(12) United States Patent
Takashima et al.

(10) Patent No.: US 9,073,821 B2
(45) Date of Patent: Jul. 7, 2015

(54) HYDROXAMIC ACID DERIVATIVE

(75) Inventors: Hajime Takashima, Tokyo (JP); Risa Tsuruta, Tokyo (JP); Tetsuya Yabuuchi, Tokyo (JP); Yusuke Oka, Tokyo (JP); Hiroki Urabe, Tokyo (JP); Yoichiro Suga, Tokyo (JP); Masato Takahashi, Tokyo (JP); Fumito Uneuchi, Tokyo (JP); Hironori Kotsubo, Toyama (JP); Muneo Shoji, Toyama (JP); Yasuko Kawaguchi, Toyama (JP)

(73) Assignees: TAISHO PHARMACEUTICAL CO., LTD, Tokyo (JP); TOYAMA CHEMICAL CO., LTD., Tokyo (JP)

( * ) Notice: Subject to any disclaimer, the term of this patent is extended or adjusted under 35 U.S.C. 154(b) by 111 days.

(21) Appl. No.: 13/642,320

(22) PCT Filed: Apr. 20, 2011

(86) PCT No.: PCT/JP2011/059737
§ 371 (c)(1),
(2), (4) Date: Nov. 20, 2012

(87) PCT Pub. No.: WO2011/132712
PCT Pub. Date: Oct. 27, 2011

(65) Prior Publication Data
US 2013/0072677 A1    Mar. 21, 2013

(30) Foreign Application Priority Data
Apr. 20, 2010   (JP) ................................. 2010-096852

(51) Int. Cl.
*C07C 259/06* (2006.01)
*C07C 323/62* (2006.01)
(Continued)

(52) U.S. Cl.
CPC .............. *C07C 259/06* (2013.01); *C07C 271/22* (2013.01); *C07C 271/28* (2013.01); *C07C 311/08* (2013.01); *C07C 317/28* (2013.01); *C07C 317/44* (2013.01); *C07C 323/41* (2013.01); *C07C 323/62* (2013.01); *C07C 2101/02* (2013.01); *C07C 2101/04* (2013.01);
(Continued)

(58) Field of Classification Search
CPC .. C07C 259/06; C07C 323/62; C07D 305/06; C07D 305/08; C07D 307/14; C07D 307/18; C07D 307/52; C07D 307/54; C07D 307/78; C07D 307/82; C07D 307/87; C07D 317/30; C07D 317/60; C07D 317/18; C07D 319/20; C07D 333/24; C07D 295/08; C07D 295/12; C07D 295/14; C07D 295/16; C07D 285/12; C07D 277/20; C07D 277/30; C07D 277/62; C07D 277/66; C07D 271/12; C07D 267/10; C07D 265/30; C07D 265/38; C07D 263/14; C07D 263/32; C07D 263/56; C07D 261/08; C07D 241/04; C07D 239/26; C07D 235/04; C07D 233/61; C07D 231/12; C07D 231/56; C07D 231/61; C07D 217/04; C07D 217/12; C07D 215/14; C07D 213/38; C07D 213/4054; C07D 213/61; C07D 213/64; C07D 213/14; C07D 211/18; C07D 211/38; C07D 211/46; C07D 211/56; C07D 211/70; C07D 209/08; C07D 209/12; C07D 209/14; C07D 209/44; C07D 209/52; C07D 207/10; C07D 207/12; C07D 207/27; C07D 207/327; C07D 205/04; C07D 205/12
USPC .......... 562/621; 514/575; 540/545; 544/58.2, 544/106, 242, 336, 358; 546/134, 139, 184, 546/329; 548/215, 240, 300, 356, 400, 452, 548/950; 549/13, 65, 356, 395, 429
See application file for complete search history.

(56) References Cited

U.S. PATENT DOCUMENTS 7,126,001 B2 * 10/2006 Breslow et al. ................ 546/171
8,722,686 B2 * 5/2014 Brown et al. .................. 514/256
(Continued)

FOREIGN PATENT DOCUMENTS

JP      2006519772      8/2006
WO      0059874         10/2000
(Continued)

OTHER PUBLICATIONS

Livermore, "Multiple Mechanisms of Antimicrobial Resistance in *Psuedomonas aeruginosa*: Our Worst Nightmare?", Antimicrobial Resistance, 34:634-640 (2002).
(Continued)

Primary Examiner — Venkataraman Balasubramanian
(74) Attorney, Agent, or Firm — Sughrue Mion, PLLC

(57) ABSTRACT

Provided is a novel compound which is useful as a pharmaceutical composition by inhibiting an LpxC activity, thereby exhibiting potent antimicrobial activity against gram-negative bacteria including *Pseudomonas aeruginosa* and its drug resistant bacteria. Provided is a hydroxamic acid derivative represented by the following general formula [1] or a pharmaceutically acceptable salt thereof:

[Chemical formula 1]

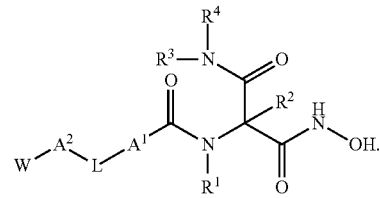

17 Claims, No Drawings

(51) Int. Cl.

| | |
|---|---|
| *C07D 305/06* | (2006.01) |
| *C07D 307/14* | (2006.01) |
| *C07D 317/30* | (2006.01) |
| *C07D 319/18* | (2006.01) |
| *C07D 295/08* | (2006.01) |
| *C07D 285/12* | (2006.01) |
| *C07D 271/12* | (2006.01) |
| *C07D 265/30* | (2006.01) |
| *C07D 263/14* | (2006.01) |
| *C07D 261/08* | (2006.01) |
| *C07D 241/04* | (2006.01) |
| *C07C 271/22* | (2006.01) |
| *C07C 271/28* | (2006.01) |
| *C07C 311/08* | (2006.01) |
| *C07C 317/28* | (2006.01) |
| *C07C 317/44* | (2006.01) |
| *C07C 323/41* | (2006.01) |
| *C07D 205/12* | (2006.01) |
| *C07D 207/12* | (2006.01) |
| *C07D 207/27* | (2006.01) |
| *C07D 207/327* | (2006.01) |
| *C07D 209/12* | (2006.01) |
| *C07D 209/14* | (2006.01) |
| *C07D 209/44* | (2006.01) |
| *C07D 209/52* | (2006.01) |
| *C07D 211/18* | (2006.01) |
| *C07D 211/38* | (2006.01) |
| *C07D 211/46* | (2006.01) |
| *C07D 211/56* | (2006.01) |
| *C07D 211/70* | (2006.01) |
| *C07D 213/38* | (2006.01) |
| *C07D 213/40* | (2006.01) |
| *C07D 213/54* | (2006.01) |
| *C07D 213/61* | (2006.01) |
| *C07D 213/64* | (2006.01) |
| *C07D 213/65* | (2006.01) |
| *C07D 213/70* | (2006.01) |
| *C07D 213/74* | (2006.01) |
| *C07D 213/81* | (2006.01) |
| *C07D 215/14* | (2006.01) |
| *C07D 217/12* | (2006.01) |
| *C07D 231/56* | (2006.01) |
| *C07D 257/04* | (2006.01) |
| *C07D 263/32* | (2006.01) |
| *C07D 263/56* | (2006.01) |
| *C07D 265/38* | (2006.01) |
| *C07D 267/10* | (2006.01) |
| *C07D 277/20* | (2006.01) |
| *C07D 277/30* | (2006.01) |
| *C07D 277/62* | (2006.01) |
| *C07D 277/66* | (2006.01) |
| *C07D 295/12* | (2006.01) |
| *C07D 295/14* | (2006.01) |
| *C07D 295/16* | (2006.01) |
| *C07D 305/08* | (2006.01) |
| *C07D 307/18* | (2006.01) |
| *C07D 307/52* | (2006.01) |
| *C07D 307/54* | (2006.01) |
| *C07D 307/78* | (2006.01) |
| *C07D 307/82* | (2006.01) |
| *C07D 307/87* | (2006.01) |
| *C07D 309/04* | (2006.01) |
| *C07D 309/14* | (2006.01) |
| *C07D 317/60* | (2006.01) |
| *C07D 319/20* | (2006.01) |
| *C07D 333/24* | (2006.01) |
| *C07D 405/06* | (2006.01) |
| *C07D 413/06* | (2006.01) |
| *C07D 471/04* | (2006.01) |
| *C07D 471/10* | (2006.01) |
| *C07D 487/08* | (2006.01) |
| *C07D 491/20* | (2006.01) |
| *C07D 498/08* | (2006.01) |
| *C07F 9/09* | (2006.01) |
| C07D 239/26 | (2006.01) |
| C07D 235/04 | (2006.01) |
| C07D 233/61 | (2006.01) |
| C07D 231/12 | (2006.01) |
| C07D 217/04 | (2006.01) |
| C07D 211/14 | (2006.01) |
| C07D 209/08 | (2006.01) |
| C07D 207/10 | (2006.01) |
| C07D 205/04 | (2006.01) |

(52) U.S. Cl.
CPC .......... *C07C 2101/08* (2013.01); *C07C 2101/14* (2013.01); *C07C 2101/16* (2013.01); *C07C 2101/18* (2013.01); *C07C 2102/08* (2013.01); *C07D 205/04* (2013.01); *C07D 205/12* (2013.01); *C07D 207/10* (2013.01); *C07D 207/12* (2013.01); *C07D 207/27* (2013.01); *C07D 207/327* (2013.01); *C07D 209/08* (2013.01); *C07D 209/12* (2013.01); *C07D 209/14* (2013.01); *C07D 209/44* (2013.01); *C07D 209/52* (2013.01); *C07D 211/14* (2013.01); *C07D 211/18* (2013.01); *C07D 211/38* (2013.01); *C07D 211/46* (2013.01); *C07D 211/56* (2013.01); *C07D 211/70* (2013.01); *C07D 213/38* (2013.01); *C07D 213/40* (2013.01); *C07D 213/54* (2013.01); *C07D 213/61* (2013.01); *C07D 213/64* (2013.01); *C07D 213/65* (2013.01); *C07D 213/70* (2013.01); *C07D 213/74* (2013.01); *C07D 213/81* (2013.01); *C07D 215/14* (2013.01); *C07D 217/04* (2013.01); *C07D 217/12* (2013.01); *C07D 231/12* (2013.01); *C07D 231/56* (2013.01); *C07D 233/61* (2013.01); *C07D 235/04* (2013.01); *C07D 257/04* (2013.01); *C07D 261/08* (2013.01); *C07D 263/14* (2013.01); *C07D 263/32* (2013.01); *C07D 263/56* (2013.01); *C07D 265/30* (2013.01); *C07D 265/38* (2013.01); *C07D 267/10* (2013.01); *C07D 271/12* (2013.01); *C07D 277/20* (2013.01); *C07D 277/30* (2013.01); *C07D 277/62* (2013.01); *C07D 277/66* (2013.01); *C07D 285/12* (2013.01); *C07D 295/08* (2013.01); *C07D 295/12* (2013.01); *C07D 295/14* (2013.01); *C07D 295/16* (2013.01); *C07D 305/06* (2013.01); *C07D 305/08* (2013.01); *C07D 307/14* (2013.01); *C07D 307/18* (2013.01); *C07D 307/52* (2013.01); *C07D 307/54* (2013.01); *C07D 307/78* (2013.01); *C07D 307/82* (2013.01); *C07D 307/87* (2013.01); *C07D 309/04* (2013.01); *C07D 309/14* (2013.01); *C07D 317/30* (2013.01); *C07D 317/60* (2013.01); *C07D 319/18* (2013.01); *C07D 319/20* (2013.01); *C07D 333/24* (2013.01); *C07D 405/06* (2013.01); *C07D 413/06* (2013.01); *C07D 471/04* (2013.01);

C07D 471/10 (2013.01); C07D 487/08 (2013.01); C07D 491/20 (2013.01); C07D 498/08 (2013.01); C07F 9/091 (2013.01)

(56) References Cited

U.S. PATENT DOCUMENTS

| | | |
|---|---|---|
| 2007/0066646 A1 | 3/2007 | Clauzel et al. |
| 2007/0129371 A1 | 6/2007 | Nakamoto et al. |
| 2010/0135960 A1 | 6/2010 | Or et al. |

FOREIGN PATENT DOCUMENTS

| | | |
|---|---|---|
| WO | 0230873 | 4/2002 |
| WO | 2004058728 | 7/2004 |
| WO | 2004062601 | 7/2004 |
| WO | 2007069020 | 6/2007 |
| WO | 2008045671 | 4/2008 |
| WO | 2008154642 | 12/2008 |
| WO | 2010017060 | 2/2010 |
| WO | 2010031750 | 3/2010 |
| WO | 2010032147 | 3/2010 |
| WO | 2011005355 | 1/2011 |

OTHER PUBLICATIONS

Eldere, "Multicentre surveillance of Psuedomonas aeruginosa susceptibility patterns in nosocominal infections", Journal of Antimicrobial Chemotherapy, 51:347-352 (2003).

Beall et al., "Sequence Analysis, transcriptional organization, and insertional mutagenesis of the envA gene of Escherichia coli", Journal of Bacteriology, 169(12):5408-5415 (1987).

Kline et al., "Potent, Novel in Vitro Inhibitors of the Psuedomonas aeruginosa Deacetylase LpxC", Journal of Medicinal Chemistry, 45:3112-3129 (2002).

Mikamo et al., "Surveillance on Psuedomonas aeruginosa Isolated in Gifu Prefecture", The Japanese Journal of Antibiotics, 59(5):355-363 (2006).

Young et al., "The envA Permeability/Cell Division Gene of Escherichia coli Encodes the Second Enzyme of Lipid a Biosynthesis", Journal of Biological Chemistry, 270(51):30384-30391 (1995).

Barb et al., "Structure of the deacetylase LpxC bound to the antibiotic CHIR-090: Time-dependent inhibition and specificity in ligand binding", PNAS, 104(47):18433-18438 (2007).

Lee et al., "Species-Specific and Inhibitor-Dependent Conformations of LpxC: Implications for Antibiotic Design", Chemistry & Biology, 18:38-47 (2011).

Liang et al., "Synthesis, structures and antibiotic activities of LpxC inhibitors based on the diacetylene scaffold", Bioorganic & Medicinal Chemistry, 19:852-860 (2011).

Mansoor et al., "Design and synthesis of potent Gram-positive specific LpxC inhibitors", Bioorganic & Medicinal Chemistry Letters, 21:1155-1161 (2011).

* cited by examiner

HYDROXAMIC ACID DERIVATIVE

CROSS REFERENCE TO RELATED APPLICATIONS

This application is a National Stage of International Application No. PCT/JP2011/059737 filed Apr. 20, 2011, claiming priority based on Japanese Patent Application No. 2010-096852 filed Apr. 20, 2010, the contents of all of which are incorporated herein by reference in their entirety.

TECHNICAL FIELD

This invention relates to novel hydroxamic acid derivatives or salts thereof, which exhibit an activity for inhibiting uridyl-diphospho (UDP)-3-O-acyl-N-acetylglucosamine deacetylase (LpxC) and antimicrobial pharmaceuticals comprising the same.

BACKGROUND ART

Gram-negative bacteria have an outer membrane composed of a lipid bilayer inexistent in gram-positive bacteria, and thus tend to be more resistant to drugs, as compared with gram-positive bacteria, due to the problem of drug permeability. Gram-negative bacteria are also known to have a plurality of drug efflux proteins, which are known to be involved in drug resistance (Non-Patent Document 1). Furthermore, lipopolysaccharide (LPS), one of the main constituents of the outer membrane, greatly takes part in toxicity as an endotoxin.

Among gram-negative bacteria, *Pseudomonas aeruginosa*, in particular, is known to have a strong tendency to show natural resistance to various antimicrobial agents. *Pseudomonas aeruginosa* is a weakly toxic bacterial species which is found commonly and widely in natural environment and living environment, but is normally not pathogenic to healthy persons. However, *Pseudomonas aeruginosa* is a pathogenic microorganism causing a serious acute infection, such as sepsis, to patients with serious underlying diseases; patients, called compromised hosts, using immunosuppressants because of transplantation or the like; or patients subjected to medical care such as medical catheterization, endotracheal intubation, or surgical operation. Thus, *Pseudomonas aeruginosa* is one of important microorganisms causing opportunistic infections or nosocomial infections. In recent years, *Pseudomonas aeruginosa*, which has gained resistance to carbapenem drugs, quinolone drugs or aminoglycoside drugs expected to be essentially effective against *Pseudomonas aeruginosa*, has been clinically isolated in medical settings (Non-Patent Document 2). Moreover, multi-drug resistant *Pseudomonas aeruginosa* which has obtained resistance to all of these three types of drugs has been isolated (Non-Patent Document 3). Infections with multi-drug resistant *Pseudomonas aeruginosa* have posed worldwide major problems as intractable infectious diseases, because there have been few useful therapeutic drugs. Hence, there is a keen demand for the development of a drug having a novel mechanism of action.

UDP-3-O-acyl-N-acetylglucosamine deacetylase (LpxC) is an enzyme in charge of the synthesis of lipid A (hydrophobic anchor of LPS which is the constituent of the outer membrane). Lipid A biosynthesis consists of reactions in 10 stages, and LpxC catalyzes the second stage of the biosynthesis reactions to remove the acetyl group of UDP-3-O-acyl-N-acetylglucosamine (Non-Patent Document 4). Lipid A is a component essential for the formation of the outer membrane, and is consequently indispensable for the survival of gram-negative bacteria (Non-Patent Document 5). LpxC is one of the rate-determining important enzymes during the process of lipid A biosynthesis, and is an indispensable enzyme for lipid A biosynthesis. Thus, a drug inhibiting the activity of LpxC is highly expected to be capable of becoming an antimicrobial agent effective against gram-negative bacteria including *Pseudomonas aeruginosa*, particularly against drug resistant *Pseudomonas aeruginosa*, because such a drug has a mechanism of action different from those of conventional drugs.

LpxC inhibitors have hitherto been known from Patent Documents 1 to 4 and Non-Patent Documents 6 to 10 teaching inhibitors with amide structures, Patent Document 5 teaching an inhibitor with a urea structure, and Patent Document 6 teaching an inhibitor with an ether structure. However, the compound of the present invention is not known to have LpxC-inhibiting activity.

CITATION LIST

Patent Documents

Patent Document 1: International Publication Ser. No. 04/062,601 pamphlet
Patent Document 2: International Publication Ser. No. 07/069,020 pamphlet
Patent Document 3: International Publication Ser. No. 08/154,642 pamphlet
Patent Document 4: International Publication Ser. No. 10/031,750 pamphlet
Patent Document 5: International Publication Ser. No. 10/017,060 pamphlet
Patent Document 6: International Publication Ser. No. 10/032,147 pamphlet

Non-Patent Documents

Non-Patent Document 1: Antimicrobial Resistance (2002) March 1, 34, pp. 634-640.
Non-Patent Document 2: J. Antimicrob. Chemother. (2003) January 14, 51, pp. 347-352.
Non-Patent Document 3: Jpn. J. Antibiotics (2006), 59(5), pp. 355-363.
Non-Patent Document 4: J. Biol. Chem. (1995) December 22, 270, pp. 30384-30391.
Non-Patent Document 5: J. Bacteriol. (1987), 169, pp. 5408-5415.
Non-Patent Document 6: J. Med. Chem. (2002), 45, pp. 3112-3129.
Non-Patent Document 7: Proc. Natl. Acad. Sci. USA (2007), 104, pp. 18433-18438.
Non-Patent Document 8: Chem. Biol. (2011), 18, pp. 38-47.
Non-Patent Document 9: Bioorg. Med. Chem. (2011), 19, pp. 852-860.
Non-Patent Document 10: Bioorg. Med. Chem. Lett. (2011), 21, pp. 1155-1161.

SUMMARY OF INVENTION

Technical Problems

An object of the present invention is to provide a novel compound which exhibits potent antimicrobial activity against gram-negative bacteria, including *Pseudomonas* aeruginosa, and their drug resistant strains by inhibiting LpxC, and which is useful as a pharmaceutical drug.

Solution to Problems

The present inventors have conducted in-depth studies in an attempt to find out a compound having LpxC-inhibiting activity. As a result, they have found that a compound represented by the following general formula [1] or a pharmaceutically acceptable salt thereof attains the above object. Based on this finding, they have accomplished the present invention. The present invention will be described below.

The present invention provides (1) a compound represented by the following general formula [1] or a pharmaceutically acceptable salt thereof:

[Chemical formula 1]

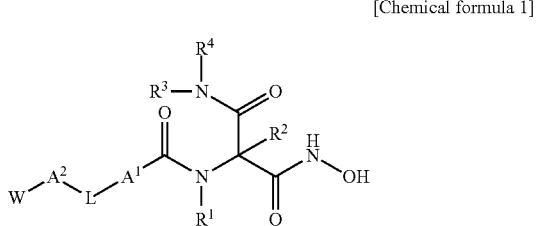

[1]

wherein $R^1$ and $R^2$ are the same or different and each represent a hydrogen atom, a $C_{1-6}$ alkyl group, a $C_{3-8}$ cycloalkyl group or a $C_{1-6}$ alkoxy group (the $C_{1-6}$ alkyl group, the $C_{1-6}$ alkoxy group and the $C_{3-8}$ cycloalkyl group may be substituted with 1 to 3 substituents which are the same or different and are selected from "a halogen atom, a hydroxy group, a $C_{3-8}$ cycloalkyl group, a $C_{1-6}$ alkoxy group, a $C_{3-8}$ cycloalkoxy group, an amino group, a $C_{1-6}$ alkylamino group, a di($C_{1-6}$ alkyl)amino group, —N($R^{11}$)COR$^{12}$, —N($R^{11}$)SO$_2R^{12}$, a cyano group, a carboxy group, a carbamoyl group, —CON($R^{13}$)($R^{14}$), —SO$_2$N($R^{13}$)($R^{14}$), a $C_{1-6}$ alkylthio group, a $C_{1-6}$ alkylsulfonyl group, an aryloxy group, an aryl group, and a heterocyclic group"), $R^{11}$, $R^{12}$, $R^{13}$ and $R^{14}$ are the same or different and each represent a hydrogen atom or a $C_{1-6}$ alkyl group, $R^{13}$ and $R^{14}$, together with the nitrogen atom to which they are attached, may form a saturated or unsaturated 5- or 6-membered ring which may further contain one or more nitrogen atoms, oxygen atoms or sulfur atoms, $R^3$ represents a hydrogen atom or a $C_{1-6}$ alkyl group (the $C_{1-6}$ alkyl group may be substituted with 1 to 3 substituents which are the same or different and are selected from "a halogen atom, a hydroxy group, a $C_{1-6}$ alkoxy group, a $C_{3-8}$ cycloalkoxy group, an amino group, a $C_{1-6}$ alkylamino group, and a di($C_{1-6}$ alkyl)amino group"), $R^4$ represents a hydrogen atom,
a hydroxy group,
a $C_{1-6}$ alkoxy group,
a $C_{3-8}$ cycloalkoxy group,
an amino group,
a $C_{1-6}$ alkylamino group,
a di($C_{1-6}$ alkyl)amino group,
a $C_{1-6}$ alkyl group, a $C_{3-8}$ cycloalkyl group
(the $C_{1-6}$ alkyl group and the $C_{3-8}$ cycloalkyl group may be substituted with 1 to 3 substituents which are the same or different and are selected from "a halogen atom, a hydroxy group, a $C_{3-8}$ cycloalkyl group, a $C_{1-6}$ alkoxy group, a $C_{3-8}$ cycloalkoxy group, an amino group, a $C_{1-6}$ alkylamino group, a di($C_{1-6}$ alkyl)amino group, —N($R^{41}$)COR$^{42}$, —N($R^{41}$)SO$_2R^{42}$, a cyano group, a carboxy group, —CON($R^{43}$)($R^{44}$), —SO$_2$N($R^{43}$)($R^{44}$), a $C_{1-6}$ alkylthio group, a $C_{1-6}$ alkylsulfonyl group, an aryl group, an aryloxy group, and a heterocyclic group (the aryl group, the aryloxy group, and the heterocyclic group may be substituted with 1 to 3 substituents which are the same or different and are selected from "a halogen atom, a $C_{1-6}$ alkyl group, a $C_{3-8}$ cycloalkyl group, a benzyl group, a $C_{1-6}$ haloalkyl group, a $C_{1-6}$ hydroxyalkyl group, a $C_{2-8}$ alkoxyalkyl group, a hydroxy group, a $C_{1-6}$ alkoxy group, a $C_{3-8}$ cycloalkoxy group, an amino group, a $C_{1-6}$ alkylamino group, a di($C_{1-6}$ alkyl)amino group, —N($R^{45}$)COR$^{46}$, —N($R^{45}$)SO$_2R^{46}$, a cyano group, a carboxy group, —CON($R^{47}$)($R^{48}$), —SO$_2$N($R^{47}$)($R^{48}$), a $C_{1-6}$ alkylthio group, and a $C_{1-6}$ alkylsulfonyl group")"), an aryl group, or a heterocyclic group (the aryl group and the heterocyclic group may be substituted with 1 to 3 substituents which are the same or different and are selected from "a halogen atom, a $C_{1-6}$ alkyl group, a $C_{3-8}$ cycloalkyl group, a $C_{1-6}$ haloalkyl group, a $C_{1-6}$ hydroxyalkyl group, a $C_{2-8}$ alkoxyalkyl group, a hydroxy group, a $C_{1-6}$ alkoxy group, a $C_{3-8}$ cycloalkoxy group, an amino group, a $C_{1-6}$ alkylamino group, a di($C_{1-6}$ alkyl)amino group, —N($R^{45}$)COR$^{46}$, —N($R^{45}$)SO$_2R^{46}$, a cyano group, a carboxy group, —CON($R^{47}$)($R^{48}$), —SO$_2$N($R^{47}$)($R^{48}$), a $C_{1-6}$ alkylthio group, and a $C_{1-6}$ alkylsulfonyl group"), $R^{41}$, $R^{42}$, $R^{43}$, $R^{44}$, $R^{45}$, $R^{46}$, $R^{47}$ and $R^{48}$ are the same or different and each represent a hydrogen atom or a $C_{1-6}$ alkyl group, $R^{43}$ and $R^{44}$, together with the nitrogen atom to which they are attached, may form a saturated or unsaturated 5- or 6-membered ring which may further contain one or more nitrogen atoms, oxygen atoms or sulfur atoms, $R^{47}$ and $R^{48}$, together with the nitrogen atom to which they are attached, may form a saturated or unsaturated 5- or 6-membered ring which may further contain one or more nitrogen atoms, oxygen atoms or sulfur atoms, $R^3$ and $R^4$, together with the nitrogen atom to which they are attached, may form a saturated or unsaturated 5- or 6-membered ring which may further contain one or more nitrogen atoms, oxygen atoms or sulfur atoms, $A^1$ represents a divalent aryl group, a divalent heterocyclic group, or a $C_{3-8}$ cycloalkylene group (the divalent aryl group, the divalent heterocyclic group and the $C_{3-8}$ cycloalkylene group may be substituted with 1 to 4 substituents which are the same or different and are selected from the following group of substituents, $R^a$):

the group of substituents, $R^a$, consists of a halogen atom, a hydroxy group, an amino group (the amino group may be substituted with a $C_{2-6}$ alkanoyl group or one or two $C_{1-6}$ alkyl groups), a carboxy group, a carbamoyl group, a $C_{1-6}$ alkyl group, a $C_{3-8}$ cycloalkyl group, a $C_{2-6}$ alkenyl group, and a $C_{1-6}$ alkoxy group (the $C_{1-6}$ alkyl group, the $C_{3-8}$ cycloalkyl group, the $C_{2-6}$ alkenyl group, and the $C_{1-6}$ alkoxy group may be substituted with 1 to 4 substituents which are the same or different and are selected from "a halogen atom, a hydroxy group, an amino group, a carboxy group, a $C_{1-6}$ alkylaminocarbonyl group, and a $C_{1-6}$ alkoxycarbonyl group"), L represents —C≡C—, —C≡C—C≡C—, —C≡C—(CH$_2$)$_m$—O—, —CH=CH—, —CH=CH—C≡C—, —C≡C—CH=CH—, —O—, —S—, —NR$^5$—, —CONR$^5$—, —NR$^5$CO—, a divalent heterocyclic group, —(CH$_2$)$_m$—NR$^5$—, —(CH$_2$)$_m$—O—, —NR$^5$—(CH$_2$)$_m$—, —O—(CH$_2$)$_m$—, —ON=CH—, a C$_{1-4}$ alkylene group, or a bond, R$^5$ represents a hydrogen atom, a C$_{1-6}$ alkyl group, a C$_{3-8}$ cycloalkyl group, or an aryl group, m denotes 1, 2 or 3, A$^2$ represents a divalent aryl group, a divalent heterocyclic group, a divalent partially saturated fused polycyclic hydrocarbon ring group, a C$_{3-8}$ cycloalkylene group, a C$_{3-8}$ cycloalkenylene group, a C$_{1-4}$ alkylene group, or a C$_{2-4}$ alkenylene group (the divalent aryl group, the divalent heterocyclic group, the divalent partially saturated fused polycyclic hydrocarbon ring group, the C$_{3-8}$ cycloalkenylene group, the C$_{3-8}$ cycloalkylene group, the C$_{1-4}$ alkylene group, and the C$_{2-4}$ alkenylene group may be substituted with 1 to 4 substituents which are the same or different and are selected from the following group of substituents, R$^b$):

the group of substituents, R$^b$, consists of a halogen atom, an optionally protected hydroxy group, a mercapto group, a cyano group, a nitro group, an optionally protected amino group, an optionally protected formyl group, an optionally protected carboxy group, a carbamoyl group, a sulfo group, a ureido group, a guanidido group, a C$_{1-6}$ alkyl group, a C$_{3-8}$ cycloalkyl group, a C$_{1-6}$ haloalkyl group, a C$_{1-6}$ hydroxyalkyl group, a C$_{1-6}$ alkoxy group, a C$_{1-6}$ alkylamino group, a di(C$_{1-6}$ alkyl)amino group, a C$_{1-6}$ alkoxycarbonyl group, a C$_{2-6}$ alkanoyl group, and an aryl group, W represents R$^6$—X$^1$—, R$^6$—X$^2$—Y$^1$—X$^1$—, R$^6$—X$^4$—Y$^1$—X$^2$—Y$^3$—X$^3$—, Q-X$^1$—Y$^2$—X$^3$—, or Q-X$^1$—Y$^1$—X$^2$—Y$^3$—X$^3$—, Y$^2$ represents —O—, —NR$^7$—, —CO—, —NR$^7$CO—, —CONR$^7$—, —S(O)$_n$—, —OCO—, —COO—, —NR$^7$SO$_2$—, —SO$_2$—NR$^7$—, —OCOO—, —OCONR$^7$—, —NR$^7$CONR$^8$—, or a bond, Y$^1$ and Y$^3$ are the same or different and each represent —O—, —NR$^7$—, —CO—, —NR$^7$CO—, —CONR$^7$—, —S(O)$_n$—, —OCO—, —COO—, —NR$^7$SO$_2$—, —SO$_2$NR$^7$—, —OCOO—, —OCONR$^7$—, or —NR$^7$CONR$^8$—, n denotes 0, 1 or 2, X$^1$ and X$^3$ are the same or different and each represent a C$_{1-10}$ alkylene group, a C$_{2-10}$ alkenylene group, a C$_{2-10}$ alkynylene group, a C$_{3-8}$ cycloalkylene group, —C$_{1-6}$ alkylene-C$_{3-8}$ cycloalkylene-C$_{1-6}$ alkylene- (the C$_{1-10}$ alkylene group, the C$_{2-10}$ alkenylene group, the C$_{2-10}$ alkynylene group, the C$_{3-8}$ cycloalkylene group, and the —C$_{1-6}$ alkylene-C$_{3-8}$ cycloalkylene-C$_{1-6}$ alkylene- may be substituted with 1 to 4 substituents which are the same or different and are selected from a group of substituents, R$^c$, to be shown below), or a bond, X$^2$ and X$^4$ are the same or different and each represent a C$_{1-10}$ alkylene group, a C$_{2-10}$ alkenylene group, a C$_{2-10}$ alkynylene group, or —C$_{1-6}$ alkylene-C$_{3-8}$ cycloalkylene-C$_{1-6}$ alkylene- (the C$_{1-10}$ alkylene group, the C$_{2-10}$ alkenylene group, the C$_{2-10}$ alkynylene group, and the —C$_{1-6}$ alkylene-C$_{3-8}$ cycloalkylene-C$_{1-6}$ alkylene- may be substituted with 1 to 4 substituents which are the same or different and are selected from the group of substituents, R$^c$, to be shown below), Q represents a C$_{3-8}$ cycloalkyl group, an aryl group, or a heterocyclic group (the C$_{3-8}$ cycloalkyl group, the aryl group and the heterocyclic group may be substituted with 1 to 4 substituents which are the same or different and are selected from the group of substituents, R$^c$, to be shown below, and the heterocyclic group may have the different carbon atoms on the ring bridged with a C$_{1-6}$ alkylene group or —C$_{1-6}$ alkylene-O—C$_{1-6}$ alkylene-), R$^6$ represents a hydrogen atom, a halogen atom, an optionally protected hydroxy group, a mercapto group, a cyano group, a nitro group, an optionally protected amino group, an optionally protected formyl group, an optionally protected carboxy group, a carbamoyl group, a sulfo group, an optionally protected phosphate group, a ureido group, a guanidido group, R$^7$—O—NR$^8$—CO—, R$^8$—ON=CR$^9$—, R$^8$—ON=CR$^9$—NH—, R$^7$—O—NR$^8$—CH=N—, (R$^7$)(R$^8$)N—N=CH—, R$^8$—O—NR$^8$—, N≡C—NR$^8$— or a C$_{1-6}$ alkoxy group (the C$_{1-6}$ alkoxy group may be substituted with 1 to 3 hydroxy groups), R$^7$ and R$^8$ are the same or different and each represent a hydrogen atom, a C$_{1-6}$ alkyl group, a C$_{3-8}$ cycloalkyl group, an aryl group, or a heterocyclic group (the C$_{1-6}$ alkyl group, the C$_{3-8}$ cycloalkyl group, the aryl group and the heterocyclic group may be substituted with 1 to 4 substituents which are the same or different and are selected from the group of substituents, R$^c$, to be shown below), R$^9$ represents a hydrogen atom, a C$_{1-6}$ alkyl group, a C$_{3-8}$ cycloalkyl group, an amino group, or a C$_{1-6}$ alkylamino group, and the group of substituents, R$^c$, consists of a halogen atom, a hydroxy group, a cyano group, a nitro group, an amino group (the amino group may be substituted with a C$_{2-6}$ alkanoyl group or one or two C$_{1-6}$ alkyl groups), a carboxy group, a carbamoyl group, a ureido group, a guanidido group, a C$_{1-6}$ alkyl group (the C$_{1-6}$ alkyl group may be substituted with a heterocyclic group), a C$_{1-6}$ hydroxyalkyl group, a C$_{1-6}$ haloalkyl group, a C$_{3-8}$ cycloalkyl group, a C$_{1-6}$ alkoxy group (the C$_{1-6}$ alkoxy group may be substituted with 1 to 3 substituents which are the same or different and are selected from a hydroxy group, a halogen atom, a C$_{3-8}$ cycloalkyl group, a C$_{1-6}$ alkoxy group, an aryl group and a heterocyclic group), a C$_{3-8}$ cycloalkoxy group, a C$_{1-6}$ alkoxycarbonyl group, a C$_{1-6}$ alkoxycarbonylamino group, a C$_{2-6}$ alkanoyl group, a C$_{1-6}$ alkylsulfonyl group, a C$_{1-6}$ alkylthio group, an aryl group, a heterocyclic group (the aryl group and the heterocyclic group may be substituted with 1 to 4 substituents which are the same or different and are selected from "a halogen atom, a hydroxy group, a cyano group, a nitro group, an amino group, a carboxy group and a C$_{1-6}$ alkyl group"), a C$_{1-6}$ alkylidene group (the C$_{1-6}$ alkylidene group may be substituted with a C$_{1-6}$ alkoxy group), a C$_{3-8}$ cycloalkylidene group, a monocyclic saturated heteroclidene group (the monocyclic saturated heterocyclidene group may be substituted with 1 to 2 C$_{1-6}$ alkyl groups), and a hydroxyaminocarbonyl group;

(2) the compound represented by the following general formula [1] or the pharmaceutically acceptable salt thereof, according to the item (1) above:

[Chemical formula 2]

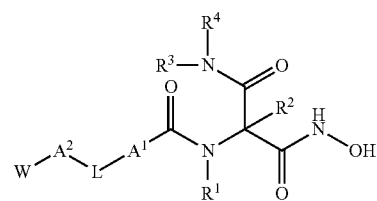

[1]
where
$R^1$ and $R^2$ are the same or different and each represent a hydrogen atom, a $C_{1-6}$ alkyl group, a $C_{3-8}$ cycloalkyl group or a $C_{1-6}$ alkoxy group (the $C_{1-6}$ alkyl group, the $C_{1-6}$ alkoxy group and the $C_{3-8}$ cycloalkyl group may be substituted with 1 to 3 substituents which are the same or different and are selected from "a halogen atom, a hydroxy group, a $C_{3-8}$ cycloalkyl group, a $C_{1-6}$ alkoxy group, a $C_{3-8}$ cycloalkoxy group, an amino group, a $C_{1-6}$ alkylamino group, a di($C_{1-6}$ alkyl)amino group, —N($R^{11}$)COR$^{12}$, —N($R^{11}$)SO$_2$R$^{12}$, a cyano group, a carboxy group, a carbamoyl group, —CON($R^{13}$)($R^{14}$), —SO$_2$N($R^{13}$)($R^{14}$), a $C_{1-6}$ alkylthio group, a $C_{1-6}$ alkylsulfonyl group, an aryloxy group, an aryl group, and a heterocyclic group"), $R^{11}$, $R^{12}$, $R^{13}$ and $R^{14}$ are the same or different and each represent a hydrogen atom or a $C_{1-6}$ alkyl group, $R^{13}$ and $R^{14}$, together with the nitrogen atom to which they are attached, may form a saturated or unsaturated 5- or 6-membered ring which may further contain one or more nitrogen atoms, oxygen atoms or sulfur atoms, $R^3$ represents a hydrogen atom or a $C_{1-6}$ alkyl group (the $C_{1-6}$ alkyl group may be substituted with 1 to 3 substituents which are the same or different and are selected from "a halogen atom, a hydroxy group, a $C_{1-6}$ alkoxy group, a $C_{3-8}$ cycloalkoxy group, an amino group, a $C_{1-6}$ alkylamino group, and a di($C_{1-6}$ alkyl)amino group"), $R^4$ represents
a hydrogen atom,
a hydroxy group,
a $C_{1-6}$ alkoxy group,
a $C_{3-8}$ cycloalkoxy group,
an amino group,
a $C_{1-6}$ alkylamino group,
a di($C_{1-6}$ alkyl)amino group,
a $C_{1-6}$ alkyl group, a $C_{3-8}$ cycloalkyl group
(the $C_{1-6}$ alkyl group and the $C_{3-8}$ cycloalkyl group may be substituted
with 1 to 3 substituents which are the same or different and are selected from "a halogen atom, a hydroxy group, a $C_{3-8}$ cycloalkyl group, a $C_{1-6}$ alkoxy group, a $C_{3-8}$ cycloalkoxy group, an amino group, a $C_{1-6}$ alkylamino group, a di($C_{1-6}$ alkyl)amino group, —N($R^{41}$)COR$^{42}$, —N($R^{41}$)SO$_2$R$^{42}$, a cyano group, a carboxy group, —CON($R^{43}$)($R^{44}$), —SO$_2$N($R^{43}$)($R^{44}$), a $C_{1-6}$ alkylthio group, a $C_{1-6}$ alkylsulfonyl group, an aryl group, an aryloxy group, and a heterocyclic group (the aryl group, the aryloxy group, and the heterocyclic group may be substituted with 1 to 3 substituents which are the same or different and are selected from "a halogen atom, a $C_{1-6}$ alkyl group, a $C_{3-8}$ cycloalkyl group, a benzyl group, a $C_{1-6}$ haloalkyl group, a $C_{1-6}$ hydroxyalkyl group, a $C_{2-8}$ alkoxyalkyl group, a hydroxy group, a $C_{1-6}$ alkoxy group, a $C_{3-8}$ cycloalkoxy group, an amino group, a $C_{1-6}$ alkylamino group, a di($C_{1-6}$ alkyl)amino group, —N($R^{45}$)COR$^{46}$, —N($R^{45}$)SO$_2$R$^{46}$, a cyano group, a carboxy group, —CON($R^{47}$)($R^{48}$), —SO$_2$N($R^{47}$)($R^{48}$), a $C_{1-6}$ alkylthio group, and a $C_{1-6}$ alkylsulfonyl group")"), an aryl group, or a heterocyclic group
(the aryl group and the heterocyclic group may be substituted with 1 to 3 substituents which are the same or different and are selected from "a halogen atom, a $C_{1-6}$ alkyl group, a $C_{3-8}$ cycloalkyl group, a $C_{1-6}$ haloalkyl group, a $C_{1-6}$ hydroxyalkyl group, a $C_{2-8}$ alkoxyalkyl group, a hydroxy group, a $C_{1-6}$ alkoxy group, a $C_{3-8}$ cycloalkoxy group, an amino group, a $C_{1-6}$ alkylamino group, a di($C_{1-6}$ alkyl)amino group, —N($R^{45}$)COR$^{46}$, —N($R^{45}$)SO$_2$R$^{46}$, a cyano group, a carboxy group, —CON($R^{47}$)($R^{48}$), —SO$_2$N($R^{47}$)($R^{48}$), a $C_{1-6}$ alkylthio group, and a $C_{1-6}$ alkylsulfonyl group"), $R^{41}$, $R^{42}$, $R^{43}$, $R^{44}$, $R^{45}$, $R^{46}$, $R^{47}$ and $R^{48}$ are the same or different and each represent a hydrogen atom or a $C_{1-6}$ alkyl group, $R^{43}$ and $R^{44}$, together with the nitrogen atom to which they are attached, may form a saturated or unsaturated 5- or 6-membered ring which may further contain one or more nitrogen atoms, oxygen atoms or sulfur atoms, $R^{47}$ and $R^{48}$, together with the nitrogen atom to which they are attached, may form a saturated or unsaturated 5- or 6-membered ring which may further contain one or more nitrogen atoms, oxygen atoms or sulfur atoms, $R^3$ and $R^4$, together with the nitrogen atom to which they are attached, may form a saturated or unsaturated 5- or 6-membered ring which may further contain one or more nitrogen atoms, oxygen atoms or sulfur atoms, $A^1$ represents a divalent aryl group, a divalent heterocyclic group, or a $C_{3-8}$ cycloalkylene group (the divalent aryl group, the divalent heterocyclic group and the $C_{3-8}$ cycloalkylene group may be substituted with 1 to 4 substituents which are the same or different and are selected from the following group of substituents, $R^a$):

the group of substituents, $R^a$, consists of a halogen atom, a hydroxy group, an amino group (the amino group may be substituted with a $C_{2-6}$ alkanoyl group or one or two $C_{1-6}$ alkyl groups), a carboxy group, a carbamoyl group, a $C_{1-6}$ alkyl group, a $C_{3-8}$ cycloalkyl group, a $C_{2-6}$ alkenyl group, and a $C_{1-6}$ alkoxy group (the $C_{1-6}$ alkyl group, the $C_{3-8}$ cycloalkyl group, the $C_{2-6}$ alkenyl group, and the $C_{1-6}$ alkoxy group may be substituted with 1 to 4 substituents which are the same or different and are selected from "a halogen atom, a hydroxy group, an amino group, a carboxy group, a $C_{1-6}$ alkylaminocarbonyl group, and a $C_{1-6}$ alkoxycarbonyl group"), L represents —C≡C—, —C≡C—C≡C—, —O—, —S—, —NR$^5$—, —CONR$^5$—, —NR$^5$CO—, a divalent heterocyclic group, —(CH$_2$)$_m$—NR$^5$—, —(CH$_2$)$_m$—O—, —NR$^5$—(CH$_2$)$_m$—, —O—(CH$_2$)$_m$—, —ON=CH—, a $C_{1-4}$ alkylene group, or a bond, $R^5$ represents a hydrogen atom, a $C_{1-6}$ alkyl group, a $C_{3-8}$ cycloalkyl group, or an aryl group, m denotes 1, 2 or 3, $A^2$ represents a divalent aryl group, a divalent heterocyclic group, a divalent partially saturated fused polycyclic hydrocarbon ring group, a $C_{3-8}$ cycloalkylene group, a $C_{1-4}$ alkylene group, or a $C_{2-4}$ alkenylene group (the divalent aryl group, the divalent heterocyclic group, the divalent partially saturated fused polycyclic hydrocarbon ring group, the $C_{3-8}$ cycloalkenylene group, $C_{1-4}$ alkylene group, and the $C_{2-4}$ alkenylene group may be substituted with 1 to 4 substituents which are the same or different and are selected from the following group of substituents, $R^b$):

the group of substituents, $R^b$, consists of a halogen atom, an optionally protected hydroxy group, a mercapto group, a cyano group, a nitro group, an optionally protected amino group, an optionally protected formyl group, an optionally protected carboxy group, a carbamoyl group, a sulfo group, a ureido group, a guanidido group, a $C_{1-6}$ alkyl group, a $C_{3-8}$ cycloalkyl group, a $C_{1-6}$ haloalkyl group, a $C_{1-6}$ hydroxyalkyl group, a $C_{1-6}$ alkoxy group, a $C_{1-6}$ alkylamino group, a di($C_{1-6}$ alkyl)amino group, a $C_{1-6}$ alkoxycarbonyl group, a $C_{2-6}$ alkanoyl group, and an aryl group, W represents $R^6—X^1—$, $R^6—X^2—Y^1—X^1—$, $R^6—X^4—Y^1—X^2—Y^3—X^3—$, $Q-X^1—Y^2—X^3—$, or $Q-X^1—Y^1—X^2—Y^3—X^3—$, $Y^2$ represents $—O—$, $—NR^7—$, $—CO—$, $—NR^7CO—$, $—CONR^7—$, $—S(O)_n—$, $—OCO—$, $—COO—$, $—NR^7SO_2—$, $—SO_2—NR^7—$, $—OCOO—$, $—OCONR^7—$, $—NR^7CONR^8—$, or a bond, $Y^1$ and $Y^3$ are the same or different and each represent $—O—$, $—NR^7—$, $—CO—$, $—NR^7CO—$, $—CONR^7—$, $—S(O)_n—$, $—OCO—$, $—COO—$, $—NR^7SO_2—$, $—SO_2NR^7—$, $—OCOO—$, $—OCONR^7—$, or $—NR^7CONR^8—$, n denotes 0, 1 or 2, $X^1$ and $X^3$ are the same or different and each represent a $C_{1-10}$ alkylene group, a $C_{2-10}$ alkenylene group, a $C_{2-10}$ alkynylene group, (the $C_{1-10}$ alkylene group, the $C_{2-10}$ alkenylene group and the $C_{2-10}$ alkynylene group may be substituted with 1 to 4 substituents which are the same or different and are selected from a group of substituents, $R^c$, to be shown below), or a bond, $X^2$ and $X^4$ are the same or different and each represent a $C_{1-10}$ alkylene group, a $C_{2-10}$ alkenylene group, a $C_{2-10}$ alkynylene group, or $—C_{1-6}$ alkylene-$C_{3-8}$ cycloalkylene-$C_{1-6}$ alkylene- (the $C_{1-10}$ alkylene group, the $C_{2-10}$ alkenylene group, the $C_{2-10}$ alkynylene group, and the $—C_{1-6}$ alkylene-$C_{3-8}$ cycloalkylene-$C_{1-6}$ alkylene- may be substituted with 1 to 4 substituents which are the same or different and are selected from the group of substituents, $R^c$, to be shown below), Q represents a $C_{3-8}$ cycloalkyl group, an aryl group, or a heterocyclic group (the $C_{3-8}$ cycloalkyl group, the aryl group and the heterocyclic group may be substituted with 1 to 4 substituents which are the same or different and are selected from the group of substituents, $R^c$, to be shown below), $R^6$ represents a hydrogen atom, a halogen atom, an optionally protected hydroxy group, a mercapto group, a cyano group, a nitro group, an optionally protected amino group, an optionally protected formyl group, an optionally protected carboxy group, a carbamoyl group, a sulfo group, an optionally protected phosphate group, a ureido group, a guanidido group, $R^7—O—NR^8—CO—$, $R^8—ON=CR^9—$, $R^8—ON=CR^9—NH—$, $R^7—O—NR^8—CH=N—$, $(R^7)(R^8)N—N=CH—$, $R^8—O—NR^8—$, $N≡C—NR^8—$, $R^7$ and $R^8$ are the same or different and each represent a hydrogen atom, a $C_{1-6}$ alkyl group, a $C_{3-8}$ cycloalkyl group, an aryl group, or a heterocyclic group (the $C_{1-6}$ alkyl group, the $C_{3-8}$ cycloalkyl group, the aryl group and the heterocyclic group may be substituted with 1 to 4 substituents which are the same or different and are selected from the group of substituents, $R^c$, to be shown below), $R^9$ represents a hydrogen atom, a $C_{1-6}$ alkyl group, a $C_{3-8}$ cycloalkyl group, an amino group, or a $C_{1-6}$ alkylamino group, and the group of substituents, $R^c$, consists of a halogen atom, a hydroxy group, a cyano group, a nitro group, an amino group (the amino group may be substituted with a $C_{2-6}$ alkanoyl group or one or two $C_{1-6}$ alkyl groups), a carboxy group, a carbamoyl group, a ureido group, a guanidido group, a $C_{1-6}$ alkyl group (the $C_{1-6}$ alkyl group may be substituted with a heterocyclic group), a $C_{1-6}$ hydroxyalkyl group, a $C_{1-6}$ haloalkyl group, a $C_{3-8}$ cycloalkyl group, a $C_{1-6}$ alkoxy group (the $C_{1-6}$ alkoxy group may be substituted with 1 to 3 hydroxy groups), a $C_{3-8}$ cycloalkoxy group, a $C_{1-6}$ alkoxycarbonyl group, a $C_{1-6}$ alkoxycarbonylamino group, a $C_{2-6}$ alkanoyl group, a $C_{1-6}$ alkylsulfonyl group, a $C_{1-6}$ alkylthio group, an aryl group, a heterocyclic group (the aryl group and the heterocyclic group may be substituted with 1 to 4 substituents which are the same or different and are selected from "a halogen atom, a hydroxy group, a cyano group, a nitro group, an amino group, a carboxy group and a $C_{1-6}$ alkyl group");

(3) the compound or the pharmaceutically acceptable salt thereof, according to the item (1) or (2) above, wherein $R^1$ is a hydrogen atom or a $C_{1-6}$ alkyl group (the $C_{1-6}$ alkyl group may be substituted with the same or different 1 to 3 halogen atoms);

(4) the compound or the pharmaceutically acceptable salt thereof, according to the item (3) above, wherein $R^1$ is a $C_{1-6}$ alkyl group (the $C_{1-6}$ alkyl group may be substituted with the same or different 1 to 3 halogen atoms);

(5) the compound or the pharmaceutically acceptable salt thereof, according to the item (4) above, wherein $R^1$ is a methyl group;

(6) the compound or the pharmaceutically acceptable salt thereof, according to any one of the items (1) to (5) above, wherein $R^2$ is a hydrogen atom;

(7) the compound or the pharmaceutically acceptable salt thereof, according to any one of the items (1) to (5) above, wherein $R^2$ is a methyl group;

(8) the compound or the pharmaceutically acceptable salt thereof, according to any one of the items (1) to (7) above, wherein $R^3$ is a hydrogen atom, and $R^4$ is a $C_{1-6}$ alkyl group (the $C_{1-6}$ alkyl group may be substituted with a phenyl group or a monocyclic aromatic heterocyclic group (the phenyl group and the monocyclic aromatic heterocyclic group may be substituted with 1 to 3 substituents which are the same or different and are selected from "a halogen atom, a $C_{1-6}$ alkyl group, a $C_{3-8}$ cycloalkyl group, a $C_{1-6}$ haloalkyl group, a $C_{1-6}$ hydroxyalkyl group, a $C_{2-8}$ alkoxyalkyl group, a hydroxy group, a $C_{1-6}$ alkoxy group, a $C_{3-8}$ cycloalkoxy group, an amino group, a $C_{1-6}$ alkylamino group, a di($C_{1-6}$ alkyl)amino group, $—N(R^{45})COR^{46}$, $—CON(R^{47})(R^{48})$"));

(9) the compound or the pharmaceutically acceptable salt thereof, according to the item (8) above, wherein $R^3$ is a hydrogen atom, and $R^4$ is a methyl group;

(10) the compound or the pharmaceutically acceptable salt thereof, according to any one of the items (1) to (9) above, wherein $A^1$ is a phenylene group (the phenylene group may be substituted with 1 to 4 substituents which are the same or different and are selected from "a halogen atom, a hydroxy group, an amino group and a $C_{1-6}$ alkyl group");

(11) the compound or the pharmaceutically acceptable salt thereof, according to the item (10) above, wherein $A^1$ is a phenylene group;

(12) the compound or the pharmaceutically acceptable salt thereof, according to any one of the items (1) to (11) above, wherein L is $—C≡C—$, $—C≡C—C≡C—$, $—CH=CH—$, $—CH=CH—C≡C—$, $—C≡C—CH=CH—$, an ethylene group, or a bond;

(13) the compound or the pharmaceutically acceptable salt thereof, according to the item (12) above, wherein L is a bond or $—C≡C—$;

(14) the compound or the pharmaceutically acceptable salt thereof, according to the item (13) above, wherein L is a bond;
(15) the compound or the pharmaceutically acceptable salt thereof, according to the item (13) above, wherein L is —C≡C—;
(16) the compound or the pharmaceutically acceptable salt thereof, according to any one of the items (1) to (15) above, wherein
$A^2$ is a divalent aryl group (the divalent aryl group may be substituted with 1 to 4 substituents which are the same or different and are selected from "a halogen atom, a hydroxy group, an amino group and a $C_{1-6}$ alkyl group"), a divalent monocyclic aromatic heterocyclic group (the divalent monocyclic aromatic heterocyclic group contains, as a ring-constituting atom, any 1 to 3 atoms selected from a nitrogen atom, an oxygen atom and a sulfur atom, and may be substituted with 1 to 4 substituents which are the same or different and are selected from "a halogen atom, a hydroxy group, an amino group and a $C_{1-6}$ alkyl group"), a divalent fused ring aromatic heterocyclic group, or a divalent fused ring heterocyclic group having a partially saturated monocycle (the divalent fused ring aromatic heterocyclic group, and the divalent fused ring heterocyclic group having a partially saturated monocycle contain, as a ring-constituting atom, any 1 to 4 atoms selected from a nitrogen atom, an oxygen atom and a sulfur atom, have a benzene ring or a pyridine ring as at least one of the rings constituting the fused ring, and may be substituted with 1 to 4 substituents which are the same or different and are selected from "a halogen atom, a hydroxy group, an amino group and a $C_{1-6}$ alkyl group");
(17) the compound or the pharmaceutically acceptable salt thereof, according to the item (16) above, wherein
$A^2$ is a phenylene group or a divalent group represented by the following formula [2]

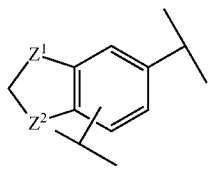

[Chemical formula 3]

[2]
where
$Z^1$ and $Z^2$ are the same or different and each represent —CH$_2$—, —O—, —NH—, —N(CH$_3$)—, or —S—, with the exception of a case where $Z^1$ and $Z^2$ both represent —CH$_2$—;
(18) the compound or the pharmaceutically acceptable salt thereof, according to the item (16) above, wherein
$A^2$ is a phenylene group, a pyridinediyl group, a pyrimidinediyl group, a 2,4-furandiyl group, a pyrazolediyl group, a pyrrolediyl group, a "divalent fused ring aromatic heterocyclic group composed of a 5-membered ring and a 6-membered ring", or a "divalent fused ring heterocyclic group having a partially saturated monocycle, which is composed of a 5-membered ring and a 6-membered ring" (the phenylene group, the pyridinediyl group, the pyrimidinediyl group, the 2,4-furandiyl group, the pyrazolediyl group, the pyrrolediyl group, the "divalent fused ring aromatic heterocyclic group composed of a 5-membered ring and a 6-membered ring", and the "divalent fused ring heterocyclic group having a partially saturated monocycle, which is composed of a 5-membered ring and a 6-membered ring" may be substituted with 1 to 4 substituents which are the same or different and are selected from "a halogen atom, a hydroxy group, an amino group and a $C_{1-6}$ alkyl group");
(19) the compound or the pharmaceutically acceptable salt thereof, according to any one of the items (1) to (18) above, wherein
W is $R^6$—$X^1$—,
$X^1$ is a methylene group or a bond,
$R^6$ is a hydrogen atom, an optionally protected hydroxy group, or $R^8$—ON═$CR^9$—,
$R^8$ is a hydrogen atom or a $C_{1-6}$ alkyl group (the $C_{1-6}$ alkyl group may be substituted with 1 to 4 substituents which are the same or different and are selected from a group of substituents, $R^c$, to be shown below),
$R^9$ is a hydrogen atom, a $C_{1-6}$ alkyl group, a $C_{3-8}$ cycloalkyl group, an amino group, or a $C_{1-6}$ alkylamino group, and the group of substituents, $R^c$, consists of a halogen atom and a hydroxy group;
(20) the compound or the pharmaceutically acceptable salt thereof, according to any one of the items (1) to (18) above, wherein
W is $R^6$—$X^2$—$Y^1$—$X^1$—,
$Y^1$ is —O— or —$NR^7$—,
$X^1$ is a methylene group, an ethylene group (the methylene group and the ethylene group may be substituted with 1 to 2 methyl groups), a $C_{3-8}$ cycloalkylene group, or a bond,
$X^2$ is a $C_{1-4}$ alkylene group (the $C_{1-4}$ alkylene group may be substituted with 1 to 4 substituents which are the same or different and are selected from a group of substituents, $R^c$, to be shown below),
$R^6$ is a hydrogen atom, a halogen atom, an optionally protected hydroxy group, or a $C_{1-6}$ alkoxy group,
$R^7$ is a hydrogen atom, a $C_{1-6}$ alkyl group or a $C_{3-8}$ cycloalkyl group (the $C_{1-6}$ alkyl group and the $C_{3-8}$ cycloalkyl group may be substituted with 1 to 4 substituents which are the same or different and are selected from the following group of substituents, $R^c$), and
the group of substituents, $R^c$, consists of a halogen atom, a hydroxy group, and a $C_{1-6}$ alkyl group;
(21) the compound or the pharmaceutically acceptable salt thereof, according to any one of the items (1) to (18) above, wherein
W is Q-$X^1$—$Y^2$—$X^3$—,
$Y^2$ is —O—, —$NR^7$—, or a bond,
$X^1$ is a $C_{1-4}$ alkylene group (the $C_{1-4}$ alkylene group may be substituted with 1 to 4 substituents which are the same or different and are selected from a group of substituents, $R^c$, to be shown below), or a bond,
$X^3$ is a methylene group, an ethylene group (the methylene group and the ethylene group may be substituted with 1 to 2 methyl groups), a $C_{3-8}$ cycloalkylene group, or a bond,
Q is a $C_{3-8}$ cycloalkyl group, an aryl group, or a heterocyclic group (the $C_{3-8}$ cycloalkyl group, the aryl group, or the heterocyclic group may be substituted with 1 to 4 substituents which are the same or different and are selected from the group of substituents, $R^c$, shown below
$R^7$ is a hydrogen atom, a $C_{1-6}$ alkyl group or a $C_{3-8}$ cycloalkyl group (the $C_{1-6}$ alkyl group and the $C_{3-8}$ cycloalkyl group may be substituted with 1 to 4 substituents which are the same or different and are selected from the following group of substituents, $R^c$), and the group of substituents, $R^c$, consists of a halogen atom, a hydroxy group, a $C_{1-6}$ alkyl group, a $C_{1-6}$ hydroxyalkyl group, a $C_{1-6}$ haloalkyl group, a $C_{3-8}$ cycloalkyl group, a $C_{1-6}$ alkoxy group (the $C_{1-6}$ alkoxy group may be substituted with 1 to 3 hydroxy groups or halogen atoms), a $C_{3-8}$ cycloalkoxy group, a $C_{2-6}$ alkanoyl group, a $C_{1-6}$ alkylidene group (the $C_{1-6}$ alkylidene group may be substituted with a $C_{1-6}$ alkoxy group), and a hydroxyaminocarbonyl group;

(22) the compound or the pharmaceutically acceptable salt thereof, according to any one of the items (1) to (18) above, wherein W is a hydrogen atom, a halogen atom, a $C_{1-6}$ alkyl group, a $C_{1-6}$ alkoxy group, or a $C_{1-6}$ alkylamino group (the $C_{1-6}$ alkyl group, the $C_{1-6}$ alkoxy group and the $C_{1-6}$ alkylamino group may be substituted with 1 to 3 substituents which are the same or different and are selected from "a halogen atom, a hydroxy group, a $C_{1-6}$ alkoxy group and a morpholino group");

(23) a pharmaceutical composition comprising the compound or the pharmaceutically acceptable salt thereof according to any one of the items (1) to (22) above;

(24) an LpxC inhibitor comprising the compound or the pharmaceutically acceptable salt thereof according to any one of the items (1) to (23) above; and

(25) an antimicrobial agent comprising the compound or the pharmaceutically acceptable salt thereof according to any one of the items (1) to (24) above.

Advantageous Effects of Invention

The compound or the pharmaceutically acceptable salt thereof according to the present invention has a strong LpxC-inhibiting action, and exhibits potent antimicrobial activity against gram-negative bacteria, including *Pseudomonas aeruginosa*. Thus, the compound or its pharmaceutically acceptable salt is useful as a pharmaceutical composition and as an antimicrobial agent against these bacteria as causative bacteria.

DESCRIPTION OF EMBODIMENT

The present invention will be described in further detail below.

The terms and phrases used herein will be explained first.

In the present invention, "n-" means normal, "i-" iso, "s-" secondary, "t-" tertiary, "c-" cyclo, "o-" ortho, "m-" meta, and "p-" para.

The "halogen atom" means a fluorine atom, a chlorine atom, a bromine atom, and an iodine atom.

The "$C_{1-6}$ alkyl group" refers to a straight-chain or branched-chain alkyl group having 1 to 6 carbon atoms. Its examples are a methyl group, an ethyl group, a n-propyl group, a n-butyl group, a n-pentyl group, a n-hexyl group, an isopropyl group, an isobutyl group, a t-butyl group, a s-butyl group, an isopentyl group, a neopentyl group, a t-pentyl group, and a 1,2-dimethylpropyl group.

The "$C_{1-6}$ hydroxyalkyl group" refers to an alkyl group in which one or more of the hydrogen atoms of the above-mentioned "$C_{1-6}$ alkyl group" has been or have been substituted with a hydroxy group or hydroxy groups. Its examples are a hydroxymethyl group, a 1-hydroxyethyl group, a 2-hydroxyethyl group, a 2-hydroxypropyl group, a 3-hydroxypropyl group, a 1-hydroxybutyl group, a 2-hydroxybutyl group, a 3-hydroxybutyl group, a 4-hydroxybutyl group, a 1-hydroxypentyl group, a 5-hydroxypentyl group, a 1-hydroxyhexyl group, a 6-hydroxyhexyl group, a 2-hydroxymethyl-1-hydroxypropyl group, a 2,2-dihydroxymethyl-1-hydroxypropyl group, and a 2-hydroxymethyl-1-hydroxypentyl group.

The "$C_{1-6}$ haloalkyl group" refers to an alkyl group in which one or more of the hydrogen atoms of the above-mentioned "$C_{1-6}$ alkyl group" has been or have been substituted with a halogen atom or halogen atoms. Its examples are a fluoromethyl group, a difluoromethyl group, a trifluoromethyl group, a 2,2,2-trifluoroethyl group, a 2,2,2-trichloroethyl group, a pentafluoroethyl group, a 3,3,3-trifluoropropyl group, a perfluoropropyl group, a 4-fluorobutyl group, a 4-chlorobutyl group, and a 4-bromobutyl group.

The "$C_{2-8}$ alkoxyalkyl group" refers to an alkoxyalkyl group having a total of 2 to 8 carbon atoms. Its examples are a methoxymethyl group, a 1-methoxyethyl group, a 1-methoxypropyl group, a 2-methoxypropyl group, a 1-methoxybutyl group, a 1-methoxypentyl group, a 1-ethoxyethyl group, a 1-ethoxypropyl group, a 1-ethoxybutyl group, a 1-propoxyethyl group, a 1-isopropoxyethyl group, and a 1-propoxypropyl group.

The "$C_{3-8}$ cycloalkyl group" refers to a cycloalkyl group having 3 to 8 carbon atoms. Its examples are a c-propyl group, a c-butyl group, a c-pentyl group, a c-hexyl group, a c-heptyl group, and a c-octyl group.

The "$C_{2-6}$ alkenyl group" refers to a straight-chain or branched-chain alkenyl group with 2 to 6 carbon atoms which has one or more double bonds at any position(s) of the above-mentioned "$C_{1-6}$ alkyl group". Its examples are a vinyl group, a 1-propenyl group, a 2-propenyl group, an isopropenyl group, a 2-butenyl group, a 1,3-butadienyl group, a 2-pentenyl group, a 3-pentenyl group, and a 2-hexenyl group.

The "$C_{2-6}$ alkynyl group" refers to a straight-chain or branched-chain alkynyl group with 2 to 6 carbon atoms which has one or more triple bonds at any position(s) of the above-mentioned "$C_{1-6}$ alkyl group". Its examples are an ethynyl group, a 1-propynyl group, a 2-propynyl group, a 1-butynyl group, a 3-butynyl group, a 1-pentynyl group, a 4-pentynyl group, a 1-hexynyl group, and a 5-hexynyl group.

The "$C_{3-8}$ cycloalkenyl group" refers to a cycloalkyl group with 3 to 8 carbon atoms which has one or more double bonds at any position(s) of the above-mentioned "$C_{3-8}$ cycloalkyl group". Its examples are a c-butenyl group, a c-pentenyl group, a c-hexenyl group, a c-hexadienyl group, a c-heptenyl group, and a c-octenyl group.

The "$C_{1-6}$ alkoxy group" refers to a straight-chain or branched-chain alkoxy group having 1 to 6 carbon atoms. Its examples are a methoxy group, an ethoxy group, a 1-propoxy group, an isopropoxy group, a 1-butoxy group, a 1-methyl-1-propoxy group, a t-butoxy group, and a 1-pentyloxy group.

The "$C_{3-8}$ cycloalkoxy group" refers to a cycloalkoxy group having 3 to 8 carbon atoms. Its examples are a c-propyloxy group, a c-butyloxy group, a c-pentyloxy group, and a c-hexyloxy group.

The "$C_{1-6}$ alkylthio group" refers to a straight-chain or branched-chain alkylthio group having 1 to 6 carbon atoms. Its examples are a methylthio group, an ethylthio group, a n-propylthio group, an isopropylthio group, a n-butylthio group, a s-butylthio group, a t-butylthio group, a 1,1-dimethylpropylthio group, a n-pentylthio group, an isopentylthio group, and a n-hexylthio group.

The "$C_{1-6}$ alkylamino group" refers to a straight-chain or branched-chain alkylamino group having 1 to 6 carbon atoms. Its examples are a methylamino group, an ethylamino group, a n-propylamino group, an isopropylamino group, a n-butylamino group, a s-butylamino group, a t-butylamino group, a 1,1-dimethylpropylamino group, a n-pentylamino group, an isopentylamino group, and a n-hexylamino group.

The "di($C_{1-6}$ alkyl)amino group" refers to a dialkylamino group having two straight-chain or branched-chain alkyl groups each having 1 to 6 carbon atoms. Its examples are a dimethylamino group, a diethylamino group, a di(n-propyl)amino group, a diisopropylamino group, a di(n-butyl)amino group, a di(s-butyl)amino group, a di(t-butyl)amino group, a di(1,1-dimethylethyl)amino group, a di(n-pentyl)amino group, a diisopentylamino group, and a di(n-hexyl)amino group.

The "$C_{2-6}$ alkanoyl group" refers to a straight-chain or branched-chain alkanoyl group having 2 to 6 carbon atoms. Its examples are an acetyl group, a propionyl group, a butyryl group, and a pivaloyl group.

The "$C_{1-6}$ alkoxycarbonyl group" refers to a carbonyl group having a straight-chain or branched-chain alkoxy group having 1 to 6 carbon atoms. Its examples are a methoxycarbonyl group, an ethoxycarbonyl group, and an isopropoxycarbonyl group.

The "$C_{1-6}$ alkylaminocarbonyl group" refers to a carbonyl group having a straight-chain or branched-chain alkylamino group having 1 to 6 carbon atoms. Its examples are a methylaminocarbonyl group, an ethylaminocarbonyl group, and an isopropylaminocarbonyl group.

The "$C_{1-6}$ alkoxycarbonylamino group" refers to an amino group having a $C_{1-6}$ alkoxycarbonyl group. Its examples are a methoxycarbonylamino group, an ethoxycarbonylamino group, a n-propoxycarbonylamino group, an isopropoxycarbonylamino group, and a t-butoxycarbonylamino group.

The "$C_{1-6}$ alkylsulfonyl group" refers to a straight-chain or branched-chain alkylsulfonyl group having 1 to 6 carbon atoms. Its examples are a methylsulfonyl group, an ethylsulfonyl group, and a propylsulfonyl group.

The "aryl group" refers to a monocyclic to tetracyclic aromatic carbocyclic group composed of 6 to 18 carbon atoms. Its examples are a phenyl group, a naphthyl group, an anthryl group, a phenanthrenyl group, a tetracenyl group, and a pyrenyl group.

The "aryloxy group" refers to the above-mentioned "aryl group" having an oxy group bound thereto. Its examples are a phenoxy group and a naphthyloxy group.

The "fused polycyclic hydrocarbon ring group" refers to a bicyclic to tetracyclic carbocyclic group having 6 to 18 carbon atoms, and includes, for example, not only a bicyclic to tetracyclic aryl group such as a naphthyl group, an anthryl group, a phenanthrenyl group, a tetracenyl group, or a pyrenyl group, but also a fluorenyl group, an indenyl group, and an acenaphthylenyl group.

The "partially saturated fused polycyclic hydrocarbon ring group" refers to a fused polycyclic hydrocarbon ring group having a part hydrogenated. Its examples are an indanyl group and an acenaphthenyl group.

The "heterocyclic group" refers to a "monocyclic heterocyclic group", a "fused ring heterocyclic group", or a "spiro ring heterocyclic group" which contains, as a ring-constituting atom(s), any 1 to 5 atoms selected from a nitrogen atom, an oxygen atom and a sulfur atom. If the hetero atom is a sulfur atom, a dioxide compound is also included in the present invention.

The "monocyclic heterocyclic group" refers to a heterocyclic group of a monocyclic type, in which the number of the atoms on the ring is 3 to 8, among the above-mentioned "heterocyclic groups". The monocyclic heterocyclic group includes a "monocyclic saturated heterocyclic group", a "monocyclic aromatic heterocyclic group", and a "partially saturated monocyclic aromatic heterocyclic group".

The "fused ring heterocyclic group" refers to a heterocyclic group of a fused ring type composed of 6 to 14 ring-constituting atoms, among the above-mentioned "heterocyclic groups". The fused ring heterocyclic group includes a "fused ring saturated heterocyclic group", a "fused ring aromatic heterocyclic group", and a "fused ring heterocyclic group having a partially saturated monocycle".

The "spiro ring heterocyclic group" refers to a heterocyclic group, which is constituted by a total of 6 to 14 ring-constituting atoms and formed by two rings sharing one spiro carbon atom, among the above-mentioned "heterocyclic groups". This spiro ring heterocyclic group may be substituted with 1 to 3 oxo groups, and includes, for example, a 2-oxa-6-azaspiro[3.3]heptanyl group, a 1-oxa-6-azaspiro[3.3]heptanyl group, a 6-oxa-1-azaspiro[3.3]heptanyl group, a 1-oxo-2,8-diazaspiro[4.5]decanyl group, a 1,4-dioxa-8-azaspiro[4.5]decanyl group, a 2-azaspiro[3.3]heptyl group, a 7-oxa-2-azaspiro[3.5]nonyl group, a 5,8-oxa-2-azaspiro[3.4]octyl group, a 1,4-dioxa-8-azaspiro[4.5]decanyl group, and a 1-oxaspiro[4.5]decanyl group.

The "monocyclic saturated heterocyclic group" refers to a monocyclic heterocyclic group having a ring constituted only by saturated bonds, and may be substituted with 1 to 2 oxo groups. Its examples are an aziridinyl group, an azetidinyl group, a pyrrolidinyl group, a 2-oxopyrrolidinyl group, a piperidinyl group, a piperazinyl group, a 3-oxopiperazinyl group, a morpholinyl group, a thiomorpholinyl group (the sulfur atom on the ring may be oxidized), a homopiperazinyl group, a homomorpholinyl group (oxazepanyl group), an imidazolidinyl group, a pyrazolidinyl group, an oxazolidinyl group, a 2-oxo-1,3-oxazolidin-3-yl group, an isoxazolidinyl group, a 2,3-dioxopiperazinyl group, an oxetan-2-yl group, an oxetan-3-yl group, a 1,3-dioxolanyl group, a tetrahydrofuranyl group, a tetrahydropyranyl group, a tetrahydro-2H-thiopyranyl group, a dithiolanyl group, and a thiolanyl group.

The "monocyclic aromatic heterocyclic group" includes, for example, a pyridyl group, a pyridazinyl group, a pyrimidinyl group, a pyrazinyl group, a thienyl group, a pyrrolyl group, a thiazolyl group, an isothiazolyl group, a pyrazolyl group, an imidazolyl group, a furyl group, an oxazolyl group, an isoxazolyl group, an oxadiazolyl group, a 1,3,4-thiadiazolyl group, a 1,2,3-triazolyl group, a 1,2,4-triazolyl group, and a tetrazolyl group.

The "partially saturated monocyclic aromatic heterocyclic group" refers to a monocyclic aromatic heterocyclic group, in which some of the bonds constituting the ring are saturated, and includes those substituted with 1 or 2 oxo groups. Its examples are a 4,5-dihydro-1H-imidazolyl group, a 1,2,3,6-tetrahydropyridyl group, a 4H-1,3-oxazinyl group, and a 5,6-dihydro-4H-1,3-oxazinyl group.

The "fused ring saturated heterocyclic group" refers to a fused ring heterocyclic group having rings constituted only by saturated bonds, and may be substituted with 1 to 3 oxo groups. Its examples are an octahydro-1H-isoindolyl group, a decahydroquinolyl group, a decahydroisoquinolyl group, a hexahydro-2H-[1,4]dioxino[2,3-c]pyrrolyl group, and a 3-azabicyclo[3.1.0]hex-3-yl group.

The "fused ring aromatic heterocyclic group" includes, for example, a quinolyl group, an isoquinolyl group, a naphthyridinyl group (for example, a 1,6-naphthyridinyl group, a 1,7-naphthyridinyl group, and a 1,8-naphthyridinyl group), a quinazolinyl group, a benzofuranyl group, a benzothienyl group, an indolyl group, a benzoxazolyl group, a benzisoxazolyl group (for example, a benz[c]isoxazolyl group, a benz[d]isoxazolyl group), a 1H-indazolyl group, a 2H-indazolyl group, a benzimidazolyl group, a benzoxadiazolyl group (for example, a benz[1,2,5]oxadiazolyl group, a benz[1,2,3]oxadiazolyl group, a benz[2,1,3]oxadiazolyl group), a benzothiazolyl group, a benzothiadiazolyl group (for example, a [1,2,5]thiadiazolyl group, and a benzo[1,2,3]thiadiazolyl group), an indolizinyl group, a benzofurazanyl group, a thienopyridyl group (for example, a thieno[2,3-b]pyridyl group, and a [3,2-b]pyridyl group), a pyrazolopyridyl group, an imidazopyridyl group (for example, an imidazo[1,5-a]pyridyl group, an imidazo[1,2-a]pyridyl group, and a 3H-imidazo[4,5-b]pyridyl group), an imidazopyrazinyl group (for example, an imidazo[1,5-a]pyrazinyl group, an imidazo[1,2-a]pyrazinyl group), a pyrazolopyrimidinyl group (for example, a pyrazolo[1,5-a]pyrimidinyl group, a pyrazolo[1,5-c]pyrimidinyl group), a triazolopyrimidinyl group (for example, a [1,2,3]triazolo[1,5-a]pyrimidinyl group, a [1,2,3]triazolo[1,5-c]pyrimidinyl group, a [1,2,4]triazolo[1,5-a]pyrimidinyl group, a [1,2,4]triazolo[1,5-c]pyrimidinyl group), a thienothienyl group (for example, a thieno[2,3-b]thienyl group, a thieno[3,2-b]thienyl group), and an imidazothiazolyl group (for example, an imidazo[2,1-b]thiazolyl group, an imidazo[5,1-b]thiazolyl group).

The "fused ring heterocyclic group having a partially saturated monocycle" refers to a fused ring aromatic heterocyclic group having a monocycle in which some of the bonds constituting the rings are saturated, and this fused ring heterocyclic group may be substituted with 1 to 3 oxo groups. Its examples are a 1,3-dihydrobenzimidazol-2-onyl group, a 2-benzoxazolinonyl group, an octahydroisoindolyl group, a 2H-pyrido[3,2-b]-1,4-oxazin-3(4H)-on-yl group, a 3-oxo-3,4-dihydro-2H-pyrido[3,2-b][1,4]oxazin-6-yl group, a [1,3]dioxolo[4,5-b]pyridyl group, a 2,3-dihydrobenzo[b]thienyl group, a 2,3-dihydro-1-benzofuran-5-yl group, a 2,3-dihydro-1-benzofuran-6-yl group, a 1,3-dihydro-2-benzofuran-5-yl group, a 2,3-dihydro-1H-indol-5-yl group, a 1,3-benzodioxol-5-yl group, a 2,3-dihydro-1,4-benzodioxin-2-yl group, a 2,3-dihydro-1,4-benzodioxin-6-yl group, a 3-oxo-3,4-dihydro-2H-1,4-benzoxazin-6-yl group, a 1,4-benzodioxanyl group, a 2H-benz[b][1,4]oxazin-3(4H)-on-yl group, a 3,4-dihydro-2H-benzo[b][1,4]dioxepinyl group, an indolinyl group, a 2H-isoindolinyl group, a chromanyl group, a chromonyl group, an isochromanyl group, and a 1,2,3,4-tetrahydroisoquinolyl group.

The "4- to 7-membered nitrogen-containing saturated heterocyclic group" refers to a monocyclic saturated heterocyclic group composed of 4 to 7 ring-constituting atoms and containing 1 or 2 nitrogen atoms, among the aforementioned "monocyclic saturated heterocyclic groups". This nitrogen-containing saturated heterocyclic group may contain 1 or 2 oxygen atoms as a ring-constituting atom(s), and may be substituted with 1 to 2 oxo groups. Its examples are an azetidinyl group, a pyrrolidinyl group, a piperidinyl group, a piperazinyl group, a morpholinyl group, a homopiperazinyl group, a homomorpholinyl group, an imidazolidyl group, a pyrazolidinyl group, an oxazolidinyl group, an isoxazolidinyl group, and a 2,3-dioxopiperazinyl group.

The "nitrogen-containing saturated spiro ring group" refers to a spiro ring heterocyclic group constituted by a total of 7 to 11 ring-constituting atoms and containing 1 to 2 nitrogen atoms in the rings, among the aforementioned "spiro ring heterocyclic groups", and may be substituted with 1 to 2 oxo groups. Its examples are a 2-oxa-6-azaspiro[3.3]heptanyl group, a 1-oxa-6-azaspiro[3.3]heptanyl group, a 1-oxo-2,8-diazaspiro[4.5]decanyl group, a 1,4-dioxa-8-azaspiro[4.5]decanyl group, a 2-azaspiro[3.3]heptyl group, a 7-oxa-2-azaspiro[3.5]nonyl group, a 5,8-oxa-2-azaspiro[3.4]octyl group, and a 1,4-dioxa-8-azaspiro[4.5]decanyl group.

The "$C_{1-4}$ alkylene group" refers to a straight-chain or branched-chain alkylene group having 1 to 4 carbon atoms. Its examples are —$CH_2$—, —$(CH_2)_2$—, —$(CH_2)_3$—, —$CH_2$—$CH(CH_3)$—, —$C(CH_3)_2$—, —$(CH_2)_4$—, —$(CH_2)_2$—$CH(CH_3)$—, —$CH_2$—$CH(CH_3)$—$CH_2$—, and —$CH(CH_3)$—$(CH_2)_2$—.

The "$C_{1-6}$ alkylene group" refers to a straight-chain or branched-chain alkylene group having 1 to 6 carbon atoms. Its examples are —$(CH_2)_5$—, —$(CH_2)_3$—$CH(CH_3)$—, —$(CH_2)_2$—$CH(C_2H_5)$—, —$(CH_2)_6$—, —$(CH_2)_3$—$CH(CH_3)$—$CH_2$—, and —$CH_2$—$CH(CH_3)$—$(CH_2)_3$—, in addition to the above-mentioned examples of the "$C_{1-4}$ alkylene group".

The "$C_{1-10}$ alkylene group" refers to a straight-chain or branched-chain alkylene group having 1 to 10 carbon atoms. Its examples are —$(CH_2)_7$—, —$(CH_2)_5$—$CH(CH_3)$—, —$(CH_2)_4$—$CH(C_2H_5)$—, —$(CH_2)_8$—, —$(CH_2)_6$—$CH(CH_3)$—$CH_2$—, and —$CH_2$—$CH(CH_3)$—$(CH_2)_7$—, in addition to the above-mentioned examples of the "$C_{1-6}$ alkylene group".

The "$C_{3-8}$ cycloalkylene group" refers to a divalent group formed by eliminating any two hydrogen atoms from a cycloalkane having 3 to 8 carbon atoms. Its examples are a 1,1-c-propylene group, a 1,2-c-propylene group, a 1,1-c-butylene group, a 1,2-c-butylene group, a 1,3-c-butylene group, a 1,2-c-pentylene group, a 1,1-c-hexylene group, a 1,2-c-hexylene group, a 1,3-c-hexylene group, a 1,4-c-hexylene group, and a 1,3-c-heptylene group.

The "$C_{2-4}$ alkenylene group" refers to a straight-chain or branched-chain alkenylene group having 2 to 4 carbon atoms which has one or more double bonds in the chain. Its examples are —CH=CH—, —CH=CH—$CH_2$—, —$CH_2$—CH=CH—, —CH=$C(CH_3)$—, —$(CH_2)_2$—CH=CH—, —$CH(CH_3)$—CH=CH—, —$CH_2$—CH=CH—$CH_2$—, and —CH=CH—CH=CH—.

The "$C_{2-6}$ alkenylene group" refers to a straight-chain or branched-chain alkenylene group having 2 to 6 carbon atoms which has one or more double bonds in the chain. Its examples are —$(CH_2)_3$—CH=CH—, —$(CH_2)_2$—CH=$C(CH_3)$—, —$(CH_2)_4$—CH=CH—, and —$(CH_2)_2$—CH=$C(C_2H_5)$—, in addition to the examples of the "$C_{2-4}$ alkenylene group" mentioned above.

The "$C_{2-10}$ alkenylene group" refers to a straight-chain or branched-chain alkenylene group having 2 to 10 carbon atoms which has one or more double bonds in the chain. Its examples are —$(CH_2)_5$—CH=CH—, —$(CH_2)_5$—CH=$C(CH_3)$—, —$(CH_2)_6$—CH=CH—, and —$(CH_2)_6$—CH=$C(C_2H_5)$—, in addition to the examples of the "$C_{2-6}$ alkenylene group" mentioned above.

The "$C_{3-8}$ cycloalkenylene group" refers to a cycloalkylene group having 3 to 8 carbon atoms which has one or more double bonds at any position(s) of the above-mentioned "$C_{3-8}$ cycloalkylene group". Its examples are a c-butenylene group, a c-pentenylene group, a c-hexenylene group, a c-hexadienylene group, a c-heptenylene group, and a c-octenylene group.

The "$C_{2-10}$ alkynylene group" refers to a straight-chain or branched-chain alkynylene group having 2 to 10 carbon atoms which has one or more triple bonds in the chain. Its example is a divalent group having a triple bond formed by further eliminating a hydrogen atom from the carbon atom in the double bond moiety of the "$C_{2-10}$ alkenylene group" mentioned above.

The "—$C_{1-6}$alkylene-$C_{3-8}$cycloalkylene-$C_{1-6}$alkylene-" refers to a divalent group composed of a $C_{1-6}$alkylene group, a $C_{3-8}$cycloalkylene group, and a $C_{1-6}$alkylene group bound together. Its examples are divalent groups represented by the following formula [3]:

[Chemical formula 4]

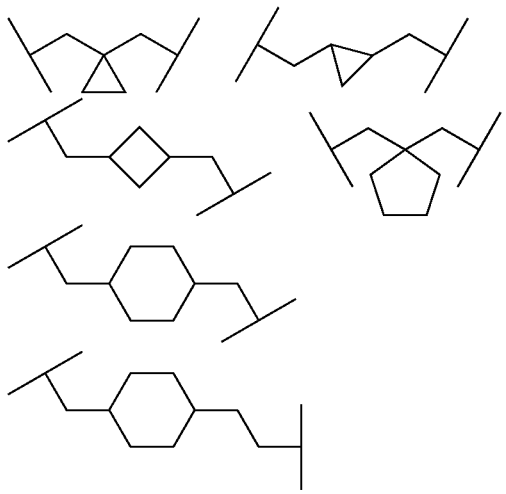

[3]

The "$C_{1-6}$ alkylidene group" refers to a straight-chain or branched-chain alkylidene group having 1 to 6 carbon atoms, and includes, for example, a methylidene group, an ethylidene group, a n-propylidene group, a n-butylidene group, an isopropylidene group, a n-pentylidene group, and a n-hexylidene group.

The "$C_{3-8}$ cycloalkylidene group" refers to a cycloalkylidene group having 3 to 8 carbon atoms, and includes, for example, a cyclopropylidene group, a cyclobutylidene group, a cyclopentylidene group, a cyclohexylidene group, a cycloheptylidene group, and a cyclooctylidene group.

The "monocyclic saturated heterocyclidene group" refers to a divalent group formed by further eliminating one hydrogen atom, which has been bound to a carbon atom providing a free valence, from a monocyclic saturated heterocyclic group. Its examples are an azetidin-3-ylidene group, a pyrrolidin-3-ylidene group, a piperidin-3-ylidene group, a piperidin-4-ylidene group, a homopiperidin-4-ylidene group, a tetrahydrofuran-3-ylidene group, and a tetrahydropyran-4-ylidene group.

The "divalent aryl group" refers to a divalent group formed by eliminating any two hydrogen atoms from a monocyclic, bicyclic, tricyclic or tetracyclic aromatic carbocyclic group composed of 6 to 18 carbon atoms. Its examples are divalent groups formed by eliminating any two hydrogen atoms from benzene, naphthalene, azulene, fluorene, phenanthrene, anthracene, and pyrene.

The "divalent partially saturated fused polycyclic hydrocarbon ring group" refers to a divalent group formed by further eliminating any one hydrogen atom from the aforementioned "partially saturated fused polycyclic hydrocarbon ring group". Its examples are divalent groups formed by eliminating any one hydrogen atom from an indanyl group and an acenaphthenyl group.

The "divalent heterocyclic group" refers to a divalent group formed by further eliminating any one hydrogen atom from the aforementioned "heterocyclic group". Its examples include a "divalent monocyclic heterocyclic group", a "divalent fused ring heterocyclic group", and a "divalent spiro ring heterocyclic group".

The "divalent monocyclic heterocyclic group" refers to a divalent group formed by further eliminating any one hydrogen atom from the aforementioned "monocyclic heterocyclic group". The divalent monocyclic heterocyclic group includes a "divalent monocyclic saturated heterocyclic group", a "divalent monocyclic aromatic heterocyclic group", and a "divalent partially saturated monocyclic aromatic heterocyclic group".

The "divalent fused ring heterocyclic group" refers to a divalent group formed by further eliminating any one hydrogen atom from the aforementioned "fused ring heterocyclic group". The divalent fused ring heterocyclic group includes a "divalent fused ring saturated heterocyclic group", a "divalent fused ring aromatic heterocyclic group", and a "divalent fused ring heterocyclic group having a partially saturated monocycle".

The "divalent spiro ring heterocyclic group" refers to a divalent group formed by further eliminating any one hydrogen atom from the aforementioned "spiro ring heterocyclic group". Its examples are divalent groups formed by eliminating any one hydrogen atom from a 2-oxa-6-azaspiro[3.3]heptanyl group, a 1-oxa-6-azaspiro[3.3]heptanyl group, a 1-oxo-2,8-diazaspiro[4.5]decanyl group, a 1,4-dioxa-8-azaspiro[4.5]decanyl group, a 2-azaspiro[3.3]heptyl group, a 7-oxa-2-azaspiro[3.5]nonyl group, a 5,8-oxa-2-azaspiro[3.4]octyl group, a 1,4-dioxa-8-azaspiro[4.5]decanyl group, and a 1-oxaspiro[4.5]decanyl group.

The "divalent monocyclic saturated heterocyclic group" refers to a divalent group formed by further eliminating any one hydrogen atom from the aforementioned "monocyclic saturated heterocyclic group". Its examples are divalent groups formed by eliminating any one hydrogen atom from an aziridinyl group, an azetidinyl group, a pyrrolidinyl group, a 2-oxopyrrolidinyl group, a piperidinyl group, a piperazinyl group, a 3-oxopiperazinyl group, a morpholinyl group, a thiomorpholinyl group (the sulfur atom on the ring may be oxidized), a homopiperazinyl group, a homomorpholinyl group (oxazepanyl group), an imidazolidyl group, a pyrazolidinyl group, an oxazolidinyl group, a 2-oxo-1,3-oxazolidin-3-yl group, an isoxazolidinyl group, a 2,3-dioxopiperazinyl group, an oxetan-2-yl group, an oxetan-3-yl group, a 1,3-dioxolanyl group, a tetrahydrofuranyl group, a tetrahydropyranyl group, a tetrahydro-2H-thiopyranyl group, a dithiolanyl group, and a thiolanyl group.

The "divalent monocyclic aromatic heterocyclic group" refers to a divalent group formed by further eliminating any one hydrogen atom from the aforementioned "monocyclic aromatic heterocyclic group". Its examples are divalent groups formed by eliminating any one hydrogen atom from a pyridyl group, a pyridazinyl group, a pyrimidinyl group, a pyrazinyl group, a thienyl group, a pyrrolyl group, a thiazolyl group, an isothiazolyl group, a pyrazolyl group, an imidazolyl group, a furyl group, an oxazolyl group, an isoxazolyl group, an oxadiazolyl group, a 1,3,4-thiadiazolyl group, a 1,2,3-triazolyl group, and a 1,2,4-triazolyl group.

The "divalent partially saturated monocyclic aromatic heterocyclic group" refers to a divalent group formed by further eliminating any one hydrogen atom from the aforementioned "partially saturated monocyclic aromatic heterocyclic group". Its examples are divalent groups formed by eliminating any one hydrogen atom from a 4,5-dihydro-1H-imidazolyl group, a 1,2,3,6-tetrahydropyridyl group, a 4H-1,3-oxazinyl group, and a 5,6-dihydro-4H-1,3-oxazinyl group.

The "divalent fused ring saturated heterocyclic group" refers to a divalent group formed by further eliminating any one hydrogen atom from the aforementioned "fused ring saturated heterocyclic group". Its examples are divalent groups formed by eliminating any one hydrogen atom from an octahydro-1H-isoindolyl group, a decahydroquinolyl group, a decahydroisoquinolyl group, a hexahydro-2H-[1,4]dioxino[2,3-c]pyrrolyl group, and a 3-azabicyclo[3.1.0]hex-3-yl group.

The "divalent fused ring aromatic heterocyclic group" refers to a divalent group formed by further eliminating any one hydrogen atom from the aforementioned "fused ring aromatic heterocyclic group". Its examples are divalent groups formed by eliminating any one hydrogen atom from a quinolyl group, an isoquinolyl group, a naphthyridinyl group (for example, a 1,6-naphthyridinyl group, a 1,7-naphthyridinyl group, and a 1,8-naphthyridinyl group), a quinazolinyl group, a benzofuranyl group, a benzothienyl group, an indolyl group, a benzoxazolyl group, a benzisoxazolyl group (for example, a benz[c]isoxazolyl group, a benz[d]isoxazolyl group), a 1H-indazolyl group, a 2H-indazolyl group, a benzimidazolyl group, a benzoxadiazolyl group (for example, a benz[1,2,5]oxadiazolyl group, a benz[1,2,3]oxadiazolyl group, a benz[2,1,3]oxadiazolyl group), a benzodiazolyl group, a benzothiadiazolyl group (for example, a [1,2,5]thiadiazolyl group, and a benzo[1,2,3]thiadiazolyl group), an indolizinyl group, a benzofurazanyl group, a thienopyridyl group (for example, a thieno[2,3-b]pyridyl group, and a [3,2-b]pyridyl group), a pyrazolopyridyl group, an imidazopyridyl group (for example, an imidazo[1,5-a]pyridyl group, an imidazo[1,2-a]pyridyl group, and a 3H-imidazo[4,5-b]pyridyl group), an imidazopyrazinyl group (for example, an imidazo[1,5-a]pyrazinyl group, an imidazo[1,2-a]pyrazinyl group), a pyrazolopyrimidinyl group (for example, a pyrazolo[1,5-a]pyrimidinyl group, a pyrazolo[1,5-c]pyrimidinyl group), a triazolopyrimidinyl group (for example, a [1,2,3]triazolo[1,5-a]pyrimidinyl group, a [1,2,3]triazolo[1,5-c]pyrimidinyl group, a [1,2,4]triazolo[1,5-a]pyrimidinyl group, a [1,2,4]triazolo[1,5-c]pyrimidinyl group), a thienothienyl group (for example, a thieno[2,3-b]thienyl group, a thieno[3,2-b]thienyl group), and an imidazothiazolyl group (for example, an imidazo[2,1-b]thiazolyl group, an imidazo[5,1-b]thiazolyl group).

The "divalent fused ring aromatic heterocyclic group composed of a 5-membered ring and a 6-membered ring" refers to a divalent aromatic heterocyclic group constituted by the ring condensation of a 5-membered ring and a 6-membered ring, among the aforementioned "divalent fused ring aromatic heterocyclic groups". Its examples are divalent groups formed by eliminating any one hydrogen atom from a benzofuranyl group, a benzothienyl group, an indolyl group, a benzoxazolyl group, a benzisoxazolyl group (for example, a benz[c]isoxazolyl group, a benz[d]isoxazolyl group), a 1H-indazolyl group, a 2H-indazolyl group, a benzimidazolyl group, a benzoxadiazolyl group (for example, a benz[1,2,5]oxadiazolyl group, a benz[1,2,3]oxadiazolyl group, a benz[2,1,3]oxadiazolyl group), a benzodiazolyl group, a benzothiadiazolyl group (for example, a [1,2,5]thiadiazolyl group, and a benzo[1,2,3]thiadiazolyl group), an indolizinyl group, a benzofurazanyl group, a thienopyridyl group (for example, a thieno[2,3-b]pyridyl group, and a [3,2-b]pyridyl group), a pyrazolopyridyl group, an imidazopyridyl group (for example, an imidazo[1,5-a]pyridyl group, an imidazo[1,2-a]pyridyl group, and a 3H-imidazo[4,5-b]pyridyl group), an imidazopyrazinyl group (for example, an imidazo[1,5-a]pyrazinyl group, an imidazo[1,2-a]pyrazinyl group), a pyrazolopyrimidinyl group (for example, a pyrazolo[1,5-a]pyrimidinyl group, a pyrazolo[1,5-c]pyrimidinyl group), and a triazolopyrimidinyl group (for example, a [1,2,3]triazolo[1,5-a]pyrimidinyl group, a [1,2,3]triazolo[1,5-c]pyrimidinyl group, a [1,2,4]triazolo[1,5-a]pyrimidinyl group, a [1,2,4]triazolo[1,5-c]pyrimidinyl group).

The "divalent fused ring heterocyclic group having a partially saturated monocycle" refers to a divalent group formed by further eliminating any one hydrogen atom from the aforementioned "fused ring heterocyclic group having a partially saturated monocycle". Its examples are divalent groups formed by eliminating any one hydrogen atom from a 1,3-dihydrobenzimidazol-2-onyl group, a 2-benzoxazolinonyl group, an octahydroisoindolyl group, a 2H-pyrido[3,2-b]-1,4-oxazin-3(4H)-on-yl group, a 3-oxo-3,4-dihydro-2H-pyrido[3,2-b][1,4]oxazin-6-yl group, a [1,3]dioxolo[4,5-b]pyridyl group, a 2,3-dihydrobenzo[b]thienyl group, a 2,3-dihydro-1-benzofuran-5-yl group, a 2,3-dihydro-1-benzofuran-6-yl group, a 1,3-dihydro-2-benzofuran-5-yl group, a 2,3-dihydro-1H-indol-5-yl group, a 1,3-benzodioxol-5-yl group, a 2,3-dihydro-1,4-benzodioxin-2-yl group, a 2,3-dihydro-1,4-benzodioxin-6-yl group, a 3-oxo-3,4-dihydro-2H-1,4-benzoxazin-6-yl group, a 1,4-benzodioxanyl group, a 2H-benz[b][1,4]oxazin-3(4H)-on-yl group, a 3,4-dihydro-2H-benzo[b][1,4]dioxepinyl group, an indolinyl group, a 2H-isoindolinyl group, a chromanyl group, a chromonyl group, an isochromanyl group, and a 1,2,3,4-tetrahydroisoquinolyl group.

The "divalent fused ring heterocyclic group having a partially saturated monocycle, which is composed of a 5-membered ring and a 6-membered ring" refers to a divalent heterocyclic group constituted by the ring condensation of a 5-membered ring and a 6-membered ring, among the aforementioned "divalent fused ring heterocyclic groups having a partially saturated monocycle". Its examples are divalent groups formed by eliminating any one hydrogen atom from a 1,3-dihydrobenzimidazol-2-onyl group, a 2-benzoxazolinonyl group, an octahydroisoindolyl group, a [1,3]dioxolo[4,5-b]pyridyl group, a 2,3-dihydrobenzo[b]thienyl group, a 2,3-dihydro-1-benzofuran-5-yl group, a 2,3-dihydro-1-benzofuran-6-yl group, a 1,3-dihydro-2-benzofuran-5-yl group, a 2,3-dihydro-1H-indol-5-yl group, a 1,3-benzodioxol-5-yl group, an indolinyl group, and a 2H-isoindolinyl group.

The "saturated or unsaturated 5- or 6-membered ring which is formed together with the nitrogen atom to which they are attached and which may further contain one or more nitrogen atoms, oxygen atoms or sulfur atoms" includes, for example, a pyrrolidinyl group, a piperidinyl group, a piperazinyl group, a morpholinyl group, a thiomorpholinyl group, and a 1,2,3,6-tetrahydropyridyl group.

The "optionally protected hydroxy group" means an unprotected or protected hydroxy group.

The "protected hydroxy group" means a hydroxy group protected with a "protective group for a hydroxy group".

The "protective group for a hydroxy group" includes all groups usable usually as protective groups for a hydroxy group, and includes, for example, the groups described in P. G. M. Wuts et al., Protective Groups in Organic Synthesis, 4th Ed., 2006, John Wiley & Sons, Inc. Its examples are a $C_{1-6}$ alkyl group optionally substituted with a $C_{1-6}$ alkoxy group (a methyl group, a methoxymethyl group, a t-butoxymethyl group, etc.), a benzyloxymethyl group, a tetrahydropyranyl group, a tetrahydrofuranyl group, a benzyl group optionally substituted with a substituent selected from "a halogen atom, a $C_{1-6}$ alkoxy group, and a nitro group" (a benzyl group, a p-methoxybenzyl group, a p-nitrobenzyl group, and a p-chlorobenzyl group, etc.), a $C_{1-6}$ alkoxycarbonyl group optionally substituted with 1 to 3 substituents selected from "a halogen atom and an aryl group" (a methoxycarbonyl group, a t-butoxycarbonyl group, a 2,2,2-trichloroethoxycarbonyl group, a benzyloxycarbonyl group, and a 9-fluorenylmethoxycarbonyl group, etc.), a benzoyl group, a $C_{2-6}$ alkanoyl group optionally substituted with 1 to 3 halogen atoms (an acetyl group, a chloroacetyl group, a trichloroacetyl group, a trifluoroacetyl group, and a pivaloyl group, etc.), and a silyl group having 3 substituents which are the same or different and are selected from "a $C_{1-6}$ alkyl group and an aryl group" (a trimethylsilyl group, a triethylsilyl group, a t-butyldimethylsilyl group, and a t-butyldiphenylsilyl group, etc.).

The "optionally protected amino group" means an unprotected or protected amino group.

The "protected amino group" means an amino group protected with a "protective group for an amino group".

The "protective group for an amino group" includes all groups usable usually as protective groups for an amino group, and includes, for example, the groups described in P. G. M. Wuts et al., Protective Groups in Organic Synthesis, 4th Ed., 2006, John Wiley & Sons, Inc. Its examples are a benzyl group optionally substituted with a substituent selected from "a halogen atom, a $C_{1-6}$ alkoxy group, and a nitro group" (a benzyl group, a p-methoxybenzyl group, a p-nitrobenzyl group, and a p-chlorobenzyl group, etc.), a $C_{1-6}$ alkoxycarbonyl group optionally substituted with 1 to 3 substituents selected from "a halogen atom and an aryl group" (a methoxycarbonyl group, a t-butoxycarbonyl group, a 2,2,2-trichloroethoxycarbonyl group, a benzyloxycarbonyl group, and a 9-fluorenylmethoxycarbonyl group, etc.), an aryl group, a dialkylaminoalkylidene group (an N,N-dimethylaminomethylene group, and an N,N-diethylaminomethylene group, etc.), a formyl group, a $C_{2-6}$ alkanoyl group optionally substituted with 1 to 3 halogen atoms (an acetyl group, a chloroacetyl group, a trichloroacetyl group, a trifluoroacetyl group, and a pivaloyl group, etc.), and a benzoyl group.

The "optionally protected carboxy group" means an unprotected or protected carboxy group.

The "protected carboxy group" means a carboxy group protected with a "protective group for a carboxy group".

The "protective group for a carboxy group" includes all groups usable usually as protective groups for a carboxy group, and includes, for example, the groups described in P. G. M. Wuts et al., Protective Groups in Organic Synthesis, 4th Ed., 2006, John Wiley & Sons, Inc. Its examples are a $C_{1-6}$ alkyl group optionally substituted with a $C_{1-6}$ alkoxy group (a methyl group, an ethyl group, a t-butyl group, a methoxymethyl group, and a t-butoxymethyl group, etc.), and a benzyl group optionally substituted with a substituent selected from "a halogen atom, a $C_{1-6}$ alkoxy group, and a nitro group" (a benzyl group, a p-methoxybenzyl group, a p-nitrobenzyl group, and a p-chlorobenzyl group, etc.).

The "optionally protected phosphate group" means an unprotected or protected phosphate group.

The "protected phosphate group" means a phosphate group protected with a "protective group for a phosphate group".

The "protective group for a phosphate group" includes all groups usable usually as protective groups for a phosphate group, and includes, for example, the groups described in P. G. M. Wuts et al., Protective Groups in Organic Synthesis, 4th Ed., 2006, John Wiley & Sons, Inc. Its examples are a $C_{1-6}$ alkyl group optionally substituted with a cyano group (a methyl group, an ethyl group, a t-butyl group, and a 2-cyanoethyl group, etc.), and a benzyl group optionally substituted with a substituent selected from "a halogen atom and a nitro group" (a benzyl group, a p-chlorobenzyl group, and a p-nitrobenzyl group, etc.).

The "optionally protected formyl group" means an unprotected or protected formyl group.

The "protected formyl group" includes a formyl group protected with any of groups usable as ordinary formyl-protecting groups, and there can be named the groups described in P. G. M. Wuts et al., Protective Groups in Organic Synthesis, 4th Ed., 2006, John Wiley & Sons, Inc. Its examples are a 1,1-dimethoxymethyl group, a 1,1-diethoxymethyl group, a 1,3-dioxanyl group, a 1,3-dioxolanyl group, a 1,3-dithianyl group, and a 1,3-dithiolanyl group.

The "protective group for an acetylene group" includes all groups usable usually as protective groups for an acetylene group, and includes, for example, the groups described in P. G. M. Wuts et al., Protective Groups in Organic Synthesis, 4th Ed., 2006, John Wiley & Sons, Inc. Its example is a silyl group having 3 substituents which are the same or different and are selected from "a $C_{1-6}$ alkyl group and an aryl group" (a trimethylsilyl group, a triethylsilyl group, a triisopropylsilyl group, a t-butyldimethylsilyl group, and a t-butyldiphenylsilyl group, etc.).

The "leaving group" includes, for example, a halogen atom, a methylsulfonyloxy group, a trifluoromethylsulfonyloxy group, and a p-toluenesulfonyloxy group.

The "antimicrobial agent" refers to a substance which has the ability to act on bacteria, such as gram-positive bacteria or gram-negative bacteria, thereby suppressing their growth or destroying them. The antimicrobial agent may be one which keeps down propagation of bacteria, or kills some of bacteria to decrease their count. Examples of gram-positive bacteria are the genus *Staphylococcus* (*Staphylococcus aureus, Staphylococcus epidermidis*, etc.), the genus *Streptococcus* (*Streptococcus pyogenes, Streptococcus agalactiae, Streptococcus pneumoniae*, etc.), and the genus *Enterococcus* (*Enterococcus faecalis, Enterococcus faecium*, etc.). Examples of gram-negative bacteria are the genus *Pseudomonas* (*Pseudomonas aeruginosa*, etc.), the genus *Escherichia* (*Escherichia coli*, etc.), the genus *Klebsiella* (*Klebsiella pneumoniae, Klebsiella oxytoca*, etc.), the genus *Haemophilus* (*Haemophilus influenzae, Haemophilus parainfluenzae*, etc.), the genus *Bordetella* (*Bordetella pertussis, Bordetella bronchiseptica*, etc.), the genus *Serratia* (*Serratia marcescens*, etc.), the genus *Proteus* (*Proteus mirabilis*, etc.), the genus *Enterobacter* (*Enterobacter cloacae*, etc.), the genus *Campylobacter* (*Campylobacter jejuni*, etc.), the genus *Citrobacter*, the genus *Vibrio* (*Vibrio parahaemolyticus, Vibrio cholerae*, etc.), the genus *Morganella* (*Morganella morganii*, etc.), the genus *Salmonella* (*Salmonella typhi, Salmonella paratyphi*, etc.), the genus *Shigella* (*Shigella dysenteriae*, etc.), the genus *Acinetobacter* (*Acinetobacter baumannii, Acinetobacter calcoaceticus*, etc.), the genus *Legionella* (*Legionella pneumophila*, etc.), the genus *Bacteroides* (*Bacteroides fragilis*, etc.), the genus *Neisseria* (*Neisseria gonorrhoeae, Neisseria meningitides*, etc.), the genus *Moraxella* (*Moraxella catarrhalis*, etc.), the genus *Chlamydia* (*Chlamydia trachomatis, Chlamydia psittaci*, etc.), and the genus *Helicobacter* (*Helicobacter pylori*, etc.).

The preferred embodiments of the compound according to the present invention are as follows:

Preferred $R^1$ is a hydrogen atom or a $C_{1-6}$ alkyl group (the $C_{1-6}$ alkyl group may be substituted with the same or different 1 to 3 halogen atoms). Further preferred $R^1$ is a $C_{1-6}$ alkyl group (the $C_{1-6}$ alkyl group may be substituted with the same or different 1 to 3 halogen atoms), and can be expected to enhance antibacterial activity in vitro or in vivo and increase water solubility. Even more preferred $R^1$ is a methyl group or an ethyl group, and the most preferred $R^1$ is a methyl group.

Preferred $R^2$ is a hydrogen atom or a methyl group, and more preferred $R^2$ is a methyl group.

Preferred $R^3$ is a hydrogen atom.

Preferred $R^4$ is a $C_{1-6}$ alkyl group (the $C_{1-6}$ alkyl group may be substituted with a phenyl group or a monocyclic aromatic heterocyclic group (the phenyl group and the monocyclic aromatic heterocyclic group may be substituted with 1 to 3 substituents which are the same or different and are selected from "a halogen atom, a $C_{1-6}$ alkyl group, a $C_{3-8}$ cycloalkyl group, a $C_{1-6}$ haloalkyl group, a $C_{1-6}$ hydroxyalkyl group, a $C_{2-8}$ alkoxyalkyl group, a hydroxy group, a $C_{1-6}$ alkoxy group, a $C_{3-8}$ cycloalkoxy group, an amino group, a $C_{1-6}$ alkylamino group, a di($C_{1-6}$ alkyl)amino group, —N($R^{45}$)$COR^{46}$, —CON($R^{47}$)($R^{48}$)")). More preferred $R^4$ is a methyl group (the methyl group may be substituted with a monocyclic aromatic heterocyclic group (the monocyclic aromatic heterocyclic group may be substituted with the same or different 1 to 3 $C_{1-6}$ alkyl groups)). The most preferred $R^4$ is a methyl group.

Preferred $A^1$ is a phenylene group (the phenylene group may be substituted with 1 to 4 substituents which are the same or different and are selected from "a halogen atom, a hydroxy group, an amino group, and a $C_{1-6}$ alkyl group"). More preferred $A^1$ is a phenylene group, provided that the phenylene group is preferably bound as in the following formula [4]:

[Chemical Formula 5]

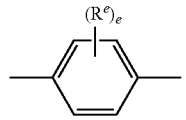

[4]

where $R^e$ represents a halogen atom, a hydroxy group, an amino group, or a $C_{1-6}$ alkyl group, and e denotes 0, 1, 2, 3 or 4.

Preferred L is —C≡C—, —C≡C—C≡C—, —CH=CH—, —CH=CH—C≡C—, —C≡C—CH=CH—, an ethylene group, or a bond, and more preferred L is —C≡C— or a bond.

Preferred $A^2$ is a divalent aryl group (the divalent aryl group may be substituted with 1 to 4 substituents which are the same or different and are selected from "a halogen atom, a hydroxy group, an amino group, and a $C_{1-6}$ alkyl group"), a divalent monocyclic aromatic heterocyclic group (the divalent monocyclic aromatic heterocyclic group contains, as a ring-constituting atom(s), any 1 to 3 atoms selected from a nitrogen atom, an oxygen atom and a sulfur atom, and may be substituted with 1 to 4 substituents which are the same or different and are selected from "a halogen atom, a hydroxy group, an amino group and a $C_{1-6}$ alkyl group"), a divalent fused ring aromatic heterocyclic group, or a divalent fused ring heterocyclic group having a partially saturated monocycle (the divalent fused ring aromatic heterocyclic group, and the divalent fused ring heterocyclic group having a partially saturated monocycle contain, as a ring-constituting atom, any 1 to 4 atoms selected from a nitrogen atom, an oxygen atom and a sulfur atom, have a benzene ring or a pyridine ring as at least one of the rings constituting the fused ring, and may be substituted with 1 to 4 substituents which are the same or different and are selected from "a halogen atom, a hydroxy group, an amino group and a $C_{1-6}$ alkyl group").

A more preferred embodiment of $A^2$ is a phenylene group or a divalent functional group represented by the following formula [5]

[Chemical Formula 6]

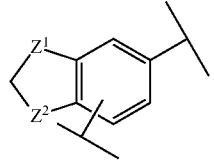

[5]

where $Z^1$ and $Z^2$ are the same or different and each represent —$CH_2$—, —O—, —NH—, —N($CH_3$)—, or —S—, with the exception of a case where $Z^1$ and $Z^2$ both represent —$CH_2$—.

Another more preferred embodiment of $A^2$ is a phenylene group, a pyridinediyl group, a pyrimidinediyl group, a 2,4-furandiyl group, a pyrazolediyl group, a pyrrolediyl group, a "divalent fused ring aromatic heterocyclic group composed of a 5-membered ring and a 6-membered ring", or a "divalent fused ring heterocyclic group having a partially saturated monocycle, which is composed of a 5-membered ring and a 6-membered ring" (the phenylene group, the pyridinediyl group, the pyrimidinediyl group, the 2,4-furandiyl group, the pyrazolediyl group, the pyrrolediyl group, the "divalent fused ring aromatic heterocyclic group composed of a 5-membered ring and a 6-membered ring", and the "divalent fused ring heterocyclic group having a partially saturated monocycle, which is composed of a 5-membered ring and a 6-membered ring" may be substituted with 1 to 4 substituents which are the same or different and are selected from "a halogen atom, a hydroxy group, an amino group and a $C_{1-6}$ alkyl group"). The most preferred $A^2$ is a phenylene group or a 2,4-furandiyl group.

A preferred embodiment of W is a hydrogen atom, a halogen atom, a $C_{1-6}$ alkyl group, a $C_{1-6}$ alkoxy group, a $C_{1-6}$ alkylamino group (the $C_{1-6}$ alkyl group, the $C_{1-6}$ alkoxy group, and the $C_{1-6}$ alkylamino group may be substituted with 1 to 3 substituents which are the same or different and are selected from "a halogen atom, a hydroxy group, a $C_{1-6}$ alkoxy group, and a morpholino group").

Another preferred embodiment of W is $R^6$—$X^1$—
where
$X^1$ represents a methylene group or a bond,
$R^6$ represents a hydrogen atom, an optionally protected hydroxy group, or $R^8$—ON=$CR^9$—,
$R^8$ represents a hydrogen atom or a $C_{1-6}$ alkyl group (the $C_{1-6}$ alkyl group may be substituted with 1 to 4 substituents which are the same or different and are selected from a group of substituents, $R^c$, to be shown below),
$R^9$ represents a hydrogen atom, a $C_{1-6}$ alkyl group, a $C_{3-8}$ cycloalkyl group, an amino group, or a $C_{1-6}$ alkylamino group, and
the group of substituents, $R^c$, consists of a halogen atom and a hydroxy group.

Another preferred embodiment of W is $R^6$—$X^2$—$Y^1$—$X^1$—
where
$Y^1$ represents —O— or —$NR^7$—,
$X^1$ represents a methylene group, an ethylene group (the methylene group and the ethylene group may be substituted with 1 to 2 substituents which are the same or different and are selected from a methyl group and a $C_{3-8}$ cycloalkyl group), a cyclopropylene group, or a bond,
$X^2$ represents a $C_{1-4}$ alkylene group (the $C_{1-4}$ alkylene group may be substituted with 1 to 4 substituents which are the same or different and are selected from a group of substituents, $R^c$, to be shown below),
$R^6$ represents a hydrogen atom, a halogen atom, an optionally protected hydroxy group, or a $C_{1-6}$ alkoxy group,
$R^7$ represents a hydrogen atom, a $C_{1-6}$ alkyl group or a $C_{3-8}$ cycloalkyl group (the $C_{1-6}$ alkyl group and the $C_{3-8}$ cycloalkyl group may be substituted with 1 to 4 substituents which are the same or different and are selected from the following group of substituents, $R^c$), and
the group of substituents, $R^c$, consists of a halogen atom, a hydroxy group, and a $C_{1-6}$ alkyl group.

Another preferred embodiment of W is Q-X$^1$—Y$^2$—X$^3$—,
where

Y$^2$ represents —O—, —NR$^7$—, or a bond,

X$^1$ represents a C$_{1-4}$ alkylene group (the C$_{1-4}$ alkylene group may be substituted with 1 to 4 substituents which are the same or different and are selected from a group of substituents, R$^c$, to be shown below), or a bond, X$^3$ represents a methylene group, an ethylene group (the methylene group and the ethylene group may be substituted with 1 to 2 methyl groups), a cyclopropylene group, or a bond, Q represents a C$_{3-8}$ cycloalkyl group, an aryl group, or a heterocyclic group (the C$_{3-8}$ cycloalkyl group, the aryl group, and the heterocyclic group may be substituted with 1 to 4 substituents which are the same or different and are selected from the group of substituents, R$^c$, shown below, R$^7$ represents a hydrogen atom, a C$_{1-6}$ alkyl group or a C$_{3-8}$ cycloalkyl group (the C$_{1-6}$ alkyl group and the C$_{3-8}$ cycloalkyl group may be substituted with 1 to 4 substituents which are the same or different and are selected from the following group of substituents, R$^c$), and the group of substituents, R$^c$, consists of a halogen atom, a hydroxy group, a C$_{1-6}$ alkyl group, a C$_{1-6}$ hydroxyalkyl group, a C$_{1-6}$ haloalkyl group, a C$_{3-8}$ cycloalkyl group, a C$_{1-6}$ alkoxy group (the C$_{1-6}$ alkoxy group may be substituted with 1 to 3 hydroxy groups or halogen atoms), a C$_{3-8}$ cycloalkoxy group, a C$_{2-6}$ alkanoyl group, a C$_{1-6}$ alkylidene group (the C$_{1-6}$ alkylidene group may be substituted with a C$_{1-6}$ alkoxy group), and a hydroxyaminocarbonyl group.

When W is Q-X$^1$—Y$^2$—X$^3$—, still another preferred embodiment is one in which Y$^2$ is a bond, X$^1$ is a bond, X$^3$ is a methylene group, an ethylene group (the methylene group and the ethylene group may be substituted with 1 to 2 methyl groups), a cyclopropylene group, or a bond, Q is a heterocyclic group (the heterocyclic group may be substituted with 1 to 4 substituents which are the same or different and are selected from the group of substituents, R$^c$, shown below), and the group of substituents, R$^c$, consists of a halogen atom, a hydroxy group, a C$_{1-6}$ alkyl group, a C$_{1-6}$ hydroxyalkyl group, a C$_{1-6}$ haloalkyl group, a C$_{3-8}$ cycloalkyl group, a C$_{1-6}$ alkoxy group (the C$_{1-6}$ alkoxy group may be substituted with 1 to 3 hydroxy groups or halogen atoms), a C$_{3-8}$ cycloalkoxy group, a C$_{2-6}$ alkanoyl group, a C$_{1-6}$ alkylidene group (the C$_{1-6}$ alkylidene group may be substituted with a C$_{1-6}$ alkoxy group), and a hydroxyaminocarbonyl group, provided that the heterocyclic group is a 4- to 7-membered nitrogen-containing saturated heterocyclic group represented by the following formula [6]

[Chemical Formula 7]

[6]

where n1 denotes 0, 1, 2, 3 or 4, and R$^c$ is as defined above, or a nitrogen-containing saturated spiro ring group represented by the following formula [7]:

[Chemical Formula 8]

[7]

When W is Q-X$^1$—Y$^2$—X$^3$—, still another preferred embodiment is one in which Y$^2$ represents —NR$^7$—, X$^1$ represents a C$_{1-4}$ alkylene group (the C$_{1-4}$ alkylene group may be substituted with 1 to 4 substituents which are the same or different and are selected from a group of substituents, R$^c$, to be shown below), or a bond, X$^3$ represents a methylene group, an ethylene group (the methylene group and the ethylene group may be substituted with 1 to 2 methyl groups), a cyclopropylene group, or a bond, Q represents a C$_{3-8}$ cycloalkyl group, a phenyl group, a pyridyl group, a pyrimidyl group, a pyrazinyl group, a furanyl group, an oxazolyl group, or an isoxazolyl group (the C$_{3-8}$ cycloalkyl group, the phenyl group, the pyridyl group, the pyrimidyl group, the pyrazinyl group, the furanyl group, the oxazolyl group, and the isoxazolyl group may be substituted with 1 to 4 substituents which are the same or different and are selected from the group of substituents, R$^c$, shown below), R$^7$ represents a hydrogen atom, a C$_{1-6}$ alkyl group or a C$_{3-8}$ cycloalkyl group (the C$_{1-6}$ alkyl group and the C$_{3-8}$ cycloalkyl group may be substituted with 1 to 4 substituents which are the same or different and are selected from the following group of substituents, R$^c$), and the group of substituents, R$^c$, consists of a halogen atom, a hydroxy group, a C$_{1-6}$ alkyl group, a C$_{1-6}$ hydroxyalkyl group, a C$_{1-6}$ haloalkyl group, a C$_{3-8}$ cycloalkyl group, a C$_{1-6}$ alkoxy group (the C$_{1-6}$ alkoxy group may be substituted with 1 to 3 hydroxy groups or halogen atoms), a C$_{3-8}$ cycloalkoxy group, a C$_{2-6}$ alkanoyl group, a C$_{1-6}$ alkylidene group (the C$_{1-6}$ alkylidene group may be substituted with a C$_{1-6}$ alkoxy group), and a hydroxyaminocarbonyl group.

A preferred embodiment of the compound according to the present invention is as follows:

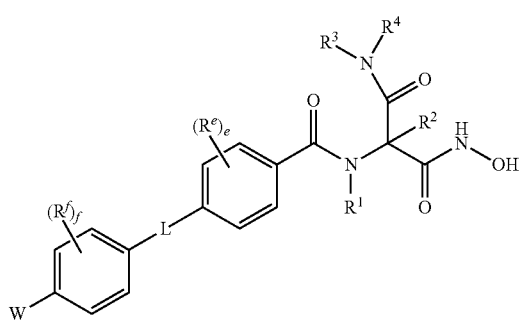

[Chemical Formula 9]

[8]

where the definitions and preferred embodiment of R$^1$, R$^2$, R$^3$, R$^4$, L, R$^e$, R$^f$, e, f and W are as described above.

Another preferred form of the compound according to the present invention is as follows:

[Chemical Formula 10]

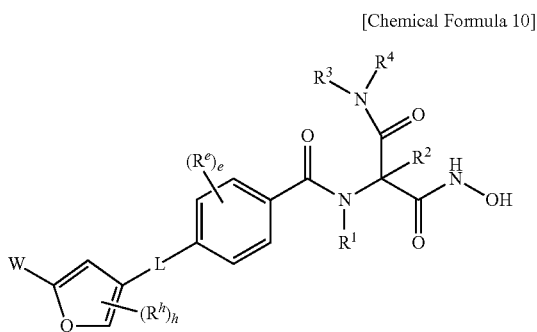

[9]

where the definitions and preferred forms of $R^1$, $R^2$, $R^3$, $R^4$, L, $R^e$, e, and W are as described above, $R^h$ represents a halogen atom, a hydroxy group, an amino group, or a $C_{1-6}$ alkyl group, and h denotes 0, 1, 2 or 3.

In Formula [9], particularly preferred W represents $$R^6-X^1- \quad (1)$$

where $X^1$ represents a methylene group or a bond, $R^6$ represents a hydrogen atom, an optionally protected hydroxy group, or $R^8-ON=CH-$, $R^8$ represents a hydrogen atom or a $C_{1-6}$ alkyl group (the $C_{1-6}$ alkyl group may be substituted with 1 to 4 substituents which are the same or different and are selected from the following group of substituents, $R^c$), and the group of substituents, $R^c$, consists of a halogen atom and a hydroxy group;

$$R^6-X^2-Y^1-X^1- \quad (2)$$

where $Y^1$ represents $-O-$ or $-NH-$, $X^1$ represents a methylene group or an ethylene group, $X^2$ represents a $C_{1-4}$ alkylene group (the $C_{1-4}$ alkylene group may be substituted with the same or different 1 to 4 halogen atoms), and $R^6$ represents a hydrogen atom, a halogen atom, an optionally protected hydroxy group, or a $C_{1-6}$ alkoxy group, $$Q-X^1-Y^2-X^3-, \quad (3)$$

where $Y^2$ represents $-O-$ or $-NH-$, $X^1$ represents a $C_{1-4}$ alkylene group or a bond, $X^3$ represents a methylene group, an ethylene group (the methylene group and the ethylene group may be substituted with 1 to 2 methyl groups), a cyclopropylene group, or a bond, Q represents a $C_{3-8}$ cycloalkyl group (the $C_{3-8}$ cycloalkyl group may be substituted with 1 to 4 substituents which are the same or different and are selected from the following group of substituents, $R^c$), and the group of substituents, $R^c$, consists of a halogen atom, a hydroxy group, a $C_{1-6}$ alkyl group, a $C_{1-6}$ hydroxyalkyl group, a $C_{1-6}$ haloalkyl group, a $C_{3-8}$ cycloalkyl group, a $C_{1-6}$ alkoxy group (the $C_{1-6}$ alkoxy group may be substituted with 1 to 3 hydroxy groups or halogen atoms), a $C_{3-8}$ cycloalkoxy group, a $C_{2-6}$ alkanoyl group, a $C_{1-6}$ alkylidene group (the $C_{1-6}$ alkylidene group may be substituted with a $C_{1-6}$ alkoxy group), and a hydroxyaminocarbonyl group; or $$Q-X^1-Y^2-X^3-, \quad (4)$$

where $Y^2$ is a bond, $X^1$ is a bond, $X^3$ is a methylene group, an ethylene group (the methylene group and the ethylene group may be substituted with 1 to 2 methyl groups), a cyclopropylene group, or a bond, Q is a heterocyclic group (the heterocyclic group may be substituted with 1 to 4 substituents which are the same or different and are selected from the following group of substituents, $R^c$), and the group of substituents, $R^c$, consists of a halogen atom, a hydroxy group, a $C_{1-6}$ alkyl group, a $C_{1-6}$ hydroxyalkyl group, a $C_{1-6}$ haloalkyl group, a $C_{3-8}$ cycloalkyl group, a $C_{1-6}$ alkoxy group (the $C_{1-6}$ alkoxy group may be substituted with 1 to 3 hydroxy groups or halogen atoms), a $C_{3-8}$ cycloalkoxy group, a $C_{2-6}$ alkanoyl group, a $C_{1-6}$ alkylidene group (the $C_{1-6}$ alkylidene group may be substituted with a $C_{1-6}$ alkoxy group), and a hydroxyaminocarbonyl group, provided that the heterocyclic group is a 4- to 7-membered nitrogen-containing saturated heterocyclic group represented by the following formula [6]

[Chemical Formula 11]

[6]

where n1 denotes 0, 1, 2, 3 or 4, and $R^c$ is as defined above.

Examples of the preferred compounds in the present invention are as follows:

(2S)-N-hydroxy-N',2-dimethyl-2-{methyl[(4-{[4-(1,4-oxazepan-4-ylmethyl)phenyl]ethynyl}phenyl)carbonyl]amino}propanediamide, (2S)-N-hydroxy-N',2-dimethyl-2-(methyl{[4-({4-[(oxetan-3-ylamino)methyl]phenyl}ethynyl)phenyl]carbonyl}amino)propanediamide, (2S)-N-hydroxy-N',2-dimethyl-2-{methyl[(4-{[4-(2-oxa-6-azaspiro[3.3]hept-6-ylmethyl)phenyl]ethynyl}phenyl)carbonyl]amino}propanediamide, (2S)-N-hydroxy-2-{[(4-{[5-(methoxymethyl)furan-3-yl]ethynyl}phenyl)carbonyl](methyl)amino}-N',2-dimethylpropanediamide, (2S)-2-[{[4-({4-[(3-ethoxyazetidin-1-yl)methyl]phenyl}ethynyl)phenyl]carbonyl}(methyl)amino]-N-hydroxy-N',2-dimethylpropanediamide, (2S)-N-hydroxy-2-[{[4-({4-[(3-methoxyazetidin-1-yl)methyl]phenyl}ethynyl)phenyl]carbonyl}(methyl)amino]-N',2-dimethylpropanediamide, and (2S)-2-[{[4-({5-[(cyclopropylamino)methyl]furan-3-yl}ethynyl)phenyl]carbonyl}(methyl)amino]-N-hydroxy-N',2-dimethylpropanediamide.

The compounds represented by the formula [1] of the present invention have asymmetric carbon. The compounds of the present invention may be used in racemic form or as a specific enantiomer.

As the specific enantiomer, the compounds represented by the following formula [10] are preferred:

[Chemical Formula 12]

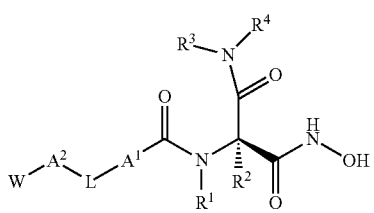

[10]

where the definitions and preferred forms of $R^1$, $R^2$, $R^3$, $R^4$, $A^1$, $A^2$, L and W are as described previously.

The compounds of the present invention can exist as tautomers, stereoisomers such as geometrical isomers, and optical isomers, and the present invention includes them. The present invention also includes various hydrates, solvates and polymorphic substances of the compounds of the invention and their salts.

In the present invention, the pharmaceutically acceptable salts refer to salts which are used in chemotherapy and prevention of bacterial infections. Their examples are salts with acids such as acetic acid, propionic acid, butyric acid, formic acid, trifluoroacetic acid, maleic acid, tartaric acid, citric acid, stearic acid, succinic acid, ethylsuccinic acid, malonic acid, lactobionic acid, gluconic acid, glucoheptonic acid, benzoic acid, methanesulfonic acid, ethanesulfonic acid, 2-hydroxyethanesulfonic acid, benzenesulfonic acid, p-toluenesulfonic acid (tosic acid), laurylsulfuric acid, malic acid, aspartic acid, glutamic acid, adipic acid, cysteine, N-acetylcysteine, hydrochloric acid, hydrobromic acid, phosphoric acid, sulfuric acid, hydriodic acid, nicotinic acid, oxalic acid, picric acid, thiocyanic acid, undecanoic acid, acrylic polymer, and carboxyvinyl polymer; salts with inorganic bases such as lithium salt, sodium salt, potassium salt, magnesium salt and calcium salt; salts with organic amines such as morpholine and piperidine; and salts with amino acids.

Among the compounds of the present invention are compounds which function as prodrugs when administered. The preferred compounds functioning as prodrugs are those having a phosphate group as $R^6$. It is preferred for a group of the compounds, which function as prodrugs, to have the following features:

(1) The prodrug compound itself may have LpxC enzyme inhibiting activity or antimicrobial activity, but such activity is not essential.
(2) After the compound is administered, a functional group which functions as a prodrug is cut off with a suitable enzyme in vivo, and thereby converted into a compound exhibiting the desired pharmacological activity. If, on this occasion, the prodrug itself has antimicrobial activity, it may show a pharmacological effect in the prodrug form, without undergoing cleavage by the in vivo enzyme. Moreover, the prodrug compound and the compound formed by cutting with the in vivo enzyme may be coexistent.
(3) Provision as a prodrug can be expected to increase solubility in water, enhance and prolong drug efficacy, reduce adverse reactions and toxicity, and improve stability. Particularly preferably, an increase in water solubility can be expected. If the prodrug is used as an injection or a drip infusion, for example, it becomes possible to achieve improvements in administration conditions, such as a decrease in the amount of the liquid administered, thus expecting enhanced efficacy ascribed to an increase in the amount of the active ingredient and a rise in its blood level.

The compound of the present invention can be made into a medicinal preparation upon combination with one or more pharmaceutically acceptable carriers, excipients or diluents. Examples of such carriers, excipients and diluents include water, lactose, dextrose, fructose, sucrose, sorbitol, mannitol, polyethylene glycol, propylene glycol, starch, gum, gelatin, alginate, calcium silicate, calcium phosphate, cellulose, aqueous syrup, methyl cellulose, polyvinyl pyrrolidone, alkylparahydroxybenzosorbate, talc, magnesium stearate, stearic acid, glycerin, sesame oil, olive oil, soy oil, and various other seed oils. Moreover, the above carriers, excipients or diluents can be mixed, as needed, with commonly used additives such as thickeners, binders, disintegrants, pH regulators, and solvents, and can be prepared as an oral or parenteral drug, such as tablets, pills, capsules, granules, powders, liquids, emulsions, suspensions, ointments, injections, or skin patchs, by a customary pharmaceutical technology.

The compound of the present invention can be administered orally or parenterally to an adult patient in a dose of 1 to 5,000 mg as a single daily dose or as divided portions per day. This dose can be increased or decreased, as appropriate, according to the type of the disease to be treated, or the age, body weight, symptoms, etc. of the patient. The compound of the present invention can also be used in combination with other drugs.

The compound of the present invention can be synthesized, for example, by methods to be shown below, but the present invention is in no way limited to these methods of manufacturing the compound.

(Scheme 1)

[Chemical Formula 13]

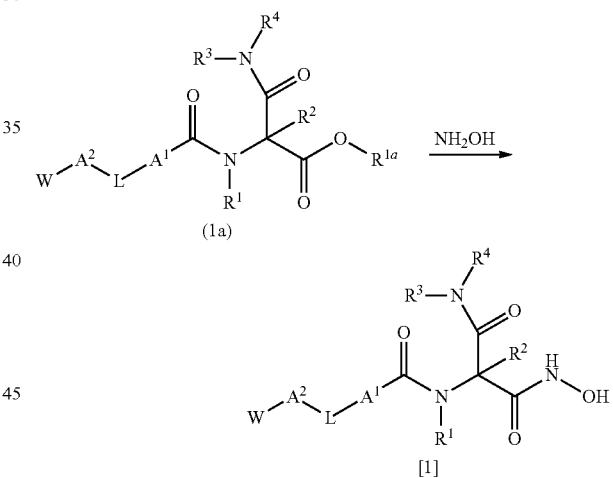

A compound represented by the general formula (1a) (where $R^{1a}$ is a protective group for a carboxy group, and the other symbols are as defined above) is reacted with hydroxylamine in the presence or absence of a base, such as sodium methoxide, whereby the compound represented by the general formula [1] can be obtained.

(Scheme 2)

[Chemical Formula 14]

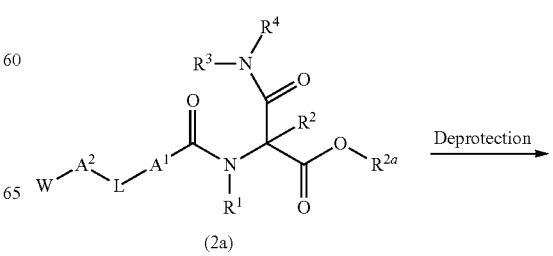

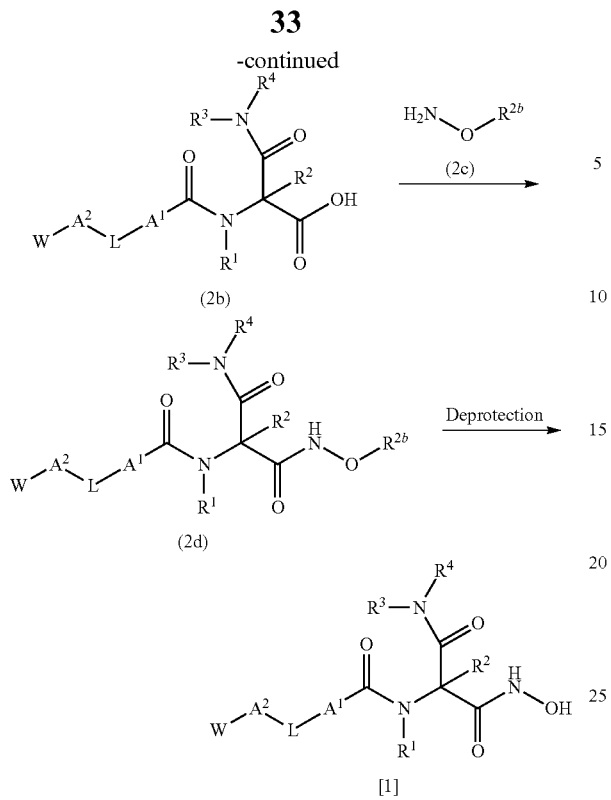

(2b)

(2d)

[1]

A compound represented by the general formula (2a) (where $R^{2a}$ is a protective group for a carboxy group, and the other symbols are as defined above) is subjected to a deprotection reaction under appropriate conditions in accordance with the type of the protective group for the carboxy group, whereby a compound represented by the general formula (2b) (where the symbols are as defined above) can be obtained. Then, the compound of the general formula (2b) is reacted with a hydroxylamine compound represented by the general formula (2c) (where $R^{2b}$ is a protective group for a hydroxy group or a hydrogen atom), in the presence of a condensing agent and in the presence or absence of a base, whereby a compound represented by the general formula (2d) (where the symbols are as defined above) can be obtained. Alternatively, an acid chloride or an acid anhydride of the compound represented by the general formula (2b) is reacted with the hydroxylamine compound represented by the general formula (2c) in the presence or absence of a base, whereby the compound represented by the general formula (2d) can be obtained. Furthermore, when $R^{2b}$ is the protective group for a hydroxy group, a deprotection reaction is performed under appropriate conditions in accordance with the type of this protective group, whereupon the compound represented by the general formula [1] can be obtained.

The compounds represented by the general formulas (1a), (2a) and (2d) can be obtained, for example, by the method described in Scheme 3, 4a, 4b, 5a, 5b, 6 or 7.

(Scheme 3)

[Chemical Formula 15]

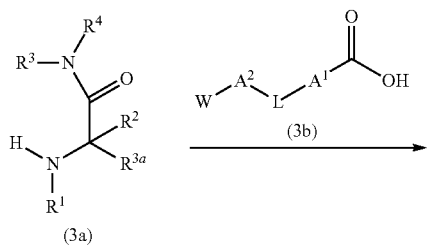

(3a)

(3c)

A compound represented by the general formula (3a) (where $R^{3a}$ is a protected carboxy group, or —CONH—OR$^{3b}$ (where $R^{ab}$ is a protective group for a hydroxy group), and the other symbols are as defined above), and a compound represented by the general formula (3b) (where the symbols are as defined above) are reacted in the presence of a condensing agent and in the presence or absence of a base, whereby a compound represented by the general formula (3c) (where the symbols are as defined above) can be obtained. Alternatively, an acid chloride or an acid anhydride of the compound represented by the general formula (3b) is reacted with the compound represented by the general formula (3a) in the presence or absence of a base, whereby the compound represented by the general formula (3c) can be obtained.

From the compound represented by the general formula (3c), the compound represented by the general formula [1] can be obtained in accordance with the method of Scheme 1 or 2.

(Scheme 4a)

[Chemical Formula 16]

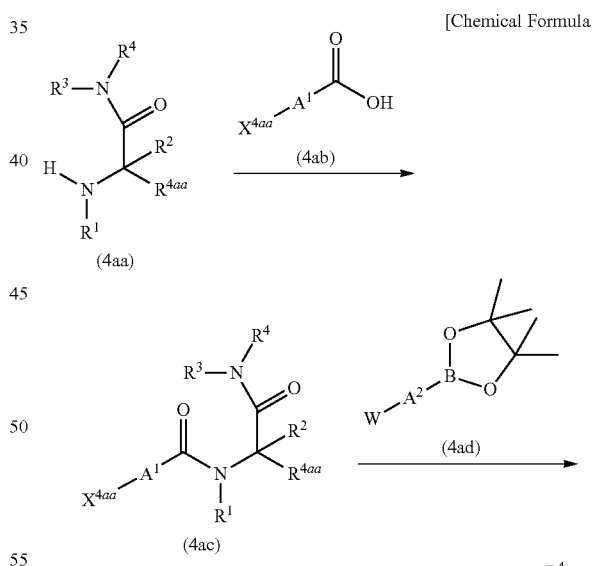

A compound represented by the general formula (4aa) (where $R^{4aa}$ is a protected carboxy group, or —CONH—

OR$^{4ab}$ (where R$^{4ab}$ is a protective group for a hydroxy group), and the other symbols are as defined above), and a compound represented by the general formula (4ab) (where X$^{4aa}$ is a leaving group, and the other symbols are as defined above) are reacted in the presence of a condensing agent and in the presence or absence of a base, whereby a compound represented by the general formula (4ac) (where the symbols are as defined above) can be obtained. Alternatively, an acid chloride or an acid anhydride of the compound represented by the general formula (4ab) is reacted with the compound represented by the general formula (4aa) in the presence or absence of a base, whereby the compound represented by the general formula (4ac) can be obtained. Then, the compound of the general formula (4ac) is subjected to a coupling reaction with a compound represented by the general formula (4ad) (where the symbols are as defined above) in the presence of a catalyst, such as tetrakis(triphenylphosphine)palladium or (1,3-bis(2,6-diisopropylphenyl)imidazolidene)(3-chloropyridyl)palladium(II) dichloride, in the presence or absence of a base, and in the presence or absence of a ligand, whereby a compound represented by the general formula (4ae) (where the symbols are as defined above) can be obtained.

From the compound represented by the general formula (4ae), the compound represented by the general formula [1] can be obtained in accordance with the method of Scheme 1 or 2.

A compound represented by the general formula (4ba) (where R$^{4ba}$ is a protected carboxy group, or —CONH—OR$^{4bb}$ (where R$^{4bb}$ is a protective group for a hydroxy group), and the other symbols are as defined above), and a compound represented by the general formula (4bb) (where the symbols are as defined above) are reacted in the presence of a condensing agent and in the presence or absence of a base, whereby a compound represented by the general formula (4bc) (where the symbols are as defined above) can be obtained. Alternatively, the compound represented by the general formula (4ac) shown in Scheme 4a is subjected to a coupling reaction with a diboron compound, such as bis(pinacolato)diboron, in the presence of a catalyst, such as bistetrakis(triphenylphosphine)palladium(II) dichloride, in the presence or absence of a base, and in the presence or absence of a ligand, whereby the compound represented by the general formula (4bc) can be obtained. The compound of the general formula (4bc) is subjected to a coupling reaction with a compound represented by the general formula (4bd) (where X$^{4ba}$ is a leaving group, and the other symbols are as defined above) in the presence of a catalyst, such as tetrakis(triphenylphosphine)palladium or (1,3-bis(2,6-diisopropylphenyl)imidazolidene)(3-chloropyridyl)palladium(II) dichloride, in the presence or absence of a base, and in the presence or absence of a ligand, whereby a compound represented by the general formula (4be) (where the symbols are as defined above) can be obtained.

From the compound represented by the general formula (4be), the compound represented by the general formula [1] can be obtained in accordance with the method of (Scheme 4b)

[Chemical Formula 17]

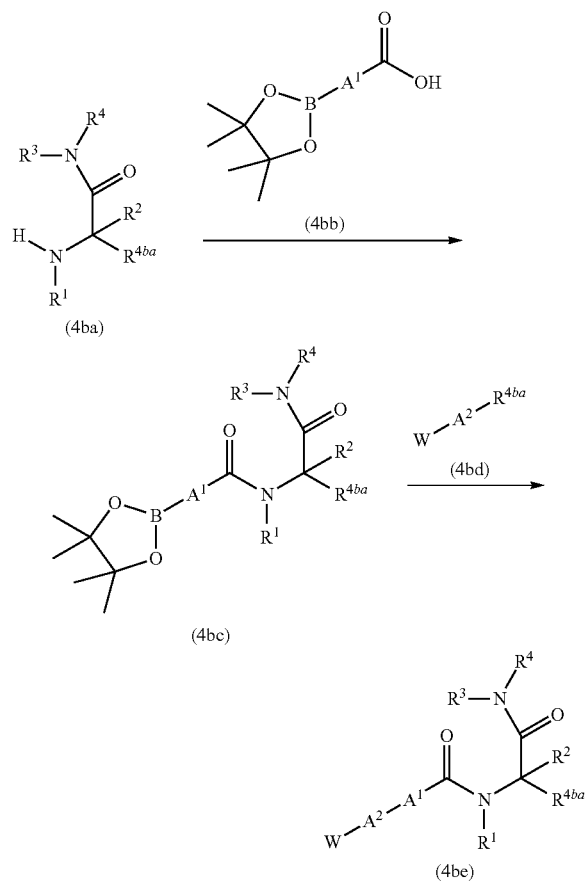

(Scheme 5a)

[Chemical Formula 18]

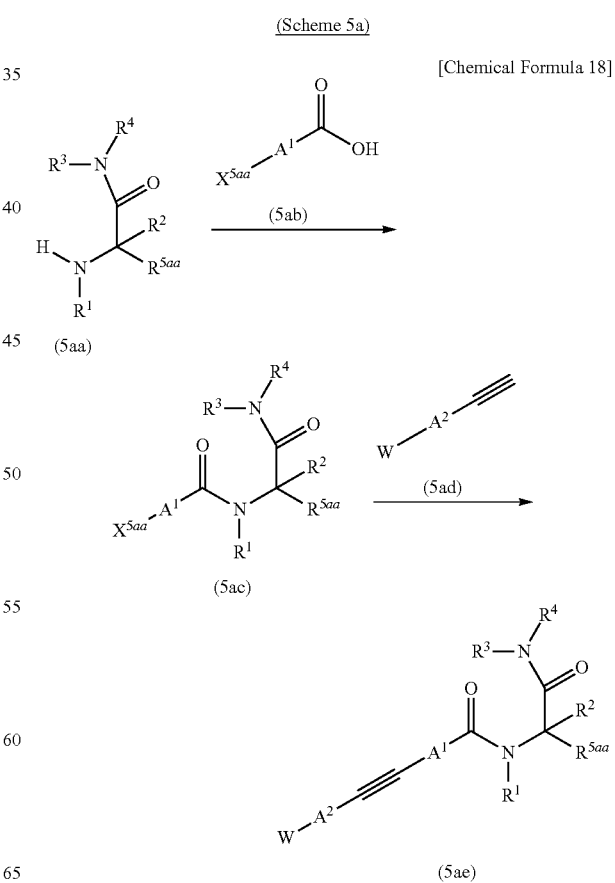

A compound represented by the general formula (5aa) (where $R^{5aa}$ is a protected carboxy group, or —CONH—$OR^{5ab}$ (where $R^{5ab}$ is a protective group for a hydroxy group), and the other symbols are as defined above), and a compound represented by the general formula (5ab) (where $X^{5aa}$ is a leaving group, and the other symbols are as defined above) are reacted in the presence of a condensing agent and in the presence or absence of a base, whereby a compound represented by the general formula (5ac) (where the symbols are as defined above) can be obtained. Alternatively, an acid chloride or an acid anhydride of the compound represented by the general formula (5ab) is reacted with the compound represented by the general formula (5aa) in the presence or absence of a base, whereby the compound represented by the general formula (5ac) can be obtained. Then, the compound of the general formula (5ac) is subjected to a coupling reaction with a compound represented by the general formula (5ad) (where the symbols are as defined above) in the presence of a catalyst, such as bis(triphenylphosphine)dichloropalladium and copper iodide, in the presence or absence of a base, and in the presence or absence of a ligand, whereby a compound represented by the general formula (5ae) (where the symbols are as defined above) can be obtained.

From the compound represented by the general formula (5ae), the compound represented by the general formula [1] can be obtained in accordance with the method of Scheme 1 or 2.

(Scheme 5b)

[Chemical Formula 19]

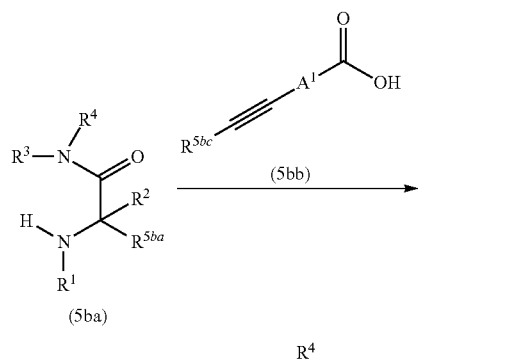

(5ba)

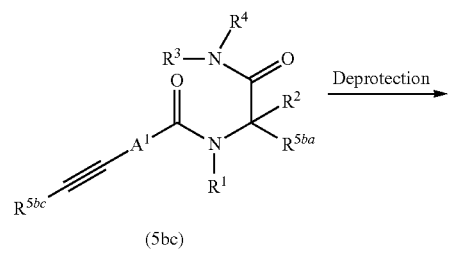

(5bc)

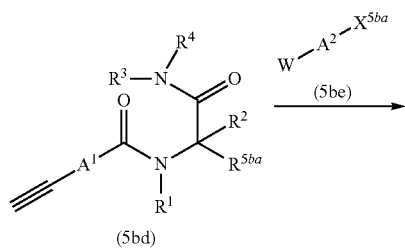

(5bd)

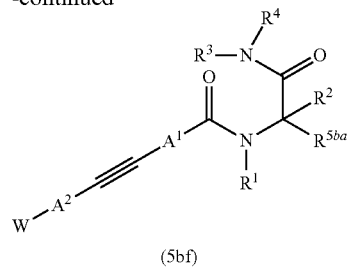

(5bf)

A compound represented by the general formula (5ba) (where $R^{5ba}$ is a protected carboxy group, or —CONH—$OR^{5bb}$ (where $R^{5bb}$ is a protective group for a hydroxy group), and the other symbols are as defined above), and a compound represented by the general formula (5bb) (where $R^{5bc}$ is a protective group for an acetylene group, and the other symbols are as defined above) are reacted in the presence of a condensing agent and in the presence or absence of a base, whereby a compound represented by the general formula (5bc) (where the symbols are as defined above) can be obtained. Alternatively, an acid chloride or an acid anhydride of the compound represented by the general formula (5bb) is reacted with the compound represented by the general formula (5ba) in the presence or absence of a base, whereby the compound represented by the general formula (5bc) (where the symbols are as defined above) can be obtained. Alternatively, the compound represented by the general formula (5ac) shown in Scheme 5a is reacted with $R^{5bc}$-protected acetylene in the presence of a catalyst, such as bis(triphenylphosphine)dichloropalladium and copper iodide, in the presence or absence of a base, and in the presence or absence of a ligand, whereby the compound represented by the general formula (5bc) can be obtained. The compound of the general formula (5bc) is subjected to a deprotection reaction under appropriate conditions according to the type of the protective group $R^{5bc}$, whereby a compound represented by the general formula (5bd) (where the symbols are as defined above) can be obtained. Further, the compound of the general formula (5bd) is subjected to a coupling reaction with a compound represented by the general formula (5be) (where $X^{5ba}$ is a leaving group, and the other symbols are as defined above) in the presence of a catalyst, such as bis(triphenylphosphine)dichloropalladium and copper iodide, in the presence or absence of a base, and in the presence or absence of a ligand, whereby a compound represented by the general formula (5bf) (where the symbols are as defined above) can be obtained.

From the compound represented by the general formula (5bf), the compound represented by the general formula [1] can be obtained in accordance with the method of Scheme 1 or 2.

(Scheme 6)

[Chemical Formula 20]

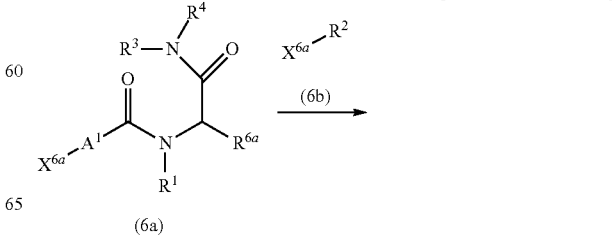

(6a)

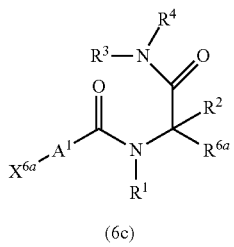

(6c)

A compound represented by the general formula (6a) (where $X^{6a}$ is a leaving group, $R^{6a}$ is a protected carboxy group, or —CONH—$OR^{6b}$ (where $R^{6b}$ is a protective group for a hydroxy group), and the other symbols are as defined above), and a compound represented by the general formula (6b) (where $X^{6b}$ is a leaving group, and the other symbols are as defined above) are reacted in the presence of a base, whereby a compound represented by the general formula (6c) can be obtained.

From the compound represented by the general formula (6c), the compound represented by the general formula [1] can be obtained in accordance with the method of Scheme 4a or 5a.

A compound represented by the general formula (7a) (where $R^{7a}$ and $R^{7b}$ are the same or different protective groups for a carboxy group, and the other symbols are as defined above), and a compound represented by the general formula (7b) (where the symbols are as defined above) are reacted in the presence of a condensing agent and in the presence or absence of a base, whereby a compound represented by the general formula (7c) (where the symbols are as defined above) can be obtained. The compound of the general formula (7c) is reacted with a compound represented by the general formula (7d) (where the symbols are as defined above) in the presence or absence of a base, whereby a compound represented by the general formula (7e) (where the symbols are as defined above) can be obtained. Alternatively, the compound of the general formula (7c) is subjected to a deprotection reaction, in which only $R^{7b}$ is removed, under appropriate conditions according to the types of the two protective groups $R^{7a}$ and $R^{7b}$ for a carboxy group, to form a monocarboxylic acid compound represented by the general formula (7f) (where the symbols are as defined above). Then, the compound of the general formula (7f) is reacted with the compound of the general formula (7d) in the presence of a condensing agent and in the presence or absence of a base, whereby the compound represented by the general formula (Scheme 7)

[Chemical Formula 21]

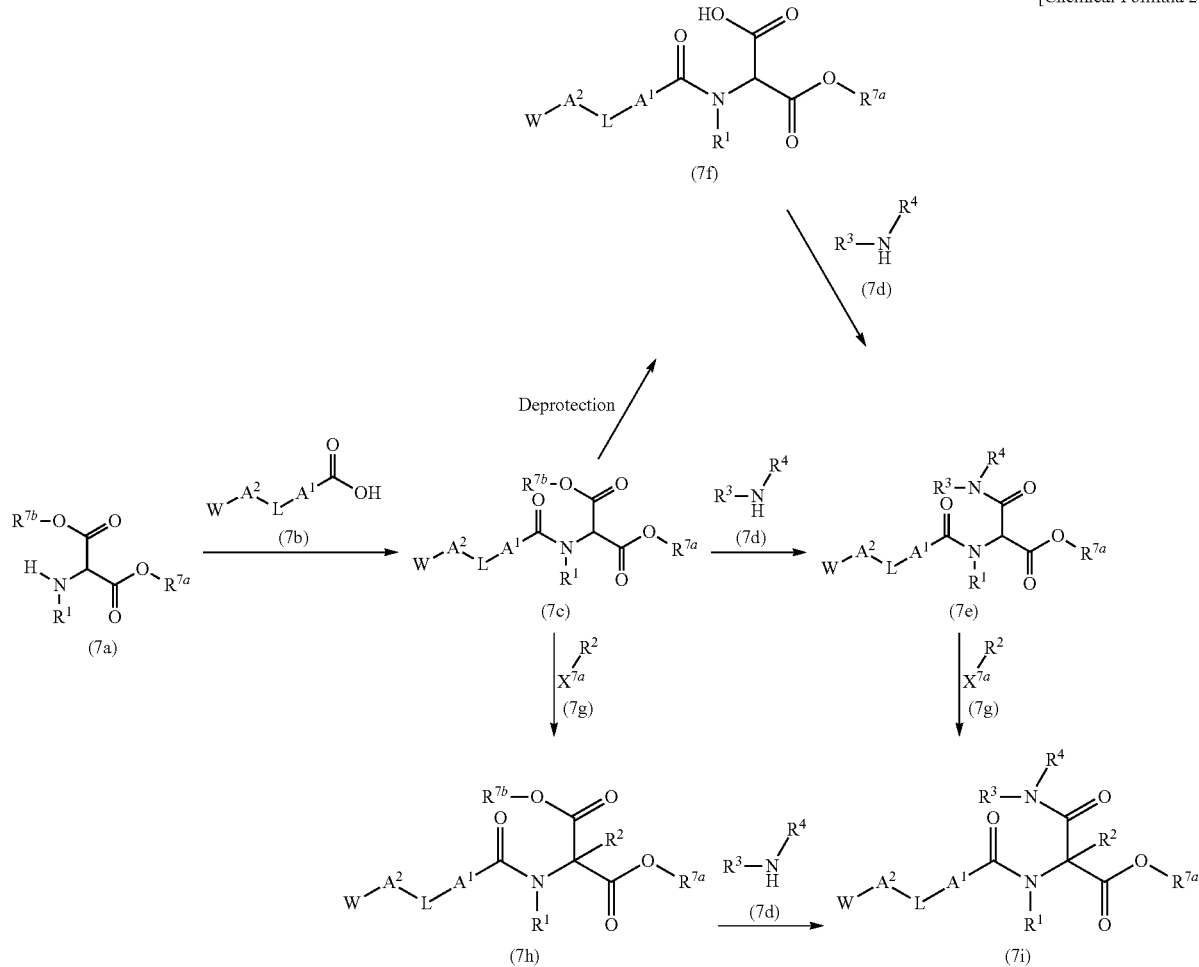

(7e) can be obtained. When $R^{7a}$ and $R^{7b}$ are both ethyl groups, for example, only $R^{7b}$ can be removed for deprotection by performing the reaction in an absolute ethanol solvent with the use of one equivalent of potassium hydroxide, as described in the literature (Bioorg. Med. Chem. (2007), 15, pp. 63-76).

On the other hand, the compound represented by the general formula (7c) and a compound represented by the general formula (7g) (where $X^{7a}$ is a leaving group, and the other symbols are as defined above) are reacted in the presence of a base, whereby a compound represented by the general formula (7h) (where the symbols are as defined above) can be obtained. The compound of the general formula (7h) is reacted with the compound of the general formula (7d) in the presence or absence of a base, whereby a compound represented by the general formula (71) (where the symbols are as defined above) can be obtained. The compound of the general formula (7h) is subjected to a deprotection reaction, in which only $R^{7b}$ is removed, under appropriate conditions according to the types of the two protective groups $R^{7a}$ and $R^{7b}$ for a carboxy group, to form a monocarboxylic acid compound. Then, this monocarboxylic acid compound is reacted with the compound of the general formula (7d) in the presence of a condensing agent and in the presence or absence of a base, whereby the compound represented by the general formula (7i) can be obtained. Alternatively, the compound represented by the general formula (7e) is reacted with the compound represented by the general formula (7g) in the presence of a base, whereby the compound represented by the general formula (7i) can be obtained.

From the compound represented by the general formula (7e) or (7i), the compound represented by the general formula [1] can be obtained in accordance with the method of Scheme 1 or 2.

The compounds represented by the general formulas (3a), (4aa), (4ba), (5aa), (5ba) and (7a) can be obtained, for example, by the method described in Scheme 8, 9, 10 or 11.

(Scheme 8)

[Chemical Formula 22]

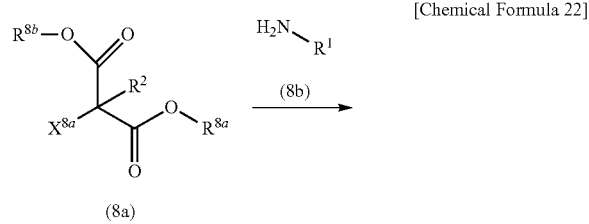

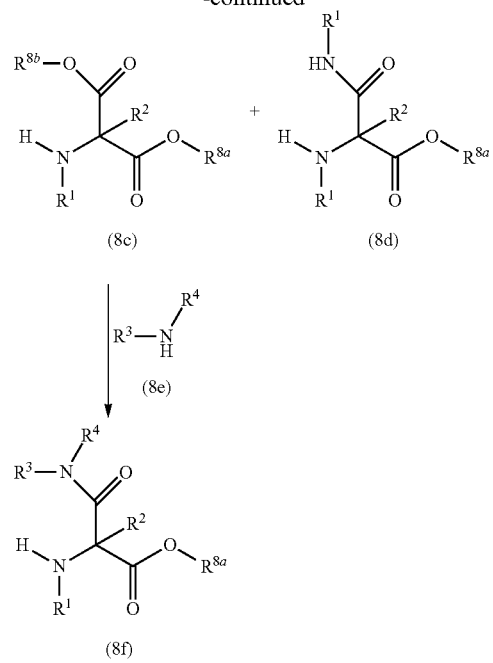

A compound represented by the general formula (8a) (where $X^{8a}$ is a leaving group, and $R^{8a}$ and $R^{8b}$ are the same or different protective groups for a carboxy group), and a compound represented by the general formula (8b) are reacted in the presence or absence of a base, whereby a compound represented by the general formula (8c) (where the symbols are as defined above) and a compound represented by the general formula (8d) (where the symbols are as defined above) can be obtained. The compound of the general formula (8c) is reacted with a compound represented by the general formula (8e) in the presence or absence of a base, whereby a compound represented by the general formula (8f) (where the symbols are as defined above) can be obtained. Alternatively, the compound of the general formula (8a) is subjected to a deprotection reaction, in which only $R^{8b}$ is removed, under appropriate conditions according to the types of the two protective groups $R^{8a}$ and $R^{8b}$ for a carboxy group, to form a monocarboxylic acid compound. Then, the monocarboxylic acid compound is reacted with the compound of the general formula (8e) in the presence of a condensing agent and in the presence or absence of a base, whereby the compound represented by the general formula (8f) can be obtained.

From the compound represented by the general formula (8d) or (8f), the compound represented by the general formula [1] can be obtained in accordance with the method of Scheme 3, 4a, 4b, 5a or 5b.

[Chemical Formula 23]
(Scheme 9)
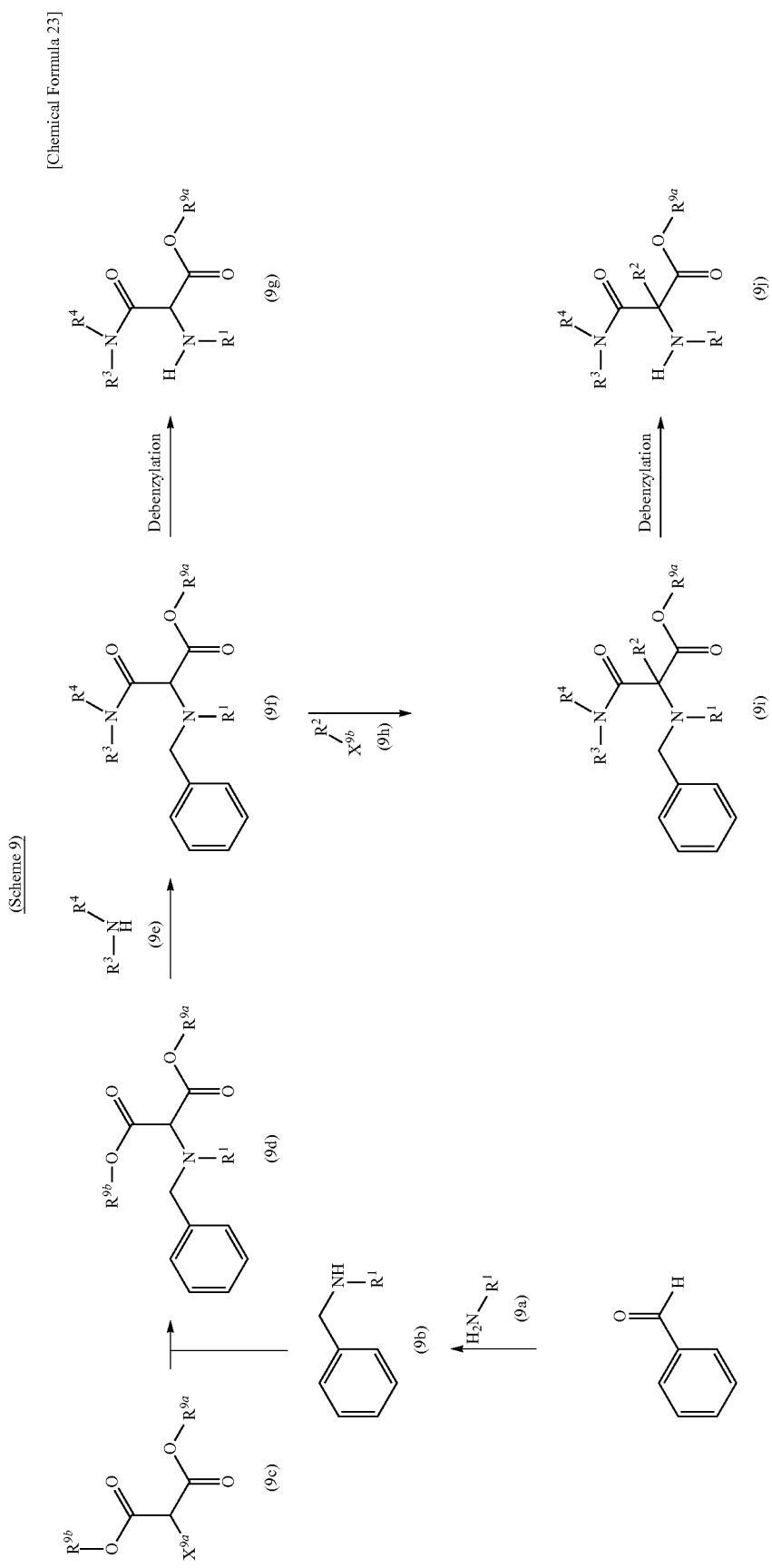

A compound represented by the general formula (9a) (where the symbols are as defined above), and benzaldehyde are reacted in the presence of a reducing agent, such as sodium triacetoxyborohydride, sodium cyanoborohydride or sodium borohydride, in the presence or absence of a metal salt, such as zinc chloride, whereby a compound represented by the general formula (9b) (where the symbols are as defined above) can be obtained. Then, the compound of the general formula (9b) is reacted with a compound represented by the general formula (9c) (where $X^{9a}$ is a leaving group, and $R^{9a}$ and $R^{9b}$ are the same or different protective groups for a carboxy group) in the presence or absence of a base, whereby a compound represented by the general formula (9d) (where the symbols are as defined above) can be obtained. The compound of the general formula (9d) is reacted with a compound represented by the general formula (9e) (where the symbols are as defined above) in the presence or absence of a base, whereby a compound represented by the general formula (9f) (where the symbols are as defined above) can be obtained. Alternatively, the compound of the general formula (9d) is subjected to a deprotection reaction, in which only $R^{9b}$ is removed, under appropriate conditions according to the types of the two protective groups $R^{9a}$ and $R^{9b}$ for a carboxy group, to form a monocarboxylic acid compound. Then, the monocarboxylic acid compound is reacted with a compound represented by the general formula (9h) in the presence of a condensing agent and in the presence or absence of a base, whereby the compound represented by the general formula (9f) can be obtained. The compound of the general formula (9f) is debenzylated in the presence of a catalyst, such as palladium on carbon or palladium hydroxide, and in the presence of hydrogen or formic acid, whereby a compound represented by the general formula (9g) (where the symbols are as defined above) can be obtained.

On the other hand, the compound of the general formula (9f) is reacted with the compound represented by the general formula (9h) (where $X^{9b}$ is a leaving group, and the other symbols are as defined above) in the presence of a base, whereby a compound represented by the general formula (9i) (where the symbols are as defined above) can be obtained. The compound of the general formula (9i) is debenzylated in the presence of a catalyst, such as palladium on carbon or palladium hydroxide, and in the presence of hydrogen or formic acid, whereby a compound represented by the general formula (9j) (where the symbols are as defined above) can be obtained.

From the compound represented by the general formula (9g) or (9j), the compound represented by the general formula [1] can be obtained in accordance with the method of Scheme 3, 4a, 4b, 5a or 5b.

(Scheme 10)

[Chemical formula 24]

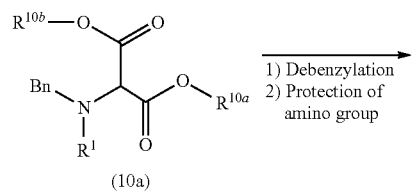

(10a)

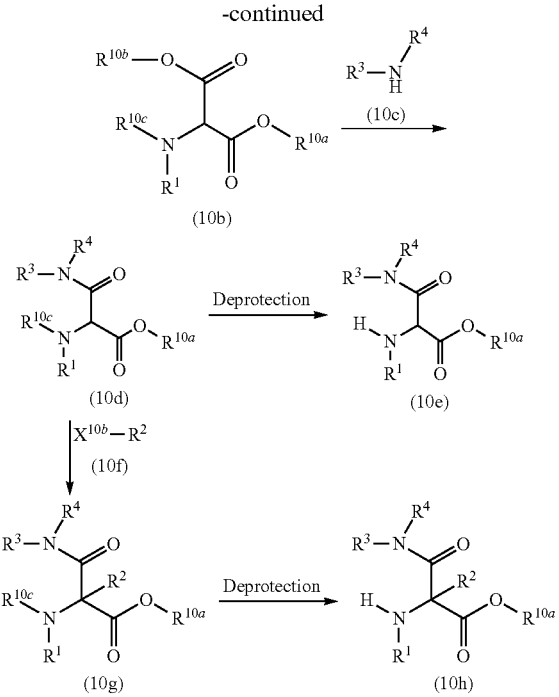

A compound represented by the general formula (10a) (where $R^{10a}$ and $R^{10b}$ are the same or different protective groups for a carboxy group, Bn is a benzyl group, and the other symbols are as defined above), which has been obtained in accordance with the method of Scheme 9, is debenzylated in the presence of a catalyst, such as palladium on carbon or palladium hydroxide, and in the presence of hydrogen or formic acid. Then, a protection reaction for an amino group is performed under appropriate conditions according to the type of the protective group for an amino group (e.g., a t-butoxycarbonyl group). As a result, a compound represented by the general formula (10b) (where $R^{10c}$ is a protective group for an amino group, and the other symbols are as defined above) can be obtained. The compound of the general formula (10b) is reacted with a compound represented by the general formula (10c) (where the symbols are as defined above) in the presence or absence of a base, whereby a compound represented by the general formula (10d) (where the symbols are as defined above) can be obtained. Alternatively, the compound of the general formula (10b) is subjected to a deprotection reaction, in which only $R^{10b}$ is removed, under appropriate conditions according to the types of the two protective groups $R^{10a}$ and $R^{10b}$ for a carboxy group, to form a monocarboxylic acid compound. Then, the monocarboxylic acid compound is reacted with the compound represented by the general formula (10c) in the presence of a condensing agent and in the presence or absence of a base, whereby the compound represented by the general formula (10d) can be obtained. The compound of the general formula (10d) is subjected to a deprotection reaction under appropriate conditions according to the type of the protective group for an amino group, whereby a compound represented by the general formula (10e) (where the symbols are as defined above) can be obtained.

The compound of the general formula (10d) is reacted with a compound represented by the general formula (10f) (where $X^{10b}$ is a leaving group, and the other symbols are as defined above) in the presence of a base, whereby a compound represented by the general formula (10g) (where the symbols are as defined above) can be obtained. The compound of the general formula (10g) is subjected to a deprotection reaction under appropriate conditions according to the type of the protective group for an amino group, whereby a compound represented by the general formula (10h) (where the symbols are as defined above) can be obtained.

From the compound represented by the general formula (10e) or (10h), the compound represented by the general formula [1] can be obtained in accordance with the method of Scheme 3, 4a, 5b, 5a or 5b.

formula (11d) (where the symbols are as defined above) can be obtained. Then, the compound of the general formula (11d) is subjected to a deprotection reaction under appropriate conditions according to the type of the protective group for the amino group, whereby a compound represented by the general formula (11e) (where the symbols are as defined above) can be obtained. From the compound represented by the general formula (11e), the compound represented by the general formula [1] can be obtained in accordance with the method of Scheme 3, 4a, 4b, 5a or 5b.

The compounds represented by the general formulas (3b), (4ad), (4bb), (5ad) and (7b) can be obtained, for example, by the method described in Scheme 12a or 12b.

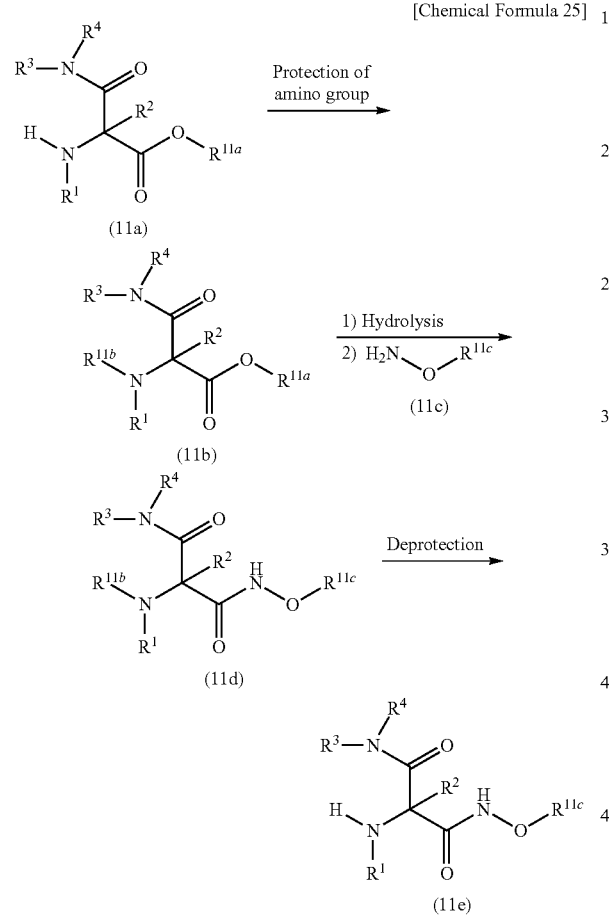

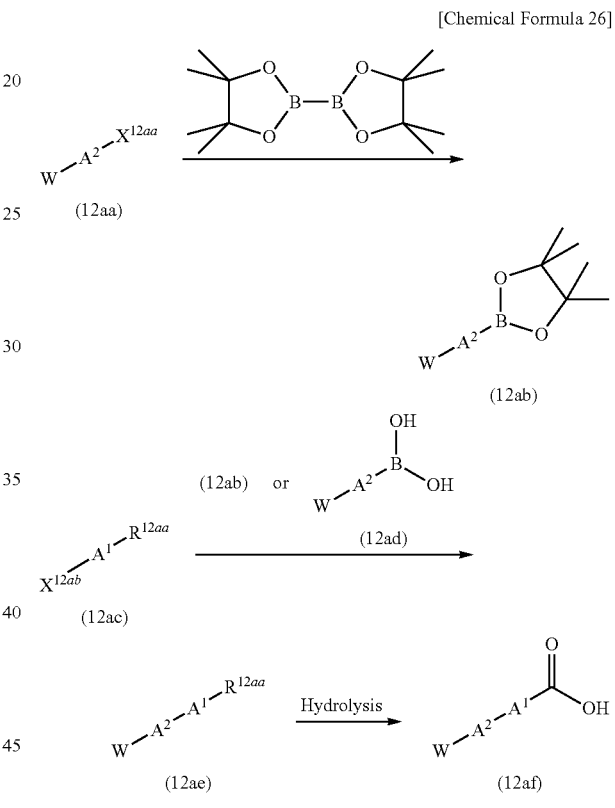

A compound represented by the general formula (11a) (where $R^{11a}$ is a protective group for a carboxy group, and the other symbols are as defined above), which has been obtained in accordance with the method of Scheme 8, 9 or 10, is subjected to a reaction for protection of an amino group under appropriate conditions according to the type of a protective group for an amino group. As a result, a compound represented by the general formula (11b) (where $R^{11b}$ is a protective group for an amino group, and the other symbols are as defined above) can be obtained. The compound of the general formula (11b) can be subjected to a deprotection reaction under appropriate conditions according to the type of the protective group for the carboxy group, and is then reacted with a compound represented by the general formula (11c) (where $R^{11c}$ is a protective group for a hydroxy group) in the presence of a condensing agent and in the presence or absence of a base, whereby a compound represented by the general A compound represented by the general formula (12aa) (where $X^{12aa}$ is a leaving group, and the other symbols are as defined above) is reacted with a diboron compound, such as bis(pinacolato)diboron, in the presence of a catalyst, such as 1,1'-bis(diphenylphosphino)ferrocenedichloropalladium, in the presence or absence of a base, and in the presence or absence of a ligand, whereby a compound represented by the general formula (12ab) (where the symbols are as defined above) can be obtained. Then, a compound represented by the general formula (12ac) (where $X^{12ab}$ is a leaving group, $R^{12a}$ is a carboxy group, a protected carboxy group, or a cyano group, and the other symbols are as defined above) is subjected to a coupling reaction with the compound of the general formula (12ab) or a compound represented by the general formula (12ad) (where the symbols are as defined above) in the presence of a catalyst, such as tetrakis(triphenylphosphine)palladium, in the presence or absence of a base, and in the presence or absence of a ligand, whereby a compound represented by the general formula (12ae) (where the symbols are as defined above) can be obtained. Further, when $R^{12aa}$ of the compound of the general formula (12ae) is a protective group for the carboxy group or is a cyano group, this compound is hydrolyzed under basic or acidic conditions, whereby a compound represented by the general formula (12af) (where the symbols are as defined above) can be obtained. The reactions may be interchanged and their sequence may be changed such that the compound of the general formula (12ac) is converted into a boronic acid ester, which is then reacted with the compound of the generation formula (12aa), whereby the compound of the general formula (12af) can be obtained.

From the compound represented by the general formula (12ab) or (12af), the compound represented by the general formula [1] can be obtained in accordance with the method of Scheme 3, 4a, 4b or 7.

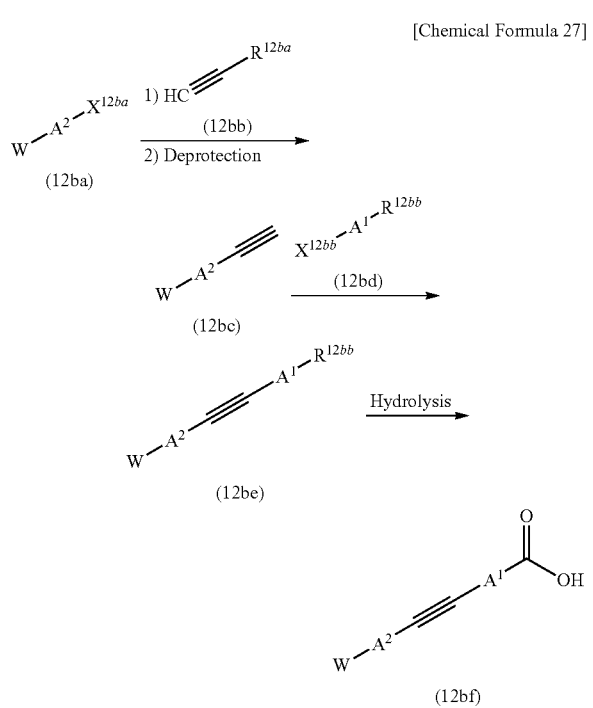

(Scheme 12b)

[Chemical Formula 27]

per iodide, in the presence or absence of a base, and in the presence or absence of a ligand, whereby a compound represented by the general formula (12be) (where the symbols are as defined above) can be obtained. Further, when $R^{12bb}$ of the compound represented by the general formula (12be) is a protective group for the carboxy group or is a cyano group, this compound is hydrolyzed under basic or acidic conditions, whereby a compound represented by the general formula (12bf) (where the symbols are as defined above) can be obtained. The sequence of the reactions may be changed such that the compound of the general formula (12bd) is converted into an acetylene compound, which is then reacted with the compound of the generation formula (12ba), whereby the compound of the general formula (12bf) can be obtained.

From the compound represented by the general formula (12bc) or (12bf), the compound represented by the general formula [1] can be obtained in accordance with the method of Scheme 3, 5a, 5b or 7.

The compounds described in Schemes 1 to 12 can be obtained, for example, by the methods described in Schemes 13 to 23 as well.

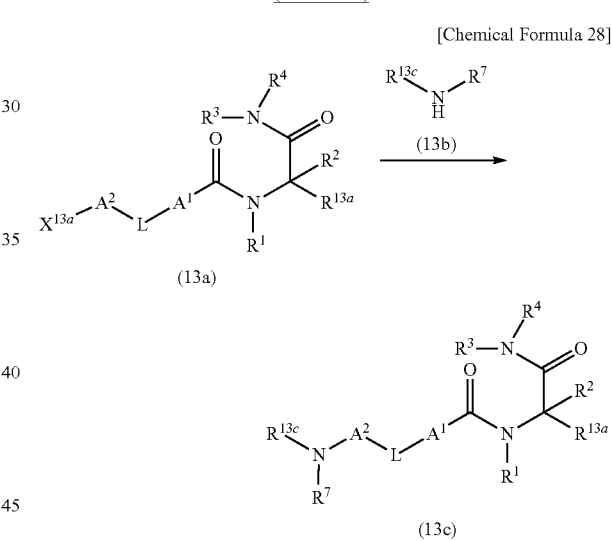

(Scheme 13)

[Chemical Formula 28]

A compound represented by the general formula (12ba) (where $X^{12ba}$ is a leaving group, and the other symbols are as defined above) is subjected to a coupling reaction with a compound represented by the general formula (12bb) (where $R^{12ba}$ is a protective group for an acetylene group), in the presence of a catalyst, such as bis(triphenylphosphine)dichloropalladium and copper iodide, in the presence or absence of a base, and in the presence or absence of a ligand. Then, the reaction product is subjected to a deprotection reaction under appropriate conditions according to the type of the protective group $R^{12ba}$, whereby a compound represented by the general formula (12bc) (where the symbols are as defined above) can be obtained. Further, the compound of the general formula (12bc) is subjected to a coupling reaction with a compound represented by the general formula (12bd) (where $X^{12bb}$ is a leaving group, $R^{12bb}$ is a carboxy group, a protected carboxy group, or a cyano group, and the other symbols are as defined above) in the presence of a catalyst, such as bis(triphenylphosphine)dichloropalladium and cop- A compound represented by the general formula (13a) (where $X^{13a}$ is a leaving group, $R^{13a}$ is a carboxy group, a protected carboxy group, or —CONH—OR$^{13b}$ (where R$^{13b}$ is a protective group for a hydroxy group), and the other symbols are as defined above), which has been obtained in accordance with the method of Scheme 2, 3, 4a, 4b, 5a, 5b or 7, is reacted with a compound represented by the general formula (13b) (where $R^{13c}$ is $R^9$—$X^2$—, $R^9$—$X^4$—$Y^1$—$X^2$, Q-$X^1$— or Q-$X^1$—$Y^1$—$X^2$—, and the other symbols are as defined above), in the presence or absence of a catalyst, in the presence or absence of a base, and in the presence or absence of a ligand, whereby a compound represented by the general formula (13c) (where the symbols are as defined above) can be obtained.

From the compound represented by the general formula (13c), the compound represented by the general formula [1] can be obtained in accordance with the method of Scheme 1 or 2.

(Scheme 14)

[Chemical Formula 29]

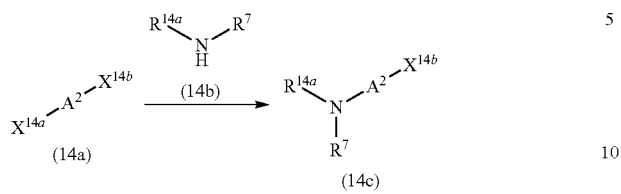

A compound represented by the general formula (14a) (where $X^{14a}$ and $X^{14b}$ are groups to be eliminated, and the other symbols are as defined above) is reacted with a compound represented by the general formula (14b) (where $R^{14a}$ is $R^9$—$X^2$—, $R^9$—$X^4$—$Y^1$—$X^2$—, Q-$X^1$— or Q-$X^1$—$Y^1$—$X^2$—, and the other symbols are as defined above), in the presence or absence of a catalyst, in the presence or absence of a base, and in the presence or absence of a ligand, whereby a compound represented by the general formula (14c) (where the symbols are as defined above) can be obtained.

From the compound represented by the general formula (14c), the compound represented by the general formula [1] can be obtained in accordance with the method of Scheme 4b, 5b, 12a or 12b.

(Scheme 15)

[Chemical Formula 30]

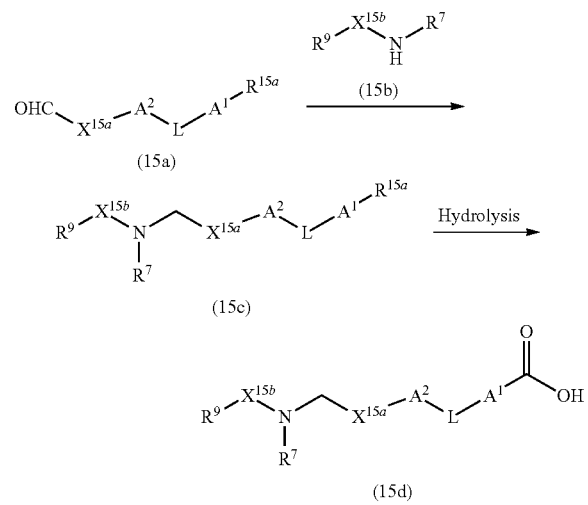

A compound represented by the general formula (15a) (where $X^{15a}$ is a group which, together with an adjacent methylene group, forms —$X^1$— or —$X^2$—$Y^3$—$X^3$—, $R^{15a}$ is a protected carboxy group or a cyano group, and the other symbols are as defined above), which has been obtained in accordance with the method of Scheme 12a or 12b, is reacted with a compound represented by the general formula (15b) (where $X^{15b}$ is —$X^2$— or —$X^4$—, and the other symbols are as defined above), in the presence of a reducing agent, such as sodium triacetoxyborohydride, sodium cyanoborohydride or sodium borohydride, and in the presence or absence of a metal salt, such as zinc chloride, whereby a compound represented by the general formula (15c) (where the symbols are as defined above) can be obtained. Then, the compound of the general formula (15c) is hydrolyzed under basic or acidic conditions, whereby a compound represented by the general formula (15d) (where the symbols are as defined above) can be obtained.

From the compound represented by the general formula (15d), the compound represented by the general formula [1] can be obtained in accordance with the method of Scheme 3 or 7.

(Scheme 16)

[Chemical Formula 31]

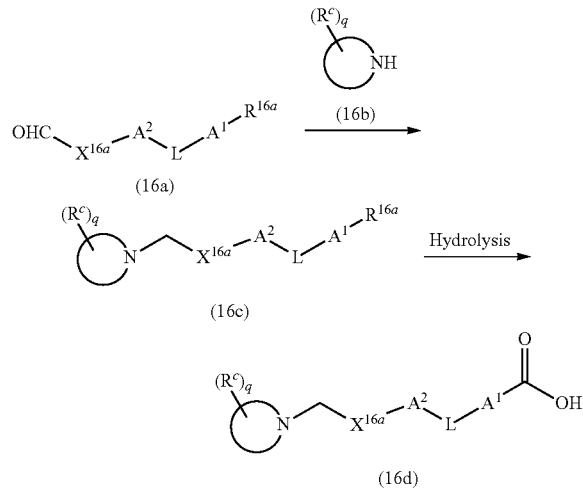

A compound represented by the general formula (16a) (where $X^{16a}$ is a group which, together with an adjacent methylene group, forms —$X^1$— or —$X^2$—$Y^3$—$X^3$—, $R^{16a}$ is a protected carboxy group or a cyano group, and the other symbols are as defined above), which has been obtained in accordance with the method of Scheme 12a or 12b, is reacted with a compound represented by the general formula (16b) (where the symbols are as defined above), in the presence of a reducing agent, such as sodium triacetoxyborohydride, sodium cyanoborohydride or sodium borohydride, and in the presence or absence of a metal salt, such as zinc chloride, whereby a compound represented by the general formula (16c) (where the symbols are as defined above) can be obtained. Here, the formula (16b)

[Chemical Formula 32]

(16b)

represents a 4- to 7-membered nitrogen-containing saturated heterocyclic group (in which q denotes 0, 1, 2, 3 or 4, and the other symbols are as defined above). Then, the compound of the general formula (16c) is hydrolyzed under basic or acidic conditions, whereby a compound represented by the general formula (16d) (where the symbols are as defined above) can be obtained.

From the compound represented by the general formula (16d), the compound represented by the general formula [1] can be obtained in accordance with the method of Scheme 3 or 7.

(Scheme 17)

[Chemical Formula 33]

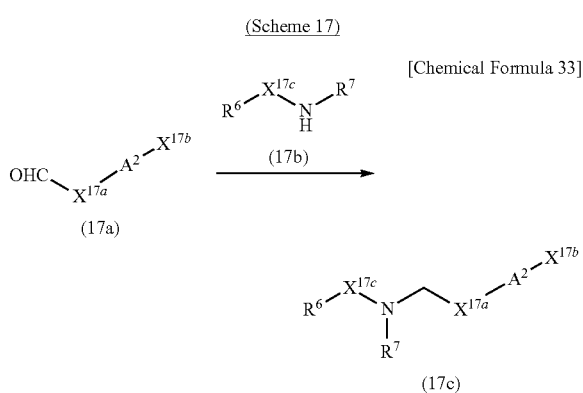

A compound represented by the general formula (17a) (where $X^{17a}$ is a group which, together with an adjacent methylene group, forms —$X^1$— or —$X^2$—$Y^3$—$X^3$—, $X^{17b}$ is a leaving group, and the other symbols are as defined above) is reacted with a compound represented by the general formula (17b) ($X^{17c}$ is —$X^2$— or —$X^4$—, and the other symbols are as defined above), in the presence of a reducing agent, such as sodium triacetoxyborohydride, sodium cyanoborohydride or sodium borohydride, and in the presence or absence of a metal salt, such as zinc chloride, whereby a compound represented by the general formula (17c) (where the symbols are as defined above) can be obtained.

From the compound represented by the general formula (17c), the compound represented by the general formula [1] can be obtained in accordance with the method of Scheme 4b, 5b, 12a or 12b.

(Scheme 18)

[Chemical Formula 34]

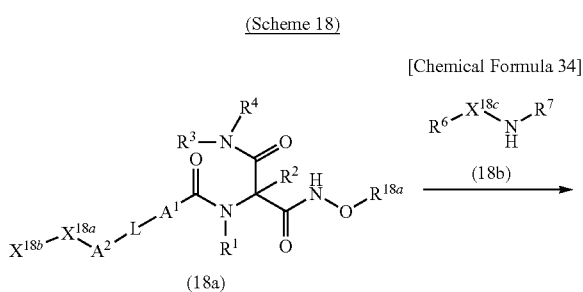

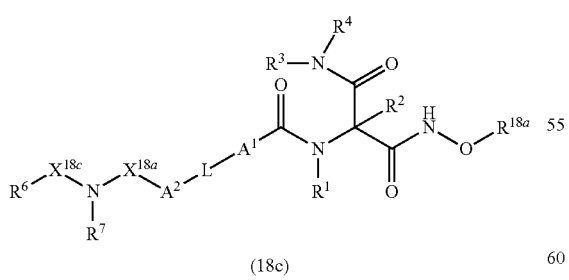

A compound represented by the general formula (18a) (where $X^{18a}$ is —$X^1$— or —$X^2$—$Y^3$—$X^3$—, $X^{18b}$ is a leaving group, $R^{18a}$ is a protective group for a hydroxy group, and the other symbols are as defined above), which has been obtained in accordance with the method of Scheme 2, 3, 4a, 4b, 5a, 5b or 7, is reacted with a compound represented by the general formula (18b) (where $X^{18c}$ is —$X^2$— or —$X^4$—, and the other symbols are as defined above), in the presence or absence of a base, whereby a compound represented by the general formula (18c) (where the symbols are as defined above) can be obtained.

From the compound represented by the general formula (18c), the compound represented by the general formula [1] can be obtained in accordance with the method of Scheme 2.

(Scheme 19)

[Chemical Formula 35]

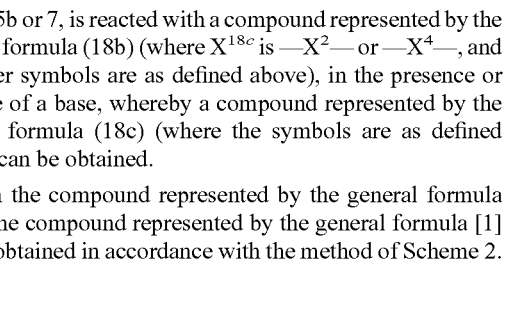

A compound represented by the general formula (19a) (where $X^{19a}$ is —$X^1$—$Y^2$—$X^3$— or —$X^1$—$Y^1$—$X^2$—$Y^3$—$X^3$—, $X^{19b}$ is a leaving group, $R^{19a}$ is a protective group for a hydroxy group, and the other symbols are as defined above), which has been obtained in accordance with the method of Scheme 2, 3, 4a, 4b, 5a, 5b or 7, is reacted with a compound represented by the general formula (19b) (where the symbols are as defined above), in the presence or absence of a base, whereby a compound represented by the general formula (19c) (where the symbols are as defined above) can be obtained.

From the compound represented by the general formula (19c), the compound represented by the general formula [1] can be obtained in accordance with the method of Scheme 2.

(Scheme 20)

[Chemical Formula 36]

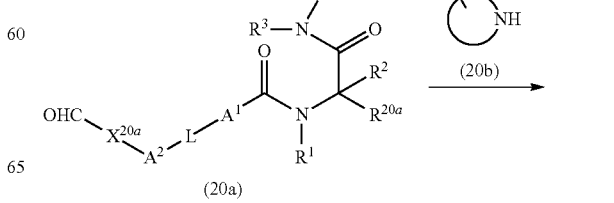

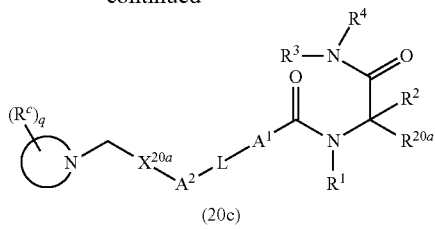

(20c)

A compound represented by the general formula (20a) (where $X^{20a}$ is a group which, together with an adjacent methylene group, forms —$X^1$— or —$X^2$—$Y^3$—$X^3$—, $R^{20a}$ is a carboxy group, a protected carboxy group or —CONH—$OR^{20b}$ (where $R^{20b}$ is a protective group for a hydroxy group), and the other symbols are as defined above), which has been obtained in accordance with the method of Scheme 2, 3, 4a, 4b, 5a, 5b or 7, is reacted with a compound represented by the general formula (20b) (where the symbols are as defined above), in the presence of a reducing agent, such as sodium triacetoxyborohydride, sodium cyanoborohydride or sodium borohydride, and in the presence or absence of a metal salt, such as zinc chloride, whereby a compound represented by the general formula (20c) (where the symbols are as defined above) can be obtained.

From the compound represented by the general formula (20c), the compound represented by the general formula [1] can be obtained in accordance with the method of Scheme 1 or 2.

(Scheme 21)

[Chemical Formula 37]

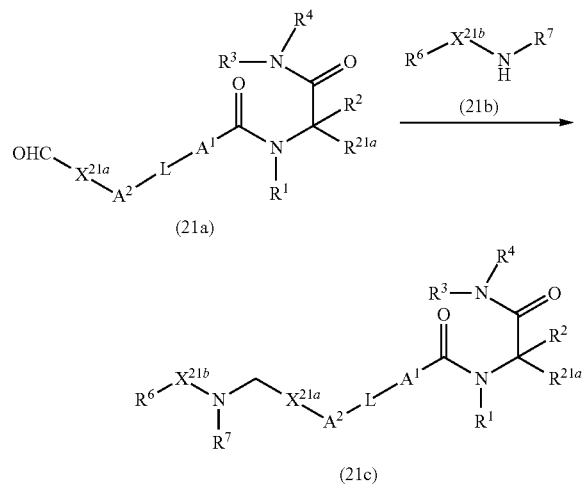

A compound represented by the general formula (21a) (where $X^{21a}$ is a group which, together with an adjacent methylene group, forms —$X^1$— or —$X^2$—$Y^3$—$X^3$—, $R^{21a}$ is a carboxy group, a protected carboxy group or —CONH—$OR^{21b}$ (where $R^{21b}$ is a protective group for a hydroxy group), and the other symbols are as defined above), which has been obtained in accordance with the method of Scheme 2, 3, 4a, 4b, 5a, 5b or 7, is reacted with a compound represented by the general formula (21b) (where $X^{21b}$ is —$X^2$— or —$X^4$—, and the other symbols are as defined above), in the presence of a reducing agent, such as sodium triacetoxyborohydride, sodium cyanoborohydride or sodium borohydride, and in the presence or absence of a metal salt, such as zinc chloride, whereby a compound represented by the general formula (21c) (where the symbols are as defined above) can be obtained.

From the compound represented by the general formula (21c), the compound represented by the general formula [1] can be obtained in accordance with the method of Scheme 1 or 2.

(Scheme 22)

[Chemical Formula 38]

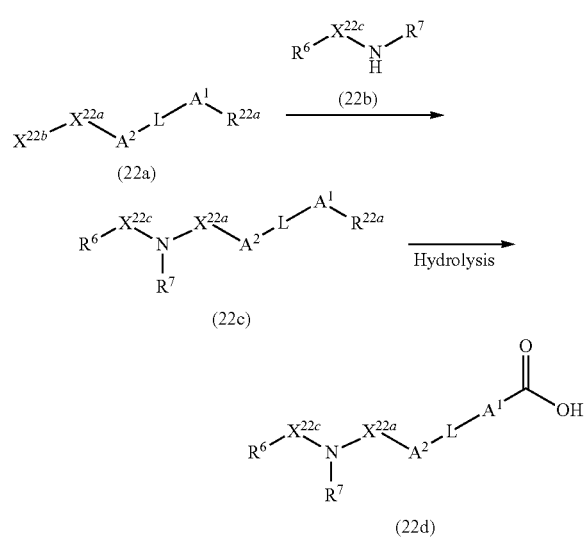

A compound represented by the general formula (22a) (where $X^{22a}$ is —$X^1$— or —$X^2$—$Y^3$—$X^3$—, $X^{22b}$ is a leaving group, $R^{22a}$ is a protected carboxy group or a cyano group, and the other symbols are as defined above), which has been obtained in accordance with the method of Scheme 12a or 12b, is reacted with a compound represented by the general formula (22b) (where $X^{22c}$ is —$X^2$— or —$X^4$—, and the other symbols are as defined above), in the presence or absence of a base, whereby a compound represented by the general formula (22c) (where the symbols are as defined above) can be obtained. Then, the compound of the general formula (22c) is hydrolyzed under basic or acidic conditions, whereby a compound represented by the general formula (22d) (where the symbols are as defined above) can be obtained.

From the compound represented by the general formula (22d), the compound represented by the general formula [1] can be obtained in accordance with the method of Scheme 3 or 7.

(Scheme 23)

[Chemical Formula 39]

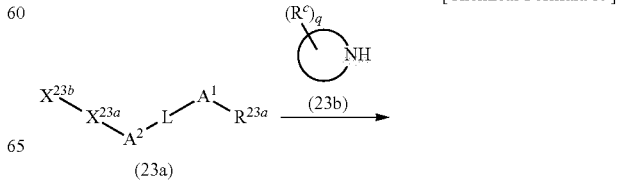

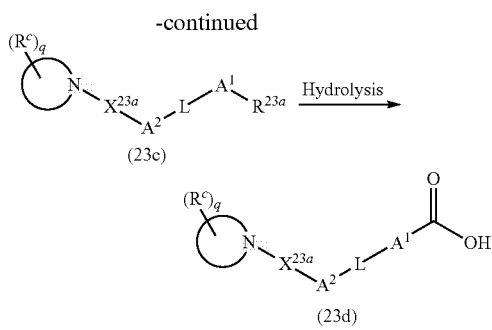

(23c)

(23d)

A compound represented by the general formula (23a) (where $X^{23a}$ is —$X^1$—$Y^2$—$X^3$— or —$X^1$—$Y^1$—$X^2$—$Y^3$—$X^3$—, $X^{23a}$ is a leaving group, $R^{23a}$ is a protected carboxy group or a cyano group, and the other symbols are as defined above), which has been obtained in accordance with the method of Scheme 12a or 12b, is reacted with a compound represented by the general formula (23b) (where the symbols are as defined above), in the presence or absence of a base, whereby a compound represented by the general formula (23c) (where the symbols are as defined above) can be obtained. Then, the compound of the general formula (23c) is hydrolyzed under basic or acidic conditions, whereby a compound represented by the general formula (23d) (where the symbols are as defined above) can be obtained.

From the compound represented by the general formula (23d), the compound represented by the general formula [1] can be obtained in accordance with the method of Scheme 3 or 7.

In the methods of synthesis shown above, the sequence of the reaction steps can be changed as needed. If an amino group, a hydroxy group, a formyl group, and a carboxy group are present in the compounds obtained in the respective reaction steps and their intermediates, the reactions can be performed, with the protective groups for them being removed for deprotection or being used in appropriately changed combinations.

Unless otherwise specified, examples of the base used in any of the above reactions are sodium carbonate, potassium carbonate, cesium carbonate, sodium hydrogen carbonate, potassium hydrogen carbonate, sodium acetate, potassium acetate, potassium hydroxide, sodium hydroxide, lithium hydroxide, sodium amide, sodium methoxide, potassium t-butoxide, sodium hydride, lithium hydride, triethylamine, diisopropylethylamine, dimethylaniline, diethylaniline, pyridine, pyrrolidine, and N-methylmorpholine.

Examples of the acid are inorganic acids such as hydrochloric acid, hydrobromic acid, sulfuric acid, nitric acid, phosphoric acid, and polyphosphoric acid, and organic acids such as p-toluenesulfonic acid, methanesulfonic acid, trifluoroacetic acid, formic acid, and acetic acid.

Examples of the condensing agent are o-(7-azabenzotriazol-1-yl)-N,N,N',N'-tetramethyluronium hexafluorophosphate, 1-(3-dimethylaminopropyl)-3-ethylcarbodiimide hydrochloride, dicyclohexylcarbodiimide, carbonyldiimidazole, 2-chloro-1-methylpyridinium iodide, 4-(4,6-dimethoxy-1,3,5-triazin-2-yl)-4-methylmorpholine chloride, o-(7-azabenzotriazol-1-yl)-N,N,N',N'-tetramethyluronium hexafluorophosphate, and benzotriazol-1-yl-oxy-tris-pyrrolidino-phosphonium hexafluorophosphate.

Examples of the activator used in employing the method conducted via an acid chloride or an acid anhydride are thionyl chloride, oxalyl chloride, phosphoryl chloride, acetic anhydride, and chloroformic esters.

Examples of the catalyst are palladium acetate, palladium chloride, bis(triphenylphosphine)palladium(II) dichloride, tetrakis(triphenylphosphine)palladium, bis(acetonitrile)dichloropalladium, bis(benzonitrile)dichloropalladium, tris(dibenzylideneacetone)dipalladium, bis(dibenzylideneacetone)palladium, 1,1'-bis(diphenylphosphino)ferrocenedichloropalladium, bis(tricyclohexylphosphine)dichloropalladium, bis(tri-o-tolylphosphine)dichloropalladium, bis(tri-t-butylphosphine)dichloropalladium, (1,3-bis(2,6-diisopropylphenyl)imidazolidene)(3-chloropyridyl)palladium(II) dichloride, palladium on carbon, palladium hydroxide, and copper iodide.

Examples of the ligand are tri-t-butylphosphine, tricyclohexylphosphine, triphenylphosphine, tritolylphosphine, tributyl phosphite, tricyclohexyl phosphite, triphenyl phosphite, 1,1'-bis(diphenylphosphino)ferrocene, 2,2'-bis(diphenylphosphino)-1,1'-binaphthyl, 2-dicyclohexylphosphino-2',6'-dimethoxybiphenyl, 2-dicyclohexylphosphino-2',4',6'-triisopropylbiphenyl, 2-(di-t-butylphosphino)-2',4',6'-triisopropylbiphenyl, and 2-(di-t-butylphosphino)biphenyl.

Examples of the oxidizing agent are inorganic and organic peroxides such as potassium permanganate, chromium oxide, potassium dichromate, hydrogen peroxide, m-chloroperbenzoic acid, urea hydrogen peroxide adduct/phthalic anhydride, t-butyl hydroperoxide, and cumene hydroperoxide, selenium dioxide, lead(IV) acetate, t-butyl hypochlorite, sodium hypochlorite, and 1,1,1-triacetoxy-1,1-dihydro-1,2-benziodoxol-3(1H)-one.

Examples of the reducing agent are hydrogenated complex compounds such as lithium aluminum hydride, sodium triacetoxyborohydride, sodium cyanoborohydride, sodium borohydride, lithium borohydride, and diisobutylaluminum hydride, boranes, sodium, and sodium amalgam.

Examples of the metal salt are zinc chloride, zirconium chloride, indium chloride, and magnesium chloride.

The solvent is not limited, if it is stable under the reaction conditions concerned, is inert, and does not impede the reaction. Examples of the solvent are polar solvents (e.g., water and alcoholic solvents such as methanol, ethanol and isopropanol), inert solvents (e.g., halogenated hydrocarbon-based solvents such as chloroform, methylene chloride, dichloroethane, and carbon tetrachloride, ether-based solvents such as diethyl ether, diisopropyl ether, tetrahydrofuran, 1,4-dioxane, and dimethoxyethane, aprotic solvents such as dimethylformamide, dimethyl sulfoxide, ethyl acetate, t-butyl acetate, acetonitrile, and propionitrile, aromatics such as benzene, toluene and anisole, or hydrocarbons such as cyclohexane), and mixtures of these solvents.

The reaction can be performed at an appropriate temperature selected from a range of from −78° C. to the boiling point of the solvent used in the reaction, at ordinary pressure or under pressurized conditions, and under microwave irradiation or the like.

Hereinbelow, the present invention will be described in further detail by examples of intermediate synthesis, Examples, and Test Examples. The compounds of the present invention are in no way limited to the compounds described in the Examples presented below.

Unless otherwise described, the support used in silica gel chromatography was Silica Gel 60N produced by KANTO CHEMICAL CO., INC., the support used in NH type silica gel chromatography was Chromatorex NH-DM1020 produced by FUJI SILYSIA CHEMICAL LTD., and the support used in reversed phase silica gel chromatography was ODS-A-AA12S50 of YMC CO., LTD. Preparative silica gel thin-layer chromatography used PLC Plate Silica Gel 60F$_{254}$ produced by Merck Ltd. Cellpure used was a product of Advanced Minerals Corporation. A phase separator used was a product of Biotage Ltd. NMR spectrum was shown by proton NMR, in which tetramethylsilane was used as an internal standard, and δ value was shown in ppm.

In LC-MS, HPLC was performed using Agilent 1100, and MS (ESI) was performed using MicroMass Platform LC. The following column, solvent and measuring conditions were used:
Column: Waters, SunFire™ C18, 2.5 μm, 4.6×50 mm Column
Solvent: $CH_3CN$ (0.10% $CF_3COOH$), $H_2O$ (0.10% $CF_3COOH$)
Measuring conditions: Gradient elution for 0 to 0.5 min (10% $CH_3CN$)→5.5 min (80% $CH_3CN$)→6.0 to 6.3 min (99% $CH_3CN$)

LC-preparative procedure used GILSON Preparative HPLC system. The column, solvent and measuring conditions used in the LC-preparative procedure were as follows:
Column: Waters, SunFire™ Prep C18, OBD™ 5.0 μm, 30×50 mm Column
Solvent: $CH_3CN$ (0.1% $CF_3COOH$), $H_2O$ (0.1% $CF_3COOH$)
Measuring conditions: Gradient elution for 0 to 2 min (10% $CH_3CN$)→11 min (80% $CH_3CN$)→13.5 min (95% $CH_3CN$)

Abbreviations used in the Examples are shown below.
(+)-CSA: (+)-10-camphorsulfonic acid
AcOEt: Ethyl acetate
AcOBu: n-Butyl acetate
APCI: Atmospheric pressure chemical ionization
aq.: Aqueous solution
Boc: t-Butoxycarbonyl
Bn: Benzyl
Bu: Butyl
DEAD: Diethyl azodicarboxylate
DIPEA: N,N-diisopropylethylamine
DMF: N,N-dimethylformamide
DMSO-$d_6$: Hexadeuterodimethyl sulfoxide
ESI: Electrospray ionization
Et: Ethyl
HATU: O-(7-azabenzotriazol-1-yl)-N,N,N',N'-tetramethyluronium hexafluorophosphate
HOBt.$H_2O$: 1-Hydroxybenzotriazole monohydrate
IPA: Isopropyl alcohol
IPE: Diisopropyl ether
LC: Liquid chromatography
LDA: Lithium diisopropylamide
Me: Methyl
NMP: 1-Methyl-2-pyrrolidone
PEPPSI: (1,3-bis(2,6-diisopropylphenyl)imidazolidene)(3-chloropyridyl)palladium(II) dichloride
$PdCl_2(dppf).CH_2Cl_2$: 1,1'-bis(diphenylphosphino)ferrocenepalladium(II) chloride dichloromethane complex
$PdCl_2(PPh_3)_2$: Bis(triphenylphosphine)palladium(II) dichloride
PPTS: Pyridine 4-methylbenzenesulfonate
$(p-Tol)_3P$: Tri(4-methylphenyl)phosphine
p-TsOH.$H_2O$: p-Toluenesulfonic acid monohydrate
TBAF: Tetra-n-butylammonium fluoride
TEA: triethylamine
TFA: Trifluoroacetic acid
THF: Tetrahydrofuran
THP: Tetrahydropyranyl
TMS: Trimethylsilyl
TIPS: Triisopropylsilyl
TsCl: 4-Methylbenzenesulfonyl chloride
WSC.HCl: 1-Ethyl-3-(3-dimethylaminopropyl)carbodiimide hydrochloride
s: Singlet
br.s.: Broad singlet
d: Doublet
dd: Double doublet
dt: Double triplet
m: Multiplet
t: Triplet
td: Triple doublet
tt: Triple triplet
q: Quartet
quin: Quintet First, a description will be presented of methods for synthesizing shared intermediates utilized when synthesizing the compounds of the present invention. Schemes for the synthesis of the intermediates are as shown below.

[Chemical Formula 40]

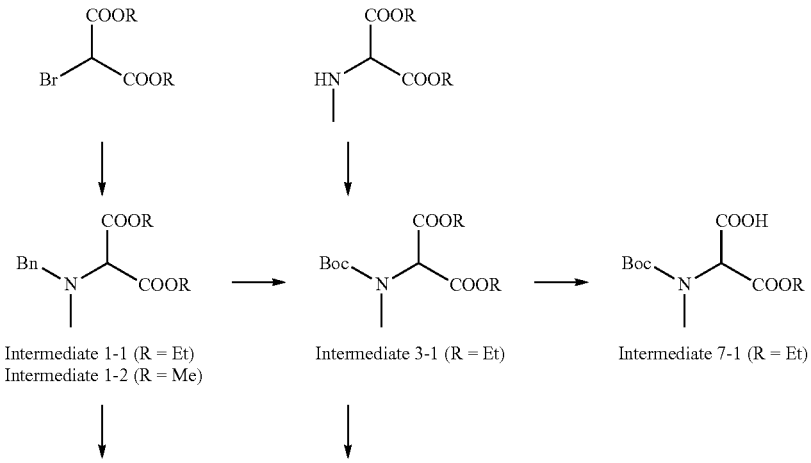

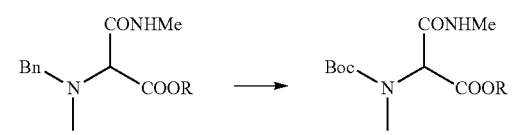
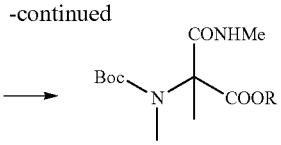
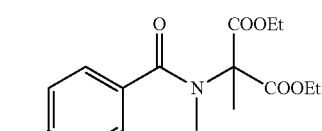

Intermediate 2-2 (R = Me)    Intermediate 4-2 (R = Me)    Intermediate 8-2 (R = Me)    Intermediate 16

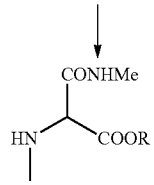
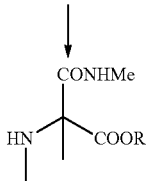
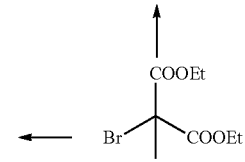

Intermediate 5-2 (R = Me, hydrochloride)    Intermediate 9-1 (R = Et)
Intermediate 9-2 (R = Me, hydrochloride)

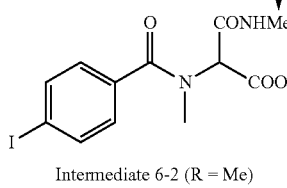
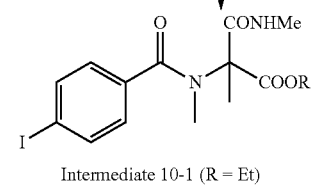
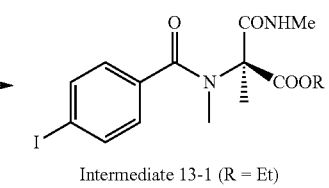

Intermediate 6-2 (R = Me)    Intermediate 10-1 (R = Et)    Intermediate 13-1 (R = Et)
Intermediate 10-2 (R = Me)

Chiral resolution

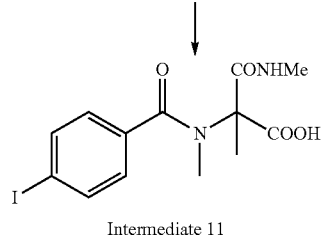
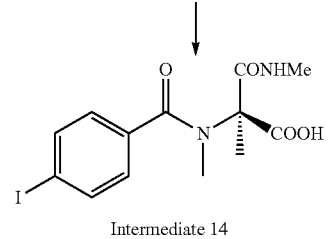

Intermediate 11    Intermediate 14

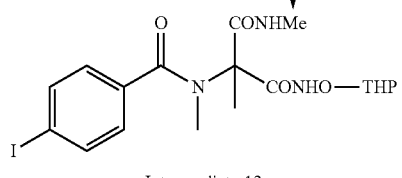
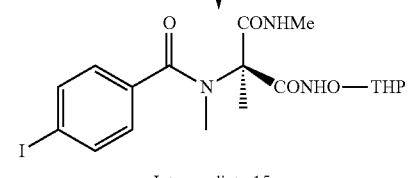

Intermediate 12    Intermediate 15

SYNTHESIS OF INTERMEDIATE 1-1

Diethyl [benzyl(methyl)amino]propanedioate

[Chemical Formula 41]

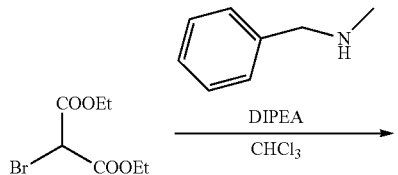

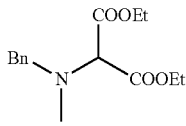

Using diethyl bromopropanedioate (8.5 g), the same procedure as in the method described in the literature (Tetrahedron, 2005, Vol. 61, pp. 8722-8739) was performed to obtain diethyl [benzyl(methyl)amino]propanedioate (Intermediate 1-1, colorless oil) (6.7 g, 67%).

MS (ESI): 280 (M+H)$^+$ $^1$H NMR (600 MHz, CHLOROFORM-d) δ ppm 1.25-1.35 (6 H, m), 2.46 (3 H, s), 3.82 (2 H, s), 4.16 (1 H, s), 4.21-4.31 (4 H, m), 7.22-7.41 (5 H, m)

SYNTHESIS OF INTERMEDIATE 1-2

Dimethyl [benzyl(methyl)amino]propanedioate

[Chemical Formula 42]

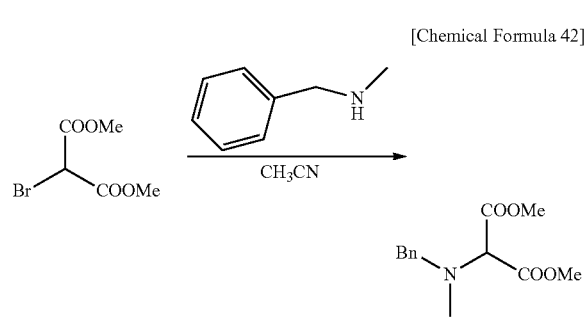

To an acetonitrile (60 mL) solution of N-methylbenzylamine (15 mL), an acetonitrile (10 mL) solution of dimethyl bromomalonate (12 g) was added dropwise at room temperature, and the mixture was stirred for 6 hours at room temperature. Toluene (0.20 L) was added, insolubles were filtered off, and the filtrate was concentrated under reduced pressure. To the residue, toluene (0.10 L) and OH type silica gel (6.0 g) were added, and the mixture was stirred for 20 minutes at room temperature and then filtered. The filtrate was concentrated under reduced pressure to obtain dimethyl [benzyl (methyl)amino]propanedioate (pale yellow oil) (14 g, 96%).

$^1$H NMR (400 MHz, CHLOROFORM-d) δ ppm 2.46 (3 H, s), 3.60-4.00 (2 H, m), 3.79 (6 H, br. s.), 4.20 (1 H, s), 7.20-7.50 (5 H, m)

SYNTHESIS OF INTERMEDIATE 2-2

({[1-Methoxy-3-(methylamino]-1,3-dioxopropan-2-yl](methyl)amino}methyl)benzene

[Chemical Formula 43]

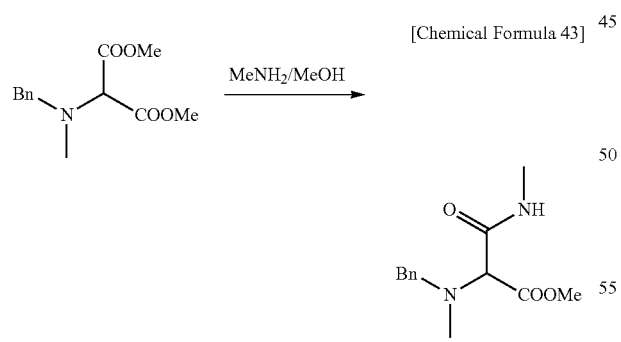

To a methanol (39 mL) solution of dimethyl [benzyl(methyl)amino]propanedioate (Intermediate 1-2, 13 g), a 9 mol/L-methylamine-methanol solution (14 mL) was added at room temperature, followed by stirring the mixture for 26 hours at room temperature. The reaction mixture was concentrated under reduced pressure, whereafter ethyl acetate and water were added to the resulting residue to isolate the organic layer. The extract was washed with brine, and dried over anhydrous sodium sulfate. Then, the desiccant was filtered out, and the solvent was distilled off under reduced pressure. The resulting residue was purified by OH type silica gel column chromatography (hexane/ethyl acetate=50/50→chloroform/acetone=95/5) to obtain ({[1-methoxy-3-(methylamino)-1,3-dioxopropan-2-yl](methyl) amino}methyl)benzene (pale yellow oil) (7.1 g, 56%).

$^1$H NMR (400 MHz, CHLOROFORM-d) δ ppm 2.37 (3 H, s), 2.87 (3 H, d, J=5.1 Hz), 3.60-3.85 (2 H, m), 3.81 (3 H, s), 3.98 (1 H, s), 6.90-7.00 (1 H, m), 7.20-7.40 (5 H, m)

SYNTHESIS (1) OF INTERMEDIATE 3-1

Diethyl [(t-butoxycarbonyl)(methyl)amino]propanedioate

[Chemical Formula 44]

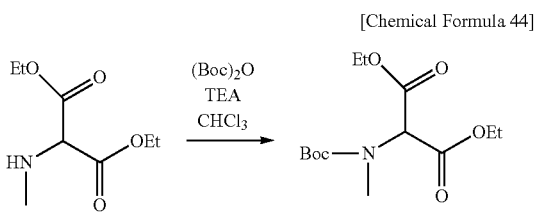 [SMILES: CCOC(=O)C(NC)C(=O)OCC ; CCOC(=O)C(C(=O)OCC)N(C)C(=O)OC(C)(C)C]

Diethyl (methylamino)propanedioate was obtained by the same method as the method of synthesis described in the literature (Tetrahedron, 2005, Vol. 61, pp. 8722-8739). To a chloroform (1.7 L) solution of this diethyl (methylamino) propanedioate (0.17 kg), TEA (0.25 L) and di-tert-butyl dicarbonate (0.18 kg) were added. After the mixture was stirred for 14 hours at room temperature, the reaction mixture was concentrated. The resulting residue was purified by OH type silica gel column chromatography (gradient elution with hexane/ethyl acetate=97/3→80/20) to obtain diethyl [(t-butoxycarbonyl)(methyl)amino]propanedioate (Intermediate 3-1, yellow oil) (0.21 kg, 82%).

MS (ESI): 312 (M+Na)$^+$ $^1$H NMR (600 MHz, CHLOROFORM-d) δ ppm 1.27-1.34 (6 H, m), [1.44], 1.48 (9 H, s), 2.95 (3 H, s), 4.23-4.31 (4 H, m), [5.11], 5.51 (1 H, s)

SYNTHESIS (2) OF INTERMEDIATE 3-1

Diethyl [(t-butoxycarbonyl)(methyl)amino]propanedioate

[Chemical Formula 45]

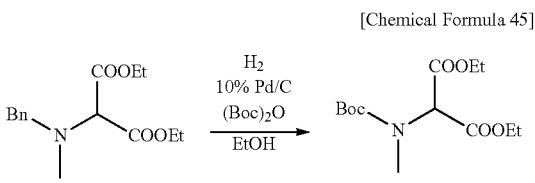 [SMILES: "EtOH" ; CCOC(=O)C(C(=O)OCC)N(C)Cc1ccccc1 ; CCOC(=O)C(C(=O)OCC)N(C)C(=O)OC(C)(C)C]

10% Pd—C (0.16 kg) and di-t-butyl dicarbonate (0.42 kg) were added to an ethanol (5.3 L) solution of diethyl [benzyl (methyl)amino]propanedioate (Intermediate 1-1, 0.55 kg), and the mixture was stirred in a hydrogen atmosphere for 24 hours at room temperature. Then, the reaction mixture was filtered through Celite, and the solvent was distilled off under reduced pressure. 10% Pd—C (71 g) was added to an ethanol (3.5 L) solution of the resulting residue, and the mixture was stirred again in a hydrogen atmosphere for 6 hours at room temperature. Then, the reaction mixture was filtered through Celite, and the solvent was distilled off under reduced pressure. The resulting residue was purified by OH type silica gel column chromatography (gradient elution with hexane/ethyl acetate=98/2→60/40) to obtain diethyl [(t-butoxycarbonyl)(methyl)amino]propanedioate (Intermediate 3-1, colorless oil) (0.42 kg, 74%).

MS (ESI): 312 (M+Na)$^+$, 288 (M−H)$^−$ $^1$H NMR (600 MHz, CHLOROFORM-d) δ ppm 1.27-1.34 (6 H, m), [1.44], 1.48 (9 H, s), 2.95 (3 H, s), 4.19-4.32 (4 H, m), [5.11], 5.51 (1 H, s)

SYNTHESIS OF INTERMEDIATE 4-2

N$^2$-(t-butoxycarbonyl)-N,N$^2$,O-trimethyl-3-oxoserinamide

[Chemical Formula 46]

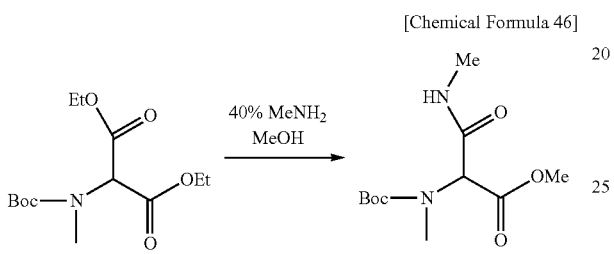

A 40% methylamine-methanol solution (67 mL) was added to a methanol (2.1 L) solution of diethyl [(t-butoxycarbonyl)(methyl)amino]propanedioate (Intermediate 3-1, 0.21 kg), and the mixture was stirred for 19 hours at room temperature. Further, a 40% methylamine-methanol solution (23 mL) was added, and the mixture was stirred for 4 days at the same temperature. Then, ethyl acetate (0.30 L) was added, and citric acid monohydrate (81 g) was slowly added under ice cooling, followed by stirring the mixture for 30 minutes under ice cooling. The precipitated solid was filtered, and the solvent was distilled off under reduced pressure. The resulting residue was purified by OH type silica gel column chromatography (gradient elution with hexane/ethyl acetate=75/25→15/85) to obtain N$^2$-(t-butoxycarbonyl)-N,N$^2$,O-trimethyl-3-oxoserinamide (Intermediate 4-2, yellow oil) (63 g, 34%).

MS (ESI): 283 (M+Na)$^+$ $^1$H NMR (600 MHz, CHLOROFORM-d) δ ppm 1.44 (9 H, br. s.), 2.86 (3 H, br. s.), 2.99 (3 H, br. s.), 3.80 (3 H, s), [4.64], 5.11 (1 H, br. s.), [6.85], 7.13 (1 H, br. s.)

SYNTHESIS (1) OF INTERMEDIATE 5-2

N,N$^2$,O-trimethyl-3-oxoserinamide hydrochloride

[Chemical Formula 47]

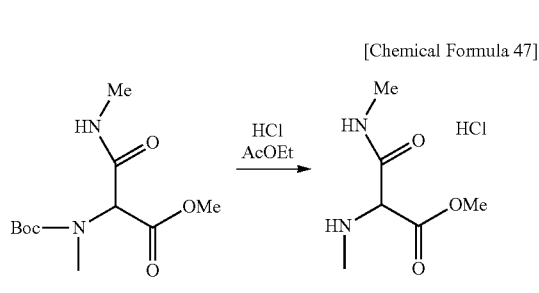 [SMILES: CNC(=O)C(C(=O)OC)N(C)C(=O)OC(C)(C)C ; CNC(=O)C(NC)C(=O)OC ; Cl]

A 4.0 mol/L-hydrochloric acid-ethyl acetate solution (0.13 L) was added to an ethyl acetate (0.19 L) solution of N$^2$-(t-butoxycarbonyl)-N,N$^2$,O-trimethyl-3-oxoserinamide (Intermediate 4-2, 62 g), and the mixture was stirred for 24 hours at room temperature. The precipitated solid was filtered off, and washed with ethyl acetate to obtain N,N$^2$,O-trimethyl-3-oxoserinamide hydrochloride (Intermediate 5-2, white solid) (39 g, 84%).

MS (ESI): 161 (M+H)$^+$ $^1$H NMR (600 MHz, DMSO-d$_6$) δ ppm 2.71 (3 H, d, J=4.58 Hz), 3.34 (3 H, s), 3.79 (3 H, s), 4.81 (1 H, s), 8.97 (1 H, br. s.), 9.69 (1 H, br. s.)

SYNTHESIS (2) OF INTERMEDIATE 5-2

N,N$^2$,O-trimethyl-3-oxoserinamide hydrochloride

[Chemical Formula 48]

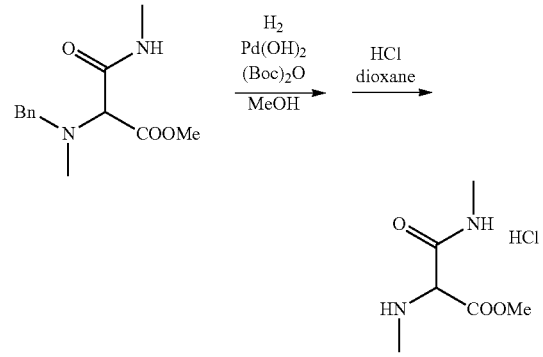

Di-t-butyl dicarbonate (19 mL) and 20% palladium hydroxide-carbon (1.4 g) were added to a methanol (50 mL) solution of ({[1-methoxy-3-(methylamino)-1,3-dioxopropan-2-yl](methyl)amino}methyl)benzene (Intermediate 2-2, 7.1 g), and the mixture was stirred in a hydrogen atmosphere for 3.5 hours at room temperature. The reaction mixture was filtered through Celite, and the solvent was concentrated under reduced pressure. To a THF (20 mL) solution of the resulting residue, a 5.7 mol/L-hydrochloric acid-1,4-dioxane solution (50 mL) was added dropwise under water cooling, and the mixture was stirred for 1 hour and 15 minutes at room temperature. IPE (0.15 L) was added, and the mixture was stirred for 15 minutes under ice cooling. The precipitated solid was filtered off, and washed with an ethyl acetate-IPE (1:2) solvent mixture to obtain N,N$^2$,O-trimethyl-3-oxoserinamide hydrochloride (pale orange solid) (4.9 g, 88%).

$^1$H NMR (400 MHz, D$_2$O) δ ppm 2.63 (3 H, s), 2.70 (3 H, s), 3.75 (3 H, s)

SYNTHESIS OF INTERMEDIATE 6-2

1-Iodo-4-{[1-methoxy-3-(methylamino)-1,3-dioxopropan-2-yl](methyl)carbamoyl}benzene

[Chemical Formula 49]

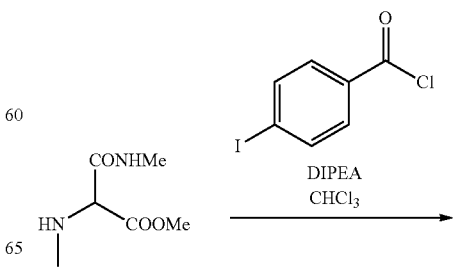

-continued

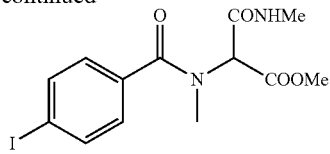

DIPEA (27 mL) was added to a chloroform (0.20 L) suspension of 4-iodobenzoyl chloride (13 g) and N,N²,O-trimethyl-3-oxoserinamide hydrochloride (Intermediate 5-2, 10 g) under ice cooling, and the mixture was stirred for 4 hours at room temperature, whereafter the reaction mixture was concentrated. The resulting residue was purified by OH type silica gel column chromatography (gradient elution with hexane/ethyl acetate=70/30→0/100) to obtain 1-iodo-4-{[1-methoxy-3-(methylamino)-1,3-dioxopropan-2-yl](methyl)carbamoyl}benzene (Intermediate 6-2, white solid) (14 g, 68%).

MS (ESI): 391 (M+H)⁺, 389 (M−H)⁻

¹H NMR (200 MHz, CHLOROFORM-d) δ ppm 2.88 (3 H, d, J=4.8 Hz), 3.11 (3 H, s), 3.84 (3 H, s), 5.45 (1 H, br. s), 7.16-7.34 (3 H, m), 7.71-7.86 (2 H, m)

SYNTHESIS OF INTERMEDIATE 7-1

N-(t-butoxycarbonyl)-O-ethyl-N-methyl-3-oxoserine

[Chemical Formula 50]

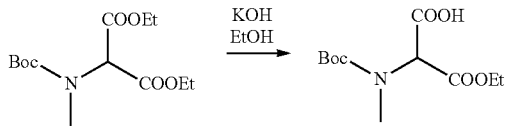

An ethanol solution (4.0 mL) of potassium hydroxide (0.19 g) prepared under ice cooling was added to an ethanol (2.0 mL) solution of diethyl [(t-butoxycarbonyl)(methyl)amino]propanedioate (Intermediate 3-1, 1.0 g), and the mixture was stirred for 23 hours at room temperature. The reaction mixture was concentrated under reduced pressure, and a 1.0 mol/L-sodium hydrogen carbonate aqueous solution was added, followed by extracting the mixture with ethyl acetate. The aqueous layer was cooled with iced water, and potassium hydrogen sulfate was added to adjust it to pH 2, followed by extracting the mixture with chloroform. The extract was dried over anhydrous sodium sulfate, and the desiccant was filtered out. Then, the solvent was distilled off under reduced pressure to obtain N-(t-butoxycarbonyl)-O-ethyl-N-methyl-3-oxoserine (Intermediate 7-1, light yellow oil) (0.26 g, 29%).

MS (ESI): 284 (M+Na)⁺, 260 (M−H)⁻

¹H NMR (600 MHz, DMSO-d₆) δ ppm 1.18-1.23 (3 H, m), [1.35], 1.42 (9 H, s), [2.81], 2.84 (3 H, s), 4.14-4.20 (2 H, m), [5.01], 5.23 (1 H, s)

SYNTHESIS OF INTERMEDIATE 8-2

N²-(t-butoxycarbonyl)-N,N²,O,2-tetramethyl-3-oxoserinamide

[Chemical Formula 51]

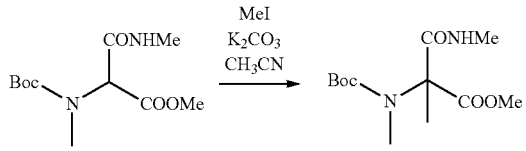

Iodomethane (1.4 mL) and potassium carbonate (1.6 g) were added to an acetonitrile (5.0 mL) solution of N²-(t-butoxycarbonyl)-N,N²,O-trimethyl-3-oxoserinamide (Intermediate 4-2, 2.0 g), and the mixture was stirred for 20 hours at room temperature under closed conditions. Iodomethane (2.8 mL) was added, and the mixture was stirred for 3 days at room temperature under closed conditions. Further, iodomethane (2.8 mL) was added, and the mixture was stirred for 1 day at room temperature under closed conditions, and then stirred for 9 hours at 50° C. After the reaction mixture was stirred for 14 hours at room temperature, potassium carbonate was filtered out. Then, the system was washed with ethyl acetate, and the reaction mixture was concentrated. The resulting residue was purified by OH type silica gel column chromatography (gradient elution with hexane/ethyl acetate=70/30→100/0) to obtain N²-(t-butoxycarbonyl)-N,N²,O,2-tetramethyl-3-oxoserinamide (Intermediate 8-2, yellow oil) (1.5 g, 78%).

MS (ESI): 275 (M+H)⁺, 297 (M+Na)⁺

¹H NMR (200 MHz, CHLOROFORM-d) δ ppm 1.40 (9 H, s), 1.64 (3 H, s), 2.85 (3 H, d, J=4.8 Hz), 3.04 (3 H, s), 3.74 (3 H, s) 8.02 (1 H, br. s.)

SYNTHESIS OF INTERMEDIATE 9-1

O-ethyl-N,N²,2-trimethyl-3-oxoserinamide

[Chemical Formula 52]

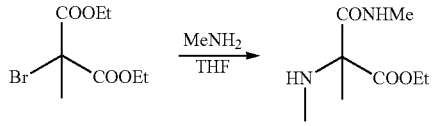

A 2.0 mol/L-methylamine-THF solution (21 mL) was added to a THF (9.0 mL) solution of diethyl bromo(methyl)propanedioate (3.0 g) under ice cooling, and the mixture was stirred for 16 hours at room temperature under closed conditions. The precipitated solid was filtered out, and the filtrate was concentrated. The resulting residue was purified by OH type silica gel column chromatography (gradient elution with chloroform/methanol=100/0→93/7) to obtain O-ethyl-N,N², 2-trimethyl-3-oxoserinamide (Intermediate 9-1, yellow oil) (2.0 g, 89%).

MS (ESI): 189 (M+H)⁺

¹H NMR (600 MHz, CHLOROFORM-d) δ ppm 1.27-1.32 (3 H, m), 1.51 (3 H, s), 2.30 (3 H, s), 2.82 (3 H, d, J=5.0 Hz), 4.13-4.33 (2 H, m), 7.17-7.25 (1 H, m)

SYNTHESIS OF INTERMEDIATE 9-2

N,N²,O,2-tetramethyl-3-oxoserinamide hydrochloride

[Chemical Formula 53]

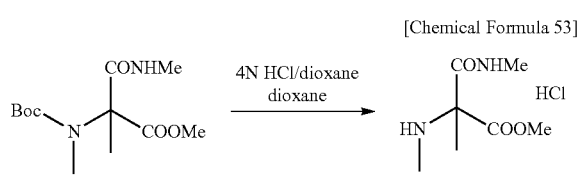

A 4.0 mol/L-hydrochloric acid-dioxane solution (5.0 mL) was added to a dioxane (5.0 mL) solution of N²-(t-butoxycarbonyl)-N,N²,O,2-tetramethyl-3-oxoserinamide (Intermediate 8-2, 1.5 g) under ice cooling, and the mixture was stirred for 18 hours at room temperature. Then, the reaction mixture was concentrated to obtain N,N²,O,2-tetramethyl-3-oxoserinamide hydrochloride (Intermediate 9-2, white solid) (1.1 g, 98%).

MS (ESI): 175 (M+H)⁺

¹H NMR (200 MHz, CHLOROFORM-d) δ ppm 1.75 (3 H, s), 2.46 (3 H, s), 2.68 (3 H, d, J=4.4 Hz), 3.80 (3 H, s) 8.60-8.67 (1 H, m), 9.85 (1 H, br. s.)

SYNTHESIS OF INTERMEDIATE 10-1

1-{[1-ethoxy-2-methyl-3-(methylamino)-1,3-dioxopropan-2-yl](methyl)carbamoyl}-4-iodobenzene

[Chemical Formula 54]

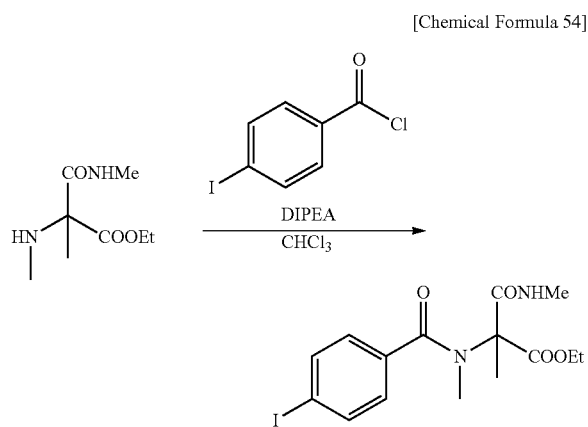

DIPEA (0.34 mL) and 4-iodobenzoyl chloride (0.13 g) were added to a chloroform (2.3 mL) solution of O-ethyl-N,N²,2-trimethyl-3-oxoserinamide (Intermediate 9-1, 0.25 g) under ice cooling, and the mixture was stirred for 40 minutes at room temperature, whereafter the reaction mixture was concentrated. The resulting residue was purified by NH type silica gel column chromatography (gradient elution with hexane/ethyl acetate=70/30→35/65) to obtain 1-{[1-ethoxy-2-methyl-3-(methylamino)-1,3-dioxopropan-2-yl](methyl)carbamoyl}-4-iodobenzene (Intermediate 10-1, yellow oil) (0.20 g, 72%).

MS (ESI): 419 (M+H)⁺, 417 (M+H)⁻

¹H NMR (600 MHz, CHLOROFORM-d) δ ppm 1.21-1.28 (3 H, m), 1.75 (3 H, s), 2.88 (3 H, d, J=4.5 Hz), 3.13 (3 H, s), 4.13-4.29 (2 H, m), 7.18-7.24 (2 H, m), 7.72-7.81 (2 H, m), 8.09-8.23 (1 H, m)

SYNTHESIS OF INTERMEDIATE 10-2

1-{[1-Methoxy-2-methyl-3-(methylamino)-1,3-dioxopropan-2-yl](methyl)carbamoyl}-4-iodobenzene

[Chemical Formula 55]

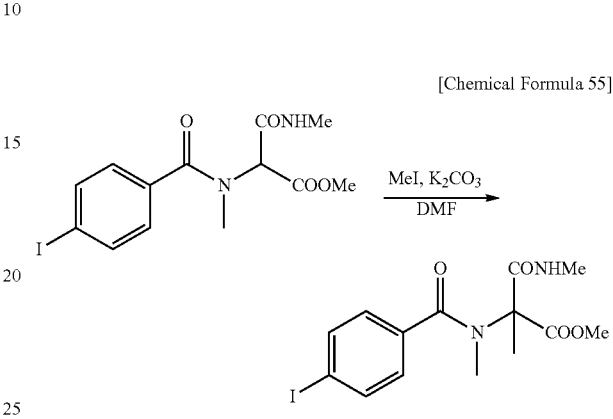

Iodomethane (1.7 mL) was added to a DMF (25 mL) solution of 1-iodo-4-{[1-methoxy-3-(methylamino)-1,3-dioxopropan-2-yl](methyl)carbamoyl}benzene (Intermediate 6-2, 2.6 g). Potassium carbonate (1.4 g) was added under water cooling, and the mixture was stirred for 1.5 hours at room temperature. Iodomethane (0.40 mL) and potassium carbonate (0.46 g) were added, and the mixture was stirred for 1 hour at room temperature. Ethyl acetate was added, and the insolubles were separated by filtration. Water was added to the filtrate, and the mixture was adjusted to pH 5 using 1 mol/L-hydrochloric acid so that the organic layer was isolated. The extract was washed sequentially with water and brine, and dried over anhydrous magnesium sulfate. Then, the desiccant was filtered out, and the solvent was distilled off under reduced pressure. The resulting residue was purified by OH type silica gel column chromatography (gradient elution with chloroform/acetone=100/0→80/20), and was further purified by OH type silica gel column chromatography (gradient elution with chloroform/acetone=196/4→175/25) to obtain 1-{[1-methoxy-2-methyl-3-(methylamino)-1,3-dioxopropan-2-yl](methyl)carbamolyl}-4-iodobenzene (colorless oil) (2.3 g, 82%).

¹H NMR (400 MHz, CHLOROFORM-d) δ ppm 1.75 (3 H, s), 2.88 (3 H, d, J=4.9 Hz), 3.13 (3 H, s), 3.75 (3 H, s), 7.21-7.25 (2 H, m), 7.74-7.80 (2 H, m), 8.09-8.19 (1 H, m)

SYNTHESIS OF INTERMEDIATE 11

1-{[2-carboxy-1-(methylamino)-1-oxopropan-2-yl](methyl)carbamoyl}-4-iodobenzene

[Chemical Formula 56]

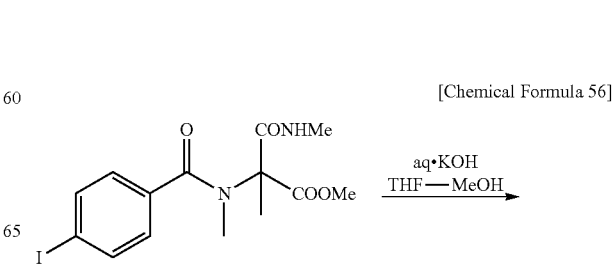

H, m), 7.18-7.31 (2 H, m), [6.97], 7.61 (1 H, br. s.) 7.72-7.83 (2 H, m), [10.04], 10.46 (1 H, s)

ISOLATION OF INTERMEDIATE 13-1

1-{[(2S)-1-ethoxy-2-methyl-3-(methylamino)-1,3-dioxopropan-2-yl](methyl)carbamolyl}-4-iodobenzene

[Chemical Formula 58]

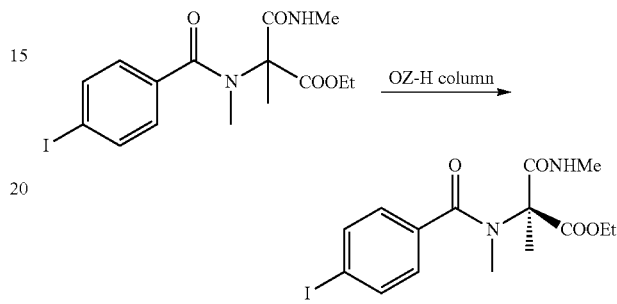

1-{[1-ethoxy-2-methyl-3-(methylamino)-1,3-dioxopropan-2-yl](methyl)carbamolyl}-4-iodobenzene (Intermediate 10-1, 0.26 kg) was isolated and purified by supercritical fluid chromatography (SFC). Purification was performed under the following conditions: (Isolation conditions: column: CHIRALCEL OZ-H, column size: 3 cm I.D.×25 cm L, mobile phase: $CO_2$/ethanol/acetonitrile=80/16/4 <v/v/v>, flow velocity: 85 mL/min, column temperature: 25° C., detection wavelength: 240 nm). As a result, 1-{[(2S)-1-ethoxy-2-methyl-3-(methylamino)-1,3-dioxopropan-2-yl](methyl) carbamolyl}-4-iodobenzene (Intermediate 13-1, light yellow oil) was obtained (0.12 kg).

$[\alpha]_D$; −37.4 (C:0.10, chloroform)

SYNTHESIS OF INTERMEDIATE 14

1-{[(2S)-2-carboxy-1-(methylamino)-1-oxopropan-2-yl](methyl)carbamolyl}-4-iodobenzene

[Chemical Formula 59]

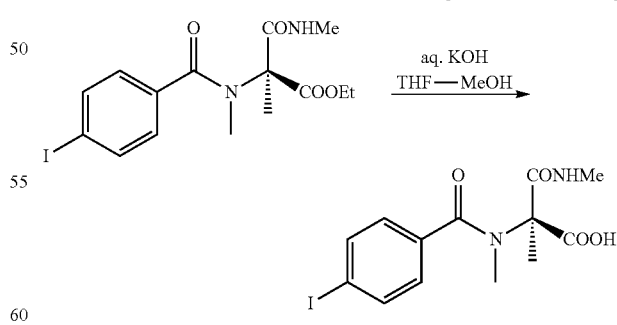

A solution of potassium hydroxide (15 g) in water (54 mL) was added dropwise to a THF (72 mL)-methanol (36 mL) solution of 1-{[(2S)-1-ethoxy-2-methyl-3-(methylamino)-1,3-dioxopropan-2-yl](methyl)carbamoyl}-4-iodobenzene (Intermediate 13-1, 36 g) at room temperature, and the mixture was stirred for 30 minutes at room temperature. The

---

-continued

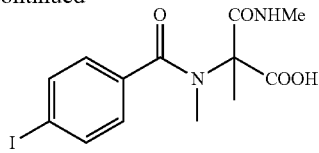

A 1.7 mol/L-potassium hydroxide aqueous solution (0.55 mL) was added to a THF (1.0 mL)-MeOH (1.0 mL) solution of 1-{[1-methoxy-2-methyl-3-(methylamino)-1,3-dioxopropan-2-yl](methyl)carbamoyl}-4-iodobenzene (Intermediate 10-2, 0.12 g), and the mixture was stirred for 3 hours at room temperature. The reaction mixture was adjusted to pH 5 with a 10% aqueous solution of citric acid, and extracted with a chloroform-methanol mixture. The organic layer was washed with brine, and dried over anhydrous sodium sulfate. The desiccant was filtered out, and then the solvent was distilled off under reduced pressure to obtain 1-{[2-carboxy-1-(methylamino)-1-oxopropan-2-yl](methyl)carbamoyl}-4-iodobenzene (Intermediate 11, orange solid) (91 mg, 80%).

MS (ESI): 413 (M+Na)$^+$ $^1$H NMR (200 MHz, CHLOROFORM-d) δ ppm 1.80 (3 H, s), 2.84 (3 H, d, J=4.8 Hz) 3.22 (3 H, s), 7.12-7.37 (3 H, m), 7.69-7.82 (2 H, m)

SYNTHESIS OF INTERMEDIATE 12

2-[(4-Iodobenzoyl)(methyl)amino]-N,2-dimethyl-N'-(tetrahydro-2H-pyran-2-yloxy)propanediamide

[Chemical Formula 57]

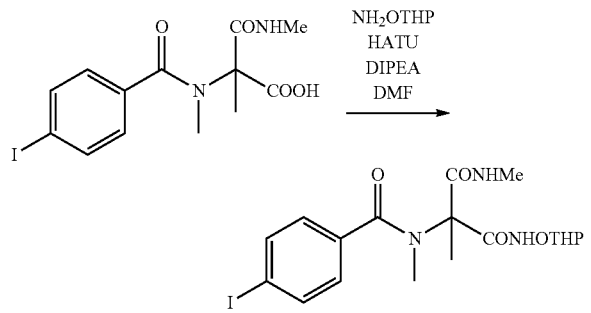

DIPEA (0.11 mL) and O-(tetrahydro-2H-pyran-2-yl)hydroxylamine (24 mg) were added to a DMF (5.0 mL) solution of 1-{[2-carboxy-1-(methylamino)-1-oxopropan-2-yl](methyl)carbamoyl}-4-iodobenzene (Intermediate 11, 81 mg) and HATU (120 mg) under ice cooling, and the mixture was stirred for 2 hours at room temperature. Water was added, and the mixture was extracted with chloroform. Then, the organic layer was washed with brine, and dried over magnesium sulfate. The desiccant was filtered out, and then the solvent was distilled off under reduced pressure. The resulting residue was purified by NH type silica gel column chromatography (gradient elution with chloroform/methanol=100/0→95/5) to obtain 2-[(4-iodobenzoyl)(methyl)amino]-N,2-dimethyl-N'-(tetrahydro-2H-pyran-2-yloxy)propanediamide (Intermediate 12, light yellow oil) (59 mg, 57%).

MS (ESI): 512 (M+Na)$^+$, 488 (M−H)$^−$ $^1$H NMR (600 MHz, CHLOROFORM-d) δ ppm 1.50-1.99 (6 H, m), [1.80], 1.81 (3 H, s), 2.76-2.92 (3 H, m), [3.14], 3.17 (3 H, s), 3.51-3.70 (1 H, m), 3.80-4.06 (1 H, m), 4.89-5.03 (1 reaction mixture was added dropwise to a mixture of water (0.36 L) and 12 mol/L of hydrochloric acid (36 mL) at room temperature, and the mixture was stirred for 30 minutes under ice cooling. The precipitate was filtered off, and washed with ice-cooled water. A suspension of the resulting solids in ethyl acetate (75 mL) and water (25 mL) was stirred for 30 minutes, then separated by filtration, and washed with ethyl acetate to obtain 1-{[(2S)-2-carboxy-1-(methylamino)-1-oxopropan-2-yl](methyl)carbamoyl}-4-iodobenzene (Intermediate 14, white solid) (21 g, 62%).

MS (ESI): 413 (M+Na)$^+$, 389 (M−H)$^−$ $^1$H NMR (400 MHz, CHLOROFORM-d) δ ppm 1.82 (3 H, s), 2.87 (3 H, d, J=4.9 Hz), 3.26 (3 H, s), 6.70-6.85 (1 H, m), 7.22-7.26 (2 H, m), 7.76-7.82 (2 H, m)

SYNTHESIS OF INTERMEDIATE 15

(2S)-2-[(4-Iodobenzoyl)(methyl)amino]-N,2-dimethyl-N'-(tetrahydro-2H-pyran-2-yloxy)propanediamide

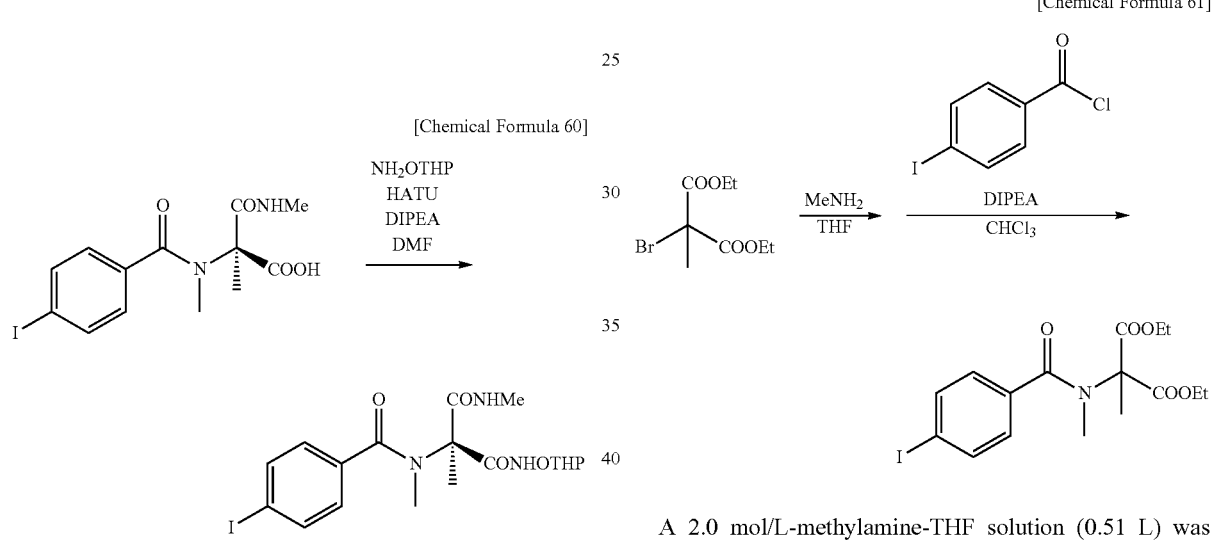

[Chemical Formula 60]

DIPEA (5.3 mL) was added to a DMF (16 mL) solution of 1-{[(2S)-2-carboxy-1-(methylamino)-1-oxopropan-2-yl](methyl)carbamoyl}-4-iodobenzene (Intermediate 14, 4.0 g) and O-(tetrahydropyran-2-yl)hydroxylamine (1.6 g), and HATU (5.9 g) was added under water cooling. The mixture was stirred for 2 hours under ice cooling, and then stirred for 1 hour at room temperature. Water and ethyl acetate were sequentially added, and the organic layer was isolated. The extract was washed sequentially with water and brine, and dried over anhydrous sodium sulfate. OH type silica gel (4.0 g) was added, and the mixture was filtered for 10 minutes at room temperature. Then, the silica gel was filtered out, and the solvent was distilled off under reduced pressure. A mixed solvent (IPE:ethyl acetate=10:1) was added to the resulting residue, and the supernatant was removed. This procedure was repeated twice, and then a solvent mixture of ethyl acetate (6.0 mL) and IPA (6.0 mL) was added to the resulting residue. The solids were collected by filtration to obtain (2S)-2-[(4-iodobenzoyl)(methyl)amino]-N,2-dimethyl-N'-(tetrahydro-2H-pyran-2-yloxy)propanediamide (Intermediate 15, white solid) (1.3 g, 26%). Moreover, the residue obtained from the filtrate was purified by OH type silica gel column chromatography (ethyl acetate/hexane=50/50→gradient elution with chloroform/acetone=100/0→85/15) to obtain (2S)-2-[(4-iodobenzoyl)(methyl)amino]-N,2-dimethyl-N'-(tetrahydro-2H-pyran-2-yloxy)propanediamide (Intermediate 15, white solid) (1.7 g, 34%).

MS (ESI): 512 (M+Na)$^+$, 488 (M−H)$^−$ $^1$H NMR (400 MHz, CHLOROFORM-d) δ ppm 1.50-2.00 (6 H, m), [1.83], 1.84 (3 H, s), 2.85-2.90 (3 H, m), [3.18], 3.20 (3 H, s), 3.55-3.72 (1 H, m), 3.85-4.10 (1 H, m), 4.95-5.05 (1 H, m), [7.01], 7.66 (1 H, br. s.), 7.25-7.32 (2 H, m), 7.81 (2 H, d, J=8.3 Hz), [10.10], 10.52 (1 H, s)

SYNTHESIS OF INTERMEDIATE 16

Diethyl [(4-iodobenzoyl)(methyl)amino](methyl)propanedioate

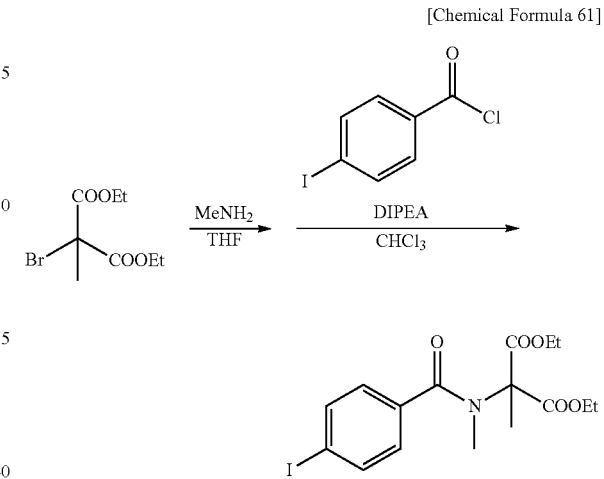

[Chemical Formula 61]

A 2.0 mol/L-methylamine-THF solution (0.51 L) was added to a THF (0.23 L) solution of diethyl bromo(methyl)propanedioate (81 g) under ice cooling, and the mixture was stirred for 16 hours at room temperature under closed conditions. The precipitated solid was filtered out, and the filtrate was concentrated. The resulting residue was purified by OH type silica gel column chromatography (gradient elution with chloroform/methanol=100/0→92/8) to obtain a yellow oil (38 g). DIPEA (86 mL) and 4-iodobenzoyl chloride (53 g) were added to a chloroform (0.53 L) solution of the yellow oil (38 g) under ice cooling, and the mixture was stirred for 1 hour at room temperature, whereafter the reaction mixture was concentrated. The resulting residue was purified by NH type silica gel column chromatography (gradient elution with hexane/ethyl acetate=30/70→0/100). Upon addition of IPE, the precipitated solid was collected by filtration, and purified by OH type silica gel column chromatography (gradient elution with chloroform/methanol=100/0→95/5) to obtain diethyl [(4-iodobenzoyl)(methyl)amino]methyl)propanedioate (Intermediate 16-1, white solid) (3.3 g, yield upon the 2 steps: 1.1%).

$^1$H NMR (600 MHz, CHLOROFORM-d) δ ppm 1.30 (6 H, t, J=7.0 Hz), 1.81 (3 H, s), 2.93 (3 H, s), 4.17-4.36 (4 H, m), 7.20-7.28 (2 H, m), 7.71-7.81 (2 H, m)

Next, the process for preparing the compound of the present invention will be described in detail with reference to Examples.

EXAMPLE 1

2-[(Biphenyl-4-ylcarbonyl)(methyl)amino]-N-hydroxy-N'-methylpropanediamide (Compound 1)

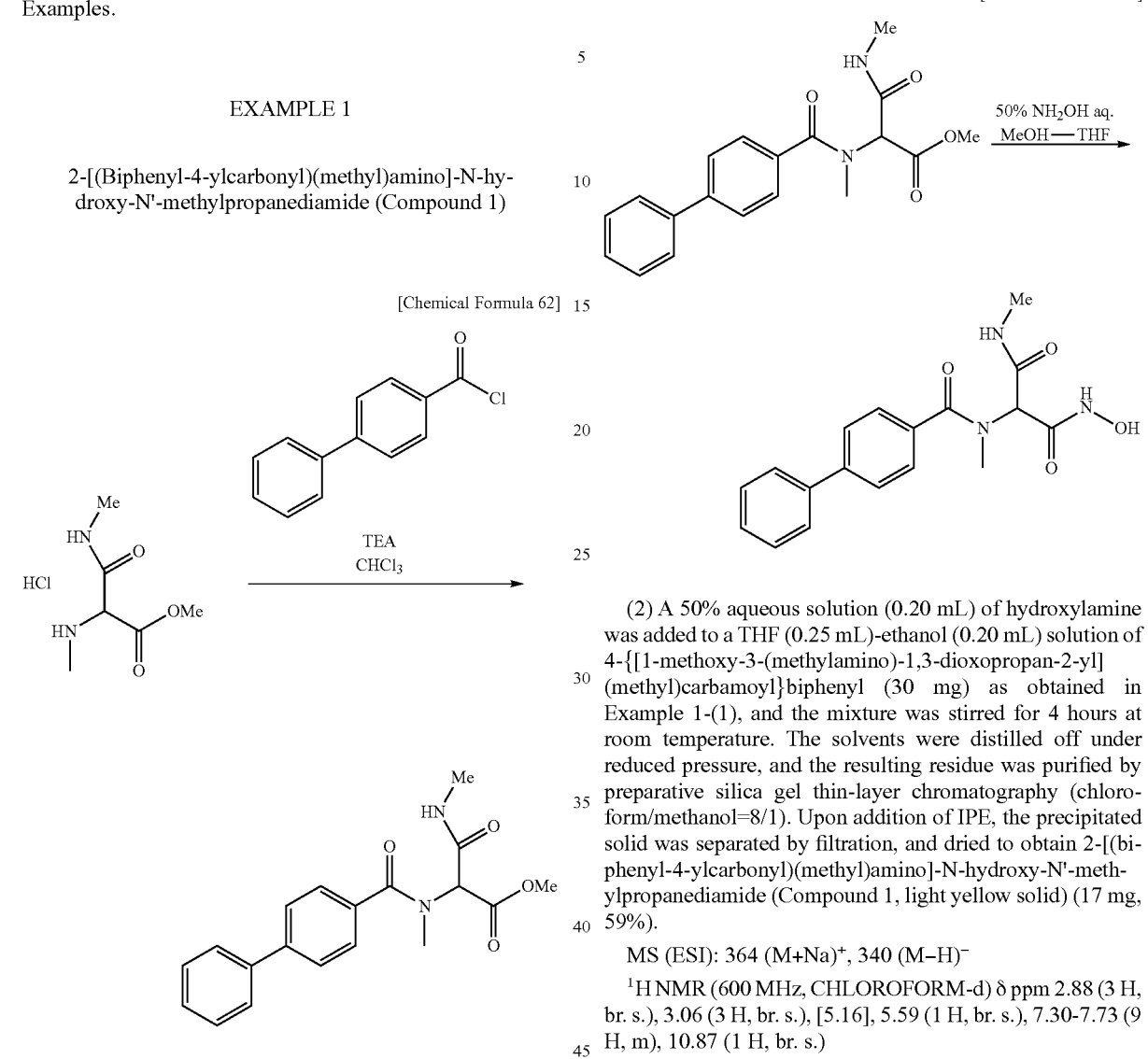

(1) 4-Phenylbenzoyl chloride (2.23 g) was added little by little to a chloroform (20 mL) solution of N,N²,O-trimethyl-3-oxoserinamide hydrochloride (Intermediate 5-2, 2.02 g) and triethylamine (2.18 g) under ice cooling, and the mixture was stirred for 30 minutes at the same temperature and for 1 hour, with the temperature raised to room temperature. Water was added to the reaction mixture, and the system was extracted with chloroform. The extract was dried over anhydrous magnesium sulfate, and the desiccant was filtered out, whereafter the solvent was distilled off under reduced pressure. The resulting residue was purified by OH type silica gel column chromatography (gradient elution with chloroform/methanol=98/2→90/10) to obtain 4-{[1-methoxy-3-(methylamino)-1,3-dioxopropan-2-yl](methyl)carbamoyl}biphenyl (yellow solid) (3.0 g, 86%).

MS (ESI): 363 (M+Na)⁺, 339 (M–H)⁻

¹H NMR (600 MHz, CHLOROFORM-d) δ ppm 2.90 (3 H, d, J=4.58 Hz), 3.20 (3 H, s), 3.85 (3 H, s), [5.14], 5.50 (1 H, br. s.), 7.18-7.23 (1 H, m), 7.39 (1 H, d, J=7.34 Hz), 7.46 (2 H, t, J=7.79 Hz), 7.55-7.69 (6 H, m)

(2) A 50% aqueous solution (0.20 mL) of hydroxylamine was added to a THF (0.25 mL)-ethanol (0.20 mL) solution of 4-{[1-methoxy-3-(methylamino)-1,3-dioxopropan-2-yl](methyl)carbamoyl}biphenyl (30 mg) as obtained in Example 1-(1), and the mixture was stirred for 4 hours at room temperature. The solvents were distilled off under reduced pressure, and the resulting residue was purified by preparative silica gel thin-layer chromatography (chloroform/methanol=8/1). Upon addition of IPE, the precipitated solid was separated by filtration, and dried to obtain 2-[(biphenyl-4-ylcarbonyl)(methyl)amino]-N-hydroxy-N'-methylpropanediamide (Compound 1, light yellow solid) (17 mg, 59%).

MS (ESI): 364 (M+Na)⁺, 340 (M–H)⁻

¹H NMR (600 MHz, CHLOROFORM-d) δ ppm 2.88 (3 H, br. s.), 3.06 (3 H, br. s.), [5.16], 5.59 (1 H, br. s.), 7.30-7.73 (9 H, m), 10.87 (1 H, br. s.)

EXAMPLE 2

N-hydroxy-N'-methyl-2-(methyl {[4'-(methylamino)biphenyl-4-yl]carbonyl}amino)propanediamide (Compound 2)

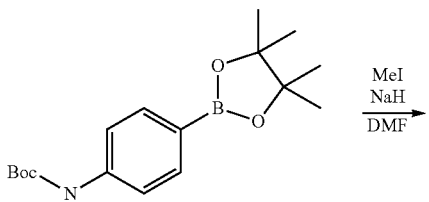

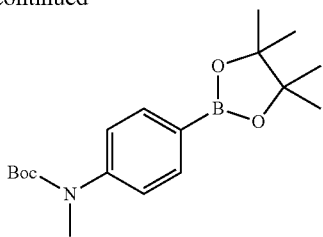

(1) 60% Sodium hydride (0.55 g) and methyl iodide (1.2 mL) were added to a DMF (6.0 mL) solution of t-butyl(4-(4,4,5,5-tetramethyl-1,3,2-dioxaborolan-2-yl)phenyl)carbamate (2.0 g), and the mixture was stirred for 18 hours at room temperature. Ethyl acetate and water were added to the reaction mixture, and the organic layer was isolated. The extract was washed sequentially with water and brine, and dried over anhydrous sodium sulfate. Then, the desiccant was filtered out, whereafter the solvent was distilled off under reduced pressure. Hexane was added to the residue, and the precipitated solid was collected by filtration to obtain t-butyl=methyl (4-(4,4,5,5-tetramethyl-1,3,2-dioxaborolan-2-yl)phenyl)carbamate (white solid) (1.46 g, 70%).

$^1$H NMR (400 MHz, CHLOROFORM-d) δ ppm 1.34 (12H, s), 1.45 (9H, s), 3.27 (3H, s), 7.24 (2H, d, J=8.4 Hz), 7.76 (2H, d, J=8.4 Hz)

[Chemical Formula 65]

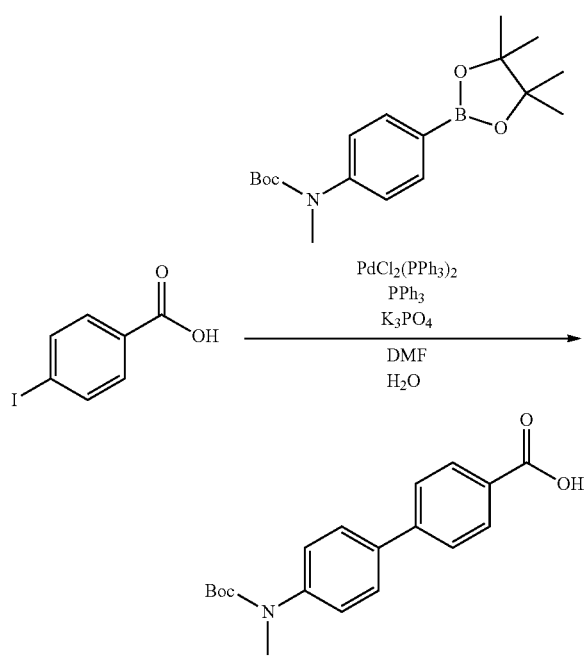

(2) PdCl$_2$(PPh$_3$)$_2$ (119 mg), triphenylphosphine (89 mg), potassium phosphate (1.44 g) and water (1.7 mL) were added to a DMF (17 mL) solution of t-butyl=methyl(4-(4,4,5,5-tetramethyl-1,3,2-dioxaborolan-2-yl)phenyl)carbamate (846 mg), as obtained in Example 2-(1), and 4-iodobenzoic acid (420 mg), and the mixture was stirred in a nitrogen atmosphere for 3.5 hours at 90° C. After the reaction mixture was allowed to cool, ethyl acetate and water were added, and the mixture was adjusted to pH 3 with 1 mol/L of hydrochloric acid. The organic layer was isolated, and the extract was washed sequentially with water and brine. The system was dried over anhydrous magnesium sulfate and, after addition of silica gel (10.0 g), the mixture was stirred for 15 minutes at room temperature. The desiccant and the silica gel were filtered out, and then the solvent was distilled off under reduced pressure. Hexane was added to the residue, and the precipitated solid was collected by filtration, and washed with an IPE/hexane=1/1 solvent mixture. IPE was added to the resulting solid, and the mixture was stirred for 15 minutes at room temperature. Then, the remaining solid was collected by filtration to obtain 4'-((t-butoxycarbonyl)(methyl)amino)biphenyl-4-carboxylic acid (light brown solid) (396 mg, 71%).

$^1$H NMR (400 MHz, DMSO-d$_6$) δ ppm 1.42 (9H, s), 3.23 (3H, s), 7.41 (2H, d, J=8.5 Hz), 7.72 (2H, d, J=8.5 Hz), 7.80 (2H, d, J=8.3 Hz), 8.01 (2H, d, J=8.3 Hz), 12.80-13.14 (1H, br. s.)

[Chemical Formula 66]

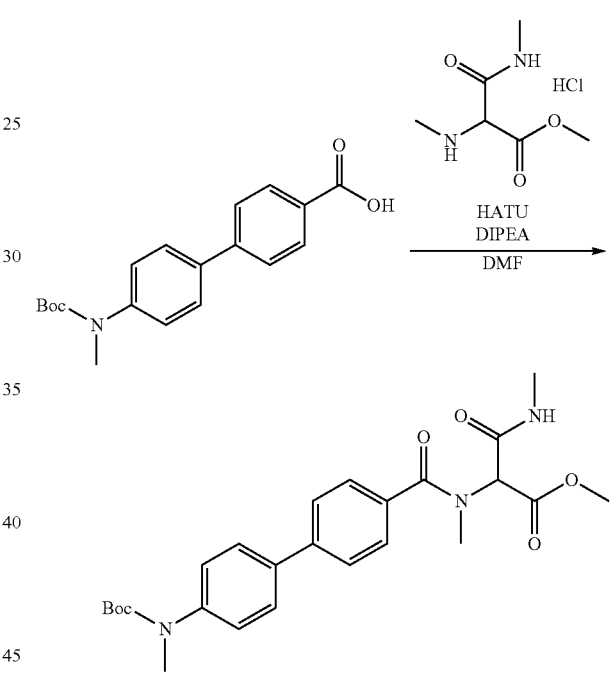

(3) N,N$^2$,O-trimethyl-3-oxoserinamide hydrochloride (Intermediate 5-2, 90 mg), HATU (0.17 g) and DIPEA (0.16 mL) were added to a DMF (2.0 mL) solution of 4'-((t-butoxycarbonyl)(methyl)amino)biphenyl-4-carboxylic acid (0.10 g), as obtained in Example 2-(2), and the mixture was stirred for 16 hours at room temperature. Ethyl acetate and water were added to the reaction mixture to isolate the organic layer, and the extract was washed sequentially with water and brine. The system was dried over anhydrous sodium sulfate and, after separation of the desiccant by filtration, the solvent was distilled off under reduced pressure. The residue was purified by silica gel column chromatography (hexane/ethyl acetate=1/3) to obtain 4-((t-butoxycarbonyl)(methyl)amino)-4'-(((2-methoxy-1-((methylamino)carbonyl)-2-oxoethyl)(methyl)amino)carbonyl)biphenyl (white foam) (73 mg, 51%).

$^1$H NMR (400 MHz, CHLOROFORM-d) δ ppm 1.48 (9H, s), 2.90 (3H, d, J=4.9 Hz), 3.20 (3H, s), 3.31 (3H, s), 3.85 (3H, s), 5.49 (1H, s), 7.16-7.23 (1H, m), 7.34 (2H, d, J=8.3 Hz), 7.52-7.67 (6H, m)

[Chemical Formula 67]

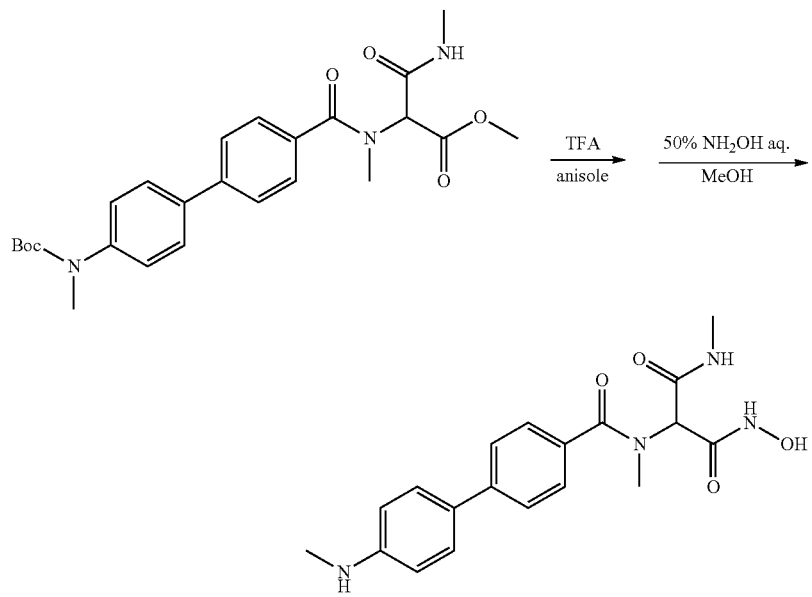

(4) TFA (1.0 mL) was added to an anisole (1.0 mL) solution of 4-((t-butoxycarbonyl)(methyl)amino)-4'-(((2-methoxy-1-((methylamino)carbonyl)-2-oxoethyl)(methyl)amino)carbonyl)biphenyl (60 mg), as obtained in Example 2-(3), and the mixture was stirred for 1 hour at room temperature. IPE was added to the reaction mixture, and the supernatant was removed. A 50% aqueous solution (1.5 mL) of hydroxylamine was added to a methanol (2.0 mL) solution of the resulting residue, and the mixture was stirred for 1 hour at room temperature. Water was added to the reaction mixture, and the mixture was adjusted to pH 6 with 6 mol/L of hydrochloric acid. Then, ethyl acetate was added to isolate the organic layer, and the aqueous layer was extracted with ethyl acetate. The extract was dried over anhydrous sodium sulfate and, after separation of the desiccant by filtration, the solvent was distilled off under reduced pressure. The resulting residue was purified by preparative silica gel thin-layer chromatography (chloroform/methanol=5/1) to obtain N-hydroxy-N'-methyl-2-(methyl {[4'-(methylamino)biphenyl-4-yl]carbonyl}amino)propanediamide (Compound 2, light yellow solid) (20 mg, 42%).

MS (ESI): 393 (M+Na)$^+$, 369 (M−H)$^−$ $^1$H NMR (400 MHz, CD$_3$OD) δ ppm 2.80 (6H, br. s.), 3.12 (3H, s), 6.69 (2H, d, J=8.6 Hz), 7.35-7.69 (6H, m)

EXAMPLE 3

N-hydroxy-2-[{[4'-(methoxymethyl)biphenyl-4-yl]carbonyl}(methyl)amino]-N'-methylpropanediamide (Compound 4)

[Chemical Formula 68]

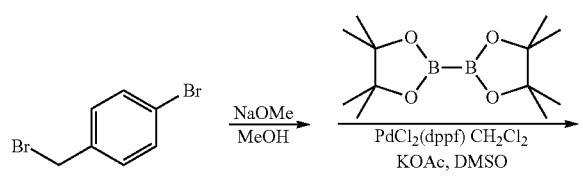

-continued

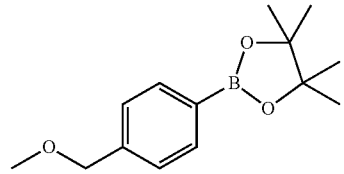

(1) A 28% sodium methoxide-methanol solution (5.0 g) was added to a methanol (40 mL) solution of 1-bromo-4-(bromomethyl)benzene (5.0 g) at room temperature, and the mixture was stirred for 21 hours at room temperature. Water was added to the reaction mixture, and the mixture was extracted with diethyl ether, whereafter the organic layer was dried over anhydrous magnesium sulfate. The desiccant was filtered out, and the filtrate was concentrated under reduced pressure. To a DMSO solution (40 mL) of the resulting residue, 4,4,4',4',5,5,5',5'-octamethyl-2,2'-bi-1,3,2-dioxaborolane (7.6 g), PdCL$_2$(dppf).CH$_2$Cl$_2$ (0.82 g), and potassium acetate (5.9 g) were added, followed by stirring the mixture for 4 hours at 100° C. After the system was allowed to cool, water (0.10 L) and ethyl acetate (0.10 L) were added, and the precipitated insolubles were filtered out. The filtrate was extracted with ethyl acetate, and the organic layer was washed with brine, and dried over anhydrous magnesium sulfate. The desiccant was filtered out, and the solvent was distilled off under reduced pressure. The resulting residue was purified by OH type silica gel chromatography (gradient elution with hexane/ethyl acetate=90/10→80/20) to obtain 2-[4-(methoxymethyl)phenyl]-4,4,5,5-tetramethyl-1,3,2-dioxaborolane (light green solid) (4.1 g, 82%).

MS (ESI): 249 (M+H)$^+$ $^1$H NMR (200 MHz, CHLOROFORM-d) δ ppm 1.34 (12 H, s), 3.38 (3 H, s), 4.48 (2 H, s), 7.30-7.38 (2 H, m), 7.76-7.83 (2 H, m)

[Chemical Formula 69]

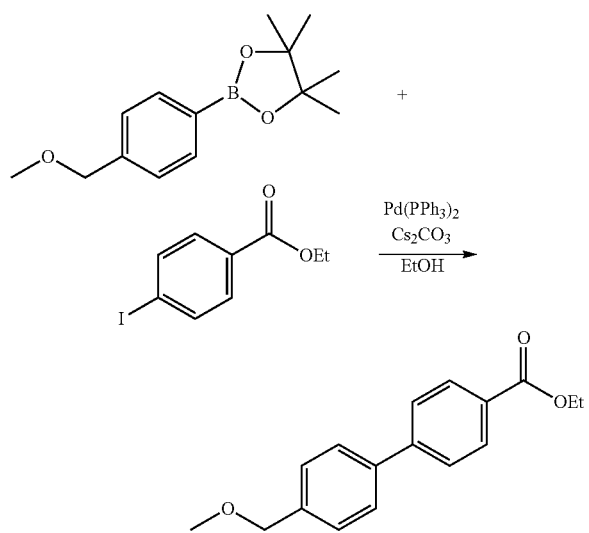

(2) Ethyl 4-iodobenzoate (5.5 g), tetrakis(triphenylphosphine)palladium (1.2 g), and cesium carbonate (9.8 g) were added to an ethanol (0.10 L) solution of 2-[4-(methoxymethyl)phenyl]-4,4,5,5-tetramethyl-1,3,2-dioxaborolane (4.1 g), as obtained in Example 3-(1). The mixture was stirred for 30 minutes at 80° C., and then the solvent was distilled off under reduced pressure. The resulting residue was purified by OH type silica gel chromatography (hexane/ethyl acetate=85/15) to obtain ethyl 4'-(methoxymethyl)biphenyl-4-carboxylate (light yellow solid) (3.5 g, 80%).

MS (ESI/APCI Dual): 271 (M+H)$^+$ $^1$H NMR (200 MHz, CHLOROFORM-d) δ ppm 1.43 (3 H, t, J=7.0 Hz), 3.43 (3 H, s), 4.42 (2 H, q, J=7.0 Hz), 4.51 (2 H, s), 7.41-7.45 (2 H, m), 7.57-7.70 (4 H, m), 8.06-8.15 (2 H, m)

[Chemical Formula 70]

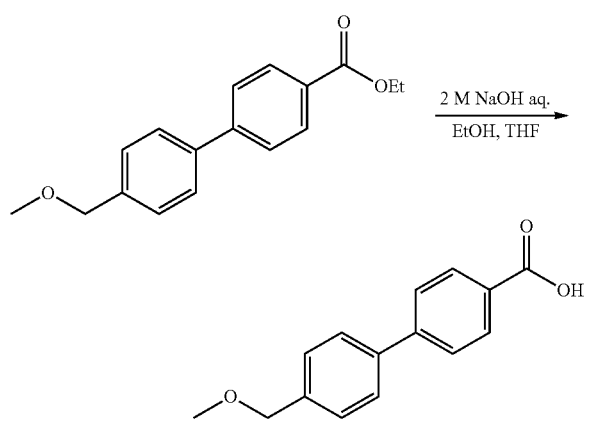

(3) Ethanol (20 mL) and a 2.0 mol/L aqueous solution (10 mL) of sodium hydroxide were added to a THF (20 mL) solution of ethyl 4'-(methoxymethyl)biphenyl-4-carboxylate (3.5 g) as obtained in Example 3-(2), and the mixture was stirred for 1 hour at 80° C. Water was added to the reaction mixture, and the mixture was neutralized with an aqueous solution of hydrochloric acid. Then, the precipitate was collected by filtration to obtain 4'-(methoxymethyl)biphenyl-4-carboxylic acid (gray solid) (3.0 g, 96%).

MS (ESI/APCI Dual): 241 (M−H)$^-$ $^1$H NMR (600 MHz, DMSO-d$_6$) δ ppm 3.32 (3 H, s), 4.46 (2 H, s), 7.41-7.43 (2 H, m), 7.69-7.72 (4 H, m), 7.97-8.01 (2 H, m)

[Chemical Formula 71]

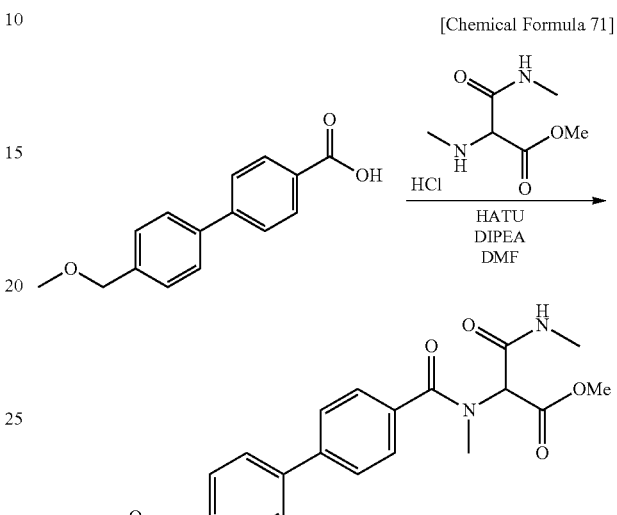

(4) Intermediate 5-2 (0.39 g), HATU (0.57 g) and DIPEA (0.80 mL) were added to a DMF (6.0 mL) solution of 4'-(methoxymethyl)biphenyl-4-carboxylic acid (0.36 g) as obtained in Example 3-(3), and the mixture was stirred for 30 minutes at 80° C. Then, brine was added to the reaction mixture, the mixture was extracted with ethyl acetate, and the organic layer was dried over anhydrous magnesium sulfate. The desiccant was filtered out, and the filtrate was concentrated under reduced pressure. The resulting residue was purified by NH type silica gel chromatography (gradient elution with hexane/ethyl acetate=50/50→0/100) to obtain 4-(methoxymethyl)-4'-{[1-methoxy-3-(methylamino)-1,3-dioxopropan-2-yl](methyl)carbamoyl}biphenyl (yellow oil) (0.40 g, 69%).

MS (ESI/APCI Dual): 385 (M+H)$^+$, 407 (M+Na)$^+$, 383 (M−H)$^-$ $^1$H NMR (600 MHz, CHLOROFORM-d) δ ppm 2.88 (3 H, d, J=4.6 Hz), 3.19 (3 H, s), 3.43 (3 H, s), 3.84 (3 H, s), 4.51 (2 H, s), 5.52 (1 H, s), 7.27 (1 H, br. s.), 7.43-7.44 (2 H, m), 7.56-7.67 (6 H, m)

[Chemical Formula 72]

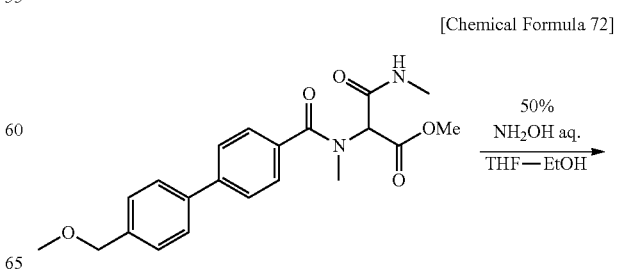

-continued

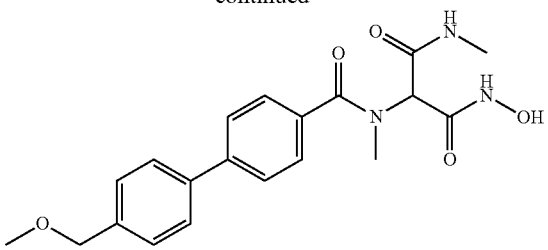

(5) Ethanol (5.0 mL) and a 50% aqueous solution (5.0 mL) of hydroxylamine were added to a tetrahydrofuran (5.0 mL) solution of 4-(methoxymethyl)-4'-{[1-methoxy-3-(methylamino)-1,3-dioxopropan-2-yl](methyl)carbamoyl}biphenyl (0.40 g) as obtained in Example 3-(4), and the mixture was stirred for 2 hours at room temperature. Then, the reaction mixture was concentrated under reduced pressure, and purified by preparative silica gel thin-layer chromatography (chloroform/methanol=85/15). IPE was added, and the precipitated solid was filtered off and dried to obtain N-hydroxy-2-[{[4'-(methoxymethyl)biphenyl-4-yl]carbonyl}(methyl)amino]-N'-methylpropanediamide (Compound 4, pink solid) (0.18 g, 46%).

MS (ESI/APCI Dual): 408 (M+Na)$^+$, 384 (M−H)$^-$ $^1$H NMR (600 MHz, CD$_3$OD) δ ppm 2.83 (3 H, br. s.), 3.12 (3 H, s), 3.40 (3 H, s), 4.51 (2 H, s), 7.44 (2 H, d, J=8.25 Hz), 7.57-7.78 (6 H, m)

Compounds 3, 5, 6, 8, 40, 43, 52, 56, 58, 61, 94, 112, 114, 115, 153, 165, 169, 176, 179 to 185, 187 to 192, 195 to 197, 199 to 203, 208, 211 to 216, 220, 222 to 224, 226 to 231, 233, 236 to 241, 243, 244, 246 to 248, 251 to 262, 265, 266, 269 to 271, 278, 279, 281, 282, 285 to 287, 290, 291, 298, 299, 308 to 312, 344, 347, 352, 442 to 452, 456 to 460, 462, 463, 467 to 470, 474, 475, 479, 480, 499, 502 and 519 were synthesized by the same methods as in Example 3 with the use of the corresponding materials.

EXAMPLE 4

N-hydroxy-N'-methyl-2-[methyl({4'-[3-(morpholin-4-yl)propoxy]biphenyl-4-yl}carbonyl)amino]propanediamide (Compound 7)

N-hydroxy-N'-methyl-2-[methyl({4'-[3-(morpholin-4-yl)propoxy]biphenyl-4-yl}carbonyl)amino]propanediamide 4-methylbenzenesulfonate (Compound 7b)

[Chemical Formula 73]

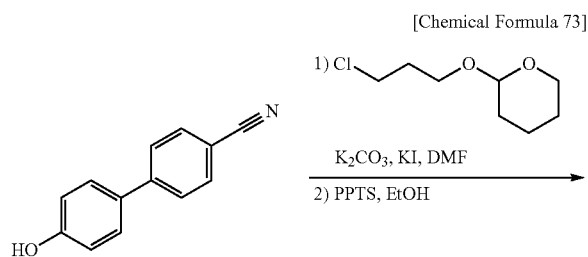

-continued

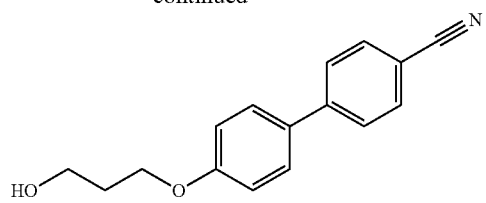

(1) 2-(3-Chloropropoxy)tetrahydro-2H-pyran (11 g), potassium carbonate (11 g), and potassium iodide (4.4 g) were added to a DMF (0.10 L) solution of 4'-hydroxybiphenyl-4-carbonitrile (10 g), and the mixture was stirred for 5 hours at 100° C. Water was added to the reaction mixture, and the mixture was extracted with ethyl acetate. Then, the organic layer was washed with brine, and dried over anhydrous magnesium sulfate. The desiccant was filtered out, and the solvent was distilled off under reduced pressure. PPTS (1.3 g) was added to an ethanol (0.10 L) solution of the resulting residue, and the mixture was stirred for 1 hour at 60° C. The solvent was distilled off under reduced pressure, and the resulting residue was purified by OH type silica gel chromatography (gradient elution with hexane/ethyl acetate=80/20→20/80) to obtain 4'-(3-hydroxypropoxy)biphenyl-4-carbonitrile (white solid) (12 g, 88%).

MS (ESI/APCI Dual): 434 (M+H)$^+$, 456 (M+Na)$^+$, 432 (M−H)$^-$ $^1$H NMR (600 MHz, CHLOROFORM-d) δ ppm 2.09 (2 H, quin, J=6.0 Hz), 3.87-3.91 (2 H, m), 4.19 (2 H, t, J=6.0 Hz), 7.00-7.03 (2 H, m), 7.52-7.55 (2 H, m), 7.63-7.65 (2 H, m), 7.68-7.70 (2 H, m)

[Chemical Formula 74]

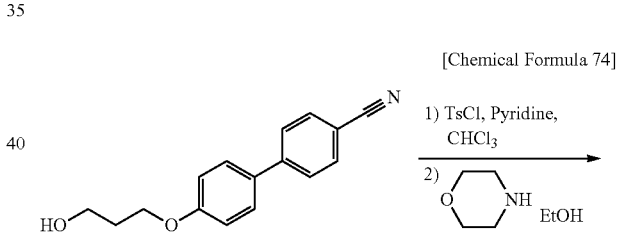

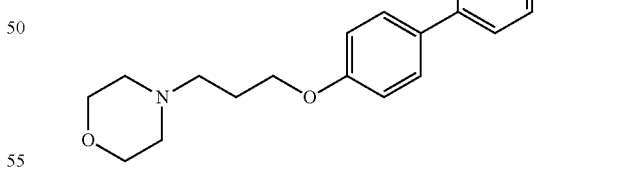

(2) TsCl (12 g) and pyridine (10 mL) were added to a chloroform (0.1 L) solution of 4'-(3-hydroxypropoxy)biphenyl-4-carbonitrile (5.1 g) as obtained in Example 4-(1), and the mixture was stirred overnight at room temperature. Chloroform was added to the reaction mixture, and the mixture was washed with a 1.0 mol/L hydrochloric acid aqueous solution and a 1.0 mol/L sodium hydrogen carbonate aqueous solution. After the organic layer was dried over anhydrous magnesium sulfate, the desiccant was filtered out, and the solvent was distilled off under reduced pressure. IPE was added to the resulting residue, and the precipitated solid was collected by filtration. Then, ethanol (40 mL) and morpholine (8.8 mL) were added, and the mixture was stirred for 1 hour at 80° C. The reaction mixture was distilled under reduced pressure, and the resulting residue was purified by OH type silica gel chromatography (gradient elution with hexane/ethyl acetate=50/50→90/10) to obtain 4'-[3-(morpholin-4-yl)propoxy]biphenyl-4-carbonitrile (light brown solid) (5.1 g, 79%).

MS (ESI/APCI Dual): 323 (M+H)$^+$ $^1$H NMR (200 MHz, CHLOROFORM-d) δ ppm 1.93-2.07 (2 H, m), 2.44-2.59 (6 H, m), 3.69-3.76 (4 H, m), 4.08 (2 H, t, J=6.7 Hz), 6.95-7.04 (2 H, m), 7.48-7.57 (2 H, m), 7.60-7.72 (4 H, m)

(morpholin-4-yl)propoxy]biphenyl-4-carbonitrile (5.1 g) as obtained in Example 4-(2), and the mixture was refluxed for 12 hours. The solvent was distilled off under reduced pressure, and water (0.20 L) was added to the resulting residue. Under ice cooling, concentrated hydrochloric acid (25 mL) and a 1.0 mol/L potassium hydrogen sulfate aqueous solution (30 mL) were added to neutralize the mixture. The precipitate solid was filtered off, and then washed with water to obtain 4'-[3-(morpholin-4-yl)propoxy]biphenyl-4-carboxylic acid (white solid) (5.5 g, 100%).

MS (ESI/APCI Dual): 283 (M–H)$^-$ $^1$H NMR (600 MHz, DMSO-d$_6$) δ ppm 2.12-2.24 (2 H, m), 2.91-3.61 (6 H, m), 3.75-4.04 (4 H, m), 4.13 (2 H, t, J=6.0 Hz), 7.05-7.09 (2 H, m), 7.69-7.72 (2 H, m), 7.74-7.77 (2 H, m), 7.98-8.00 (2 H, m)

[Chemical Formula 76]

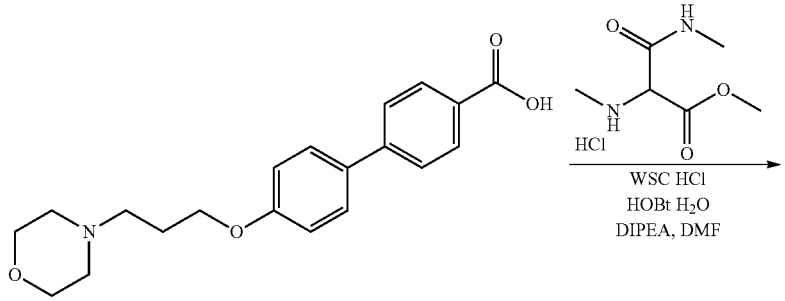

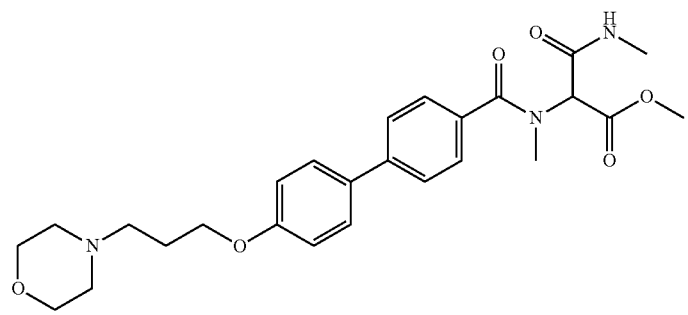

[Chemical Formula 75]

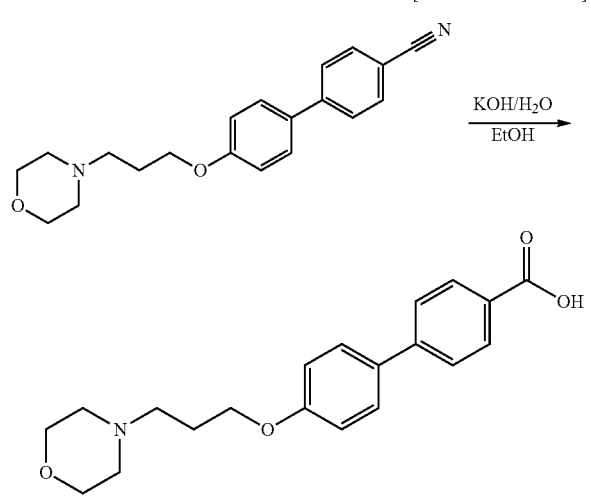

(3) An aqueous solution (40 mL) of 8.0 mol/L potassium hydroxide was added to an ethanol (0.12 L) solution of 4'-[3-

(4) Intermediate 5-2 (0.24 g), WSC·HCl (0.29 g), HOBt·H$_2$O (0.20 g), and DIPEA (0.27 mL) were added to a DMF (5.0 mL) solution of 4'-[3-(morpholin-4-yl)propoxy]biphenyl-4-carboxylic acid (0.34 g) as obtained in Example 4-(3), and the mixture was stirred for 2 hours at room temperature. Then, an aqueous solution of sodium hydrogen carbonate was added to the reaction mixture, and the mixture was extracted with ethyl acetate. The organic layer was washed with brine, and dried over anhydrous magnesium sulfate. Then, the desiccant was filtered out, and the solvent was distilled off under reduced pressure. The resulting residue was purified by NH type silica gel chromatography (gradient elution with hexane/ethyl acetate=50/50→0/100) to obtain 4-{3-[(4'-{[1-methoxy-3-(methylamino)-1,3-dioxopropan-2-yl](methyl)carbamoyl}biphenyl-4-yl)oxy]propyl}morpholine (colorless oil) (0.11 g, 23%).

MS (ESI/APCI Dual): 484 (M+H)$^+$, 506 (M+Na)$^+$, 482 (M–H)$^-$ $^1$H NMR (600 MHz, CHLOROFORM-d) δ ppm 2.01 (2 H, quin, J=6.8 Hz), 2.48-2.50 (4H, m), 2.55 (2H, t, J=6.8 Hz), 2.91 (3 H, d, J=5.0 Hz), 3.20 (3 H, br. s.), 3.73-3.75 (4 H, m), 3.85 (3 H, s), 4.09 (2 H, t, J=6.8 Hz), 5.48 (1 H, s), 6.99-7.00 (2 H, m), 7.17-7.18 (1 H, m), 7.53-7.63 (6 H, m)

[Chemical Formula 76]

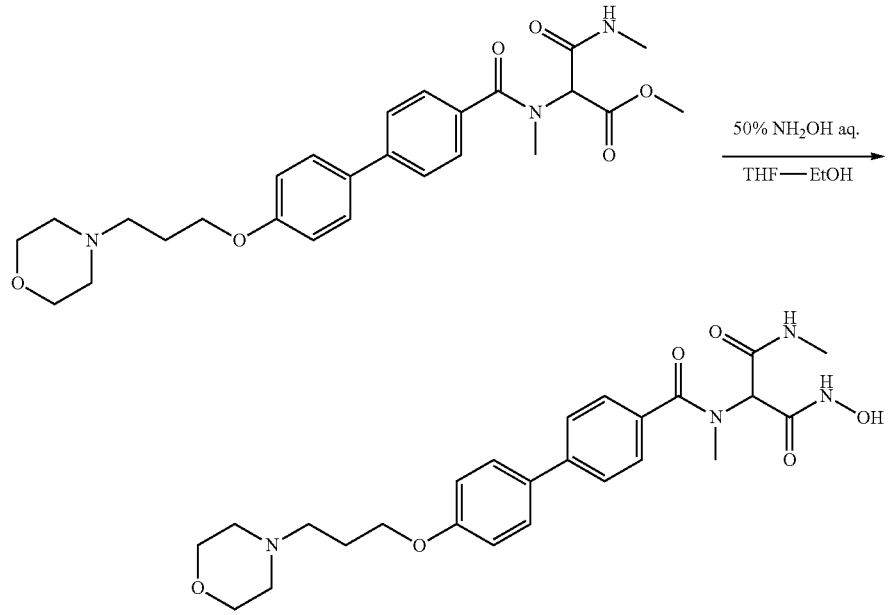

(5) Ethanol (1.0 mL) and a 50% aqueous solution (1.0 mL) of hydroxylamine were added to a THF (1.0 mL) solution of 4-{3-[(4'-{[1-methoxy-3-(methylamino)-1,3-dioxopropan-2-yl](methyl)carbamoyl}biphenyl-4-yl)oxy]propyl}morpholine (0.11 g) as obtained in Example 4-(4), and the mixture was stirred for 2 hours at room temperature. Then, the reaction mixture was concentrated under reduced pressure. The resulting residue was purified by preparative silica gel thin-layer chromatography (chloroform/methanol=90/10), and then recrystallized from ethyl acetate/hexane to obtain N-hydroxy-N'-methyl-2-[methyl({4'-[3-(morpholin-4-yl)propoxy]biphenyl-4-yl}carbonyl)amino]propanediamide (Compound 7, light brown solid) (43 mg, 39%).

MS (ESI/APCI Dual): 485 (M+H)$^+$, 507 (M+Na)$^+$, 483 (M−H)$^−$ $^1$H NMR (600 MHz, DMSO-d$_6$) δ ppm 1.84-1.92 (2 H, m), 2.33-2.40 (4 H, m), 2.41-2.46 (2 H, m), 2.67 (3 H, br. s.), 2.98 (3 H, s), 3.54-3.61 (4 H, m), 4.03-4.10 (2 H, m), 5.36, [5.84] (1 H, br. s.), 7.01-7.06 (2 H, m), 7.32-7.74 (6 H, m), 8.14 (1 H, br. s.), 9.04 (1 H, br. s.), 10.85 (1 H, br. s.)

[Chemical Formula 78]

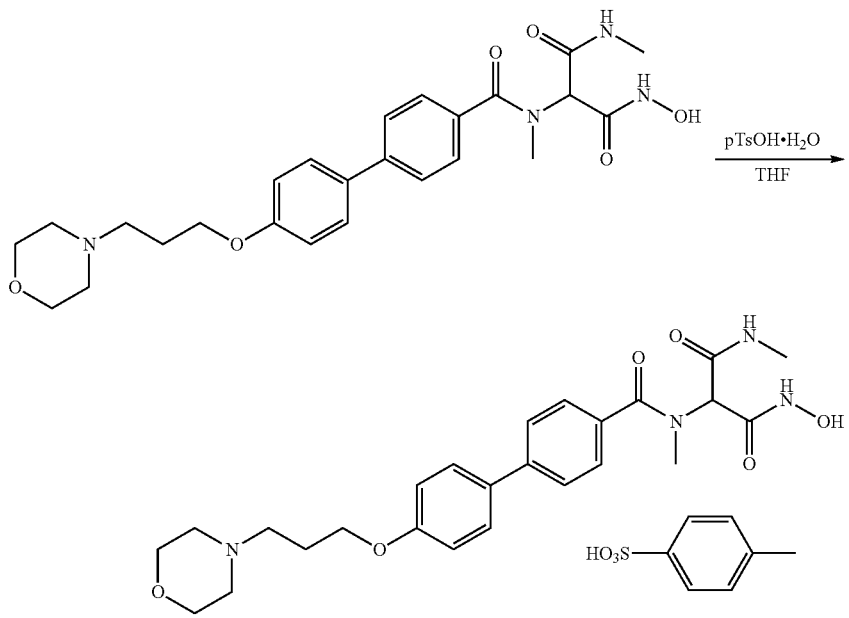

(6) To a THF (1.0 mL) suspension of N-hydroxy-N'-methyl-2-[methyl({4'-[3-(morpholin-4-yl)propoxy]biphenyl-4-yl}carbonyl)amino]propanediamide (Compound 7, 24 mg)

as obtained in Example 4-(5), p-TsOH.H₂O (9.5 mg) was added, and the mixture was stirred for 10 minutes at room temperature. The precipitate was collected by filtration to obtain N-hydroxy-N'-methyl-2-[methyl({4'-[3-(morpholin-4-yl)propoxy]biphenyl-4-yl}carbonyl)amino]propanediamide 4-methylbenzenesulfonate (Compound 7b, white solid) (26 mg, 79%).

MS (ESI/APCI Dual): 485 (M+H)⁺, 483 (M−H)⁻

¹H NMR (600 MHz, CD₃OD) δ ppm 2.18-2.29 (2H, m), 2.36 (3H, s), 2.83 (3H, br. s.), 3.12 (3H, br. s.), 3.17-3.40 (8H, m), 3.90 (2H, br. s.), 4.12-4.19 (2H, m), 7.04 (2H, d, J=8.7 Hz), 7.22 (2H, d, J=8.3 Hz), 7.54-7.77 (8H, m)

EXAMPLE 5

N-hydroxy-N'-methyl-2-[methyl(4-{[4-(1,4-oxazepan-4-ylmethyl)phenyl]ethynyl}benzoyl)amino]propanediamide (Compound 168)

[Chemical Formula 79]

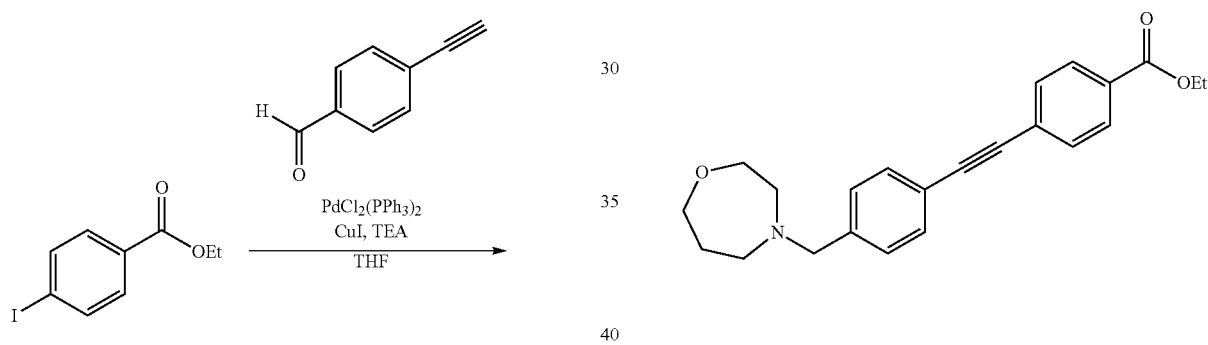

resulting residue was purified by OH type silica gel chromatography (gradient elution with hexane/chloroform=80/20→0/100) to obtain ethyl 4-[(4-formylphenyl)ethynyl]benzoate (yellow solid) (16 g, 69%).

¹H NMR (600 MHz, CHLOROFORM-d) δ ppm 1.41 (3 H, t, J=7.3 Hz), 4.40 (2 H, q, J=7.3 Hz), 7.62 (2 H, d, J=8.7 Hz), 7.70 (2 H, d, J=7.8 Hz), 7.89 (2 H, d, J=7.8 Hz), 8.05 (2 H, d, J=8.7 Hz), 10.04 (1 H, s)

[Chemical Formula 80]

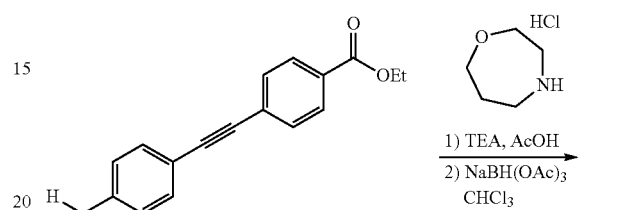

(1) 4-Ethynylbenzaldehyde (10 g) obtained by the same method as the synthesis method described in the literature (Tetrahedron Letters, 2007, Vol. 48(33), pp. 5817-5820), PdCl₂(PPh₃)₂ (3.4 g), CuI (1.5 g), and triethylamine (32 mL) were added to a THF (0.25 L) solution of ethyl 4-iodobenzoate (20 g). The mixture was stirred for 3 hours at room temperature, and the reaction mixture was concentrated. The (2) 1,4-Oxazepane hydrochloride (1.6 g) and acetic acid (0.90 mL) were added to a chloroform (20 mL) solution of ethyl 4-[(4-formylphenyl)ethynyl]benzoate (2.1 g) as obtained in Example 5-(1), and the mixture was stirred for 3.5 hours at room temperature, and then for 2 hours at 60° C. Then, sodium triacetoxyborohydride (2.7 g) was added, and the mixture was stirred for 16 hours at room temperature. A saturated aqueous solution of sodium hydrogen carbonate was added to the reaction mixture, and the mixture was extracted with chloroform. The organic layer was washed with brine, and dried over anhydrous sodium sulfate. Then, the desiccant was filtered out, and the solvent was distilled off under reduced pressure. The resulting residue was purified by OH type silica gel chromatography (gradient elution with chloroform/methanol=100/0→93/7) to obtain ethyl 4-{[4-(1,4-oxazepan-4-ylmethyl)phenyl]ethynyl}benzoate (yellow solid) (1.5 g, 52%).

MS (ESI): 364 (M+H)⁺

¹H NMR (600 MHz, CHLOROFORM-d) δ ppm 1.41 (3 H, t, J=6.9 Hz), 1.85-1.94 (2 H, m), 2.64-2.75 (4 H, m), 3.67 (2 H, s), 3.70-3.75 (2 H, m), 3.80-3.86 (2 H, m), 4.39 (2 H, q, J=6.9 Hz), 7.36 (2 H, d, J=7.8 Hz), 7.45-7.61 (4 H, m), 7.99-8.05 (2 H, m)

[Chemical Formula 81]

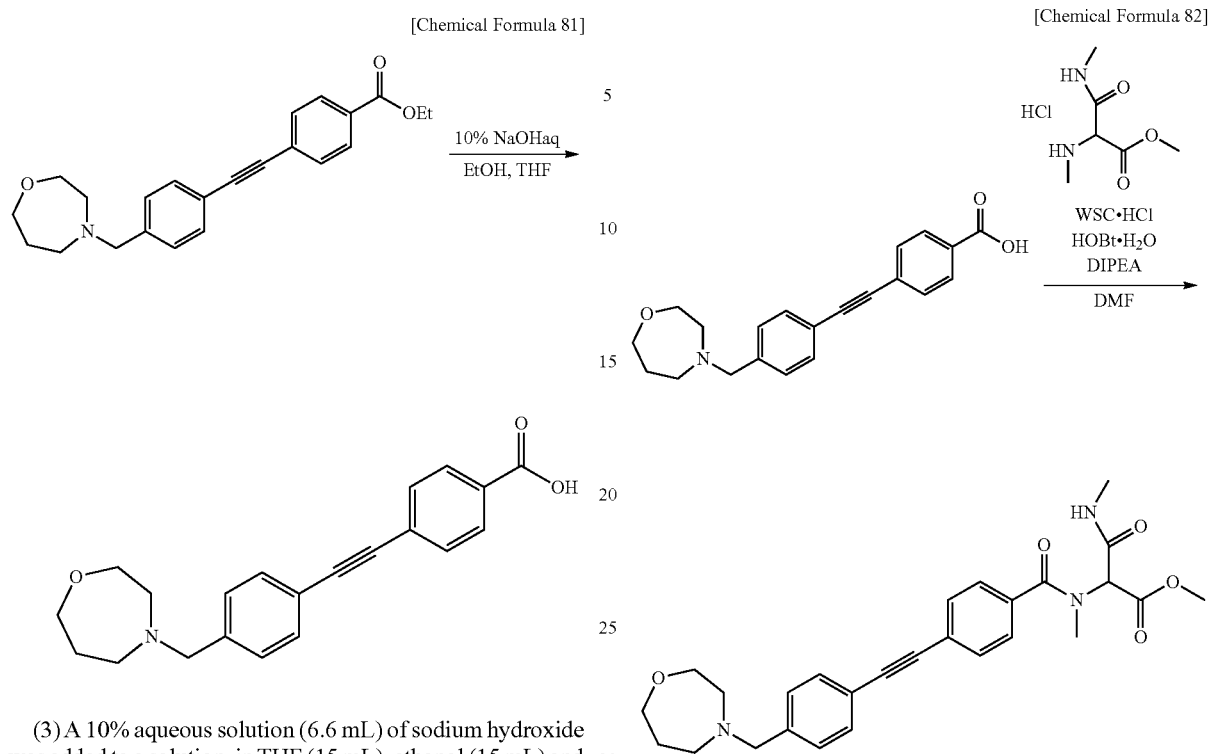

(3) A 10% aqueous solution (6.6 mL) of sodium hydroxide was added to a solution, in THF (15 mL), ethanol (15 mL) and water (10 mL), of ethyl 4-{[4-(1,4-oxazepan-4-ylmethyl) phenyl]ethynyl}benzoate (1.5 g) as obtained in Example 5-(2). The mixture was stirred for 3 hours at room temperature, and then the reaction mixture was neutralized with acetic acid (5.0 mL). The reaction mixture was concentrated, and water was added. The precipitated solid was filtered off and dried to obtain 4-{[4-(1,4-oxazepan-4-ylmethyl)phenyl] ethynyl}benzoic acid (white solid) (0.92 g, 67%).

MS (ESI): 336 (M+H)$^+$, 334 (M+H)$^-$ $^1$H NMR (600 MHz, DMSO-d$_6$) δ ppm 1.77-1.84 (2 H, m), 2.58-2.67 (4 H, m), 3.58-3.73 (6 H, m), 7.40 (2 H, d, J=8.3 Hz), 7.54 (2 H, d, J=8.3 Hz), 7.63 (2 H, d, J=8.3 Hz), 7.95 (2 H, d, J=8.3 Hz)

(4) The same reaction as in Example 4-(4) was performed using 4-{[4-(1,4-oxazepan-4-ylmethyl)phenyl] ethynyl}benzoic acid (0.25 g) as obtained in Example 5-(3), and N,N$^2$,O-trimethyl-3-oxoserinamide hydrochloride (Intermediate 5-2, 0.18 g), to obtain 4-{4-[(4-{[1-methoxy-3-(methylamino)-1,3-dioxopropan-2-yl](methyl) carbamoyl}phenyl)ethynyl]benzyl}-1,4-oxazepane (white solid) (0.11 g, 30%).

MS (ESI): 478 (M+H)$^+$, 476 (M+H)$^-$ $^1$H NMR (600 MHz, CHLOROFORM-d) δ ppm 1.85-1.97 (2 H, m), 2.64-2.77 (4 H, m), 2.90 (3 H, d, J=4.6 Hz), 3.12-3.18 (3 H, m), 3.66-3.78 (4 H, m), 3.80-3.87 (5 H, m), 5.46 (1 H, s), 7.12-7.22 (1 H, m), 7.36 (2 H, d, J=6.9 Hz), 7.41-7.67 (6 H, m)

[Chemical Formula 83]

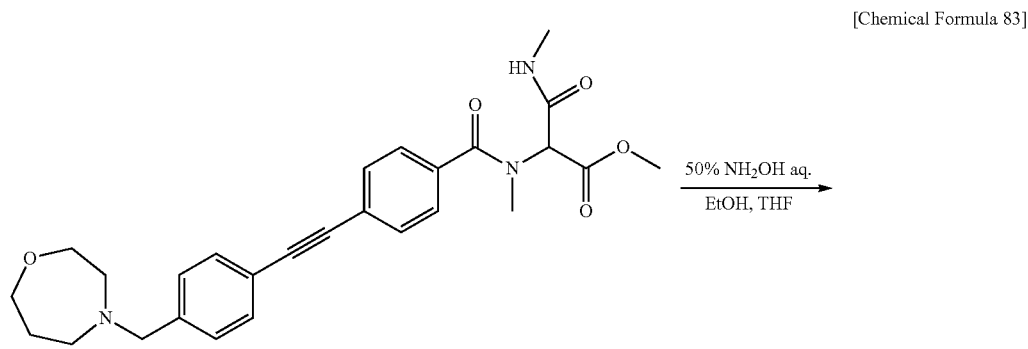

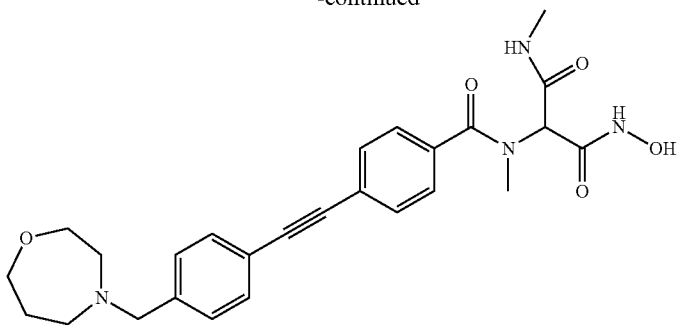

(5) The same procedure as in Example 4-(5) was performed using 4-{4-[(4-{[1-methoxy-3-(methylamino)-1,3-dioxopropan-2-yl](methyl)carbamoyl}phenyl)ethynyl]benzyl}-1,4-oxazepane (0.11 g) as obtained in Example 5-(4), to obtain N-hydroxy-N'-methyl-2-[methyl(4-{[4-(1,4-oxazepan-4-ylmethyl)phenyl]ethynyl}benzoyl)amino]propanediamide (Compound 168, white solid) (40 mg, 37%).

MS (ESI): 479 (M+H)$^+$, 477 (M−H)$^−$ $^1$H NMR (600 MHz, CHLOROFORM-d) δ ppm 1.90-1.99 (2 H, m), 2.65-2.81 (4 H, m), 2.90 (3 H, d, J=5.0 Hz), 3.01 (3 H, s), 3.68-3.78 (4 H, m), 3.81-3.86 (2 H, m), 5.58 (1 H, br. s.), 7.38 (2 H, d, J=7.3 Hz), 7.50 (2 H, d, J=7.8 Hz), 7.53-7.63 (4 H, m)

EXAMPLE 6

2-({[4-(4-Cyclopropylbuta-1,3-diyn-1-yl)phenyl]carbonyl}(methyl)amino)-N-hydroxy-N'-methylpropanediamide (Compound 507)

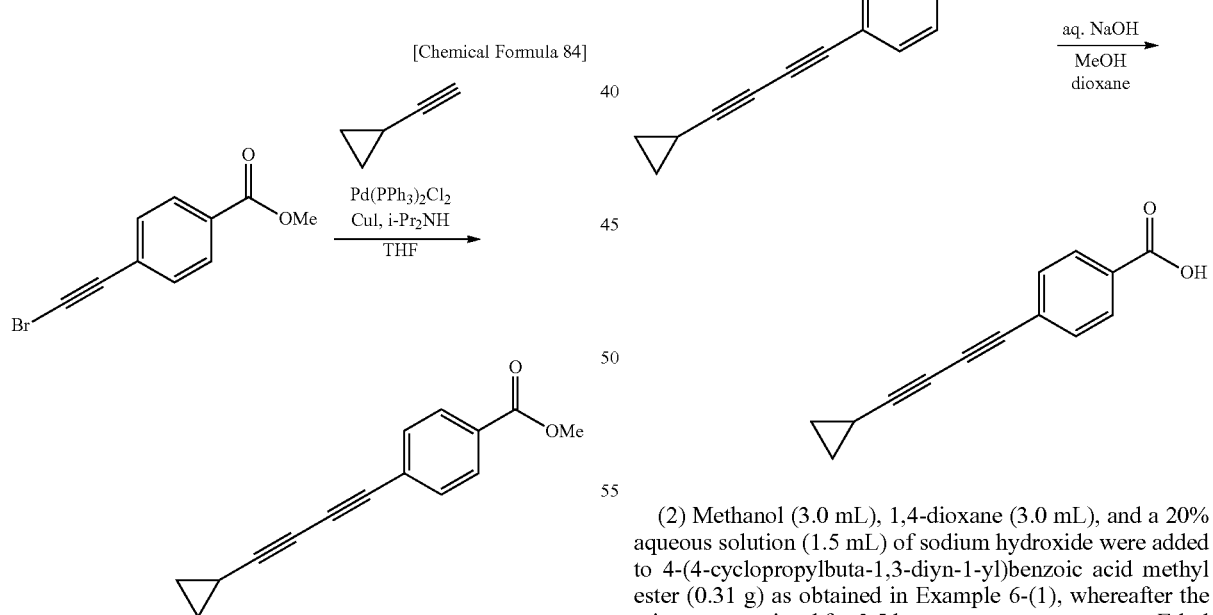

(1) To a THF (6.5 mL) solution of 4-(bromoethynyl)benzoic acid methyl ester (0.65 g) as obtained by the method described in the patent (WO2008/154642), PdCl$_2$(PPh$_3$)$_2$ (95 mg), CuI (52 mg), diisopropylamine (1.5 mL), and ethynylcyclopropane (0.30 mL) were added in a nitrogen atmosphere under water cooling, followed by stirring the mixture for 1.5 hours. Ethyl acetate and water were added, and the mixture was adjusted to pH 5 with 6 mol/L of hydrochloric acid to isolate the organic layer. The extract was dried over anhydrous magnesium sulfate, and then the desiccant was filtered out. The solvent was distilled off under reduced pressure, and the resulting residue was purified by OH type silica gel column chromatography (gradient elution with hexane/ethyl acetate=95/5→92/8). Hexane was added to the resulting solid, which was filtered off to obtain 4-(4-cyclopropylbuta-1,3-diyn-1-yl)benzoic acid methyl ester (light brown solid) (0.31 g, 51%).

$^1$H NMR (400 MHz, CHLOROFORM-d) δ ppm 0.82-0.95 (4 H, m), 1.37-1.47 (1 H, m), 3.91 (3 H, s), 7.51 (2 H, d, J=8.2 Hz), 7.96 (2 H, d, J=8.2 Hz)

(2) Methanol (3.0 mL), 1,4-dioxane (3.0 mL), and a 20% aqueous solution (1.5 mL) of sodium hydroxide were added to 4-(4-cyclopropylbuta-1,3-diyn-1-yl)benzoic acid methyl ester (0.31 g) as obtained in Example 6-(1), whereafter the mixture was stirred for 2.5 hours at room temperature. Ethyl acetate and water were added, and the mixture was adjusted to pH 3 with 6 mol/L of hydrochloric acid to isolate the organic layer. The extract was dried over anhydrous magnesium sulfate, and then the desiccant was filtered out. The solvent was distilled off under reduced pressure to obtain 4-(4-cyclopropylbuta-1,3-diyn-1-yl)benzoic acid (dark brown solid) (0.28 g, 94%).

$^1$H NMR (400 MHz, DMSO-d$_6$) δ ppm 0.70-1.05 (4 H, m), 1.50-1.65 (1 H, m), 7.63 (2 H, d, J=8.3 Hz), 7.92 (2 H, d, J=8.3 Hz), 13.21 (1 H, br. s.)

[Chemical Formula 86]

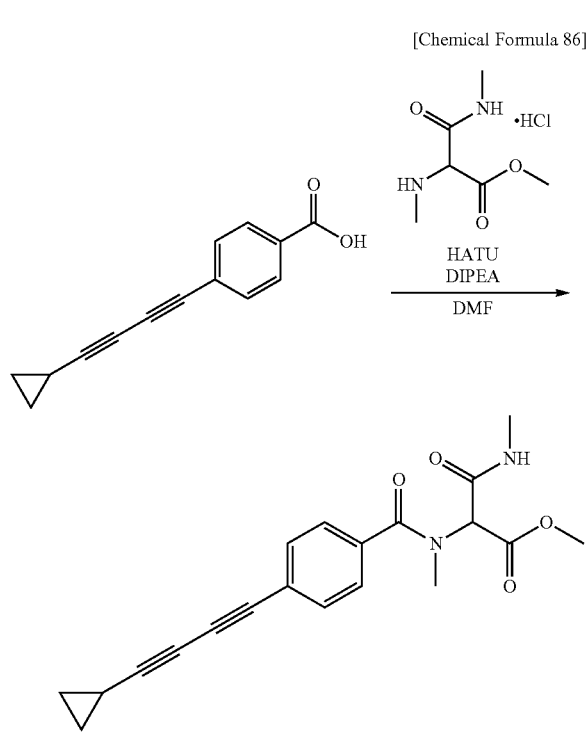

(3) HATU (1.1 g) and DIPEA (1.0 mL) were added to a DMF (4.0 mL) solution of 4-(4-cyclopropylbuta-1,3-diyn-1-yl)benzoic acid (0.42 g) as obtained in Example 6-(2), whereafter the mixture was stirred for 2.5 hours at room temperature. Then, N,N$^2$,O-trimethyl-3-oxoserinamide hydrochloride (Intermediate 5-2, 0.59 g) was added, and the mixture was stirred for 40 minutes at 70 to 80° C. The reaction mixture was cooled to room temperature, and ethyl acetate and water were added to isolate the organic layer. The extract was washed sequentially with water and brine, and dried over anhydrous magnesium sulfate. The desiccant was filtered out, and then the solvent was distilled off under reduced pressure to obtain 1-(4-cyclopropylbuta-1,3-diyn-1-yl)-4-{[1-methoxy-3-(methylamino)-1,3-dioxopropan-2-yl](methyl)carbamoyl}benzene (brown oil) (0.81 g).

$^1$H NMR (400 MHz, CHLOROFORM-d) δ ppm 0.81-0.95 (4 H, m), 1.37-1.51 (1 H, m), 2.88 (3 H, d, J=4.8 Hz), 3.11 (3 H, s), 3.83 (3 H, s), 5.44 (1 H, s), 7.15-7.35 (1 H, m), 7.35-7.57 (4 H, m)

[Chemical Formula 87]

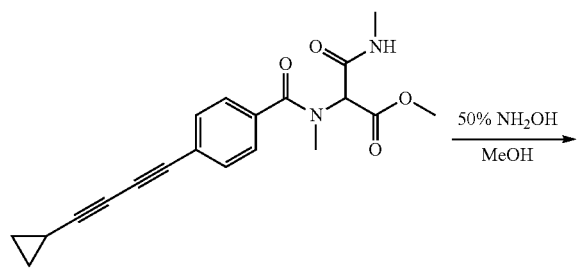

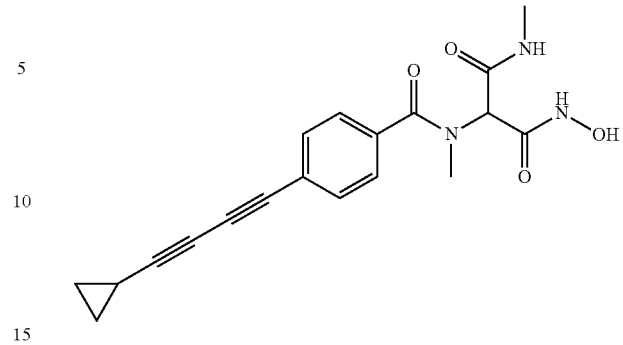

(4) To a methanol (2.0 mL) solution of 1-(4-cyclopropylbuta-1,3-diyn-1-yl)-4-{[1-methoxy-3-(methylamino)-1,3-dioxopropan-2-yl](methyl)carbamoyl}benzene (0.81 g) as obtained in Example 6-(3), a 50% aqueous solution (1.0 mL) of hydroxylamine was added under ice cooling. After the mixture was stirred for 30 minutes under ice cooling, it was stirred for 2.5 hours under water cooling. A 50% aqueous solution (1.0 mL) of hydroxylamine was added, whereafter the mixture was stirred for 30 minutes under water cooling. Ethyl acetate and water were added to the reaction mixture, and the mixture was adjusted to pH 5 with 6 mol/L of hydrochloric acid, whereafter the organic layer was isolated. The extract was washed sequentially with water and brine, and dried over anhydrous magnesium sulfate. Then, the desiccant was filtered out, and the solvent was distilled off under reduced pressure. Chloroform and IPE were added to the resulting residue, and the mixture was filtered. The resulting solid was purified by OH type silica gel column chromatography (chloroform/methanol=10/1) to obtain 2-({[4-(4-cyclopropylbuta-1,3-diyn-1-yl)phenyl]carbonyl}(methyl)amino)-N-hydroxy-N'-methylpropanediamide (Compound 507, white solid) (0.16 g, yield upon the 2 steps: 20%).

MS (ESI): 376 (M+Na)$^+$, 352 (M−H)$^−$ $^1$H NMR (400 MHz, CD$_3$ OD) δ ppm 0.73-0.80 (2 H, m), 0.87-0.95 (2 H, m), 1.41-1.50 (1 H, m), 2.80 (3 H, s), 3.04 (3 H, s), 7.30-7.57 (4 H, m)

Compounds 476, 484, 492, 493, 500, 509, 511 and 529 were synthesized by the same methods as in Example 3 with the use of the corresponding materials.

EXAMPLE 7

2-[(Biphenyl-4-ylcarbonyl)(methyl)amino]-N-hydroxy-N'-[(5-methyl-1,2-oxazol-3-yl)methyl]propanediamide (Compound 172)

[Chemical Formula 88]

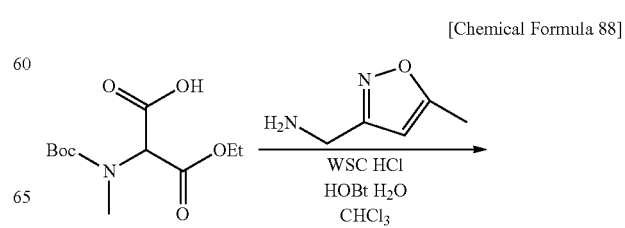

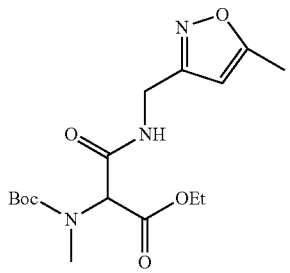

(1) N-(t-butoxycarbonyl)-O-ethyl-N-methyl-3-oxoserine (Intermediate 7-1, 2.3 g), 1-(5-methyl-1,2-oxazol-3-yl)methanamine (1.0 g), WSC.HCl (2.4 g), HOBt.H$_2$O (1.9 g), and chloroform (24 mL) were stirred overnight at room temperature. A saturated aqueous solution of sodium hydrogen carbonate was added to the reaction mixture, and the mixture was extracted with chloroform. The extract was dried over anhydrous magnesium sulfate, and the desiccant was filtered out. Then, the solvent was distilled off under reduced pressure, and the resulting residue was purified by OH type silica gel column chromatography (gradient elution with chloroform/methanol=98/2→92/8) to obtain 3-({[N-(t-butoxycarbonyl)-O-ethyl-N-methyl-3-oxoseryl]amino}methyl)-5-methyl-1,2-oxazole (pale yellow oil) (2.1 g, 67%).

MS (ESI): 378 (M+Na)$^+$, 354 (M−H)$^−$ $^1$H NMR (600 MHz, CHLOROFORM-d) δ ppm 1.24-1.34 (3 H, m), [1.38], 1.48 (9 H, br. s.), 2.39 (3 H, s), 2.96-3.06 (3 H, m), 4.21-4.30 (2 H, m), 4.44-4.57 (2 H, m), [4.63], 5.01 (1 H, br. s.), 6.00 (1 H, s), 7.57, [7.81] (1 H, br. s.)

(2) 4.0 mol/L hydrochloric acid-ethyl acetate (1.0 mL) was added to an ethyl acetate (2.0 mL) solution of 3-({[N-(t-butoxycarbonyl)-O-ethyl-N-methyl-3-oxoseryl]amino}methyl)-5-methyl-1,2-oxazole (0.30 g) as obtained in Example 7-(1), and the mixture was stirred overnight at room temperature. The reaction mixture was concentrated under reduced pressure, and chloroform (2.0 mL), TEA (0.27 g) and 4-phenylbenzoyl chloride (0.18 g) were added to the resulting residue under cooling with iced water, whereafter the mixture was stirred overnight at room temperature. The reaction mixture was purified by OH type silica gel column chromatography (gradient elution with chloroform/methanol=98/2→96/4) to obtain 3-({[N-(biphenyl-4-ylcarbonyl)-O-ethyl-N-methyl-3-oxoseryl]amino}methyl)-5-methyl-1,2-oxazole (colorless oil) (0.15 g, 40%).

MS (ESI): 458 (M+Na)$^+$, 434 (M−H)$^−$ $^1$H NMR (600 MHz, DMSO-d$_6$) δ ppm 1.22-1.30 (m, 3 H), 2.39 (3 H, s), 2.97-3.04 (3 H, m), 4.17-4.24 (2 H, m), 4.38 (2 H, d, J=5.0 Hz), [5.01], 5.64 (1 H, br. s), 6.10-6.18 (1 H, m), 7.36-7.82 (10 H, m)

[Chemical Formula 90]

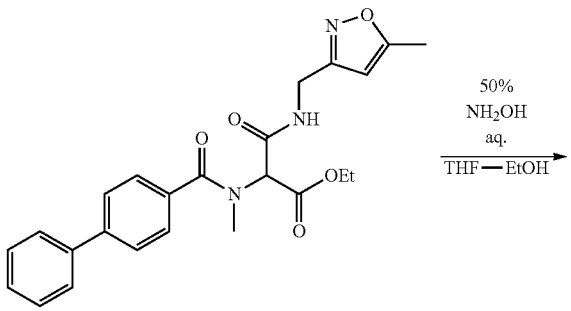

[Chemical Formula 89]

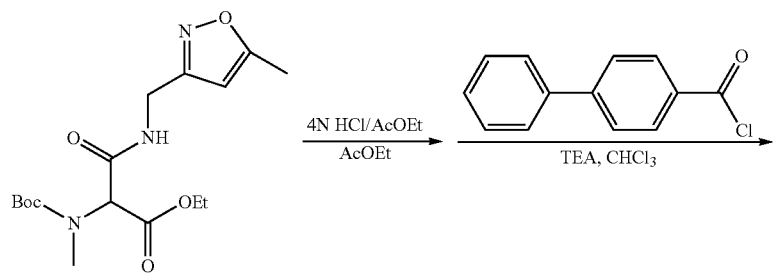

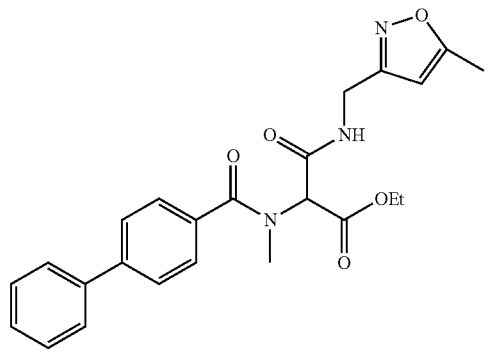

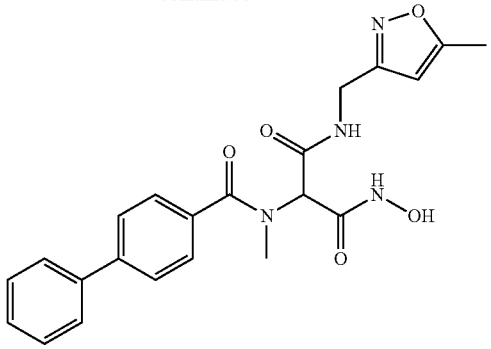

(3) Using 3-({[N-(biphenyl-4-ylcarbonyl)-O-ethyl-N-methyl-3-oxoseryl]amino}methyl)-5-methyl-1,2-oxazole (0.15 g) as obtained in Example 7-(2), the same procedure as in Example 4-(5) was performed to obtain 2-[(biphenyl-4-ylcarbonyl)(methyl)amino]-N-hydroxy-N'-[(5-methyl-1,2-oxazol-3-yl)methyl]propanediamide (Compound 172, white solid) (63 mg, 45%).

MS (ESI): 445 (M+Na)$^+$, 421 (M−H)$^-$ $^1$H NMR (600 MHz, DMSO-d$_6$) δ ppm 2.38 (3 H, s), 3.00 (3 H, s), 4.35 (2 H, br. s.) [4.75], 5.45 (1 H, br. s.), 6.19 (1 H, br. s.), 7.36-7.61 (5 H, m), 7.67-7.80 (4 H, m), 8.85 (1 H, br. s.), 9.10 (1 H, br. s.), 10.93 (1 H, br. s.)

Compounds 116, 118 to 126, 128 to 147, 149 to 152, 155 to 158, 170 to 173, 175, 177 and 178 were synthesized by the same methods as in Example 7 with the use of the corresponding materials.

EXAMPLE 8

2-[(Biphenyl-4-ylcarbonyl)amino]-N-hydroxy-N',2-dimethylpropanediamide (Compound 164)

[Chemical Formula 91]

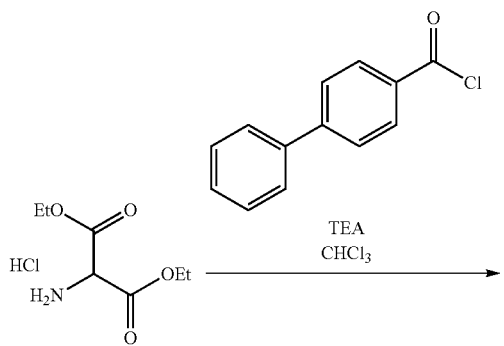

(1) 4-Phenylbenzoyl chloride (4.3 g) was added little by little to a chloroform (80 mL) solution of diethyl aminopropanedioate hydrochloride (4.3 g) and TEA (8.4 mL) under ice cooling, and the mixture was stirred for 3 hours at the same temperature. A saturated aqueous solution of sodium hydrogen carbonate was added to the reaction mixture, and the mixture was extracted with chloroform. The extract was dried over anhydrous magnesium sulfate, and the desiccant was filtered out. Then, the solvent was distilled off under reduced pressure, and the resulting residue was purified by OH type silica gel column chromatography (chloroform/methanol=20/1) to obtain diethyl [(biphenyl-4-ylcarbonyl)amino]propanedioate (white solid) (6.7 g, 95%).

MS (ESI): 356 (M+H)$^+$, 378 (M+Na)$^+$ $^1$H NMR (600 MHz, CHLOROFORM-d) δ ppm 1.35 (6 H, t, J=7.2 Hz), 4.28-4.39 (4 H, m), 5.38 (1 H, d, J=6.6 Hz), 7.16 (1 H, d, J=6.6 Hz), 7.41 (1 H, tt, J=7.5, 1.3 Hz), 7.48 (2 H, t, J=7.5 Hz), 7.63 (2 H, dd, J=7.5, 1.3 Hz), 7.70 (2 H, d, J=8.5 Hz), 7.94 (2 H, d, J=8.5 Hz)

[Chemical Formula 92]

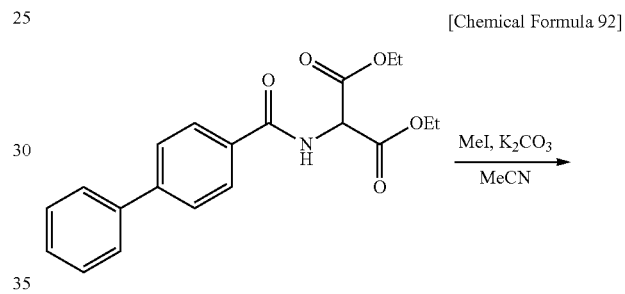

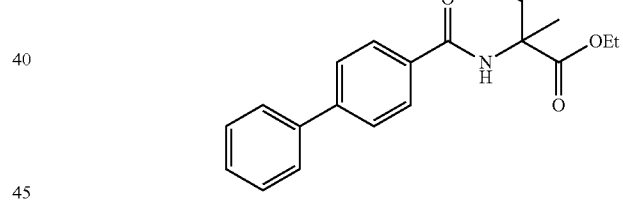

(2) Methyl iodide (0.18 g) was added to an acetonitrile (5.0 mL) suspension of diethyl [(biphenyl-4-ylcarbonyl)amino]propanedioate (0.36 g) as obtained in Example 8-(1) and potassium carbonate (0.20 g). The mixture was stirred for 14 hours at room temperature under closed conditions. Water was added to the reaction mixture, and the mixture was extracted with chloroform. The extract was dried over anhydrous magnesium sulfate, and the desiccant was filtered out. Then, the solvent was distilled off under reduced pressure, and the resulting residue was purified by OH type silica gel column chromatography (gradient elusion with hexane/ethyl acetate=80/20→50/50) to obtain diethyl [(biphenyl-4-ylcarbonyl)amino]methyl)propanedioate (white solid) (0.24 g, 66%).

MS (ESI): 370 (M+H)$^+$ $^1$H NMR (600 MHz, CHLOROFORM-d) δ ppm 1.27 (6 H, t, J=7.1 Hz), 1.88 (3 H, s), 4.24-4.33 (4 H, m), 7.38 (1 H, tt, J=7.7, 1.2 Hz), 7.46 (2 H, t, J=7.7 Hz), 7.58 (1 H, br. s), 7.61 (2 H, dd, J=7.7, 1.2 Hz), 7.67 (2 H, d, J=8.4 Hz), 7.89 (2 H, d, J=8.4 Hz)

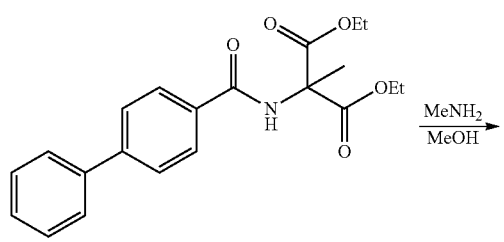

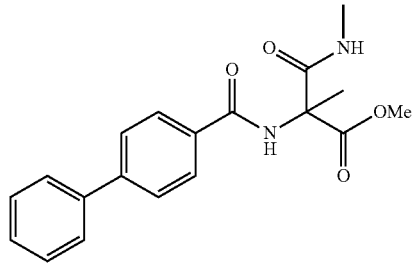

(3) A 40% methylamine-methanol solution (61 mg) was added to a methanol (3.0 mL) solution of diethyl [(biphenyl-4-ylcarbonyl)amino]methyl)propanedioate (0.24 g) as obtained in Example 8-(2), and the mixture was stirred overnight at room temperature under closed conditions. The reaction mixture was concentrated under reduced pressure, and the resulting residue was purified by silica gel column chromatography (gradient elution with hexane/ethyl acetate=50/50→30/70) to obtain 4-{[1-methoxy-2-methyl-3-(methylamino)-1,3-dioxopropan-2-yl]carbamoyl}biphenyl (white solid) (70 mg, 31%).

MS (ESI): 341 (M+Na)$^+$, 375 (M+Cl)$^-$ $^1$H NMR (600 MHz, CHLOROFORM-d) δ ppm 1.92 (3 H, s), 2.89-2.92 (3 H, m), 3.79 (3 H, s), 6.34-6.39 (1 H, m), 7.37-7.41 (1 H, m), 7.45-7.49 (2 H, m), 7.60-7.64 (2 H, m), 7.66-7.70 (2 H, m), 7.89 (1 H, br. s), 7.91-7.94 (2 H, m)

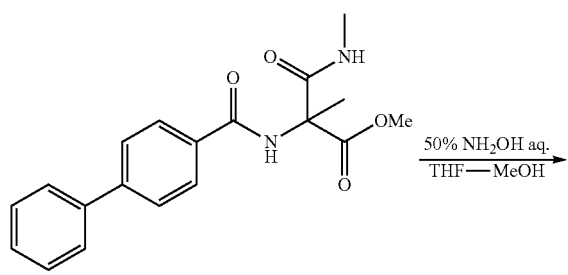

(4) Using 4-{[1-methoxy-2-methyl-3-(methylamino)-1,3-dioxopropan-2-yl]carbamoyl}biphenyl (70 mg) as obtained in Example 8-(3), the same procedure as in Example 4-(5) was performed to obtain 2-[(biphenyl-4-ylcarbonyl)amino]-N-hydroxy-N', 2-dimethylpropanediamide (Compound 164, white solid) (10 mg, 15%).

MS (ESI): 364 (M+Na)$^+$, 340 (M−H)$^-$ $^1$H NMR (600 MHz, DMSO-d$_6$) δ ppm 1.66 (3 H, s), 2.63 (3 H, d, J=4.6 Hz), 7.40-7.44 (1 H, m), 7.48-7.54 (2 H, m), 7.75 (2 H, d, J=8.7 Hz), 7.80 (2 H, d, J=8.3 Hz), 7.96 (2 H, d, J=8.3 Hz), 8.16 (1 H, br. s.), 8.90 (1 H, br. s.), 10.89 (1 H, br. s.)

EXAMPLE 9

2-[(Biphenyl-4-ylcarbonyl)(cyclopropyl)amino]-N-hydroxy-N'-methylpropanediamide (Compound 127)

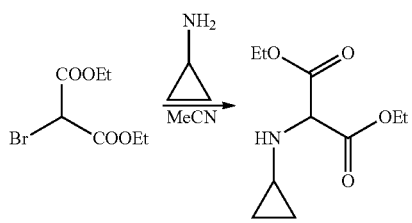

(1) Cyclopropylamine (0.30 mL) was added to an acetonitrile (10 mL) solution of diethyl bromopropanedioate (1.0 g), and the mixture was stirred for 16 hours at room temperature. The precipitated solid was filtered out, and the filtrate was concentrated under reduced pressure. Then, the resulting residue was purified by OH type silica gel column chromatography (gradient elution with hexane/ethyl acetate=90/10→70/30) to obtain diethyl (cyclopropylamino)propanedioate (colorless oil) (0.57 g, 63%).

MS (ESI): 216 (M+H)$^+$, 214 (M+H)$^-$ $^1$H NMR (600 MHz, CHLOROFORM-d) δ ppm 0.37-0.52 (4 H, m), 1.22-1.34 (6 H, m), 2.15-2.22 (1 H, m), 4.17-4.28 (4 H, m), 4.82 (1 H, s)

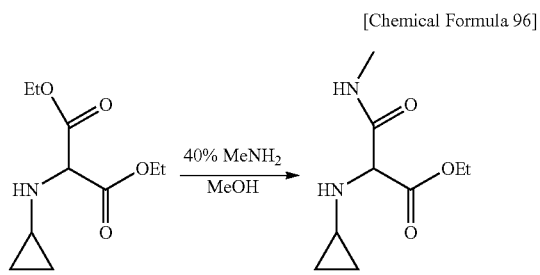

(2) A 40% methylamine-methanol solution (86 μL) was added to a methanol (2.0 mL) solution of diethyl (cyclopropylamino)propanedioate (0.20 g) as obtained in Example 9-(1), and the mixture was stirred for 5 days at room temperature, whereafter the reaction mixture was concentrated. The resulting residue was purified twice by OH type silica gel column chromatography (gradient elution with chloroform/methanol=100/0→95/5) to obtain N$^2$-cyclopropyl-N,O-dimethyl-3-oxoseriamide (colorless oil) (58 mg, 31%).

MS (ESI): 201 (M+H)$^+$ $^1$H NMR (600 MHz, CHLOROFORM-d) δ ppm 0.29-0.34 (1 H, m), 0.42-0.53 (3 H, m), 2.14-2.20 (1 H, m), 2.80-2.83 (3 H, m), 3.83 (3 H, s), 4.00 (1 H, s), 6.94 (1 H, br. s.)

[Chemical Formula 97]

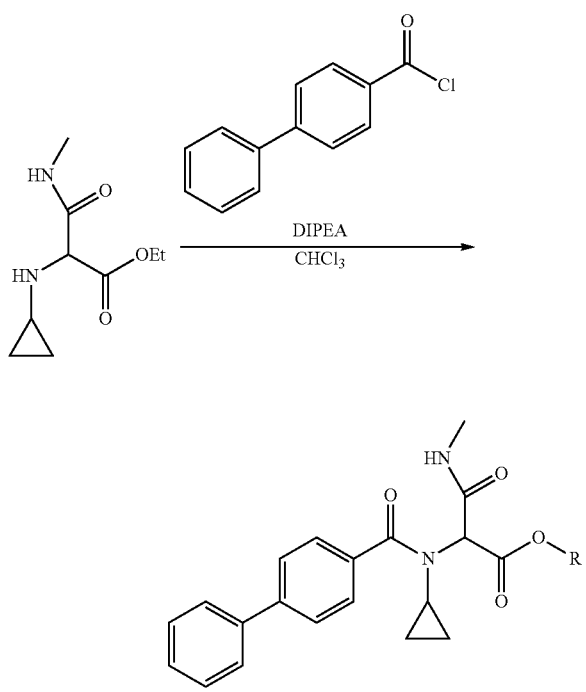

R = Et, Me (3) Under ice cooling, DIPEA (0.11 mL) and 4-phenylbenzoyl chloride (78 mg) were added to a chloroform (0.70 mL) solution of $N^2$-cyclopropyl-N,O-dimethyl-3-oxoseriamide (70 mg) as obtained in Example 9-(2). The mixture was stirred for 15 hours at room temperature and for 4.5 hours under ice cooling, whereafter the reaction mixture was concentrated. The resulting residue was purified twice by OH type silica gel column chromatography (gradient elution with chloroform/methanol=100/0→95/5) to obtain a mixture of 4-{cyclopropyl[1-ethoxy-3-(methylamino)-1,3-dioxopropan-2-yl]carbamoyl}biphenyl and 4-{cyclopropyl[1-methoxy-3-(methylamino)-1,3-dioxopropan-2-yl]carbamoyl}biphenyl (yellow oil) (34 mg, 26%).

MS (ESI): 403 (M+Na)⁺, 379 (M–H)⁻, 389 ((M+Na)⁺, 365 (M–H)⁻

¹H NMR (600 MHz, CHLOROFORM-d) δ ppm 0.41-0.70 (4 H, m), 1.24-1.36 (3 H, m), 2.13-2.21 (1 H, m), [2.80], 2.89 (3 H, d, J=5.0 Hz), [3.81, [3.82]] (3 H, s), 4.21-4.33 (2 H, m), 4.61, [4.65] (1 H, s), 7.35-7.49 (3 H, m), 7.58-7.95 (7 H, m)

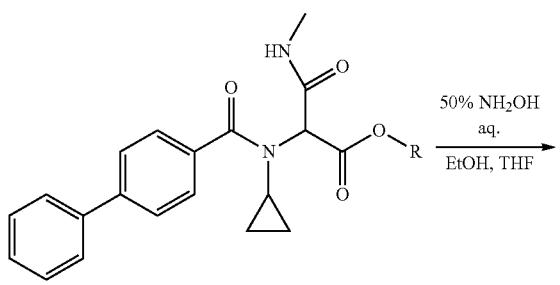

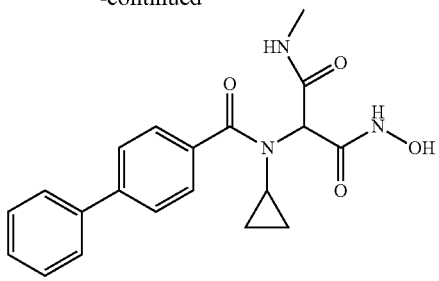

R = Et, Me (4) Using the mixture (34 mg) of 4-{cyclopropyl[1-ethoxy-3-(methylamino)-1,3-dioxopropan-2-yl]carbamoyl}biphenyl and 4-{cyclopropyl[1-methoxy-3-(methylamino)-1,3-dioxopropan-2-yl]carbamoyl}biphenyl as obtained in Example 9-(3), the same procedure as in Example 4-(5) was performed to obtain 2-[(biphenyl-4-ylcarbonyl)(cyclopropyl)amino]-N-hydroxy-N'-methylpropanediamide (Compound 127, white solid) (3.2 mg, 10%).

MS (ESI): 390 (M+Na)⁺, 366 (M–H)⁻

¹H NMR (600 MHz, CHLOROFORM-d) δ ppm 0.44-0.69 (4 H, m), 2.88 (3 H, d, J=4.6 Hz), 3.07-3.13 (1 H, m), 5.18 (1 H, s), 7.02-7.19 (1 H, m), 7.36-7.42 (1 H, m), 7.44-7.50 (2 H, m), 7.60-7.70 (4 H, m), 7.76 (2 H, d, J=8.3 Hz), 10.92 (1 H, br. s.)

Compounds 154 and 198 were synthesized by the same methods as in Example 9 with the use of the corresponding materials.

EXAMPLE 10

2-[{[4-({4-[(Cyclopropylamino)methyl]phenyl}ethynyl)phenyl]carbonyl}(methyl)amino]-n-hydroxy-n'-methylpropanediamide (Compound 301)

[Chemical Formula 99]

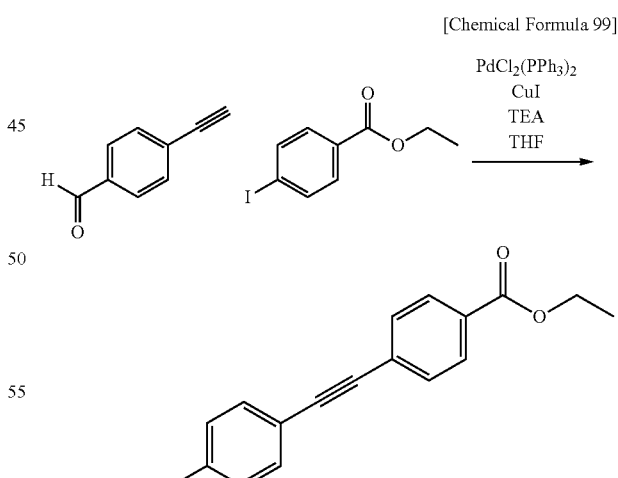

(1) TEA (46 mL) was added to a THF (0.40 L) suspension of ethyl 4-iodobenzoate (30 g), 4-ethynylbenzaldehyde (14 g) obtained by the synthesis method described in the literature (Tetrahedron Letters, 2007, Vol. 48(33), pp. 5817-5820), PdCl₂(PPh₃)₂ (3.9 g), and CuI (2.1 g), and the mixture was stirred for 4 hours at 45° C. After the reaction mixture was allowed to cool, water was added, and the mixture was extracted with ethyl acetate. The organic layer was washed with brine, and dried over anhydrous sodium sulfate. The desiccant was filtered out, and the solvent was distilled off under reduced pressure. Hexane/ethyl acetate (1:1 (v/v)) was added to the resulting residue, the mixture was stirred, and then the precipitate was filtered off and dried. The filtrate was concentrated, and then the same procedure was performed. As a result, ethyl 4-[(4-formylphenyl)ethynyl]benzoate (yellow solid) was obtained (27 g, 88%).

ME (ESI/APCI Dual): 279 (M+H)$^+$ $^1$H NMR (200 MHz, CHLOROFORM-d) δ ppm 1.41 (3 H, t, J=7.3 Hz), 4.40 (2 H, q, J=7.3 Hz), 7.52-7.78 (4 H, m), 7.81-8.18 (4 H, m), 10.04 (1 H, s)

[Chemical Formula 100]

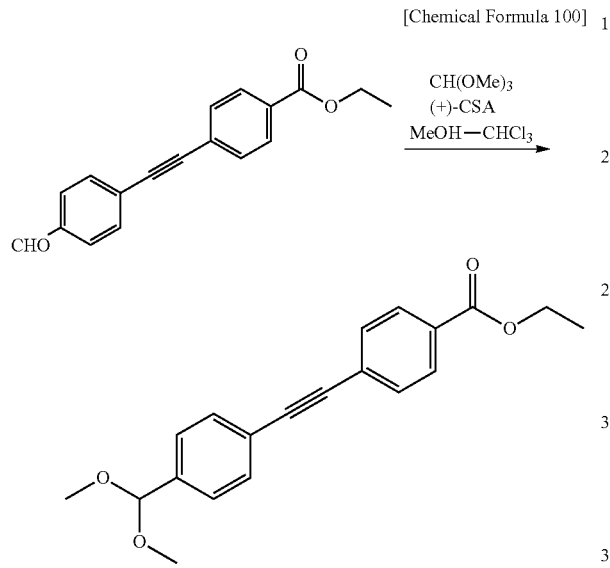

(2) Trimethyl orthoformate (51 g) and (+)-CSA (2.3 g) were added to a methanol (0.40 L)-chloroform (0.10 L) mixed solution of ethyl 4-[(4-formylphenyl)ethynyl]benzoate (27 g) as obtained in Example 10-(1), and the mixture was stirred for 3 hours at room temperature. A saturated aqueous solution of sodium hydrogen carbonate was added to the reaction mixture, and the mixture was extracted with chloroform. The organic layer was dried over anhydrous magnesium sulfate, and then the desiccant was filtered out. Then, the solvent was distilled off under reduced pressure, and the resulting residue was purified by OH type silica gel chromatography (gradient elution with hexane/ethyl acetate=95/5→80/20) to obtain ethyl 4-{[4-(dimethoxymethyl)phenyl]ethynyl}benzoate (white solid) (21 g, 67%).

MS (ESI/APCI Dual): 325 (M+H)$^+$ $^1$H NMR (200 MHz, DMSO-d$_6$) δ ppm 1.33 (3 H, t, J=7.2 Hz), 3.26 (6 H, s), 4.33 (2 H, q, J=7.2 Hz), 5.43 (1 H, s), 7.36-7.78 (6 H, m), 7.91-8.07 (2 H, m)

[Chemical Formula 101]

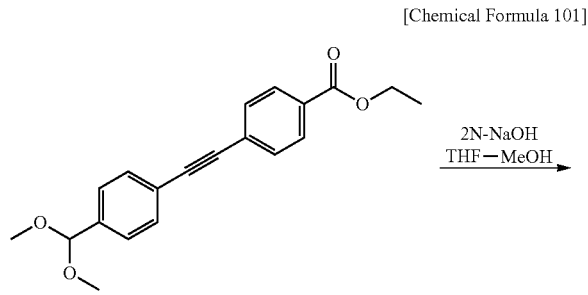

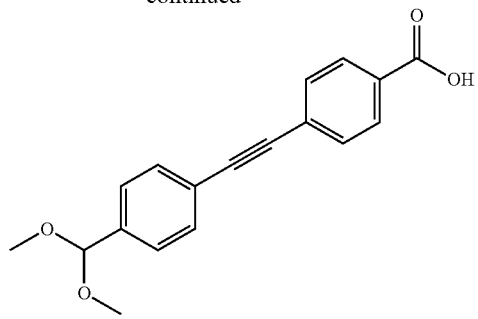

(3) A 2.0 mol/L sodium hydroxide aqueous solution (0.10 L) was added to a THF (0.25 L)-methanol (0.25 L) solution of ethyl 4-{[4-(dimethoxymethyl)phenyl]ethynyl}benzoate (21 g) as obtained in Example 10-(2), and the mixture was stirred for 3 hours at room temperature. The solvent was distilled off, and then water and acetic acid were added to the residue to adjust it to pH 4. The precipitate was filtered off and dried. Hexane/ethyl acetate (3:1 (v/v)) was added, and the mixture was stirred for a while. The precipitate was filtered off and dried to obtain 4-{[4-(dimethoxymethyl)phenyl]ethynyl}benzoic acid (white solid) (15 g, 75%).

MS (ESI/APCI Dual): 295 (M-H)$^-$ $^1$H NMR (200 MHz, DMSO-d$_6$) δ ppm 3.26 (6 H, s), 5.43 (1 H, s), 7.36-7.67 (6 H, m), 7.85-8.00 (2 H, m)

[Chemical Formula 102]

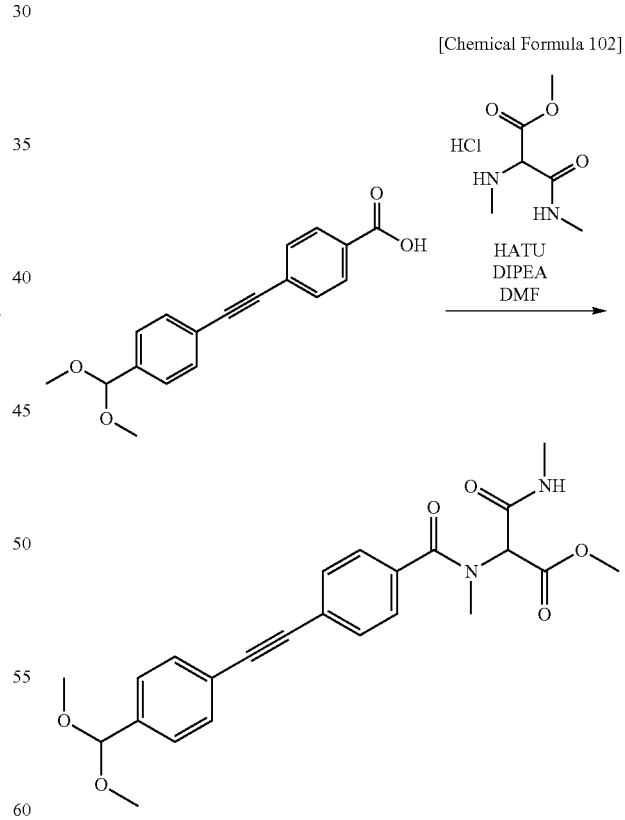

(4) DIPEA (8.8 mL) and N,N$^2$,O-trimethyl-3-oxoserinamide hydrochloride (Intermediate 5-2, 3.3 g) were added to a DMF (50 mL) solution of 4-{[4-(dimethoxymethyl)phenyl]ethynyl}benzoic acid (5.0 g) as obtained in Example 10-(3) and HATU (9.6 g), and the mixture was stirred for 2 hours at 80° C. A saturated aqueous solution of sodium hydrogen carbonate was added to the reaction mixture, and the mixture was extracted with ethyl acetate. The organic layer was washed with brine, and dried over anhydrous magnesium sulfate. The desiccant was filtered out, and the solvent was distilled off under reduced pressure. The resulting residue was purified by NH type silica gel chromatography (gradient elution with hexane/ethyl acetate=50/50→0/100) to obtain 1-(dimethoxymethyl)-4-[(4-{[1-methoxy-3-(methylamino)-1,3-dioxopropan-2-yl](methyl)carbamoyl}phenyl)ethynyl]benzene (yellow oil) (6.6 g, 89%).

MS (ESI/APCI Dual): 439 (M+H)$^+$, 461 (M+Na)$^+$, 437 (M−H)$^−$ $^1$H NMR (200 MHz, DMSO-d$_6$) δ ppm 2.69 (3 H, d, J=4.4 Hz), 2.93 (3 H, s), 3.26 (6 H, s), 3.72 (3 H, s), 5.43 (1 H, s), 5.58 (1 H, s), 7.24-7.73 (8 H, m), 8.50 (1 H, br. d, J=4.4 Hz)

[Chemical Formula 103]

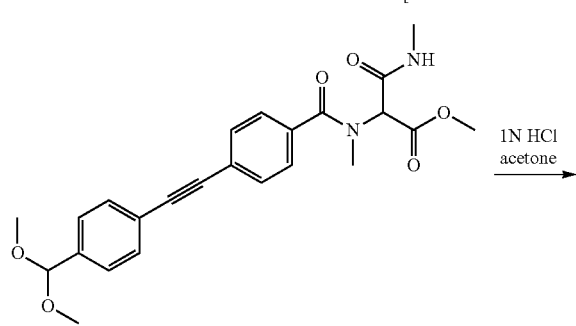

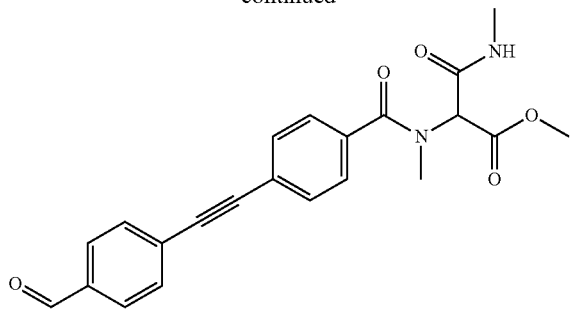

(5) Under ice cooling, a 1.0 mol/L hydrochloric acid aqueous solution (4.0 mL) was added to an acetone (50 mL) solution of 1-(dimethoxymethyl)-4-[(4-{[1-methoxy-3-(methylamino)-1,3-dioxopropan-2-yl](methyl)carbamoyl}phenyl)ethynyl]benzene (6.5 g) as obtained in Example 10-(4), and the mixture was stirred for 15 hours at room temperature. The solvent was distilled off, and then hexane/AcOEt (20:1 (v/v)) was added to the residue, whereafter the mixture was stirred for a while. Then, the precipitate was filtered off and dried to obtain 1-formyl-4-[(4-{[1-methoxy-3-(methylamino)-1,3-dioxopropan-2-yl](methyl)carbamoyl}phenyl)ethynyl]benzene (white solid) (4.6 g, 79%).

MS (ESI/APCI Dual): 393 (M+H)$^+$, 415 (M+Na)$^+$, 391 (M−H)$^−$ $^1$H NMR (200 MHz, CHLOROFORM-d) δ ppm 2.90 (3 H, d, J=4.8 Hz), 3.15 (3 H, s), 3.86 (3 H, s), 5.47 (1 H, br. s), 7.20 (1 H, br. s.), 7.44-7.97 (8 H, m), 10.03 (1 H, s)

[Chemical Formula 104]

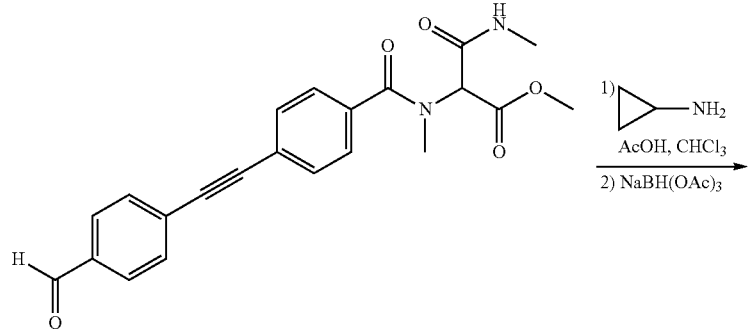

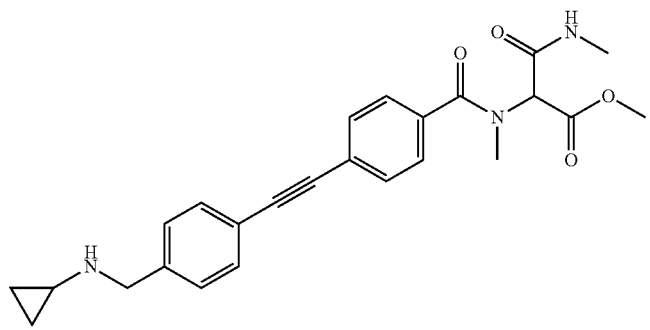

(6) Cyclopropylamine (0.15 g) and acetic acid (0.16 g) were added to a chloroform (20 mL) solution of 1-formyl-4-[(4-{[1-methoxy-3-(methylamino)-1,3-dioxopropan-2-yl](methyl)carbamoyl}phenyl)ethynyl]benzene (1.0 g) as obtained in Example 10-(5), and the mixture was stirred for 2.5 hours at room temperature. Then, sodium triacetoxyborohydride (0.89 g) was added, and the mixture was stirred for 15 hours at room temperature. A saturated aqueous solution of sodium hydrogen carbonate was added to the reaction mixture, and then the mixture was extracted with chloroform. The organic layer was washed with brine, and dried over anhydrous sodium sulfate. Then, the desiccant was filtered out, and the solvent was distilled off under reduced pressure. The resulting residue was purified by OH type silica gel chromatography (gradient elution with hexane/ethyl acetate=34/66→1/100) to obtain 1-[(cyclopropylamino)methyl]-4-[(4-{[1-methoxy-3-(methylamino)-1,3-dioxopropan-2-yl](methyl)carbamoyl}phenyl)ethynyl]benzene (colorless foam) (0.84 g, 74%).

MS (ESI/APCI Dual): 434 (M+H)$^+$, 456 (M+Na)$^+$, 432 (M−H)$^−$ $^1$H NMR (200 MHz, CHLOROFORM-d) δ ppm 0.34-0.49 (4 H, m), 2.10-2.20 (1 H, m), 2.89 (3 H, d, J=4.8 Hz), 3.14 (3 H, s), 3.84 (3 H, s), 3.86 (2 H, s), 5.48 (1 H, s), 7.23-7.34 (3 H, m), 7.48-7.60 (6 H, m)

[Chemical Formula 105]

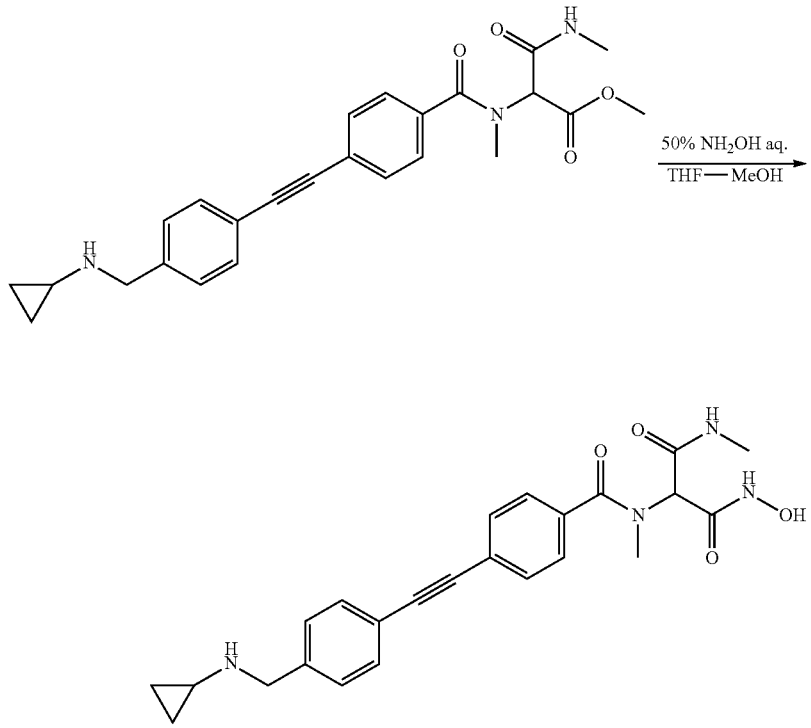

(7) Using 1-[(cyclopropylamino)methyl]-4-[(4-{[1-methoxy-3-(methylamino)-1,3-dioxopropan-2-yl](methyl)carbamoyl}phenyl)ethynyl]benzene (0.84 g) as obtained in Example 10-(6), the same procedure as in Example 4-(5) was performed to obtain 2-[{[4-({4-[(cyclopropylamino)methyl]phenyl}ethynyl)phenyl]carbonyl}(methyl)amino]-N-hydroxy-N'-methylpropanediamide (Compound 301, white solid) (0.56 g, 84%).

MS (ESI/APCI Dual): 435 (M+H)$^+$, 457 (M+Na)$^+$, 433 (M−H)$^−$ $^1$H NMR (600 MHz, CD$_3$OD) δ ppm 0.38-0.41 (2 H, m), 0.46-0.49 (2 H, m), 2.14 (1 H, tt, J=6.9, 3.6 Hz), 2.82 (3 H, br. s.), 3.08 (3 H, s), 3.83 (2 H, s), 7.38-7.39 (2 H, m), 7.42-7.64 (6 H, m)

Compounds 300, 302 to 305, 313 to 318, 321 to 323, 325 to 334, 336, 337, 353 to 356, 359 to 363, 365, 366, 368 to 374, 378, 383, 384, 386 to 388, 391 to 393, 482, 485, 486, 489, 490, 494, 495, 497, 505, 510, 512, 513, 515, 522, 524, 525, 527, 530, 532, 533, 535, 537 to 540, 542, 543, 546, 551, and 552 were synthesized by the same methods as in Example 10 with the use of the corresponding materials.

EXAMPLE 11

2-{[(4-{[4-(2,3-dihydroxypropoxy)phenyl]ethynyl}phenyl)carbonyl](methyl)amino}-N-hydroxy-N'-methylpropanediamide (Compound 320)

MS (ESI): 349 (M+Na)$^+$, 361 (M+Cl)$^-$ $^1$H NMR (200 MHz, DMSO-d$_6$) δ ppm 3.45 (2 H, t, J=5.7 Hz), 3.73-4.14 (6 H, m), 4.62-4.74 (1 H, m), 4.98 (1 H, d, J=4.8 Hz), 7.01 (2 H, d, J=8.8 Hz), 7.44-7.72 (4 H, m), 7.98 (2 H, d, J=8.8 Hz)

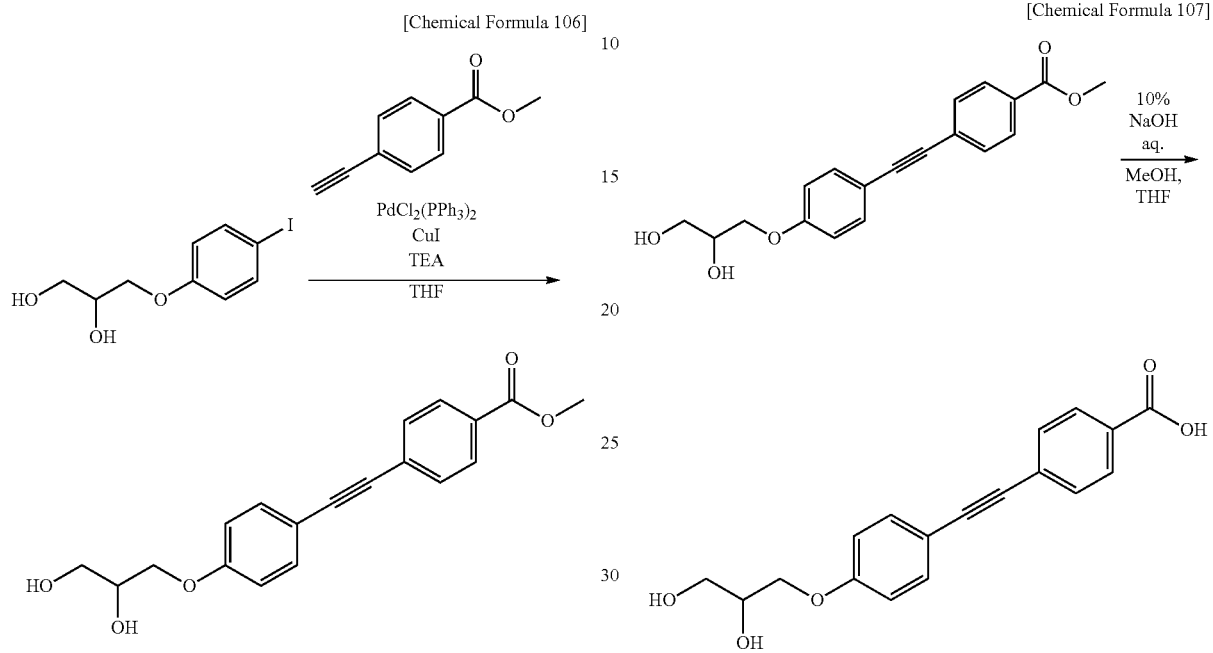

(1) Methyl 4-ethynylbenzoate (0.95 g) obtained by the same method as the synthesis method described in the literature (Journal of the American Chemical Society, 2010, Vol. 132(30), pp. 10391-10397), PdCl$_2$(PPh$_3$)$_2$ (0.21 g), CuI (0.11 g) and TEA (2.5 mL) were added to a THF (35 mL) solution of 3-(4-iodophenoxy)propane-1,2-diol (1.8 g) obtained by the same method as the synthesis method described in the literature (Russian Journal of Organic Chemistry (Translation of Zhurnal Organicheskoi Khimii), 2002, Vol. 38(2), pp. 213-219), and the mixture was stirred for 2 hours at room temperature. The reaction mixture was concentrated, and ethyl acetate-chloroform was added. The precipitated solid was filtered off and dried to obtain methyl 4-{[4-(2,3-dihydroxypropoxy)phenyl]ethynyl}benzoate (orange solid) (0.92 g, 47%).

(2) A 10% aqueous solution (5.5 mL) of sodium hydroxide was added to a THF (25 mL)-MeOH (15 mL) solution of methyl 4-{[4-(2,3-dihydroxypropoxy)phenyl]ethynyl}benzoate (0.92 g) as obtained in Example 11-(1), and the mixture was stirred for 3.5 hours at room temperature. Then, acetic acid (1.2 mL) was added for neutralization. The reaction mixture was concentrated, and water was added. The precipitated solid was filtered off and dried to obtain 4-{[4-(2,3-dihydroxypropoxy)phenyl]ethynyl}benzoic acid (light green solid) (0.80 g, 91%).

MS (ESI): 335 (M+Na)$^+$, 311 (M−H)$^-$ $^1$H NMR (200 MHz, DMSO-d$_6$) δ ppm 3.42-3.53 (3 H, m), 3.65-4.17 (4 H, m), 6.80-7.98 (8 H, m)

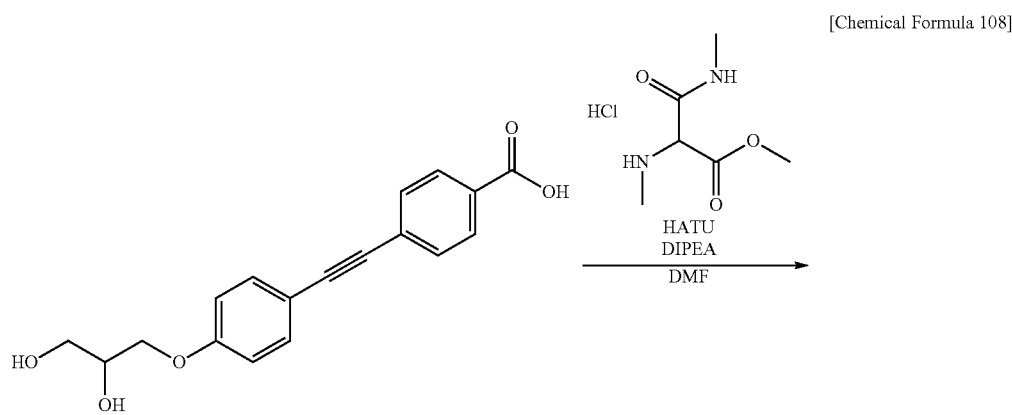

-continued

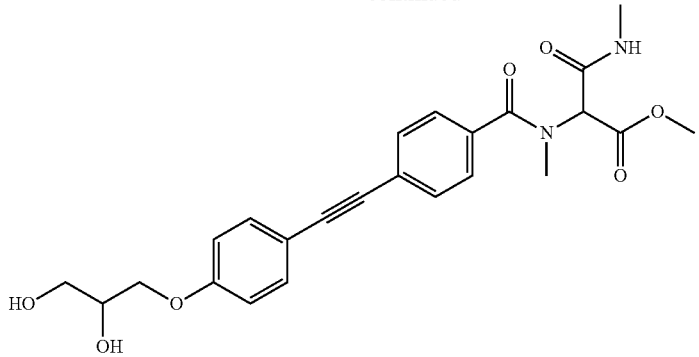

(3) N,N²,O-trimethyl-3-oxoserinamide hydrochloride (Intermediate 5-2, 0.13 g), HATU (0.17 g) and DIPEA (0.33 mL) were added to a DMF (2.0 mL) solution of 4-{[4-(2,3-dihydroxypropoxy)phenyl]ethynyl}benzoic acid (0.20 g) as obtained in Example 11-(2), and the mixture was stirred for 1 hour at 80° C. A saturated aqueous solution of sodium hydrogen carbonate was added to the reaction mixture, and the mixture was extracted with chloroform. The organic layer was washed with brine, and dried over anhydrous magnesium sulfate. The desiccant was filtered out, and the solvent was distilled off under reduced pressure. The resulting residue was purified by NH type silica gel column chromatography (gradient elution with ethyl acetate/methanol=99/1→88/12) to obtain 1-(2,3-dihydroxypropoxy)-4-[(4-{[1-methoxy-3-(methylamino)-1,3-dioxopropan-2-yl](methyl) carbamoyl}phenyl)ethynyl]benzene (white solid) (23 mg, 8.0%).

MS (ESI): 477 (M+Na)⁺, 453 (M−H)⁻

¹H NMR (600 MHz, CHLOROFORM-d) δ ppm 2.86-2.93 (3 H, m), 3.15 (3 H, s), 3.83 (3 H, br. s.), 4.01-4.18 (5 H, m), 5.45 (1 H, s), 6.85-6.95 (2 H, m), 7.17-7.23 (1 H, m), 7.42-7.59 (6 H, m)

[Chemical Formula 109]

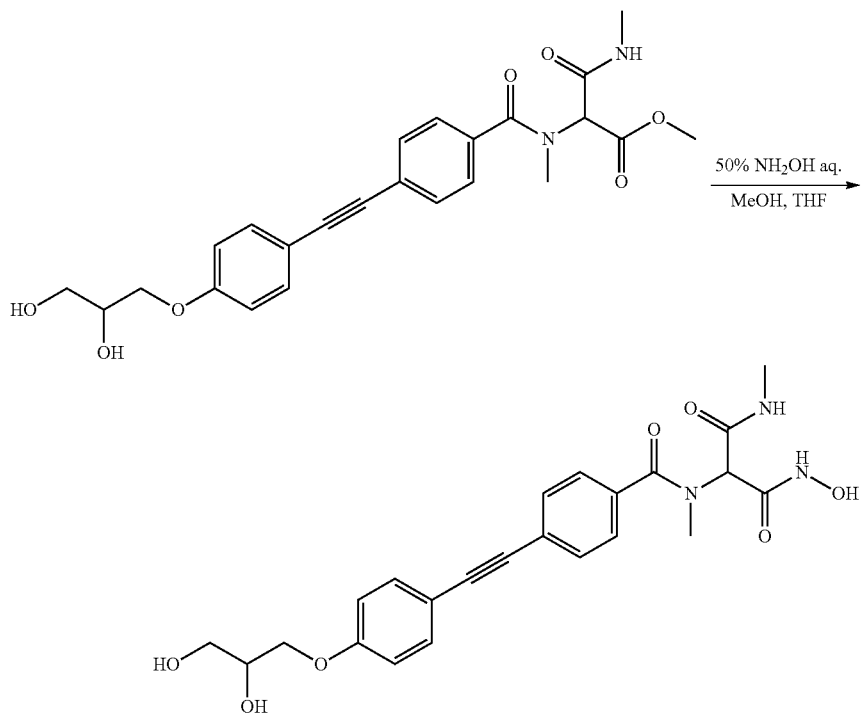

(4) Using 1-(2,3-dihydroxypropoxy)-4-[(4-{[1-methoxy-3-(methylamino)-1,3-dioxopropan-2-yl](methyl) carbamoyl}phenyl)ethynyl]benzene (23 mg) as obtained in Example 11-(3), the same procedure as in Example 4-(5) was performed to obtain 2-{[(4-{[4-(2,3-dihydroxypropoxy)phenyl]ethynyl}phenyl)carbonyl](methyl)amino}-N-hydroxy-N'-methylpropanediamide (Compound 320, white solid) (3.0 mg, 14%).

MS (ESI): 478 (M+Na)⁺, 454 (M−H)⁻

¹H NMR (600 MHz, CD₃OD) δ ppm 2.82 (3 H, br. s.), 3.08 (3 H, s), 3.61-3.73 (2 H, m), 3.93-4.05 (2 H, m), 4.06-4.14 (1 H, m), 6.98 (2 H, d, J=9.2 Hz), 7.40-7.65 (6 H, m)

Compound 335 was synthesized by the same methods as in Example 11 using the corresponding materials.

EXAMPLE 12

2-[(Biphenyl-4-ylcarbonyl)(methyl)amino]-N-hydroxy-N',2-dimethylpropanediamide (Compound 324)

[Chemical Formula 110]

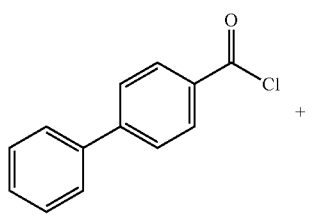

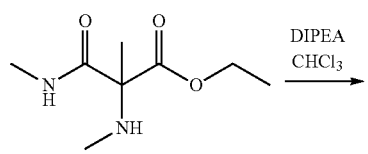

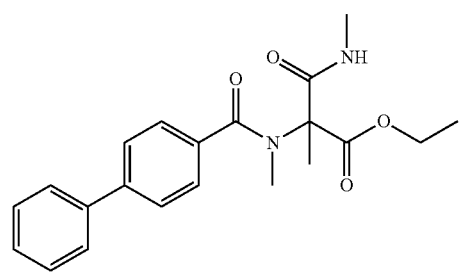

[Chemical Formula 111]

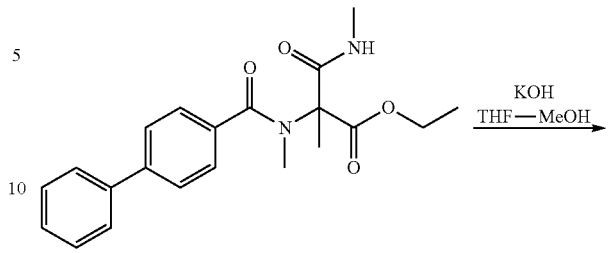

(1) DIPEA (1.0 mL) and 4-phenylbenzoyl chloride (0.50 g) were added in this order to a chloroform (10 mL) solution of O-ethyl-N,N²,2-trimethyl-3-oxoserinamide (Intermediate 9-1, 0.69 g), and the mixture was stirred for 5 hours at room temperature. A saturated aqueous solution of sodium hydrogen carbonate was added to the reaction mixture, and the mixture was extracted with chloroform. The organic layer was dried over anhydrous magnesium sulfate, whereafter the desiccant was filtered out, and the solvent was distilled off under reduced pressure. The resulting residue was purified by OH type silica gel chromatography (gradient elution with hexane/ethyl acetate=60/40→25/75) to obtain 4-{[1-ethoxy-2-methyl-3-(methylamino)-1,3-dioxopropan-2-yl](methyl)carbamoyl}biphenyl (colorless oil) (0.79 g, 66%).

MS (ESI/APCI Dual): 391 (M+Na)⁺

¹H NMR (600 MHz, CHLOROFORM-d) δ ppm 1.28 (3 H, t, J=7.1 Hz), 1.78 (3 H, s), 2.90 (3 H, d, J=5.0 Hz), 3.19 (3 H, s), 4.13-4.32 (2 H, m), 7.33-7.50 (3 H, m), 7.52-7.70 (6 H, m), 8.14-8.24 (1 H, m)

(2) A 0.84 mol/L potassium hydroxide aqueous solution (3.0 mL) was added to an ethanol (3.0 mL)-THF (3.0 mL) solution of 4-{[1-ethoxy-2-methyl-3-(methylamino)-1,3-dioxopropan-2-yl](methyl)carbamoyl}biphenyl (0.30 g) as obtained in Example 12-(1), and the mixture was stirred for 4.5 hours at room temperature. Under ice cooling, water and a 2.0 mol/L potassium hydrogen sulfate aqueous solution were added to adjust the mixture to pH 7, followed by extracting the mixture with chloroform. The organic layer was dried over anhydrous magnesium sulfate, and then the desiccant was filtered out. The solvent was distilled off under reduced pressure to obtain 4-{[2-carboxy-1-(methylamino)-1-oxopropan-2-yl](methyl)carbamoyl}biphenyl (orange solid) (0.29 g, 82%).

MS (ESI/APCI Dual): 363 (M+Na)⁺, 295 (M-CO₂-H)⁻

¹H NMR (600 MHz, CHLOROFORM-d) δ ppm 1.85 (3 H, s), 2.89 (3 H, d, J=4.6 Hz), 3.34 (3 H, s), 6.68 (1 H, br. s.), 7.34-7.51 (3 H, m), 7.53-7.70 (6 H, m)

[Chemical Formula 112]

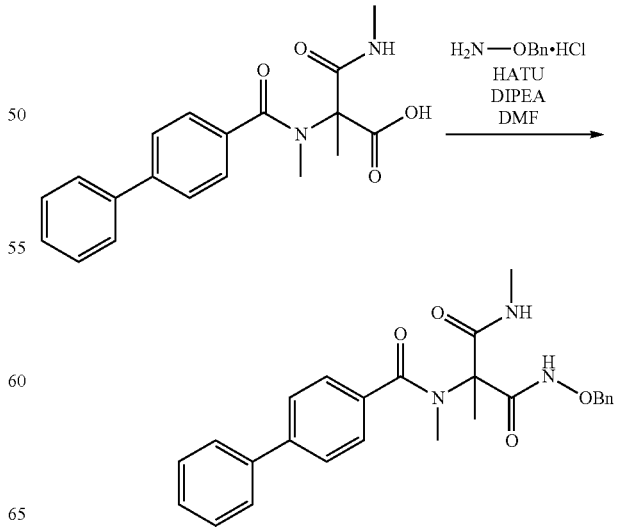

(3) DIPEA (0.30 mL), HATU (0.35 g) and O-benzylhydroxylamine hydrochloride (0.14 g) were added in this order, under ice cooling, to a DMF (5.0 mL) solution of 4-{[2-carboxy-1-(methylamino)-1-oxopropan-2-yl](methyl)carbamoyl}biphenyl (0.23 g) as obtained in Example 12-(2), and the mixture was stirred for 1 hour under ice cooling and for 3 hours at room temperature. A saturated aqueous solution of sodium hydrogen carbonate was added to the reaction mixture, and the mixture was extracted with ethyl acetate. The organic layer was dried over anhydrous magnesium sulfate, whereafter the desiccant was filtered out, and the solvent was distilled off under reduced pressure. The resulting residue was purified by OH type silica gel chromatography (gradient elution with hexane/ethyl acetate=70/30→0/100) and (gradient elution with chloroform/methanol=98/2→95/5) to obtain N-(benzyloxy)-2-[(biphenyl-4-ylcarbonyl)(methyl)amino]-N',2-dimethylpropanediamide (light brown oil) (0.22 g, 75%).

MS (ESI/APCI Dual): 468 (M+Na)$^+$, 444 (M−H)$^−$, $^1$H NMR (600 MHz, CHLOROFORM-d) δ ppm 1.78 (3 H, s), 2.84 (3 H, d, J=4.6 Hz), 3.21 (3 H, s), [4.84], 4.94 (2 H, s), 7.14-7.23 (1 H, m), 7.28-7.54 (10 H, m), 7.57-7.66 (4 H, m), 10.14 (1 H, s)

[Chemical Formula 113]

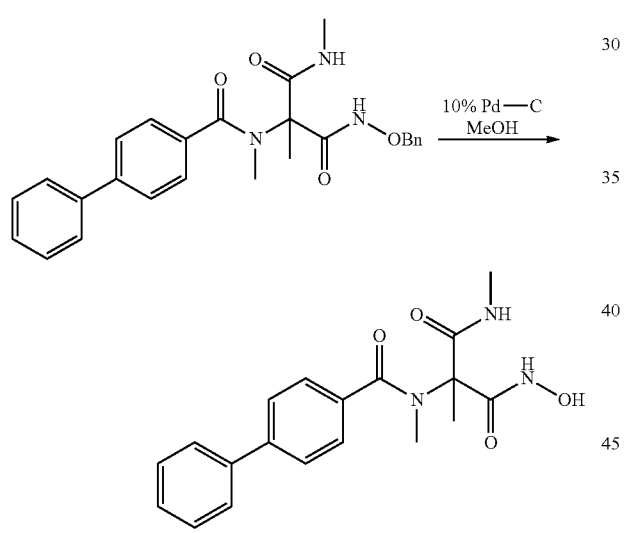

(4) 10% Pd—C (36 mg) was added to a methanol (3.0 mL) solution of N-(benzyloxy)-2-[(biphenyl-4-ylcarbonyl)(methyl)amino]-N',2-dimethylpropanediamide (0.10 g) as obtained in Example 12-(3), and the mixture was stirred in a hydrogen atmosphere for 4 hours at room temperature. The reaction mixture was filtered through Celite, and the solvent was distilled off. The residue was purified by preparative silica gel thin-layer chromatography (chloroform/methanol=14/1) to obtain 2-[(biphenyl-4-ylcarbonyl)(methyl)amino]-N-hydroxy-N',2-dimethylpropanediamide (Compound 324, yellow solid) (38 mg, 48%).

MS (ESI/APCI Dual): 378 (M+Na)$^+$, 394 (M+K)$^+$, 354 (M−H)$^−$ $^1$H NMR (600 MHz, CD$_3$OD) δ ppm 1.76 (3 H, s), 2.78 (3 H, s), 3.20 (3 H, s), 7.33-7.38 (1 H, m), 7.42-7.47 (2 H, m), 7.59-7.66 (4 H, m), 7.71 (2 H, d, J=8.7 Hz)

Compounds 342, 348 to 350, and 521 were synthesized by the same methods as in Example 12 using the corresponding materials.

EXAMPLE 13

(2S)-2-[(biphenyl-4-ylcarbonyl)(methyl)amino]-N-hydroxy-N',2-dimethylpropanediamide (Compound 341)

[Chemical Formula 114]

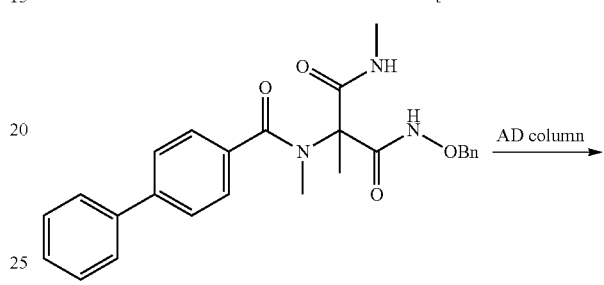

(1) N-(benzyloxy)-2-[(biphenyl-4-ylcarbonyl)(methyl)amino]-N',2-dimethylpropanediamide (80 mg) as obtained in Example 12-(3) was isolated and purified using a chiral column. (Isolation conditions: column: CHIRALPAK AD, column size: 2 cm I.D.×25 cm L, mobile phase: hexane/IPA=50/50 <v/v>, flow velocity: 10 mL/min, column temperature: 25° C., detection wavelength: 254 nm) Purification under these conditions obtained (2S)-N-(benzyloxy)-2-[(biphenyl-4-ylcarbonyl)(methyl)amino]-N',2-dimethylpropanediamide (white solid) (29 mg, 36%).

[α]$_D$; +26.8 (C:0.10, chloroform)

$^1$H NMR (600 MHz, CHLOROFORM-d) δ ppm 1.78 (3 H, s), 2.84 (3 H, d, J=4.6 Hz), 3.21 (3 H, s), [4.84], 4.94 (2 H, s), 7.16-7.23 (1 H, m), 7.28-7.67 (14 H, m), 10.10-10.17 (1 H, m)

[Chemical Formula 115]

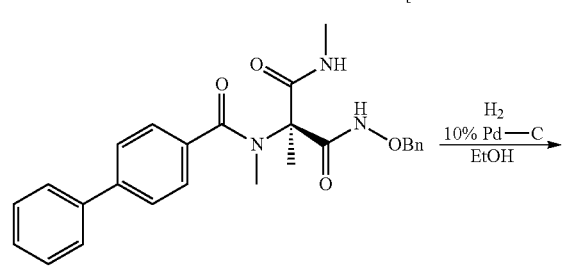

-continued

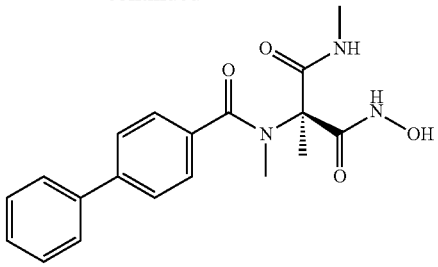

(2) 10% Pd—C (7.0 mg) was added to a methanol (2.6 mL) solution of (2S)-N-(benzyloxy)-2-[(biphenyl-4-ylcarbonyl)(methyl)amino]-N',2-dimethylpropanediamide (21 mg) as obtained in Example 13-(1), and the mixture was stirred in a hydrogen atmosphere for 6 hours at room temperature. The reaction mixture was filtered through Celite, and the solvent was distilled off under reduced pressure. The resulting residue was purified by preparative silica gel thin-layer chromatography (chloroform/methanol=6/1) to obtain (2S)-2-[(biphenyl-4-ylcarbonyl)(methyl)amino]-N-hydroxy-N',2-dimethylpropanediamide (Compound 341, white solid) (4.2 mg, 27%).

$[\alpha]_D$; +8.3 (C:0.17, methanol)

MS (ESI): 378 (M+Na)$^+$, 354 (M–H)$^-$ $^1$H NMR (600 MHz, CHLOROFORM-d) δ ppm 1.84 (3 H, s), 2.86 (3 H, d, J=5.0 Hz), 3.27 (3 H, s), 6.72-6.77 (1 H, m), 7.36-7.42 (1 H, m), 7.44-7.50 (2 H, m), 7.58-7.63 (4 H, m), 7.63-7.68 (2 H, m), 10.56-10.67 (1 H, m)

EXAMPLE 14

2-[{[4-({4-[1-(cyclopropylamino)ethyl]phenyl}ethynyl)phenyl]carbonyl}(methyl)amino]-N-hydroxy-N'-methylpropanediamide (Compound 357)

[Chemical Formula 116]

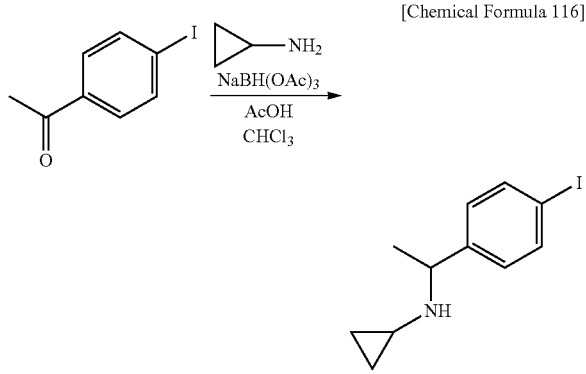

(1) Cyclopropylamine (0.85 g), acetic acid (0.89 g), and sodium triacetoxyborohydride (3.2 g) were added to a chloroform (20 mL) solution of 1-(4-iodophenyl)ethanone (1.2 g), and the mixture was stirred in a nitrogen atmosphere for 24 hours at room temperature. A saturated aqueous solution of sodium hydrogen carbonate was added to the reaction mixture, and then the mixture was extracted with chloroform. Then, the organic layer was washed with brine, and dried over anhydrous magnesium sulfate. Then, the desiccant was filtered out, and the solvent was distilled off under reduced pressure. The resulting residue was purified by OH type silica gel chromatography (hexane/ethyl acetate=80/20) to obtain N-[1-(4-iodophenyl)ethyl]cyclopropylamine (colorless oil) (1.3 g, 95%).

MS (ESI/APCI Dual): 288 (M+H)$^+$ $^1$H NMR (200 MHz, CHLOROFORM-d) δ ppm 0.22-0.41 (4 H, m), 1.34 (3 H, d, J=6.6 Hz), 1.88-2.00 (1 H, m), 3.82 (1 H, q, J=6.6 Hz), 7.03-7.12 (2 H, m), 7.59-7.68 (2 H, m)

[Chemical Formula 117]

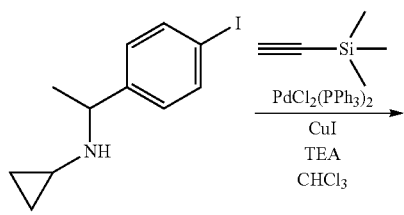

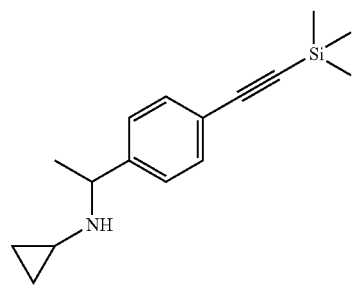

(2) Ethynyl(trimethyl)silane (80 mg), PdCl$_2$(PPh$_3$)$_2$ (29 mg), CuI (16 mg), and TEA (0.25 g) were added to a chloroform (5.0 mL) solution of N-[1-(4-iodophenyl)ethyl]cyclopropylamine (0.23 g) as obtained in Example 14-(1), and the mixture was stirred in a nitrogen atmosphere for 24 hours at room temperature. Further, stirring was continued for 2 hours at 45° C., and then PdCl$_2$(PPh$_3$)$_2$ (29 mg) was added. After the system was refluxed in a nitrogen atmosphere for 5 hours, the reaction mixture was concentrated. The resulting residue was purified by OH type silica gel chromatography (hexane/ethyl acetate=85/15) to obtain N-(1-{4-[(trimethylsilyl)ethynyl]phenyl}ethyl)cyclopropylamine (brown oil) (0.14 g, 66%).

MS (ESI/APCI Dual): 258 (M+H)$^+$ $^1$H NMR (600 MHz, CHLOROFORM-d) δ ppm 0.21-0.39 (4 H, m), 0.25 (9 H, s), 1.34 (3 H, d, J=6.9 Hz), 1.91-1.94 (1 H, m), 3.84 (1 H, q, J=6.9 Hz), 7.24-7.25 (2 H, m), 7.41-7.43 (2 H, m)

[Chemical Formula 118]

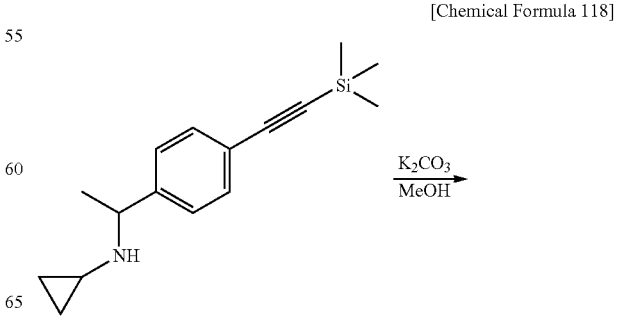

-continued

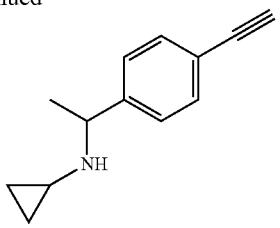

(3) Potassium carbonate (96 mg) was added to a methanol (3.0 mL) solution of N-(1-{4-[(trimethylsilyl)ethynyl]phenyl}ethyl)cyclopropylamine (0.12 g) as obtained in Example 14-(2), and the mixture was stirred in a nitrogen atmosphere for 30 minutes at room temperature. After the solid was filtered out, the reaction mixture was concentrated. The resulting residue was purified by OH type silica gel chromatography (hexane/ethyl acetate=95/5) to obtain N-[1-(4-ethynylphenyl)ethyl]cyclopropylamine (colorless oil) (85 mg, 100%).

MS (ESI/APCI Dual): 186 (M+H)$^+$ $^1$H NMR (200 MHz, CHLOROFORM-d) δ ppm 0.20-0.42 (4 H, m), 1.36 (3 H, d, J=6.9 Hz), 1.88-2.00 (1 H, m), 3.04 (1 H, s), 3.85 (1 H, q, J=6.9 Hz), 7.23-7.30 (2 H, m), 7.42-7.49 (2 H, m)

[Chemical Formula 119]

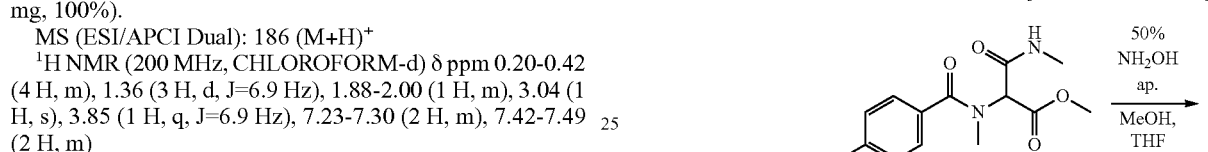

(4) Intermediate 6-2 (0.11 g), PdCl$_2$(PPh$_3$)$_2$ (10 mg), CuI (5.0 mg), and TEA (28 mg) were added to a chloroform (5.0 mL) solution of N-[1-(4-ethynylphenyl)ethyl]cyclopropylamine (51 mg) as obtained in Example 14-(3), and the mixture was stirred in a nitrogen atmosphere for 2 hours at room temperature, whereafter the reaction mixture was concentrated. The resulting residue was purified by OH type silica gel chromatography (ethyl acetate) to obtain 1-[1-(cyclopropylamino)ethyl]-4-[(4-{[1-methoxy-3-(methylamino)-1,3-dioxopropan-2-yl](methyl)carbamoyl}phenyl)ethynyl]benzene (light yellow foam) (0.10 g, 85%).

MS (ESI/APCI Dual): 448 (M+H)$^+$, 470 (M+Na)$^+$, 446 (M−H)$^−$ $^1$H NMR (200 MHz, CHLOROFORM-d) δ ppm 0.25-0.42 (4 H, m), 1.38 (3 H, d, J=6.6 Hz), 1.90-2.02 (1 H, m), 2.89 (3 H, d, J=4.8 Hz), 3.14 (3 H, br. s), 3.84 (3 H, s), 3.88 (1 H, q, J=6.6 Hz), 5.48 (1 H, br. s), 7.24-7.36 (3 H, m), 7.48-7.60 (6 H, m)

[Chemical Formula 120]

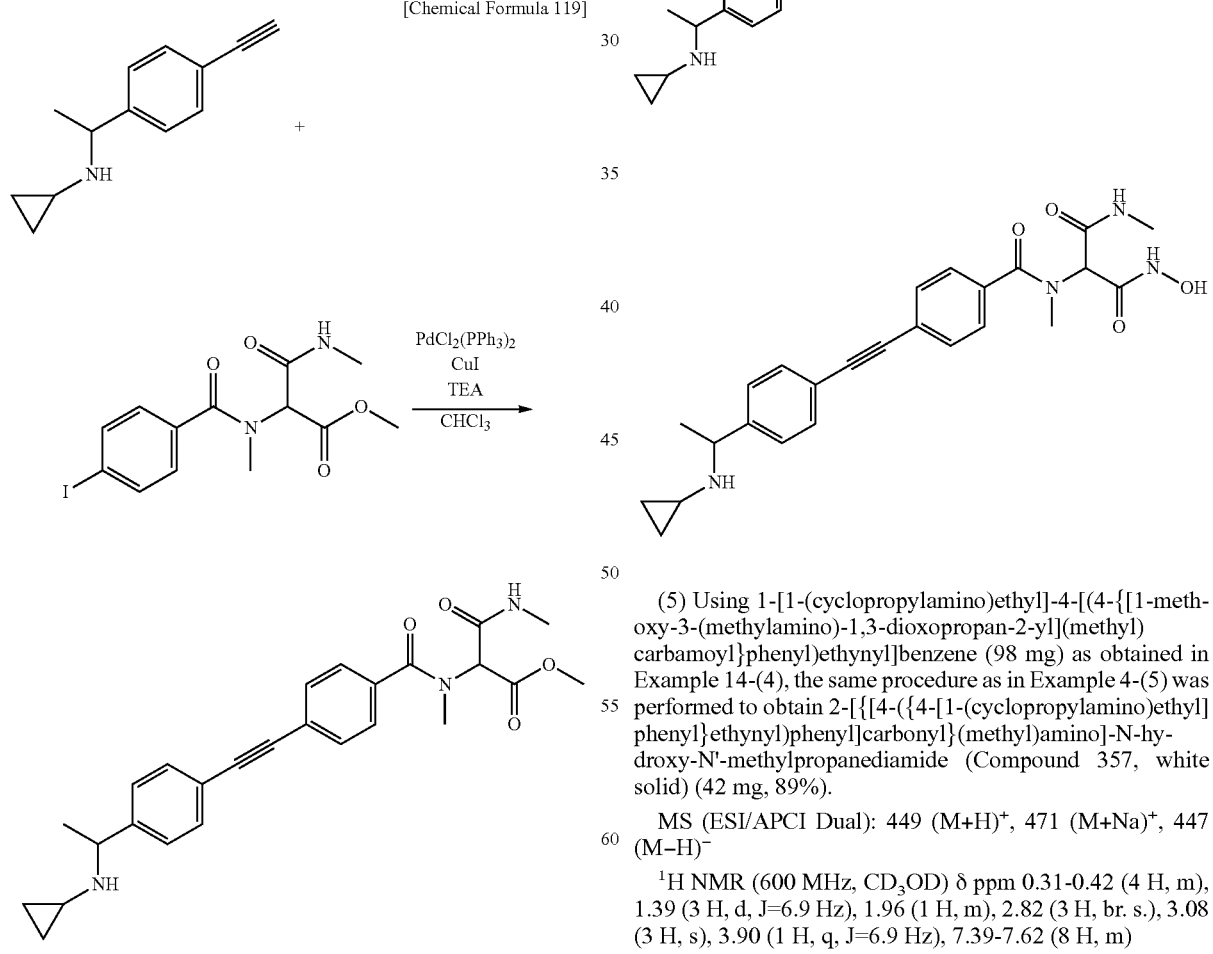

(5) Using 1-[1-(cyclopropylamino)ethyl]-4-[(4-{[1-methoxy-3-(methylamino)-1,3-dioxopropan-2-yl](methyl)carbamoyl}phenyl)ethynyl]benzene (98 mg) as obtained in Example 14-(4), the same procedure as in Example 4-(5) was performed to obtain 2-[{[4-({4-[1-(cyclopropylamino)ethyl]phenyl}ethynyl)phenyl]carbonyl}(methyl)amino]-N-hydroxy-N'-methylpropanediamide (Compound 357, white solid) (42 mg, 89%).

MS (ESI/APCI Dual): 449 (M+H)$^+$, 471 (M+Na)$^+$, 447 (M−H)$^−$ $^1$H NMR (600 MHz, CD$_3$OD) δ ppm 0.31-0.42 (4 H, m), 1.39 (3 H, d, J=6.9 Hz), 1.96 (1 H, m), 2.82 (3 H, br. s.), 3.08 (3 H, s), 3.90 (1 H, q, J=6.9 Hz), 7.39-7.62 (8 H, m)

Compounds 358, 367, 375, 379, 381, 382, 385, 407, 455, 461, 464, 465, 471 to 473, 483, 487, 488, 491, 496, 498, 501, 503, 504, 506, 508, 514, 516 to 518, 523, 536, 544, 545, 547,

EXAMPLE 15

N-hydroxy-N',2-dimethyl-2-{[(4-{[4-(1,4-oxazepan-4-ylmethyl)phenyl]ethynyl}phenyl)carbonyl]amino}propanediamide (Compound 380)

[Chemical Formula 121]

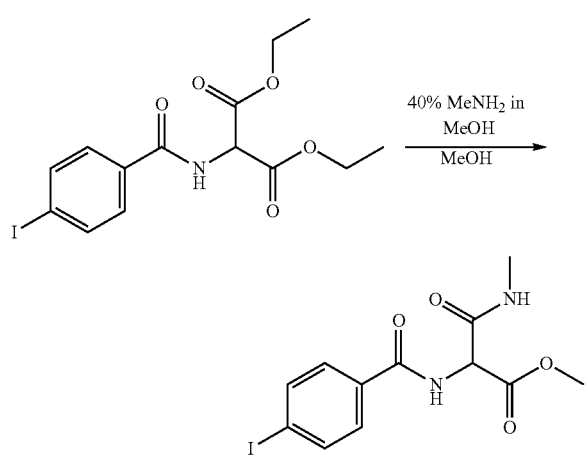

(1) A 40% methylamine-methanol solution (0.80 mL) was added to a methanol (90 mL) solution of diethyl {[(4-iodophenyl)carbonyl]amino}propandioate (4.1 g) obtained by the same method as the synthesis method described in the literature (Organic & Biomolecular Chemistry, 2005, Vol. 3(19), pp. 3531-3539), and the mixture was stirred for 19 hours at room temperature. Further, a 40% methylamine-methanol solution (0.24 mL) was added, and the mixture was stirred for 19 hours at the same temperature, followed by concentrating the reaction mixture. The resulting residue was purified by OH type silica gel column chromatography (gradient elution with chloroform/ethanol=95/5→90/10) to obtain 1-iodo-4-{[1-methoxy-3-(methylamino)-1,3-dioxopropan-2-yl]carbamoyl}benzene (white solid) (1.5 g, 39%).

MS (ESI): 377 (M+H)$^+$, 411 (M+Cl)$^-$ $^1$H NMR (600 MHz, CHLOROFORM-d) δ ppm 2.90 (3 H, d, J=5.2 Hz), 3.84 (3 H, s), 5.19 (1 H, d, J=6.2 Hz), 6.44-6.50 (1 H, m), 7.38-7.44 (1 H, m), 7.58 (2 H, d, J=8.7 Hz), 7.82 (2 H, d, J=8.7 Hz)

[Chemical Formula 122]

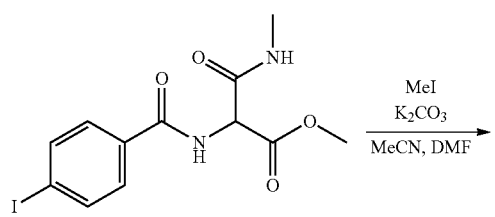

(2) Methyl iodide (0.35 mL) was added to an acetonitrile (40 mL)-DMF (16 mL) suspension of 1-iodo-4-{[1-methoxy-3-(methylamino)-1,3-dioxopropan-2-yl]carbamoyl}benzene (1.5 g) as obtained in Example 15-(1) and potassium carbonate (0.81 g), and the mixture was stirred for 4 days at room temperature under closed conditions. Water was added to the reaction mixture, and the mixture was extracted with chloroform. The extract was dried over anhydrous magnesium sulfate, and the desiccant was filtered out, whereafter the solvent was distilled off under reduced pressure. The resulting residue was purified by OH type silica gel column chromatography (gradient elution with hexane/ethyl acetate=45/55→14/86) to obtain 1-iodo-4-{[1-methoxy-2-methyl-3-(methylamino)-1,3-dioxopropan-2-yl]carbamoyl}benzene (colorless oil) (1.3 g, 82%).

MS (ESI): 391 (M+H)$^+$, 425 (M+Cl)$^-$ $^1$H NMR (600 MHz, CHLOROFORM-d) δ ppm 1.89 (3 H, s), 2.96 (3 H, s), 3.77 (3 H, s), 6.34 (1 H, br. s.), 7.53-7.59 (2 H, m), 7.78-7.83 (2 H, m), 7.85 (1 H, s)

[Chemical Formula 123]

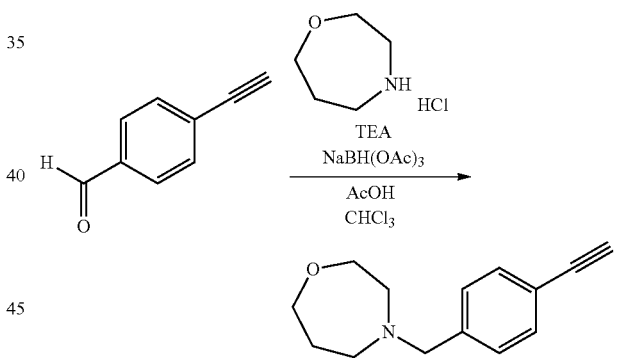

(3) 1,4-Oxazepane hydrochloride (1.0 g) and TEA (1.1 mL) were added to a chloroform (20 mL) solution of 4-ethynylbenzaldehyde (1.0 g) obtained by the same method as the synthesis method described in the literature (Tetrahedron Letters, 2007, Vol. 48(33), pp. 5817-5820). The mixture was stirred for 30 minutes at room temperature, and acetic acid (0.45 mL) was added, followed by stirring the mixture for 1 hour at room temperature. Then, sodium triacetoxyborohydride (2.4 g) was added, and the mixture was stirred for 15 hours at room temperature. A saturated aqueous solution of sodium hydrogen carbonate was added to the reaction mixture, and then the mixture was extracted with chloroform. The organic layer was washed with brine, and dried over anhydrous sodium sulfate. Then, the desiccant was filtered out, and the solvent was distilled off under reduced pressure. The resulting residue was purified by NH type silica gel chromatography (gradient elution with hexane/ethyl acetate=90/10→60/40) to obtain 4-(4-ethynylbenzyl)-1,4-oxazepane (yellow solid) (1.4 g, 87%).

MS (ESI): 216 (M+H)$^+$ $^1$H NMR (200 MHz, CHLOROFORM-d) δ ppm 1.78-1.99 (2 H, m), 2.58-2.75 (4 H, m), 3.05 (1 H, s), 3.60-3.75 (4 H, m), 3.77-3.91 (2 H, m), 7.26-7.50 (4 H, m)

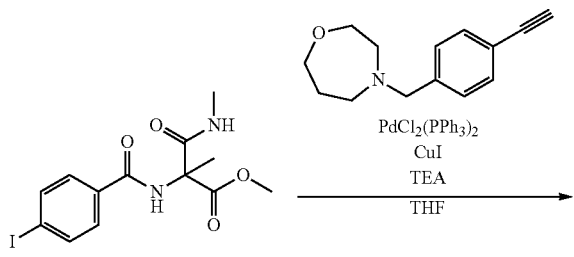

[Chemical Formula 124]

solution of 1-iodo-4-{[1-methoxy-2-methyl-3-(methylamino)-1,3-dioxopropan-2-yl]carbamoyl}benzene (0.16 g) as obtained in Example 15-(2). The mixture was stirred for 2 hours at room temperature, and then the reaction mixture was concentrated. The resulting residue was purified by OH type silica gel chromatography (gradient elution with hexane/ethyl acetate=57/43→3/97) to obtain 4-{4-[(4-{[1-methoxy-2-methyl-3-(methylamino)-1,3-dioxopropan-2-yl]carbamoyl}phenyl)ethynyl]benzyl}-1,4-oxazepane (yellow foam) (0.12 g, 65%).

MS (ESI): 478 (M+H)$^+$, 512 (M+Cl)$^-$ $^1$H NMR (600 MHz, CHLOROFORM-d) δ ppm 1.56 (3 H, s), 1.87-1.93 (2 H, m), 2.66-2.74 (4 H, m), 2.90 (3 H, d, J=4.5 Hz), 3.67 (2 H, s), 3.70-3.74 (2 H, m), 3.77 (3 H, s), 3.80-3.88 (2 H, m), 6.32 (1 H, d, J=4.5 Hz), 7.36 (2 H, d, J=7.8 Hz), 7.50 (2 H, d, J=7.8 Hz), 7.60 (2 H, d, J=8.3 Hz), 7.83 (2 H, d, J=8.3 Hz)

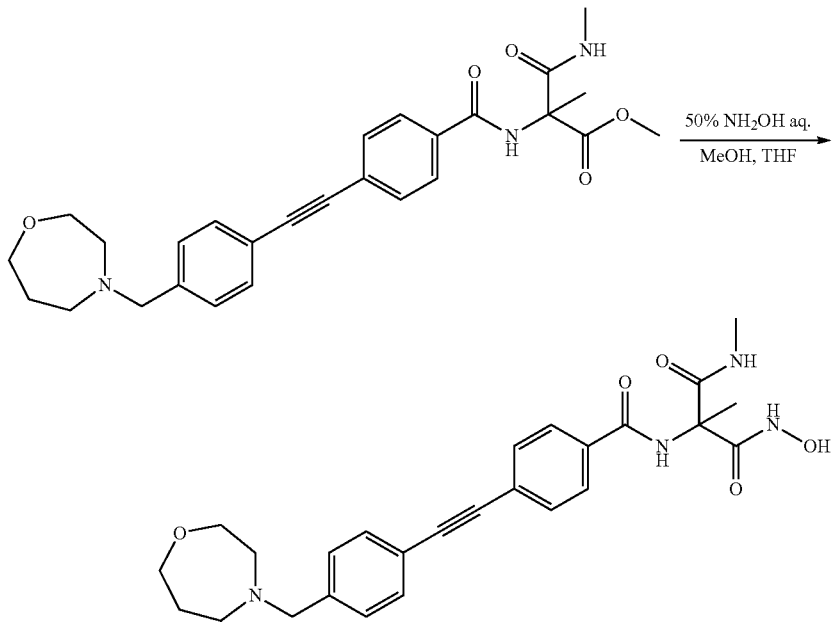

[Chemical Formula 125]

-continued

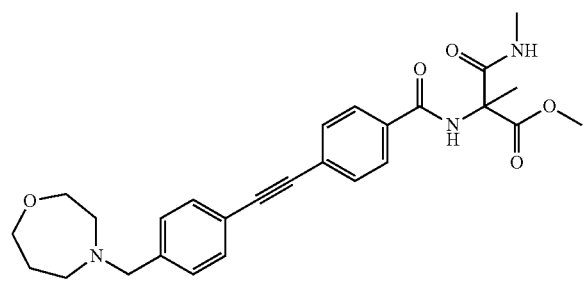

(4) 4-(4-Ethynylbenzyl)-1,4-oxazepane (79 mg) as obtained in Example 15-(3), PdCl$_2$(PPh$_3$)$_2$ (14 mg), CuI (9.0 mg), and TEA (0.16 mL) were added to a THF (2.0 mL)

(5) Using 4-{4-[(4-{[1-methoxy-2-methyl-3-(methylamino)-1,3-dioxopropan-2-yl]carbamoyl}phenyl)ethynyl]benzyl}-1,4-oxazepane (74 mg) as obtained in Example 15-(4), the same procedure as in Example 4-(5) was performed to obtain N-hydroxy-N',2-dimethyl-2-{[(4-{[4-(1,4-oxazepan-4-ylmethyl)phenyl]ethynyl}phenyl)carbonyl]amino}propanediamide (Compound 380, white solid) (6.2 mg, 8.0%).

MS (ESI): 479 (M+H)$^+$, 477 (M−H)$^-$ $^1$H NMR (600 MHz, CD$_3$OD) δ ppm 1.77 (3 H, s), 1.88-1.95 (2 H, m), 2.68-2.75 (4 H, m), 2.77 (3 H, s), 3.69-3.75 (4 H, m), 3.79-3.84 (2 H, m), 7.41 (2 H, d, J=8.3 Hz), 7.51 (2 H, d, J=8.3 Hz), 7.62 (2 H, d, J=8.7 Hz), 7.92 (2 H, d, J=8.7 Hz)

EXAMPLE 16

(2S)-N-hydroxy-N',2-dimethyl-2-[methyl(4-{[4-(1,4-oxazepan-4-ylmethyl)phenyl]ethynyl}benzoyl)amino]propanediamide (Compound 376)

[Chemical Formula 126]

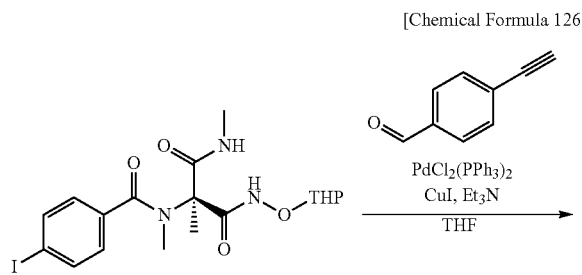

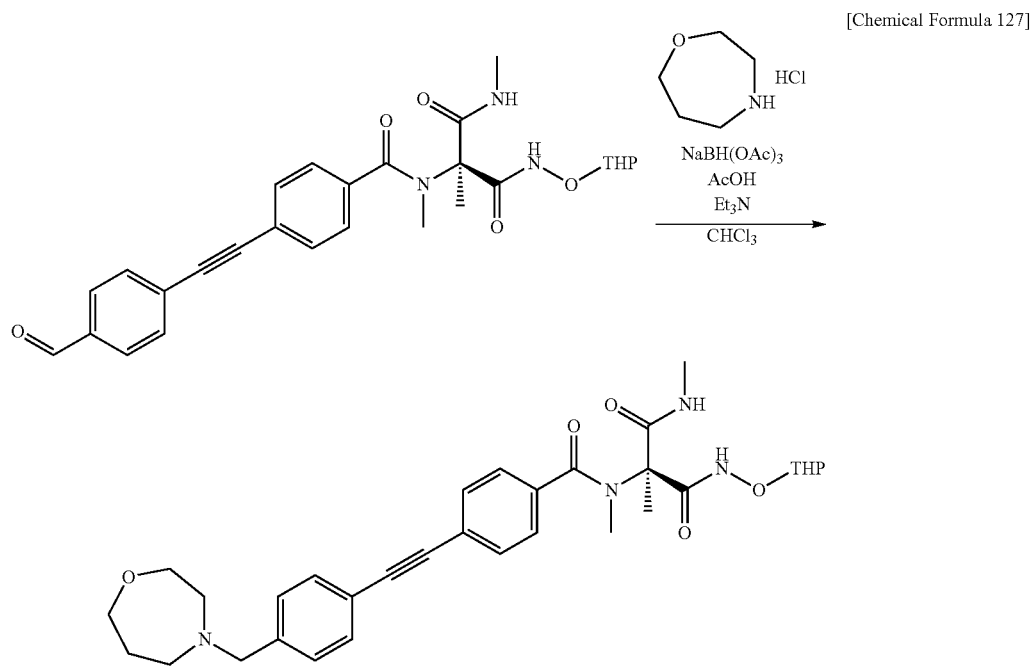

[Chemical Formula 127]

-continued

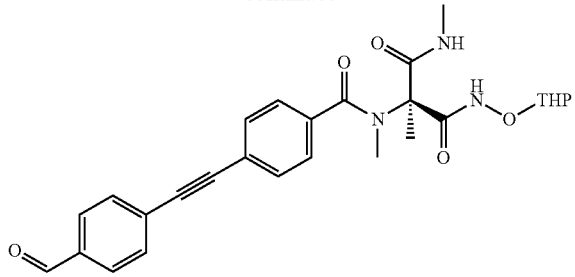

(1) TEA (10 mL) was added dropwise to a mixture of (2S)-2-[(4-iodobenzoyl)(methyl)amino]-N,2-dimethyl-N'-(tetrahydro-2H-pyran-2-yloxy)propanediamide (Intermediate 15, 12 g), 4-ethynylbenzaldehyde (4.1 g), PdCl$_2$(PPh$_3$)$_2$ (0.85 g), CuI (0.46 g), and THF (60 mL) at room temperature in a nitrogen atmosphere, and the mixture was stirred for 2 hours and 15 minutes at room temperature. Ethyl acetate (0.20 L), OH type silica gel (12 g), cellpure (5.9 g) and activated carbon (0.60 g) were added, the insolubles were filtered out, and the filtrate was concentrated under reduced pressure. The resulting residue was purified by OH type silica gel column chromatography (ethyl acetate/hexane=50/50, followed by gradient elution with chloroform/acetone=100/0→80/20). Then, ethyl acetate and IPE were added to the resulting solid, and the solid was filtered off and washed with IPE to obtain (2S)-2-[{4-[(4-formylphenyl)ethynyl]benzoyl}(methyl)amino]-N,2-dimethyl-N'-(tetrahydro-2H-pyran-2-yloxy)propanediamide (yellow brown solid) (9.0 g, 76%).

MS (ESI): 514 (M+Na)$^+$, 490 (M−H)$^−$ $^1$H NMR (400 MHz, CHLOROFORM-d) δ ppm 1.50-2.00 (6 H, m), [1.82], 1.83 (3 H, s), 2.84-2.90 (3 H, m), [3.17], 3.20 (3 H, s), 3.52-3.70 (1 H, m), 3.80-4.10 (1 H, m), 4.94-5.02 (1 H, m), [6.95-7.05], 7.47-7.57 (1 H, m), 7.52-7.58 (2 H, m), 7.58-7.64 (2 H, m), 7.69 (2 H, d, J=8.0 Hz), 7.89 (2 H, d, J=8.1 Hz), 10.03 (1 H, s), [10.07], 10.49 (1 H, s)

(2) TEA (1.6 mL) and acetic acid (0.8 mL) were added to a chloroform (13 mL) solution of (2S)-2-[{4-[(4-formylphenyl)ethynyl]benzoyl}(methyl)amino]-N,2-dimethyl-N'-(tetrahydro-2H-pyran-2-yloxy)propanediamide (3.7 g) as obtained in Example 16-(1) and homomorpholine hydrochloride (1.6 g). Under ice cooling, sodium triacetoxyborohydride (2.6 g) was added in divided portions in a nitrogen atmosphere, and the mixture was stirred for 3.5 hours at room temperature. Water and ethyl acetate were added, the mixture was adjusted to pH 7.5 with a 1 mol/L sodium hydroxide aqueous solution, and then the organic layer was isolated. The extract was washed with brine, and dried over anhydrous sodium sulfate. Then, the desiccant was filtered out, and the solvent was distilled off under reduced pressure. The resulting residue was purified by OH type silica gel column chromatography (gradient elution with chloroform/acetone=100/0→60/40, followed by chloroform/methanol=90/10) to obtain (2S)-N,2-dimethyl-2-[methyl(4-{[4-(1,4-oxazepan-4-ylmethyl)phenyl]ethynyl}benzoyl)amino]-N'-(tetrahydro-2H-pyran-2-yloxy)propanediamide (light yellow solid) (3.0 g, 69%).

¹H NMR (400 MHz, CHLOROFORM-d) δ ppm 1.50-2.00 (8 H, m), [1.81], 1.82 (3 H, s), 2.66-2.74 (4 H, m), 2.83-2.89 (3 H, m), [3.17], 3.20 (3 H, s), 3.50-4.10 (8 H, m), 4.93-5.03 (1 H, m), [6.95-7.05], 7.60-7.70 (1 H, m), 7.35 (2 H, d, J=8.0 Hz), 7.46-7.55 (4 H, m), 7.57 (2 H, d, J=8.0 Hz), [10.09], 10.50 (1 H, s)

¹H NMR (600 MHz, CD₃OD) δ ppm 1.77 (3 H, s), 1.89-1.95 (2 H, m), 2.69-2.76 (4 H, m), 2.79 (3 H, s), 3.17 (3 H, s), 3.71 (2 H, s), 3.71-3.75 (2 H, m), 3.81 (2 H, t, J=6.0 Hz), 7.36-7.62 (8 H, m)

Compounds 396, 397, 409, 414, 416, 417, 419, 421, 427, 429 to 432, 439 to 441, 531, 534, 541, 548, 549, 553 to 561, 565 to 567, 569 to 571, 577 to 578, 587, 591, 594, 598, 607, 610, 611, 613 to 615, 617 to 620, 625, 631 and 634 were synthesized by the same methods as in Example 16 with the use of the corresponding materials.

[Chemical Formula 128]

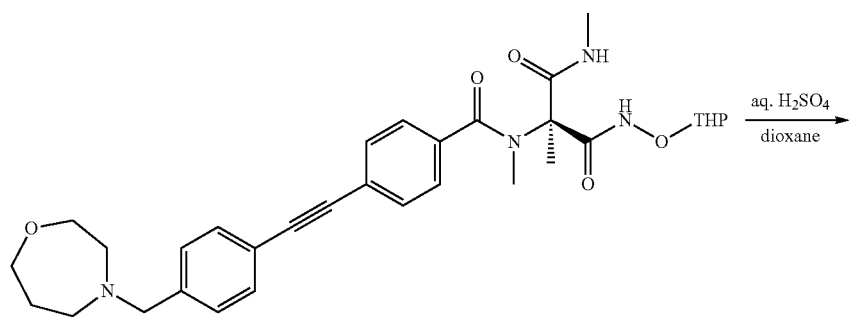

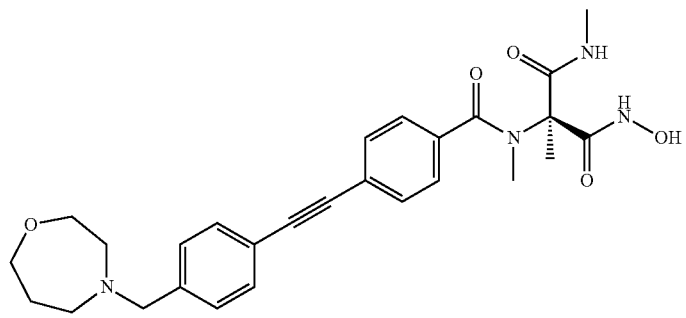

(3) A 1 mol/L sulfuric acid aqueous solution (16 mL) was added dropwise, under water cooling, to a 1,4-dioxane (6.0 mL) suspension of (2S)-N,2-dimethyl-2-[methyl(4-{[4-(1,4-oxazepan-4-ylmethyl)phenyl]ethynyl}benzoyl)amino]-N'-(tetrahydro-2H-pyran-2-yloxy)propanediamide (3.0 g) as obtained in Example 16-(2), and the mixture was stirred for 2 hours and 50 minutes at room temperature. Water and ethyl acetate were added, and the aqueous layer was isolated. The isolate was adjusted to pH 7 with 20% sodium hydroxide and a saturated aqueous solution of sodium hydrogen carbonate, and then ethyl acetate and sodium chloride were added, followed by isolating the organic layer. The extract was washed with brine, and dried over anhydrous sodium sulfate. Then, the desiccant was filtered out, and the solvent was distilled off under reduced pressure. The resulting residue was purified by OH type silica gel column chromatography (gradient elution with chloroform/acetone=100/0→60/40, followed by gradient elution with chloroform/methanol=98/2→90/10) to obtain (2S)-N-hydroxy-N',2-dimethyl-2-[methyl(4-{[4-(1,4-oxazepan-4-ylmethyl)phenyl]ethynyl}benzoyl)amino]propanediamide (Compound 376, pale yellow solid) (1.7 g, 65%).

MS (ESI): 493 (M+H)⁺, 491 (M−H)⁻

EXAMPLE 16-1

(2S)-2-[({4-[(4-{[3-(2-fluoroethoxy)azetidin-1-yl]methyl}phenyl)ethynyl]phenyl}carbonyl)(methyl)amino]-N-hydroxy-N',2-dimethylpropanediamide (Compound 559)

[Chemical Formula 129]

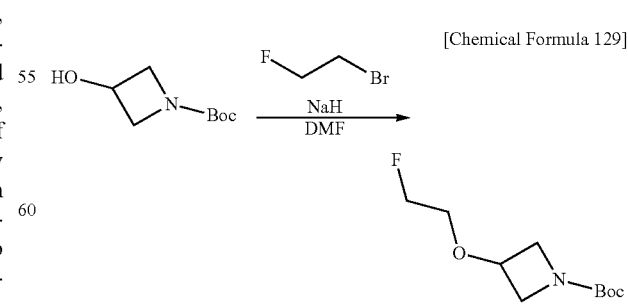

(1) 60% Sodium hydride (0.18 g) was added to a DMF (5.0 mL) solution of 3-hydroxyazetidine-1-carboxylic acid t-butyl ester (0.52 g) under ice cooling, and the mixture was stirred for 30 minutes at room temperature. 1-Bromo-2-fluoroethane (0.45 mL) was added under ice cooling, and the mixture was stirred for 2 hours at room temperature, then for 1.5 hours at 50° C., and further for 1.5 hours at 70° C. The reaction mixture was cooled to room temperature, and ethyl acetate and a saturated aqueous solution of ammonium chloride were added, whereafter the organic layer was isolated. The extract was washed with water and brine in this order, and dried over anhydrous sodium sulfate. Then, the desiccant was filtered out, and the solvent was distilled off under reduced pressure. The resulting residue was purified by OH type silica gel column chromatography (gradient elution with hexane/ethyl acetate=80/20→70/30) to obtain 3-(2-fluoroethoxy)azetidine-1-carboxylic acid t-butyl ester (colorless oil) (0.30 g, 46%).

$^1$H NMR (400 MHz, CHLOROFORM-d) δ ppm 1.44 (9 H, s), 3.58-3.64 (1 H, m), 3.65-3.72 (1 H, m), 3.82-3.92 (2 H, m), 4.03-4.14 (2 H, m), 4.24-4.33 (1 H, m), 4.46-4.53 (1 H, m), 4.59-4.65 (1 H, m)

[Chemical Formula 130]

(2) To a 1,4-dioxane (0.9 mL) solution of 3-(2-fluoroethoxy)azetidine-1-carboxylic acid t-butyl ester (0.30 g) as obtained in Example 16-1-(1), methanol (0.15 mL) was added, and then a 4.0 mol/L HCl-1,4-dioxane solution (1.7 mL) was added, and the mixture was stirred for 3 hours at room temperature. IPE (10 mL) was added to the reaction mixture, and the supernatant was removed. This procedure was repeated 3 times to obtain 3-(2-fluoroethoxy)azetidine hydrochloride (colorless oil) (0.20 g, 94%).

$^1$H NMR (600 MHz, D$_2$O) δ ppm 3.58-3.63 (1 H, m), 3.67-3.71 (1 H, m), 3.90-3.98 (2 H, m), 4.17-4.25 (2 H, m), 4.40-4.50 (2 H, m), 4.52-4.56 (1 H, m)

[Chemical Formula 131]

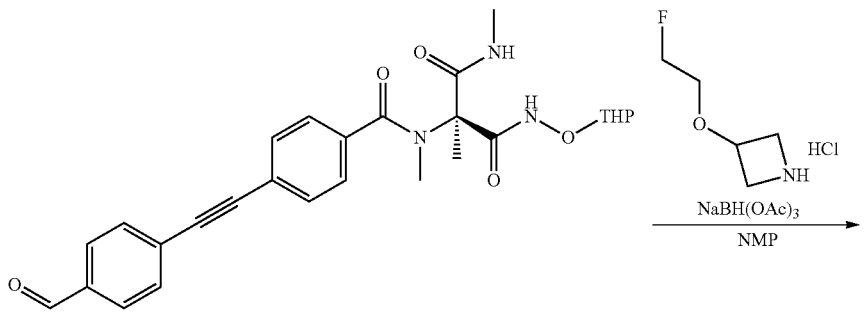

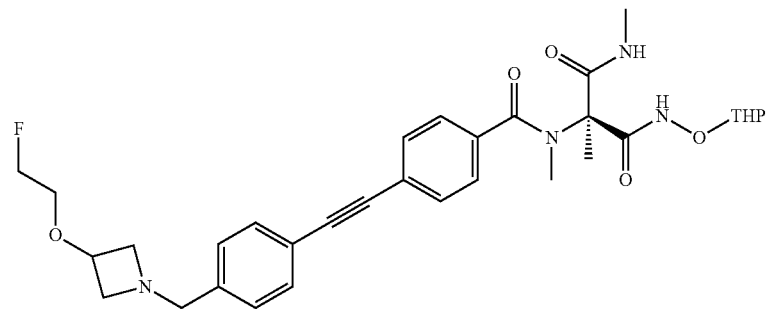

(3) Sodium triacetoxyborohydride (0.10 g) was added to a solution in NMP (1.5 mL) of (2S)-2-[{4-[(4-formylphenyl)ethynyl]benzoyl}(methyl)amino]-N,2-dimethyl-N'-(tetrahydro-2H-pyran-2-yloxy)propanediamide (0.15 g) as obtained in Example 16-(1) and 3-(2-fluoroethoxy)azetidine hydrochloride (63 mg) as obtained in Example 16-1-(2), under ice cooling in a nitrogen atmosphere. The mixture was stirred for 40 minutes at room temperature. Water and ethyl acetate were added, and the mixture was adjusted to pH 7.5 with a saturated aqueous solution of sodium hydrogen carbonate, whereafter the organic layer was isolated. The extract was washed with brine, and dried over anhydrous sodium sulfate. Then, the desiccant was filtered out, and the solvent was distilled off under reduced pressure. The resulting residue was purified by OH type silica gel column chromatography (gradient elution with chloroform/acetone=80/20→50/50) to obtain (2S)-2-[{4-[(4-{[3-(2-fluoroethoxy)azetidin-1-yl]methyl}phenyl)ethynyl]benzoyl}(methyl)amino]-N,2-dimethyl-N'-(tetrahydro-2H-pyran-2-yloxy)propanediamide (yellow oil) (0.14 g, 81%).

$^1$H NMR (400 MHz, CHLOROFORM-d) δ ppm 1.40-1.95 (6 H, m), [1.81], 1.82 (3 H, s), 2.80-2.90 (3 H, m), 2.95-3.05 (2 H, m), [3.17], 3.20 (3 H, s), 3.50-3.80 (7 H, m), 3.80-4.10 (1 H, m), 4.15-4.25 (1 H, m), 4.45-4.65 (2 H, m), 4.90-5.05 (1 H, m), [6.95-7.05], 7.60-7.70 (1 H, m), 7.25-7.40 (2 H, m), 7.45-7.60 (6 H, m), [10.09], 10.50 (1 H, br. s.)

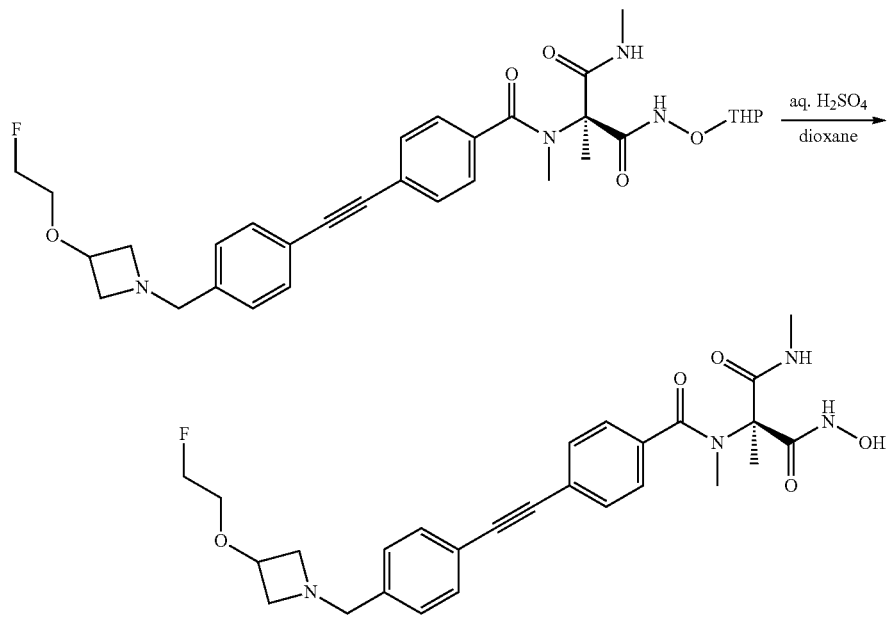

(4) From (2S)-2-[{4-[(4-{[3-(2-fluoroethoxy)azetidin-1-yl]methyl}phenyl)ethynyl]benzoyl}(methyl)amino]-N,2-dimethyl-N'-(tetrahydro-2H-pyran-2-yloxy)propanediamide (0.14 g) as obtained in Example 16-1-(3), (2S)-2-[({4-[(4-{[3-(2-fluoroethoxy)azetidin-1-yl]methyl}phenyl)ethynyl]phenyl}carbonyl)(methyl)amino]-N-hydroxy-N',2-dimethylpropanediamide (Compound 559, yellow solid) (77 mg, 60%) was obtained in the same manner as in Example 16-(3).

MS (ESI): 512 (M+H)$^+$, 510 (M−H)$^−$ $^1$H NMR (400 MHz, CD$_3$OD) δ ppm 1.77 (3 H, s), 2.79 (3 H, s), 3.08-3.14 (2 H, m), 3.16 (3 H, s), 3.56-3.74 (4 H, m), 3.70 (2 H, s), 4.16-4.25 (1 H, m), 4.40-4.45 (1 H, m), 4.52-4.57 (1 H, m), 7.25-7.40 (2 H, m), 7.45-7.65 (6 H, m)

EXAMPLE 16-2

(2S)-2-[{[4-({4-[(3-ethoxyazetidin-1-yl)methyl]phenyl}ethynyl)phenyl]carbonyl}(methyl)amino]-N-hydroxy-N',2-dimethylpropanediamide (Compound 557)

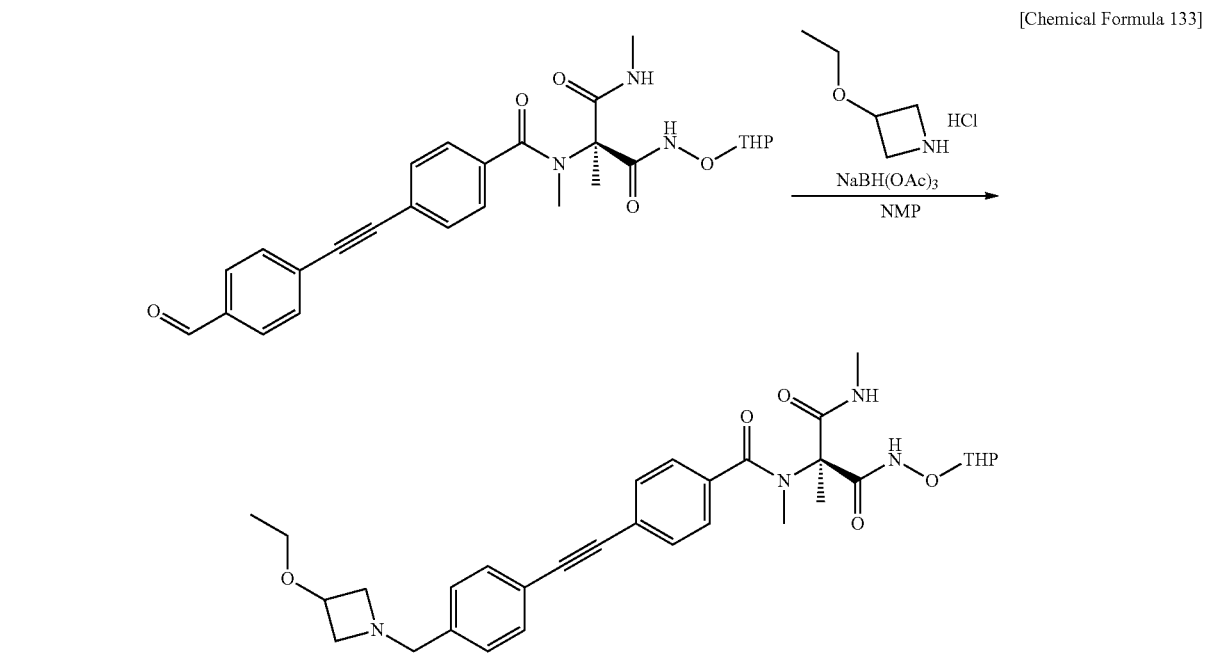

(1) From (2S)-2-[{4-[(4-formylphenyl)ethynyl]benzoyl}(methyl)amino]-N,2-dimethyl-N'-(tetrahydro-2H-pyran-2-yloxy)propanediamide (0.30 g) as obtained in Example 16-(1) and 3-ethoxyazetidine hydrochloride (0.11 g), there was obtained (2S)-2-{[4-({4-[(3-ethoxyazetidin-1-yl)methyl]phenyl}ethynyl)benzoyl](methyl)amino}-N,2-dimethyl-N'-(tetrahydro-2H-pyran-2-yloxy)propanediamide (yellow solid) (0.26 g, 74%) in the same manner as in Example 16-1-(3).

$^1$H NMR (400 MHz, CHLOROFORM-d) δ ppm 1.20 (3 H, t, J=7.1 Hz), 1.35-1.95 (6 H, m), [1.81], 1.82 (3 H, s), 2.80-2.90 (3 H, m), 2.95-3.00 (2 H, m), [3.17], 3.20 (3 H, s), 3.40-3.45 (2 H, m), 3.49 (2 H, s), 3.50-3.70 (3 H, m), 3.80-4.05 (1 H, m), 4.10-4.20 (1 H, m), 4.90-5.05 (1 H, m), [6.95-7.05], 7.60-7.70 (1 H, m), 7.25-7.35 (2 H, m), 7.45-7.60 (6 H, m), [10.08], 10.49 (1 H, br. s.)

[Chemical Formula 134]

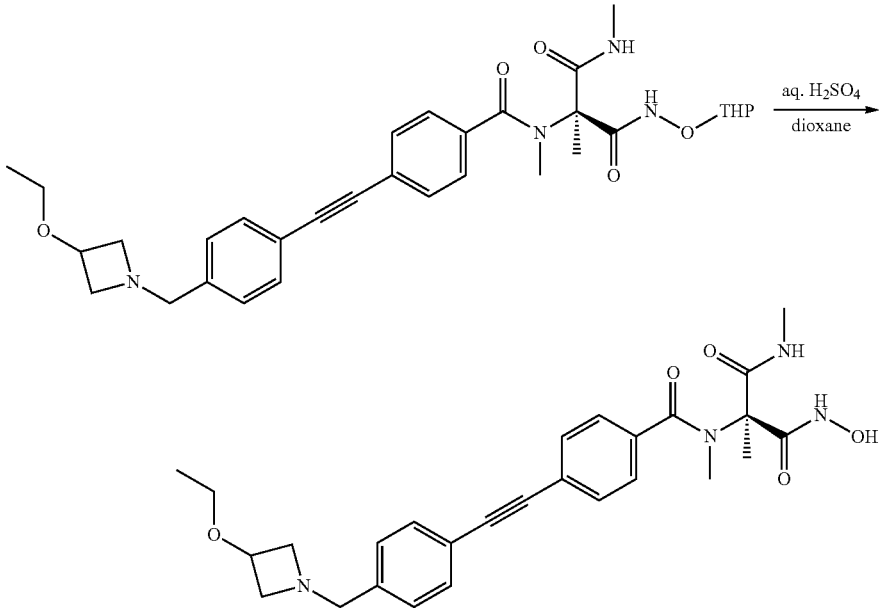

(2) From (2S)-2-{[4-({4-[(3-ethoxyazetidin-1-yl)methyl]phenyl}ethynyl)benzoyl](methyl)amino}-N,2-dimethyl-N'-(tetrahydro-2H-pyran-2-yloxy)propanediamide (0.26 g) as obtained in Example 16-2-(1), (2S)-2-[{[4-({4-[(3-ethoxyazetidin-1-yl)methyl]phenyl}ethynyl)phenyl]carbonyl}(methyl)amino]-N-hydroxy-N',2-dimethylpropanediamide was obtained (Compound 557, yellow solid) (0.14 g, 62%) in the same manner as in Example 16-(3).

MS (ESI): 493 (M+H)$^+$, 491 (M−H)$^−$ $^1$H NMR (400 MHz, CD$_3$OD) δ ppm 1.16 (3 H, t, J=7.0 Hz), 1.77 (3 H, s), 2.79 (3 H, s), 3.06-3.12 (2 H, m), 3.16 (3 H, s), 3.35-3.50 (2 H, m), 3.58-3.76 (4 H, m), 4.08-4.20 (1 H, m), 7.25-7.40 (2 H, m), 7.45-7.70 (6 H, m)

EXAMPLE 16-3

(2S)-N-hydroxy-2-[{[4-({4-[(3-methoxyazetidin-1-yl)methyl]phenyl}ethynyl)phenyl]carbonyl}(methyl)amino]-N',2-dimethylpropanediamide (Compound 567)

[Chemical Formula 135]

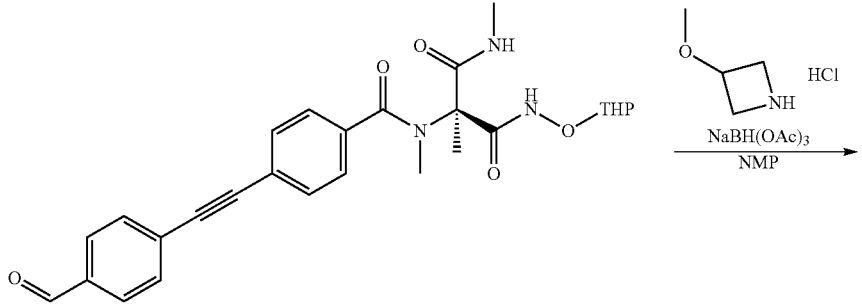

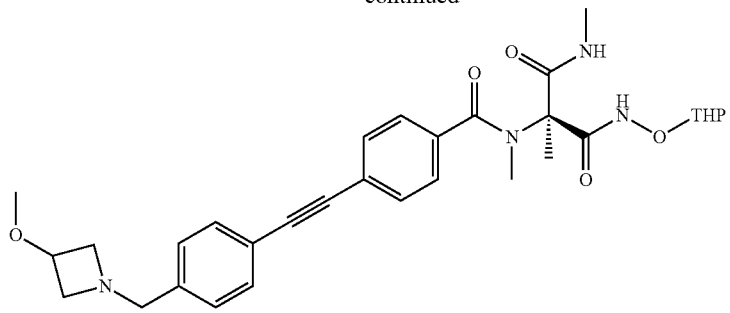

(1) From (2S)-2-[{4-[(4-formylphenyl)ethynyl]benzoyl}(methyl)amino]-N,2-dimethyl-N'-(tetrahydro-2H-pyran-2-yloxy)propanediamide (0.50 g) as obtained in Example 16-(1) and 3-methoxyazetidine hydrochloride (0.16 g), there was obtained (2S)-2-{[4-({4-[(3-methoxyazetidin-1-yl)methyl]phenyl}ethynyl)benzoyl](methyl)amino}-N,2-dimethyl-N'-(tetrahydro-2H-pyran-2-yloxy)propanediamide (yellow solid) (0.39 g, 68%) in the same manner as in Example 16-1-(3).

$^1$H NMR (400 MHz, CHLOROFORM-d) δ ppm 1.55-1.95 (6 H, m), [1.81], 1.82 (3 H, s), 2.80-2.90 (3 H, m), 2.90-3.00 (2 H, m), [3.17], 3.20 (3 H, s), 3.26 (3 H, s), 3.50-3.70 (5 H, m), 3.80-4.15 (2 H, m), 4.90-5.05 (1 H, m), [6.95-7.05], 7.60-7.70 (1 H, m), 7.20-7.30 (2 H, m), 7.45-7.60 (6 H, m), [10.08], 10.49 (1 H, br. s.)

[Chemical Formula 136]

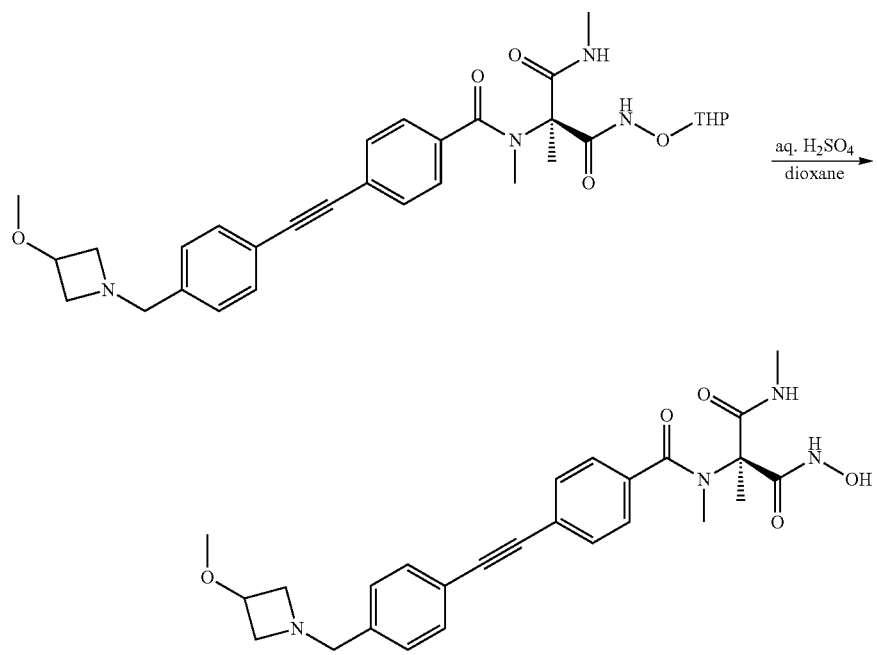

(2) From (2S)-2-{[4-({4-[(3-methoxyazetidin-1-yl)methyl]phenyl}ethynyl)benzoyl](methyl)amino}-N,2-dimethyl-N'-(tetrahydro-2H-pyran-2-yloxy)propanediamide (0.39 g) as obtained in Example 16-3-(1), (2S)-N-hydroxy-2-[{[4-({4-[(3-methoxyazetidin-1-yl)methyl]phenyl}ethynyl)phenyl]carbonyl}(methyl)amino]-N',2-dimethylpropanediamide (Compound 567, white solid) was obtained (0.26 g, 79%) in the same manner as in Example 16-(3).

MS (ESI): 479 (M+H)$^+$, 477 (M−H)$^−$ $^1$H NMR (400 MHz, CD$_3$OD) δ ppm 1.77 (3 H, s), 2.79 (3 H, s), 3.02-3.12 (2 H, m), 3.16 (3 H, s), 3.25 (3 H, s), 3.56-3.64 (2 H, m), 3.69 (2 H, s), 4.02-4.13 (1 H, m), 7.32 (2 H, d, J=8.3 Hz), 7.45-7.65 (6 H, m)

EXAMPLE 16-4

(2S)-2-[{[4-({4-[(cyclopropylamino)methyl]phenyl}ethynyl)phenyl]carbonyl}(methyl)amino]-N-hydroxy-N',2-dimethylpropanediamide (Compound 553)

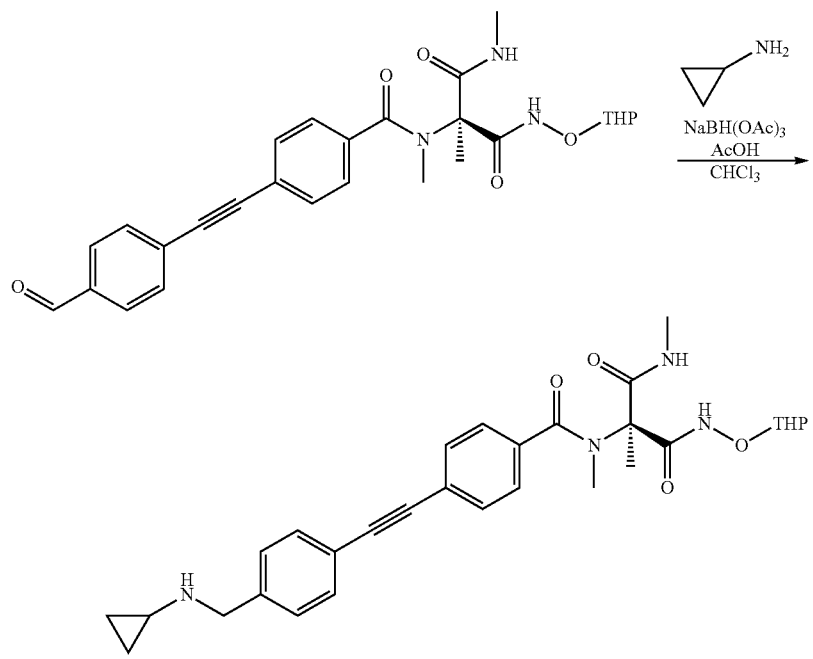

[Chemical Formula 137]

(1) From (2S)-2-[{4-[(4-formylphenyl)ethynyl]benzoyl}(methyl)amino]-N,2-dimethyl-N'-(tetrahydro-2H-pyran-2-yloxy)propanediamide (0.30 g) as obtained in Example 16-(1) and cyclopropylamine (0.19 mL), there was obtained (2S)-2-{[4-({4-[(cyclopropylamino)methyl]phenyl}ethynyl)benzoyl](methyl)amino}-N,2-dimethyl-N'-(tetrahydro-2H-pyran-2-yloxy)propanediamide (white solid) (0.20 g, 62%) in the same manner as in Example 16-(2).

$^1$H NMR (400 MHz, CHLOROFORM-d) δ ppm 0.35-0.40 (4 H, m), 1.40-1.95 (6 H, m), [1.82], 1.83 (3 H, s), 2.10-2.20 (1 H, m), 2.80-2.90 (3 H, m), [3.17], 3.20 (3 H, s), 3.86 (2 H, br. s.), 3.90-4.15 (2 H, m), 4.90-5.05 (1 H, m), 7.20-7.35 (2 H, m), 7.40-7.60 (6 H, m)

[Chemical Formula 138]

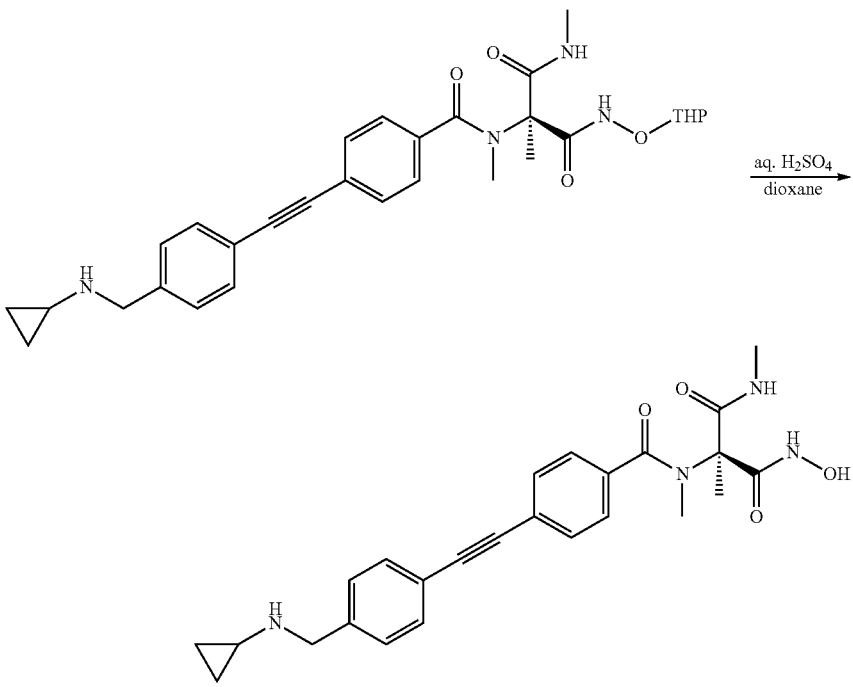

(2) From (2S)-2-{[4-({4-[(cyclopropylamino)methyl]phenyl}ethynyl)benzoyl](methyl)amino}-N,2-dimethyl-N'-(tetrahydro-2H-pyran-2-yloxy)propanediamide (0.20 g) as obtained in Example 16-4-(1), (2S)-2-[{[4-({4-[(cyclopropylamino)methyl]phenyl}ethynyl)phenyl]carbonyl}(methyl)amino]-N-hydroxy-N',2-dimethylpropanediamide (Compound 553, yellow solid) was obtained (0.11 g, 68%) in the same manner as in Example 16-(3).

MS (ESI): 450 (M+H)$^+$, 448 (M−H)$^−$ $^1$H NMR (400 MHz, CD$_3$OD) δ ppm 0.35-0.50 (4 H, m), 1.77 (3 H, s), 2.08-2.17 (1 H, m), 2.79 (3 H, s), 3.17 (3 H, s), 3.82 (2 H, s), 7.38 (2 H, d, J=8.5 Hz), 7.46-7.61 (6 H, m)

EXAMPLE 16-5

(2S)-N-hydroxy-2-[{[4-({4-[(4-methoxypiperidin-1-yl)methyl]phenyl}ethynyl)phenyl]carbonyl}(methyl)amino]-N',2-dimethylpropanediamide (Compound 565)

[Chemical Formula 139]

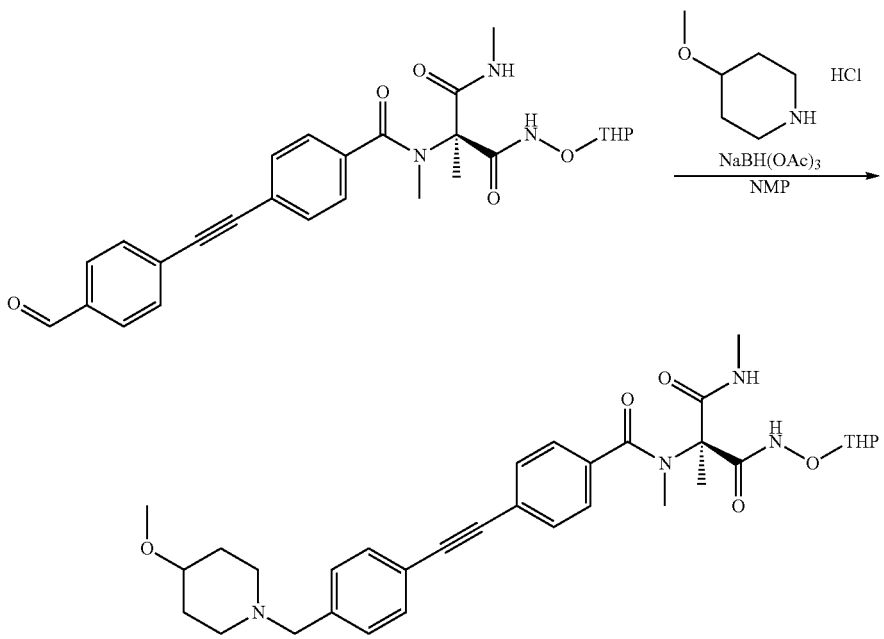

(1) From (2S)-2-[{4-[(4-formylphenyl)ethynyl]benzoyl}(methyl)amino]-N,2-dimethyl-N'-(tetrahydro-2H-pyran-2-yloxy)propanediamide (0.15 g) as obtained in Example 16-(1) and 4-methoxypiperidine hydrochloride (60 mg), there was obtained (2S)-2-{[4-({4-[(4-methoxypiperidin-1-yl)methyl]phenyl}ethynyl)benzoyl](methyl)amino}-N,2-dimethyl-N'-(tetrahydro-2H-pyran-2-yloxy)propanediamide (yellow solid) (0.13 g, 74%) in the same manner as in Example 16-1-(3).

$^1$H NMR (400 MHz, CHLOROFORM-d) δ ppm 1.50-1.95 (10 H, m), [1.81], 1.82 (3 H, s), 2.05-2.20 (2 H, m), 2.65-2.75 (2 H, m), 2.80-2.90 (3 H, m), 3.15-3.25 (1 H, m), [3.17], 3.20 (3 H, s), 3.34 (3 H, br. s.), 3.45-3.75 (3 H, m), 3.80-4.10 (1 H, m), 4.90-5.05 (1 H, m), [6.95-7.05], 7.60-7.70 (1 H, m), 7.30-7.35 (2 H, m), 7.45-7.60 (6 H, m), [10.08], 10.50 (1 H, br. s.)

[Chemical Formula 140]

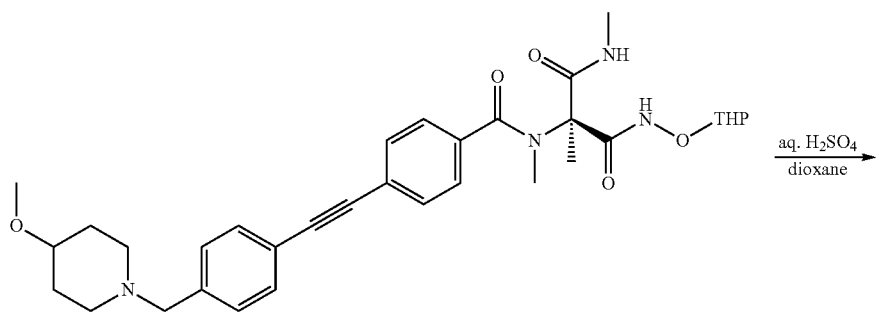

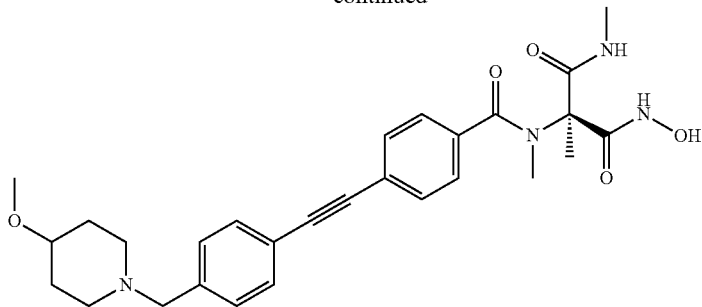

(2) From (2S)-2-{[4-({4-[(4-methoxypiperidin-1-yl)methyl]phenyl}ethynyl)benzoyl](methyl)amino}-N,2-dimethyl-N'-(tetrahydro-2H-pyran-2-yloxy)propanediamide (0.13 g) as obtained in Example 16-5-(1), (2S)-N-hydroxy-2-[{[4-({4-[(4-methoxypiperidin-1-yl)methyl]phenyl}ethynyl)phenyl]carbonyl}(methyl)amino]-N',2-dimethylpropanediamide (Compound 565, yellow solid) was obtained (49 mg, 42%) in the same manner as in Example 16-(3).

MS (ESI): 507 (M+H)$^+$, 505 (M−H)$^−$ $^1$H NMR (400 MHz, CD$_3$OD) δ ppm 1.51-1.64 (2 H, m), 1.77 (3 H, s), 1.86-1.96 (2 H, m), 2.18-2.32 (2 H, m), 2.65-2.85 (2 H, m), 2.79 (3 H, s), 3.17 (3 H, s), 3.20-3.35 (1 H, m), 3.28 (3 H, s), 3.56 (2 H, s), 7.35-7.40 (2 H, m), 7.45-7.65 (6 H, m)

EXAMPLE 16-6

(2S)-N-hydroxy-N',2-dimethyl-2-{methyl[(4-{[4-({[(3-methyloxetan-3-yl)methyl]amino}methyl)phenyl]ethynyl}phenyl)carbonyl]amino}propanediamide (Compound 578)

[Chemical Formula 141]

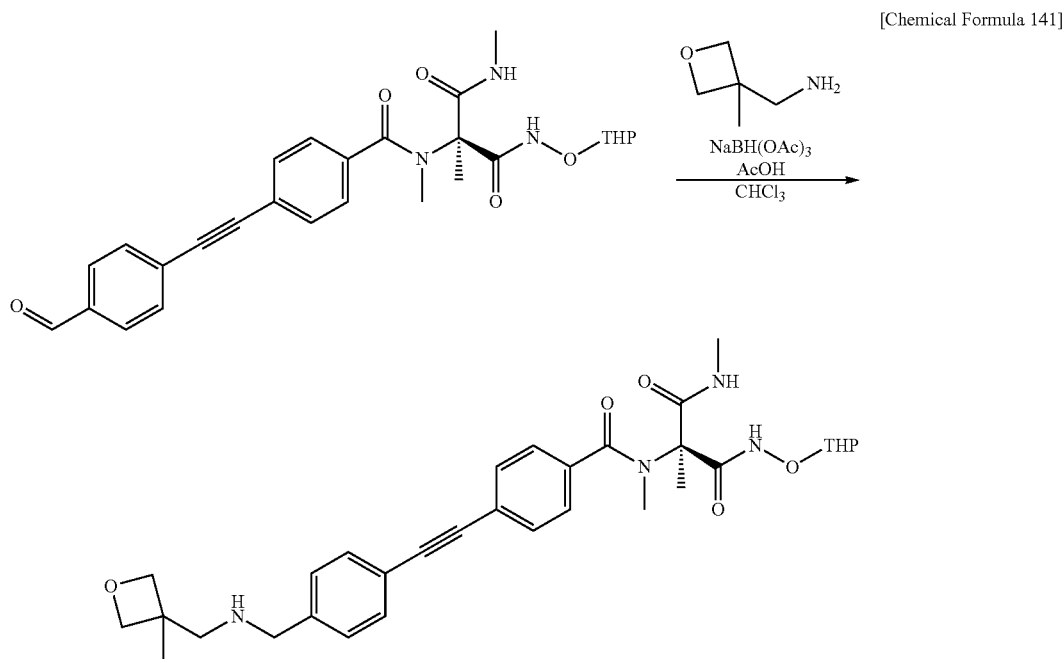

(1) From (2S)-2-[{4-[(4-formylphenyl)ethynyl]benzoyl}(methyl)amino]-N,2-dimethyl-N'-(tetrahydro-2H-pyran-2-yloxy)propanediamide (0.15 g) as obtained in Example 16-(1) and [(3-methyloxetan-3-yl)methyl]amine (63 mg), (2S)-N,2-dimethyl-2-[methyl(4-{[4-({[(3-methyloxetan-3-yl)methyl]amino}methyl)phenyl]ethynyl}benzoyl)amino]-N'-(tetrahydro-2H-pyran-2-yloxy)propanediamide (yellow solid) was obtained (0.13 g, 73%) in the same manner as in Example 16-(2).

$^1$H NMR (400 MHz, CHLOROFORM-d) δ ppm 1.32 (3 H, s), 1.40-1.95 (9 H, m), 2.63 (2 H, s), 2.80-2.90 (3 H, m), [3.17], 3.20 (3 H, s), 3.50-3.70 (1 H, m), 3.80-4.10 (1 H, m), 3.85 (2 H, s), 4.30-4.60 (4 H, m), 4.90-5.05 (1 H, m), 7.15-7.40 (2 H, m), 7.45-7.70 (6 H, m)

[Chemical Formula 142]

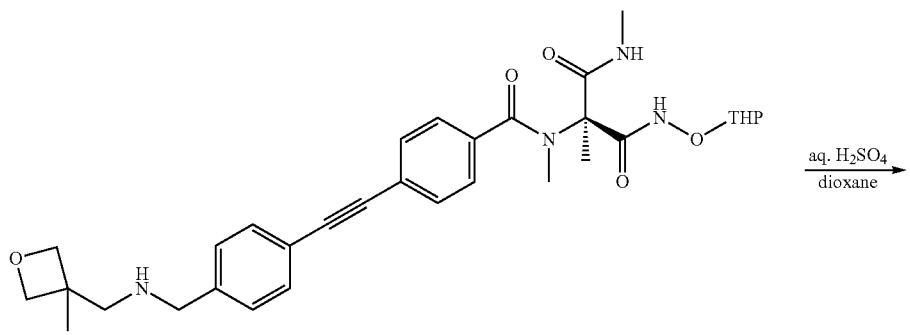

aq. H₂SO₄
────────
dioxane

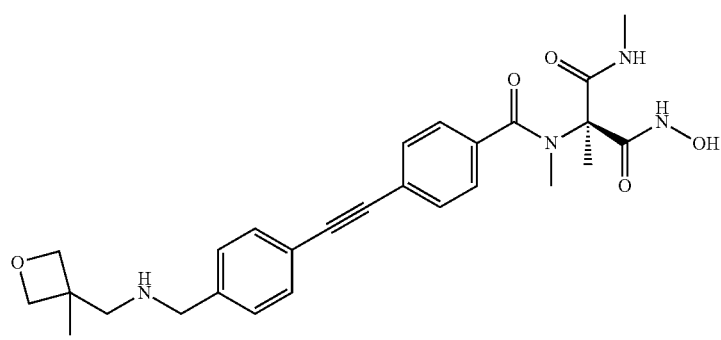

(2) From (2S)-N,2-dimethyl-2-[methyl(4-{[4-({[(3-methyloxetan-3-yl)methyl]amino}methyl)phenyl]ethynyl}benzoyl)amino]-N'-(tetrahydro-2H-pyran-2-yloxy)propanediamide (0.13 g) as obtained in Example 16-6-(1), (2S)-N-hydroxy-N',2-dimethyl-2-{methyl[(4-{[4-({[(3-methyloxetan-3-yl)methyl]amino}methyl)phenyl]ethynyl}phenyl)carbonyl]amino}propanediamide (Compound 578, yellow solid) was obtained in the same manner as in Example 16-(3) (62 mg, 55%).

MS (ESI): 493 (M+H)⁺, 491 (M−H)⁻

¹H NMR (400 MHz, CD₃OD) δ ppm 1.32 (3 H, s), 1.77 (3 H, s), 2.77 (2 H, s), 2.79 (3 H, s), 3.17 (3 H, s), 3.83 (2 H, s), 4.33 (2 H, d, J=5.9 Hz), 4.45 (2 H, d, J=5.9 Hz), 7.35-7.45 (2 H, m), 7.45-7.65 (6 H, m)

EXAMPLE 16-7

(2S)-N-hydroxy-2-[({4-[(4-{[3-(2-methoxyethoxy)azetidin-1-yl]methyl}phenyl)ethynyl]phenyl}carbonyl)(methyl)amino]-N',2-dimethylpropanediamide (Compound 577)

[Chemical Formula 143]

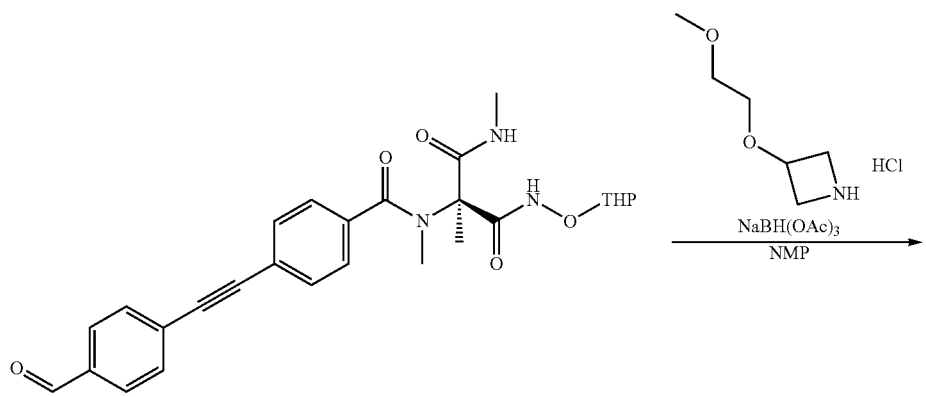

-continued

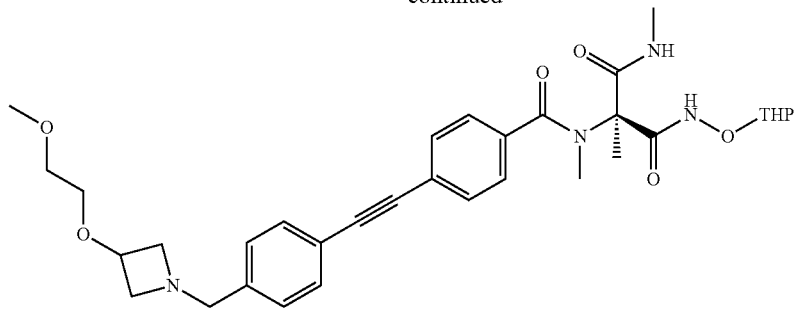

(1) From (2S)-2-[{4-[(4-formylphenyl)ethynyl]benzoyl}(methyl)amino]-N,2-dimethyl-N'-(tetrahydro-2H-pyran-2-yloxy)propanediamide (0.12 g) as obtained in Example 16-(1) and 3-(2-methoxyethoxy)azetidine hydrochloride (60 mg), (2S)-2-[{4-[(4-{[3-(2-methoxyethoxy)azetidin-1-yl]methyl}phenyl)ethynyl]benzoyl}(methyl)amino]-N,2-dimethyl-N'-(tetrahydro-2H-pyran-2-yloxy)propanediamide (yellow oil) was obtained (0.10 g, 69%) in the same manner as in Example 16-1-(3).

$^1$H NMR (400 MHz, CHLOROFORM-d) δ ppm 1.40-1.95 (6 H, m), [1.81], 1.82 (3 H, s), 2.80-2.90 (3 H, m), 2.95-3.05 (2 H, m), [3.17], 3.20 (3 H, s), 3.35 (3 H, s), 3.45-3.70 (9 H, m), 3.75-4.10 (1 H, m), 4.15-4.25 (1 H, m), 4.90-5.05 (1 H, m), [6.95-7.05], 7.60-7.70 (1 H, m), 7.20-7.30 (2 H, m), 7.45-7.60 (6 H, m), [10.10], 10.51 (1 H, br. s.)

[Chemical Formula 144]

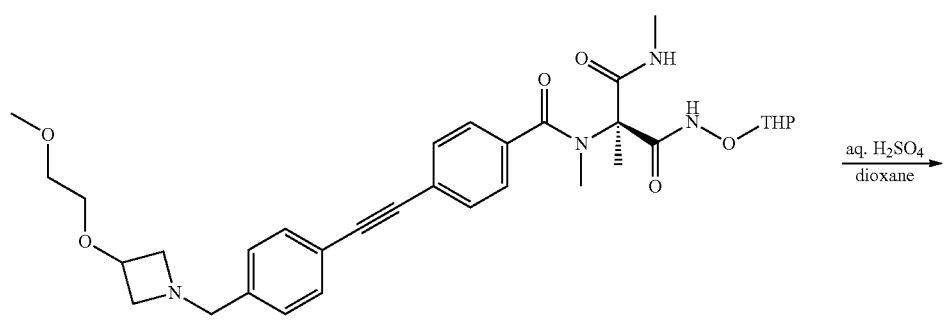

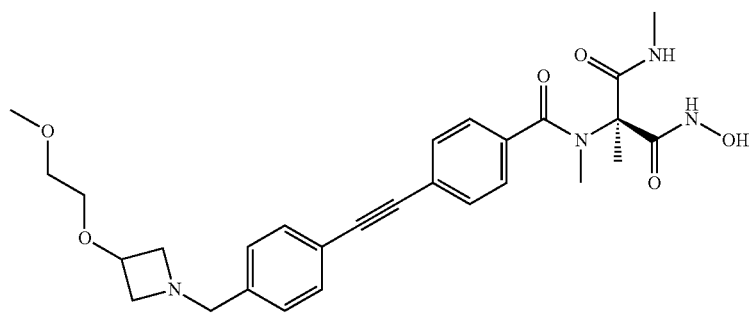

(2) From (2S)-2-[{4-[(4-{[3-(2-methoxyethoxy)azetidin-1-yl]methyl}phenyl)ethynyl]benzoyl}(methyl)amino]-N,2-dimethyl-N'-(tetrahydro-2H-pyran-2-yloxy)propanediamide (0.10 g) as obtained in Example 16-7-(1), (2S)-N-hydroxy-2-[({4-[(4-{[3-(2-methylethoxy)azetidine-1-yl]methyl}phenyl)ethynyl]phenyl}carbonyl)(methyl)amino]-N',2-dimethylpropanediamide (Compound 577, yellow solid) was obtained (61 mg, 69%) in the same manner as in Example 16-(3).

MS (ESI): 523 (M+H)$^+$, 521 (M−H)$^−$ $^1$H NMR (400 MHz, CD$_3$OD) δ ppm 1.77 (3 H, s), 2.79 (3 H, s), 3.16 (3 H, s), 3.35 (3 H, s), 3.44-3.62 (6 H, m), 3.88-3.96 (2 H, m), 4.00 (2 H, s), 4.24-4.32 (1 H, m), 7.39 (2 H, d, J=8.3 Hz), 7.52-7.65 (6 H, m)

EXAMPLE 16-8

(2S)-N-hydroxy-N',2-dimethyl-2-(methyl{[4-({4-[(oxetan-3-ylamino)methyl]phenyl}ethynyl)phenyl]carbonyl}amino)propanediamide (Compound 396)

[Chemical Formula 145]

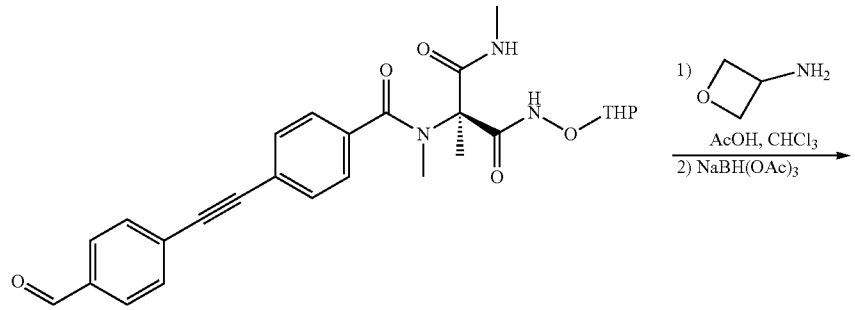

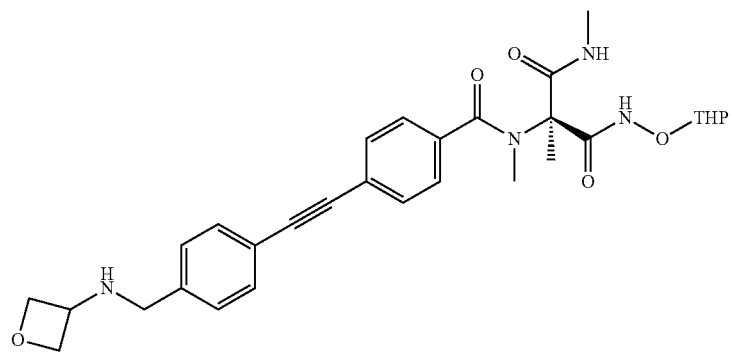

(1) The same procedure as in Example 16-(2) was performed using (2S)-2-[{4-[(4-formylphenyl)ethynyl]benzoyl}(methyl)amino]-N,2-dimethyl-N'-(tetrahydro-2H-pyran-2-yloxy)propanediamide (0.25 g) as obtained in Example 16-(1) and oxetan-3-amine (44 mg), whereby (2S)-N,2-dimethyl-2-{methyl[4-({4-[(oxetan-3-ylamino)methyl]phenyl}ethynyl)benzoyl]amino}-N'-(tetrahydro-2H-pyran-2-yloxy)propanediamide (light yellow foam) was obtained (0.24 g, 85%).

MS (ESI): 549 (M+H)$^+$, 547 (M−H)$^−$ $^1$H NMR (600 MHz, CHLOROFORM-d) δ ppm 1.56-1.91 (9 H, m), 2.82-2.89 (3 H, m), [3.17], 3.20 (3 H, s), 3.53-3.70 (1 H, m), 3.77 (2 H, s), 3.83-4.05 (2 H, m), 4.39-4.45 (2 H, m), 4.79 (2 H, t, J=6.8 Hz), 4.92-5.03 (1 H, m), 6.99 (1 H, br. s.), 7.31 (2 H, d, J=8.3 Hz), 7.46-7.60 (6 H, m), 7.60-7.66 (1 H, m)

[Chemical Formula 146]

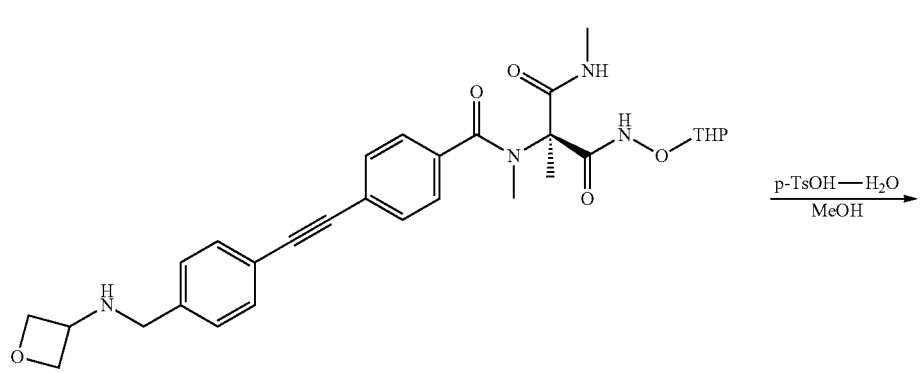

-continued

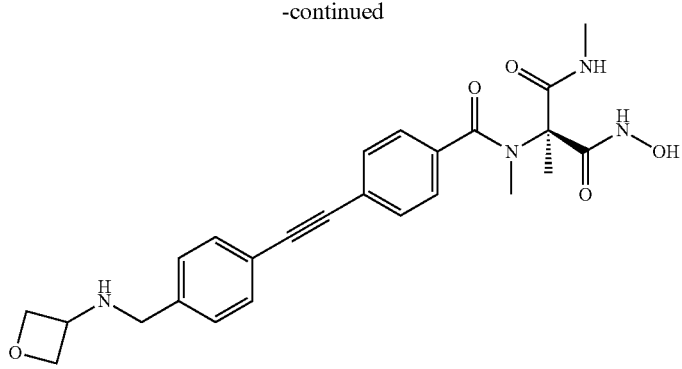

(2) To a methanol (2.0 mL) solution of (2S)-N,2-dimethyl-2-{methyl[4-({4-[(oxetan-3-ylamino)methyl]phenyl}ethynyl)benzoyl]amino}-N'-(tetrahydro-2H-pyran-2-yloxy)propanediamide (97 mg) as obtained in Example 16-8-(1), p-TsOH.H$_2$O (43 mg) was added, and the mixture was stirred for 1.5 hours at room temperature. After a saturated aqueous solution of sodium hydrogen carbonate was added to the reaction mixture, the system was extracted with chloroform. The organic layer was dried over anhydrous sodium sulfate, whereafter the desiccant was filtered out, and the solvent was distilled off under reduced pressure. The resulting residue was purified by OH type silica gel chromatography (gradient elution with chloroform/methanol=98/2→86/14). Then, IPE was added, and the precipitated solid was filtered off and dried to obtain (2S)-N-hydroxy-N',2-dimethyl-2-(methyl{[4-({4-[(oxetan-3-ylamino)methyl]phenyl}ethynyl)phenyl]carbonyl}amino)propanediamide (Compound 396, light yellow solid) (45 mg, 55%).

MS (ESI): 465 (M+H)$^+$, 463 (M−H)$^-$ $^1$H NMR (600 MHz, CD$_3$OD) δ ppm 1.77 (3 H, s), 2.79 (3 H, s), 3.14-3.19 (3 H, m), 3.72 (2 H, s), 3.95-4.04 (1 H, m), 4.39-4.48 (2 H, m), 4.66-4.73 (2 H, m), 7.37 (2 H, d, J=8.3 Hz), 7.51 (2 H, d, J=8.3 Hz), 7.54-7.64 (4 H, m)

EXAMPLE 16-9

(2S)-N-hydroxy-N',2-dimethyl-2-{methyl[(4-{[4-(2-oxa-6-azaspiro[3.3]hept-6-ylmethyl)phenyl]ethynyl}phenyl)carbonyl]amino}propanediamide (Compound 416)

[Chemical Formula 147]

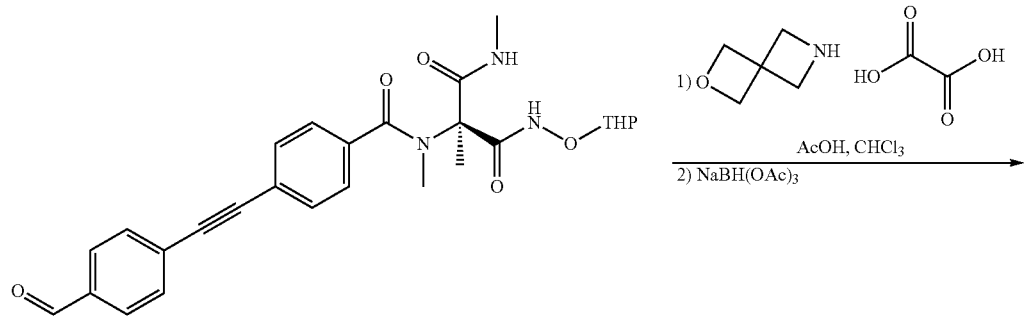

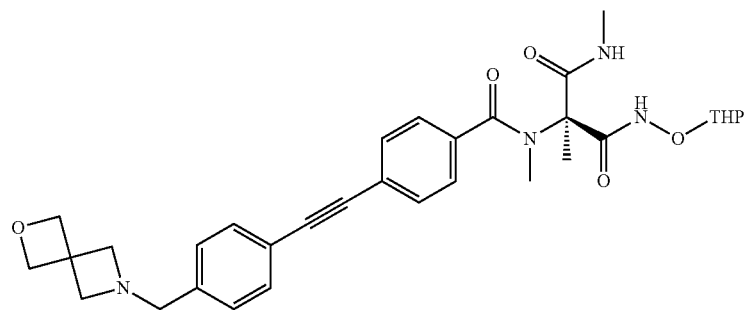

(1) The same procedure as in Example 16-(2) was performed using (2S)-2-[{4-[(4-formylphenyl)ethynyl]benzoyl}(methyl)amino]-N,2-dimethyl-N'-(tetrahydro-2H-pyran-2-yloxy)propanediamide (0.12 g) as obtained in Example 16-(1) and an oxalic acid salt (71 mg) of 2-oxa-6-azaspiro[3.3]heptane, whereby (2S)-N,2-dimethyl-2-[methyl(4-{[4-(2-oxa-6-azaspiro[3.3]hept-6-ylmethyl)phenyl] ethynyl}benzoyl)amino]-N'-(tetrahydro-2H-pyran-2-yloxy)propanediamide (yellow oil) was obtained (95 mg, 68%).

MS (ESI): 575 (M+H)$^+$, 573 (M−H)$^-$ $^1$H NMR (600 MHz, CHLOROFORM-d) δ ppm 1.61-1.90 (9 H, m), 2.84-2.87 (3 H, m), [3.17], 3.20 (3 H, s), 3.36-3.39 (4 H, m), 3.51-3.70 (3 H, m), 3.83-4.07 (1 H, m), 4.72-4.77 (4 H, m), 4.93-5.01 (1 H, m), 6.96-7.03 (1 H, m), 7.24 (2 H, d, J=7.8 Hz), 7.44-7.59 (6 H, m), 7.62 (1 H, br. s.)

[Chemical Formula 148]

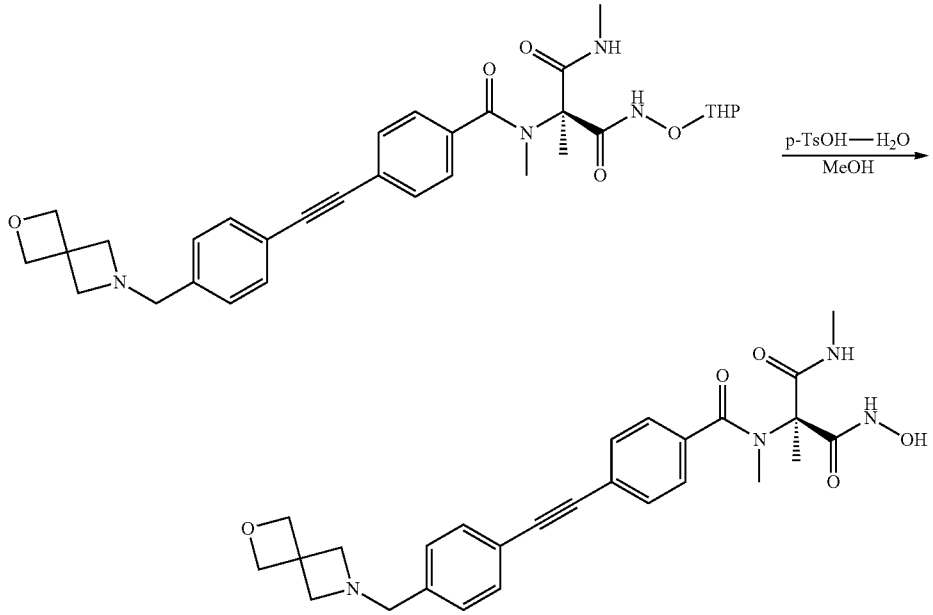

(2) The same procedure as in Example 16-8-(2) was performed using (2S)-N,2-dimethyl-2-[methyl(4-{[4-[2-oxa-6-azaspiro[3.3]hept-6-ylmethyl)phenyl]ethynyl}benzoyl)amino]-N'-(tetrahydro-2H-pyran-2-yloxy)propanediamide (95 mg) as obtained in Example 16-9-(1), whereby (2S)-N-hydroxy-N',2-dimethyl-2-{methyl[(4-{[4-(2-oxa-6-azaspiro[3.3]hept-6-ylmethyl)phenyl]ethynyl}phenyl)carbonyl]amino}propanediamide (Compound 416, light yellow solid) was obtained (23 mg, 28%).

MS (ESI): 491 (M+H)$^+$, 489 (M−H)$^-$ $^1$H NMR (600 MHz, CD$_3$OD) δ ppm 1.77 (3 H, s), 2.79 (3 H, s), 3.17 (3 H, s), 3.43-3.50 (4 H, m), 3.61 (2 H, s), 4.71-4.75 (4 H, m), 7.31 (2 H, d, J=8.3 Hz), 7.50 (2 H, d, J=8.3 Hz), 7.54-7.63 (4 H, m)

EXAMPLE 16-10

(2S)-2-[({4-[(4-{[(furan-2-ylmethyl)amino]methyl}phenyl)ethynyl]phenyl}carbonyl)(methyl)amino]-N-hydroxy-N',2-dimethylpropanediamide (Compound 417)

[Chemical Formula 149]

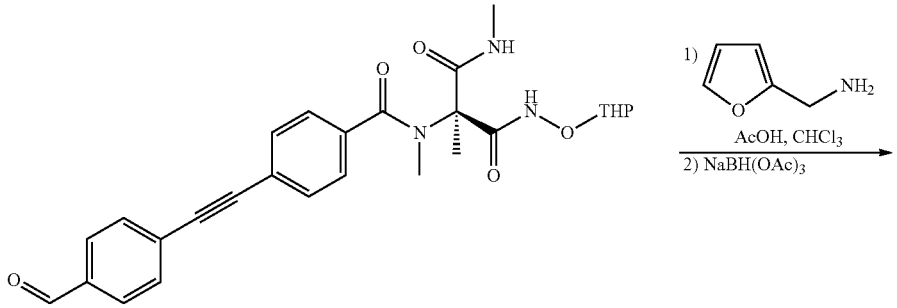

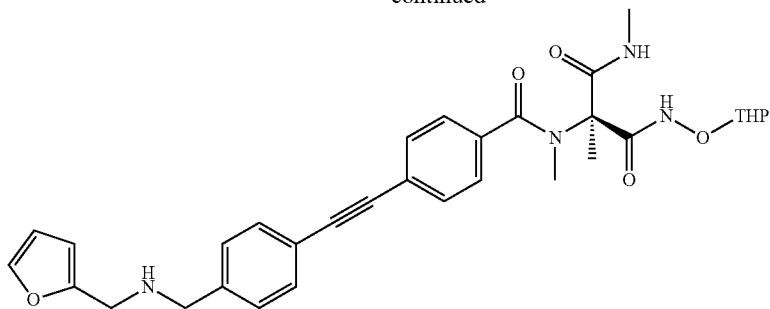

(1) The same procedure as in Example 16-(2) was performed using (2S)-2-[{4-[(4-formylphenyl)ethynyl]benzoyl}(methyl)amino]-N,2-dimethyl-N'-(tetrahydro-2H-pyran-2-yloxy)propanediamide (0.12 g) as obtained in Example 16-(1) and 1-(furan-2-yl (2) The same procedure as in Example 16-8-(2) was performed using (2S)-N,2-dimethyl-2-[methyl(4-{[4-[2-oxa-6-azaspiro[3.3]hept-6-ylmethyl)phenyl]ethynyl}benzoyl)amino]-N'-(tetrahydro-2H-pyran-2-yloxy)propanediamide (95 mg) as obtained in Example 16-9-(1), whereby (2S)-N-hydroxy-N',2-dimethyl-2-{methyl[(4-{[4-(2-oxa-6-azaspiro[3.3]hept-6-ylmethyl)phenyl]ethynyl}phenyl)carbonyl]amino}propanediamide (Compound 416, light yellow solid) was obtained (23 mg, 28%).

MS (ESI): 491 (M+H)$^+$, 489 (M−H)$^−$ $^1$H NMR (600 MHz, CD$_3$OD) δ ppm 1.77 (3 H, s), 2.79 (3 H, s), 3.17 (3 H, s), 3.43-3.50 (4 H, m), 3.61 (2 H, s), 4.71-4.75 (4 H, m), 7.31 (2 H, d, J=8.3 Hz), 7.50 (2 H, d, J=8.3 Hz), 7.54-7.63 (4 H, m)

EXAMPLE 16-10

(2S)-2-[({4-[(4-{[(furan-2-ylmethyl)amino]methyl}phenyl)ethynyl]phenyl}carbonyl)(methyl)amino]-N-hydroxy-N',2-dimethylpropanediamide (Compound 417) )methanamine (34 mg), whereby (2S)-2-[{4-[(4-{[(furan-2-ylmethyl)amino]methyl}phenyl)ethynyl]benzoyl}(methyl)amino]-N,2-dimethyl-N'-(tetrahydro-2H-pyran-2-yloxy)propanediamide (yellow oil) was obtained (93 mg, 67%).

[Chemical Formula 150]

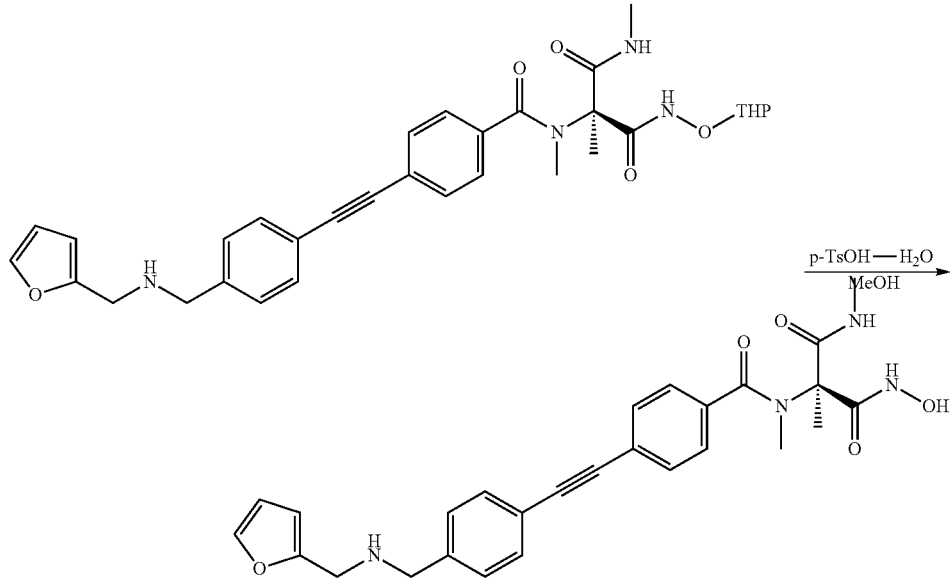

(2) The same procedure as in Example 16-8-(2) was performed using (2S)-2-[{4-[(4-{[(furan-2-ylmethyl)amino]methyl}phenyl)ethynyl]benzoyl}(methyl)amino]-N,2-dimethyl-N'-(tetrahydro-2H-pyran-2-yloxy)propanediamide (93 mg) as obtained in Example 16-10-(1), whereby (2S)-2-[({4-[(4-{[(furan-2-ylmethyl)amino]methyl}phenyl)ethynyl]phenyl}carbonyl)(methyl)amino]-N-hydroxy-N',2-dimethylpropanediamide (Compound 417, light yellow solid) was obtained (26 mg, 33%).

MS (ESI): 489 (M+H)$^+$, 487 (M−H)$^−$ $^1$H NMR (600 MHz, CD$_3$OD) δ ppm 1.77 (3 H, s), 2.79 (3 H, s), 3.17 (3 H, s), 3.71-3.83 (4 H, m), 6.23-6.41 (2 H, m), 7.37 (2 H, d, J=7.8 Hz), 7.43-7.68 (7 H, m)

EXAMPLE 17

(2S)-N-hydroxy-N',2-dimethyl-2-{methyl[(4-{[4-(1,4-oxazepan-4-ylmethyl)phenyl]ethynyl}phenyl)carbonyl]amino}propanediamide (Compound 376)

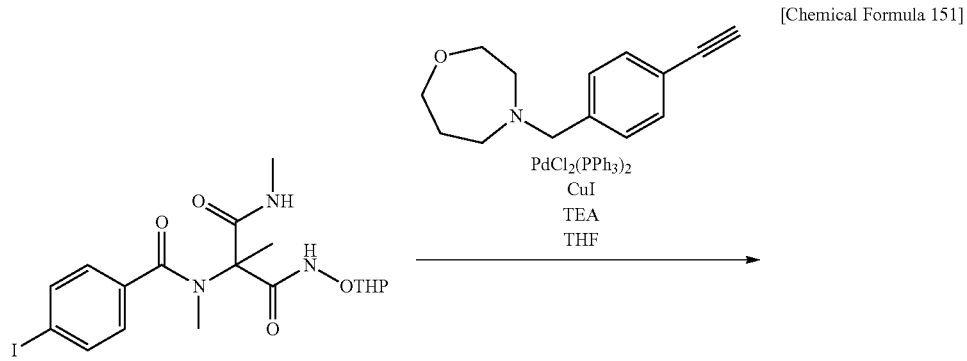

[Chemical Formula 151]

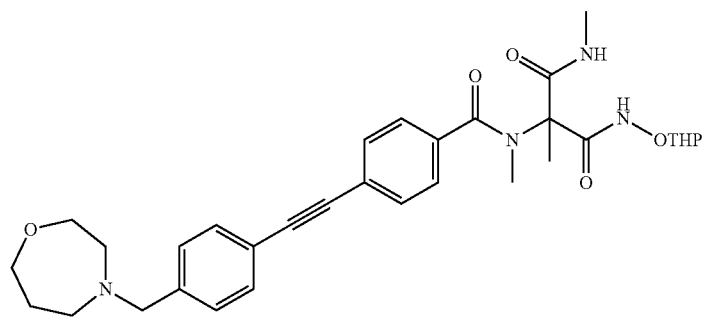

(1) TEA (0.87 mL) and a THF (5.0 mL) solution of 4-(4-ethynylbenzyl)-1,4-oxazepane (0.45 g) as obtained in Example 15-(3) were added to a THF (50 mL) suspension of 2-[(4-iodobenzoyl)(methyl)amino]-N,2-dimethyl-N'-(tetrahydro-2H-pyran-2-yloxy)propanediamide (Intermediate 12, 1.0 g), PdCl$_2$(PPh$_3$)$_2$ (73 mg) and CuI (40 mg) under ice cooling, and the mixture was stirred for 2 hours. PdCl$_2$(PPh$_3$)$_2$ (73 mg), CuI (40 mg) and TEA (0.87 mL) were added, and a THF (5.0 mL) solution of 4-(4-ethynylbenzyl)-1,4-oxazepane (0.45 g) as obtained in Example 15-(3) was further added at 60° C. The mixture was stirred for 1.5 hours, and then the reaction mixture was concentrated. The resulting residue was purified by NH type silica gel chromatography (gradient elution with ethyl acetate→chloroform/methanol=100/0→95/5) to obtain N,2-dimethyl-2-{methyl[(4-{[4-(1,4-oxazepan-4-ylmethyl)phenyl]ethynyl}phenyl)carbonyl]amino}-N'-(tetrahydro-2H-pyran-2-yloxy)propanediamide (light brown foam) (1.1 g, 93%).

MS (ESI/APCI Dual): 577 (M+H)$^+$, 599 (M+Na)$^+$, 575 (M−H)$^−$

[Chemical Formula 152]

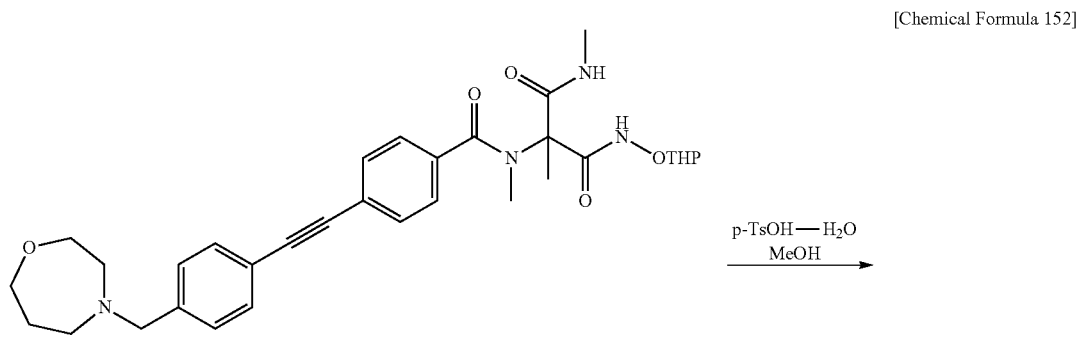

-continued

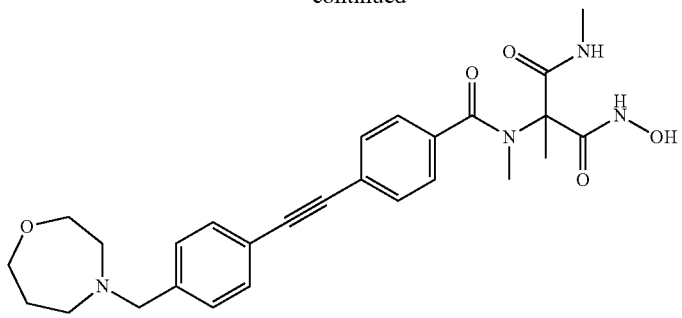

(2) To a methanol (10 mL) solution of N,2-dimethyl-2-{methyl[(4-{[4-(1,4-oxazepan-4-ylmethyl)phenyl]ethynyl}phenyl)carbonyl]amino}-N'-(tetrahydro-2H-pyran-2-yloxy)propanediamide (0.80 g) as obtained in Example 17-(1), p-TsOH.H₂O (0.32 g) was added, and the mixture was stirred for 4 hours at room temperature. After the reaction mixture was concentrated, a saturated aqueous solution of sodium hydrogen carbonate was added, and the mixture was extracted with chloroform. The organic layer was separated using a phase separator, and distilled off under reduced pressure. The resulting residue was purified by NH type silica gel chromatography (gradient elution with chloroform/methanol=100/2→90/10) to obtain N-hydroxy-N',2-dimethyl-2-{methyl[(4-{[4-(1,4-oxazepan-4-ylmethyl)phenyl]ethynyl}phenyl)carbonyl]amino}propanediamide (yellow solid) (0.48 g, 71%).

MS (ESI/APCI Dual): 493 (M+H)⁺, 491 (M−H)⁻

[Chemical Formula 153]

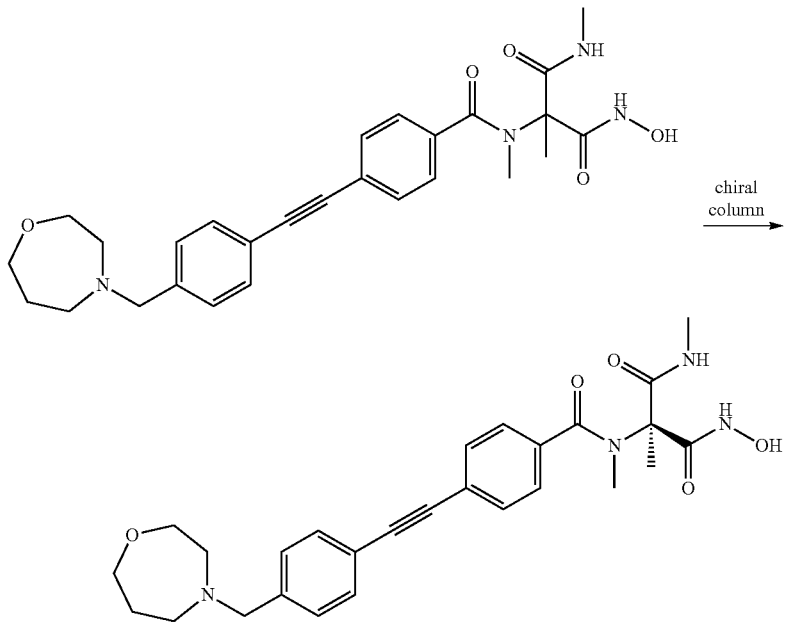

(3) N-hydroxy-N',2-dimethyl-2-{methyl[(4-{[4-(1,4-oxazepan-4-ylmethyl)phenyl]ethynyl}phenyl)carbonyl]amino}propanediamide (0.39 g) as obtained in Example 17-(2) was isolated and purified using a chiral column. (Isolation conditions: column: CHIRALPAKAD-H, column size: 2 cm I.D.×25 cm L, mobile phase: hexane/isopropyl alcohol=60/40 <v/v>, flow velocity: 10 mL/min, column temperature: 40° C., detection wavelength: 254 nm.) The resulting crude crystals were washed with IPE, and then dried to obtain (2S)-N-hydroxy-N',2-dimethyl-2-{methyl[(4-{[4-(1,4-oxazepan-4-ylmethyl)phenyl]ethynyl}phenyl)carbonyl]amino}propanediamide (Compound 376, yellow solid) (0.13 g).

[α]$_D$; +6.2 (C:0.10, methanol)

MS (ESI/APCI Dual): 493 (M+H)⁺, 491 (M−H)⁻

¹H NMR (600 MHz, CD₃OD) δ ppm 1.77 (3 H, s), 1.89-1.95 (2 H, m), 2.69-2.76 (4 H, m), 2.79 (3 H, s), 3.17 (3 H, s), 3.71 (2 H, s), 3.71-3.75 (2 H, m), 3.81 (2 H, t, J=6.0 Hz), 7.36-7.62 (8 H, m)

EXAMPLE 18

(2S)-N-hydroxy-2-{[(4-{[5-(methoxymethyl)furan-3-yl]ethynyl}phenyl)carbonyl](methyl)amino}-N',2-dimethylpropanediamide (Compound 550)

[Chemical Formula 154]

(1) Sodium borohydride (0.32 g) was added in divided portions to an ethanol (15 mL) solution of 4-bromofuran-2-carbaldehyde (3.0 g) under ice cooling, and the mixture was stirred for 1 hour at room temperature. Acetone, ethyl acetate and water were added sequentially, and the solvents were distilled off under reduced pressure. Ethyl acetate was added to the resulting residue, and the organic layer was isolated. The extract was washed with water and brine sequentially, and dried over anhydrous magnesium sulfate. Then, the desiccant was filtered out, and the solvent was distilled off under reduced pressure to obtain (4-bromofuran-2-yl)methanol (brown oil) (3.1 g, 100%).

¹H NMR (400 MHz, CHLOROFORM-d) δ ppm 1.80-1.87 (1 H, m), 4.58 (2 H, d, J=5.4 Hz), 6.36 (1 H, s), 7.40 (1 H, br. s.)

[Chemical Formula 155]

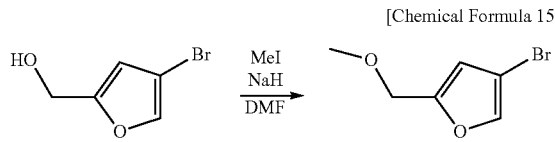

(2) Iodomethane (1.6 mL) was added to a DMF (15 mL) solution of (4-bromofuran-2-yl)methanol (3.0 g) as obtained in Example 18-(1). Under ice cooling, 60% sodium hydride (0.82 g) was added in divided portions, and the mixture was stirred for 1 hour and 40 minutes at room temperature. Ethyl acetate and water were added, and the organic layer was isolated. The extract was washed with water and brine sequentially, and dried over anhydrous magnesium sulfate. Then, the desiccant was filtered out, and the solvent was distilled off under reduced pressure to obtain partially purified 4-bromo-2-(methoxymethyl)furan (yellow oil) (3.9 g).

¹H NMR (400 MHz, CHLOROFORM-d) δ ppm 3.36 (3 H, s), 4.36 (2 H, s), 6.38 (1 H, s), 7.39-7.43 (1 H, m)

[Chemical Formula 156]

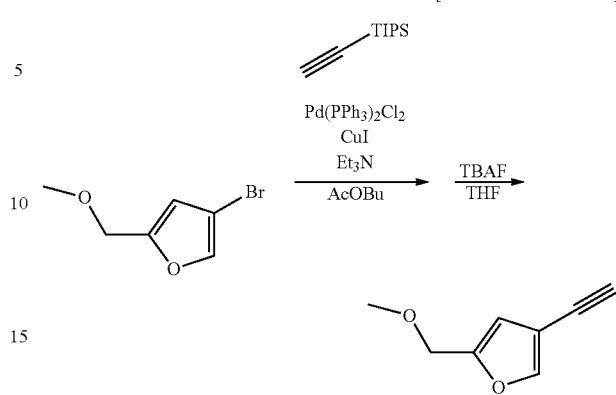

(3) A mixture of partially purified 4-bromo-2-(methoxymethyl)furan (1.9 g) as obtained in Example 18-(2), AcOBu (16 mL), CuI (0.33 g), PdCl₂(PPh₃)₂ (0.60 g), triisopropylsilylacetylene (9.6 mL) and TEA (12 mL) was stirred in a nitrogen atmosphere for 7.5 hours at 110° C. After the reaction mixture was allowed to cool, ethyl acetate (0.10 L), OH type silica gel (1.9 g), cellpure (0.95 g) and activated carbon (10 mg) were added. The insolubles were filtered out, and the filtrate was concentrated under reduced pressure. The resulting residue was purified by OH type silica gel column chromatography (gradient elution with hexane/ethyl acetate=100/0→80/20) to obtain a yellow oil (1.7 g). THF (4.0 mL) was added to this oil (0.80 g), and a 1 mol/L TBAF-THF solution (4.1 mL) was added dropwise to the mixture under ice cooling. The mixture was stirred for 30 minutes under ice cooling, and then stirred for 30 minutes at room temperature. The reaction mixture was concentrated under reduced pressure, and the resulting residue was purified by OH type silica gel column chromatography (gradient elution with hexane/ethyl acetate=100/0→90/10) to obtain 4-ethynyl-2-(methoxymethyl)furan (yellow oil) (0.24 g).

¹H NMR (400 MHz, CHLOROFORM-d) δ ppm 3.04 (1 H, s), 3.36 (3 H, s), 4.37 (2 H, s), 6.40 (1 H, s), 7.63 (1 H, s)

[Chemical Formula 157]

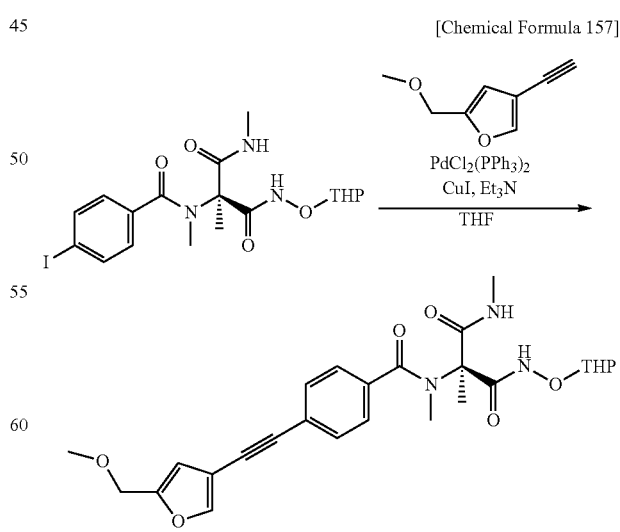

(4) PdCl₂(PPh₃)₂ (70 mg), CuI (38 mg) and TEA (1.5 mL) were added to a THF (7.0 mL) solution of 4-ethynyl-2-(methoxymethyl)furan (0.24 g) as obtained in Example 18-(3) and (2S)-2-[(4-iodobenzoyl)(methyl)amino]-N,2-dimethyl-N'-(tetrahydro-2H-pyran-2-yloxy)propanediamide (Intermediate 15, 0.51 g), and the mixture was stirred for 5.5 hours at room temperature in a nitrogen atmosphere. Ethyl acetate (30 mL), OH type silica gel (1.9 g), cellpure (0.95 g) and activated carbon (50 mg) were added, the insolubles were filtered out, and the filtrate was concentrated under reduced pressure. The resulting residue was purified by OH type silica gel column chromatography (gradient elution with ethyl acetate/hexane=75/25→100/0, followed by gradient elution with chloroform/acetone=100/0→70/30) to obtain (2S)-2-[(4-{[5-(methoxymethyl)furan-3-yl]ethynyl}benzoyl)(methyl)amino]-N,2-dimethyl-N'-(tetrahydro-2H-pyran-2-yloxy)propanediamide (yellow solid) (0.43 g, 84%).

$^1$H NMR (400 MHz, CHLOROFORM-d) δ ppm 1.50-1.95 (6 H, m), [1.81], 1.82 (3 H, s), 2.82-2.88 (3 H, m), [3.17], 3.20 (3 H, s), 3.38 (3 H, s), 3.51-3.70 (1 H, m), 3.80-4.08 (1 H, m), 4.40 (2 H, s), 4.93-5.03 (1 H, m), 6.46 (1 H, d, J=0.5 Hz), [7.00], 7.63 (1 H, br. s.), 7.46-7.56 (4 H, m), 7.66-7.70 (1 H, m), [10.10], 10.51 (1 H, br. s.)

methanol=100/0→80/20) to obtain (2S)-N-hydroxy-2-{[(4-{[5-(methoxymethyl)furan-3-yl]ethynyl}phenyl)carbonyl](methyl)amino}-N',2-dimethylpropanediamide (Compound 550, white solid) (0.25 g, 68%).

MS (ESI): 436 (M+Na)$^+$, 412 (M–H)$^-$ $^1$H NMR (400 MHz, CHLOROFORM-d) δ ppm 1.80 (3 H, s), 2.83 (3 H, d, J=4.6 Hz), 3.17 (3 H, s), 3.38 (3 H, s), 4.39 (2 H, s), 6.45 (1 H, s), 6.80-7.00 (1 H, m), 7.30-7.60 (5 H, m), 7.68 (1 H, br. s.), 10.54 (1 H, br. s.)

Compounds 403, 410, 418, 420, 422, 424, 428, 433, 435, 436, 438, 528, 575, 576, 588, 589, 593, 599, 600, 602 to 605, 609, 612, 616, 622, 630 and 633 were synthesized by the same methods as in Example 18 with the use of the corresponding materials.

[Chemical Formula 158]

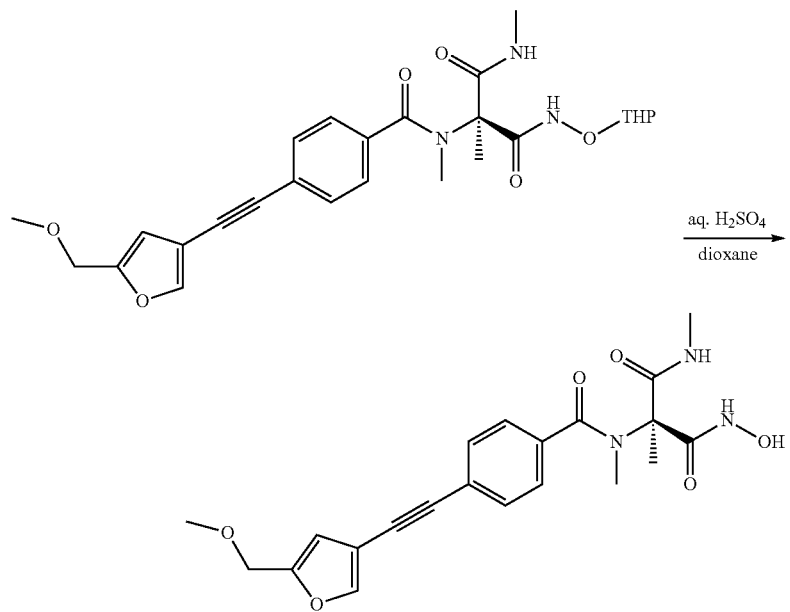

(5) A 1 mol/L sulfuric acid aqueous solution (2.6 mL) was added dropwise, under water cooling, to a 1,4-dioxane (4.0 mL) solution of (2S)-2-[(4-{[5-(methoxymethyl)furan-3-yl]ethynyl}benzoyl)(methyl)amino]-N,2-dimethyl-N'-(tetrahydro-2H-pyran-2-yloxy)propanediamide (0.43 g) as obtained in Example 18-(4), and the mixture was stirred for 3 hours and 45 minutes at room temperature. Ethyl acetate and water were added, and the mixture was adjusted to pH 6 with a saturated aqueous solution of sodium hydrogen carbonate. Then, sodium chloride was added, and the organic layer was isolated. The extract was washed with brine, and dried over anhydrous sodium sulfate. Then, the desiccant was filtered out, and the solvent was distilled off under reduced pressure. The resulting residue was purified by OH type silica gel column chromatography (gradient elution with chloroform/

EXAMPLE 19

(2S)-N-hydroxy-N',2-dimethyl-2-[methyl({4'-[2-(morpholin-4-yl)ethoxy]biphenyl-4-yl}carbonyl)amino]propanediamide (Compound 437)

[Chemical Formula 159]

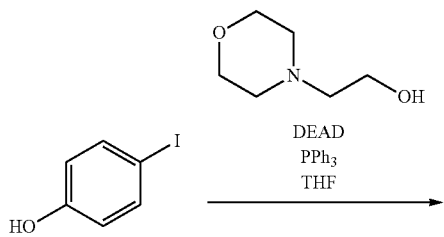

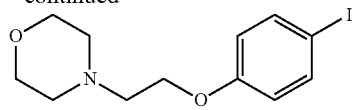

(1) 40% DEAD/toluene (2.5 mL) was added to a THF (30 mL) solution of 4-iodophenol (1.0 g), 2-morpholinoethanol (0.72 g) and triphenylphosphine (1.4 g) under ice cooling, and the mixture was stirred for 17 hours at room temperature. After the solvents were distilled off, the resulting residue was purified by NH type silica gel chromatography (gradient elution with hexane/ethyl acetate=90/0→60/40) to obtain 4-[2-(4-iodophenoxy)ethyl]morpholine (colorless oil) (1.4 g, 93%).

MS (ESI/APCI Dual): 334 (M+H)$^+$ $^1$H NMR (200 MHz, CHLOROFORM-d) δ ppm 2.47-2.64 (4 H, m), 2.79 (2 H, t, J=5.7 Hz), 3.64-3.81 (4 H, m), 4.07 (2 H, t, J=5.7 Hz), 6.59-6.77 (2 H, m), 7.46-7.63 (2 H, m)

[Chemical Formula 160]

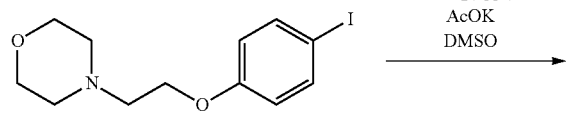

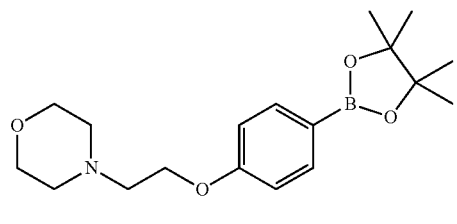

(2) A DMSO (5.0 mL) suspension of 4-[2-(4-iodophenoxy)ethyl]morpholine (0.49 g) as obtained in Example 19-(1), 4,4,4',4',5,5,5',5'-octamethyl-2,2'-bi-1,3,2-dioxaborolane (0.56 g), PdCl$_2$(dppf).CH$_2$Cl$_2$ (0.12 g), and potassium acetate (0.43 g) was stirred for 4 hours at 90° C. Water was added, and the mixture was extracted with ethyl acetate. The organic layer was washed with brine, and dried over anhydrous magnesium sulfate. Then, the desiccant was filtered out, and the solvent was distilled off under reduced pressure. The resulting residue was purified by NH type silica gel chromatography (gradient elution with hexane/ethyl acetate=90/10→70/30) to obtain 4-{2-[4-(4,4,5,5-tetramethyl-1,3,2-dioxaborolan-2-yl)phenoxy]ethyl}morpholine (colorless foam) (0.63 g).

MS (ESI/APCI Dual): 334 (M+H)$^+$ $^1$H NMR (200 MHz, CHLOROFORM-d) δ ppm 1.33 (12 H, s), 2.50-2.65 (4 H, m), 2.80 (2 H, t, J=5.7 Hz), 3.65-3.80 (4 H, m), 4.14 (2 H, t, J=5.7 Hz), 6.83-6.95 (2 H, m), 7.67-7.81 (2 H, m)

[Chemical Formula 161]

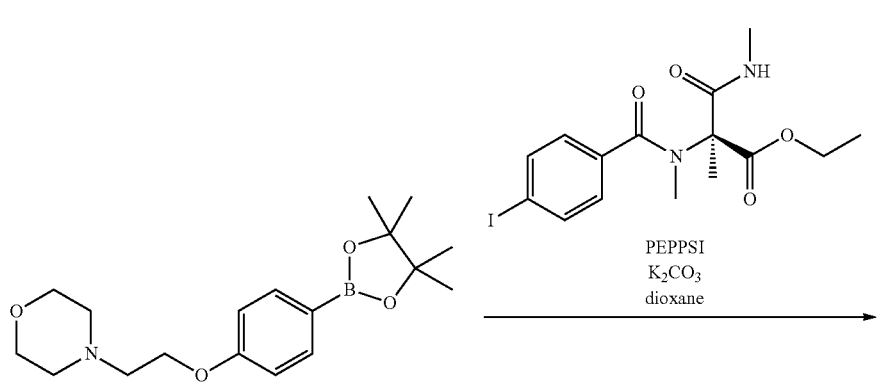

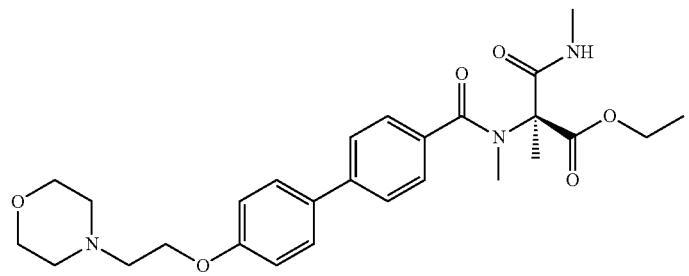

(3) A dioxane (3.0 mL) suspension of 4-{2-[4-(4,4,5,5-tetramethyl-1,3,2-dioxaborolan-2-yl)phenoxy]ethyl}morpholine (0.55 g) as obtained in Example 19-(2), 1-{[(2S)-1-ethoxy-2-methyl-3-(methylamino)-1,3-dioxopropan-2-yl](methyl)carbamoyl}-4-iodobenzene (Intermediate 13-1, 0.43 g), PEPPSI (83 mg), and potassium carbonate (0.51 g) was stirred for 8 hours at 90° C. PEPPSI (83 mg) was added, and the mixture was stirred for 2 hours at 110° C. Water was added, and the mixture was extracted with chloroform. The organic layer was separated using a phase separator, and the solvent was distilled off under reduced pressure. The resulting residue was purified by NH type silica gel chromatography (gradient elution with hexane/ethyl acetate=50/50→0/100) to obtain 4-{2-[(4'-{[(2S)-1-ethoxy-2-methyl-3-(methylamino)-1,3-dioxopropan-2-yl](methyl)carbamoyl}biphenyl-4-yl)oxy]ethyl}morpholine (light yellow oil) (96 mg, yield upon the 2 steps: 19%).

MS (ESI/APCI Dual): 498 (M+H)$^+$, 520 (M+Na)$^-$ $^1$H NMR (200 MHz, CHLOROFORM-d) δ ppm 1.17-1.38 (3 H, m), 1.78 (3 H, s), 2.52-2.68 (4 H, m), 2.76-2.96 (5 H, m), 3.19 (3 H, s), 3.65-3.83 (4 H, m), 4.05-4.35 (4 H, m), 6.90-7.07 (2 H, m), 7.44-7.66 (6 H, m), 8.07-8.29 (1 H, m)

[Chemical Formula 162]

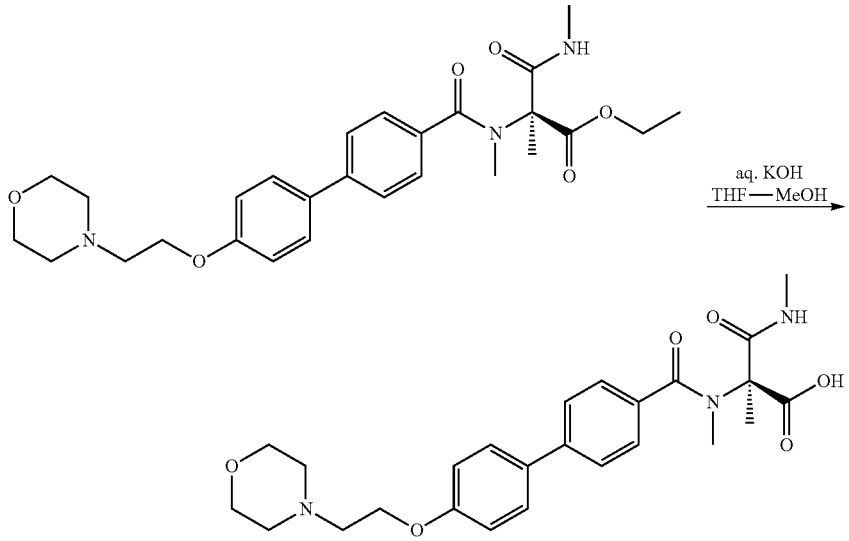

(4) An aqueous solution (2.0 mL) of potassium hydroxide (0.11 g) was added to a THF (2.0 mL)-methanol (2.0 mL) solution of 4-{2-[(4'-{[(2S)-1-ethoxy-2-methyl-3-(methylamino)-1,3-dioxopropan-2-yl](methyl)carbamoyl}biphenyl-4-yl)oxy]ethyl}morpholine (93 mg) as obtained in Example 19-(3), and the mixture was stirred for 16 hours at room temperature. The reaction mixture was adjusted to pH 6 with a 10% aqueous solution of citric acid, and extracted with chloroform. The organic layer was separated using a phase separator, and the solvent was distilled off under reduced pressure to obtain 4-{2-[(4'-{[(2S)-2-carboxy-1-(methylamino)-1-oxopropan-2-yl](methyl)carbamoyl}biphenyl-4-yl)oxy]ethyl}morpholine (light brown oil) (58 mg, 65%).

MS (ESI/APCI Dual): 470 (M+H)$^+$, 492 (M+Na)$^+$ $^1$H NMR (200 MHz, DMSO-d$_6$) δ ppm 1.64 (3 H, s), 2.44-2.56 (4 H, m), 2.59-2.80 (5 H, m), 3.05 (3 H, s), 3.49-3.66 (4 H, m), 4.15 (2 H, t, J=5.7 Hz), 6.95-7.15 (2 H, m), 7.46-7.79 (6 H, m)

[Chemical Formula 163]

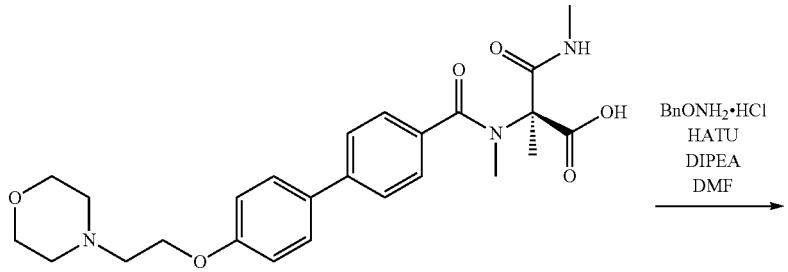

-continued

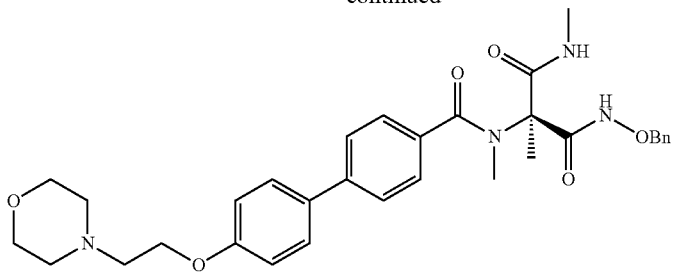

(5) DIPEA (84 μL) and O-benzylhydroxylamine hydrochloride (23 mg) were added to a DMF (3.0 mL) solution of 4-{2-[(4'-{[(2S)-2-carboxy-1-(methylamino)-1-oxopropan-2-yl](methyl)carbamoyl}biphenyl-4-yl)oxy]ethyl}morpholine (56 mg) as obtained in Example 19-(4) and HATU (68 mg) under ice cooling, and the mixture was stirred for 13 hours at room temperature, followed by stirring it for 3 hours at 80° C. Water was added, and the mixture was extracted with chloroform. The organic layer was washed with brine, and the organic layer was separated using a phase separator, whereafter the solvent was distilled off under reduced pressure. The resulting residue was purified by NH type silica gel chromatography (gradient elution with chloroform/methanol=100/0→95/5) to obtain (2S)-N-(benzyloxy)-N',2-dimethyl-2-[methyl({4'-[2-(morpholin-4-yl)ethoxy]biphenyl-4-yl}carbonyl)amino]propanediamide (light yellow solid) (35 mg, 51%).

MS (ESI/APCI Dual): 575 (M+H)$^+$, 597 (M+Na)$^+$, 573 (M−H)$^-$ $^1$H NMR (600 MHz, CHLOROFORM-d) δ ppm 1.77 (3 H, s), 2.56-2.64 (4 H, m), 2.81-2.87 (5 H, m), 3.20 (3 H, s), 3.73-3.78 (4 H, m), 4.17 (2 H, t, J=5.8 Hz), 4.91-4.97 (2 H, m), 6.95-7.05 (2 H, m), 7.13-7.22 (1 H, m), 7.28-7.62 (11 H, m), 10.14 (1 H, s)

[Chemical Formula 164]

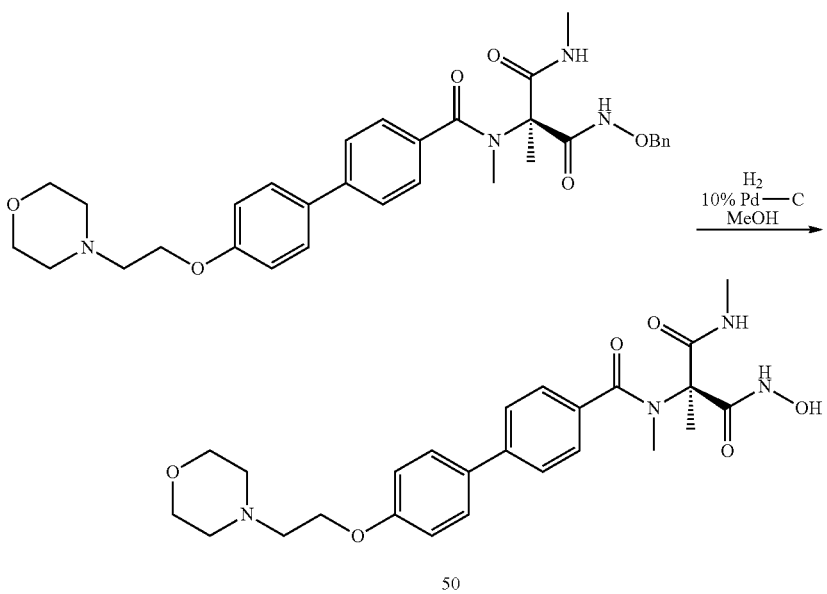

(6) 10% Pd—C (5.0 mg) was added to a methanol (3.0 mL) solution of (2S)-N-(benzyloxy)-N',2-dimethyl-2-[methyl({4'-[2-(morpholin-4-yl)ethoxy]biphenyl-4-yl}carbonyl)amino]propanediamide (27 mg) as obtained in Example 19-(5), and the mixture was stirred in a hydrogen atmosphere for 6 hours at room temperature. The reaction mixture was filtered through Celite, and the solvent was distilled off under reduced pressure. The residue was subjected to isolation and purification by LC to obtain (2S)-N-hydroxy-N',2-dimethyl-2-[methyl({4'-[2-(morpholin-4-yl)ethoxy]biphenyl-4-yl}carbonyl)amino]propanediamide (Compound 437, light yellow solid) (8.0 mg, 35%).

MS (ESI/APCI Dual): 485 (M+H)$^+$, 483 (M−H)$^-$ $^1$H NMR (600 MHz, CD$_3$OD) δ ppm 1.78 (3 H, s), 2.56-2.67 (4 H, m), 2.77-2.86 (5 H, m), 3.21 (3 H, s), 3.69-3.76 (4 H, m), 4.20 (2 H, t, J=5.6 Hz), 6.98-7.10 (2 H, m), 7.54-7.73 (6 H, m)

Compounds 399, 401, 402, 406, 408, 411 to 413, 415, 423, 426, 623, 624, 626 and 629 were synthesized by the same methods as in Example 19 with the use of the corresponding materials.

EXAMPLE 20

N-hydroxy-N'-methyl-2-[methyl({4'-[3-(morpholin-4-yl)prop-1-yn-1-yl]biphenyl-4-yl}carbonyl)amino]propanediamide (Compound 390)

[Chemical Formula 165]

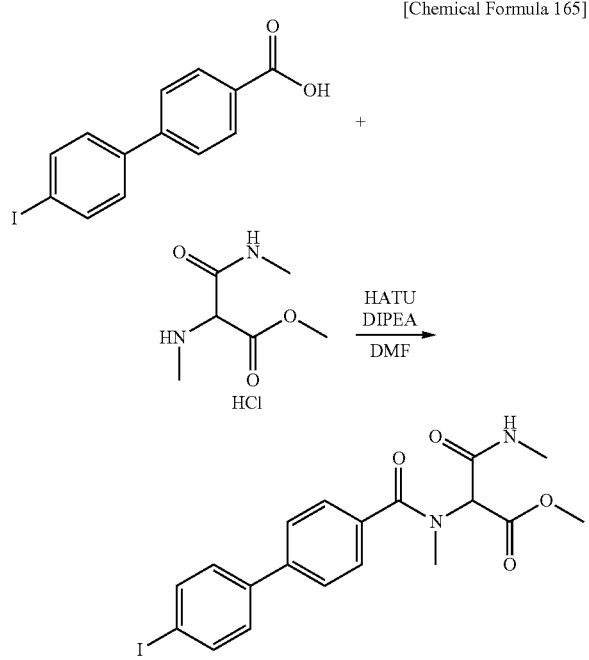

(1) Using 4'-iodobiphenyl-4-carboxylic acid (1.8 g) obtained by the same method as the synthesis method described in the literature (Zhurnal Organicheskoi Khimii, 1981, Vol. 17(12), pp. 2598-2601) and N,N²,O-trimethyl-3-oxoserinamide hydrochloride (Intermediate 5-2, 1.1 g), the same procedure as in Example 4-(4) was performed to obtain 4-iodo-4'-{[1-methoxy-3-(methylamino)-1,3-dioxopropan-2-yl](methyl)carbamoyl}biphenyl (light yellow solid) (1.5 g, 58%).

MS (ESI/APCI Dual): 467 (M+H)⁺, 489 (M+Na)⁺, 465 (M−H)⁻

¹H NMR (200 MHz, CHLOROFORM-d) δ ppm 2.91 (3 H, d, J=4.8 Hz), 3.18 (3 H, br. s.), 3.85 (3 H, s), 5.49 (1 H, s), 7.20 (1 H, m), 7.31-7.35 (2 H, m), 7.56-7.63 (4 H, m), 7.76-7.82 (2 H, m)

[Chemical Formula 166]

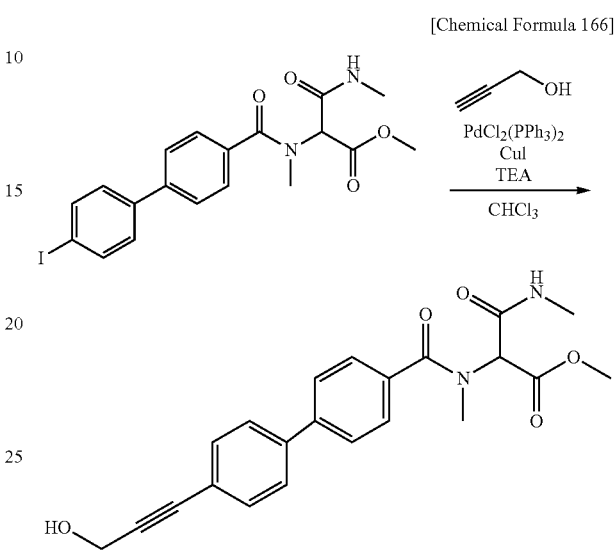

(2) Prop-2-yn-1-ol (0.19 g), PdCl₂(PPh₃)₂ (39 mg), CuI (21 mg) and TEA (0.17 g) were added to a chloroform (10 mL) solution of 4-iodo-4'-{[1-methoxy-3-(methylamino)-1,3-dioxopropan-2-yl](methyl)carbamoyl}biphenyl (0.52 g) as obtained in Example 20-(1). The mixture was stirred for 3 hours at room temperature in a nitrogen atmosphere, and then the reaction mixture was concentrated. The resulting residue was purified by OH type silica gel chromatography (gradient elution with hexane/ethyl acetate=50/50→0/100) to obtain 4-(3-hydroxyprop-1-yn-1-yl)-4'-{[1-methoxy-3-(methylamino)-1,3-dioxopropan-2-yl](methyl)carbamoyl}biphenyl (white solid) (0.28 g, 63%).

MS (ESI/APCI Dual): 395 (M+H)⁺, 417 (M+Na)⁺, 393 (M−H)⁻

¹H NMR (200 MHz, CHLOROFORM-d) δ ppm 1.83 (1 H, t, J=6.2 Hz), 2.91 (3 H, d, J=4.8 Hz), 3.19 (3 H, s), 3.85 (3 H, s), 4.51 (2 H, d, J=6.2 Hz), 5.49 (1 H, s), 7.19-7.28 (1 H, m), 7.48-7.66 (8 H, m)

[Chemical Formula 167]

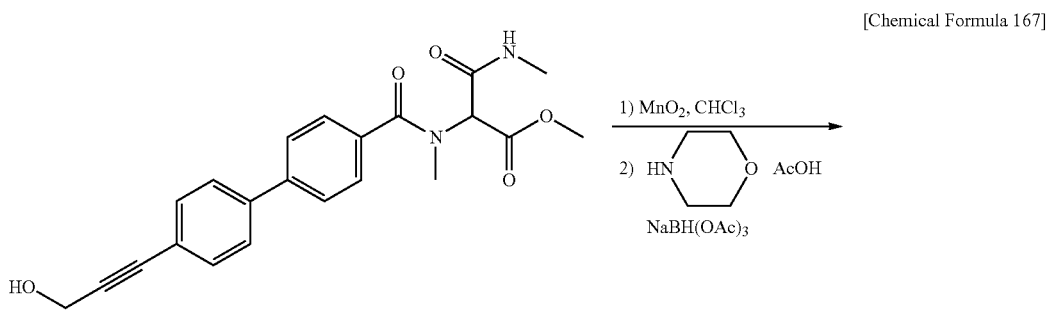

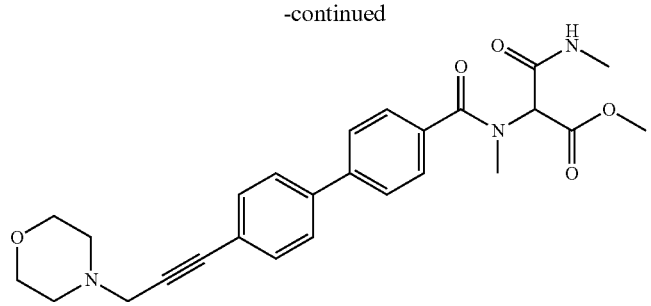

(3) Manganese dioxide (0.19 g) was added to a chloroform (15 mL) solution of 4-(3-hydroxyprop-1-yn-1-yl)-4'-{[1-methoxy-3-(methylamino)-1,3-dioxopropan-2-yl](methyl)carbamoyl}biphenyl (85 mg) as obtained in Example 20-(2), and the mixture was stirred for 2 hours at room temperature in a nitrogen atmosphere. Then, the reaction mixture was filtered, and the solvent was distilled off under reduced pressure. Morpholine (23 mg) and acetic acid were added to a chloroform (5.0 mL) solution of the resulting residue, and the mixture was stirred for 30 minutes at room temperature in a nitrogen atmosphere. Then, sodium triacetoxyborohydride (73 mg) was added, and the mixture was stirred for 4 hours at room temperature in a nitrogen atmosphere. A saturated aqueous solution of sodium hydrogen carbonate was added to the reaction mixture, and the mixture was extracted with chloroform, whereafter the organic layer was washed with brine. The organic layer was dried over anhydrous magnesium sulfate. Then, the desiccant was filtered out, and the solvent was distilled off under reduced pressure. The resulting residue was purified by OH type silica gel chromatography (gradient elution with chloroform/methanol=100/0→90/10) to obtain 4-[3-(4'-{[1-methoxy-3-(methylamino)-1,3-dioxopropan-2-yl](methyl)carbamoyl}biphenyl-4-yl)prop-2-yn-1-yl]morpholine (light yellow foam) (75 mg, 75%).

MS (ESI/APCI Dual): 464 $(M+H)^+$, 486 $(M+Na)^+$, 462 $(M-H)^-$ $^1$H NMR (200 MHz, CHLOROFORM-d) δ ppm 2.63-2.70 (4 H, m), 2.91 (3 H, d, J=4.8 Hz), 3.18 (3 H, br. s.), 3.54 (2 H, s), 3.76-3.82 (4 H, m), 3.85 (3 H, s), 5.48 (1 H, s), 7.14-7.24 (1 H, m), 7.49-7.67 (8 H, m)

[Chemical Formula 168]

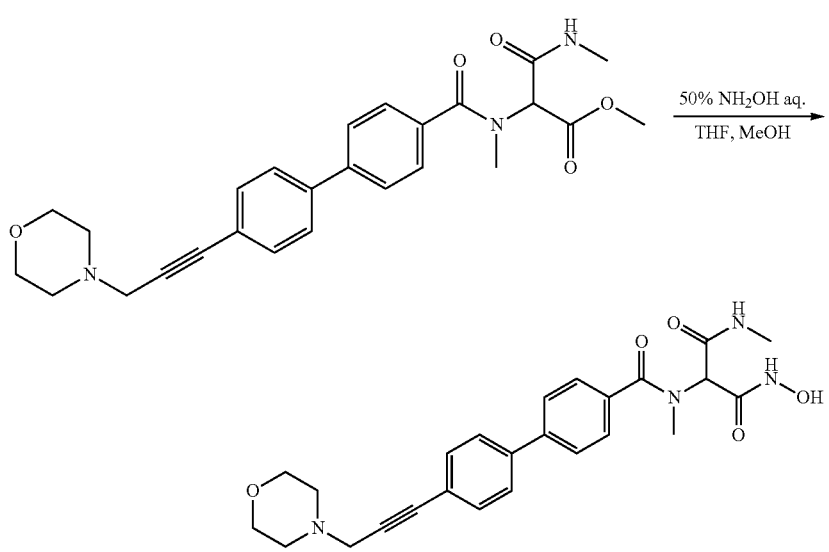

(4) Using 4-[3-(4'-{[1-methoxy-3-(methylamino)-1,3-dioxopropan-2-yl](methyl)carbamoyl}biphenyl-4-yl)prop-2-yn-1-yl]morpholine (75 mg) as obtained in Example 20-(3), the same procedure as in Example 4-(5) was performed to obtain N-hydroxy-N'-methyl-2-[methyl({4'-[3-(morpholin-4-yl)prop-1-yn-1-yl]biphenyl-4-yl}carbonyl)amino]propanediamide (Compound 390, white solid) (19 mg, 25%).

MS (ESI/APCI Dual): 465 $(M+H)^+$, 487 $(M+Na)^+$, 463 $(M-H)^-$ $^1$H NMR (600 MHz, CD$_3$OD) δ ppm 2.65-2.72 (4 H, m), 2.83 (3 H, br. s.), 3.11 (3 H, s), 3.57 (2 H, s), 3.74-3.76 (4 H, m), 7.51-7.55 (2 H, m), 7.61-7.67 (4 H, m), 7.74-7.76 (2 H, m)

Compounds 389, 398, 400 and 405 were synthesized by the same methods as in Example 20 with the use of the corresponding materials.

EXAMPLE 21

(2S)-2-{[(4-{[4-(1-aminocyclopropyl)phenyl]ethynyl}phenyl)carbonyl](methyl)amino}-N-hydroxy-N',2-dimethylpropanediamide (Compound 404)

[Chemical Formula 169]

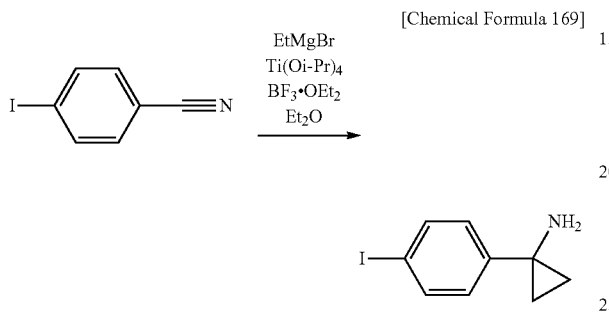

(1) Titanium(IV) isopropoxide (7.1 mL) was added to a diethyl ether (0.14 L) solution of 4-iodobenzonitrile (5.0 g) and, with the internal temperature being kept at −60° C. or lower, a THF solution (53 mL) of 0.90 mol/L ethylmagnesium bromide was added dropwise. After the mixture was stirred for 1 hour at room temperature, boron trifluoride diethyl etherate (5.4 mL) was added, and the mixture was stirred for 3 hours at room temperature. Upon addition of 1.0 mol/L hydrochloric acid (65 mL), the aqueous layer was washed with diethyl ether. A 1.0 mol/L sodium hydroxide aqueous solution was added to the washed aqueous layer to bring it to pH 9. The precipitate was filtered out using Celite, and the filtrate was extracted with ethyl acetate. The extract was dried over magnesium sulfate, whereafter the desiccant was filtered out, and the solvent was distilled off under reduced pressure. The resulting residue was purified by OH type silica gel chromatography (gradient elution with hexane/ethyl acetate=50/50→1/99) to obtain 1-(4-iodophenyl)cyclopropylamine (light yellow solid) (1.3 g, 23%).

MS (ESI/APCI Dual): 260 (M+H)$^+$ $^1$H NMR (200 MHz, CHLOROFORM-d) δ ppm 0.87-1.00 (2 H, m), 1.01-1.15 (2 H, m), 6.96-7.11 (2 H, m), 7.54-7.68 (2 H, m)

[Chemical Formula 170]

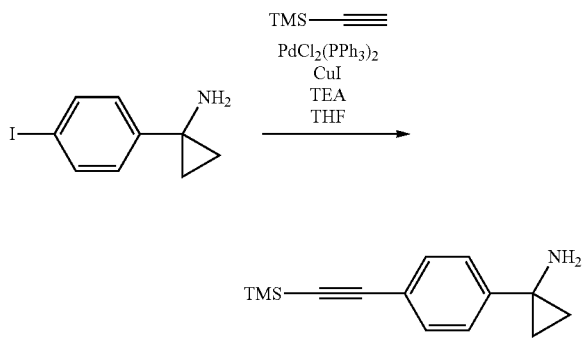

(2) TEA (0.64 mL) was added to a THF (10 mL) suspension of 1-(4-iodophenyl)cyclopropylamine (0.40 g) as obtained in Example 21-(1), PdCl$_2$(PPh$_3$)$_2$ (54 mg) and CuI (29 mg), and the mixture was stirred for 3 hours at room temperature. After the solvent was distilled off under reduced pressure, the resulting residue was purified by OH type silica gel chromatography (gradient elution with hexane/ethyl acetate=70/30→30/70) to obtain 1-{4-[(trimethylsilyl)ethynyl]phenyl}cyclopropylamine (brown oil) (0.39 g, 100%).

MS (ESI/APCI Dual): 230 (M+H)$^+$ $^1$H NMR (200 MHz, CHLOROFORM-d) δ ppm 0.24 (9 H, s), 0.90-1.04 (2 H, m), 1.05-1.18 (2 H, m), 7.13-7.29 (2 H, m), 7.32-7.49 (2 H, m)

[Chemical Formula 171]

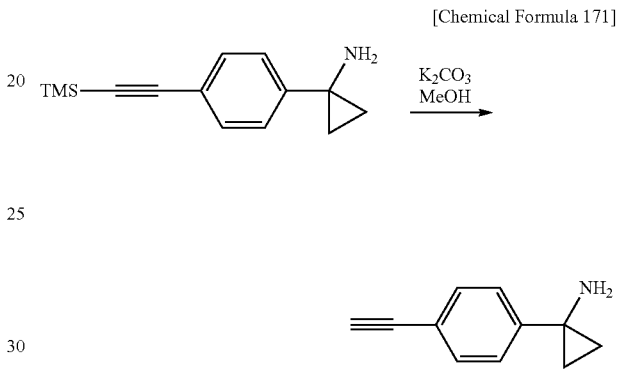

(3) Potassium carbonate (0.33 g) was added to a methanol (10 mL) solution of 1-{4-[(trimethylsilyl)ethynyl]phenyl}cyclopropylamine (0.37 g) as obtained in Example 21-(2), and the mixture was stirred for 1 hour at room temperature. After the potassium carbonate was filtered out and washed with chloroform, the solvent was distilled off under reduced pressure. The resulting residue was purified by OH type silica gel chromatography (gradient elution with hexane/AcOEt=70/30→30/70) to obtain 1-(4-ethynylphenyl)cyclopropylamine (Compound 404, yellow solid) (0.19 g, 76%).

MS (ESI/APCI Dual): 158 (M+H)$^+$ $^1$H NMR (200 MHz, CHLOROFORM-d) δ ppm 0.90-1.05 (2 H, m), 1.06-1.18 (2 H, m), 3.05 (1 H, s), 7.14-7.32 (2 H, m), 7.35-7.52 (2 H, m)

[Chemical Formula 172]

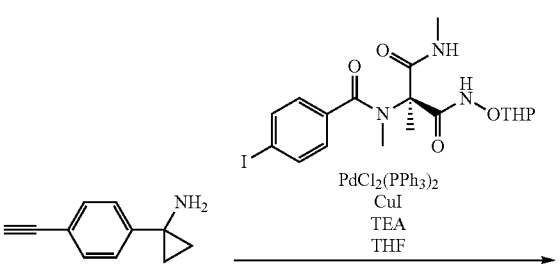

-continued

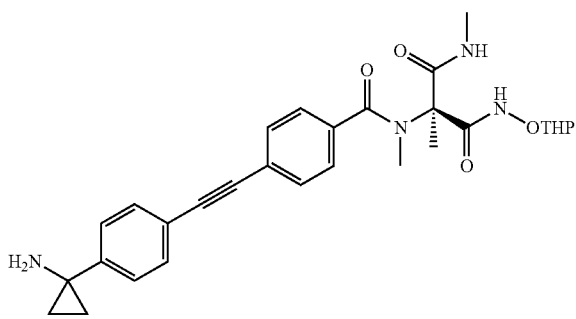

(4) TEA (84 μL) and a THF (1.0 mL) solution of 1-(4-ethynylphenyl)cyclopropylamine (32 mg) as obtained in Example 21-(3) were added to a THF (3.0 mL) suspension of Intermediate 15 (0.10 g), PdCl$_2$(PPh$_3$)$_2$ (7.0 mg) and CuI (4.0 mg), and the mixture was stirred for 2.5 hours at room temperature. After the solvent was distilled off under reduced pressure, the resulting residue was purified by OH type silica gel chromatography (gradient elution with chloroform/methanol=100/0→95/5) to obtain (2S)-2-{[(4-{[4-(1-aminocyclopropyl)phenyl]ethynyl}phenyl)carbonyl](methyl)amino}-N,2-dimethyl-N'-(tetrahydro-2H-pyran-2-yloxy)propanediamide (light yellow solid) (54 mg, 52%).

MS (ESI/APCI Dual): 519 (M+H)$^+$, 517 (M−H)$^−$ $^1$H NMR (600 MHz, CHLOROFORM-d) δ ppm 0.94-1.07 (2 H, m), 1.08-1.18 (2 H, m), [1.80], 1.82 (3 H, s), 1.41-2.21 (6 H, m), 2.77-2.91 (3 H, m), [3.17], 3.19 (3 H, s), 3.50-3.70 (1 H, m), 3.81-4.08 (1 H, m), 4.93-5.02 (1 H, m), 6.96-7.71 (9 H, m)

(5) To a methanol (3.0 mL) solution of (2S)-2-{[(4-{[4-(1-aminocyclopropyl)phenyl]ethynyl}phenyl)carbonyl](methyl)amino}-N,2-dimethyl-N'-(tetrahydro-2H-pyran-2-yloxy)propanediamide (34 mg) as obtained in Example 21-(4), p-TsOH.H$_2$O (15 mg) was added, and the mixture was stirred for 5.5 hours at room temperature. Under water cooling, the solvent was distilled off under reduced pressure, whereafter the resulting residue was isolated and purified by LC to obtain (2S)-2-{[(4-{[4-(1-aminocyclopropyl)phenyl]ethynyl}phenyl)carbonyl](methyl)amino}-N-hydroxy-N',2-dimethylpropanediamide (Compound 404, white solid) (1.8 mg, 6.0%).

MS (ESI/APCI Dual): 435 (M+H)$^+$, 433 (M−H)$^−$ $^1$H NMR (600 MHz, CD$_3$OD) δ ppm 1.00-1.05 (2 H, m), 1.07-1.13 (2 H, m), 1.77 (3 H, s), 2.79 (3 H, s), 3.17 (3 H, s), 7.32-7.39 (2 H, m), 7.43-7.63 (6 H, m)

Compound 394 was synthesized by the same methods as in Example 21 with the use of the corresponding materials.

EXAMPLE 22

2-[({4-[(1E)-4-{4-[(cyclopropylamino)methyl]phenyl}but-1-en-3-yn-1-yl]phenyl}carbonyl)(methyl)amino]-N-hydroxy-N'-methylpropanediamide (Compound 477)

[Chemical Formula 174]

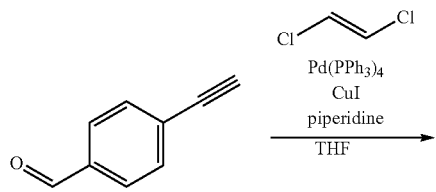

[Chemical Formula 173]

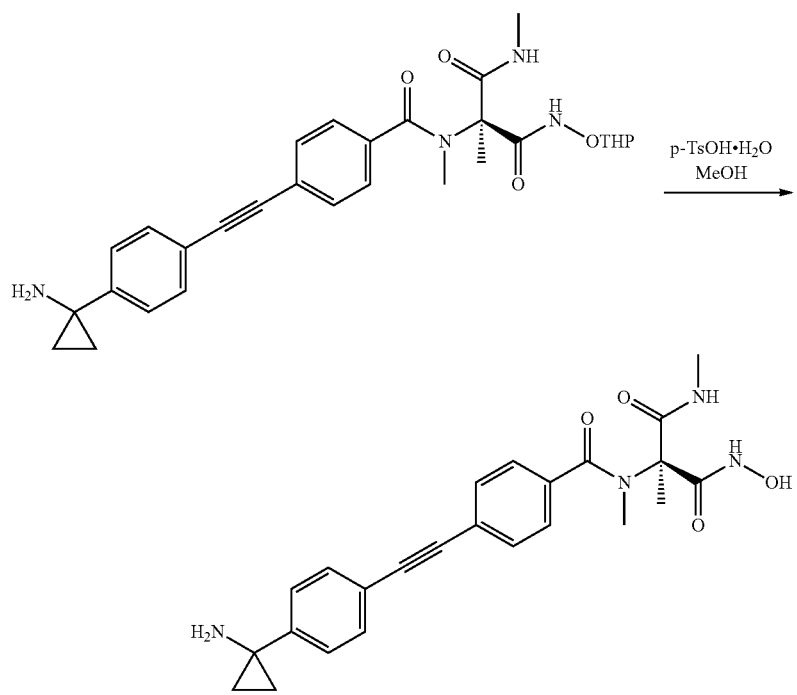

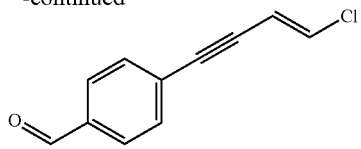

(1) 1,2-Dichloroethylene (3.0 mL), tetrakis(triphenylphosphine)palladium (0.44 g), CuI (73 mg) and piperidine (1.1 mL) were added to a THF (20 mL) solution of 4-ethynylbenzaldehyde (1.0 g), and the mixture was stirred for 22.5 hours at room temperature in a nitrogen atmosphere. IPE was added, the insolubles were filtered out, and the filtrate was concentrated under reduced pressure. The resulting residue was purified by OH type silica gel column chromatography (hexane/ethyl acetate/chloroform=9/1/1) to obtain 4-((E)-4-chlorobut-3-en-1-yn-1-yl)benzaldehyde (light brown solid) (0.87 g, 59%).

$^1$H NMR (400 MHz, CHLOROFORM-d) δ ppm 6.18 (1 H, d, J=13.7 Hz), 6.71 (1 H, d, J=13.7 Hz), 7.58 (2 H, d, J=8.3 Hz), 7.60-7.80 (2 H, m), 10.01 (1 H, s)

[Chemical Formula 175]

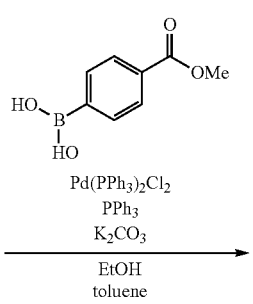

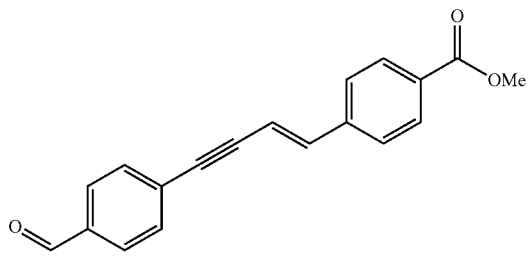

(2) 4-Methoxycarbonylphenylboronic acid (1.0 g), PdCl$_2$(PPh$_3$)$_2$ (0.18 g), triphenylphosphine (0.13 g) and potassium carbonate (1.4 g) were added to a toluene (5.0 mL)-ethanol (2.5 mL) solution of 4-((E)-4-chlorobut-3-en-1-yn-1-yl)benzaldehyde (0.97 g) as obtained in Example 22-(1), and the mixture was heated and refluxed for 3 hours in a nitrogen atmosphere. After the reaction mixture was cooled to room temperature, ethyl acetate was added, the insolubles were filtered out, and the filtrate was concentrated under reduced pressure. IPE was added to the resulting residue, and the solids were filtered out, whereafter chloroform and OH type silica gel (10 g) were added. The insolubles were filtered out, and the filtrate was concentrated under reduced pressure to obtain 4-[(1E)-4-(4-formylphenyl)but-1-en-3-yn-1-yl]benzoic acid methyl ester (light brown solid) (1.2 g, 78%).

$^1$H NMR (400 MHz, CHLOROFORM-d) δ ppm 3.93 (3 H, s), 6.51 (1 H, d, J=16.2 Hz), 7.13 (1 H, d, J=16.2 Hz), 7.50 (2 H, d, J=8.3 Hz), 7.63 (2 H, d, J=8.3 Hz), 7.83-7.90 (2 H, m), 8.00-8.06 (2 H, m), 10.02 (1 H, s)

[Chemical Formula 176]

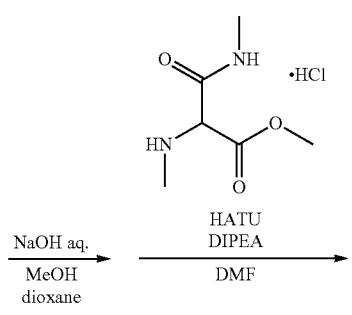

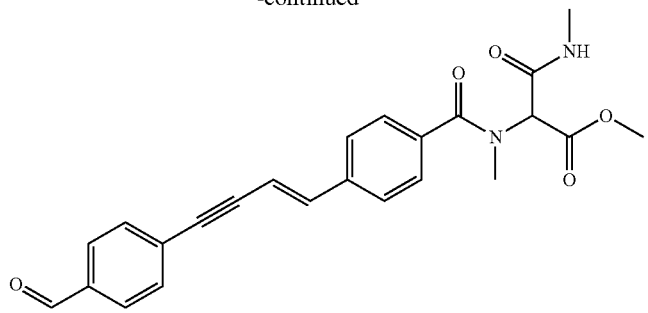

(3) A 20% aqueous solution (3.0 mL) of sodium hydroxide was added to a methanol (40 mL)-1,4-dioxane (40 mL) solution of 4-[(1E)-4-(4-formylphenyl)but-1-en-3-yn-1-yl]benzoic acid methyl ester (1.2 g) as obtained in Example 22-(2), and then the mixture was stirred for 3 hours at room temperature. A 20% aqueous solution (3.0 mL) of sodium hydroxide was added, the mixture was stirred for 30 minutes at room temperature, and a 20% aqueous solution (3.0 mL) of sodium hydroxide was further added, whereafter the mixture was stirred for 25 hours at room temperature. Water was added and, under ice cooling, the mixture was adjusted to pH 3 with 12 mol/L hydrochloric acid. The precipitate was filtered off, and washed with water and IPE to obtain a brown solid (1.0 g). DMF (10 mL), HATU (2.8 g) and DIPEA (2.5 mL) were added to the resulting solid, and the mixture was stirred for 1 hour at room temperature. $N,N^2,O$-trimethyl-3-oxoserinamide hydrochloride (Intermediate 5-2, 1.4 g) was added, and the mixture was stirred for 1 hour at 80° C. The reaction mixture was cooled to room temperature, and ethyl acetate and water were added to isolate the organic layer. The extract was washed sequentially with water and brine, and dried over anhydrous magnesium sulfate. The desiccant was filtered out, and then the solvent was distilled off under reduced pressure. The resulting residue was purified by OH type silica gel column chromatography (gradient elution with chloroform/methanol=50/1→10/1) to obtain 1-formyl-4-[(3E)-4-(4-{[1-methoxy-3-(methylamino)-1,3-dioxopropan-2-yl](methyl)carbamoyl}phenyl)but-3-en-1-yn-1-yl]benzene (yellow oil) (0.47 g, 28%).

$^1$H NMR (400 MHz, CHLOROFORM-d) δ ppm 2.90 (3 H, d, J=4.6 Hz), 3.16 (3 H, s), 3.85 (3 H, s), 5.47 (1 H, s), 6.47 (1 H, d, J=16.2 Hz), 7.11 (1 H, d, J=16.2 Hz), 7.17-7.27 (1 H, m), 7.40-7.59 (4 H, m), 7.62 (2 H, d, J=8.3 Hz), 7.83-7.90 (2 H, m), 10.02 (1 H, s)

[Chemical Formula 177]

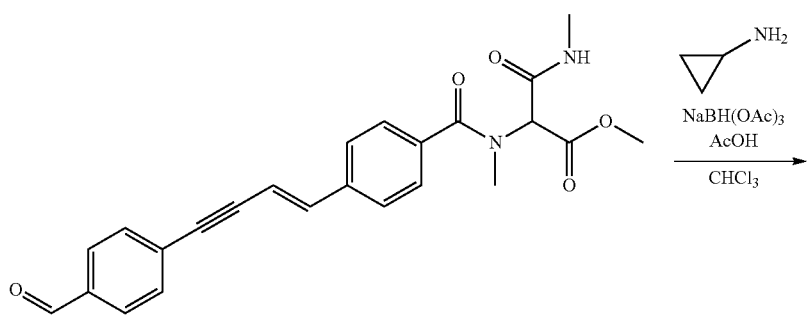

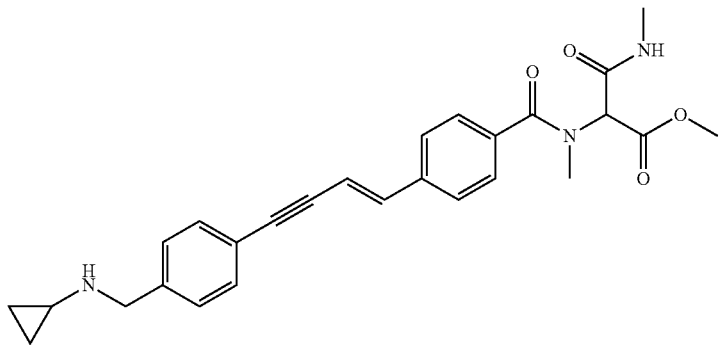

(4) Cyclopropylamine (99 μL), acetic acid (27 μL) and sodium triacetoxyborohydride (0.10 g) were added to a chloroform (4.0 mL) suspension of 1-formyl-4-[(3E)-4-(4-{[1-methoxy-3-(methylamino)-1,3-dioxopropan-2-yl](methyl)carbamoyl}phenyl)but-3-en-1-yn-1-yl]benzene (0.20 g) as obtained in Example 22-(3), and the mixture was stirred for 1 hour and 15 minutes at room temperature. Sodium triacetoxyborohydride (0.10 g) was added, and the mixture was stirred for 1.5 hours at room temperature. Water and chloroform were added, and the organic layer was isolated. The extract was dried over anhydrous sodium sulfate, and the desiccant was filtered out. The solvent was distilled off under reduced pressure to obtain 1-[(cyclopropylamino)methyl]-4-[(3E)-4-(4-{[1-methoxy-3-(methylamino)-1,3-dioxopropan-2-yl](methyl)carbamoyl}phenyl)but-3-en-1-yn-1-yl]benzene (orange oil) (0.20 g, 91%).

MS (ESI): 460 (M+H)⁺, 458 (M−H)⁻

¹H NMR (400 MHz, CHLOROFORM-d) δ ppm 0.35-0.60 (4 H, m), 2.10-2.25 (1 H, m), 2.88 (3 H, d, J=4.9 Hz), 3.16 (3 H, s), 3.84 (3 H, s), 3.87 (2 H, br. s.), 5.49 (1 H, s), 6.45 (1 H, d, J=16.2 Hz), 7.03 (1 H, d, J=16.2 Hz), 7.24-7.59 (9 H, m)

[Chemical Formula 178]

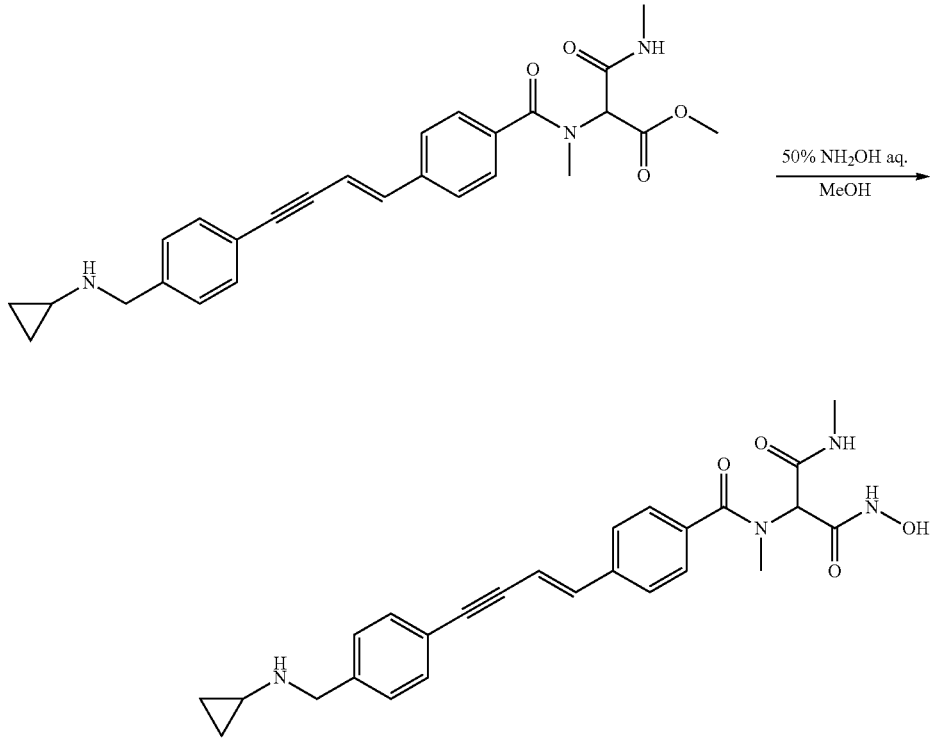

(5) A 50% aqueous solution (2.0 mL) of hydroxylamine was added, under ice cooling, to a methanol (4.0 mL) solution of 1-[(cyclopropylamino)methyl]-4-[(3E)-4-(4-{[1-methoxy-3-(methylamino)-1,3-dioxopropan-2-yl](methyl)carbamoyl}phenyl)but-3-en-1-yn-1-yl]benzene (0.20 g) as obtained in Example 22-(4), and the mixture was stirred for 30 minutes under ice cooling and then stirred for 2 hours under water cooling. Ethyl acetate and water were added to the reaction mixture to isolate the organic layer, and the extract was washed sequentially with water and brine. The precipitate was dissolved with methanol and water, and the organic layer was isolated. Chloroform, methanol and anhydrous sodium sulfate were added to the extract, and the desiccant was filtered out, whereafter the solvents were distilled off under reduced pressure. The resulting residue was purified by OH type silica gel column chromatography (gradient elution with chloroform/methanol=20/1→10/1), and further purified by preparative silica gel thin-layer chromatography (chloroform/methanol=10/1) to obtain 2-[({4-[(1E)-4-{4-[(cyclopropylamino)methyl]phenyl}but-1-en-3-yn-1-yl]phenyl}carbonyl)(methyl)amino]-N-hydroxy-N'-methylpropanediamide (Compound 477, light yellow solid) (51 mg, 25%).

MS (ESI): 461 (M+H)⁺, 459 (M−H)⁻

$^1$H NMR (400 MHz, CD$_3$ OD) δ ppm 0.39-0.55 (4 H, m), 2.12-2.20 (1 H, m), 2.85 (3 H, s), 3.12 (3 H, s), 3.85 (2 H, s), 6.64 (1 H, d, J=16.3 Hz), 7.10 (1 H, d, J=16.3 Hz), 7.35-7.70 (8 H, m)

EXAMPLE 23

2-[({4-[(3E)-4-{4-[(cyclopropylamino)methyl]phenyl}but-3-en-1-yn-1-yl]phenyl}carbonyl)(methyl)amino]-N-hydroxy-N'-methylpropanediamide (Compound 481)

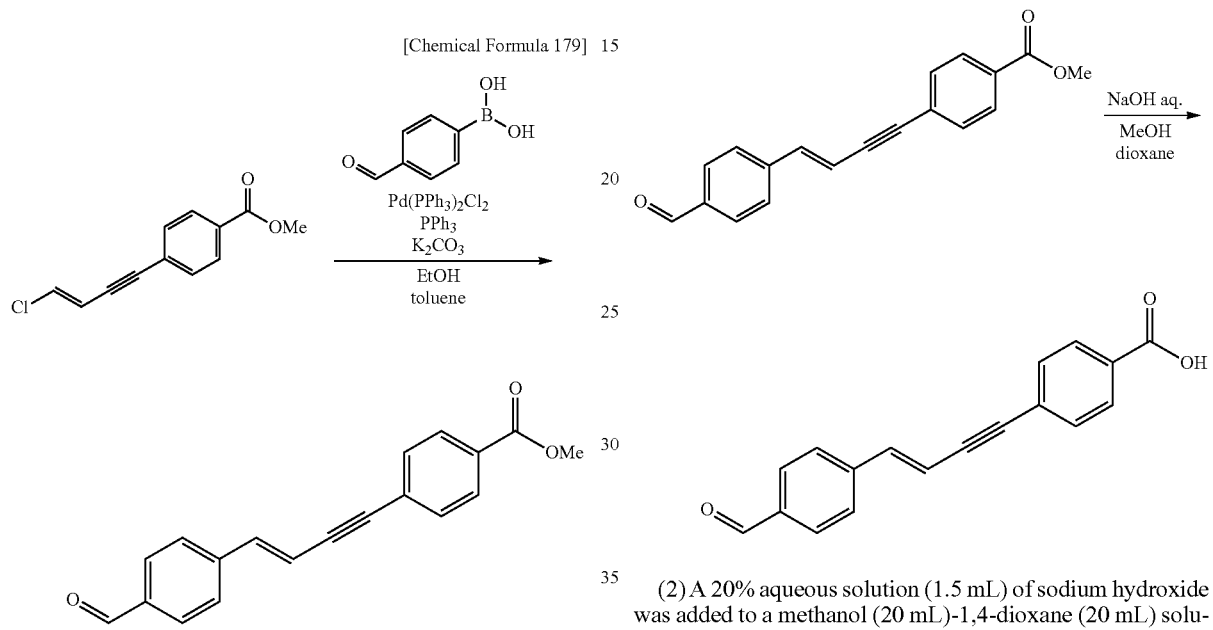

[Chemical Formula 179]

[Chemical Formula 180]

(1) 4-Formylphenylboronic acid (0.49 g), PdCl$_2$(PPh$_3$)$_2$ (0.11 g), triphenylphosphine (78 mg) and potassium carbonate (0.82 g) were added to a toluene (3.5 mL)-ethanol (1.8 mL) solution of 4-((E)-4-chlorobut-3-en-1-yn-1-yl)benzoic acid methyl ester (0.70 g) as obtained by the method described in the patent (WO2008/154642), and the mixture was heated and refluxed for 3 hours in a nitrogen atmosphere. After the reaction mixture was cooled to room temperature, ethyl acetate was added, the insolubles were filtered out, and the filtrate was concentrated under reduced pressure. IPE and IPA were added to the resulting residue, and the solids were filtered out, whereafter chloroform and OH type silica gel (10 g) were added. The insolubles were filtered out, and the filtrate was concentrated under reduced pressure to obtain 4-[(E)-4-(4-formylphenyl)but-3-en-1-yn-1-yl]benzoic acid methyl ester (orange solid) (0.59 g, 69%).

$^1$H NMR (400 MHz, CHLOROFORM-d) δ ppm 3.93 (3 H, s), 6.55 (1 H, d, J=16.2 Hz), 7.12 (1 H, d, J=16.2 Hz), 7.51-7.62 (2 H, m), 7.59 (2 H, d, J=8.3 Hz), 7.87 (2 H, d, J=8.3 Hz), 7.98-8.06 (2 H, m), 10.01 (1 H, s)

(2) A 20% aqueous solution (1.5 mL) of sodium hydroxide was added to a methanol (20 mL)-1,4-dioxane (20 mL) solution of 4-[(E)-4-(4-formylphenyl)but-3-en-1-yn-1-yl]benzoic acid methyl ester (0.59 g) as obtained in Example 23-(1), and then the mixture was stirred for 3 hours at room temperature. A 20% aqueous solution (1.5 mL) of sodium hydroxide was added, and the mixture was stirred for 30 minutes at room temperature. Water was added, and the mixture was adjusted to pH 3 with 12 mol/L hydrochloric acid. The precipitate was filtered off to obtain 4-[(E)-4-(4-formylphenyl)but-3-en-1-yn-1-yl]benzoic acid (orange solid) (0.55 g, 98%).

$^1$H NMR (400 MHz, DMSO-d$_6$) δ ppm 6.91 (1 H, d, J=16.3 Hz), 7.26 (1 H, d, J=16.3 Hz), 7.52 (2 H, d, J=8.3 Hz), 7.82 (2 H, d, J=8.3 Hz), 7.88-7.95 (4 H, m), 10.00 (1 H, s)

[Chemical Formula 181]

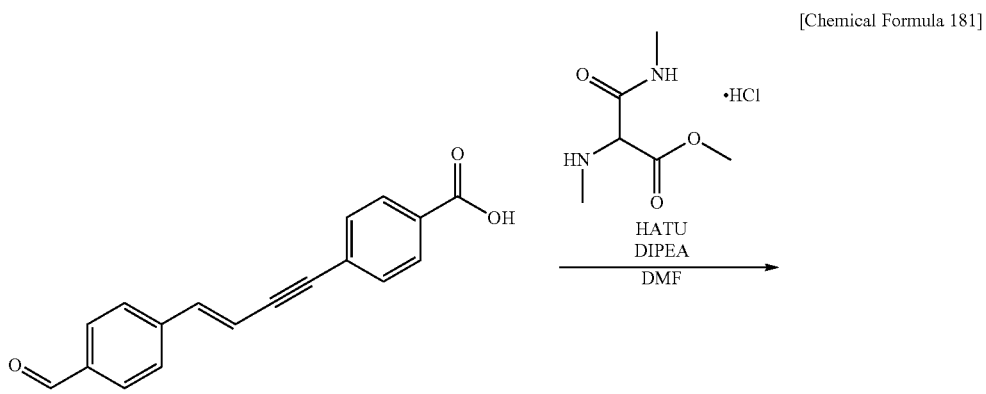

-continued

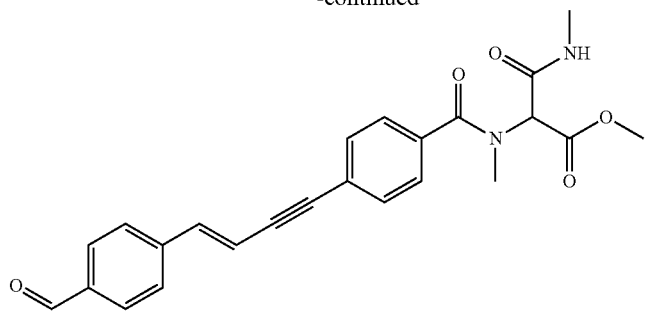

(3) HATU (1.1 g) and DIPEA (1.0 mL) were added to a DMF (5.0 mL) solution of 4-[(E)-4-(4-formylphenyl)but-3-en-1-yn-1-yl)benzoic acid (0.54 g) as obtained in Example 23-(2), and the mixture was stirred for 2 hours and 20 minutes at room temperature. HATU (1.1 g) was further added, and the mixture was stirred for 40 minutes at room temperature. $N,N^2,O$-trimethyl-3-oxoserinamide hydrochloride (Intermediate 5-2, 0.57 g) was added, and the mixture was stirred for 20 minutes at 80° C. The reaction mixture was cooled to room temperature, and ethyl acetate and water were added to isolate the organic layer. The extract was washed sequentially with water and brine, and dried over anhydrous magnesium sulfate. The desiccant was filtered out, and then the solvent was distilled off under reduced pressure. Chloroform, IPE and ethyl acetate were added to the resulting residue, the insolubles were filtered out, and the filtrate was concentrated under reduced pressure. The resulting residue was purified by OH type silica gel column chromatography (gradient elution with chloroform/methanol=100/0→10/1) to obtain 1-formyl-4-[(1E)-4-(4-{[1-methoxy-3-(methylamino)-1,3-dioxopropan-2-yl](methyl)carbamoyl}phenyl)but-1-en-3-yn-1-yl]benzene (orange oil) (0.61 g, 74%).

$^1$H NMR (400 MHz, CHLOROFORM-d) δ ppm 2.90 (3 H, d, J=4.9 Hz), 3.14 (3 H, s), 3.85 (3 H, s), 5.47 (1 H, s), 6.54 (1 H, d, J=16.2 Hz), 7.10 (1 H, d, J=16.2 Hz), 7.19-7.31 (1 H, m), 7.46-7.62 (6 H, m), 7.87 (2 H, d, J=8.3 Hz), 10.01 (1 H, s)

[Chemical Formula 182]

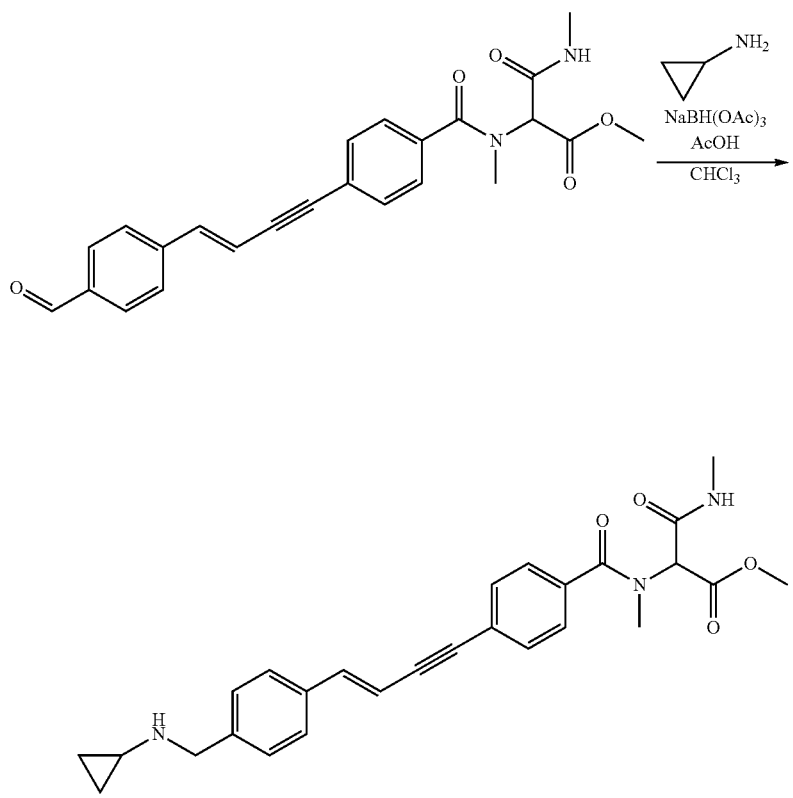

(4) Cyclopropylamine (99 μL), acetic acid (27 μL) and sodium triacetoxyborohydride (0.10 g) were added to a chloroform (4.0 mL) suspension of 1-formyl-4-[(1E)-4-(4-{[1-methoxy-3-(methylamino)-1,3-dioxopropan-2-yl](methyl)carbamoyl}phenyl)but-1-en-3-yn-1-yl]benzene (0.20 g) as obtained in Example 23-(3), and the mixture was stirred for 1 hour and 10 minutes at room temperature. Sodium triacetoxyborohydride (0.10 g) was added, and the mixture was stirred for 1 hour and 15 minutes at room temperature. Further, sodium triacetoxyborohydride (0.10 g) was added, and the mixture was stirred for 1 hour and 15 minutes at room temperature. Water and chloroform were added to isolate the organic layer, and the extract was washed with water and brine sequentially. The washed extract was dried over anhydrous sodium sulfate, and the desiccant was filtered out. Then, the solvent was distilled off under reduced pressure. The resulting residue was purified by OH type silica gel column chromatography (gradient elution with chloroform/methanol=50/1→10/1) to obtain 1-[(cyclopropylamino)methyl]-4-[(1E)-4-(4-{[1-methoxy-3-(methylamino)-1,3-dioxopropan-2-yl](methyl)carbamoyl}phenyl)but-1-en-3-yn-1-yl]benzene (orange oil) (0.18 g, 83%).

$^1$H NMR (400 MHz, CHLOROFORM-d) δ ppm 0.42-0.61 (4 H, m), 2.10-2.25 (1 H, m), 2.89 (3 H, d, J=4.9 Hz), 3.15 (3 H, s), 3.85 (3 H, s), 3.89 (2 H, br. s.), 5.47 (1 H, s), 6.37 (1 H, d, J=16.1 Hz), 7.06 (1 H, d, J=16.1 Hz), 7.20-7.60 (5 H, m), 7.32 (2 H, d, J=8.3 Hz), 7.40 (2 H, d, J=8.0 Hz)

[Chemical Formula 183]

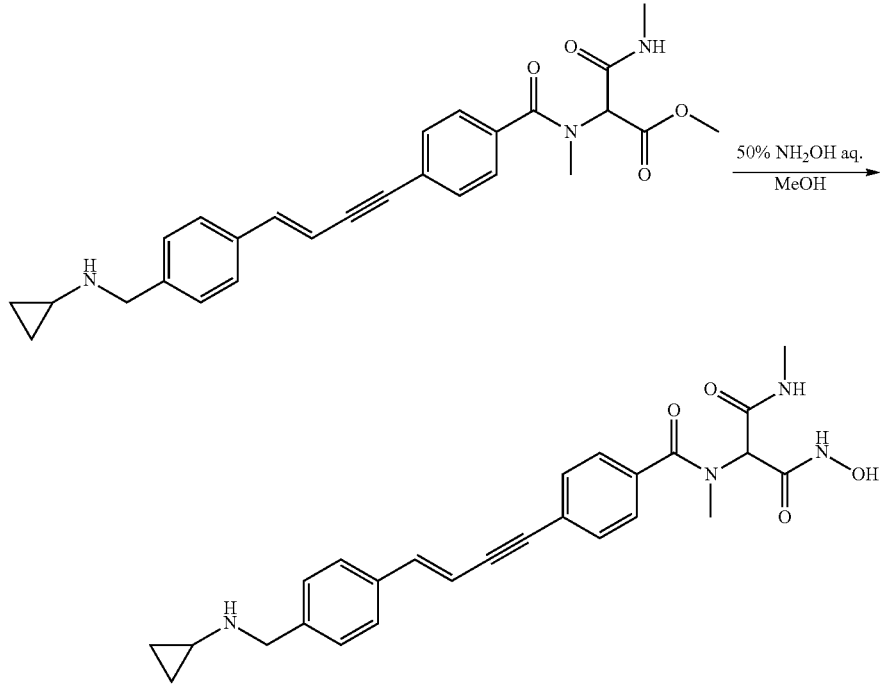

(5) A 50% aqueous solution (2.0 mL) of hydroxylamine was added, under ice cooling, to a methanol (4.0 mL) solution of 1-[(cyclopropylamino)methyl]-4-[(1E)-4-(4-{[1-methoxy-3-(methylamino)-1,3-dioxopropan-2-yl](methyl)carbamoyl}phenyl)but-1-en-3-yn-1-yl]benzene (0.18 g) as obtained in Example 23-(4), and the mixture was stirred for 25 minutes under ice cooling and then stirred for 1.5 hours under water cooling. Ethyl acetate and water were added to the reaction mixture to isolate the organic layer, and the extract was washed with water. The washed extract was dried over anhydrous sodium sulfate, the desiccant was filtered out, and the solvent was distilled off under reduced pressure. The resulting residue was purified by OH type silica gel column chromatography (gradient elution with chloroform/methanol=50/1→10/1), and further purified by preparative silica gel thin-layer chromatography (chloroform/methanol=10/1) to obtain 2-[({4-[(3E)-4-{4-[(cyclopropylamino)methyl]phenyl}but-3-en-1-yn-1-yl]phenyl}carbonyl)(methyl)amino]-N-hydroxy-N'-methylpropanediamide (Compound 481, light yellow solid) (41 mg, 23%).

MS (ESI): 461 (M+H)$^+$, 459 (M−H)$^−$ $^1$H NMR (400 MHz, CD$_3$OD) δ ppm 0.47-0.63 (4 H, m), 2.21-2.30 (1 H, m), 2.91 (3 H, s), 3.17 (3 H, s), 3.92 (2 H, s), 6.58 (1 H, d, J=16.2 Hz), 7.17 (1 H, d, J=16.2 Hz), 7.45 (2 H, d, J=8.0 Hz), 7.54-7.68 (6 H, m)

EXAMPLE 24

(2S)-2-[{[4-({5-[(cyclopropylamino)methyl]furan-3-yl}ethynyl)phenyl]carbonyl}(methyl)amino]-N-hydroxy-N',2-dimethylpropanediamide (Compound 585)

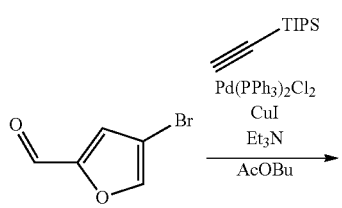

[Chemical Formula 184]

(1) Triisopropylsilylacetylene (9.0 mL) was added dropwise to a mixture of 4-bromofuran-2-carbaldehyde (2.0 g), PdCl$_2$(PPh$_3$)$_2$ (0.40 g), CuI (0.22 g), TEA (7.9 mL) and AcOBu (20 mL) at 110 to 120° C. over the course of 6 hours in a nitrogen atmosphere, and then the mixture was stirred for 2 hours. After the reaction mixture was allowed to cool, ethyl acetate (50 mL), OH type silica gel (1.0 g), cellpure (1.2 g) and activated carbon (20 mg) were added. The insolubles were filtered out, and the filtrate was concentrated under reduced pressure. The resulting residue was purified by OH type silica gel column chromatography (gradient elution with hexane/ethyl acetate=100/0→65/35) to obtain 4-[(triisopropylsilanyl)ethynyl]furan-2-carbaldehyde (black oil) (2.3 g, 72%).

$^1$H NMR (400 MHz, CHLOROFORM-d) δ ppm 0.95-1.15 (21 H, m), 7.26 (1 H, br. s.), 7.83 (1 H, d, J=0.7 Hz), 9.63 (1 H, s)

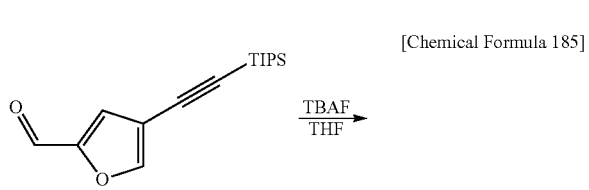

[Chemical Formula 185]

(2) A 1 mol/L-TBAF-THF solution (3.4 mL) was added dropwise, under ice cooling, to a mixture of 4-[(triisopropylsilanyl)ethynyl]furan-2-carbaldehyde (0.63 g) as obtained in Example 24-(1), THF (3.0 mL) and acetic acid (0.20 mL) over the course of 1.5 hours. Diethyl ether and water were added to the reaction mixture, and the mixture was adjusted to pH 5 with a saturated aqueous solution of ammonium chloride to isolate the organic layer. The extract was washed with brine, and the solvent was distilled off under reduced pressure. The resulting residue was purified by OH type silica gel column chromatography (gradient elution with hexane/ethyl acetate=100/0→80/20) to obtain 4-ethynylfuran-2-carbaldehyde (brown solid) (0.22 g, 80%).

$^1$H NMR (400 MHz, CHLOROFORM-d) δ ppm 3.14 (1 H, s), 7.27 (1 H, s), 7.86 (1 H, s), 9.65 (1 H, s)

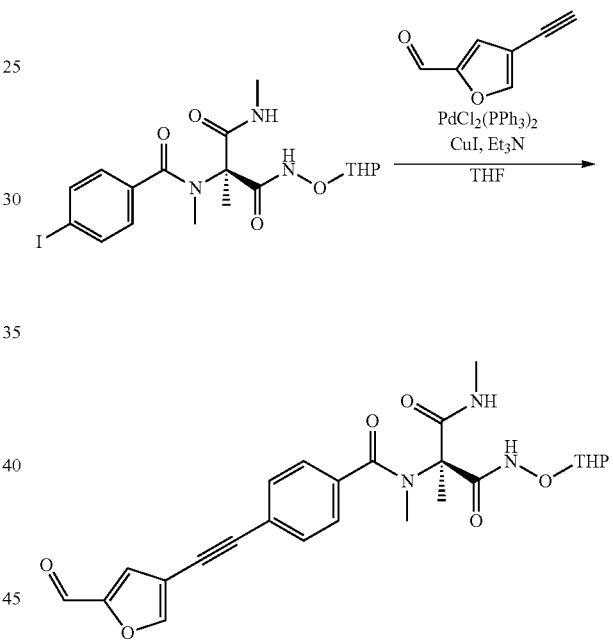

[Chemical Formula 186]

(3) From 4-ethynylfuran-2-carbaldehyde (0.21 g) as obtained in Example 24-(2) and (2S)-2-[(4-iodobenzoyl)(methyl)amino]-N,2-dimethyl-N'-(tetrahydro-2H-pyran-2-yloxy)propanediamide (Intermediate 15, 0.60 g), (2S)-2-[{4-[(5-formylfuran-3-yl)ethynyl]benzoyl}(methyl)amino]-N,2-dimethyl-N'-(tetrahydro-2H-pyran-2-yloxy)propanediamide (brown solid) was obtained (0.46 g, 78%) in the same manner as in Example 16-(1).

MS (ESI): 505 (M+Na)$^+$, 481 (M−H)$^−$ $^1$H NMR (400 MHz, CHLOROFORM-d) δ ppm 1.40-1.92 (9 H, m), 2.82-2.92 (3 H, m), 3.13-3.25 (3 H, m), 3.45-4.20 (2 H, m), 4.93-5.05 (1 H, m), 6.95-7.85 (5 H, m), 7.33 (1 H, s), 7.92 (1 H, s), 9.68 (1 H, s), [10.02], 10.70 (1 H, br. s.)

[Chemical Formula 187]

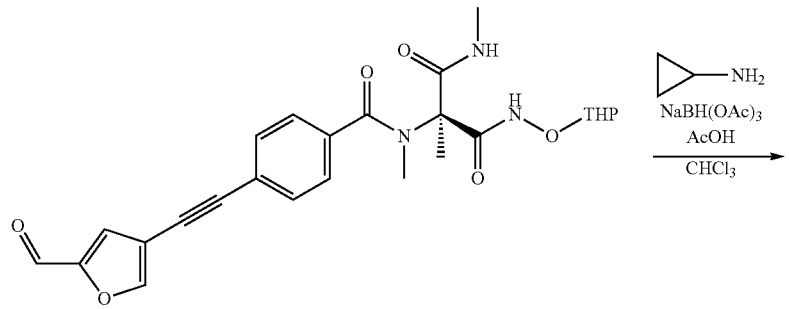

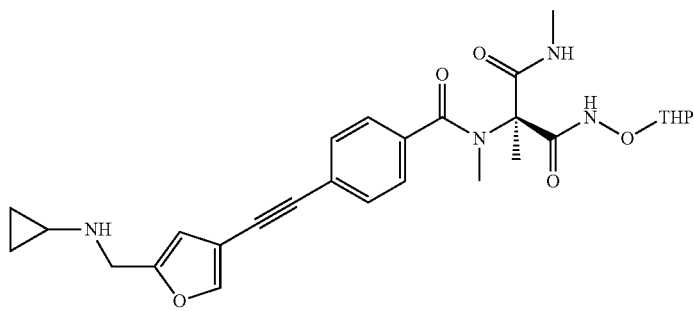

(4) From (2S)-2-[{4-[(5-formylfuran-3-yl)ethynyl]benzoyl}(methyl)amino]-N,2-dimethyl-N'-(tetrahydro-2H-pyran-2-yloxy)propanediamide (0.11 g) as obtained in Example 24-(3) and cyclopropylamine (24 μL), (2S)-2-{[4-({5-[(cyclopropylamino)methyl]furan-3-yl}ethynyl)benzoyl](methyl)amino}-N,2-dimethyl-N'-(tetrahydro-2H-pyran-2-yloxy)propanediamide (yellow solid) was obtained (62 mg, 52%) in the same manner as in Example 16-(2).

MS (ESI): 523 (M+H)$^+$, 521 (M−H)$^−$ $^1$H NMR (400 MHz, CHLOROFORM-d) δ ppm 0.35-0.50 (4 H, m), 1.45-2.00 (6 H, m), [1.81], 1.82 (3 H, s), 2.10-2.20 (1 H, m), 2.80-2.90 (3 H, m), [3.16], 3.19 (3 H, s), 3.52-4.06 (4 H, m), 4.92-5.04 (1 H, m), 6.29-6.35 (1 H, m), 6.94-7.69 (6 H, m), [10.12], 10.52 (1 H, br. s.)

[Chemical Formula 188]

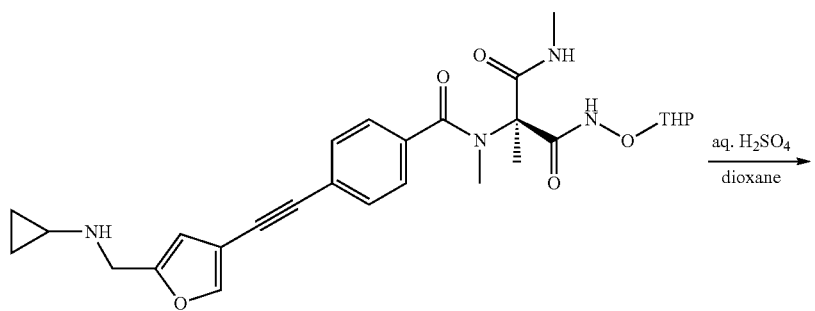

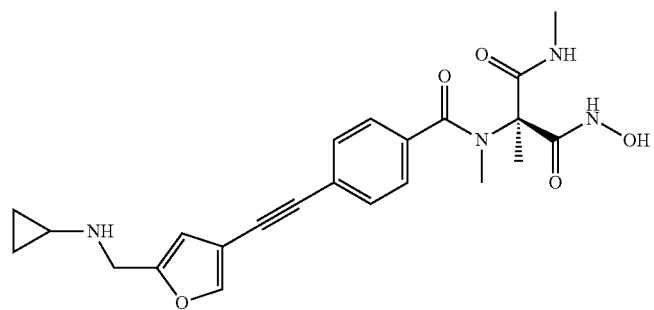

(5) From (2S)-2-{[4-({5-[(cyclopropylamino)methyl]furan-3-yl}ethynyl)benzoyl](methyl)amino}-N,2-dimethyl-N'-(tetrahydro-2H-pyran-2-yloxy)propanediamide (62 mg) as obtained in Example 24-(4), (2S)-2-[{[4-({5-[(cyclopropylamino)methyl]furan-3-yl}ethynyl)phenyl]carbonyl}(methyl)amino]-N-hydroxy-N',2-dimethylpropanediamide (Compound 585, white solid) was obtained (18 mg, 34%) in the same manner as in Example 16-(3).

MS (ESI): 439 (M+H)$^+$, 437 (M−H)$^−$ $^1$H NMR (400 MHz, CD$_3$OD) δ ppm—0.03-0.02 (2 H, m), 0.08-0.13 (2 H, m), 1.39 (3 H, s), 1.75-1.83 (1 H, m), 2.41 (3 H, s), 2.78 (3 H, s), 3.43 (2 H, s), 6.05 (1 H, s), 7.12-7.20 (4 H, m), 7.41 (1 H, s)

Compounds 583, 584 and 592 were synthesized by the same methods as in Example 24 with the use of the corresponding materials.

EXAMPLE 25

(2S)-N-hydroxy-2-[{4-[(3E)-7-methoxyhept-3-en-1-yn-1-yl]benzoyl}(methyl)amino]-N',2-dimethylpropanediamide (Compound 597)

[Chemical Formula 189]

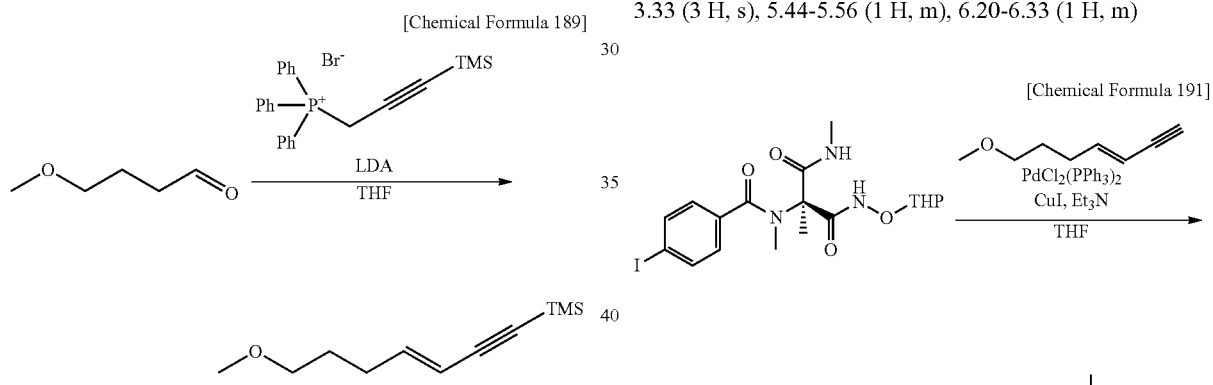

(1) A 1.1M-LDA-THF/hexane solution (6.5 mL) was added dropwise to a THF (15 mL) suspension of (3-trimethylsilyl-2-propynyl)triphenylphosphonium bromide (2.7 g) under ice cooling, and then the mixture was stirred for 40 minutes. The reaction mixture was cooled to −70° C., and a THF (5.0 mL) solution of 4-methoxybutylaldehyde (0.51 g) obtained by the methods described in a patent (WO2009/7814A1) was added dropwise. The mixture was warmed to room temperature, and then stirred for 30 minutes. The reaction mixture was cooled to −60° C., and a saturated aqueous solution of ammonium chloride and diethyl ether were added to isolate the organic layer. The extract was washed with brine, and dried over anhydrous magnesium sulfate. Then, the desiccant was filtered out, and the solvent was distilled off under reduced pressure. The resulting residue was purified by OH type silica gel column chromatography (gradient elution with hexane/diethyl ether=96/4→94/6) to obtain ((E)-7-methoxyhept-3-en-1-yn-1-yl)trimethylsilane (yellow oil) (0.74 g, 76%).

$^1$H NMR (400 MHz, CHLOROFORM-d) δ ppm 0.17 (9 H, s), 1.62-1.74 (2 H, m), 2.14-2.20 (2 H, m), 3.27-3.44 (2 H, m), 3.32 (3 H, s), 5.48-5.57 (1 H, m), 6.16-6.27 (1 H, m)

[Chemical Formula 190]

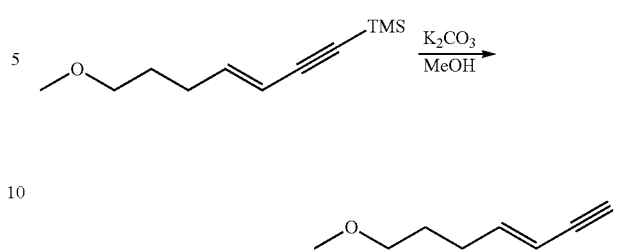

(2) Potassium carbonate (0.10 g) was added, under ice cooling, to a methanol (3.7 mL) solution of ((E)-7-methoxyhept-3-en-1-yn-1-yl)trimethylsilane (0.74 g) as obtained in Example 25-(1), and the mixture was stirred for 45 minutes at room temperature. Diethyl ether and an aqueous solution of ammonium chloride were added to isolate the organic layer. The extract was washed with brine, and dried over anhydrous magnesium sulfate. Then, the desiccant was filtered out, and the solvent was distilled off under reduced pressure to obtain (E)-7-methoxyhept-3-en-1-yn (pale yellow oil) (0.34 g, 73%).

$^1$H NMR (400 MHz, CHLOROFORM-d) δ ppm 1.57-1.78 (2 H, m), 2.14-2.29 (2 H, m), 2.79 (1 H, s), 3.27-3.45 (2 H, m), 3.33 (3 H, s), 5.44-5.56 (1 H, m), 6.20-6.33 (1 H, m)

[Chemical Formula 191]

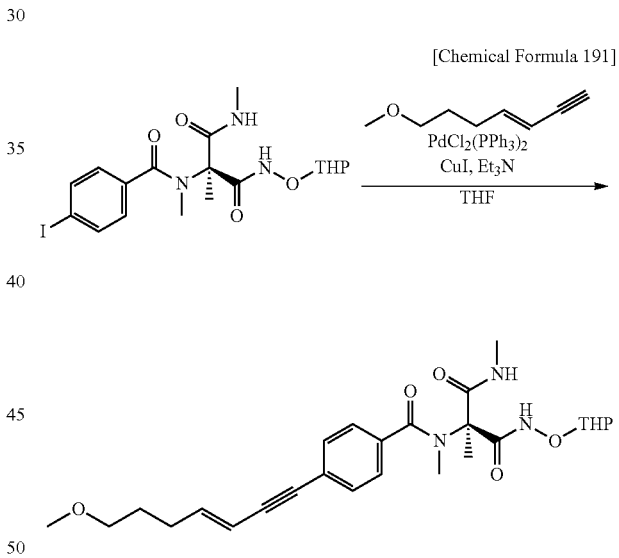

(3) From (E)-7-methoxyhept-3-en-1-yn (0.11 g) as obtained in Example 25-(2) and (2S)-2-[(4-iodobenzoyl)(methyl)amino]-N,2-dimethyl-N'-(tetrahydro-2H-pyran-2-yloxy)propanediamide (Intermediate 15, 0.15 g), (2S)-2-[{4-[(3E)-7-methoxyhept-3-en-1-yn-1-yl]benzoyl}(methyl)amino]-N,2-dimethyl-N'-(tetrahydro-2H-pyran-2-yloxy)propanediamide (brown foam) was obtained (0.15 g, 100%) in the same manner as in Example 18-(4).

$^1$H NMR (400 MHz, CHLOROFORM-d) δ ppm 1.41-1.90 (11 H, m), 2.20-2.32 (2 H, m), 2.77-2.88 (3 H, m), [3.16], 3.18 (3 H, s), 3.28-3.45 (2 H, m), 3.35 (3 H, s), 3.50-3.70 (1 H, m), 3.80-4.07 (1 H, m), 4.90-5.00 (1 H, m), 5.67-5.76 (1 H, m), 6.23-6.34 (1 H, m), [6.93-7.03], 7.57-7.70 (1 H, m), 7.35-7.52 (4 H, m), [10.07], 10.49 (1 H, s)

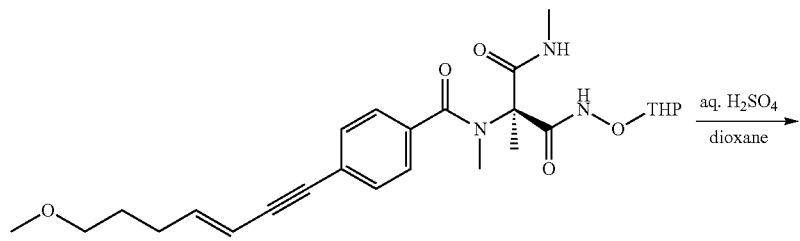

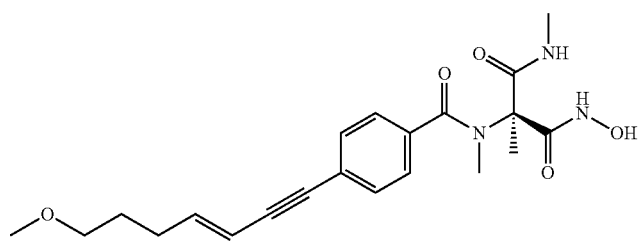

(4) From (2S)-2-[{4-[(3E)-7-methoxyhept-3-en-1-yn-1-yl]benzoyl}(methyl)amino]-N,2-dimethyl-N'-(tetrahydro-2H-pyran-2-yloxy)propanediamide (0.15 g) as obtained in Example 25-(3), (2S)-N-hydroxy-2-[{4-[(3E)-7-methoxyhept-3-en-1-yn-1-yl]benzoyl}(methyl)amino]-N',2-dimethylpropanediamide (Compound 597, light yellow solid) was obtained (54 mg, 45%) in the same manner as in Example 18-(5).

MS (ESI): 401 (M−H)⁻

¹H NMR (400 MHz, CD₃ OD) δ ppm 1.65-1.73 (2 H, m), 1.75 (3 H, s), 2.20-2.29 (2 H, m), 2.78 (3 H, s), 3.15 (3 H, s), 3.33 (3 H, s), 3.38-3.44 (2 H, m), 5.71-5.79 (1 H, m), 6.22-6.32 (1 H, m), 7.44-7.55 (4 H, m)

Compounds 590, 595, 596 and 606 were synthesized by the same methods as in Example 25 with the use of the corresponding materials.

EXAMPLE 26

(2S)-N-hydroxy-N',2-dimethyl-2-{methyl[(4-{(E)-2-[4-(morpholin-4-ylmethyl)phenyl]ethenyl}phenyl)carbonyl]amino}propanediamide (Compound 434)

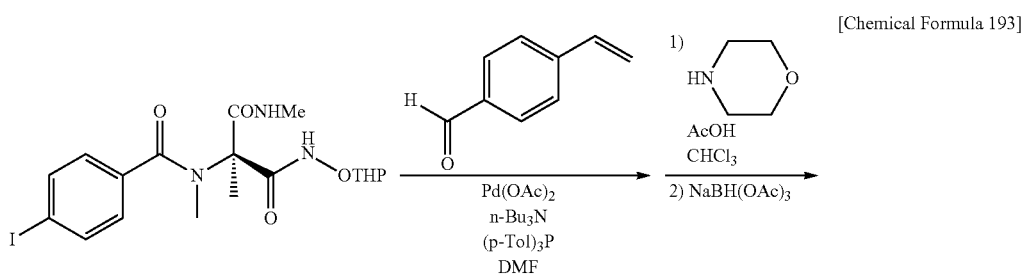

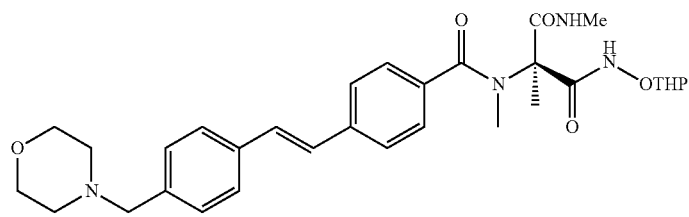

(1) Palladium acetate (12 mg), tris(4-methylphenyl)phosphine (24 mg), tri-n-butylamine (0.25 mL) were added to a DMF (1.2 ml) solution of (2S)-2-[(4-iodobenzoyl)(methyl)amino]-N,2-dimethyl-N'-(tetrahydro-2H-pyran-2-yloxy)propanediamide (Intermediate 15, 90 mg) and 4-ethenylbenzaldehyde (98 mg) obtained by the same method as the synthesis method described in the literature (Journal of Electroanalytical Chemistry, 2002, Vol. 529(1), pp. 43-50), and the mixture was stirred overnight at 80° C. The solvent was distilled off under reduced pressure, and the resulting residue was purified by OH type silica gel chromatography (gradient elution with chloroform/methanol=100/0→94/6) to obtain a crude product. Morpholine (30 µl) and acetic acid (20 µl) were added to a chloroform (1.0 ml) solution of the resulting crude product, and the mixture was stirred for 2.5 hours at room temperature. Further, sodium triacetoxyborohydride (62 mg) was added, and the mixture was stirred overnight at room temperature. A saturated aqueous solution of sodium hydrogen carbonate was added to the reaction mixture, the mixture was extracted with chloroform, and the organic layer was concentrated under reduced pressure. The resulting residue was purified by NH type silica gel chromatography (gradient elution with chloroform/methanol=100/0→94/6) to obtain (2S)-N,2-dimethyl-2-{methyl[(4-{(E)-2-[4-(morpholin-4-ylmethyl)phenyl]ethenyl}phenyl)carbonyl]amino}-N'-(tetrahydro-2H-pyran-2-yloxy)propanediamide (colorless oil) (32 mg, 31%).

MS (ESI): 565 (M+H)$^+$, 563 (M−H)$^−$ $^1$H NMR (600 MHz, CHLOROFORM-d) δ ppm 1.61-1.69 (3 H, m), 1.73-1.91 (6 H, m), 2.41-2.50 (4 H, m), 2.81-2.89 (3 H, m), [3.20], 3.23 (3 H, s), 3.51 (2 H, s), 3.54-3.76 (5 H, m), 3.83-4.06 (1 H, m), 4.95-5.03 (1 H, m), 7.01 (1 H, br. s.), 7.05-7.20 (2 H, m), 7.34 (2 H, d, J=8.3 Hz), 7.44-7.67 (7 H, m) 3.64-3.73 (4 H, m), 7.17-7.32 (2 H, m), 7.35 (2 H, d, J=7.8 Hz), 7.51-7.60 (4 H, m), 7.66 (2H, d, J=8.3 Hz)

Compounds 621, 627 and 628 were synthesized by the same methods as in Example 26 with the use of the corresponding materials.

Tests

The following pharmacological tests were conducted to verify the action of inventive compounds.

Test 1: Evaluation of the Inhibitory Activity on *Pseudomonas aeruginosa* LpxC Enzyme To assay the activity of *Pseudomonas aeruginosa* LpxC enzyme, LpxC was reacted with its substrate UDP-3-O-(R-3-hydroxydecanoyl)-N-acetylglucosamine and the amount of the reaction product was determined by quantifying the amino groups present in it.

Specifically, 12.5 ng of *Pseudomonas aeruginosa* LpxC enzyme (as acquired by preparing chromosomal DNA from *Pseudomonas aeruginosa*, subjecting the DNA to PCR (polymerase chain reaction) using LpxC specific primers to acquire *Pseudomonas aeruginosa* LpxC genes, incorporating the genes into a vector, and expressing the same with *E. coli*) was mixed with 80 µmol/L of UDP-3-O-(R-3-hydroxydecanoyl)-N-acetylglucosamine (Wako Pure Chemical Industries, Ltd.) and the mixture was incubated at room temperature for 40 minutes. The reaction was performed in 40 mmol/L of Hepes buffer solution (pH 8.0) supplemented with 0.02% Bridge 35 and 80 µmol/L of dithiothreitol. To terminate the reaction, 0.2 mol/L of borax was added to the reaction mixture; thereafter, 0.5 mg/mL of fluorescamine dissolved in anhydrous dioxane was added and the amount of the reaction product was measured at excitation and fluorescence wavelengths of 390 nm and 495 nm, respectively. An inhibition curve was constructed for each test compound by performing

[Chemical Formula 194]

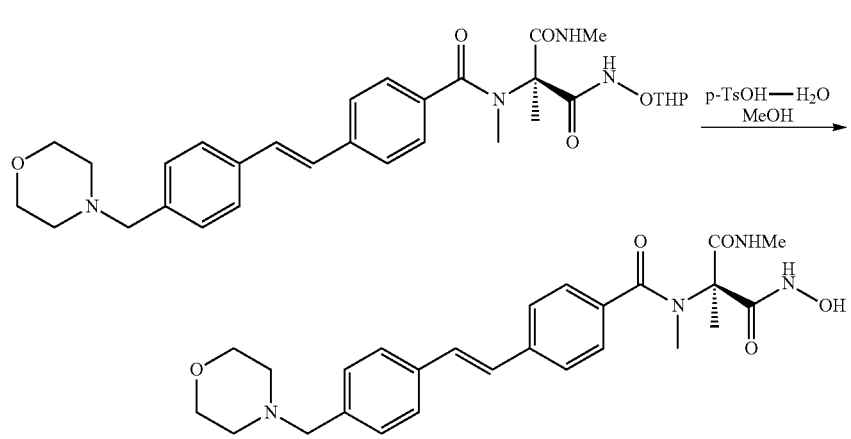

(2) Using (2S)-N,2-dimethyl-2-{methyl[(4-{(E)-2-[4-(morpholin-4-ylmethyl)phenyl]ethenyl}phenyl)carbonyl]amino}-N'-(tetrahydro-2H-pyran-2-yloxy)propanediamide (32 mg) as obtained in Example 26-(1), the same procedure as in Example 16-8-(2) was performed to obtain (2S)-N-hydroxy-N',2-dimethyl-2-{methyl[(4-{(E)-2-[4-(morpholin-4-ylmethyl)phenyl]ethenyl}phenyl)carbonyl]amino}propanediamide (Compound 434, light yellow solid) (16 mg, 61%).

MS (ESI/APCI Dual): MS (ESI): 481 (M+H)$^+$, 479 (M−H)$^−$ $^1$H NMR (600 MHz, CD$_3$OD) δ ppm 1.77 (3 H, s), 2.41-2.53 (4 H, m), 2.79 (3 H, s), 3.20 (3 H, s), 3.53 (2 H, s), the aforementioned reaction at varying concentrations of the test compound. From this inhibition curve, the concentration of the test compound at which the formation of the reaction product was suppressed by 50% was determined as the IC$_{50}$ of the test compound, which was an index for the inhibitory activity on *Pseudomonas aeruginosa* LpxC enzyme. The results for various test compounds are shown in Tables 1 to 4. As shown, the test compounds exhibited at least 25% inhibition of *Pseudomonas aeruginosa* LpxC enzyme at a concentration of 1000 nM.

Test 2: Evaluation of the Inhibitory Activity on *E. coli* LpxC Enzyme

To assay the activity of *E. coli* LpxC enzyme, LpxC was reacted with its substrate UDP-3-O-(R-3-hydroxytetradecanoyl)-N-acetylglucosamine and the amount of the reaction product was determined by quantifying the amino groups present in it.

Specifically, 12.5 ng of *E. coli* LpxC enzyme (as acquired by preparing chromosomal DNA from *E. coli*, subjecting the DNA to PCR (polymerase chain reaction) using LpxC specific primers to acquire *E. coli* LpxC genes, incorporating the genes into a vector, and expressing the same with *E. coli*) was mixed with 20 μmol/L of UDP-3-O-(R-3-hydroxytetradecanoyl)-N-acetylglucosamine (Wako Pure Chemical Industries, Ltd.) and the mixture was incubated at room temperature for 120 minutes. The reaction was performed in 40 mmol/L of 2-morpholinoethanesulfonic acid buffer solution (pH 6.5) supplemented with 0.02% Bridge 35 and 80 μmol/L of dithiothreitol. To terminate the reaction, 0.2 mol/L of borax was added to the reaction mixture; thereafter, 0.5 mg/mL of fluorescamine dissolved in anhydrous dioxane was added and the amount of the reaction product was measured at excitation and fluorescence wavelengths of 390 nm and 495 nm, respectively. An inhibition curve was constructed for each test compound by performing the aforementioned reaction at varying concentrations of the test compound. From this inhibition curve, the concentration of the test compound at which the formation of the reaction product was suppressed by 50% was determined as the $IC_{50}$ of the test compound, which was an index for the inhibitory activity on *E. coli* LpxC enzyme. The test results for representative compounds are shown in Table 4.

Test 3: Evaluation of Antimicrobial Activity

For minimum inhibitory concentration (MIC) measurement, the following broth microdilution method was applied as adapted from the standard procedure recommended by the CLSI (Clinical and Laboratory Standards Institute).

The bacteria used were *Pseudomonas aeruginosa* strain TS88 (clinical isolate), *E. coli* strain ATCC25922, and *Klebsiella pneumoniae* strain ATCC13883. After culture overnight on a heart infusion agar medium, the cells of a test bacterium were scraped off and suspended to give a turbidity of level 0.5 on the McFarland scale; the suspension was then diluted 10 fold to prepare an inoculum solution. A 0.005 mL aliquot of the inoculum solution was inoculated in a cation-adjusted Mueller-Hinton broth medium containing a test compound and cultured at 35° C. for 18 hours. A minimum drug concentration at which no cell growth was visible to the naked eye was designated as MIC. The test results for representative compounds are shown in Tables 1 and 4.

In Tables 1 to 4, NT means that no test was conducted.

In Tables 2 and 3, the test results for inhibitory activity on *Pseudomonas aeruginosa* LpxC enzyme are indicated according to the following criteria.

A: $IC_{50}$ of less than 10 nM;
B: $IC_{50}$ of at least 10 nM but less than 100 nM;
C: $IC_{50}$ of at least 100 nM and 25% or more inhibition at 1000 nM.

In Table 2, the data in the MS (ESI) column as accompanied by the indication of LC-MS retention times refer to the values detected in LC-MS ([M+H]+).

TABLE 1-1

Structural formulae of representative compounds, as well as their spectral data, inhibitory activity against *Pseudomonas aeruginosa* LpxC enzyme, and antimicrobial activity

| Compound No. | Structural formulae | MS (ESI) | $^1$H-NMR | *Pseudomonas aeruginosa* LpxC $IC_{50}$ (nmol/L) | MIC (μg/mL) *Pseudomonas aeruginosa* TS88 strain |
|---|---|---|---|---|---|
| 1 | | 364 [M + Na]+ 340 [M − H]− | $^1$H NMR (600 MHz, CHLOROFORM-d) δ ppm 2.88 (3 H, br. s.), 3.06 (3 H, br. s.), [5.16], 5.59 (1 H, br. s.), 7.30-7.73 (9H, m), 10.87 (1 H, br. s.) | 7.7 | 0.5 |
| 2 | | 393 [M + Na]+ 369 [M − H]− | $^1$H NMR (400 MHz, CD$_3$OD) δ ppm 2.80 (6H, br. s.), 3.12 (3H, s), 6.69 (2H, d, J = 8.6 Hz), 7.35-7.69 (6H, m) | 7.1 | 0.5 |

TABLE 1-1-continued

Structural formulae of representative compounds, as well as their spectral data, inhibitory activity against *Pseudomonas aeruginosa* LpxC enzyme, and antimicrobial activity

| Compound No. | Structural formulae | MS (ESI) | ¹H-NMR | *Pseudomonas aeruginosa* LpxC IC$_{50}$ (nmol/L) | MIC (μg/mL) *Pseudomonas aeruginosa* TS88 strain |
|---|---|---|---|---|---|
| 3 | | 494 [M + Na]+ 370 [M − H]− | ¹H NMR (600 MHz, DMSO-d$_6$) δ ppm 2.66 (3 H, br. s.), 2.98 (3 H, s), 3.81 (3 H, s), 5.38, [5.84] (1 H, br. s.), 7.05 (2 H, d, J = 8.71 Hz), 7.33-7.74 (6 H, m), 8.16 (1 H, br. s.), 9.03 (1 H, br. s.), 10.83 (1 H, br. s.) | 3.3 | 0.5 |
| 4 | | 425 [M − H]− | ¹H NMR (600 MHz, CD$_3$OD) δ ppm 2.83 (3 H, br. s.), 3.12 (3 H, s), 3.40 (3 H, s), 4.51 (2 H, s), 7.44 (2 H, d, J = 8.25 Hz), 7.57-7.78 (6 H, m) | 6.1 | 1 |
| 5 | | 378 [M + Na]+ 354 [M − H]− | ¹H NMR (400 MHz, CD$_3$OD) δ ppm 2.38 (3H, s), 2.82 (3H, s), 3.11 (3H, s), 5.50 (1H, s), 7.27 (2H, d, J = 8.0 Hz), 7.40-7.76 (6H, m) | 3.7 | 0.25 |
| 6 | | 382 [M + Na]+ 358 [M − H]− | ¹H NMR (400 MHz, CD$_3$OD) δ ppm 2.73 (3H, s), 3.02 (3H, s), 5.42 (1H, s), 7.06-7.15 (2H, m), 7.33-7.67 (6H, m) | 7.1 | 1 |
| 7 | | 486 [M + H]+ 484 [M − H]− | ¹H NMR (600 MHz, DMSO-d$_6$) δ ppm 1.84-1.92 (2H, m), 2.33-2.40 (4 H, m), 2.41-2.46 (2H, m), 2.67 (3H, br. s.), 2.98 (3H, s), 3.54-3.61 (4H, m), 4.03-4.10 (2 H, m), 5.36, [5.84] (1H, br. s.), 7.01-7.06 (2H, m), 7.32-7.74 (6H, m), 8.14 (1H, br. s.), 9.04 (1H, br. s.), 10.85 (1H, br. s.) | 6.7 | 2 |

TABLE 1-1-continued

Structural formulae of representative compounds, as well as their spectral data, inhibitory activity against *Pseudomonas aeruginosa* LpxC enzyme, and antimicrobial activity

| Compound No. | Structural formulae | MS (ESI) | $^1$H-NMR | *Pseudomonas aeruginosa* LpxC IC$_{50}$ (nmol/L) | MIC (μg/mL) *Pseudomonas aeruginosa* TS88 strain |
|---|---|---|---|---|---|
| 7b | | 486 [M + H]+ 484 [M − H]− | $^1$H NMR (600 MHz, CD$_3$OD) δ ppm 2.18-2.29 (2H, m), 2.36 (3H, s), 2.83 (3H, br. s.), 3.12 (3H, br. s.), 3.17-3.40 (8H, m), 3.90 (2H, br. s.), 4.12-4.19 (2H, m), 7.04 (2H, d, J = 8.7 Hz), 7.22 (2H, d, J = 8.3 Hz), 7.54-7.77 (8H, m) | NT | 2 |
| 8 | | 386 [M + H]+ 408 [M + Na]+ 384 [M − H]− | $^1$H NMR (400 MHz, CD$_3$OD) δ ppm 2.82 (3H, s), 3.10 (3H, s), 5.50 (1H, s), 5.99 (2H, s), 6.88-6.93 (1H, m), 7.11-7.19 (2H, m), 7.39-7.69 (4H, m) | 5.0 | 0.5 |
| 40 | | 397 [M + H]+ | $^1$H NMR (400 MHz, CD$_3$OD) δ ppm 2.78 (3H, s), 2.81 (3H, s), 2.93-3.01 (2H, m), 3.11 (3H, s), 3.22-3.37 (2H, m), 5.45-5.55 (1H, br), 6.55-6.61 (1H, m), 7.34-7.66 (6H, m) | 4.7 | 1 |
| 43 | | 385 [M + H]+ | $^1$H NMR (400 MHz, CD$_3$OD) δ ppm 2.82 (3H, s), 2.98 (6H, s), 3.12 (3H, s), 5.45-5.54 (1H, br), 6.84 (2H, d, J = 8.8 Hz), 7.39-7.80 (6H, m) | 7.2 | 1 |
| 52 | | 426 [M + H]+ | $^1$H NMR (400 MHz, CD$_3$OD) δ ppm 2.82 (3H, s), 3.10 (3H, s), 5.51 (1H, s), 7.37 (2H, d, J = 8.3 Hz), 7.40-7.80 (6H, m) | 4.6 | 1 |

TABLE 1-1-continued

Structural formulae of representative compounds, as well as their spectral data, inhibitory activity against *Pseudomonas aeruginosa* LpxC enzyme, and antimicrobial activity

| Compound No. | Structural formulae | MS (ESI) | ¹H-NMR | *Pseudomonas aeruginosa* LpxC IC$_{50}$ (nmol/L) | MIC (μg/mL) *Pseudomonas aeruginosa* TS88 strain |
|---|---|---|---|---|---|
| 56 | | 410 [M + H]+ | ¹H NMR (400 MHz, CD$_3$OD) δ ppm 2.82 (3H, s), 3.11 (3H, s), 5.52 (1H, s), 7.50-8.00 (8H, m) | 6.7 | 1 |
| 58 | | 512 [M + H]+ | ¹H NMR (400 MHz, CD$_3$OD) δ ppm 1.30-1.40 (2H, m), 1.45-1.65 (4H, m), 2.25-2.35 (2H, m), 2.41 (4H, br. s.), 2.72 (3H, s), 2.95-3.10 (5H, m), 3.55-3.65 (4H, m), 5.40 (1H, s), 6.61 (2H, d, J = 8.5 Hz), 7.30-7.60 (6H, m) | 8.3 | 4 |
| 61 | | 360 [M + H]+ | ¹H NMR (400 MHz, CHLOROFORM-d) δ ppm 2.90 (3H, d, J = 4.1 Hz), 3.07 (3H, s), 5.59 (1H, s), 7.22-7.59 (8H, m), 10.84 (1H, s) | 9.2 | 2 |
| 77 | | 452 [M + H]+ | ¹H NMR (400 MHz, CD$_3$OD) δ ppm 2.39 (3H, s), 2.80 (3H, s), 3.14 (3H, s), 4.47 (2H, s), 5.50-5.55 (1H, br), 6.17 (1H, s), 6.69 (2H, d, J = 8.8 Hz), 7.42-7.67 (6H, m) | 7.5 | 4 |

TABLE 1-1-continued

Structural formulae of representative compounds, as well as their spectral data, inhibitory activity against *Pseudomonas aeruginosa* LpxC enzyme, and antimicrobial activity

| Compound No. | Structural formulae | MS (ESI) | $^1$H-NMR | *Pseudomonas aeruginosa* LpxC IC$_{50}$ (nmol/L) | MIC (μg/mL) *Pseudomonas aeruginosa* TS88 strain |
|---|---|---|---|---|---|
| 94 | | 416 [M + H]+ | $^1$H NMR (400 MHz, CD$_3$OD) δ ppm 2.82 (3H, s), 3.11 (3H, s), 3.40 (3H, s), 5.45-5.55 (1H, br), 6.95 (1H, s), 6.98 (1H, d, J = 8.0 Hz), 7.15-7.25 (2H, m), 7.40-7.65 (2H, m), 7.67 (2H, d, J = 8.0 Hz) | 5.6 | 2 |
| 153 | | 424 [M + H]+ 400 [M − H]− | $^1$H NMR (600 MHz, DMSO-d$_6$ + D$_2$O) δ ppm 2.66 (3H, br. s.), 2.98 (3H, s), 3.73 (2H, t, J = 4.8 Hz), 4.04 (2H, t, J = 4.8 Hz), 7.05 (2H, d, J = 8.7 Hz), 7.55 (2H, br. s.), 7.62-7.75 (4H, m) | 5.7 | 2 |
| 172 | | 445 [M + Na]+ 421 [M − H]− | $^1$H NMR (600 MHz, DMSO-d$_6$) δ ppm 2.38 (3H, s), 3.00 (3H, s), 4.35 (2H, br. s.) [4.75], 5.45 (1H, br. s.), 6.19 (1H, br. s.), 7.36-7.61 (5H, m), 7.67-7.80 (4H, m), 8.85 (1H, br. s.), 9.10 (1H, br. s.), 10.93 (1H, br. s.) | 7.1 | 2 |
| 188 | | 406 [M + Na]+ 382 [M − H]− | $^1$H NMR (600 MHz, DMSO-d$_6$ + D$_2$O) δ ppm 2.66 (3H, s), 2.99 (3H, s), 3.25 (2H, t, J = 8.7 Hz), 4.58 (2H, t, J = 8.7 Hz), 5.37 (1H, s), 6.86 (1H, d, J = 7.8 Hz), 7.35-7.47 (2H, m), 7.48-7.56 (1H, m), 7.57-7.62 (1H, m), 7.68 (2H, m) | 5.0 | 0.5 |
| 218 | | 388 [M + Na]+ 364 [M − H]− | $^1$H NMR (600 MHz, DMSO-d$_6$) δ ppm 2.59-2.69 (3H, m), 2.91-3.01 (3H, m), 5.36 (1H, s), 7.33-7.68 (9H, m), 8.15 (1H, m), 9.05 (1H, br. s.), 10.84 (1H, br. s.) | 7.2 | 1 |

TABLE 1-1-continued

Structural formulae of representative compounds, as well as their spectral data, inhibitory activity against *Pseudomonas aeruginosa* LpxC enzyme, and antimicrobial activity

| Compound No. | Structural formulae | MS (ESI) | ¹H-NMR | *Pseudomonas aeruginosa* LpxC IC$_{50}$ (nmol/L) | MIC (µg/mL) *Pseudomonas aeruginosa* TS88 strain |
|---|---|---|---|---|---|
| 237 | | 396 [M + Na]+ 372 [M − H]− | ¹H NMR (600 MHz, CD$_3$OD) δ ppm 2.83 (3H, br. s.), 3.12 (3H, s), 5.42 (2H, d, J = 48.0 Hz), 7.50 (2H, d, J = 6.9 Hz), 7.60-7.67 (2H, m), 7.71 (2H, d, J = 7.3 Hz), 7.76 (2H, d, J = 7.3 Hz) | 4.5 | 0.5 |
| 271 | | 406 [M + Na]+ 382 [M − H]− | ¹H NMR (600 MHz, DMSO-d$_6$) δ ppm 2.66 (3H, br. s.), 2.97 (3H, s), 3.22 (2H, t, J = 8.7 Hz), 4.57 (2H, t, J = 8.7 Hz), 5.37 (1H, br. s.), 7.09 (1H, s), 7.17 (1H, d, J = 7.3 Hz), 7.32 (1H, d, J = 7.3 Hz), 7.40 (1H, br. s.), 7.54 (2H, d, J = 7.3 Hz), 7.71 (2H, d, J = 7.3 Hz), 8.13 (1H, br. s.), 9.04 (1H, br. s.) | 5.0 | 0.5 |

TABLE 2-1

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 9 | 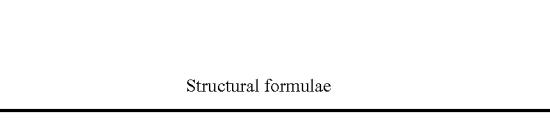 | 3.53 | 428 [M + H]+ | ¹H NMR (400 MHz, DMSO-d$_6$) δ ppm 0.15-0.25 (2H, m), 0.35-0.50 (2H, m), 0.85-1.00 (1H, m), 2.95-3.10 (2H, m), 3.70-3.85 (2H, m), 4.00-4.10 (2H, m), 7.00-7.15 (2H, m), 7.65-7.85 (4H, m), 7.90-8.10 (2H, m) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 10 | | 3.55 | 460 [M + H]+ | $^1$H NMR (400 MHz, DMSO-$d_6$) δ ppm 1.06 (6H, dd, J = 6.1, 2.2 Hz), 3.15-3.25 (2H, m), 3.25-3.45 (2H, m), 3.49-3.58 (1H, m), 3.70-3.80 (2H, m), 4.04 (2H, t, J = 4.9 Hz), 4.85-4.93 (1H, m), 5.09 (1H, d, J = 8.3 Hz), 7.06 (2H, d, J = 8.8 Hz), 7.65-7.81 (4H, m), 7.97 (2H, d, J = 8.3 Hz), 8.04-8.12 (1H, m), 8.44 (1H, d, J = 8.3 Hz), 9.09 (1H, s), 10.81 (1H, s) | B |
| 11 | | 3.10 | 471 [M + H]+ | $^1$H NMR (400 MHz, CD$_3$OD) δ ppm 3.91 (2H, t, J = 4.7 Hz), 4.11 (2H, t, J = 4.7 Hz), 4.58-4.71 (2H, m), 7.03-7.11 (2H, m), 7.58-7.69 (2H, m), 7.69-7.77 (2H, m), 7.85 (1H, s), 7.94-8.01 (2H, m), 8.91 (1H, s) | A |
| 12 | | 3.64 | 454 [M + H]+ | $^1$H NMR (400 MHz, DMSO-$d_6$) δ ppm 3.71-3.77 (2H, m), 4.04 (2H, t, J = 4.9 Hz), 4.31 (2H, d, J = 5.6 Hz), 4.90 (1H, t, J = 5.5 Hz), 5.12 (1H, d, J = 8.3 Hz), 6.27 (1H, d, J = 2.9 Hz), 6.38-6.41 (1H, m), 7.06 (2H, d, J = 8.8 Hz), 7.56-7.59 (1H, m), 7.69 (2H, d, J = 8.8 Hz), 7.75 (2H, d, J = 8.5 Hz), 7.98 (2H, d, J = 8.5 Hz), 8.50 (1H, d, J = 8.5 Hz), 8.57-8.62 (1H, m), 9.13 (1H, s), 10.91 (1H, s) | A |
| 13 | | NT | 476 [M + H]+ 498 [M + Na]+ 474 [M − H]− | $^1$H NMR (400 MHz, CD$_3$OD) δ ppm 2.70 (3H, s), 3.45-3.60 (6H, m), 3.60-3.65 (2H, m), 3.75-3.80 (2H, m), 4.05-4.15 (2H, m), 5.06 (1H, s), 6.96 (2H, d, J = 8.9 HZ), 7.54 (2H, d, J = 8.9 Hz), 7.62 (2H, d, J = 8.5 Hz), 7.87 (2H, d, J = 8.5 Hz) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 14 | | 3.33 | 432 [M + H]+ | ¹H NMR (400 MHz, CD$_3$OD) δ ppm 2.79 (3H, s), 3.60-3.75 (4H, m), 3.80-3.95 (2H, m), 4.19 (2H, t, J = 4.6 Hz), 5.15 (1H, s), 7.00-7.10 (2H, m), 7.60-7.70 (2H, m), 7.71 (2H, d, J = 8.4 Hz), 7.96 (2H, d, J = 8.4 Hz), | A |
| 15 | | 3.25 | 446 [M + H]+ | ¹H NMR (400 MHz, CD$_3$OD) δ ppm 2.82 (3H, s), 3.11 (3H, s), 3.60-3.75 (4H, m), 3.80-3.90 (2H, m), 4.15-4.25 (2H, m), 5.45-5.55 (1H, br), 7.04 (2H, d, J = 8.5 Hz), 7.40-7.75 (6H, m) | B |
| 16 | | 3.74 | 336 [M + H]+ | ¹H NMR (400 MHz, DMSO-d$_6$) δ ppm 2.62 (3H, d, J = 4.6 Hz), 5.02 (1H, d, J = 8.0 Hz), 7.48 (2H, d, J = 8.1 Hz), 8.00-8.10 (3H, m), 8.63 (1H, d, J = 8.0 Hz), 9.08 (1H, s), 10.85 (1H, s), | C |
| 17 | | 4.51 | 358 [M + H]+ | ¹H NMR (400 MHz, CD$_3$OD) δ ppm 2.72 (3H, s), 3.71 (3H, s), 5.28 (1H, s), 7.25-7.31 (1H, m), 7.32-7.41 (2H, m), 7.52-7.65 (4H, m), 7.89-7.94 (2H, m) | B |
| 18 | | 4.14 | 356 [M + H]+ | ¹H NMR (400 MHz, CD$_3$OD) δ ppm 2.25 (3H, s), 2.82 (3H, s), 3.12 (3H, s), 5.50-5.55 (1H, br), 7.16-7.31 (4H, m), 7.42 (2H, d, J = 8.0 Hz), 7.46-7.66 (2H, m) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 19 | | 4.09 | 395 [M + H]+ | ¹H NMR (400 MHz, CD$_3$OD) δ ppm 2.82 (3H, s), 3.14 (3H, s), 3.83 (3H, s), 6.49 (1H, d, J = 2.9 Hz), 7.19 (1H, d, J = 2.9 Hz), 7.42-7.52 (2H, m), 7.54-7.66 (2H, m), 7.75 (2H, d, J = 8.0 Hz), 7.84 (1H, s) | A |
| 20 | | 2.42 | 429 [M + H]+ | ¹H NMR (400 MHz, CD$_3$OD) δ ppm 1.40-1.70 (4H, m), 2.73 (3H, s), 2.95-3.15 (2H, m), 3.03 (3H, s), 3.45-3.60 (2H, m), 5.35-5.45 (1H, br), 6.61 (2H, d, J = 8.6 Hz), 7.25-7.70 (6H, m) | B |
| 21 | | 4.15 | 356 [M + H]+ | ¹H NMR (400 MHz, CD$_3$OD) δ ppm 2.39 (3H, s), 2.83 (3H, s), 2.97 (3H, s), 5.63 (1H, s), 7.32-7.48 (4H, m), 7.53 (1H, d, J = 8.3 Hz), 7.55 (1H, s), 7.59-7.67 (2H, m) | C |
| 22 | | 3.64 | 350 [M + H]+ | ¹H NMR (400 MHz, DMSO-d$_6$) δ ppm 2.65 (3H, br. s.), 2.92 (3H, s), 5.35 (1H, s), 7.35-7.75 (4H, m), 8.10-8.30 (1H, m), 9.06 (1H, s), 10.88 (1H, s), | C |
| 23 | | 4.08 | 374 [M + H]+ | ¹H NMR (400 MHz, CD$_3$OD) δ ppm 2.39 (3H, s), 2.82 (3H, s), 3.11 (3H, s), 5.51 (1H, s), 7.04 (1H, d, J = 11.7 Hz), 7.09 (1H, d, J = 8.1 Hz), 7.35-7.43 (1H, m), 7.45-7.67 (4H, m) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 24 | | 3.55 | 358 [M + H]+ | $^1$H NMR (400 MHz, CD$_3$OD) δ ppm 2.83 (3H, s), 3.09 (3H, s), 5.59 (1H, s), 7.14 (1H, s), 7.22 (1H, d, J = 7.8 Hz), 7.33-7.48 (4H, m), 7.60 (2H, d, J = 7.3 Hz) | C |
| 25 | | 5.28 | 394 [M + H]+ | $^1$H NMR (400 MHz, DMSO-d$_6$) δ ppm 0.80-0.95 (3H, m), 1.15-1.50 (8H, m), 1.60-1.80 (2H, m), 2.05-2.15 (2H, m), 2.60-2.75 (3H, m), 2.96 (3H, s), 3.95-4.10 (2H, m), 5.30 (1H, s), 6.90-7.05 (2H, m), 7.20-7.55 (2H, m), 8.00-8.20 (1H, m), 9.03 (1H, s), 10.82 (1H, s), | B |
| 26 | | 3.59 | 453 [M + H]+ | $^1$H NMR (400 MHz, CD$_3$OD) δ ppm 1.35-1.50 (2H, m), 1.75-1.90 (2H, m), 2.73 (3H, s), 3.04 (3H, s), 3.45 (2H, t, J = 6.5 Hz), 4.13 (2H, t, J = 7.1 Hz), 5.35-5.45 (1H, br), 6.41 (1H, d, J = 3.0 Hz), 7.16 (1H, d, J = 3.0 Hz), 7.30-7.55 (4H, m), 7.65 (2H, d, J = 8.3 Hz), 7.74 (1H, s) | A |
| 27 | | 3.84 | 360 [M + H]+ | $^1$H NMR (400 MHz, CD$_3$OD) δ ppm 2.82 (3H, s), 3.08 (3H, s), 5.59 (1H, s), 7.37-7.43 (1H, m), 7.44-7.52 (3H, m), 7.53-7.60 (2H, m), 7.64-7.69 (2H, m) | B |
| 28 | | 4.16 | 374 [M + H]+ | $^1$H NMR (400 MHz, CD$_3$OD) δ ppm 2.30 (3H, s), 2.82 (3H, s), 3.10 (3H, s), 5.50 (1H, s), 7.28-7.42 (3H, m), 7.45-7.66 (2H, m), 7.72 (2H, d, J = 8.3 Hz) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 29 | | 4.05 | 356 [M + H]+ | $^1$H NMR (400 MHz, CD$_3$OD) δ ppm 2.41 (3H, s), 2.82 (3H, s), 3.11 (3H, s), 5.51 (1H, s), 7.20 (1H, d, J = 7.3 Hz), 7.30-7.37 (1H, m), 7.41-7.66 (4H, m), 7.71 (2H, d, J = 8.3 Hz) | A |
| 30 | | 4.30 | 348 [M + H]+ | $^1$H NMR (400 MHz, DMSO-d$_6$) δ ppm 1.15-1.50 (5H, m), 1.65-1.90 (5H, m), 2.45-2.60 (1H, m), 2.65 (3H, d, J = 3.9 Hz), 2.94 (3H, s), 5.34 (1H, s), 7.15-7.50 (4H, m), 8.10 (1H, s), 9.04 (1H, s), 10.86 (1H, s) | B |
| 31 | | 3.27 | 425 [M + H]+ | $^1$H NMR (400 MHz, DMSO-d$_6$) δ ppm 2.60-2.70 (3H, m), 3.00 (3H, s), 3.70-3.80 (2H, m), 4.20-4.30 (2H, m), 4.90 (1H, t, J = 5.1 Hz), 5.30-5.40 (1H, br), 6.49 (1H, d, J = 3.2 Hz), 7.30-7.65 (4H, m), 7.70-7.80 (2H, m), 7.88 (1H, s), 8.15 (1H, s), 9.04 (1H, s), 10.75-11.00 (1H, br) | A |
| 32 | | NT | 407 [M + Na]+ 383 [M − H]− | $^1$H NMR (400 MHz, CD$_3$OD) δ ppm 1.25 (3H, t, J = 7.1 Hz), 2.81 (3H, s), 3.11 (3H, s), 3.16 (2H, q, J = 7.1 Hz), 5.49 (1H, s), 6.71 (2H, d, J = 8.4 Hz), 7.46 (2H, d, J = 8.0 Hz), 7.30-7.60 (2H, m), 7.64 (2H, d, J = 8.4 Hz) | A |
| 33 | | 4.00 | 469 [M + H]+ | $^1$H NMR (400 MHz, DMSO-d$_6$) δ ppm 2.67 (3H, d, J = 4.2 Hz), 3.00 (3H, s), 3.20-3.40 (3H, m), 3.78 (3H, s), 4.67 (2H, s), 4.73 (2H, s), 5.38 (1H, s), 6.56 (1H, s), 7.30-7.60 (4H, m), 7.77 (2H, d, J = 7.6 Hz), 7.88 (1H, s), 8.15 (1H, s), 9.06 (1H, s), 10.87 (1H, s) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 34 | | 4.28 | 485 [M + H]+ | ¹H NMR (400 MHz, DMSO-$d_6$) δ ppm 1.33 (3H, d, J = 7.1 Hz), 1.38 (9H, s), 2.67 (3H, d, J = 4.2 Hz), 2.98 (3H, s), 4.60-4.75 (1H, m), 5.38 (1H, s), 7.30-7.60 (5H, m), 7.66 (2H, d, J = 7.3 Hz), 7.70-7.80 (2H, m), 8.15 (1H, s), 9.06 (1H, s), 10.87 (1H, s) | B |
| 35 | | 3.84 | 338 [M + H]+ | ¹H NMR (400 MHz, DMSO-$d_6$) δ ppm 0.94 (3H, t, J = 7.1 Hz), 1.35-1.55 (2H, m), 1.60-1.80 (2H, m), 2.65 (3H, d, J = 3.0 Hz), 2.96 (3H, s), 4.01 (2H, br. s.), 5.30 (1H, s), 6.98 (2H, d, J = 7.8 Hz), 7.20-7.60 (2H, m), 8.10 (1H, s), 8.70-9.35 (1H, br), 10.83 (1H, s) | B |
| 36 | | 4.07 | 395 [M + H]+ | ¹H NMR (400 MHz, CD$_3$OD) δ ppm 2.83 (3H, s), 3.14 (3H, s), 3.86 (3H, s), 6.44 (1H, dd, J = 3.1, 0.9 Hz), 7.20 (1H, d, J = 3.1 Hz), 7.35-7.40 (1H, m), 7.55-7.70 (4H, m), 7.75-7.85 (2H, m) | A |
| 37 | | 4.00 | 322 [M + H]+ | ¹H NMR (400 MHz, CHLOROFORM-d) δ ppm 0.93 (3H, t, J = 7.3 Hz), 1.30-1.40 (2H, m), 1.55-1.65 (2H, m), 2.56-2.67 (2H, m), 2.82 (3H, s), 3.01 (3H, s), 5.58 (1H, s), 7.22 (2H, d, J = 7.1 Hz), 7.40-7.50 (3H, m) | B |
| 38 | | 3.36 | 389 [M + H]+ | ¹H NMR (400 MHz, CD$_3$OD) δ ppm 2.82 (3H, s), 2.86 (3H, s), 3.11 (3H, s), 5.49 (1H, s), 6.74-6.82 (1H, m), 7.28-7.40 (2H, m), 7.40-7.69 (4H, m) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 39 | | NT | 381 [M − H]− | $^1$H NMR (400 MHz, CD$_3$OD) δ ppm 2.83 (3H, s), 3.05 (2H, t, J = 8.3 Hz), 3.11 (3H, s), 3.49-3.57 (2H, m), 5.45-5.55 (1H, br), 6.71 (1H, d, J = 8.1 Hz), 7.39-7.66 (6H, m) | B |
| 41 | | 3.31 | 425 [M + H]+ | $^1$H NMR (400 MHz, CD$_3$OD) δ ppm 2.82 (3H, s), 3.14 (3H, s), 3.83 (3H, s), 4.77 (2H, s), 5.45-5.65 (1H, br), 6.49 (1H, s), 7.40-7.70 (4H, m), 7.75 (2H, d, J = 8.3 Hz), 7.81 (1H, s) | A |
| 42 | | 4.13 | 388 [M + H]+ | $^1$H NMR (400 MHz, DMSO-d$_6$) δ ppm 2.53 (3H, s), 2.60-2.72 (3H, m), 2.98 (3H, s), 5.37 (1H, s), 7.37 (2H, d, J = 8.5 Hz), 7.51-7.60 (2H, m), 7.68 (2H, d, J = 8.5 Hz), 7.71-7.78 (2H, m), 8.15 (1H, s), 9.07 (1H, s), 10.89 (1H, s) | A |
| 44 | | 4.50 | 485 [M + H]+ | $^1$H NMR (400 MHz, CD$_3$OD) δ ppm 1.28-1.60 (9H, m), 2.28 (3H, s), 2.82 (3H, s), 3.11 (3H, s), 3.14 (3H, s), 5.45-5.55 (1H, br), 7.17-7.43 (2H, m), 7.45-7.80 (5H, m) | B |
| 45 | | 2.42 | 385 [M + H]+ | $^1$H NMR (400 MHz, CD$_3$OD) δ ppm 2.19 (3H, s), 2.81 (3H, s), 2.87 (3H, s), 3.12 (3H, s), 6.65 (1H, d, J = 8.6 Hz), 7.35 (1H, s), 7.42 (1H, d, J = 8.6 Hz), 7.50-7.60 (2H, m), 7.64 (2H, d, J = 8.1 Hz) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 46 | 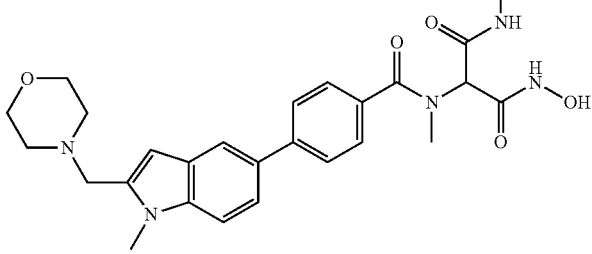 | 2.68 | 494 [M + H]+ | $^1$H NMR (400 MHz, CD$_3$OD) δ ppm 2.42 (4H, br. s.), 2.73 (3H, s), 3.04 (3H, s), 3.50-3.65 (6H, m), 3.75 (3H, s), 5.35-5.45 (1H, br), 6.35 (1H, s), 7.30-7.40 (2H, m), 7.40-7.60 (2H, m), 7.65 (2H, d, J = 8.3 Hz), 7.70 (1H, s) | B |
| 47 | 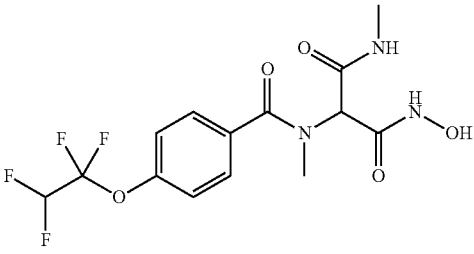 [SMILES: CNC(=O)C(C(=O)NO)N(C)C(=O)c1ccc(OC(F)(F)C(F)F)cc1] | 3.64 | 382 [M + H]+ | $^1$H NMR (400 MHz, DMSO-d$_6$) δ ppm 2.65 (3H, s), 2.93 (3H, s), 5.35 (1H, s), 6.83 (1H, t, J = 51.8 Hz), 7.30-7.65 (4H, m), 8.10-8.20 (1H, m), 9.07 (1H, s), 10.89 (1H, s) | C |
| 48 | 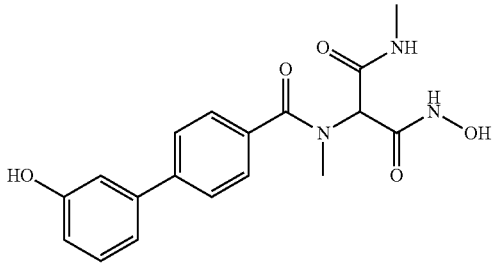 [SMILES: CNC(=O)C(C(=O)NO)N(C)C(=O)c1ccc(-c2cccc(O)c2)cc1] | 3.19 | 358 [M + H]+ | $^1$H NMR (400 MHz, CD$_3$OD) δ ppm 2.82 (3H, s), 3.11 (3H, s), 5.51 (1H, s), 6.77-6.83 (1H, m), 7.02-7.15 (2H, m), 7.22-7.31 (1H, m), 7.41-7.74 (4H, m) | B |
| 49 | 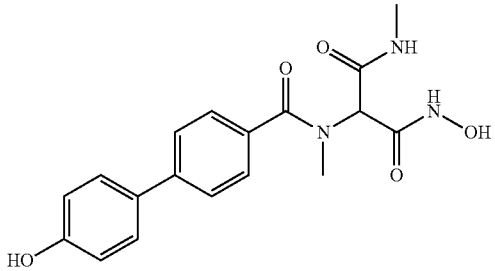 [SMILES: CNC(=O)C(C(=O)NO)N(C)C(=O)c1ccc(-c2ccc(O)cc2)cc1] | 3.08 | 358 [M + H]+ | $^1$H NMR (400 MHz, CD$_3$OD) δ ppm 2.82 (3H, s), 3.11 (3H, s), 5.45-5.55 (1H, br), 6.87 (2H, d, J = 8.8 Hz), 7.40-7.70 (6H, m) | B |
| 50 | 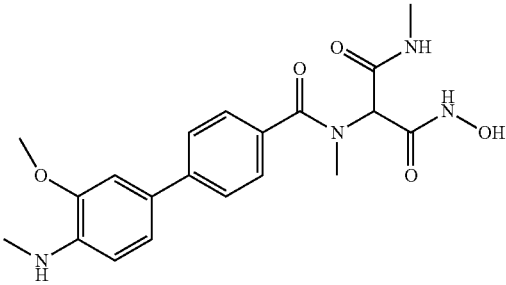 [SMILES: CNC(=O)C(C(=O)NO)N(C)C(=O)c1ccc(-c2ccc(NC)c(OC)c2)cc1] | 2.41 | 401 [M + H]+ | $^1$H NMR (400 MHz, CD$_3$OD) δ ppm 2.82 (3H, s), 2.86 (3H, s), 3.12 (3H, s), 3.92 (3H, s), 5.50 (1H, s), 6.69 (1H, d, J = 8.7 Hz), 7.13 (1H, s), 7.20 (1H, d, J = 8.7 Hz), 7.35-7.65 (2H, m), 7.68 (2H, d, J = 8.0 Hz) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 51 | | 4.14 | 408 [M + H]+ | $^1$H NMR (400 MHz, CD$_3$OD) δ ppm 2.82 (3H, s), 3.11 (3H, s), 5.51 (1H, s), 6.87 (1H, t, J = 74.0 Hz), 7.24 (2H, d, J = 8.8 Hz), 7.40-7.80 (6H, m) | A |
| 53 | | 3.02 | 427 [M + H]+ | $^1$H NMR (400 MHz, CD$_3$OD) δ ppm 2.82 (3H, s), 3.11 (3H, s), 3.16-3.22 (4H, m), 3.81-3.87 (4H, m), 5.50 (1H, s), 7.05 (2H, d, J = 8.8 Hz), 7.35-7.63 (4H, m), 7.68 (2H, d, J = 8.0 Hz) | B |
| 54 | | 2.66 | 403 [M + H]+ | $^1$H NMR (400 MHz, CD$_3$OD) δ ppm 2.82 (3H, s), 2.87 (6H, s), 3.10 (3H, s), 5.50 (1H, s), 7.02-7.09 (1H, m), 7.34-7.43 (2H, m), 7.45-7.64 (2H, m), 7.69 (2H, d, J = 8.3 Hz) | B |
| 55 | | 3.39 | 402 [M + H]+ | $^1$H NMR (400 MHz, CD$_3$OD) δ ppm 2.82 (3H, s), 3.11 (3H, s), 3.87 (3H, s), 3.90 (3H, s), 5.45-5.55 (1H, br), 7.04 (1H, d, J = 8.8 Hz), 7.20-7.30 (2H, m), 7.40-7.65 (2H, m), 7.70 (2H, d, J = 7.8 Hz) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 57 | | 4.15 | 409 [M + H]+ | $^1$H NMR (400 MHz, CD$_3$OD) δ ppm 2.43 (3H, s), 2.82 (3H, s), 3.13 (3H, s), 3.70 (3H, s), 5.50 (1H, s), 7.30-7.80 (8H, m) | A |
| 59 | | 3.76 | 360 [M + H]+ | $^1$H NMR (400 MHz, CHLOROFORM-d) δ ppm 2.90 (3H, d, J = 4.6 Hz), 3.06 (3H, s), 5.62 (1H, s), 7.13-7.48 (4H, m), 7.53-7.69 (4H, br), 10.88 (1H, s) | A |
| 60 | | 2.87 | 424 [M + H]+ | $^1$H NMR (400 MHz, CD$_3$OD) δ ppm 2.82 (3H, s), 3.10 (3H, s), 4.35 (2H, s), 5.48-5.52 (1H, br), 7.38 (2H, d, J = 8.5 Hz), 7.45-7.75 (6H, m) | C |
| 62 | | 4.63 | 418 [M + H]+ | $^1$H NMR (400 MHz, CD$_3$OD) δ ppm 3.13 (3H, s), 4.49 (2H, s), 5.56 (1H, s), 7.21-7.28 (1H, m), 7.29-7.40 (5H, m), 7.42-7.50 (2H, m), 7.56-7.77 (6H, m) | C |
| 63 | | 4.19 | 368 [M + H]+ | $^1$H NMR (400 MHz, DMSO-d$_6$) δ ppm 2.66 (3H, d, J = 3.9 Hz), 2.97 (3H, s), 5.36, (1H, s), 7.26-7.53 (7H, m), 7.59-7.73 (4H, m), 8.09-8.15 (1H, m), 9.04-9.07 (1H, m), 10.87 (1H, s) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 64 | | 2.70 | 487 [M + H]+ | $^1$H NMR (400 MHz, CD$_3$OD) δ ppm 1.95-2.10 (2H, m), 2.51 (3H, s), 2.73 (3H, s), 2.85-2.95 (4H, m), 3.02 (3H, s), 3.27 (3H, s), 3.52 (2H, t, J = 5.4 Hz), 4.02 (2H, t, J = 5.9 Hz), 6.93 (2H, d, J = 8.8 Hz), 7.30-7.60 (6H, m) | B |
| 65 | | 2.45 | 448 [M + H]+ | $^1$H NMR (400 MHz, CD$_3$OD) δ ppm 2.81 (3H, s), 3.10 (3H, s), 4.44 (2H, s), 5.48 (1H, s), 6.70 (2H, d, J = 8.8 Hz), 7.35-7.65 (7H, m), 7.86 (1H, d, J = 8.0 Hz), 8.40 (1H, d, J = 4.0 Hz), 8.56 (1H, s) | A |
| 66 | | 3.69 | 433 [M + H]+ | $^1$H NMR (400 MHz, CD$_3$OD) δ ppm 2.81 (3H, s), 3.11 (3H, s), 3.34-3.40 (2H, m), 3.39 (3H, s), 3.58-3.64 (2H, m), 5.49 (1H, s), 6.80-6.90 (1H, m), 7.28-7.38 (2H, m), 7.42-7.60 (2H, m), 7.65 (2H, d, J = 8.0 Hz) | A |
| 67 | | 3.87 | 407 [M + H]+ | $^1$H NMR (400 MHz, CD$_3$OD) δ ppm 2.82 (3H, s), 2.84 (3H, s), 3.11 (3H, s), 5.50 (1H, s), 6.49 (1H, dd, J = 13.0, 7.4 Hz), 7.13 (1H, dd, J = 12.4, 7.1 Hz), 7.35-7.65 (4H, m) | A |
| 68 | | 4.19 | 439 [M + H]+ | $^1$H NMR (400 MHz, CD$_3$OD) δ ppm 2.82 (3H, s), 2.90 (3H, s), 3.11 (3H, s), 5.50 (1H, s), 6.88 (1H, d, J = 8.0 Hz), 7.40-7.80 (6H, m) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 69 | | 3.73 | 407 [M + H]+ | ¹H NMR (400 MHz, CD₃OD) δ ppm 2.82 (3H, s), 3.01 (3H, t, J = 2.2 Hz), 3.10 (3H, s), 7.18-7.24 (2H, m), 7.40-7.70 (4H, m) | A |
| 70 | | 3.19 | 519 [M + H]+ | ¹H NMR (400 MHz, CD₃OD) δ ppm 1.88-1.98 (2H, m), 2.18 (3H, s), 2.54 (2H, t, J = 7.4 Hz), 2.73 (3H, s), 3.02 (3H, s), 3.50 (2H, s), 3.98 (2H, t, J = 6.1 Hz), 6.89 (2H, d, J = 8.8 Hz), 7.12-7.26 (5H, m), 7.30-7.54 (4H, m), 7.59 (2H, d, J = 8.1 Hz) | A |
| 71 | | 3.50 | 485 [M + H]+ | ¹H NMR (400 MHz, CD₃OD) δ ppm 1.90-2.05 (2H, m), 2.73 (3H, s), 3.02 (3H, s), 3.39 (2H, t, J = 6.8 Hz), 3.50-3.65 (2H,m), 4.00 (2H, t, J = 6.0 Hz), 4.26 (2H, t, J = 8.0 Hz), 5.41 (1H, s), 6.94 (2H, d, J = 8.8 Hz), 7.25-7.65 (6H, m) | A |
| 72 | | 4.11 | 443 [M + H]+ | ¹H NMR (400 MHz, CD₃OD) δ ppm 2.82 (3H, s), 3.05-3.13 (3H, m), 3.11 (3H, s), 5.51 (1H, s), 7.45-7.68 (4H, m) | A |
| 73 | | 3.90 | 378 [M + H]+ | ¹H NMR (400 MHz, CHLOROFORM-d) δ ppm 2.88 (3H, s), 3.07 (3H, s), 5.59 (1H, s), 7.13-7.53 (8H, m), 10.55-11.10 (1H, br) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 74 | | 2.81 | 441 [M + H]+ | ¹H NMR (400 MHz, CD₃OD) δ ppm 1.04 (9H, s), 2.83 (3H, s), 2.85 (2H, s), 3.11 (3H, s), 4.31 (2H, s), 5.52 (1H, s), 7.45-7.70 (4H, m), 7.70-7.85 (4H, m) | C |
| 75 | | 3.31 | 491 [M + H]+ | ¹H NMR (400 MHz, CD₃OD) δ ppm 2.04-2.13 (2H, m), 2.82 (3H, s), 3.11 (3H, s), 3.20-3.38 (2H, m), 4.15 (2H, J = 6.1 Hz), 5.50 (1H, s), 6.56-6.63 (1H, m), 6.63-6.68 (2H, m), 6.98-7.06 (2H, m), 7.06-7.12 (2H, m), 7.40-7.64 (4H, m), 7.64-7.72 (2H, m) | A |
| 76 | | 4.78 | 432 [M + H]+ | ¹H NMR (400 MHz, CD₃OD) δ ppm 2.81-2.90 (2H, m), 3.02 (3H, s), 3.45-3.61 (2H, m), 5.45-5.50 (1H, br), 7.15-7.32 (5H, m), 7.35-7.40 (1H, m), 7.43-7.50 (2H, m), 7.50-7.77 (6H, m) | C |
| 78 | | 3.55 | 463 [M + H]+ | ¹H NMR (400 MHz, CD₃OD) δ ppm 1.01 (3H, t, J = 7.4 Hz), 1.75-1.87 (2H, m), 2.82 (3H, s), 3.04-3.15 (2H, m), 3.11 (3H, s), 5.51 (1H, s), 7.34 (2H, d, J = 8.5 Hz), 7.39-7.88 (6H, m) | B |
| 79 | | 2.67 | 411 [M + H]+ | ¹H NMR (400 MHz, CD₃OD) δ ppm 0.22-0.28 (2H, m), 0.50-0.56 (2H, m), 1.04-1.14 (1H, m), 2.81 (3H, s), 2.98 (2H, d, J = 6.6 Hz), 3.12 (3H, s), 5.48 (1H, s), 6.72 (2H, d, J = 8.8 Hz), 7.40-7.66 (6H, m) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 80 | | NT | 378 [M + Na]+ 354 [M − H]− | ¹H NMR (400 MHz, CD₃OD) δ ppm 3.10 (3H, s), 3.20-3.40 (6H, m), 7.35-7.40 (1H, m), 7.40-7.50 (2H, m), 7.55-7.75 (6H, m) | C |
| 81 | | 3.68 | 400 [M + H]+ | ¹H NMR (400 MHz, CD₃OD) δ ppm 2.82 (3H, s), 3.10 (3H, s), 4.27 (4H, s), 6.91 (1H, d, J = 8.5 Hz), 7.05-7.20 (2H, m), 7.35-7.75 (4H, m) | A |
| 82 | | 3.49 | 427 [M + H]+ | ¹H NMR (400 MHz, CD₃OD) δ ppm 2.82 (3H, s), 3.11 (3H, s), 3.44 (3H, s), 4.65 (2H, s), 5.45-5.55 (1H, br), 7.08 (1H, d, J = 8.3 Hz), 7.30-7.85 (6H, m) | A |
| 83 | | 4.40 | 458 [M + H]+ | ¹H NMR (400 MHz, CD₃OD) δ ppm 2.82 (3H, s), 3.11 (3H, s), 6.15-6.50 (1H, m), 7.34 (2H, d, J = 8.3 Hz), 7.45-7.70 (2H, m), 7.70-7.85 (4H, m) | A |
| 84 | | 3.39 | 560 [M + H]+ | ¹H NMR (400 MHz, CD₃OD) δ ppm 1.99-2.11 (2H, m), 2.61-2.73 (6H, m), 2.82 (3H, s), 3.11 (3H, s), 3.16-3.24 (4H, m), 4.11 (2H, t, J = 6.2 Hz), 6.80-6.86 (1H, m), 6.94-7.00 (2H, m), 7.00-7.06 (2H, m), 7.18-7.26 (2H, m), 7.40-7.64 (4H, m), 7.64-7.72 (2H, m) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 85 | | 2.70 | 425 [M + H]+ | ¹H NMR (400 MHz, CD₃OD) δ ppm 0.22-0.28 (2H, m), 0.46-0.54 (2H, m), 1.00-1.08 (1H, m), 2.81 (3H, s), 3.01 (3H, s), 3.12 (3H, s), 3.25-3.34 (2H, m), 5.45-5.50 (1H, br), 6.86 (2H, d, J = 9.0 Hz), 7.34-7.60 (4H, m), 7.66 (2H, d, J = 8.3 Hz) | A |
| 86 | | 2.26 | 484 [M + H]+ | ¹H NMR (400 MHz, CD₃OD) δ ppm 1.78-1.88 (2H, m), 2.46-2.54 (6H, m), 2.81 (3H, s), 3.12 (3H, br. s.), 3.19 (2H, t, J = 6.8 Hz), 3.66-3.74 (4H, m), 6.71 (2H, d, J = 8.5 Hz), 7.40-7.66 (6H, m) | B |
| 87 | | 3.15 | 547 [M + H]+ | ¹H NMR (400 MHz, CD₃OD) δ ppm 2.25-2.40 (4H, br), 2.73 (3H, s), 3.02 (3H, s), 3.44 (2H, s), 3.50-3.65 (4H, m), 5.06 (2H, s), 5.35-5.45 (1H, br), 6.99 (2H, d, J = 8.8 Hz), 7.15-7.30 (3H, m), 7.30-7.65 (7H, m) | A |
| 88 | | 2.89 | 513 [M + H]+ | ¹H NMR (400 MHz, CD₃OD) δ ppm 1.14 (6H, d, J = 6.3 Hz), 1.74-1.88 (2H, m), 1.97-2.11 (2H, m), 2.55-2.67 (2H, m), 2.82 (3H, s), 2.86-2.97 (2H, m), 3.11 (3H, s), 3.64-3.77 (2H, m), 4.08 (2H, t, J = 6.1 Hz), 5.44-5.57 (1H, br), 7.01 (2H, d, J = 8.8 Hz), 7.38-7.74 (6H, m) | A |
| 89 | | 3.41 | 491 [M + H]+ | ¹H NMR (400 MHz, CD₃OD) δ ppm 2.82 (3H, s), 3.03 (3H, s), 3.11 (3H, s), 3.76 (2H, t, J = 5.6 Hz), 4.20 (2H, t, J = 5.6 Hz), 5.50 (1H, s), 6.62-6.68 (1H, m), 6.80 (2H, d, J = 8.0 Hz), 6.99 (2H, d, J = 8.8 Hz), 7.14-7.21 (2H, m), 7.40-7.70 (6H, m) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 90 | | 3.21 | 546 [M + H]+ | ¹H NMR (400 MHz, CD₃OD) δ ppm 2.36 (3H, s), 2.60-2.68 (4H, m), 2.83 (3H, s), 3.12 (3H, s), 3.19-3.25 (4H, m), 5.04 (2H, s), 7.00 (2H, d, J = 8.8 Hz), 7.08 (2H, d, J = 8.8 Hz), 7.35 (2H, d, J = 8.8 Hz), 7.45-7.65 (4H, m), 7.69 (2H, d, J = 8.0 Hz) | A |
| 91 | | 3.07 | 547 [M + H]+ | ¹H NMR (400 MHz, CD₃OD) δ ppm 2.46 (4H, br. s.), 2.82 (3H, s), 3.11 (3H, s), 3.53 (2H, s), 3.65-3.75 (4H, m), 5.13 (2H, s), 5.45-5.55 (1H, br), 7.08 (2H, d, J = 8.8 Hz), 7.37 (2H, d, J = 8.0 Hz), 7.43 (2H, d, J = 8.4 Hz), 7.50-7.65 (4H, m), 7.68 (2H, d, J = 8.0 Hz), | A |
| 92 | | 3.21 | 555 [M + H]+ | ¹H NMR (400 MHz, CD₃OD) δ ppm 1.90-2.10 (2H, m), 2.26 (3H, s), 2.62 (2H, t, J = 7.2 Hz), 2.82 (3H, s), 3.11 (3H, s), 3.60 (2H, s), 4.06 (2H, t, J = 5.8 Hz), 5.45-5.55 (1H, br), 6.80-7.05 (2H, m), 6.97 (2H, d, J = 8.4 Hz), 7.30-7.65 (5H, m), 7.68 (2H, d, J = 8.0 Hz), | A |
| 93 | | 3.82 | 516 [M + H]+ | ¹H NMR (400 MHz, CD₃OD) δ ppm 2.82 (3H, s), 3.11 (3H, s), 5.26 (2H, s), 5.45-5.55 (1H, br), 7.12 (2H, d, J = 8.4 Hz), 7.43-7.73 (8H, m), 8.05 (2H, d, J = 8.4 Hz) | B |
| 95 | | 3.82 | 442 [M + H]+ | ¹H NMR (400 MHz, CD₃OD) δ ppm 1.45 (3H, s), 2.82 (3H, s), 3.11 (3H, s), 4.09 (2H, s), 4.46 (2H, d, J = 5.9 Hz), 4.68 (2H, d, J = 5.9 Hz), 5.51 (1H, s), 7.08 (2H, d, J = 8.8 Hz), 7.39-7.73 (6H, m) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 96 | | 2.69 | 466 [M + H]+ | ¹H NMR (400 MHz, CD$_3$OD) δ ppm 2.22-2.32 (2H, m), 2.82 (3H, s), 3.11 (3H, s), 3.97 (2H, t, J = 5.7 Hz), 4.27 (2H, t, J = 6.8 Hz), 5.45-5.55 (1H, br), 6.95-6.98 (1H, m), 7.01 (2H, d, J = 8.8 Hz), 7.13-7.16 (1H, m), 7.40-7.63 (4H, m), 7.63-7.71 (3H, m) | A |
| 97 | | 2.86 | 518 [M + H]+ | ¹H NMR (400 MHz, CD$_3$OD) δ ppm 1.80-1.95 (2H, m), 2.28 (3H, s), 2.50-2.65 (2H, m), 2.81 (3H, s), 3.12 (3H, s), 3.05-3.20 (2H, m), 3.61 (2H, s), 6.68 (2H, d, J = 8.4 Hz), 7.20-7.40 (5H, m), 7.46 (2H, d, J = 8.0 Hz), 7.50-7.60 (2H, m), 7.63 (2H, d, J = 8.0 Hz) | B |
| 98 | | 3.92 | 492 [M + H]+ | ¹H NMR (400 MHz, CD$_3$OD) δ ppm 2.82 (3H, s), 3.11 (3H, s), 5.22 (2H, s), 5.45-5.55 (1H, br), 7.10 (2H, d, J = 8.4 Hz), 7.40-7.73 (8H, m), 8.03 (2H, d, J = 8.4 Hz) | B |
| 99 | | 3.68 | 453 [M + H]+ | ¹H NMR (400 MHz, CD$_3$OD) δ ppm 2.46 (3H, s), 2.82 (3H, s), 3.11 (3H, s), 5.00 (2H, s), 5.45-5.55 (1H, br), 7.09 (2H, d, J = 8.8 Hz), 7.43-7.65 (4H, m), 7.69 (2H, d, J = 8.0 Hz), 7.87 (1H, s) | A |
| 100 | | 2.93 | 490 [M + H]+ | ¹H NMR (400 MHz, CD$_3$OD) δ ppm 1.87-1.98 (2H, m), 2.81 (3H, s), 3.12 (3H, s), 3.17-3.38 (4H, m), 5.49 (1H, s), 6.56-6.68 (3H, m), 6.72 (2H, d, J = 8.6 Hz), 7.04-7.12 (2H, m), 7.33-7.59 (4H, m), 7.63 (2H, d, J = 8.3 Hz) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 101 | | 1.79 | 400 [M + H]+ | ¹H NMR (400 MHz, CD$_3$OD) δ ppm 2.65-2.90 (9H, m), 3.10 (3H, s), 5.50 (1H, s), 6.60-6.90 (4H, m), 7.00-7.10 (1H, m), 7.10-7.25 (2H, m), | C |
| 102 | | 2.89 | 511 [M + H]+ | ¹H NMR (400 MHz, CD$_3$OD) δ ppm 0.46-0.51 (2H, m), 0.65-0.70 (2H, m), 2.42 (2H, s), 2.46-2.56 (4H, br), 2.83 (3H, s), 3.12 (3H, s), 3.69 (4H, t, J = 4.6 Hz), 3.97 (2H, s), 5.45-5.55 (1H, br), 7.03 (2H, d, J = 8.8 Hz), 7.40-7.65 (4H, m), 7.69 (2H, d, J = 8.0 Hz) | B |
| 103 | | 2.61 | 516 [M + H]+ | ¹H NMR (400 MHz, CD$_3$OD) δ ppm 0.55-0.70 (2H, m), 1.00-1.20 (2H, m), 2.82 (3H, s), 2.95-3.45 (4H, m), 3.12 (3H, s), 5.45-5.55 (1H, br), 6.70-6.85 (2H, m), 6.90-7.05 (3H, m), 7.20-7.35 (2H, m), 7.35-7.75 (6H, m), | A |
| 104 | | NT | 561 [M + Na]+ 537 [M − H]− | ¹H NMR (400 MHz, CD$_3$OD) δ ppm 2.83 (3H, s), 3.11 (3H, s), 3.35 (3H, s), 4.09-4.17 (2H, m), 4.29-4.36 (2H, m), 5.51 (1H, s), 7.42 (2H, d, J = 8.4 Hz), 7.39-7.71 (4H, m), 7.74 (2H, d, J = 8.0 Hz) | NT |
| 105 | | NT | 354 [M + Na]+ 330 [M − H]− | ¹H NMR (400 MHz, CD$_3$OD) δ ppm 2.81 (3H, s), 3.10 (3H, s), 5.49 (1H, s), 6.85 (1H, s), 7.39-7.61 (3H, m), 7.66 (2H, d, J = 8.3 Hz), 7.99 (1H, s) | C |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 106 | | NT | 549 [M + H]+ | $^1$H NMR (400 MHz, CD$_3$OD) δ ppm 1.85-2.15 (2H, m), 2.28 (3H, s), 2.50-2.95 (2H, m), 2.73 (3H, s), 2.82 (3H, s), 3.12 (3H, s), 3.61 (2H, s), 3.90-4.15 (2H, m), 6.05-6.45 (2H, m), 6.80-7.05 (1H, m), 7.15-7.75 (9H, m) | B |
| 107 | | NT | 383 [M + Na]+ 359 [M − H]− | $^1$H NMR (400 MHz, CD$_3$OD) δ ppm 2.74 (3H, s), 3.02 (3H, s), 5.43 (1H, s), 7.35-7.75 (4H, m), 7.80-8.05 (2H, m), 8.42 (1H, d, J = 4.4 Hz) | C |
| 108 | | NT | 383 [M + Na]+ 359 [M − H]− | $^1$H NMR (400 MHz, CD$_3$OD) δ ppm 2.73 (3H, s), 3.01 (3H, s), 5.35-5.45 (1H, br), 7.35-7.65 (3H, m), 7.80-7.95 (1H, m), 7.95-8.05 (2H, m), 8.46 (1H, d, J = 2.7 Hz) | C |
| 109 | | NT | 328 [M − H]− | $^1$H NMR (600 MHz, DMSO-d$_6$) δ ppm 5.06 (1 H, d, J = 8.5 Hz), 7.40-7.44 (1 H, m), 7.47-7.53 (2 H, m), 7.74 (2 H, d, J = 7.3 Hz), 7.79 (2 H, d, J = 8.3 Hz), 8.01 (2 H, d, J = 8.3 Hz), 8.41 (1 H, d, J = 8.5 Hz) | B |
| 110 | | NT | 326 [M − H]− | $^1$H NMR (600 MHz, DMSO-d$_6$) δ ppm 2.63 (3 H, d, J = 4.6 Hz), 5.05 (1 H, d, J = 8.3 Hz), 7.42 (1 H, t, J = 8.0 Hz), 7.48-7.53 (2 H, m), 7.74 (2 H, d, J = 7.3 Hz), 7.80 (2 H, d, J = 8.3 Hz), 8.01 (2 H, d, J = 8.3 Hz), 8.03-8.06 (1 H, m), 8.44 (1 H, d, J = 8.3 Hz), 9.05 (1 H, br. s.), 10.87 (1 H, br. s.) | B |
| 111 | | NT | 312 [M − H]− | $^1$H NMR (600 MHz, DMSO-d$_6$) δ ppm 5.02 (1 H, d, J = 8.3 Hz), 7.39-7.45 (2 H, m), 7.48-7.53 (3H, m), 7.74 (2H, d, J = 9.2 Hz), 7.80 (2 H, d, J = 8.7 Hz), 8.00 (2 H, d, J = 8.7 Hz), 8.39 (1 H, d, J = 8.3 Hz), 9.08 (1 H, s), 10.84 (1 H, s) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 112 | | NT | 485 [M + H]+ 483 [M − H]− | $^1$H NMR (600 MHz, DMSO-$d_6$) δ ppm 1.76-1.82 (2H, m), 1.85-1.90 (2H, m), 2.57-2.68 (9H, m), 3.58-3.63 (2H, m), 3.67 (2H, t, J = 6.0 Hz), 4.07 (2H, t, J = 6.4 Hz), 5.05 (1H, d, J = 8.3 Hz), 7.04 (2H, d, J = 8.7 Hz), 7.68 (2H, d, J = 8.7 Hz), 7.74 (2H, d, J = 8.7 Hz), 7.97 (2H, d, J = 8.7 Hz), 8.01-8.07 (1H, m), 8.39 (1H, d, J = 8.3 Hz), 9.07 (1H, br. s.) | A |
| 113 | | NT | 410 [M + Na]+ 386 [M − H]− | $^1$H NMR (600 MHz, DMSO-$d_6$) δ ppm 2.64 (3 H, s), 3.72-3.76 (2 H, m), 4.05 (2 H, t, J = 5.0 Hz), 4.88 (1 H, t, J = 5.5 Hz), 5.05 (1 H, d, J = 8.3 Hz), 6.39 (1 H, s), 7.06 (2 H, d, J = 8.7 Hz), 7.69 (2 H, d, J = 8.7 Hz), 7.75 (2 H, d, J = 8.3 Hz), 7.97 (2 H, d, J = 8.3 Hz), 8.04 (1 H, d, J = 4.6 Hz), 8.40 (1 H, d, J = 8.3 Hz), 9.06 (1 H, br. s.) | A |
| 114 | | NT | 387 [M + H]+ 385 [M − H]− | $^1$H NMR (600 MHz, DMSO-$d_6$) δ ppm 2.60 (3 H, d, J = 4.1 Hz), 3.12-3.16 (2 H, m), 3.57 (2 H, t, J = 6.2 Hz), 4.71 (1 H, br. s.), 4.86 (1 H, d, J = 5.0 Hz), 5.18 (1 H, br. s.), 5.83 (1 H, t, J = 5.7 Hz), 6.40 (1 H, br. s.), 6.69 (2 H, d, J = 8.7 Hz), 7.51 (2 H, d, J = 8.7 Hz), 7.67 (2 H, d, J = 8.3 Hz), 7.87 (2 H, d, J = 8.3 Hz), 7.99 (1 H, d, J = 4.1 Hz), 8.08 (1 H, br. s.) | B |
| 115 | | NT | 432 [M + Na]+ 409 [M − H]− | $^1$H NMR (600 MHz, DMSO-$d_6$) δ ppm 2.63 (3 H, d, J = 4.6 Hz), 3.11-3.17 (2 H, m), 3.52-3.59 (2 H, m), 4.69-4.76 (1 H, m), 5.02 (1 H, d, J = 7.8 Hz), 6.11-6.17 (1 H, m), 6.61 (2 H, d, J = 8.7 Hz), 7.28 (2 H, d, J = 8.7 Hz), 7.55 (2 H, d, J = 8.3 Hz), 7.91 (2 H, d, J = 8.3 Hz), 8.04 (1 H, d, J = 5.0 Hz), 8.46 (1 H, d, J = 7.8 Hz), 9.04 (1 H, br. s.) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 116 | | NT | 451 [M + H]+ 449 [M − H]− | $^1$H NMR (600 MHz, DMSO-$d_6$) δ ppm 3.69-3.77 (2 H, m), 4.05 (2 H, t, J = 5.0 Hz), 4.84-4.92 (1 H, m), 5.30 (1 H, d, J = 7.8 Hz), 6.40 (1 H, br. s.), 7.06 (2 H, d, J = 8.7 Hz), 7.38 (1 H, dd, J = 8.3, 4.6 Hz), 7.70 (2 H, d, J = 8.7 Hz), 7.76 (2 H, d, J = 8.3 Hz), 8.00-8.07 (3 H, m), 8.30 (1 H, dd, J = 4.6, 1.4 Hz), 8.75-8.83 (2 H, m), 9.13 (1 H, br. s.), 10.41 (1 H, br. s.) | B |
| 117 | | NT | 465 [M + H]+ 463 [M − H]− | $^1$H NMR (600 MHz, DMSO-$d_6$) δ ppm 1.78-1.83 (2 H, m), 2.59-2.64 (7 H, m), 3.60-3.62 (2 H, m), 3.67 (2 H, s), 3.70 (2 H, t, J = 6.0 Hz), 5.03 (1 H, d, J = 8.3 Hz), 7.40 (2 H, d, J = 8.3 Hz), 7.54 (2 H, d, J = 8.3 Hz), 7.65 (2 H, d, J = 8.7 Hz), 7.96 (2 H, d, J = 8.7 Hz), 8.03-8.07 (1 H, m), 8.54 (1 H, d, J = 8.3 Hz), 9.07 (1 H, s), 10.86 (1 H, br. s.) | A |
| 118 | | NT | 400 [M − H]− | $^1$H NMR (600 MHz, DMSO-$d_6$) δ ppm 2.88 (3 H, s), 3.09 (3 H, s), 3.71-3.76 (2H, m), 4.04 (2 H, t, J = 5.0 Hz), 4.88 (1 H, t, J = 5.7 Hz), 5.44-5.49 (1 H, m), 7.05 (2 H, d, J = 8.7 Hz), 7.69 (2 H, d, J = 8.7 Hz), 7.74 (2 H, d, J = 8.5 Hz), 7.96 (2 H, d, J = 8.5 Hz), 8.48-8.55 (1 H, m), 8.97 (1 H, br. s.) | C |
| 119 | | NT | 452 [M + Na]+ 428 [M − H]− | $^1$H NMR (600 MHz, DMSO-$d_6$) δ ppm 1.28 (9 H, s), 3.72-3.76 (2 H, m), 4.05 (2 H, t, J = 4.8 Hz), 4.88 (1 H, t, J = 5.7 Hz), 5.02 (1 H, d, J = 8.3 Hz), 7.06 (2 H, d, J = 8.7 Hz), 7.63 (1 H, br. s.), 7.69 (2 H, d, J = 8.7 Hz), 7.75 (2 H, d, J = 8.7 Hz), 7.95 (2 H, d, J = 8.7 Hz), 8.27 (1 H, d, J = 8.3 Hz), 9.01 (1 H, br. s.), 10.80 (1 H, s) | C |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 120 | | NT | 464 [M + H]+ 462 [M − H]− | ¹H NMR (600 MHz, DMSO-$d_6$) δ ppm 3.72-3.76 (2 H, m), 4.04 (2 H, t, J = 5.0 Hz), 4.33 (2 H, d, J = 6.0 Hz), 4.88 (1 H, t, J = 5.5 Hz), 5.12 (1 H, d, J = 7.3 Hz), 6.39 (1 H, s), 7.05 (2 H, d, J = 8.7 Hz), 7.20-7.34 (5 H, m), 7.69 (2 H, d, J = 8.7 Hz), 7.75 (2 H, d, J = 8.7 Hz), 7.98 (3 H, d, J = 8.7 Hz), 8.45 (1 H, d, J = 7.3 Hz), 8.62 (1 H, t, J = 6.0 Hz), 9.02 (1 H, s) | A |
| 121 | | NT | 412 [M − H]− | ¹H NMR (600 MHz, DMSO-$d_6$) δ ppm 0.42-0.48 (2 H, m), 0.60-0.67 (2 H, m), 2.64-2.69 (1 H, m), 3.72-3.76 (2 H, m), 4.05 (2 H, t, J = 5.0 Hz), 4.88 (1 H, t, J = 5.7 Hz), 5.02 (1 H, d, J = 8.5 Hz), 7.06 (2 H, d, J = 9.2 Hz), 7.69 (2 H, d, J = 9.2 Hz), 7.75 (2 H, d, J = 8.5 Hz), 7.96 (2 H, d, J = 8.5 Hz), 8.17 (1 H, d, J = 4.1 Hz), 8.36 (1 H, d, J = 8.5 Hz), 9.07 (1 H, s), 10.83 (1 H, br. s.) | B |
| 122 | | NT | 416 [M − H]− | ¹H NMR (600 MHz, DMSO-$d_6$) δ ppm 3.11-3.24 (2 H, m), 3.40-3.45 (2 H, m), 3.71-3.76 (2 H, m), 4.05 (2 H, t, J = 5.0 Hz), 4.67-4.71 (1 H, m), 4.86-4.90 (1 H, m), 5.09 (1 H, d, J = 8.3 Hz), 7.06 (2 H, d, J = 8.7 Hz), 7.69 (2 H, d, J = 8.7 Hz), 7.75 (2 H, d, J = 8.5 Hz), 7.97 (2 H, d, J = 8.5 Hz), 8.06 (1 H, t, J = 5.5 Hz), 8.44 (1 H, d, J = 8.3 Hz), 9.08 (1 H, br. s.) | B |
| 123 | | NT | 445 [M + H]+ 443 [M − H]− | ¹H NMR (600 MHz, DMSO-$d_6$) δ ppm 2.21 (6 H, br. s.), 2.37-2.49 (2 H, m), 3.20-3.26 (2 H, m), 3.72-3.77 (2 H, m), 4.05 (2 H, t, J = 5.0 Hz), 4.88 (1 H, t, J = 5.5 Hz), 5.07 (1 H, d, J = 8.3 Hz), 7.06 (2 H, d, J = 8.7 Hz), 7.69 (2 H, d, J = 8.7 Hz), 7.75 (2 H, d, J = 8.3 Hz), 7.97 (2 H, d, J = 8.3 Hz), 8.05-8.11 (1 H, m), 8.44 (1 H, d, J = 8.3 Hz), 9.09 (1 H, br. s.), 10.95 (1 H, br. s.) | C |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 124 | | NT | 463 [M − H]− | $^1$H NMR (600 MHz, DMSO-$d_6$) δ ppm 3.17 (2H, d, J = 5.0 Hz), 3.71-3.77 (2H, m), 4.04 (2H, t, J = 5.0 Hz), 4.36 (2H, d, J = 6.0 Hz), 4.85-4.91 (1H, m), 5.16 (1H, d, J = 8.3 Hz), 7.02-7.09 (2H, m), 7.29 (2H, d, J = 6.0 Hz), 7.66-7.71 (2H, m), 7.75 (2H, d, J = 8.7 Hz), 8.00 (2H, d, J = 8.3 Hz), 8.46-8.51 (2H, m), 8.58 (1H, d, J = 8.3 Hz), 8.74 (1H, t, J = 6.2 Hz) | A |
| 125 | | NT | 478 [M + H]+ 476 [M − H]− | $^1$H NMR (600 MHz, DMSO-$d_6$) δ ppm 2.72 (2 H, t, J = 7.6 Hz), 3.28-3.29 (1 H, m), 3.34-3.37 (1 H, m), 3.72-3.77 (2 H, m), 4.05 (2 H, t, J = 5.0 Hz), 4.88 (1 H, t, J = 5.5 Hz), 5.05 (1 H, d, J = 8.3 Hz), 7.06 (2 H, d, J = 8.7 Hz), 7.16-7.23 (3 H, m), 7.24-7.28 (2 H, m), 7.68-7.71 (2 H, m), 7.76 (2 H, d, J = 8.3 Hz), 7.97 (2 H, d, J = 8.7 Hz), 8.19 (1 H, t, J = 5.5 Hz), 8.38 (1 H, d, J = 8.3 Hz), 9.03 (1 H, br. s.), 10.76 (1 H, s) | B |
| 126 | | NT | 514 [M + Na]+ 490 [M − H]− | $^1$H NMR (600 MHz, DMSO-$d_6$) δ ppm 1.67-1.76 (2 H, m), 2.55-2.60 (2 H, m), 3.08-3.14 (2 H, m), 3.72-3.77 (2 H, m), 4.05 (2 H, t, J = 5.0 Hz), 4.88 (1 H, t, J = 5.5 Hz), 5.07 (1 H, d, J = 8.3 Hz), 6.40 (1 H, s), 7.06 (2 H, d, J = 8.7 Hz), 7.14-7.29 (5 H, m), 7.69 (2 H, d, J = 8.7 Hz), 7.75 (2 H, d, J = 8.7 Hz), 7.97 (2 H, d, J = 8.7 Hz), 8.14 (1 H, t, J = 5.5 Hz), 8.40 (1 H, d, J = 8.3 Hz), 9.09 (1 H, br. s.) | A |
| 127 | | NT | 390 [M + Na]+ 366 [M − H]− | $^1$H NMR (600 MHz, CHLOROFORM-d) δ ppm 0.44-0.69 (4 H, m), 2.88 (3 H, d, J = 4.6 Hz), 3.07-3.13 (1 H, m), 5.18 (1 H, s), 7.02-7.19 (1 H, m), 7.36-7.42 (1 H, m), 7.44-7.50 (2 H, m), 7.60-7.70 (4 H, m), 7.76 (2 H, d, J = 8.3 Hz), 10.92 (1 H, br. s.) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 128 | | NT | 464 [M + Na]+ 440 [M − H]− | ¹H NMR (600 MHz, DMSO-$d_6$) δ ppm 1.61-1.69 (2 H, m), 1.74-1.82 (2 H, m), 1.89-1.97 (2 H, m), 2.37-2.44 (1 H, m), 3.08-3.19 (2 H, m), 3.72-3.76 (2 H, m), 4.05 (2 H, t, J = 5.0 Hz), 4.88 (1 H, t, J = 5.5 Hz), 5.06 (1 H, d, J = 8.5 Hz), 7.06 (2 H, d, J = 8.7 Hz), 7.69 (2 H, d, J = 8.7 Hz), 7.75 (2 H, d, J = 8.5 Hz), 7.96 (2 H, d, J = 8.5 Hz), 8.05 (1 H, t, J = 5.7 Hz), 8.36 (1 H, d, J = 8.5 Hz), 9.06 (1 H, br. s.), 10.82 (1 H, br. s.) | A |
| 129 | | NT | 463 [M − H]− | ¹H NMR (600 MHz, DMSO-$d_6$) δ ppm 3.70-3.78 (2H, m), 4.04 (2H, t, J = 5.0 Hz), 4.36 (2H, d, J = 6.0 Hz), 4.88 (1H, t, J = 5.5 Hz), 5.13 (1H, d, J = 8.3 Hz), 7.05 (2H, d, J = 8.7 Hz), 7.30-7.38 (1H, m), 7.64-7.72 (3H, m), 7.75 (2H, d, J = 8.7 Hz), 7.99 (2H, d, J = 8.7 Hz), 8.42-8.52 (2H, m), 8.55 (1H, d, J = 8.3 Hz), 8.70 (1H, t, J = 6.0 Hz), 9.11 (1 H, br. s.) | A |
| 130 | | NT | 463 [M − H]− | ¹H NMR (600 MHz, DMSO-$d_6$) δ ppm 3.70-3.78 (2H, m), 4.04 (2H, t, J = 5.0 Hz), 4.37-4.48 (2H, m), 4.85-4.92 (1H, m), 5.17 (1H, d, J = 8.1 Hz), 7.01-7.10 (2H, m), 7.24-7.29 (1H, m), 7.36 (1H, d, J = 7.8 Hz), 7.66-7.71 (2H, m), 7.72-7.78 (3H, m), 7.99 (2H, d, J = 8.7 Hz), 8.49 (1H, d, J = 4.6 Hz), 8.55 (1H, d, J = 8.1 Hz), 8.76 (1H, t, J = 6.0 Hz), 9.12 (1H, br. s.) | A |
| 131 | | NT | 454 [M + Na]+ 430 [M − H]− | ¹H NMR (600 MHz, DMSO-$d_6$) δ ppm 3.25 (3 H, s), 3.27-3.30 (2 H, m), 3.34-3.38 (2 H, m), 3.72-3.76 (2 H, m), 4.05 (2 H, t, J = 5.0 Hz), 4.88 (1 H, t, J = 5.5 Hz), 5.08 (1 H, d, J = 8.3 Hz), 7.06 (2 H, d, J = 8.7 Hz), 7.69 (2 H, d, J = 8.7 Hz), 7.75 (2 H, d, J = 8.3 Hz), 7.96 (2 H, d, J = 8.3 Hz), 8.15 (1 H, t, J = 5.5 Hz), 8.41 (1 H, d, J = 8.3 Hz), 9.06 (1H, br. s.), 10.85 (1 H, br. s.) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 132 | | NT | 470 [M + Na]+ 446 [M − H]− | ¹H NMR (600 MHz, DMSO-$d_6$) δ ppm 2.07 (3 H, s), 2.46-2.55 (2 H, m), 3.27-3.33 (2 H, m), 3.72-3.76 (2 H, m), 4.05 (2 H, t, J = 5.0 Hz), 4.87-4.90 (1 H, m), 5.05 (1 H, d, J = 8.3 Hz), 7.06 (2 H, d, J = 8.7 Hz), 7.69 (2 H, d, J = 8.7 Hz), 7.75 (2 H, d, J = 8.5 Hz), 7.97 (2 H, d, J = 8.5 Hz), 8.23-8.26 (1 H, m), 8.41 (1 H, d, J = 8.3 Hz), 9.02 (1 H, br. s.) | A |
| 133 | | NT | 491 [M + Na]+ 467 [M − H]− | ¹H NMR (600 MHz, DMSO-$d_6$) δ ppm 2.37 (3 H, s), 3.72-3.77 (2 H, m), 4.04-4.07 (2 H, m), 4.30 (2 H, d, J = 5.0 Hz), 4.88 (1 H, t, J = 5.5 Hz), 5.11 (1 H, d, J = 8.3 Hz), 6.12 (1 H, s), 6.39 (1 H, s), 7.06 (2H, d, J = 8.7 Hz), 7.69 (2 H, d, J = 8.7 Hz), 7.75 (2 H, d, J = 8.3 Hz), 7.98 (2 H, d, J = 8.3 Hz), 8.51 (1 H, d, J = 8.3 Hz), 8.70 (1 H, t, J = 5.5 Hz), 9.08 (1 H, br. s.) | A |
| 134 | | NT | 480 [M + Na]+ 459 [M − H]− | ¹H NMR (600 MHz, DMSO-$d_6$) δ ppm 1.47-1.56 (1 H, m), 1.73-1.90 (3 H, m), 3.15-3.21 (2 H, m), 3.57 3.64 (1 H, m), 3.70-3.78 (3 H, m), 3.83-3.89 (1 H, m), 4.05 (2 H, t, J = 5.5 Hz), 4.88 (1 H, t, J = 5.5 Hz), 5.07 (1 H, d, J = 8.3 Hz), 7.06 (2 H, d, J = 8.7 Hz), 7.67-7.71 (3 H, m), 7.75 (2 H, d, J = 8.7 Hz), 7.96 (2 H, d, J = 7.8 Hz), 8.05-8.14 (1 H, m), 8.39 (1 H, br. s.), 9.06 (1 H, br. s.) | A |
| 135 | | NT | 457 [M − H]− | ¹H NMR (600 MHz, DMSO-$d_6$) δ ppm 1.79 (3 H, s), 3.07-3.19 (4 H, m), 3.74 (2 H, t, J = 5.0 Hz), 4.05 (2 H, t, J = 5.0 Hz), 4.88 (1 H, br. s.), 5.05 (1 H, d, J = 8.3 Hz), 6.40 (1 H, br. s.), 7.06 (2 H, d, J = 8.7 Hz), 7.69 (2 H, d, J = 8.7 Hz), 7.75 (2 H, d, J = 8.7 Hz), 7.99 (2 H, d, J = 8.7 Hz), 8.14-8.19 (1 H, m), 8.45 (1 H, d, J = 8.3 Hz) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 136 | | NT | 442 [M − H]− | ¹H NMR (600 MHz, DMSO-$d_6$) δ ppm 0.84 (9H, s), 2.80-2.87 (1H, m), 3.01-3.09 (1H, m), 3.71-3.77 (2H, m), 4.05 (2H, t, J = 5.0 Hz), 4.88 (1H, t, J = 5.7 Hz), 5.11 (1H, d, J = 8.3 Hz), 7.06 (2H, d, J = 8.7 Hz), 7.69 (2H, d, J = 8.7 Hz), 7.75 (2H, d, J = 8.3 Hz), 7.91-8.00 (3H, m), 8.36 (1H, d, J = 8.3 Hz), 9.07 (1H, br. s.) | B |
| 137 | | NT | 460 [M + Na]+ 436 [M − H]− | ¹H NMR (600 MHz, DMSO-$d_6$) δ ppm 3.48-3.59 (1H, m), 3.74 (2H, t, J = 5.0 Hz), 4.05 (2H, t, J = 5.0 Hz), 4.88 (1H, br. s.), 5.01-5.19 (1H, m), 5.88-6.13 (1H, m), 6.40 (1H, br. s.), 7.06 (2H, d, J = 8.7 Hz), 7.69 (2H, d, J = 8.7 Hz), 7.72-7.78 (2H, m), 7.97 (2H, t, J = 9.2 Hz), 8.31-8.60 (2H, m) | B |
| 138 | | NT | 516 [M + Na]+ 492 [M − H]− | ¹H NMR (600 MHz, DMSO-$d_6$) δ ppm 3.42-3.54 (2 H, m), 3.71-3.78 (2 H, m), 3.98-4.07 (4 H, m), 4.88 (1 H, t, J = 5.5 Hz), 5.11 (1 H, d, J = 8.3 Hz), 6.90-6.96 (3 H, m), 7.06 (2 H, d, J = 8.7 Hz), 7.25-7.31 (2 H, m), 7.69 (2 H, d, J = 8.7 Hz), 7.75 (2 H, d, J = 8.7 Hz), 7.97 (2 H, d, J = 8.7 Hz), 8.35 (1 H, t, J = 5.5 Hz), 8.48 (1 H, d, J = 8.3 Hz), 9.06 (1 H, br. s.) | A |
| 139 | | NT | 424 [M + Na]+ 400 [M − H]− | ¹H NMR (600 MHz, DMSO-$d_6$) δ ppm 1.03 (3 H, t, J = 7.1 Hz), 3.07-3.17 (2 H, m), 3.72-3.76 (2 H, m), 4.05 (2 H, t, J = 5.0 Hz), 4.88 (1 H, t, J = 5.5 Hz), 5.03 (1 H, d, J = 8.3 Hz), 7.06 (2 H, d, J = 8.7 Hz), 7.69 (2 H, d, J = 8.7 Hz), 7.75 (2 H, d, J = 8.5 Hz), 7.96 (2 H, d, J = 8.5 Hz), 8.07-8.11 (1 H, m), 8.36 (1 H, d, J = 8.3 Hz), 9.02 (1 H, br. s.), 10.88 (1 H, br. s.) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 140 | | NT | 468 [M + H]+ 466 [M − H]− | ¹H NMR (600 MHz, DMSO-$d_6$) δ ppm 3.70-3.80 (5H, m), 4.05 (2H, t, J = 5.0 Hz), 4.19-4.30 (2H, m), 4.83-4.93 (1H, m), 5.11 (1H, d, J = 8.3 Hz), 6.07-6.15 (1H, m), 7.06 (2H, d, J = 8.7 Hz), 7.54-7.61 (1H, m), 7.65-7.71 (2H, m), 7.75 (2H, d, J = 8.7 Hz), 7.96 (2H, d, J = 8.7 Hz), 8.38-8.52 (2H, m), 9.09 (1H, br. s.) | A |
| 141 | | NT | 485 [M + H]+ 483 [M − H]− | ¹H NMR (600 MHz, DMSO-$d_6$) δ ppm 1.74-1.80 (2 H, m), 1.85-1.92 (2 H, m), 3.27-3.34 (2 H, m), 3.41 (2 H, t, J = 6.9 Hz), 3.71-3.76 (2 H, m), 3.89-3.98 (2 H, m), 4.05 (2 H, t, J = 5.0 Hz), 4.86-4.90 (1 H, m), 5.19 (1 H, d, J = 8.3 Hz), 7.06 (2 H, d, J = 8.7 Hz), 7.69 (2 H, d, J = 8.7 Hz), 7.75 (2 H, d, J = 8.7 Hz), 7.97 (2 H, d, J = 8.7 Hz), 8.23-8.27 (1 H, m), 8.55 (1 H, d, J = 8.3 Hz), 9.11 (1 H, br. s.) | A |
| 142 | | NT | 438 [M + Na]+ 414 [M − H]− | ¹H NMR (600 MHz, DMSO-$d_6$) δ ppm 0.84 (3 H, t, J = 7.6 Hz), 1.38-1.47 (2 H, m), 3.02-3.09 (2 H, m), 3.72-3.76 (2 H, m), 4.05 (2 H, t, J = 5.0 Hz), 4.88 (1 H, t, J = 5.5 Hz), 5.05 (1 H, d, J = 8.3 Hz), 7.06 (2 H, d, J = 8.7 Hz), 7.69 (2 H, d, J = 8.7 Hz), 7.75 (2 H, d, J = 8.5 Hz), 7.96 (2 H, d, J = 8.5 Hz), 8.04-8.09 (1 H, m), 8.36 (1 H, d, J = 8.3 Hz), 9.06 (1 H, br. s.), 10.84 (1 H, br. s.) | B |
| 143 | | NT | 438 [M + Na]+ 414 [M − H]− | ¹H NMR (600 MHz, DMSO-$d_6$) δ ppm 1.06 (3 H, d, J = 6.4 Hz), 1.09 (3 H, d, J = 6.4 Hz), 3.72-3.77 (2 H, m), 3.81-3.89 (1 H, m), 4.05 (2 H, t, J = 5.0 Hz), 4.88 (1 H, t, J = 5.5 Hz), 5.04 (1 H, d, J = 8.3 Hz), 7.06 (2 H, d, J = 8.7 Hz), 7.69 (2 H, d, J = 8.7 Hz), 7.75 (2 H, d, J = 8.3 Hz), 7.93 (1 H, d, J = 7.3 Hz), 7.96 (2 H, d, J = 8.3 Hz), 8.36 (1 H, d, J = 8.3 Hz) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 144 | | NT | 481 [M + Na]+ | ¹H NMR (600 MHz, DMSO-d$_6$) δ ppm 2.85 (3 H, s), 2.96 (3 H, s), 3.72-3.76 (2 H, m), 3.98-4.03 (2 H, m), 4.05 (2 H, t, J = 5.0 Hz), 4.88 (1 H, t, J = 5.5 Hz), 5.19 (1 H, d, J = 7.8 Hz), 7.06 (2 H, d, J = 8.7 Hz), 7.69 (2 H, d, J = 8.7 Hz), 7.75 (2 H, d, J = 8.3 Hz), 7.97 (2 H, d, J = 8.3 Hz), 8.21 (1 H, t, J = 5.0 Hz), 8.56 (1 H, d, J = 7.8 Hz), 9.12 (1 H, br. s.) | A |
| 145 | | NT | 473 [M + H]+ 471 [M − H]− | ¹H NMR (600 MHz, DMSO-d$_6$) δ ppm 1.91-1.97 (3 H, m), 2.76-2.97 (3 H, m), 3.18-3.38 (4 H, m), 3.71-3.77 (2 H, m), 4.05 (2 H, t, J = 5.0 Hz), 4.89 (1 H, br. s.), 5.01-5.10 (1 H, m), 7.06 (2 H, d, J = 8.7 Hz), 7.69 (2 H, d, J = 8.7 Hz), 7.75 (2 H, d, J = 8.3 Hz), 7.94-8.01 (2 H, m), 8.14-8.30 (1 H, m), 8.35-8.46 (1 H, m) | B |
| 146 | | NT | 490 [M + Na]+ 466 [M − H]− | ¹H NMR (600 MHz, DMSO-d$_6$) δ ppm 3.70-3.79 (5H, m), 4.04 (2H, t, J = 5.0 Hz), 4.37 (2H, d, J = 5.5 Hz), 4.88 (1H, t, J = 4.1 Hz), 5.11 (1H, d, J = 8.1 Hz), 6.11-6.21 (1H, m), 7.05 (2H, d, J = 8.7 Hz), 7.24-7.32 (1H, m), 7.69 (2H, d, J = 8.7 Hz), 7.75 (2H, d, J = 8.3 Hz), 7.97 (2H, d, J = 8.3 Hz), 8.49 (1H, d, J = 8.1 Hz), 8.59 (1H, t, J = 5.5 Hz) | A |
| 147 | | NT | 490 [M + Na]+ 466 [M − H]− | ¹H NMR (600 MHz, DMSO-d$_6$) δ ppm 3.69-3.81 (5H, m), 4.04 (2H, t, J = 5.0 Hz), 4.09-4.18 (2H, m), 4.88 (1H, br. s.), 5.07 (1H, d, J = 8.3 Hz), 7.06 (2H, d, J = 9.2 Hz), 7.31 (1H, s), 7.54 (1H, s), 7.69 (2H, d, J = 9.2 Hz), 7.75 (2H, d, J = 8.3 Hz), 7.96 (2H, d, J = 8.3 Hz), 8.34-8.45 (2H, m) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 148 | | NT | 412 [M + Na]+ 388 [M − H]− | $^1$H NMR (600 MHz, DMSO-d$_6$) δ ppm 3.74 (2 H, t, J = 5.0 Hz), 4.05 (2 H, t, J = 5.0 Hz), 5.05 (1 H, d, J = 8.3 Hz), 7.06 (2 H, d, J = 8.7 Hz), 7.69 (2 H, d, J = 8.7 Hz), 7.74 (2 H, d, J = 8.3 Hz), 7.96 (2 H, d, J = 8.3 Hz), 8.34 (1 H, d, J = 8.3 Hz) | B |
| 149 | | NT | 522 [M + H]+ 520 [M − H]− | $^1$H NMR (600 MHz, DMSO-d$_6$) δ ppm 3.31-3.41 (1 H, m), 3.45-3.53 (1 H, m), 3.71-3.77 (2 H, m), 3.89-3.95 (1 H, m), 4.05 (2 H, t, J = 5.0 Hz), 4.19-4.25 (1 H, m), 4.26-4.33 (1 H, m), 4.88 (1 H, t, J = 5.5 Hz), 5.09-5.12 (1 H, m), 6.79-6.84 (2 H, m), 6.84-6.88 (2 H, m), 7.06 (2 H, d, J = 8.7 Hz), 7.69 (2 H, d, J = 8.7 Hz), 7.73-7.77 (2 H, m), 7.95-8.00 (2 H, m), 8.38-8.45 (1 H, m), 8.52-8.59 (1 H, m) | A |
| 150 | | NT | 479 [M + H]+ 477 [M − H]− | $^1$H NMR (600 MHz, DMSO-d$_6$) δ ppm 2.43 (3 H, s), 3.72-3.76 (2 H, m), 4.04 (2 H, t, J = 5.0 Hz), 4.32-4.42 (2 H, m), 4.88 (1 H, t, J = 5.5 Hz), 5.17 (1 H, d, J = 8.3 Hz), 7.06 (2 H, d, J = 9.2 Hz), 7.10-7.15 (2 H, m), 7.63 (1 H, t, J = 7.6 Hz), 7.69 (2 H, d, J = 9.2 Hz), 7.75 (2 H, d, J = 8.5 Hz), 8.00 (2 H, d, J = 8.5 Hz), 8.55 (1 H, d, J = 8.3 Hz), 8.72 (1 H, t, J = 6.0 Hz), 9.14 (1 H, br. s.) | A |
| 151 | | NT | 479 [M + H]+ 477 [M − H]− | $^1$H NMR (600 MHz, DMSO-d$_6$) δ ppm 2.89 (2 H, t, J = 7.3 Hz), 3.41-3.51 (2 H, m), 3.71-3.77 (2H, m), 4.05 (2 H, t, J = 5.0 Hz), 4.88 (1 H, t, J = 5.3 Hz), 5.06 (1 H, d, J = 8.3 Hz), 7.06 (2 H, d, J = 8.7 Hz), 7.17-7.22 (1 H, m), 7.25 (1 H, d, J = 7.8 Hz), 7.64-7.68 (1 H, m), 7.70 (2 H, d, J = 8.7 Hz), 7.75 (2 H, d, J = 8.5 Hz), 7.97 (2 H, d, J = 8.5 Hz), 8.24 (1 H, t, J = 5.7 Hz), 8.42 (1 H, d, J = 8.3 Hz), 8.44-8.47 (1 H, m), 9.09 (1 H, br. s.) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 152 | | NT | 558 [M + Na]+ | ¹H NMR (600 MHz, DMSO-$d_6$) δ ppm 3.72-3.76 (2 H, m), 4.04 (2 H, t, J = 5.0 Hz), 4.22-4.34 (2 H, m), 4.58 (2 H, s), 4.88 (1 H, br. s.), 5.07-5.11 (1 H, m), 6.89-6.93 (1 H, m), 7.05 (2 H, d, J = 8.7 Hz), 7.27-7.30 (1 H, m), 7.69 (2 H, d, J = 8.7 Hz), 7.75 (2 H, d, J = 8.5 Hz), 7.97 (2 H, d, J = 8.5 Hz), 8.41-8.46 (1 H, m), 8.68 (1 H, t, J = 5.7 Hz) | A |
| 154 | | NT | 426 [M − H]− | ¹H NMR (600MHz, CHLOROFORM-d) δ ppm 0.44-0.66 (4 H, m), 2.89 (3 H, s), 3.07-3.13 (1 H, m), 3.98-4.03 (2 H, m), 4.15 (2 H, d, J = 4.1 Hz), 5.19 (1 H, s), 7.02 (2 H, d, J = 8.7 Hz), 7.36-7.41 (1 H, m), 7.56-7.60 (2 H, m), 7.62 (2 H, d, J = 8.7 Hz), 7.74 (2 H, d, J = 8.7 Hz), 10.92 (1 H, br. s.) | B |
| 155 | | NT | 486 [M + H]+ 484 [M − H]− | ¹H NMR (600 MHz, DMSO-$d_6$) δ ppm 3.39-3.49 (1H, m), 3.74 (2H, br. s.), 4.05 (2H, t, J = 4.8 Hz), 4.60-4.68 (1H, m), 4.88 (1H, br. s.), [5.06], 5.14 (1H, d, J = 8.3 Hz), 7.06 (2H, d, J = 8.7 Hz), 7.69 (2H, d, J = 8.7 Hz), 7.75 (2H, d, J = 8.3 Hz), 7.93-8.03 (2H, m), 8.33-8.59 (1H, m), 9.03 (1H, t, J = 6.0 Hz) | A |
| 156 | | NT | 468 [M + H]+ 466 [M − H]− | ¹H NMR (600 MHz, DMSO-$d_6$) δ ppm 3.58 (3 H, s), 3.72-3.76 (2H, m), 4.05 (2 H, t, J = 5.0 Hz), 4.37-4.40 (2H, m), 4.87 (1 H, t, J = 5.3 Hz), 5.14 (1 H, d, J = 8.3 Hz), 6.78 (1 H, s), 7.05 (2 H, d, J = 8.7 Hz), 7.09 (1 H, s), 7.68 (2 H, d, J = 8.7 Hz), 7.74 (2 H, d, J = 8.3 Hz), 7.96 (2 H, d, J = 8.3 Hz), 8.49 (1 H, d, J = 8.3 Hz), 8.62 (1 H, t, J = 5.5 Hz), 9.07 (1 H, br. s.), 11.13 (1 H, br. s.) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 157 | | NT | 455 [M + H]+ 453 [M − H]− | $^1$H NMR (600 MHz, DMSO-$d_6$) δ ppm 3.71-3.77 (2 H, m), 4.05 (2 H, t, J = 4.8 Hz), 4.22 (2 H, d, J = 5.5 Hz), 4.87 (1 H, t, J = 5.5 Hz), 5.11 (1 H, d, J = 8.3 Hz), 7.06 (2 H, d, J = 8.7 Hz), 7.69 (2 H, d, J = 8.7 Hz), 7.75 (2 H, d, J = 8.3 Hz), 7.89 (1 H, s), 7.98 (2 H, d, J = 8.3 Hz), 8.32 (1 H, s), 8.50 (1 H, d, J = 8.3 Hz), 8.56 (1 H, t, J = 5.5 Hz), 9.11 (1 H, br. s.) | A |
| 158 | | NT | 468 [M + H]+ 466 [M − H]− | $^1$H NMR (600 MHz, DMSO-$d_6$) δ ppm 3.59 (3 H, s), 3.72-3.76 (2 H, m), 4.05 (2 H, t, J = 5.0 Hz), 4.16 (2 H, d, J = 5.5 Hz), 4.87 (1 H, t, J = 5.4 Hz), 5.10 (1 H, d, J = 8.3 Hz), 6.94 (1 H, s), 7.06 (2 H, d, J = 8.7 Hz), 7.49 (1 H, s), 7.68 (2 H, d, J = 8.7 Hz), 7.75 (2 H, d, J = 8.7 Hz), 7.96 (2 H, d, J = 8.7 Hz), 8.34 (1 H, t, J = 5.5 Hz), 8.40 (1 H, d, J = 8.3 Hz), 9.05 (1 H, br. s.) | A |
| 159 | | NT | 378 [M + Na]+ 354 [M − H]− | $^1$H NMR (600 MHz, CHLOROFORM-d) δ ppm 1.10-1.22 (3 H, m), 2.89 (3 H, br. s.), 3.45-3.66 (2 H, m), 5.02 (1 H, br. s.), 7.37-7.42 (1 H, m), 7.42-7.50 (2 H, m), 7.55-7.72 (6 H, m) | B |
| 160 | | NT | 563 [M + H]+ 561 [M − H]− | $^1$H NMR (600 MHz, DMSO-$d_6$) δ ppm 1.79-1.85 (1 H, m), 1.97-2.05 (1 H, m), 2.68-2.77 (2 H, m), 3.08-3.20 (3 H, m), 3.41-3.55 (3 H, m), 3.71-3.79 (3 H, m), 4.05 (2 H, t, J = 5.0 Hz), 4.88 (1 H, t, J = 5.7 Hz), 5.03-5.08 (1 H, m), 7.06 (2 H, d, J = 8.7 Hz), 7.21-7.34 (5 H, m), 7.69 (2 H, d, J = 8.7 Hz), 7.75 (2 H, dd, J = 8.3, 1.4 Hz), 7.92-8.00 (2 H, m), 8.13-8.18 (1 H, m), 8.39 (1 H, br. s.) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 161 | | NT | 419 [M + H]+ 417 [M − H]− | $^1$H NMR (600 MHz, CHLOROFORM-d) δ ppm 3.17 (3 H, br. s.), 4.53-4.73 (2 H, m), 5.60 (1 H, br. s.), 7.21-7.27 (2 H, m), 7.36-7.41 (1 H, m), 7.44-7.49 (2 H, m), 7.55-7.63 (6 H, m), 7.70 (1 H, t, J = 7.3 Hz), 8.33 (1 H, br. s.), 8.58 (1 H, d, J = 4.1 Hz) | B |
| 162 | | NT | 473 [M + H]+ 471 [M − H]− | $^1$H NMR (600 MHz, DMSO-$d_6$) δ ppm 2.27-2.33 (2 H, m), 2.56-2.60 (1 H, m), 2.71-2.78 (1 H, m), 3.08-3.12 (2 H, m), 3.35-3.42 (2 H, m), 3.70 (1 H, d, J = 11.0 Hz), 3.72-3.77 (2 H, m), 4.02-4.07 (2 H, m), 4.88 (1 H, t, J = 5.5 Hz), 5.08 (1 H, d, J = 8.7 Hz), 7.06 (2 H, d, J = 8.7 Hz), 7.69 (2 H, d, J = 8.7 Hz), 7.75 (2 H, d, J = 8.3 Hz), 7.96 (2 H, d, J = 8.3 Hz), 8.08-8.15 (1 H, m), 8.41 (1 H, br. s.), 9.08 (1 H, br. s.) | B |
| 163 | | NT | 404 [M + Na]+ 380 [M − H]− | $^1$H NMR (600 MHz, CHLOROFORM-d) δ ppm 1.47-1.72 (2 H, m), 2.02-2.18 (4 H, m), 2.89 (3 H, d, J = 4.6 Hz), 4.42-4.50 (1 H, m), 4.86 (1 H, br. s.), 6.97 (1 H, br. s.), 7.37-7.41 (1 H, m), 7.47 (2 H, t, J = 7.8 Hz), 7.61 (4 H, d, J = 7.8 Hz), 7.65-7.69 (2 H, m), 10.61 (1 H, br. s.) | B |
| 164 | | NT | 364 [M + Na]+ 340 [M − H]− | $^1$H NMR (600 MHz, DMSO-$d_6$) δ ppm 1.66 (3 H, s), 2.63 (3 H, d, J = 4.6 Hz), 7.40-7.44 (1 H, m), 7.48-7.54 (2 H, m), 7.75 (2 H, d, J = 8.7 Hz), 7.80 (2 H, d, J = 8.3 Hz), 7.96 (2 H, d, J = 8.3 Hz), 8.16 (1 H, br. s.), 8.90 (1 H, br. s.), 10.89 (1 H, br. s.) | C |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 165 | | NT | 422 [M + Na]+ 398 [M − H]− | ¹H NMR (600 MHz, DMSO-$d_6$) δ ppm 1.71-1.79 (2 H, m), 2.62-2.70 (5 H, m), 2.98 (3 H, s), 3.41-3.47 (2 H, m), 4.48 (1 H, t, J = 5.0 Hz), 5.38, [4.69] (1 H, br. s.), 7.31 (2 H, d, J = 7.8 Hz), 7.38-7.59 (2 H, m), 7.63 (2 H, d, J = 7.8 Hz), 7.69-7.77 (2 H, m), 8.14 (1 H, br. s.), 9.04 (1 H, br. s.), 10.86 (1 H, br. s.) | A |
| 166 | | NT | 408 [M + Na]+ | ¹H NMR (600 MHz, CHLOROFORM-d) δ ppm 2.84 (3 H, br. s), 3.40-3.56 (5 H, m), 3.71-4.13 (2 H, m), [4.65], 5.18 (1 H, br. s.), 7.36-7.41 (1 H, m), 7.44-7.49 (2 H, m), 7.51-7.69 (6 H, m), 7.89 (1 H, br. s.), 8.23 (1 H, br. s.) | B |
| 167 | | NT | 465 [M + H]+ 463 [M − H]− | ¹H NMR (600 MHz, DMSO-$d_6$ + $D_2O$) δ ppm 2.31-2.38 (4 H, m), 2.66 (3 H, br. s.), 2.94 (3 H, br. s.), 3.50 (2 H, s), 3.56-3.61 (4 H, m), 7.38 (2 H, d, J = 8.3 Hz), 7.47-7.66 (6 H, m) | A |
| 168 | | NT | 479 [M + H]+ 477 [M − H]− | ¹H NMR (600 MHz, CHLOROFORM-d) δ ppm 1.90-1.99 (2 H, m), 2.65-2.81 (4 H, m), 2.90 (3 H, d, J = 5.0 Hz), 3.01 (3 H, s), 3.68-3.78 (4 H, m), 3.81-3.86 (2 H, m), 5.58 (1 H, br. s.), 7.38 (2 H, d, J = 7.3 Hz), 7.50 (2 H, d, J = 7.8 Hz), 7.53-7.63 (4 H, m) | A |
| 169 | | NT | 343 [M + H]+ 341 [M − H]− | ¹H NMR (600 MHz, DMSO-$d_6$) δ ppm 2.67 (3H, br. s.), 2.97 (3H, br. s.), 5.39 (1H, br. s.), 7.44-7.67 (2H, m), 7.70-7.82 (2H, m), 7.83-7.98 (2H, m), 8.17 (1H, br. s.), 8.59-8.74 (2H, m), 9.06 (1H, br. s.) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 170 | | NT | 420 [M + H]+ 418 [M − H]− | ¹H NMR (600 MHz, DMSO-$d_6$ + $D_2O$) δ ppm 3.06 (3 H, s), 4.59 (2 H, s), 7.38-7.46 (2 H, m), 7.50 (2 H, t, J = 7.8 Hz), 7.52-7.62 (2 H, m), 7.70-7.81 (4 H, m), 8.80 (2 H, d, J = 5.0 Hz) | C |
| 171 | | NT | 392 [M + Na]+ 368 [M − H]− | ¹H NMR (600 MHz, DMSO-$d_6$) δ ppm 0.80-0.93 (3 H, m), 1.46 (2 H, d, J = 6.4 Hz), 2.99 (3 H, s), 3.05-3.16 (2 H, m), [4.68], 5.37 (1 H, br. s.), 7.35-7.61 (5 H, m), 7.66-7.80 (4 H, m), 8.23 (1 H, br. s.), 9.04 (1 H, br. s.), 10.85 (1 H, br. s.) | C |
| 173 | | NT | 435 [M + Na]+ 411 [M − H]− | ¹H NMR (600 MHz, DMSO-$d_6$) δ ppm 2.87 (3 H, br. s.), 2.99 (3 H, br. s.), 3.02 (3 H, br. s.), 3.85-4.16 (2 H, m), 5.60 (1 H, br. s.), 7.38-7.43 (1 H, m), 7.44-7.58 (4 H, m), 7.68-7.80 (4 H, m), 8.64 (1 H, br. s.), 9.14 (1 H, br. s.), 11.27 (1 H, br. s.) | C |
| 174 | | NT | 414 [M + Na]+ 390 [M − H]− | ¹H NMR (600 MHz, DMSO-$d_6$) δ ppm 2.61 (3 H, br. s), 3.75-4.08 (2 H, m), 4.73, [5.19] (1 H, br. s), 6.05-6.34 (1 H, m), 7.36-7.56 (5 H, m), 7.69-7.87 (4 H, m), 8.06-8.45 (1 H, m), 9.05 (1 H, br. s.), 10.88-11.34 (1 H, m) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 175 | | NT | 390 [M + Na]+ 366 [M − H]− | ¹H NMR (600 MHz, DMSO-$d_6$) δ ppm 0.40-0.55 (2 H, m), 0.58-0.74 (2 H, m), 2.64-2.75 (1 H, m), 3.01 (3 H, br. s.), [4.63], 5.31 (1 H, s), 7.37-7.61 (5 H, m), 7.65-7.84 (4 H, m), 8.33 (1 H, br. s.), 9.03 (1 H, br. s.), 10.81 (1 H, br. s.) | C |
| 176 | | NT | 429 [M + H]+ 427 [M − H]− | ¹H NMR (600 MHz, DMSO-$d_6$) δ ppm 2.64 (3 H, br. s.), 2.69-2.76 (2 H, m), 2.79-2.86 (2 H, m), 2.92 (3 H, s), 3.02-3.07 (2 H, m), 3.50-3.55 (2 H, m), 4.61-4.65 (1 H, m), 5.24 (1 H, t, J = 6.0 Hz), 5.34 (1 H, br. s.), 6.49 (2 H, d, J = 8.3 Hz), 6.90-6.95 (2 H, m), 7.23-7.29 (2 H, m), 7.34-7.39 (2 H, m), 8.12 (1 H, br. s.), 8.99 (1 H, s), 10.84 (1 H, s) | A |
| 177 | | NT | 419 [M + H]+ 417 [M − H]− | ¹H NMR (600 MHz, DMSO-$d_6$) δ ppm 3.00 (3 H, s), 4.30-4.50 (2 H, m), [4.75], 5.45 (1 H, br. s.), 7.34-7.44 (3 H, m), 7.50 (2 H, t, J = 7.8 Hz), 7.58 (1 H, d, J = 6.9 Hz), 7.64-7.81 (5 H, m), 8.46 (1 H, d, J = 4.6 Hz), 8.50-8.58 (1 H, m), 8.83 (1 H, br. s.), 9.10 (1 H, br. s.), 10.97 (1 H, br. s.) | B |
| 178 | | NT | 419 [M + H]+ 417 [M − H]− | ¹H NMR (600 MHz, DMSO-$d_6$) δ ppm 3.02 (3 H, s), 4.31-4.50 (2 H, m), [4.80], 5.48 (1 H, br. s.), 7.25-7.43 (4 H, m), 7.50 (2 H, t, J = 7.8 Hz), 7.56-7.61 (1 H, m), 7.67-7.80 (4 H, m), 8.51 (2 H, d, J = 5.5 Hz), 8.86 (1 H, br. s.) | C |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 179 | | NT | 423 [M + Na]+ 399 [M − H]− | $^1$H NMR (600 MHz, DMSO-$d_6$) δ ppm 2.62-2.70 (3H, m), 2.98 (3H, s), 3.14 (2H, q, J = 6.0 Hz), 3.57 (2H, q, J = 6.0 Hz), 4.70 (1H, t, J = 5.6 Hz), 5.79 (1H, t, J = 5.6 Hz), 6.68 (2H, d, J = 8.7 Hz), 7.23-7.72 (7H, m), 8.12 (1H, br. s.), 9.02 (1H, br. s.), 10.82 (1H, br. s.) | A |
| 180 | | NT | 452 [M + Na]+ 428 [M − H]− | $^1$H NMR (600 MHz, DMSO-$d_6$) δ ppm 1.53-1.63 (2H, m), 1.71-1.82 (2H, m), 2.66 (3H, br. s.), 2.98 (3H, s), 3.40-3.52 (2H, m), 4.03 (2H, t, J = 6.6 Hz), 4.45 (1H, t, J = 5.0 Hz), 5.37, [5.84] (1H, br. s.), 6.93-7.12 (2H, m), 7.30-7.79 (6H, m), 8.00-8.30 (1H, m), 9.04 (1H, br. s.) | A |
| 181 | | NT | 444 [M − H]− | $^1$H NMR (600 MHz, DMSO-$d_6$) δ ppm 1.61-1.71 (1H, m), 1.89-2.01 (1H, m), 2.66 (3H, br. s.), 2.98 (3H, br. s.), 3.32-3.40 (2H, m), 3.65 (1H, br. s.), 4.06-4.22 (2H, m), 4.49-4.73 (2H, m), 6.96-7.09 (2H, m), 7.31-7.77 (6H, m), 8.17 (1H, br. s.), 9.00 (1H, br. s.), 10.80 (1H, br. s.) | A |
| 182 | | NT | 406 [M + Na]+ 382 [M − H]− | $^1$H NMR (600 MHz, DMSO-$d_6$) δ ppm 0.92 (3 H, t, J = 7.3 Hz), 1.56-1.70 (2 H, m), 2.58-2.63 (2 H, m), 2.66 (3 H, br. s.), 2.98 (3 H, s), 5.38 (1 H, br. s.), 7.31 (2 H, d, J = 8.3 Hz), 7.34-7.80 (6 H, m), 8.02-8.27 (1 H, m), 9.05 (1 H, br. s.), 10.86 (1 H, br. s.) | A |
| 183 | | NT | 447 [M + Na]+ 423 [M − H]− | $^1$H NMR (600 MHz, DMSO-$d_6$) δ ppm 2.67 (3 H, br. s), 2.93 (3 H, br. s.), 3.13 (2 H, q, J = 5.7 Hz), 3.55 (2 H, q, J = 5.7 Hz), 4.71 (1 H, t, J = 5.7 Hz), 5.35 (1 H, s), 6.09-6.15 (1 H, m), 6.60 (2 H, d, J = 8.7 Hz), 7.27 (2 H, d, J = 8.7 Hz), 7.41-7.56 (4 H, m) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 184 | | NT | 404 [M + Na]+<br>380 [M − H]− | ¹H NMR (600 MHz, DMSO-d₆) δ ppm 2.67 (3 H, br. s.), 2.99 (3 H, s), 4.71 (1 H, br. s.), 5.39 (1 H, br. s.), 7.03 (1 H, d, J = 2.3 Hz), 7.40-7.48 (1 H, m), 7.58 (1 H, d, J = 6.4 Hz), 7.62-7.72 (2 H, m), 7.79 (2 H, d, J = 7.3 Hz), 7.99 (1 H, s), 8.05 (1 H, d, J = 2.3 Hz), 8.15 (1 H, br. s.), 9.04 (1 H, br. s.), 10.87 (1 H, br. s.) | A |
| 185 | | NT | 438 [M + Na]+<br>414 [M − H]− | ¹H NMR (600 MHz, DMSO-d₆) δ ppm 1.70-1.79 (2 H, m), 2.62-2.71 (5 H, m), 2.94 (3 H, br. s.), 3.43 (2 H, t, J = 6.4 Hz), 4.47 (1 H, br. s.), 4.64-4.69 (1 H, m), 5.48 (1 H, br. s.), 7.05-7.19 (2 H, m), 7.24-7.33 (3 H, m), 7.53 (2 H, d, J = 7.8 Hz), 8.00 (1 H, br. s.), 9.04 (1 H, br. s.) | C |
| 186 | | NT | 350 [M + Na]+<br>326 [M − H]− | ¹H NMR (600 MHz, DMSO-d₆) δ ppm 3.00 (3 H, s), [4.68], 5.36 (1 H, br. s.), 7.40 (1 H, t, J = 7.3 Hz), 7.43-7.78 (10 H, m), 9.04 (1 H, br. s.) | B |
| 187 | | NT | 436 [M + Na]+<br>412 [M − H]− | ¹H NMR (600 MHz, DMSO-d6) δ ppm 2.67 (3 H, br. s.), 2.98 (3 H, s), 3.93-4.12 (4 H, m), [4.67], 5.38 (1 H, br. s.), 5.79 (1 H, s), 7.45 (1 H, br. s.), 7.50-7.63 (4 H, m), 7.68-7.82 (4 H, m), 8.16 (1 H, br. s.), 9.04 (1 H, br. s.) | A |
| 189 | | NT | 406 [M + Na]+<br>382 [M − H]− | ¹H NMR (600 MHz, DMSO-d₆ + D₂O) δ ppm 2.68 (3 H, s), 2.98 (3 H, s), 5.40 (1 H, s), 7.46-7.69 (2 H, m), 7.98 (2 H, d, J = 7.8 Hz), 8.05 (1 H, d, J = 8.7 Hz), 8.19 (1 H, d, J = 8.7 Hz), 8.36-8.42 (1 H, m) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 190 | | NT | 343 [M + H]+ 341 [M − H]− | $^1$H NMR (600 MHz, DMSO-$d_6$) δ ppm 2.67 (3 H, br. s.), 3.02 (3 H, s), [4.69], 5.39 (1 H, br. s.), 7.45-7.56 (3 H, m), 7.78-8.26 (5 H, m), 8.77 (1 H, br. s.), 9.07 (1 H, br. s.), 10.89 (1 H, br. s.) | C |
| 191 | | NT | 414 [M − Na]− | $^1$H NMR (600 MHz, DMSO-$d_6$) δ ppm 2.66 (3H, br. s.), 2.98 (3H, s), 3.32 (3H, s), 3.62-3.75 (2H, m), 4.06-4.22 (2H, m), 5.37 (1H, br. s.), 7.05 (2H, d, J = 8.7 Hz), 7.29-7.78 (6H, m), 8.01-8.29 (1H, m), 9.04 (1H, br. s.), 10.85 (1H, br. s.) | A |
| 192 | | NT | 393 [M + H]+ 391 [M − H]− | $^1$H NMR (600 MHz, DMSO-$d_6$) δ ppm 2.68 (3 H, br. s.), 3.00 (3 H, s), [4.71], 5.40 (1 H, br. s.), 7.49-7.70 (3 H, m), 7.77-7.83 (1 H, m), 7.95-8.20 (5 H, m), 8.73 (1 H, br. s.), 9.07 (1 H, br. s.), 9.31 (1 H, s), 10.89 (1H, br. s.) | B |
| 193 | | NT | 396 [M + Na]+ 372 [M − H]− | $^1$H NMR (600 MHz, DMSO-$d_6$ + $D_2O$) δ ppm 2.65 (3 H, br. s), 3.65-3.92 (2 H, m), 4.36-4.68 (2 H, m), 7.35-7.59 (5 H, m), 7.72 (2 H, d, J = 7.3 Hz), 7.76 (2 H, d, J = 8.3 Hz) | A |
| 194 | | NT | 399 [M + H]+ 397 [M − H]− | $^1$H NMR (600 MHz, DMSO-$d_6$ + $D_2O$) δ ppm 2.17 (6 H, s), 2.66 (3 H, br. s.), 2.98 (3 H, s), 3.43 (2 H, s), 7.40 (2 H, d, J = 7.8 Hz), 7.57 (2 H, d, J = 7.3 Hz), 7.68 (2 H, d, J = 7.8 Hz), 7.76 (2 H, d, J = 7.3 Hz) | C |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 195 | | NT | 407 [M + Na]+ 483 [M − H]− | ¹H NMR (600 MHz, DMSO-$d_6$) δ ppm 2.67 (3 H, br. s.), 2.98 (3 H, s), [4.68], 5.38 (1 H, br. s.), 7.44 (1 H, br. s.), 7.55-7.60 (2 H, m), 7.70 (2 H, d, J = 8.3 Hz), 7.73-7.84 (4 H, m), 8.16 (1 H, br. s.), 8.20 (1 H, br. s.), 9.04 (1 H, br. s.), 11.31 (1 H, s) | A |
| 196 | | NT | 418 [M + Na]+ 394 [M − H]− | ¹H NMR (600 MHz, DMSO-$d_6$ + $D_2O$) δ ppm 2.67 (3 H, s), 3.00 (3 H, s), 4.08 (3 H, s), 5.39 (1 H, s), 7.33-7.50 (1 H, m), 7.58 (1 H, m, J = 6.9 Hz), 7.71-7.86 (4 H, m), 8.05-8.16 (2 H, m) | A |
| 197 | | NT | 418 [M + Na]+ 394 [M − H]− | ¹H NMR (600 MHz, DMSO-$d_6$ + $D_2O$) δ ppm 2.67 (3 H, s), 2.99 (3 H, s), 4.19 (3 H, s), 5.38 (1 H, s), 7.35-7.48 (1 H, m), 7.52-7.63 (2 H, m), 7.69 (1 H, d, J = 9.2 Hz), 7.73-7.83 (2 H, m), 8.00-8.07 (1 H, m), 8.41 (1 H, s) | B |
| 198 | | NT | 511 [M + H]+ 509 [M − H]− | ¹H NMR (600 MHz, DMSO-$d_6$) δ ppm 1.87-1.94 (2 H, m), 2.33-2.40 (4 H, m), 2.44 (2 H, t, J = 7.1 Hz), 2.67 (3 H, d, J = 4.6 Hz), 2.90-2.98 (1 H, m), 3.54-3.60 (4 H, m), 4.03-4.09 (2 H, m), 4.92 (1 H, br. s.), 7.03 (2 H, d, J = 8.7 Hz), 7.59-7.71 (6 H, m) | A |
| 199 | | NT | 397 [M − H]− | ¹H NMR (600 MHz, DMSO-$d_6$) δ ppm 2.67 (3H, br. s.), 3.00 (3H, s), 5.39 (1H, br. s.), 7.38-7.67 (2H, m), 7.80-7.97 (3H, m), 8.09-8.27 (2H, m), 8.49-8.65 (1H, m), 9.06 (1H, br. s.), 9.44 (1H, s), 10.85 (1H, br. s.) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 200 | | NT | 415 [M + Na]+ 391 [M − H]− | ¹H NMR (600 MHz, DMSO-$d_6$) δ ppm 2.68 (3H, br. s.), 3.00 (3H, s), 5.40 (1H, br. s.), 7.42-7.69 (3H, m), 7.87-8.00 (2H, m), 8.05-8.30 (3H, m), 8.37 (1H, s), 8.46 (1H, d, J = 8.3 Hz), 8.89-8.96 (1H, m), 9.06 (1H, br. s.), 10.86 (1H, br. s.) | A |
| 201 | | NT | 403 [M + Na]+ 379 [M − H]− | ¹H NMR (600 MHz, DMSO-$d_6$) δ ppm 2.67 (3 H, br. s.), 3.00 (3 H, br. s.), [4.74], 5.38 (1 H, br. s.), 6.50 (1 H, br. s.), 7.36-7.51 (3 H, m), 7.55 (2 H, d, J = 6.0 Hz), 7.76 (2 H, d, J = 6.0 Hz), 7.88 (1 H, s), 8.15 (1 H, br. s.), 9.04 (1 H, br. s.), 10.88 (1 H, br. s.), 11.18 (1 H, br. s.) | A |
| 202 | | NT | 423 [M + H]+ 421 [M − H]− | ¹H NMR (600 MHz, DMSO-$d_6$) δ ppm 2.15 (6 H, s), 2.66 (3 H, br. s.), 2.94 (3 H, s), 3.41 (2 H, s), [4.55], 5.36 (1 H, br. s.), 7.35 (2 H, d, J = 7.8 Hz), 7.38-7.66 (6 H, m), 8.18 (1 H, br. s.) | B |
| 203 | | NT | 417 [M + Na]+ 393 [M − H]− | ¹H NMR (600 MHz, DMSO-$d_6$) δ ppm 2.40 (3H, s), 2.60-2.72 (3H, m), 3.00 (3H, s), [4.74], 5.38 (1H, br. s.), 6.19 (1H, s), 7.24-7.62 (4H, m), 7.64-7.82 (3H, m), 8.02-8.26 (1H, m), 8.95-9.13 (1H, m), 10.86 (1H, br. s.), 11.00 (1H, s) | A |
| 204 | | NT | 433 [M + Na]+ 457 [M − H]− | ¹H NMR (600 MHz, DMSO-$d_6$) δ ppm 2.66 (3 H, br. s.), 2.81-2.91 (2 H, m), 2.98 (3 H, s), 3.80 (2 H, s), [4.69], 5.38 (1 H, s), 5.91-6.14 (1 H, m), 7.44 (2 H, d, J = 7.8 Hz), 7.56 (2 H, d, J = 7.8 Hz), 7.68 (2 H, d, J = 7.8 Hz), 7.76 (2 H, d, J = 7.8 Hz), 8.15 (1 H, br. s.), 9.04 (1 H, br. s.), 10.86 (1 H, br. s.) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 205 | | NT | 411 [M + H]+ 409 [M − H]− | ¹H NMR (600 MHz, DMSO-$d_6$) δ ppm 0.23-0.29 (2 H, m), 0.33-0.39 (2 H, m), 2.02-2.10 (1 H, m), 2.66 (3 H, br. s.), 2.98 (3 H, s), 3.76 (2 H, s), [4.69], 5.38 (1 H, br. s.), 7.43 (2 H, d, J = 8.3 Hz), 7.52-7.59 (2 H, m), 7.65 (2 H, d, J = 7.8 Hz), 7.75 (2 H, d, J = 7.8 Hz), 8.14 (1 H, br. s.), 9.05 (1 H, br. s.) | B |
| 206 | | NT | 479 [M + H]+ 477 [M − H]− | ¹H NMR (600 MHz, DMSO-$d_6$) δ ppm 2.40-2.54 (6 H, m), 2.66 (3 H, br. s.), 2.78 (2 H, t, J = 7.6 Hz), 2.94 (3 H, br. s.), 3.57 (4 H, t, J = 4.6 Hz), [4.56], 5.36 (1 H, br. s.), 7.31 (2 H, d, J = 8.3 Hz), 7.36-7.65 (6 H, m), 8.17 (1 H, br. s.), 9.03 (1 H, br. s.), 10.88 (1 H, br. s.) | A |
| 207 | | NT | 493 [M + H]+ 491 [M − H]− | ¹H NMR (600 MHz, DMSO-$d_6$) δ ppm 1.76-1.81 (2 H, m), 2.60-2.79 (11 H, m), 2.94 (3 H, br. s.), 3.57-3.61 (2 H, m), 3.66 (2 H, t, J = 6.0 Hz), [4.56], 5.36 (1 H, br. s.), 7.30 (2 H, d, J = 8.3 Hz), 7.35-7.65 (6 H, m), 8.17 (1 H, br. s.), 9.03 (1 H, br. s.), 10.87 (1 H, br. s.) | A |
| 208 | | NT | 503 [M + H]+ 501 [M − H]− | ¹H NMR (600 MHz, DMSO-$d_6$) δ ppm 1.84-1.99 (2H, m), 2.32-2.41 (4H, m), 2.44 (2H, t, J = 7.1 Hz), 2.66 (3H, br. s.), 2.97 (3H, s), 3.57 (4H, t, J = 4.6 Hz), 4.15 (2H, t, J = 6.4 Hz), [4.67], 5.37 (1H, br. s.), 7.23-7.31 (1H, m), 7.33-7.57 (3H, m), 7.59-7.67 (1H, m), 7.68-7.81 (2H, m), 8.01-8.31 (1H, m), 9.05 (1H, br. s.), 10.86 (1H, br. s.) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 209 | 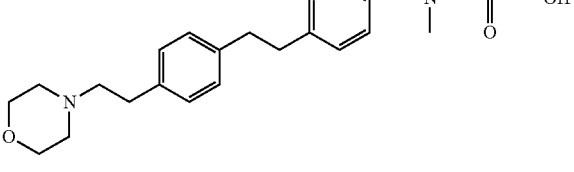 | NT | 483 [M + H]+ 481 [M − H]− | ¹H NMR (600 MHz, DMSO-$d_6$) δ ppm 2.35-2.54 (6 H, m), 2.62-2.71 (5 H, m), 2.81-2.91 (4 H, m), 2.93 (3 H, s), 3.57 (4 H, t, J = 4.6 Hz), [4.62], 5.34 (1 H, br. s.), 7.09-7.16 (4 H, m), 7.23-7.33 (2 H, m), 7.34-7.42 (2 H, m), 8.11 (1 H, br. s.), 9.02 (1 H, br. s.), 10.84 (1 H, br. s.) | A |
| 210 | 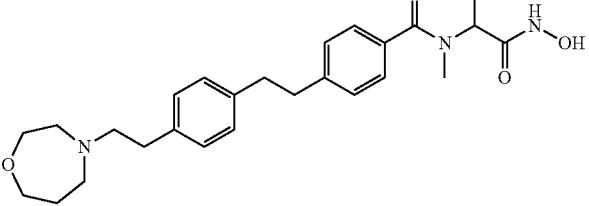 | NT | 497 [M + H]+ 495 [M − H]− | ¹H NMR (600 MHz, DMSO-$d_6$) δ ppm 1.75-1.81 (2 H, m), 2.63-2.71 (11 H, m), 2.87 (4 H, d, J = 11.9 Hz), 2.92 (3 H, s), 3.57-3.61 (2 H, m), 3.66 (2 H, t, J = 6.0 Hz), [4.60], 5.34 (1 H, br. s.), 7.09-7.15 (4 H, m), 7.25-7.32 (2 H, m), 7.35-7.40 (2 H, m), 8.12 (1 H, br. s.), 9.00 (1 H, br. s.), 10.86 (1 H, br. s.) | B |
| 211 | 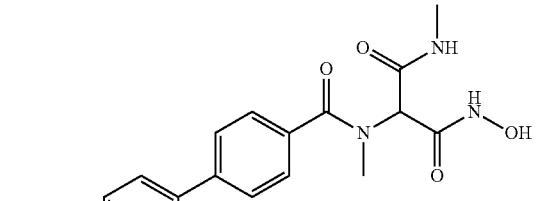 | NT | No detection | ¹H NMR (600 MHz, DMSO-$d_6$) δ ppm 1.35 (3H, t, J = 6.9 Hz), 2.66 (3H, br. s.), 2.98 (3H, s), 3.98-4.17 (2H, m), 5.37 (1H, br. s.), 7.03 (2H, d, J = 8.7 Hz), 7.31-7.78 (6H, m), 8.01-8.29 (1H, m), 9.04 (1H, br. s.), 10.84 (1H, br. s.) | A |
| 212 | 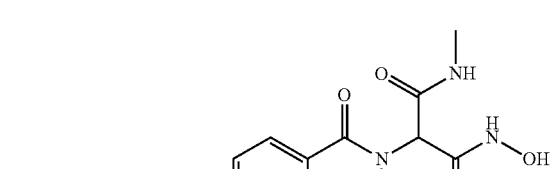 | NT | No detection | ¹H NMR (600 MHz, DMSO-$d_6$) δ ppm 1.00 (3H, t, J = 7.3 Hz), 1.67-1.84 (2H, m), 2.66 (3H, br. s.), 2.98 (3H, s), 3.90-4.06 (2H, m), 5.37 (1H, br. s.), 7.03 (2H, d, J = 8.7 Hz), 7.30-7.79 (6H, m), 8.00-8.33 (1H, m), 9.03 (1H, br. s.), 10.86 (1H, br. s.) | A |
| 213 | 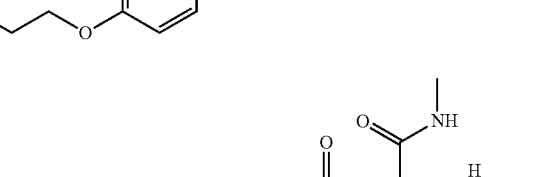 | NT | No detection | ¹H NMR (600 MHz, DMSO-$d_6$) δ ppm 1.29 (6H, d, J = 6.0 Hz), 2.66 (3H, br. s.), 2.98 (3H, s), 4.58-4.78 (1H, m), 5.37 (1H, br. s.), 7.02 (2H, d, J = 8.7 Hz), 7.28-7.78 (6H, m), 8.01-8.30 (1H, m), 9.04 (1H, br. s.), 10.86 (1H, br. s.) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 214 | | NT | 414 [M + H]+ 412 [M − H]− | ¹H NMR (600 MHz, DMSO-d$_6$) δ ppm 1.00 (6H, d, J = 6.5 Hz), 1.97-2.11 (1H, m), 2.66 (3H, br. s.), 2.98 (3H, s), 3.80 (2H, d, J = 6.5 Hz), 5.37 (1H, br. s.), 7.04 (2H, d, J = 8.7 Hz), 7.29-7.76 (6H, m), 8.01-8.28 (1H, m), 9.04 (1H, br. s.), 10.86 (1H, br. s.) | A |
| 215 | | NT | No detection | ¹H NMR (600 MHz, DMSO-d$_6$) δ ppm 1.62-1.71 (2H, m), 1.72-1.81 (2H, m), 2.66 (3H, br. s.), 2.98 (3H, s), 3.32 (3H, s), 3.38 (2H, t, J = 6.4 Hz), 4.03 (2H, t, J = 6.4 Hz), 5.37 (1H, br. s.), 7.03 (2H, d, J = 8.7 Hz), 7.30-7.80 (6H, m), 8.02-8.28 (1H, m), 9.04 (1H, br. s.), 10.85 (1H, br. s.) | A |
| 216 | | NT | 388 [M − H]− | ¹H NMR (600 MHz, DMSO-d$_6$) δ ppm 2.66 (3H, br. s.), 2.97 (3H, s), 3.89 (3H, s), 5.37 (1H, br. s.), 7.27 (1H, t, J = 8.7 Hz), 7.31-7.59 (3H, m), 7.63 (1H, d, J = 12.8 Hz), 7.70-7.80 (2H, m), 8.02-8.29 (1H, m), 9.05 (1H, br. s.), 10.86 (1H, br. s.) | A |
| 217 | | NT | 455 [M + H]+ | ¹H NMR (600 MHz, DMSO-d$_6$) δ ppm 0.17-0.21 (2 H, m), 0.32-0.38 (2 H, m), 1.82-1.88 (2 H, m), 2.02-2.08 (1 H, m), 2.66 (3 H, br. s.), 2.69-2.74 (2 H, m), 2.98 (3 H, s), 4.03-4.09 (2 H, m), [4.67-4.74], 5.37 (1 H, br. s.), 7.03 (2 H, d, J = 8.7 Hz), 7.54 (2 H, d, J = 6.9 Hz), 7.65 (2 H, d, J = 8.7 Hz), 7.71 (2 H, d, J = 6.9 Hz), 8.14 (1 H, br. s.), 9.04 (1 H, br. s.) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 219 | | NT | 419 [M + Na]+ 395 [M − H]− | ¹H NMR (600 MHz, DMSO-$d_6$) δ ppm 2.57-2.69 (3 H, m), 2.90-3.01 (3 H, m), 3.90 (3 H, s), 5.35 (1 H, s), 6.91 (1 H, d, J = 8.7 Hz), 7.26-7.67 (4 H, m), 7.81-7.97 (1 H, m), 8.09-8.26 (1 H, m), 8.43 (1 H, s), 9.04 (1 H, br. s.), 10.85 (1 H, br. s.) | A |
| 220 | | NT | 418 [M + Na]+ 394 [M − H]− | ¹H NMR (600 MHz, DMSO-$d_6$) δ ppm 2.67 (3 H, br. s.), 2.96 (3 H, s), [4.63], 5.37 (1 H, s), 7.58 (2 H, d, J = 7.3 Hz), 7.72-7.88 (4 H, m), 8.16 (1 H, br. s.), 9.05 (1 H, br. s.), 10.88 (1 H, br. s.) | B |
| 221 | | NT | 483 [M + H]+ 481 [M − H]− | ¹H NMR (600 MHz, DMSO-$d_6$) δ ppm 1.46 (2 H, quin, J = 7.6 Hz), 1.61 (2 H, quin, J = 7.6 Hz), 2.25-2.35 (6 H, m), 2.60-2.71 (5 H, m), 2.98 (3 H, s), 3.51-3.57 (4 H, m), [4.68], 5.37 (1 H, br. s.), 7.31 (2 H, d, J = 7.8 Hz), 7.56 (2 H, d, J = 7.8 Hz), 7.63 (2 H, d, J = 7.8 Hz), 7.74 (2 H, d, J = 7.8 Hz), 8.15 (1 H, br. s.), 9.05 (1 H, br. s.), 10.86 (1 H, br. s.) | A |
| 222 | | NT | 432 [M + Na]+ 408 [M − H]− | ¹H NMR (600 MHz, CHLOROFORM-d) δ ppm 2.87 (3 H, d, J = 4.6 Hz), 3.04 (3 H, s), [5.05], 5.61 (1 H, br. s.), 7.33-7.77 (9 H, m), 10.85, [11.06] (1 H, br. s.) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 223 | | NT | 416 [M + Na]+ 392 [M − H]− | $^1$H NMR (600 MHz, CHLOROFORM-d) δ ppm 2.87 (3 H, d, J = 4.1 Hz), 3.05 (3 H, br. s.), [5.07], 5.61 (1 H, br. s.), 7.22 (1 H, t, J = 8.5 Hz), 7.35-7.80 (8 H, m), 10.85, [11.07] (1 H, br. s.) | A |
| 224 | | NT | 432 [M + Na]+ 408 [M − H]− | $^1$H NMR (600 MHz, CHLOROFORM-d) δ ppm 2.91 (3 H, d, J = 4.6 Hz), 3.03 (3 H, s), 5.60 (1 H, br. s.), 7.08 (1 H, s), 7.37-7.46 (1 H, m), 7.54 (1 H, d, J = 8.7 Hz), 7.56-7.72 (5 H, m), 10.84 (1 H, br. s.) | A |
| 225 | | NT | 535 [M + H]+ 533 [M − H]− | $^1$H NMR (600 MHz, CHLOROFORM-d) δ ppm 1.97-2.08 (2 H, m), 2.40-2.65 (6 H, m), 2.92 (3 H, d, J = 4.6 Hz), 3.70-3.81 (4 H, m), 3.91-4.02 (2 H, m), 4.08 (2 H, t, J = 6.2 Hz), 4.83 (1 H, br. s), 5.83-6.08 (1 H, m), 6.95-7.01 (2 H, m), 7.49-7.81 (6 H, m) | A |
| 226 | | NT | 411 [M + Na]+ 387 [M − H]− | $^1$H NMR (600 MHz, CHLOROFORM-d) δ ppm 2.82-2.90 (6 H, m), 3.05 (3 H, br. s.), 3.98 (1 H, br. s.), [5.17], 5.60 (1 H, br. s.), 6.37 (1 H, d, J = 12.8 Hz), 6.45 (1 H, d, J = 7.8 Hz), 7.20-7.28 (1 H, m), 7.57 (6 H, br. s.), 10.88, [11.05] (1 H, br. s.) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 227 | | NT | 427 [M + Na]+ 403 [M − H]− | ¹H NMR (600 MHz, CHLOROFORM-d) δ ppm 2.86 (3 H, br. s.), 2.95 (3 H, br. s.), 3.05 (3 H, br. s.), 4.48 (1 H, br. s.), [5.14], 5.60 (1 H, br. s.), 6.71 (1 H, d, J = 8.3 Hz), 7.34-7.74 (8 H, m), 10.88, [11.06] (1 H, br. s.) | A |
| 228 | | NT | 429 [M + H]+ 427 [M − H]− | ¹H NMR (600 MHz, DMSO-d₆) δ ppm 1.82-1.95 (2H, m), 2.82 (3H, br. s.), 3.12 (3H, br. s.), 3.22 (2H, t, J = 6.9 Hz), 3.35 (3H, s), 3.52 (2H, t, J = 6.2 Hz), 6.64-6.81 (2H, m), 7.38-7.73 (6H, m) | A |
| 229 | | NT | 449 [M + Na]+ 425 [M − H]− | ¹H NMR (600 MHz, CD₃OD) δ ppm 2.82 (3H, br. s.), 3.12 (3H, br. s.), 3.35 (3H, s), 3.64-3.75 (2H, m), 4.13 (2H, m, J = 7.3 Hz), 4.30-4.44 (1H, m), 6.58 (2H, d, J = 8.3 Hz), 7.34-7.87 (6H, m) | A |
| 230 | | NT | 425 [M + Na]+ 401 [M − H]− | ¹H NMR (600 MHz, DMSO-d₆) δ ppm 1.19 (3 H, t, J = 7.1 Hz), 2.66 (3 H, br. s.), 2.98 (3 H, s), 3.13-3.20 (2 H, m), [4.70], 5.36 (1 H, br. s.), 5.61 (1 H, t, J = 4.4 Hz), 6.79 (1 H, t, J = 8.9 Hz), 7.32-7.53 (4 H, m), 7.63-7.72 (2 H, m), 8.13 (1 H, br. s.), 9.04 (1 H, br. s.), 10.85 (1 H, br. s.) | A |

TABLE 2-1-continued

Structural formulae of compounds, as well as their spectral data and inhibitory activity on Pseudomonas aeruginosa LpxC enzyme

| Compound No. | Structural formulae | LC-MS retention time (分) | MS (ESI) | ¹H-NMR | Enzyme inhibitory activity |
|---|---|---|---|---|---|
| 231 | | NT | 439 [M + Na]+ 415 [M − H]− | ¹H NMR (600 MHz, DMSO-$d_6$) δ ppm 0.93 (3 H, t, J = 7.3 Hz), 1.56-1.63 (2 H, m), 2.66 (3 H, br. s.), 2.98 (3 H, s), 3.07-3.12 (2 H, m), 5.36 (1 H, br. s.), 5.63-5.70 (1 H, m), 6.79 (1 H, t, J = 8.9 Hz), 7.32-7.55 (4 H, m), 7.62-7.72 (2 H, m), 8.13 (1 H, br. s.), 9.05 (1 H, br. s.), 10.85 (1 H, br. s.) | A |
| 232 | | NT | 441 [M + H]+ 43 [M − H]− | ¹H NMR (600 MHz, CHLOROFORM-d) δ ppm 2.44-2.52 (4 H, m), 2.89 (3 H, br. s.), 3.04 (3 H, br. s.), 3.53-3.58 (2 H, m), 3.70-3.76 (4 H, m), 5.62 (1 H, br. s.), 7.41-7.45 (2 H, m), 7.53-7.58 (2 H, m), 7.61-7.67 (4 H, m) | B |
| 233 | | NT | 400 [M + Na]+ 376 [M − H]− | ¹H NMR (600 MHz, CHLOROFORM-d) δ ppm 2.90 (3 H, d, J = 5.0 Hz), 3.06 (3 H, s), [5.17], 5.62 (1 H, br. s.), 7.01 (2 H, t, J = 7.8 Hz), 7.15 (1 H, br. s.), 7.29-7.36 (1 H, m), 7.56 (2 H, d, J = 7.8 Hz), 7.66 (2 H, d, J = 7.8 Hz), 10.86 (1 H, br. s.) | B |
| 234 | | NT | 463 [M + H]+ 461 [M − H]− | ¹H NMR (600 MHz, CD$_3$OD) δ ppm 1.45-1.51 (2 H, m), 1.58-1.64 (4 H, m), 2.43-2.51 (4 H, m), 2.82 (3 H, br. s.), 3.08 (3 H, s), 3.56 (2 H, s), 7.38 (2 H, d, J = 8.3 Hz), 7.51 (2 H, d, J = 7.8 Hz), 7.54-7.59 (2 H, m), 7.60-7.63 (2 H, m) | A |
| 235 | | NT | 383 [M − H]− | ¹H NMR (600 MHz, CD$_3$OD) δ ppm 1.14-1.23 (3 H, m), 2.81 (6 H, s), 3.53-3.61 (2 H, m), 6.70 (2 H, d, J = 8.7 Hz), 7.44-7.59 (4 H, m), 7.64 (2 H, d, J = 8.3 Hz) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 236 | | NT | 455 [M + H]+ 453 [M − H]− | ¹H NMR (600 MHz, CD$_3$OD) δ ppm 2.54-2.63 (4 H, m), 2.63-2.69 (2 H, m), 2.83 (3 H, br. s.), 2.85-2.91 (2 H, m), 3.12 (3 H, br. s.), 3.73 (4 H, t, J = 4.8 Hz), 7.34 (2 H, d, J = 7.8 Hz), 7.57-7.65 (4 H, m), 7.72 (2 H, d, J = 7.8 Hz) | A |
| 238 | | NT | 410 [M + Na]+ 386 [M − H]− | ¹H NMR (600 MHz, CD$_3$OD) δ ppm 2.83 (3 H, br. s.), 2.98-3.08 (2 H, m), 3.12 (3 H, s), 4.57-4.70 (2 H, m), 7.37 (2 H, d, J = 8.3 Hz), 7.48-7.66 (4 H, m), 7.73 (2 H, d, J = 7.8 Hz) | A |
| 239 | | NT | 449 [M + Na]+ 425 [M − H]− | ¹H NMR (500 MHz, CHLOROFORM-d) δ ppm 2.19 (3 H, s), 2.91 (3 H, d, J = 4.6 Hz), 2.98 (3 H, s), 3.05 (3 H, s), [4.59], 4.64 (2 H, s), 5.61 (1 H, br. s.), 7.28-7.36 (2 H, m), 7.56 (2 H, d, J = 7.3 Hz), 7.58-7.68 (4 H, m), 10.87 (1 H, br. s.) | B |
| 240 | | NT | 420 [M + Na]+ 396 [M − H]− | ¹H NMR (600 MHz, CD$_3$OD) δ ppm 1.36 (9 H, s), 2.83 (3 H, br. s.), 3.12 (3 H, br. s.), 7.51 (2 H, d, J = 8.3 Hz), 7.57-7.64 (4 H, m), 7.72 (2 H, d, J = 7.8 Hz) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 241 | | NT | 435 [M + Na]+ 411 [M − H]− | $^1$H NMR (600 MHz, CD$_3$OD) δ ppm 2.01 (3 H, s), 2.83 (3 H, br. s.), 3.11 (3 H, s), 4.40 (2 H, s), 7.39 (2 H, d, J = 8.3 Hz), 7.59-7.66 (4 H, m), 7.73 (2 H, d, J = 7.8 Hz) | B |
| 242 | | NT | 378 [M + Na]+ 354 [M − H]− | $^1$H NMR (600 MHz, CD$_3$OD) δ ppm 1.13-1.23 (3 H, m), 3.12 (3 H, s), 3.27-3.39 (2 H, m), 7.35-7.40 (1 H, m), 7.46 (2 H, t, J = 7.6 Hz), 7.60-7.69 (4 H, m), 7.73 (2 H, d, J = 7.3 Hz) | B |
| 243 | | NT | 471 [M + H]+ 469 [M − H]− | $^1$H NMR (600 MHz, CD$_3$OD) δ ppm 2.62 (4 H, br. s.), 2.78-2.87 (5 H, m), 3.12 (3 H, br. s.), 3.71-3.75 (4 H, m), 4.17-4.22 (2 H, m), 7.04 (2 H, d, J = 8.7 Hz), 7.43-7.64 (4 H, m), 7.69 (2 H, d, J = 7.8 Hz) | B |
| 244 | | NT | 435 [M + Na]+ 411 [M − H]− | $^1$H NMR (600 MHz, DMSO-d$_6$) δ ppm 2.66 (3 H, br. s.), 2.97 (3 H, br. s.), 3.52-3.57 (2 H, m), 4.11 (2 H, d, J = 14.7 Hz), 4.56-4.63 (1 H, m), 5.62 (1 H, br. s.), 6.48-6.55 (2 H, m), 7.36-7.70 (6 H, m) | B |
| 245 | | NT | 421 [M + Na]+ 397 [M − H]− | $^1$H NMR (600 MHz, CD$_3$OD) δ ppm 1.01 (3 H, t, J = 7.3 Hz), 1.62-1.70 (2 H, m), 2.82 (3 H, br. s.), 3.06-3.15 (5 H, m), 6.70 (2 H, d, J = 8.3 Hz), 7.46 (2 H, d, J = 8.3 Hz), 7.51-7.58 (2 H, m), 7.64 (2 H, d, J = 7.8 Hz) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 246 | | NT | 422 [M + Na]+ 398 [M − H]− | ¹H NMR (600 MHz, CD$_3$OD) δ ppm 2.83 (3H, br. s.), 2.91 (2H, t, J = 6.9 Hz), 3.12 (3H, s), 3.35 (3H, s), 3.65 (2H, t, J = 6.9 Hz), 7.34 (2H, d, J = 7.8 Hz), 7.43-7.65 (4H, m), 7.72 (2H, d, J = 7.8 Hz) | A |
| 247 | | NT | 449 [M + Na]+ 425 [M − H]− | ¹H NMR (600 MHz, DMSO-d$_6$) δ ppm 2.66 (3H, br. s.), 2.98 (3H, s), 4.12 (2H, t, J = 8.3 Hz), 4.47 (2H, m, J = 8.3 Hz), 5.38 (1H, br. s.), 7.27-7.89 (8H, m), 8.03-8.35 (1H, m), 9.04 (1 H, br. s.), 10.87 (1H, br. s.) | B |
| 248 | | NT | 463 [M + Na]+ 439 [M − H]− | ¹H NMR (600 MHz, CHLOROFORM-d) δ ppm 1.50 (9 H, s), 2.90 (3 H, d, J = 5.0 Hz), 3.04 (3 H, br. s.), 5.61 (1 H, br. s.), 5.98 (1 H, s), 7.16 (1 H, br. s.), 7.30 (1 H, br. s.), 7.58-7.71 (6 H, m), 7.81 (2 H, d, J = 7.8 Hz), 10.85 (1 H, br. s.) | B |
| 249 | | NT | 419 [M + Na]+ 395 [M − H]− | ¹H NMR (600 MHz, CHLOROFORM-d) δ ppm 2.88 (3 H, s), 3.05 (3 H, s), 3.95-4.01 (3 H, m), 4.35-4.41 (2 H, m), 5.50 (1 H, br. s.), 6.46 (2 H, d, J = 8.7 Hz), 7.26-7.29 (1 H, m), 7.35-7.38 (4 H, m), 7.51 (2 H, d, J = 8.3 Hz) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 250 | 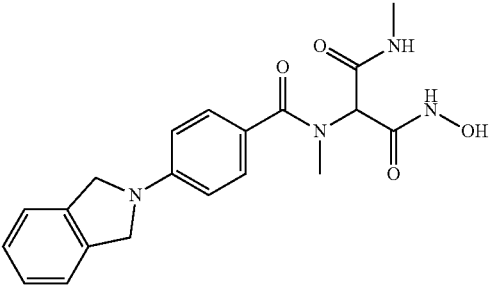 [SMILES: CNC(=O)C(C(=O)NO)N(C)C(=O)c1ccc(N2Cc3ccccc3C2)cc1] | NT | 405 [M + Na]+ 385 [M − H]− | $^1$H NMR (600 MHz, CD$_3$OD) δ ppm 2.82 (3 H, s), 3.16 (3 H, br. s.), 4.69 (4 H, s), 6.75 (2 H, d, J = 8.7 Hz), 7.31 (2 H, dd, J = 5.5, 3.2 Hz), 7.38 (2 H, dd, J = 5.5, 3.2 Hz), 7.48-7.54 (2 H, m) | B |
| 251 | 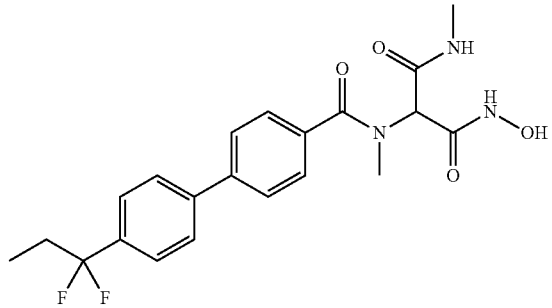 [SMILES: CCC(F)(F)c1ccc(-c2ccc(C(=O)N(C)C(C(=O)NC)C(=O)NO)cc2)cc1] | NT | 442 [M + Na]+ 418 [M − H]− | $^1$H NMR (600 MHz, CHLOROFORM-d) δ ppm 1.03 (3 H, t, J = 7.6 Hz), 2.13-2.25 (2 H, m), 2.90 (3 H, d, J = 5.0 Hz), 3.05 (3 H, br. s.), 5.61 (1 H, br. s.), 7.14 (1 H, br. s.), 7.29 (1 H, br. s.), 7.56 (2 H, d, J = 8.3 Hz), 7.61-7.73 (6 H, m), 10.85 (1 H, br .s.) | A |
| 252 | 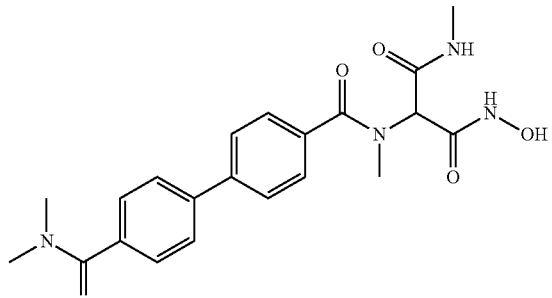 | NT | 435 [M + Na]+ 411 [M − H]− | $^1$H NMR (600 MHz, CHLOROFORM-d) δ ppm 2.91 (3 H, s), 3.05 (6 H, br. s.), 3.14 (3 H, br. s.), 5.61 (1 H, br. s.), 7.08 (1 H, br. s.), 7.30 (1 H, br. s.), 7.52 (2 H, d, J = 7.8 Hz), 7.58-7.70 (6 H, m), 10.85 (1 H, br. s.) | B |
| 253 | 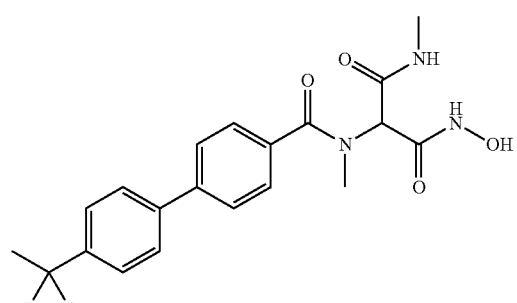 | NT | 428 [M + Na]+ 404 [M − H]− | $^1$H NMR (600 MHz, CHLOROFORM-d) δ ppm 1.97 (3 H, t, J = 18.1 Hz), 2.90 (3 H, d, J = 4.6 Hz), 3.05 (3 H, s), 5.61 (1 H, br. s.), 7.12 (1 H, br. s.), 7.29 (1 H, br. s.), 7.51-7.71 (8 H, m), 10.85 (1 H, br. s.) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 254 | | NT | 450 [M + Na]+ 426 [M − H]− | ¹H NMR (600 MHz, CD$_3$OD) δ ppm 2.64 (3H, d, J = 5.0 Hz), 2.76 (2H, s), 2.84 (2H, s), 3.06 (3H, d, J = 10.1 Hz), 7.59 (1H, d, J = 8.3 Hz), 7.69 (1H, d, J = 8.3 Hz), 7.75 (1H, d, J = 8.3 Hz), 7.77-7.85 (3H, m), 8.09 (2H, t, J = 8.7 Hz) | B |
| 255 | | NT | 426 [M + Na]+ 402 [M − H]− | ¹H NMR (600 MHz, CD$_3$OD) δ ppm 2.83 (3 H, br. s.), 3.12 (3 H, br. s.), 4.23-4.25 (1 H, m), 4.28-4.30 (1 H, m), 4.69-4.71 (1 H, m), 4.76-4.79 (1 H, m), 7.06 (2 H, d, J = 8.7 Hz), 7.57-7.63 (4 H, m), 7.69 (2 H, d, J = 8.3 Hz) | A |
| 256 | | NT | 433 [M + Na]+ 409 [M − H]− | ¹H NMR (600 MHz, CD$_3$OD) δ ppm 1.98-2.12 (4H, m), 2.82 (3H, br. s.), 3.13 (3H, br. s.), 6.66 (2H, d, J = 8.7 Hz), 7.45-7.74 (6H, m) | A |
| 257 | | NT | 449 [M + Na]+ 425 [M − H]− | ¹H NMR (600 MHz, DMSO-d$_6$) δ ppm 0.85-0.95 (3 H, m), 1.50-1.61 (2 H, m), 2.67 (3 H, br. s.), 2.98 (3 H, s), 3.24 (2 H, q, J = 6.7 Hz), [4.67], 5.38 (1 H, br. s.), 7.41-7.64 (2 H, m), 7.76-7.88 (4 H, m), 7.96 (2 H, d, J = 7.8 Hz), 8.15 (1 H, br. s.), 8.47-8.56 (1 H, m), 9.05 (1 H, br. s.), 10.90 (1 H, br. s.) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 258 | | NT | 444 [M + Na]+ 420 [M − H]− | $^1$H NMR (600 MHz, DMSO-d$_6$) δ ppm 2.66 (3 H, br. s.), 2.97 (3 H, s), 5.38 (1 H, br. s.), 7.39-7.62 (4 H, m), 7.70-7.86 (3 H, m), 8.15 (1 H, br. s.), 9.04 (1 H, br. s.), 10.85 (1 H, br. s.) | A |
| 259 | | NT | 437 [M + Na]+ 413 [M − H]− | $^1$H NMR (600 MHz, DMSO-d$_6$) δ ppm 2.56 (3 H, s), 2.66 (3 H, br. s.), 2.98 (3 H, s), 3.29-3.30 (3 H, m), 3.80 (2 H, s), 5.38 (1 H, br. s.), 7.41-7.59 (4 H, m), 7.68 (2 H, d, J = 7.8 Hz), 7.77 (2 H, d, J = 7.8 Hz), 8.14 (1 H, br. s.), 9.04 (1 H, br. s), 10.86 (1 H, br. s) | B |
| 260 | | NT | 421 [M + Na]+ 397 [M − H]− | $^1$H NMR (600 MHz, DMSO-d$_6$) δ ppm 2.66 (3 H, br. s.), 2.98 (3 H, s), 3.92 (3 H, s), 5.38 (1 H, br. s.), 7.59 (2 H, d, J = 6.4 Hz), 7.72 (2 H, d, J = 8.3 Hz), 7.75-7.84 (4 H, m), 8.15 (1 H, br. s.), 8.29 (1 H, s), 9.04 (1 H, br. s), 10.86 (1 H, br. s) | A |
| 261 | | NT | 408 [M + Na]+ 384 [M − H]− | $^1$H NMR (600 MHz, CD$_3$OD) δ ppm 1.47 (3H, d, J = 6.9 Hz), 2.83 (3H, br. s.), 3.12 (3H, br. s.), 4.85-4.92 (1H, m), 7.43-7.79 (8H, m) | B |
| 262 | | NT | 422 [M + Na]+ 398 [M − H]− | $^1$H NMR (600 MHz, CD$_3$OD) δ ppm 1.56 (6H, s), 2.83 (3H, br. s.), 3.12 (3H, br. s.), 7.43-7.81 (8H, m) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 263 | | NT | 481 [M + H]+ 479 [M − H]− | ¹H NMR (600 MHz, CD₃OD) δ ppm 2.02-2.09 (2 H, m), 2.19-2.27 (2 H, m), 2.65-2.73 (4 H, m), 2.82 (3 H, br. s.), 3.04-3.08 (2 H, m), 3.12 (3 H, br. s.), 4.06-4.13 (2 H, m), 5.66-5.73 (1 H, m), 5.76-5.82 (1 H, m), 7.02 (2 H, d, J = 8.7 Hz), 7.54-7.64 (4 H, m), 7.68 (2 H, d, J = 7.8 Hz) | B |
| 264 | | NT | 519 [M + H]+ 517 [M − H]− | ¹H NMR (600 MHz, CD₃OD) δ ppm 1.96-2.07 (6 H, m), 2.58-2.67 (6 H, m), 2.83 (3 H, br. s.), 3.12 (3 H, br. s.), 4.05-4.13 (2 H, m), 7.02 (2 H, d, J = 8.7 Hz), 7.55-7.63 (4 H, m), 7.68 (2 H, d, J = 8.3 Hz) | A |
| 265 | | NT | 426 [M + H]+ 424 [M − H]− | ¹H NMR (600 MHz, CD₃OD) δ ppm 2.83 (3 H, br. s.), 2.97 (3 H, s), 3.09 (3 H, s), 3.12 (3 H, br. s.), 3.82 (2 H, s), 7.36 (2 H, d, J = 7.8 Hz), 7.59-7.67 (4 H, m), 7.73 (2 H, d, J = 7.3 Hz) | B |
| 266 | | NT | 463 [M + Na]+ 439 [M − H]− | ¹H NMR (600 MHz, CD₃OD) δ ppm 2.72 (2 H, t, J = 7.7 Hz), 2.83 (3 H, br. s.), 2.93 (3 H, s), 2.96 (2 H, t, J = 7.7 Hz), 2.99 (3 H, s), 3.12 (3 H, s), 7.34 (2 H, d, J = 7.8 Hz), 7.57-7.64 (4 H, m), 7.72 (2 H, d, J = 7.8 Hz) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (%) | MS (ESI) | $^1$H-NMR | Enzyme inhibitory activity |
|---|---|---|---|---|---|
| 267 | | NT | 440 [M + H]+ 438 [M − H]− | $^1$H NMR (600 MHz, CD$_3$OD) δ ppm 2.36 (3H, s), 2.58-2.70 (4H, m), 2.82 (3H, br. s.), 3.12 (3H, s), 3.24-3.31 (4H, m), 7.06 (2H, d, J = 8.7 Hz), 7.41-7.76 (6H, m) | B |
| 268 | | NT | 401 [M + H]+ 409 [M − H]− | $^1$H NMR (600 MHz, CHLOROFORM-d) δ ppm 1.78-1.91 (4 H, m), 2.46 (2 H, d, J = 8.3 Hz), 2.90 (3 H, d, J = 5.0 Hz), 3.04 (3 H, s), 3.48-3.50 (1 H, m), 3.94-4.01 (1 H, m), 5.61 (1 H, br. s.), 6.62 (2 H, d, J = 8.7 Hz), 7.45 (2 H, d, J = 8.3 Hz), 7.56-7.63 (4 H, m) | A |
| 269 | | NT | 436 [M + Na]+ 412 [M − H]− | $^1$H NMR (600 MHz, CD$_3$OD) δ ppm 1.68 (6 H, s), 2.82 (3 H, br. s.), 3.11 (3 H, br. s.), 6.81 (1 H, d, J = 7.8 Hz), 7.05 (1 H, s), 7.10 (1 H, d, J = 7.8 Hz), 7.54-7.61 (2 H, m), 7.64 (2 H, d, J = 8.3 Hz) | A |
| 270 | | NT | 404 [M + Na]+ 380 [M − H]− | $^1$H NMR (600 MHz, DMSO-d$_6$) δ ppm 2.67 (3 H, br. s.), 2.99 (3 H, s), 5.39 (1 H, br. s.), 7.01 (1 H, d, J = 1.4 Hz), 7.58 (2 H, d, J = 7.3 Hz), 7.64 (1 H, d, J = 8.3 Hz), 7.76 (1 H, d, J = 8.3 Hz), 7.84 (2 H, d, J = 7.3 Hz), 7.97 (1 H, s), 8.05 (1 H, d, J = 14 Hz), 9.05 (1 H, br. s.), 10.87 (1 H, br. s.) | NT |
| 272 | | NT | 422 [M + Na]+ 398 [M − H]− | $^1$H NMR (600 MHz, DMSO-d$_6$) δ ppm 2.66 (3 H, br. s.), 2.98 (3 H, s), 5.37 (1 H, br. s.), 7.27 (2 H, d, J = 8.7 Hz), 7.39 (1 H, br. s.), 7.49-7.55 (2 H, m), 7.60 (2 H, d, J = 8.7 Hz), 7.66-7.73 (2 H, m) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 273 | 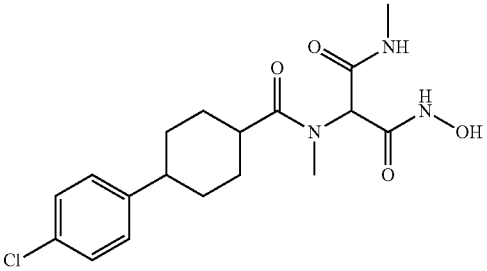 [SMILES: CNC(=O)C(C(=O)NO)N(C)C(=O)C1CCC(c2ccc(Cl)cc2)CC1] | NT | 404 [M + Na]+ 380 [M − H]− | ¹H NMR (600 MHz, CD$_3$OD) δ ppm 1.52-1.69 (4 H, m), 1.87-2.03 (4 H, m), 2.53-2.60 (1 H, m), 2.76-2.83 (4 H, m), 3.19 (3 H, s), 5.41 (1 H, s), 7.20-7.23 (2 H, m), 7.24-7.27 (2 H, m) | C |
| 274 | 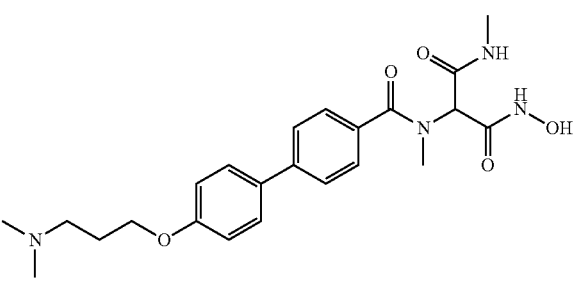 [SMILES: CNC(=O)C(C(=O)NO)N(C)C(=O)c1ccc(-c2ccc(OCCCN(C)C)cc2)cc1] | NT | 443 [M + H]+ 441 [M − H]− | ¹H NMR (600 MHz, CD$_3$OD) δ ppm 1.92-2.08 (2H, m), 2.32 (6H, s), 2.54-2.68 (2H, m), 2.82 (3H, br. s.), 3.12 (3H, br. s.), 4.08 (2H, t, J = 6.2 Hz), 7.02 (2H, d, J = 8.7 Hz), 7.41-7.77 (6H, m) | B |
| 275 | 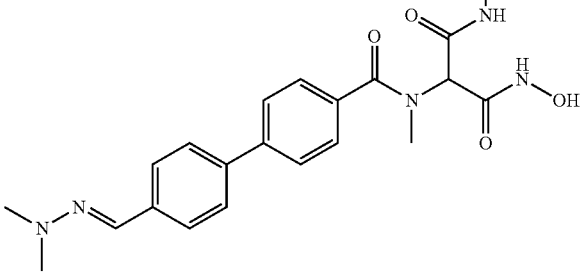 | NT | 434 [M + Na]+ 410 [M − H]− | ¹H NMR (600 MHz, DMSO-d$_6$) δ ppm 2.66 (3 H, br. s.), 2.94 (6 H, s), 2.98 (3 H, s), 5.38 (1 H, br. s.), 7.53-7.60 (2 H, m), 7.63 (2 H, d, J = 8.3 Hz), 7.67-7.73 (2 H, m), 7.77 (2 H, d, J = 8.3 Hz), 8.15 (1 H, br. s.), 9.04 (1 H, br. s.) | A |
| 276 | 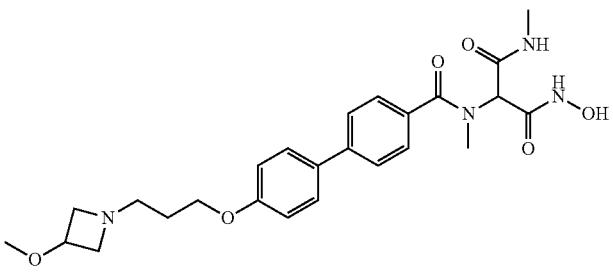 [SMILES: CNC(=O)C(C(=O)NO)N(C)C(=O)c1ccc(-c2ccc(OCCCN3CC(OC)C3)cc2)cc1] | NT | 485 [M + H]+ 483 [M − H]− | ¹H NMR (600 MHz, CD$_3$OD) δ ppm 1.82-1.92 (2H, m), 2.68-2.76 (2H, m), 2.83 (3H, br. s.), 3.01-3.07 (2H, m), 3.12 (3H, br. s.), 3.26 (3H, s), 3.57-3.73 (2H, m), 3.96-4.14 (3H, m), 7.01 (2H, d, J =8.7 Hz), 7.39-7.75 (6H, m) | A |
| 277 | 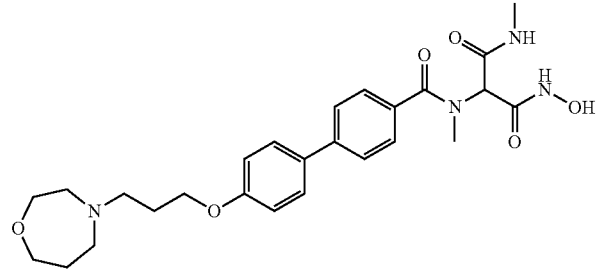 [SMILES: CNC(=O)C(C(=O)NO)N(C)C(=O)c1ccc(-c2ccc(OCCCN3CCCOCC3)cc2)cc1] | NT | 499 [M + H]+ 497 [M − H]− | ¹H NMR (600 MHz, CD$_3$OD) δ ppm 1.94 (4H, d, J = 6.0 Hz), 2.71-2.91 (9H, m), 3.12 (3H, br. s.), 3.71-3.86 (4H, m), 4.04-4.15 (2H, m), 7.02 (2H, d, J = 8.7 Hz), 7.41-7.78 (6H, m) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 278 | | NT | 393 [M + Na]+ 369 [M − H]− | $^1$H NMR (600 MHz, CD$_3$OD) δ ppm 2.77-2.86 (6 H, m), 3.11 (3 H, s), 6.65 (1 H, dd, J = 7.8, 2.1 Hz), 6.84-6.89 (1 H, m), 6.91 (1 H, d, J = 7.8 Hz), 7.21 (1 H, t, J = 7.8 Hz), 7.41-7.63 (2 H, m), 7.69 (2 H, d, J = 7.8 Hz) | B |
| 279 | | NT | 394 [M + Na]+ 370 [M − H]− | $^1$H NMR (600 MHz, CD$_3$OD) δ ppm 2.83 (3 H, br. s.), 3.12 (3 H, s), 3.86 (3 H, s), 5.52 (1 H, s), 6.95 (1 H, dd, J = 8.0, 2.3 Hz), 7.15-7.20 (1 H, m), 7.23 (1 H, d, J = 8.0 Hz), 7.37 (1 H, t, J = 8.0 Hz), 7.44-7.66 (2 H, m), 7.72 (2 H, d, J = 7.8 Hz) | B |
| 280 | | NT | 452 [M + Na]+ 428 [M − H]− | $^1$H NMR (600 MHz, CD$_3$OD) δ ppm 1.33 (6H, s), 2.83 (3H, br. s.), 3.12 (3H, br. s.), 3.83 (2H, s), 7.05 (2H, d, J = 8.7 Hz), 7.60 (6H, br. s.) | A |
| 281 | | NT | 396 [M + H]+ 394 [M − H]− | $^1$H NMR (600 MHz, CD$_3$OD) δ ppm 2.83 (3 H, br. s.), 3.14 (3 H, br. s.), 3.94 (3 H, s), 7.61-7.70 (4 H, m), 7.79 (2 H, d, J = 7.8 Hz), 7.94 (1 H, s), 8.17 (1 H, s) | B |
| 282 | | NT | 396 [M + H]+ 394 [M − H]− | $^1$H NMR (600 MHz, CD$_3$OD) δ ppm 2.84 (3 H, br. s.), 3.14 (3 H, br. s.), 3.96 (3 H, s), 7.50-7.95 (7 H, m), 8.17 (1 H, br. s.) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 283 | | NT | 504 [M + H]+ 526 [M + Na]+ 502 [M − H]− | ¹H NMR (600 MHz, CD$_3$OD) δ ppm 2.54-2.64 (4 H, m), 2.67-2.88 (5 H, m), 3.12 (3 H, br. s.), 3.67-3.75 (4 H, m), 4.15-4.31 (2 H, m), 4.96-5.11 (1 H, m), 5.51 (1 H, s), 7.06 (2 H, d, J = 8.3 Hz), 7.62 (4 H, d, J = 8.3 Hz), 7.66-7.73 (2 H, m) | A |
| 284 | | NT | 379 [M + Na]+ 355 [M − H]− | ¹H NMR (600 MHz, CD$_3$OD) δ ppm 2.82 (3 H, br. s.), 3.12 (3 H, br. s.), 6.79 (2 H, d, J = 8.3 Hz), 7.43 (2 H, d, J = 7.8 Hz), 7.51-9.59 (2 H, m), 7.64 (2 H, d, J = 7.8 Hz) | B |
| 285 | | NT | 422 [M + Na]+ 398 [M − H]− | ¹H NMR (600 MHz, CHLOROFORM-d) δ ppm 1.27 (3 H, t, J = 7.0 Hz), 2.91 (3 H, d, J = 5.0 Hz), 3.05 (3 H, s), 3.59 (2 H, q, J = 7.0 Hz), 4.56 (2 H, s), 5.62 (1 H, br. s.), 6.92 (1 H, br. s), 7.45 (2 H, d, J = 8.3 Hz), 7.59 (2 H, d, J = 7.8 Hz), 7.62-7.69 (4 H, m), 10.86 (1 H, br. s) | A |
| 286 | | NT | 501 [M + H]+ 499 [M − H]− | ¹H NMR (600 MHz, CD$_3$OD) δ ppm 1.81-1.90 (2H, m), 2.39-2.56 (6H, m), 2.83 (3H, br. s.), 3.04 (2H, t, J = 7.1 Hz), 3.11 (3H, s), 3.62-3.74 (4H, m), 7.44 (2H, d, J = 8.3 Hz), 7.49-7.78 (6H, m) | A |
| 287 | | NT | 510 [M + H]+ 508 [M − H]− | ¹H NMR (600 MHz, CD$_3$OD) δ ppm 1.73-1.86 (1H, m), 2.13-2.26 (1H, m), 2.41-2.58 (6H, m), 2.59-2.68 (1H, m), 2.82 (3H, br. s.), 3.03-3.17 (4H, m), 3.30-3.36 (1H, m), 3.38-3.45 (1H, m), 3.46-3.53 (1H, m), 3.66-3.77 (4H, m), 6.65 (2H, d, J = 8.7 Hz), 7.35-7.72 (6H, m) | A |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | ¹H-NMR | Enzyme inhibitory activity |
|---|---|---|---|---|---|
| 288 | | NT | 501 [M + H]+ 499 [M − H]− | ¹H NMR (600 MHz, CD$_3$OD) δ ppm 1.97-2.03 (2 H, m), 2.58-2.62 (2 H, m), 2.67-2.70 (4 H, m), 2.76-2.80 (4 H, m), 2.83 (3 H, br. s.), 3.12 (3 H, br. s.), 4.08 (2 H, t, J = 6.2 Hz), 7.01 (2 H, d, J = 8.7 Hz), 7.58-7.62 (4 H, m), 7.68 (2 H, d, J = 8.3 Hz) | A |
| 289 | | NT | 533 [M + H]+ 531 [M − H]− | ¹H NMR (600 MHz, CD$_3$OD) δ ppm 1.95-2.04 (2 H, m), 2.74 (2 H, t, J = 7.1 Hz), 2.83 (3 H, br. s.), 3.01-3.05 (4 H, m), 3.07-3.14 (7 H, m), 4.11 (2 H, t, J = 6.2 Hz), 7.02 (2 H, d, J = 8.7 Hz), 7.57-7.63 (4 H, m), 7.68 (2 H, d, J = 8.3 Hz) | A |
| 290 | | NT | 406 [M + Na]+ 382 [M − H]− | ¹H NMR (600 MHz, CHLOROFORM-d) δ ppm 2.90 (3 H, d, J = 4.6 Hz), 3.05 (3 H, br. s.), 5.17 (4 H, br. s.), 5.61 (1 H, br. s.), 7.28-7.68 (8 H, m), 10.86 (1 H, br. s.) | A |
| 291 | | NT | 454 [M + Na]+ 430 [M − H]− | ¹H NMR (200 MHz, CHLOROFORM-d) δ ppm 2.86 (3 H, d, J = 4.4 Hz), 3.05 (s, 3 H) 3.16 (2 H, t, J = 7.0 Hz), 3.39 (s, 3 H) 3.62 (2 H, t, J = 7.0 Hz), 5.61 (1 H, br. s.), 7.34-7.69 (10 H, m) | A |
| 292 | | NT | 346 [M − H]− | ¹H NMR (400 MHz, DMSO-d$_6$) δ ppm 2.66 (3H, d, J = 3.9 Hz), 2.98 (3H, s), 5.36 (1H, s), 7.29-7.42 (1H, br), 7.47-7.56 (1H, m), 7.60-7.65 (1H, m), 7.65-7.70 (1H, m), 7.81 (2H, d, J = 7.6 Hz), 7.96-8.01 (1H, m), 8.10-8.18 (1H, m), 9.06 (1H, s), 10.74-10.95 (1H, br) | B |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 293 | | NT | 508 [M + H]+ 530 [M + Na]+ 506 [M − H]− | $^1$H NMR (400 MHz, CD$_3$OD) δ ppm 1.85-2.05 (2H, m), 2.81 (3H, s), 3.11 (3H, s), 3.15-3.40 (4H, m), 5.45-5.55 (1H, br), 6.50-6.65 (1H, m), 6.65-6.80 (3H, m), 6.85-7.00 (2H, m), 7.35-7.70 (6H, m) | NT |
| 294 | | NT | 520 [M + H]+ 542 [M + Na]+ 518 [M − H]− | $^1$H NMR (400 MHz, CD$_3$OD) δ ppm 1.90-2.05 (2H, m), 2.63 (3H, s), 2.72 (3H, s), 3.02 (3H, s), 3.15-3.35 (2H, m), 3.96 (2H, t, J = 6.1 Hz), 5.40 (1H, s), 6.05-6.20 (3H, m), 6.63 (2H, d, J = 8.8 Hz), 6.90 (1H, dd, J = 8.0, 8.0 Hz), 7.20-7.65 (6H, m) | NT |
| 295 | | NT | 357 [M + H]+ 355 [M − H]− | $^1$H NMR (400 MHz, CD$_3$OD) δ ppm 2.59 (3 H, s), 2.82 (3 H, s), 3.11 (3 H, s), 7.25 (1 H, d, J = 7.6 Hz), 7.40-7.95 (4 H, m), 8.04 (2 H, d, J = 7.6 Hz) | C |
| 296 | | NT | 373 [M + H]+ 371 [M − H]− | $^1$H NMR (400 MHz, CD$_3$OD) δ ppm 2.82 (3 H, s), 3.11 (3 H, s), 4.00 (3 H, s), 5.45-5.60 (1 H, br.), 6.75 (1 H, d, J = 8.0 Hz), 7.40-7.80 (4 H, m), 8.17 (2 H, d, J = 7.2 Hz) | C |
| 297 | | NT | 409 [M − H]− | $^1$H NMR (400 MHz, CD$_3$OD) δ ppm 2.83 (3 H, s), 3.10 (3 H, s), 5.53 (1 H, s), 7.50-7.80 (2 H, m), 8.10-8.40 (4 H, m), 8.96 (1 H, s) | C |

TABLE 2-1-continued

Structural formulae of compounds, as well as their spectral data and inhibitory activity on *Pseudomonas aeruginosa* LpxC enzyme

| Compound No. | Structural formulae | LC-MS retention time (分) | MS (ESI) | $^1$H-NMR | Enzyme inhibitory activity |
|---|---|---|---|---|---|
| 298 | | NT | 382 [M + H]+ 404 [M + Na]+ 380 [M − H]− | $^1$H NMR (600 MHz, CD$_3$OD) δ ppm 2.83 (3 H, br. s), 3.12 (3 H, s), 7.30 (1 H, d, J = 6.4 Hz), 7.87 (9 H, m), 8.53 (1 H, d, J = 6.8 Hz) | NT |
| 299 | | NT | 366 [M + Na]+ 342 [M − H]− | $^1$H NMR (600 MHz, CD$_3$OD) δ ppm [2.80], 2.83 (3 H, s), [3.15], 3.26 (3 H, s), 7.50-7.59 (3 H, m), 8.11-8.20 (2 H, m), 8.98, [9.08] (1 H, s), [9.09], 9.17 (1 H, s) | C |

TABLE 3-1

Structural formulae of compounds, as well as their spectral data and inhibitory activity on *Pseudomonas aeruginosa* LpxC enzyme

| Compound No. | Structural formulae | Kind of salt | MS(ESI) | $^1$H-NMR | Enzyme inhibitory activity |
|---|---|---|---|---|---|
| 300 | | Free | 441[M + H]+ 463[M + Na]+ 439[M − H]− | $^1$H NMR (600 MHz, CD$_3$OD) δ ppm 2.82 (3 H, br. s.), 2.89 (2 H, dt, J = 27.5, 5.0 Hz), 3.08 (3 H, s), 3.84 (2 H, s), 4.54 (2 H, dt, J = 47.7, 5.0 Hz), 7.37-7.64 (8 H, m) | A |
| 301 | | Free | 435[M + H]+ 457[M + Na]+ 433[M − H]− | $^1$H NMR (600 MHz, CD$_3$OD) δ ppm 0.38-0.41 (2 H, m), 0.46-0.49 (2 H, m), 2.14 (1 H, tt, J = 6.9, 3.6 Hz), 2.82 (3 H, br. s.), 3.08 (3 H, s), 3.83 (2 H, s), 7.38-7.39 (2 H, m), 7.42-7.64 (6 H, m) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | $^1$H-NMR | Enzyme inhibitory activity |
|---|---|---|---|---|---|
| 302 | | Free | 459[M + H]+ 481[M + Na]+ 457[M − H]− | $^1$H NMR (600 MHz, CD$_3$OD) δ ppm 2.82 (3 H, br. s.), 2.91 (2 H, td, J = 15.5, 4.4 Hz), 3.08 (3 H, s), 3.85 (2 H, s), 5.91 (1 H, tt, J = 56.2, 4.4 Hz), 7.35-7.64 (8 H, m) | NT |
| 303 | | Free | 491[M + H]+ 513[M + Na]+ 489[M − H]− | $^1$H NMR (600 MHz, CHLOROFORM-d) δ ppm 1.84-1.88 (2 H, m), 1.97-2.00 (2 H, m), 2.33-2.38 (2 H, m), 2.51-2.55 (2 H, m), 2.88 (3 H, d, J = 4.6 Hz), 3.01 (3 H, br. s.), 3.47 (2 H, s), 4.24-4.32 (2 H, m), 5.58 (1 H, br. s.), 7.29-7.35 (3 H, m), 7.46-7.50 (2 H, m), 7.54-7.59 (4 H, m) | NT |
| 304 | | Free | 478[M + H]+ 476[M − H]− | $^1$H NMR (600 MHz, DMSO-d$_6$) δ ppm 2.18 (3 H, s), 2.25-2.60 (8 H, m), 2.66 (3 H, s), 2.93 (3 H, s), 3.49 (2 H, s), 7.32-7.67 (8 H, m), 8.13 (1 H, br. s.), 9.05 (1 H, br. s.), 10.86 (1 H, br. s.) | A |
| 305 | | Free | 535[M + Na]+ 511[M − H]− | $^1$H NMR (600 MHz, CD$_3$OD) δ ppm 2.82 (3 H, br. s.), 2.96-3.00 (4 H, m), 3.08 (3 H, s), 3.10-3.14 (4 H, m), 3.72 (2 H, s), 7.39-7.63 (8 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 306 | | Free | 418[M + Na]+ 394[M − H]− | ¹H NMR (600 MHz, CD$_3$OD) δ ppm 2.82 (3 H, br. s.), 3.08 (3 H, s), 4.63 (2 H, s), 7.36-7.63 (8 H, m) | NT |
| 307 | | Free | 353[M + Na]+ 329[M − H]− | ¹H NMR (600 MHz, CD$_3$OD) δ ppm 2.82 (3 H, br. s.), 3.12 (3 H, br. s.), 6.31-6.32 (2 H, m), 7.26-7.27 (2 H, m), 7.51-7.70 (4 H, m) | C |
| 308 | | Free | 370[M + Na]+ 346[M − H]− | ¹H NMR (600 MHz, CD$_3$OD) δ ppm 2.82 (3 H, br. s.), 3.11 (3 H, br. s.), 7.08-7.16 (1 H, m), 7.38-7.79 (6 H, m) | B |
| 309 | | Free | 366[M + Na]+ 342[M − H]− | ¹H NMR (600 MHz, CD$_3$OD) δ ppm 2.84 (3 H, br. s.), 3.11 (3 H, s), 5.54 (1 H, br. s.), 7.66-7.77 (2 H, m), 8.16-8.27 (2 H, m), 8.55-8.61 (1 H, m), 8.67-8.75 (1 H, m), 9.18 (1 H, s) | C |
| 310 | | Free | 355[M + Na]+ 331[M − H]− | ¹H NMR (600 MHz, CD$_3$OD) δ ppm 2.83 (3 H, br. s.), 3.09 (3 H, s), 7.54-7.70 (3 H, m), 7.83-7.85 (2 H, m), 8.29 (1 H, s) | C |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 311 | | Free | 366[M + Na]+ 342[M − H]− | ¹H NMR (600 MHz, CD$_3$OD) δ ppm 2.84 (3 H, br. s.), 3.11 (3 H, s), 7.34-7.46 (1 H, m), 7.58-7.75 (2 H, m), 8.43-8.59 (2 H, m), 8.81-8.94 (2 H, m) | C |
| 312 | | Free | 404[M + Na]+ 380[M − H]− | ¹H NMR (600 MHz, DMSO-d$_6$) δ ppm 2.67 (3 H, s), 2.99 (3 H, s), 5.38 (1 H, br. s.), 7.27-7.31 (1 H, m), 7.35-7.37 (1 H, m), 7.55 (1 H, s), 7.58-7.64 (1 H, m), 7.66 (1 H, d, J = 7.3 Hz), 7.70 (1 H, d, J = 7.3 Hz), 8.01 (2 H, m), 8.15 (1 H, m), 9.06 (1 H, s), 10.88 (1 H, br. s.) | A |
| 313 | | Free | 453[M + H]+ 475[M + Na]+ 451[M − H]− | ¹H NMR (600 MHz, CD$_3$OD) δ ppm 2.82 (3 H, br. s.), 3.08 (3 H, s), 3.26-3.68 (4 H, m), 3.72 (2 H, s), 5.07-5.21 (1 H, m), 7.29-7.67 (8 H, m) | NT |
| 314 | | Free | 493[M + H]+ 491[M − H]− | ¹H NMR (600 MHz, CHLOROFORM-d) δ ppm 1.22-1.81 (5 H, m), 2.53 (2 H, d, J = 6.4 Hz), 2.90 (3 H, d, J = 5.0 Hz), 3.00 (3 H, s), 3.36-3.42 (2 H, m), 3.82 (2 H, s), 3.94-3.99 (2H, m), 7.31-7.62 (8 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 315 | | Free | 483[M + H]+<br>505[M + Na]+<br>481[M − H]− | ¹H NMR (600 MHz, CD₃OD) δ ppm 2.67-2.73 (4 H, m), 2.82 (3 H, br. s.), 3.08 (3 H, s), 3.62 (4 H, s), 3.75 (2 H, s), 7.39-7.67 (8 H, m) | A |
| 316 | | Free | 449[M + H]+<br>471[M + Na]+<br>447[M − H]− | ¹H NMR (600 MHz, CD₃OD) δ ppm 1.63-1.77 (2 H, m), 1.78-1.87 (2 H, m), 2.14-2.22 (2 H, m), [2.79] 2.80 (3 H, br. s.), 3.08 (3 H, s), 3.27-3.33 (1 H, m), 3.70 (2 H, s), 7.35-7.66 (8 H, m) | B |
| 317 | | Free | 463[M + H]+<br>485[M + Na]+<br>461[M − H]− | ¹H NMR (600 MHz, CD₃OD) δ ppm 1.39-1.48 (2 H, m), 1.53-1.62 (2 H, m), 1.69-1.78 (2 H, m), 1.89-1.97 (2 H, m), [2.79] 2.82 (3 H, br. s.), 3.08 (3 H, s), 3.11-3.14 (1 H, m), 3.81 (2 H, s), 7.37-7.64 (8 H, m) | NT |
| 318 | | Free | 477[M + H]+<br>499[M + Na]+<br>475[M − H]− | ¹H NMR (600 MHz, CD₃OD) δ ppm 1.13-1.35 (5 H, m), 1.65-1.67 (1 H, m), 1.75-1.82 (2 H, m), 1.98-2.00 (2 H, m), 2.52-2.56 (1 H, m), [2.79] 2.82 (3 H, s.), 3.08 (3 H, s), 3.85 (2 H, s), 7.37-7.64 (8 H, m) | B |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 319 | | Free | 424[M + H]+ 400[M − H]− | ¹H NMR (600 MHz, CD$_3$OD) δ ppm 2.80 (3 H, s), 3.09 (3 H, br. s.), 3.79 (3 H, s), 5.06 (2 H, s), 6.92-6.93 (2 H, m), 7.03-7.08 (2 H, m), 7.35-7.37 (2 H, m), 7.46-7.53 (2 H, m) | B |
| 320 | | Free | 478[M + Na]+ 454[M − H]− | ¹H NMR (600 MHz, CD$_3$OD) δ ppm 2.82 (3 H, br. s.), 3.08 (3 H, s), 3.61-3.73 (2 H, m), 3.93-4.05 (2 H, m), 4.06-4.14 (1 H, m), 6.98 (2 H, d, J = 9.2 Hz), 7.40-7.65 (6 H, m) | A |
| 321 | | Free | 465[M + H]+ 487[M + Na]+ 463[M − H]− | ¹H NMR (600 MHz, CD$_3$OD) δ ppm 1.46 (3 H, s), 2.82 (3 H, br. s.), 3.08 (3 H, s), 3.15 (2 H, d, J = 8.5 Hz), 3.35 (2 H, d, J = 8.5 Hz), 3.72 (2 H, s), 7.31-7.65 (8 H, m) | A |
| 322 | | Free | 477[M + H]+ 475[M − H]− | ¹H NMR (600 MHz, CD$_3$OD) δ ppm 2.82 (3 H, br. s.), 3.08 (3 H, s), 3.45 (4 H, s), 3.61 (2 H, s), 4.73 (4 H, s), 7.31 (2 H, d, J = 8.3 Hz), 7.46-7.64 (6 H, m) | A |
| 323 | | CF$_3$COOH | 481[M + H]+ | ¹H NMR (600 MHz, CD$_3$OD) δ ppm 1.25 (6 H, s), 1.84 (2 H, t, J = 7.5 Hz), 2.82 (3 H, br. s.), 3.07 (3 H, s), 3.21 (2 H, t, J = 7.5 Hz), 4.25 (2 H, s), 7.50-7.67 (8 H, m) | B |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 324 | | Free | 378[M + Na]+<br>394[M + K]+<br>354[M − H]− | ¹H NMR (600 MHz, CD₃OD) δ ppm 1.76 (3 H, s), 2.78 (3 H, s), 3.20 (3 H, s), 7.33-7.38 (1 H, m), 7.42-7.47 (2 H, m), 7.59-7.66 (4 H, m), 7.71 (2 H, d, J = 8.7 Hz) | A |
| 325 | | Free | 520[M + H]+<br>518[M − H]− | ¹H NMR (600 MHz, CD₃OD) δ ppm 1.74-1.80 (2 H, m), 1.98-2.06 (2 H, m), 2.34-2.39 (2 H, m), 2.56-2.61 (2 H, m), 2.82 (3 H, br. s.), 3.08 (3 H, s), 3.32-3.38 (20 H, m), 3.41-3.46 (2 H, m), 3.79 (2 H, s), 7.39 (2 H, d, J = 7.8 Hz), 7.49-7.64 (6 H, m) | NT |
| 326 | | CF₃COOH | 492[M + H]+<br>490[M − H]− | ¹H NMR (600 MHz, CD₃OD) δ ppm 2.05-2.17 (4 H, m), 2.82 (3 H, br. s.), 3.07 (3 H, s), 3.34-3.61 (8 H, m), 4.30 (2 H, s), 7.51-7.66 (8 H, m) | NT |
| 327 | | CF₃COOH | 491[M + H]+<br>513[M + Na]+<br>489[M − H]− | ¹H NMR (600 MHz, CD₃OD) δ ppm 1.21-2.19 (10 H, m), 2.70-2.76 (4 H, m), 2.82 (3 H, br. s.), 3.07 (3 H, s), 4.20 (1 H, d, J = 13.1 Hz), 4.53 (1 H, d, J = 13.1 Hz), 7.52-7.70 (8 H, m) | B |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 328 | | Free | 451[M + H]+<br>473[M + Na]+<br>449[M − H]− | ¹H NMR (600 MHz, CD$_3$OD) δ ppm 1.24 (9 H, s), [2.79] 2.82 (3 H, s), 3.06 (3 H, s), 3.80 (2 H, s), 7.38-7.63 (8 H, m) | B |
| 329 | | Free | 465[M + H]+<br>487[M + Na]+<br>463[M − H]− | ¹H NMR (600 MHz, CD$_3$OD) δ ppm 0.91 (9 H, s), 2.33 (2 H, s), 2.82 (3 H, br. s.), 3.08 (3 H, s), 3.81 (2 H, s), 7.37-7.40 (2 H, m), 7.42-7.64 (6 H, m) | A |
| 330 | | Free | 485[M + H]+<br>507[M + Na]+<br>483[M − H]− | ¹H NMR (600 MHz, CD$_3$OD) δ ppm 2.82 (3 H, br. s.) 3.08 (3 H, s) 3.75 (2 H, s) 3.77 (2 H, s) 7.23-7.64 (8 H, m) | A |
| 331 | | Free | 508[M + H]+<br>506[M − H]− | ¹H NMR (600 MHz, CD$_3$OD) δ ppm 2.40-2.46 (4 H, m), 2.52 (2 H, t, J = 6.4 Hz), 2.74 (2 H, t, J = 6.4 Hz), 2.82 (3 H, br. s.), 3.08 (3 H, s), 3.64-3.71 (4 H, m), 3.83 (2 H, s), 7.39 (2 H, d, J = 8.3 Hz), 7.48-7.67 (6 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 332 | | Free | 546[M + H]+ 544[M − H]− | ¹H NMR (600 MHz, CD$_3$OD) δ ppm 1.88-1.96 (2 H, m), 1.96-2.02 (2 H, m), 2.16-2.26 (2 H, m), 2.76-2.89 (8 H, m), 3.08 (3 H, s), 3.33-3.39 (4 H, m), 3.58 (2 H, s), 7.39 (2 H, d, J = 7.8 Hz), 7.47-7.65 (6 H, m) | NT |
| 333 | | Free | 465[M + H]+ 463[M − H]− | ¹H NMR (600 MHz, CD$_3$OD) δ ppm 1.69-1.77 (1 H, m), 2.11-2.19 (1 H, m), 2.49-2.60 (2 H, m), 2.73-2.85 (5 H, m), 3.08 (3 H, s), 3.64-3.74 (2 H, m), 4.32-4.39 (1 H, m), 7.39 (2 H, d, J = 8.3 Hz), 7.47-7.65 (6 H, m) | NT |
| 334 | | Free | 479[M + Na]+ 477[M − H]− | ¹H NMR (600 MHz, CD$_3$OD) δ ppm 1.62-2.20 (4 H, m), 2.82 (3 H, br. s.), 3.08 (3 H, s), 3.25-4.12 (4 H, m), 4.31-4.39 (3 H, m), 7.50-7.70 (8 H, m) | A |
| 335 | | Free | 478[M + Na]+ 454[M − H]− | ¹H NMR (600 MHz, CD$_3$OD) δ ppm 2.82 (3 H, br. s.), 3.08 (3 H, s), 3.71-3.82 (4 H, m), 4.39-4.45 (1 H, m), 7.04 (2 H, d, J = 8.7 Hz), 7.46 (2 H, d, J = 8.7 Hz), 7.50-7.61 (4 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 336 | | Free | 493[M + H]+ 515[M + Na]+ 491[M − H]− | ¹H NMR (600 MHz, CD$_3$OD) δ ppm 1.14-1.20 (3 H, m), 1.88-1.96 (2 H, m), 2.67-2.76 (4 H, m), 2.81 (3 H, br. s.), 3.46-3.57 (2 H, m), 3.68-3.76 (4 H, m), 3.79-3.85 (2 H, m), 7.40 (2 H, d, J = 8.3 Hz), 7.50 (2 H, d, J = 8.3 Hz), 7.53-7.65 (4 H, m) | A |
| 337 | | Free | 473[M + Na]+ 449[M − H]− | ¹H NMR (600 MHz, CD$_3$OD) δ ppm 2.82 (3 H, br. s.), 3.08 (3 H, s), 3.73 (2 H, s), 3.96-4.04 (1 H, m), 4.40-4.46 (2 H, m), 4.68-4.73 (2 H, m), 7.37 (2 H, d, J = 8.3 Hz), 7.50 (2 H, d, J = 7.8 Hz), 7.54-7.65 (4 H, m) | |
| 338 | | Free | 426[M + H]+ 448[M + Na]+ 424[M − H]− | ¹H NMR (600 MHz, CD$_3$OD) δ ppm 2.81 (3 H, s), 3.12 (3 H, br. s.), 3.25-3.47 (8 H, m), 6.83-6.89 (1 H, m), 6.98-7.08 (4 H, m), 7.22-7.29 (2 H, m), 7.36-7.57 (2 H, m) | |
| 339 | | Free | 574[M + Na]+ 550[M − H]− | ¹H NMR (600 MHz, CD$_3$OD) δ ppm 2.71-2.88 (6 H, m), 3.07 (6 H, br. s.), 3.81 (3 H, s), 7.35-7.72 (8 H, m) | |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 340 | 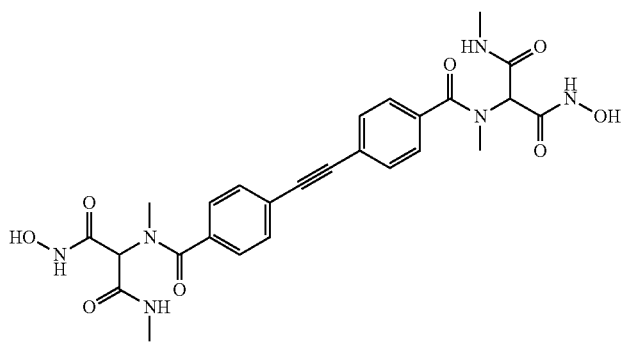 [SMILES: CNC(=O)C(C(=O)NO)N(C)C(=O)c1ccc(C#Cc2ccc(C(=O)N(C)C(C(=O)NC)C(=O)NO)cc2)cc1] | Free | 551[M − H]− | ¹H NMR (600 MHz, CD$_3$OD) δ ppm 2.80 (6 H, br. s.), 3.05 (6 H, br. s.), 7.36-7.53 (2 H, m), 7.53-7.69 (6 H, m) | |
| 341 | 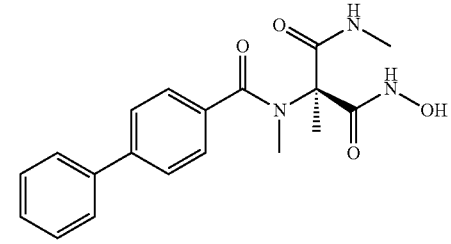 [SMILES: CNC(=O)[C@@](C)(C(=O)NO)N(C)C(=O)c1ccc(-c2ccccc2)cc1] | Free | 378[M + Na]+ 354[M − H]− | ¹H NMR (600 MHz, CHLOROFORM-d) δ ppm 1.84 (3 H, s), 2.86 (3 H, d, J = 5.0 Hz), 3.27 (3 H, s), 6.72-6.77 (1 H, m), 7.36-7.42 (1 H, m), 7.44-7.50 (2 H, m), 7.58-7.63 (4 H, m), 7.63-7.68 (2 H, m), 10.56-10.67 (1 H, m) | |
| 342 | 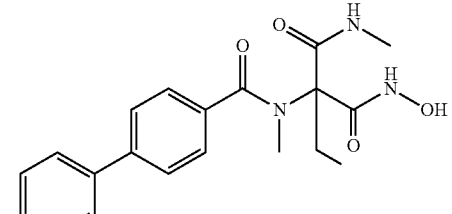 | Free | 392[M + Na]+ 368[M − H]− | ¹H NMR (600 MHz, CHLOROFORM-d) δ ppm 1.07 (3 H, t, J = 7.6 Hz), 2.11-2.32 (2 H, m), 2.85 (3 H, d, J = 5.0 Hz), 3.31 (3 H, s), 6.78 (1 H, br. s.), 7.36-7.49 (4 H, m), 7.60 (4 H, d, J = 7.8 Hz), 7.63-7.67 (2 H, m), 10.87 (1 H, br. s.) | |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 343 | | Free | 378[M + Na]+ 354[M − H]− | ¹H NMR (600 MHz, CHLOROFORM-d) δ ppm 1.84 (3 H, s), 2.86 (3 H, d, J = 5.0 Hz), 3.28 (3 H, s), 6.66-6.75 (1 H, m), 7.37-7.42 (1 H, m), 7.47 (2 H, t, J = 7.6 Hz), 7.58-7.63 (4 H, m), 7.64-7.68 (2 H, m), 10.65 (1 H, br. s) | C |
| 344 | | Free | 399[M + H]+ 421[M + Na]+ 397[M − H]− | ¹H NMR (600 MHz, CD₃OD) δ ppm [2.80] 2.84 (3 H, br. s.), 3.08 (3 H, s), 7.45-7.49 (1 H, m), 7.54-7.58 (1 H, m), 7.72-7.73 (2 H, m), 8.02-8.07 (2 H, m), 8.21-8.22 (2 H, m) | B |
| 345 | | Free | 402[M + Na]+ 378[M − H]− | ¹H NMR (600 MHz, CD₃OD) δ ppm 1.77 (3 H, s), 2.79 (3 H, s), 3.17 (3 H, s), 7.35-7.42 (3 H, m), 7.50-7.65 (6 H, m) | A |
| 346 | | Free | 493[M + H]+ 491[M − H]− | ¹H NMR (400 MHz, CD₃OD) δ ppm 1.77 (3 H,s), 1.87-1.95 (2 H, m), 2.67-2.75 (4 H, m), 2.79 (3 H, s), 3.17 (3 H, s), 3.67-3.75 (2 H, m), 3.70 (2 H, s), 3.78-3.83 (2 H, m), 7.40 (2 H, d, J = 8.0 Hz), 7.47-7.52 (2 H, m), 7.53-7.63 (4 H, m) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 347 | | Free | 405[M + Na]+ 381[M − H]− | ¹H NMR (600 MHz, CD$_3$OD) δ ppm 2.84 (3 H, s), 3.12 (3 H, s), 7.41-7.48 (2 H, m), 7.68-7.80 (4 H, m), 8.35-8.36 (2 H, m) | C |
| 348 | | Free | 408[M + Na]+ 384[M − H]− | ¹H NMR (600 MHz, CD$_3$OD) δ ppm 1.78 (3 H, s), 2.80 (3 H, s), 3.21 (3 H, s), 3.84 (3 H, s), 6.97-7.05 (2 H, m), 7.55-7.71 (6 H, m) | A |
| 349 | | Free | 392[M + Na]+ 368[M − H]− | ¹H NMR (600 MHz, CD$_3$OD) δ ppm 1.78 (3 H, s), 2.38 (3 H, s), 2.80 (3 H, s), 3.21 (3 H, s), 7.24-7.31 (2 H, m), 7.51-7.73 (6 H, m) | A |
| 350 | | Free | 499[M + H]+ 521[M + Na]+ 497[M − H]− | ¹H NMR (600 MHz, CD$_3$OD) δ ppm 1.78 (3 H, s), 1.97-2.06 (2 H, m), 2.49-2.55 (4 H, m), 2.56-2.61 (2 H, m), 2.80 (3 H, s), 3.21 (3 H, s), 3.69-3.76 (4 H, m), 4.06-4.13 (2 H, m), 7.02 (2 H, d, J = 8.7 Hz), 7.57-7.63 (4 H, m), 7.68 (2 H, d, J = 8.3 Hz) | A |
| 351 | | Free | 528[M + Na]+ 504[M − H]− | ¹H NMR (600 MHz, CD$_3$OD) δ ppm 1.78 (3 H, s), 2.80 (3 H, s), 3.21 (3 H, s), 3.81-3.90 (2 H, m), 4.11-4.27 (2 H, m), 4.63 (2 H, s), 7.01-7.73 (13 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 352 | | Free | 442[M + Na]+ 418[M − H]− | ¹H NMR (600 MHz, CD₃OD) δ ppm 2.84 (3 H, br. s.), 3.11 (3 H, s), 3.16 (3 H, s), 7.46-8.08 (8 H, m) | B |
| 353 | | Free | 493[M + Na]+ 469[M − H]− | ¹H NMR (600 MHz, CD₃OD) δ ppm 2.82 (3 H, br. s.), 3.08 (3 H, s), 3.59-3.67 (4 H, m), 3.79 (2 H, s), 7.36 (2 H, d, J = 7.8 Hz), 7.51 (2 H, d, J = 7.8 Hz), 7.54-7.65 (4 H, m) | NT |
| 354 | | Free | 513[M + H]+ 511[M − H]− | ¹H NMR (600 MHz, CD₃OD) δ ppm 1.83-1.91 (2 H, m), 2.63-2.69 (4 H, m), 2.82 (3 H, br. s.), 3.08 (3 H, s), 3.81 (2 H, s), 7.12-7.20 (3 H, m), 7.22-7.27 (2 H, m), 7.36 (2 H, d, J = 8.3 Hz), 7.51 (2 H, d, J = 7.8 Hz), 7.53-7.64 (4 H, m) | NT |
| 355 | | Free | 481[M + H]+ 503[M + Na]+ 479[M − H]− | ¹H NMR (600 MHz, CD₃OD) δ ppm 1.07 (3 H, t, J = 7.0 Hz), 2.59 (2 H, q, J = 7.0 Hz), 2.67 (2 H, t, J = 6.0 Hz), [2.77], 2.82 (3 H, br. s.), 3.06 (3 H, s), 3.30 (3 H, s), 3.50 (2 H, t, J = 6.0 Hz), 3.67 (2 H, s), 7.35-7.63 (8 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 356 | | Free | 489[M + H]+<br>501[M + Na]+<br>487[M − H]− | ¹H NMR (600 MHz, CD$_3$OD) δ ppm 2.82 (3 H, br. s.), 3.08 (3 H, s), 3.68 (3 H, s), 3.80 (2 H, s), 3.83 (2 H, s), 6.86-7.00 (2 H, m), 7.37-7.63 (8 H, m) | NT |
| 357 | | Free | 449[M + H]+<br>471[M + Na]+<br>447[M − H]− | ¹H NMR (600 MHz, CD$_3$OD) δ ppm 0.31-0.42 (4 H, m), 1.39 (3 H, d, J = 6.9 Hz), 1.96 (1 H, m), 2.82 (3 H, br. s.), 3.08 (3 H, s), 3.90 (1 H, q, J = 6.9 Hz), 7.39-7.62 (8 H, m) | NT |
| 358 | | Free | 409[M + H]+<br>407[M − H]− | ¹H NMR (600 MHz, CD$_3$OD) δ ppm 1.62 (3 H, d, J = 6.9 Hz), 2.82 (3 H, br. s.), 3.08 (3 H, s), 4.45 (1 H, q, J = 6.9 Hz), 7.43-7.67 (8 H, m) | B |
| 359 | | Free | 501[M + H]+<br>523[M + Na]+<br>499[M − H]− | ¹H NMR (600 MHz, CD$_3$OD) δ ppm 2.54 (3 H, s), 2.82 (3 H, br. s.), 3.08 (3 H, s), 3.84 (2 H, s), 3.91 (2 H, s), 7.39 (2 H, d, J = 8.3 Hz), 7.47-7.64 (6 H, m), 8.49 (1 H, s), 8.50 (1 H, s) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 360 | | Free | 487[M + H]+ 509[M + Na]+ 485[M − H]− | ¹H NMR (600 MHz, CD₃OD) δ ppm 2.82 (3 H, br. s.), 3.08 (3 H, s), 3.89 (2 H, s), 4.02 (2 H, s), 7.36-7.44 (3 H, m), 7.47-7.65 (6 H, m), 8.77 (2 H, d, J = 5.0 Hz) | NT |
| 361 | | Free | 505[M + H]+ 527[M + Na]+ 503[M − H]− | ¹H NMR (600 MHz, CD₃OD) δ ppm 2.82 (3 1.44-1.78 (13 H, m), 2.44 (2 H, d, J = 6.9 Hz), [2.79], 2.82 (3 H, br. s.), 3.08 (3 H, s), 3.78 (2 H, s), 7.37-7.63 (8 H, m) | NT |
| 362 | | Free | 491[M + H]+ 513[M + Na]+ 489[M − H]− | ¹H NMR (600 MHz, CD₃OD) δ ppm 0.86-1.81 (11 H, m), 2.44 (2 H, d, J = 6.4 Hz), 2.82 (3 H, br. s.), 3.08 (3 H, s), 3.79 (2 H, s), 7.37-7.62 (8 H, m) | NT |
| 363 | | Free | 486[M + H]+ 484[M − H]− | ¹H NMR (600 MHz, CD₃OD) δ ppm 2.79 (3 H, br. s.), 3.05 (3 H, s), 3.82 (2 H, s), 3.89 (2 H, s), 7.29-7.63 (10 H, m), 7.79-7.83 (1 H, m), 8.50-8.51 (1 H, m) | NT |
| 364 | | Free | 466[M + Na]+ 442[M − H]− | ¹H NMR (600 MHz, CD₃OD) δ ppm 1.67-1.74 (2 H, m), 1.76 (3 H, s), 1.82-1.89 (2 H, m), 2.78 (3 H, s), 3.20 (3 H, s), 3.62 (2 H, t, J = 6.6 Hz), 4.04 (2 H, t, J = 6.2 Hz), 6.99 (2 H, d, J = 8.7 Hz), 7.54-7.60 (4 H, m), 7.66 (2 H, d, J = 8.7 Hz) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 365 | | Free | 485[M + H]+ 507[M + Na]+ 483[M − H]− | ¹H NMR (600 MHz, CD$_3$OD) δ ppm 2.22-2.33 (2 H, m), 2.71-2.92 (7 H, m), 3.08 (3 H, s), 3.67 (2 H, s), 7.38 (2 H, d, J = 7.8 Hz), 7.51 (2 H, d, J = 7.8 Hz), 7.54-7.65 (4 H, m) | NT |
| 366 | | Free | 511[M + H]+ 509[M − H]− | ¹H NMR (600 MHz, CD$_3$OD) δ ppm 2.70-2.76 (4 H, m), 2.82 (3 H, br. s.), 3.08 (3 H, s), 3.36 (6 H, br. s.), 3.47-3.53 (4 H, m), 3.74 (2 H, s), 7.40 (2 H, d, J = 7.8 Hz), 7.48 (2 H, d, J = 7.8 Hz), 7.52-7.65 (4 H, m) | NT |
| 367 | | Free | 479[M + H]+ 501[M + Na]+ 477[M − H]− | ¹H NMR (600 MHz, CD$_3$OD) δ ppm 1.38 (3 H, d, J = 6.4 Hz), 2.33-2.40 (2 H, m), 2.49-2.56 (2 H, m), 2.82 (3 H, br. s.), 3.08 (3 H, s), 3.38 (1 H, q, J = 6.4 Hz), 3.64-3.70 (4 H, m), 7.36-7.63 (8 H, m) | A |
| 368 | | Free | 513[M + H]+ 511[M − H]− | ¹H NMR (600 MHz, CD$_3$OD) δ ppm 2.30 (3 H, s), 2.62-2.67 (2 H, m), 2.77-2.85 (5 H, m), 3.08 (3 H, s), 3.61 (2 H, s), 7.15-7.64 (13 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 369 | 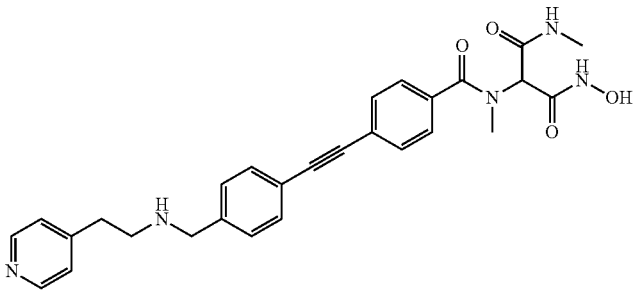 [SMILES: CNC(=O)C(C(=O)NO)N(C)C(=O)c1ccc(C#Cc2ccc(CNCCc3ccncc3)cc2)cc1] | Free | 500[M + H]+<br>498[M − H]− | ¹H NMR (600 MHz, CD$_3$OD) δ ppm 2.82 (3 H, br. s.), 2.85-2.90 (4 H, m), 3.08 (3 H, s), 3.81 (2 H, s), 7.30-7.31 (2 H, m), 7.34-7.38 (2 H, m), 7.49-7.63 (6 H, m), 8.41-8.42 (2 H, m) | NT |
| 370 | 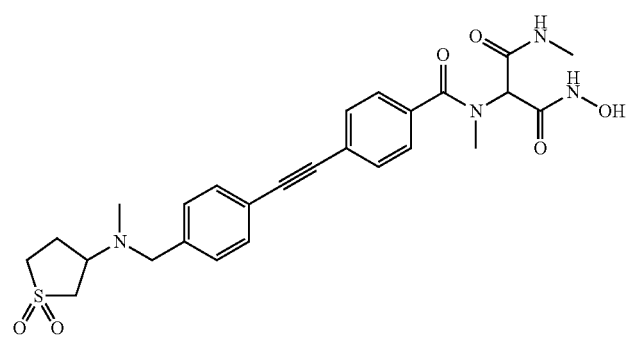 [SMILES: CNC(=O)C(C(=O)NO)N(C)C(=O)c1ccc(C#Cc2ccc(CN(C)C3CCS(=O)(=O)C3)cc2)cc1] | Free | 527[M + H]+<br>549[M + Na]+<br>525[M − H]− | ¹H NMR (600 MHz, CD$_3$OD) δ ppm 2.18-2.26 (1 H, m), 2.23 (3 H, s), 2.42-2.46 (1 H, m), 2.82 (3 H, br. s.), 3.05-3.14 (5 H, m), 3.23-3.33 (2 H, m), 3.52-3.58 (1 H, m), 3.59-3.68 (2 H, m), 7.36-7.63 (8 H, m) | NT |
| 371 | 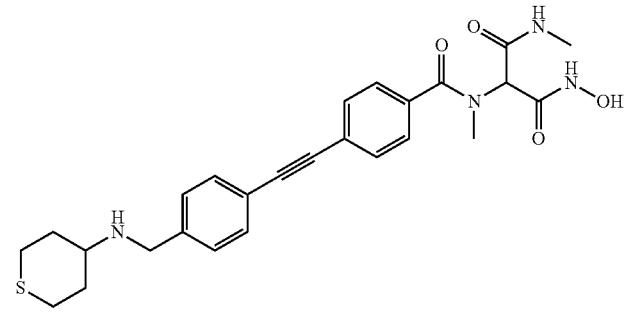 [SMILES: CNC(=O)C(C(=O)NO)N(C)C(=O)c1ccc(C#Cc2ccc(CNC3CCSCC3)cc2)cc1] | Free | 495[M + H]+<br>493[M − H]− | ¹H NMR (600 MHz, CD$_3$OD) δ ppm 1.51-1.62 (2 H, m), 2.22-2.29 (2 H, m), 2.51-2.59 (1 H, m), 2.61-2.68 (4 H, m), 2.82 (3 H, br. s.), 3.08 (3 H, s), 3.86 (2 H, s), 7.40 (2 H, d, J = 8.3 Hz), 7.47-7.64 (6 H, m) | NT |
| 372 | 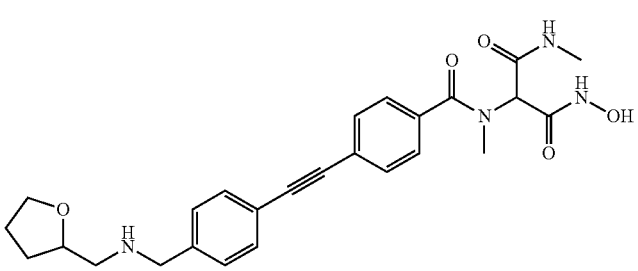 [SMILES: CNC(=O)C(C(=O)NO)N(C)C(=O)c1ccc(C#Cc2ccc(CNCC3CCCO3)cc2)cc1] | Free | 479[M + H]+<br>477[M − H]− | ¹H NMR (600 MHz, CD$_3$OD) δ ppm 1.50-1.60 (1 H, m), 1.86-1.94 (2 H, m), 1.98-2.06 (1 H, m), 2.60-2.72 (2 H, m), 2.82 (3 H, br. s.), 3.08 (3 H, s), 3.70-3.78 (1 H, m), 3.80-3.88 (3 H, m), 4.00-4.07 (1 H, m), 7.39 (2 H, d, J = 8.3 Hz), 7.48-7.65 (6 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | $^1$H-NMR | Enzyme inhibitory activity |
|---|---|---|---|---|---|
| 373 | | Free | 506[M + H]+<br>504[M − H]− | $^1$H NMR (600 MHz, CD$_3$OD) δ ppm 2.08 (3 H, s), 2.40-2.52 (4 H, m), 2.82 (3 H, br. s.), 3.08 (3 H, s), 3.52-3.62 (6 H, m), 7.36-7.64 (8 H, m) | NT |
| 374 | | Free | 486[M + H]+<br>484[M − H]− | $^1$H NMR (600 MHz, CD$_3$OD) δ ppm 2.82 (3 H, br. s.), 3.08 (3 H, s), 3.78-3.84 (4 H, m), 7.36-7.65 (9 H, m), 7.80-7.91 (1 H, m), 8.40-8.47 (1 H, m), 8.49-8.56 (1 H, m) | NT |
| 375 | | Free | 465[M + H]+<br>487[M + Na]+<br>463[M − H]− | $^1$H NMR (600 MHz, CD$_3$OD) δ ppm 2.82 (3 H, s), 2.50 (4 H, m), 2.82 (3 H, br. s.), 3.08 (3 H, s), 3.54 (2 H, s), 3.69-3.71 (4 H, m), 7.35-7.62 (8 H, m) | B |
| 376 | | Free | 493[M + H]+<br>491[M − H]− | $^1$H NMR (600 MHz, CD$_3$OD) δ ppm 2.82 (3 H, s), 1.89-1.95 (2 H, m), 2.69-2.76 (4 H, m), 2.79 (3 H, s), 3.17 (3 H, s), 3.71 (2 H, s), 3.71-3.75 (2 H, m), 3.81 (2 H, t, J = 6.0 Hz), 7.36-7.62 (8 H, m) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 377 | | Free | 493[M + H]+<br>491[M − H]− | ¹H NMR (600 MHz, CD$_3$OD) δ ppm 1.77 (3 H, s), 1.89-1.95 (2 H, m), 2.69-2.76 (4 H, m), 2.79 (3 H, s), 3.17 (3 H, s), 3.71 (2 H, s), 3.71-3.75 (2 H, m), 3.81 (2 H, t, J = 6.0 Hz), 7.36-7.62 (8 H, m) | A |
| 378 | | Free | 501[M + H]+<br>523[M + Na]+<br>499[M − H]− | ¹H NMR (600 MHz, CD$_3$OD) δ ppm 2.82 (3 H, br. s.), 3.02 (3 H, s), 3.06-3.09 (4 H, m), 3.08 (3 H, s), 3.82 (2 H, s), 7.38-7.62 (8 H, m) | A |
| 379 | | Free | 435[M + H]+<br>433[M − H]− | ¹H NMR (600 MHz, CD$_3$OD) δ ppm 0.38-0.47 (4 H, m), 2.20-2.22 (1 H, m), 2.80 (3 H, br. s.), 3.15 (3 H, s), 3.80 (2 H, s), 7.33-7.60 (8 H, m) | B |
| 380 | | Free | 479[M + H]+<br>477[M − H]− | ¹H NMR (600 MHz, CD$_3$OD) δ ppm 1.77 (3 H, s), 1.88-1.95 (2 H, m), 2.68-2.75 (4 H, m), 2.77 (3 H, s), 3.69-3.75 (4 H, m), 3.79-3.84 (2 H, m), 7.41 (2 H, d, J = 8.3 Hz), 7.51 (2 H, d, J = 8.3 Hz), 7.62 (2 H, d, J = 8.7 Hz), 7.92 (2 H, d, J = 8.7 Hz) | B |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 381 | | Free | 509[M + H]+<br>507[M − H]− | ¹H NMR (600 MHz, CD$_3$OD) δ ppm 1.95 (2 H, quin, J = 5.8 Hz), 2.82 (3 H, br. s.), 2.88-2.92 (4 H, m), 3.02 (2 H, t, J = 5.8 Hz), 3.08 (3 H, s), 3.76 (2 H, m), 3.80 (2 H, t, J = 6.0 Hz), 4.17 (2 H, t, J = 5.8 Hz), 6.95-6.99 (2 H, m), 7.45-7.59 (6 H, m) | A |
| 382 | | Free | 495[M + H]+<br>493[M − H]− | ¹H NMR (600 MHz, CD$_3$OD) δ ppm 2.59-2.61 (4 H, m), 2.81-2.83 (5 H, m), 3.08 (3 H, s), 3.68-3.73 (4 H, m), 4.18 (2 H, t, J = 5.4 Hz), 6.94-6.99 (2 H, m), 7.46-7.47 (2 H, m), 7.50-7.61 (4 H, m) | A |
| 383 | | Free | 493[M + H]+<br>491[M − H]− | ¹H NMR (600 MHz, CD$_3$OD) δ ppm 1.50-1.68 (2 H, m), 1.84-1.97 (2 H, m), 2.19-2.34 (2 H, m), 2.68-2.88 (5 H, m), 3.08 (3 H, s), 3.21-3.36 (4 H, m), 3.57 (2 H, s), 7.32-7.66 (8 H, m) | A |
| 384 | | Free | 493[M + H]+<br>491[M − H]− | ¹H NMR (600 MHz, CD$_3$OD) δ ppm 1.11 (6 H, d, J = 30.6 Hz), 1.77 (2 H, t, J = 10.8 Hz), 2.74 (2 H, d, J = 10.8 Hz), 2.82 (3 H, br. s.), 3.08 (3 H, s), 3.53 (2 H, s), 3.63-3.73 (2 H, m), 7.30-7.69 (8 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 385 | | Free | 447[M + H]+ 469[M + Na]+ 445[M − H]− | ¹H NMR (600 MHz, CD₃OD) δ ppm 0.51-0.59 (4 H, m), 2.13 (1 H, m), 2.82 (3 H, br. s.), 3.08 (3 H, s), 4.07-4.08 (4 H, m), 7.26-7.29 (1 H, m), 7.38-7.45 (2 H, m), 7.52-7.64 (4 H, m) | A |
| 386 | | Free | 531[M + H]+ 529[M − H]− | ¹H NMR (600 MHz, CD₃OD) δ ppm m 1.59-1.69 (2 H, m), 1.84-1.93 (2 H, m), 2.09-2.27 (3 H, m), 2.83 (3 H, br. s.), 3.00-3.07 (2 H, m), 3.09 (3 H, s), 3.63 (2 H, s), 7.37-7.64 (8 H, m) | NT |
| 387 | | Free | 531[M + H]+ 553[M + Na]+ 529[M − H]− | ¹H NMR (600 MHz, CD₃OD) δ ppm 1.28-1.35 (1 H, m), 1.58-1.64 (1 H, m), 1.76-1.79 (1 H, m), 1.93-2.03 (3 H, m), 2.36-2.44 (1 H, m), 2.82 (3 H, br. s.), 2.87-2.89 (1 H, m) 3.02-3.04 (1 H, m), 3.08 (3 H, s), 3.59 (2 H, s), 7.36-7.62 (8 H, m) | NT |
| 388 | | Free | 493[M + H]+ 491[M − H]− | ¹H NMR (600 MHz, CD₃OD) δ ppm 0.37-0.53 (4 H, m), 1.81-1.88 (1 H, m), 2.75 (2 H, s), 2.82 (3 H, br. s.), 3.08 (3 H, s), 3.29 (3 H, s), 3.50-3.57 (2 H, m), 3.82 (2 H, s), 7.35 (2 H, d, J = 8.3 Hz), 7.43-7.64 (6 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 389 | | Free | 396[M + H]+<br>418[M + Na]+<br>394[M − H]− | ¹H NMR (600 MHz, CD$_3$OD) δ ppm 2.78 (3 H, br. s.), 3.11 (3 H, s), 4.42 (2 H, s), 7.51-7.75 (8 H, m) | A |
| 390 | | Free | 465[M + H]+<br>487[M + Na]+<br>463[M − H]− | ¹H NMR (600 MHz, CD$_3$OD) δ ppm 2.65-2.72 (4 H, m), 2.83 (3 H, br. s.), 3.11 (3 H, s), 3.57 (2 H, s), 3.74-3.76 (4 H, m), 7.51-7.55 (2 H, m), 7.61-7.67 (4 H, m), 7.74-7.76 (2 H, m) | A |
| 391 | | Free | 478[M + H]+<br>500[M + Na]+<br>476[M − H]− | ¹H NMR (600 MHz, CD$_3$OD) δ ppm 2.62-2.72 (2 H, m), 2.68 (2 H, m), 2.82 (3 H, br. s.), 3.31-3.34 (2 H, m), 3.09 (3 H, s), 3.64 (2 H, s), 7.38-7.64 (8 H, m) | NT |
| 392 | | Free | 521[M + H]+<br>519[M − H]− | ¹H NMR (600 MHz, CD$_3$OD) δ ppm 1.68-1.69 (4 H, m), 2.50-2.57 (4 H, m), 2.77 (3 H, br. s.), 3.03 (3 H, s), 3.55 (2 H, s), 3.87 (4 H, s), 7.31-7.60 (8 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 393 | | Free | 479[M + H]+ 477[M − H]− | ¹H NMR (600 MHz, CD$_3$OD) δ ppm 1.75-1.86 (1 H, m), 2.05-2.15 (1 H, m), 2.48-2.67 (2 H, m), 2.68-2.77 (2 H, m), 2.82 (3 H, br. s.), 3.08 (3 H, s), 3.26 (3 H, s), 3.60-3.75 (2 H, m), 3.93-4.00 (1 H, m), 7.34-7.67 (8 H, m) | NT |
| 394 | | Free | 421[M + H]+ 419[M − H]− | ¹H NMR (600 MHz, CD$_3$OD) δ ppm 0.99-1.05 (2 H, m), 1.06-1.14 (2 H, m), 2.82 (3 H, br. s.), 3.08 (3 H, s), 7.29-7.66 (8 H, m) | B |
| 395 | | Free | 494[M + H]+ | ¹H NMR (600 MHz, CD$_3$OD) δ ppm 2.82 (3 H, br. s.), 3.06 (4 H, s), 3.53-4.05 (6 H, m), 7.33-7.66 (8 H, m) | NT |
| 396 | | Free | 465[M + H]+ 463[M − H]− | ¹H NMR (600 MHz, CD$_3$OD) δ ppm 1.77 (3 H, s), 2.79 (3 H, s), 3.14-3.19 (3 H, m), 3.72 (2 H, s), 3.95-4.04 (1 H, m), 4.39-4.48 (2 H, m), 4.66-4.73 (2 H, m), 7.37 (2 H, d, J = 8.3 Hz), 7.51 (2 H, d, J = 8.3 Hz), 7.54-7.64 (4 H, m) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 397 | | Free | 479[M + H]+ 477[M − H]− | ¹H NMR (600 MHz, CD$_3$OD) δ ppm 1.77 (3 H, s), 2.08 (3 H, s), 2.77-2.81 (3 H, m), 3.17 (3 H, s), 3.43 (2 H, s), 3.64-3.72 (1 H, m), 4.54-4.66 (4 H, m), 7.38 (2 H, d, J = 7.8 Hz), 7.48-7.64 (6 H, m) | NT |
| 398 | | Free | 428[M + Na]+ 404[M − H]− | ¹H NMR (600 MHz, CD$_3$OD) δ ppm 0.73-0.91 (4 H, m), 1.45-1.51 (1 H, m), 2.82 (3 H, br. s.), 3.11 (3 H, s), 7.39-7.75 (8 H, m) | NT |
| 399 | | Free | 422[M + Na]+ 398[M − H]− | ¹H NMR (600 MHz, CD$_3$OD) δ ppm 1.41 (3 H, t, J = 6.9 Hz), 1.78 (3 H, s), 2.80 (3 H, s), 3.21 (3 H, s), 4.08 (2 H, q, J = 6.9 Hz), 6.94-7.05 (2 H, m), 7.51-7.73 (6 H, m) | NT |
| 400 | | Free | 509[M + H]+ 507[M − H]− | ¹H NMR (600 MHz, CD$_3$OD) δ ppm 2.43-2.51 (4 H, m), 2.53-2.61 (2 H, m), 2.74 (3 H, br. s.), 3.02 (3 H, s), 3.57-3.65 (4 H, m), 3.65-3.72 (2 H, m), 4.33 (2 H, s), 7.38-7.72 (8 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 401 | | Free | 433[M + Na]+<br>409[M − H]− | ¹H NMR (600 MHz, CD$_3$OD) δ ppm 1.77 (3 H, s), 2.79 (3 H, s), 2.79 (3 H, s), 2.98 (2 H, t, J = 8.1 Hz), 3.22 (3 H, s), 3.33 (2 H, t, J = 8.1 Hz), 6.51-6.64 (1 H, m), 7.33-7.68 (6 H, m) | NT |
| 402 | | Free | 431[M + Na]+<br>407[M − H]− | ¹H NMR (600 MHz, CD$_3$OD) δ ppm 1.79 (3 H, s), 2.81 (3 H, s), 3.24 (3 H, s), 3.84 (3 H, s), 6.50 (1 H, d, J = 3.1 Hz), 7.19 (1 H, d, J = 3.1 Hz), 7.39-7.87 (7 H, m) | NT |
| 403 | | Free | 446[M + Na]+<br>422[M − H]− | ¹H NMR (600 MHz, CD$_3$OD) δ ppm 1.77 (3 H, s), 2.80 (3 H, br. s.), 3.17 (3 H, s), 3.39 (3 H, s), 4.47 (2 H, s), 7.36-7.37 (2 H, m), 7.52-7.53 (2 H, m), 7.55-7.58 (2 H, m), 7.59-7.62 (2 H, m) | NT |
| 404 | | Free | 435[M + H]+<br>433[M − H]− | ¹H NMR (600 MHz, CD$_3$OD) δ ppm 1.00-1.05 (2 H, m), 1.07-1.13 (2 H, m), 1.77 (3 H, s), 2.79 (3 H, s), 3.17 (3 H, s), 7.32-7.39 (2 H, m), 7.43-7.63 (6 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | $^1$H-NMR | Enzyme inhibitory activity |
|---|---|---|---|---|---|
| 405 | | Free | 432[M + Na]+ 408[M − H]− | $^1$H NMR (600 MHz, CD$_3$OD) δ ppm 2.83 (3 H, br. s.), 3.11 (3 H, s), 3.44 (3 H, s), 4.35 (2 H, s), 7.51-7.56 (2 H, m), 7.61-7.68 (4 H, m,) 7.75-7.76 (2 H, m,) | A |
| 406 | | Free | 424[M + Na]+ 400[M − H]− | $^1$H NMR (600 MHz, CD$_3$OD) δ ppm 1.78 (3 H, s), 2.52 (3 H, s), 2.80 (3 H, s), 3.21 (3 H, s), 7.31-7.39 (2 H, m), 7.56-7.75 (6 H, m) | NT |
| 407 | | Free | 424[M + H]+ 422[M − H]− | $^1$H NMR (600 MHz, CD$_3$OD) δ ppm 1.00 (3 H, t, J = 7.4 Hz), 1.59-1.68 (2 H, m), 2.80 (3 H, s), 3.06 (3 H, s), 3.09 (2 H, t, J = 7.0 Hz), 6.95 (1 H, dd, J = 8.7, 2.5 Hz), 7.36 (1 H, d, J = 8.7 Hz), 7.40-7.56 (2 H, m), 7.59 (2 H, d, J = 7.4 Hz), 7.89 (1 H, d, J = 2.5 Hz) | B |
| 408 | | Free | 435[M + Na]+ 411[M − H]− | $^1$H NMR (600 MHz, CD$_3$OD) δ ppm 1.78 (3 H, s), 2.80 (3 H, s), 3.21 (3 H, s), 3.95 (3 H, s), 7.63-7.74 (6 H, m), 7.77 (2 H, d, J = 8.3 Hz), 8.13 (1 H, s) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 409 | | Free | 495[M + H]+<br>493[M − H]− | ¹H NMR (600 MHz, CD$_3$OD) δ ppm 1.78 (3 H, s), 1.79-2.00 (4 H, m), 2.38-2.45 (2 H, m), 2.57-2.65 (2 H, m), 2.79 (3 H, s), 3.17 (3 H, s), 3.56 (2 H, s), 4.58-4.72 (1 H, m), 7.38 (2 H, d, J = 8.3 Hz), 7.51 (2 H, d, J = 8.3 Hz), 7.54-7.63 (4 H, m) | NT |
| 410 | | Free | 493[M + H]+<br>491[M − H]− | ¹H NMR (600 MHz, CD$_3$OD) δ ppm 1.77 (3 H, s), 2.51-2.58 (4 H, m), 2.60-2.65 (2 H, m), 2.79 (3 H, s), 2.83-2.89 (2 H, m), 3.17 (3 H, s), 3.68-3.75 (4 H, m), 7.27 (2 H, d, J = 8.3 Hz), 7.46 (2 H, d, J = 7.8 Hz), 7.52-7.62 (4 H, m) | NT |
| 411 | | Free | 422[M + Na]+<br>398[M − H]− | ¹H NMR (600 MHz, CD$_3$OD) δ ppm 1.78 (3 H, s), 2.79 (3 H, s), 3.20 (3 H, s), 5.99 (2 H, s), 6.83-6.96 (1 H, m), 7.05-7.27 (2 H, m), 7.51-7.70 (4 H, m) | NT |
| 412 | | Free | 408[M + Na]+<br>384[M − H]− | ¹H NMR (600 MHz, CD$_3$OD) δ ppm 1.78 (3 H, s), 2.80 (3 H, s), 3.21 (3 H, s), 3.84 (3 H, s), 6.97-7.06 (2 H, m), 7.56-7.72 (6 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 413 | | Free | 436[M + Na]+<br>412[M − H]− | ¹H NMR (600 MHz, CD$_3$OD) δ ppm 1.78 (3 H, s), 2.80 (3 H, s), 3.21 (3 H, s), 4.28 (4 H, s), 6.87-6.95 (1 H, m), 7.09-7.18 (2 H, m), 7.54-7.69 (4 H, m) | NT |
| 414 | | Free | 423[M + H]+<br>421[M − H]− | ¹H NMR (600 MHz, CD$_3$OD) δ ppm 1.77 (3 H, s), 2.42 (3 H, s), 2.79 (3 H, s), 3.17 (3 H, s), 3.78 (2 H, s), 7.35-7.64 (8 H, m) | NT |
| 415 | | Free | 396[M + Na]+<br>372[M − H]− | ¹H NMR (600 MHz, CD$_3$OD) δ ppm 1.77 (3 H, s), 2.80 (3 H, s), 3.21 (3 H, s), 7.13-7.74 (8 H, m) | NT |
| 416 | | Free | 491[M + H]+<br>489[M − H]− | ¹H NMR (600 MHz, CD$_3$OD) δ ppm 1.77 (3 H, s), 2.79 (3 H, s), 3.17 (3 H, s), 3.43-3.50 (4 H, m), 3.61 (2 H, s), 4.71-4.75 (4 H, m), 7.31 (2 H, d, J = 8.3 Hz), 7.50 (2 H, d, J = 8.3 Hz), 7.54-7.63 (4 H, m) | NT |
| 417 | | Free | 489[M + H]+<br>487[M − H]− | ¹H NMR (600 MHz, CD$_3$OD) δ ppm 1.77 (3 H, s), 2.79 (3 H, s), 3.17 (3 H, s), 3.71-3.83 (4 H, m), 6.23-6.41 (2 H, m), 7.37 (2 H, d, J = 7.8 Hz), 7.43-7.68 (7 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 418 | | Free | 392[M + Na]+ 368[M − H]− | ¹H NMR (600 MHz, CD$_3$OD) δ ppm 2.82 (3 H, br. s.), 3.08 (3 H, s), 3.91 (3 H, s), 6.49 (1 H, d, J = 1.7 Hz), 7.39-7.66 (5 H, m) | C |
| 419 | | Free | 500[M + H]+ 498[M − H]− | ¹H NMR (600 MHz, CD$_3$OD) δ ppm 1.77 (3 H, s), 2.79 (3 H, s), 3.17 (3 H, s), 3.78-3.83 (4 H, m), 7.36-7.45 (3 H, m), 7.49-7.64 (6 H, m), 7.83-7.89 (1 H, m), 8.44 (1 H, dd, J = 5.0, 1.6 Hz), 8.50-8.54 (1 H, m) | NT |
| 420 | | Free | 456[M + Na]+ 432[M − H]− | ¹H NMR (600 MHz, CD$_3$OD) δ ppm 2.82 (3 H, br. s.), 3.08 (3 H, s), 7.54-7.75 (8 H, m) | B |
| 421 | | Free | 500[M + H]+ 498[M − H]− | ¹H NMR (600 MHz, CD$_3$OD) δ ppm 1.77 (3 H, s), 2.79 (3 H, s), 3.17 (3 H, s), 3.85 (2 H, s), 3.92 (2 H, s), 7.27-7.65 (10 H, m), 7.77-7.84 (1 H, m), 8.49-8.53 (1 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 422 | | Free | 494[M + Na]+ 470[M − H]− | ¹H NMR (600 MHz, CD$_3$OD) δ ppm 1.77 (3 H, s), 2.79 (3 H, s), 2.88-2.92 (3 H, m), 3.17 (3 H, s), 4.47 (2 H, s), 7.49 (2 H, d, J = 7.8 Hz), 7.55-7.65 (6 H, m) | A |
| 423 | | Free | 406[M + Na]+ 382[M − H]− | ¹H NMR (300 MHz, CD$_3$OD) δ ppm 1.26 (3 H, t, J = 7.6 Hz), 1.78 (3 H, s), 2.69 (2 H, q, J = 7.6 Hz), 2.80 (3 H, s), 3.21 (3 H, s), 7.30 (2 H, d, J = 8.4 Hz), 7.54-7.64 (4 H, m), 7.68-7.74 (2 H, m) | NT |
| 424 | | Free | 391[M + Na]+ 367[M − H]− | ¹H NMR (600 MHz, CD$_3$OD) δ ppm 2.82 (3 H, br. s.), 3.08 (3 H, s), 3.66 (3 H, s), 6.20-6.21 (1 H, m), 6.61-6.62 (1 H, m), 6.95-6.96 (1 H, m), 7.46-7.52 (4 H, m) | B |
| 425 | | Free | 483[M + H]+ 481[M − H]− | ¹H NMR (600 MHz, CD$_3$OD) δ ppm 1.75 (3 H, s), 2.38-2.48 (4 H, m), 2.78 (3 H, s), 2.88-3.00 (4 H, m), 3.15 (3 H, s), 3.47 (2 H, s), 3.61-3.71 (4 H, m), 7.13 (2 H, d, J = 7.8 Hz), 7.18-7.29 (4 H, m), 7.43 (2 H, d, J = 8.3 Hz) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | $^1$H-NMR | Enzyme inhibitory activity |
|---|---|---|---|---|---|
| 426 | | Free | 436[M + Na]+ 412[M − H]− | $^1$H NMR (600 MHz, CD$_3$OD) δ ppm 1.78 (3 H, s), 1.83-1.91 (2 H, m), 2.70-2.76 (2 H, m), 2.80 (3 H, s), 3.21 (3 H, s), 3.60 (2 H, t, J = 6.6 Hz), 7.32 (2 H, d, J = 7.8 Hz), 7.58 (2 H, d, J = 7.8 Hz), 7.62 (2 H, d, J = 8.3 Hz), 7.71 (2 H, d, J = 8.3 Hz) | NT |
| 427 | | Free | 462[M + H]+ 460[M − H]− | $^1$H NMR (600 MHz, CD$_3$OD) δ ppm 1.77 (3 H, s), 2.62 (2 H, t, J = 6.8 Hz), 2.79 (3 H, s), 2.87 (2 H, t, J = 6.8 Hz), 3.17 (3 H, s), 3.83 (2 H, s), 7.36-7.63 (8 H, m) | NT |
| 428 | | Free | 418[M + Na]+ 394[M − H]− | $^1$H NMR (600 MHz, CD$_3$OD) δ ppm 2.75 (3 H, br. s.), 3.02 (3 H, s), 3.76 (3 H, s), 6.87-6.88 (2 H, m), 7.39-7.40 (2 H, m), 7.42-7.57 (4 H, m) | NT |
| 429 | | Free | 473[M + H]+ 471[M − H]− | $^1$H NMR (300 MHz, CD$_3$OD) δ ppm 1.77 (3 H, s), 2.79 (3 H, s), 2.91 (2 H, td, J = 15.5, 4.3 Hz), 3.17 (3 H, s), 3.85 (2 H, s), 5.68-6.13 (1 H, m), 7.35-7.43 (2 H, m), 7.47-7.65 (6 H, m) | NT |

TABLE 3-1-continued

Structural formulae of compounds, as well as their spectral data and inhibitory activity on Pseudomonas aeruginosa LpxC enzyme

| Compound No. | Structural formulae | Kind of salt | MS(ESI) | ¹H-NMR | Enzyme inhibitory activity |
|---|---|---|---|---|---|
| 430 | | Free | 481[M + H]+<br>479[M − H]− | ¹H NMR (300 MHz, CD₃OD) δ ppm 1.77 (3 H, s), 1.88-2.35 (2 H, m), 2.40-2.51 (1 H, m), 2.59-2.68 (1 H, m), 2.69-2.97 (2 H, m), 2.79 (3 H, s), 3.17 (3 H, s), 3.61-3.77 (2 H, m), 5.03-5.31 (1 H, m), 7.35-7.43 (2 H, m), 7.46-7.65 (6 H, m) | NT |
| 431 | | Free | 493[M + H]+<br>491[M − H]− | ¹H NMR (300 MHz, CD₃OD) δ ppm 1.35-1.54 (2 H, m), 1.77 (3 H, s), 1.83-1.95 (2 H, m), 2.67-2.78 (1 H, m), 2.79 (3 H, s), 3.17 (3 H, s), 3.33-3.45 (2 H, m), 3.83 (2 H, s), 3.89-4.00 (2 H, m), 7.35-7.44 (2 H, m), 7.46-7.65 (6 H, m) | NT |
| 432 | | Free | 507[M + H]+<br>505[M − H]− | ¹H NMR (300 MHz, CD₃OD) δ ppm 1.16-1.34 (2 H, m), 1.63-1.82 (6 H, m), 2.48 (2 H, d, J = 6.7 Hz), 2.79 (3 H, s), 3.17 (3 H, s), 3.35-3.47 (2 H, m), 3.79 (2 H, s), 3.88-3.97 (2 H, m), 7.35-7.42 (2 H, m), 7.47-7.64 (6 H, m) | NT |
| 433 | | Free | 406[M + Na]+<br>382[M − H]− | ¹H NMR (600 MHz, CD₃OD) δ ppm 1.77 (3 H, s), 2.79 (3 H, s), 3.16 (3 H, s), 3.90 (3 H, s), 7.50-7.55 (4 H, m), 7.64 (1 H, s), 7.86 (1 H, s) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 434 | | Free | 481[M + H]+ 479[M − H]− | ¹H NMR (600 MHz, CD$_3$OD) δ ppm 1.77 (3 H, s), 2.41-2.53 (4 H, m), 2.79 (3 H, s), 3.20 (3 H, s), 3.53 (2 H, s), 3.64-3.73 (4 H, m), 7.17-7.32 (2 H, m), 7.35 (2 H, d, J = 7.8 Hz), 7.51-7.60 (4 H, m), 7.66 (2 H, d, J = 8.3 Hz) | A |
| 435 | | Free | 449[M + H]+ 447[M − H]− | ¹H NMR (600 MHz, CD$_3$OD) δ ppm 0.92-0.99 (2 H, m), 0.99-1.07 (2 H, m), 1.77 (3 H, s), 2.26 (3 H, s), 2.79 (3 H, s), 3.17 (3 H, s), 7.33-7.65 (8 H, m) | NT |
| 436 | | Free | 438[M + Na]+ 414[M − H]− | ¹H NMR (600 MHz, CD$_3$OD) δ ppm 2.82 (3 H, br. s.), 3.08 (3 H, s), 3.37 (3 H, s), 4.60 (2 H, s), 7.12 (1 H, s), 7.36-7.67 (5 H, m) | B |
| 437 | | Free | 485[M + H]+ 483[M − H]− | ¹H NMR (600 MHz, CD$_3$OD) δ ppm 1.78 (3 H, s), 2.56-2.67 (4 H, m), 2.77-2.86 (5 H, m), 3.21 (3 H, s), 3.69-3.76 (4 H, m), 4.20 (2 H, t, J = 5.6 Hz), 6.98-7.10 (2 H, m), 7.54-7.73 (6 H, m) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 438 | | Free | 507[M + H]+<br>505[M − H]− | ¹H NMR (600 MHz, CD$_3$OD) δ ppm 1.77 (3 H, s), 1.88-1.98 (2 H, m), 2.75-2.89 (11 H, m), 3.17 (3 H, s), 3.73-3.77 (2 H, m), 3.77-3.82 (2 H, m), 7.04-7.73 (8 H, m) | A |
| 439 | | Free | 470[M + Na]+<br>446[M − H]− | ¹H NMR (600 MHz, CD$_3$OD) δ ppm 1.77 (3 H, s), 2.79 (3 H, s), 3.17 (3 H, s), 3.61 (2 H, s), 3.89 (2 H, s), 7.38-7.63 (8 H, m) | NT |
| 440 | | Free | 535[M + Na]+<br>533[M − H]− | ¹H NMR (600 MHz, CD$_3$OD) δ ppm 1.69-1.75 (4 H, m), 1.77 (3 H, s), 2.48-2.62 (4 H, m), 2.79 (3 H, s), 3.17 (3 H, s), 3.57 (2 H, s), 3.92 (4 H, s), 7.33-7.63 (8 H, m) | NT |
| 441 | | Free | 481[M + H]+<br>479[M − H]− | ¹H NMR (600 MHz, CD$_3$OD) δ ppm 1.73-1.85 (5 H, m), 2.65-2.72 (2 H, m), 2.80 (3 H, s), 3.17 (3 H, s), 3.31 (3 H, s), 3.41-3.48 (2 H, m), 3.76-3.82 (2 H, m), 7.34-7.41 (2 H, m), 7.46-7.64 (6 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 442 | | Free | 370[M + Na]+ 346[M − H]− | ¹H NMR (600 MHz, CD₃OD) δ ppm 1.50-1.59 (1 H, m), 1.78 (3 H, s), 1.86-1.93 (2 H, m), 1.98-2.05 (1 H, m), 2.60-2.69 (2 H, m), 2.80 (3 H, s), 3.17 (3 H, s), 3.74 (1 H, q, J = 7.4 Hz), 3.80-3.87 (3 H, m), 4.00-4.06 (1 H, m), 7.39 (2 H, d, J = 8.3 Hz), 7.52 (2 H, d, J = 8.3 Hz), 7.55-7.63 (4 H, m) | C |
| 443 | | Free | 380[M + Na]+ 356[M − H]− | ¹H NMR (600 MHz, CD₃OD) δ ppm 1.12 (6 H, d, J = 5.8 Hz), 1.78 (3 H, s), 2.80 (3 H, s), 3.00-3.05 (2 H, m), 3.17 (3 H, s), 3.59-3.65 (3 H, m), 3.68 (2 H, s), 4.17-4.23 (1 H, m), 7.33 (2 H, d, J = 8.3 Hz), 7.51 (2 H, d, J = 8.3 Hz), 7.55-7.63 (4 H, m) | C |
| 444 | | Free | 384[M + Na]+ 360[M − H]− | ¹H NMR (600 MHz, CD₃OD) δ ppm 1.61-2.20 (6 H, m), 2.81 (3 H, s), 3.05-3.13 (3 H, m), 3.33-3.37 (1 H, m), 5.79-6.03 (2 H, m), 6.99 (2 H, d, J = 8.7 Hz), 7.36-7.62 (2 H, m) | B |
| 445 | | Free | 378[M + Na]+ 354[M − H]− | ¹H NMR (600 MHz, CD₃OD) δ ppm 2.81 (3 H, br. s.), 3.05 (3 H, s), 4.01 (2 H, s), 7.15-7.50 (9 H, m) | C |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | $^1$H-NMR | Enzyme inhibitory activity |
|---|---|---|---|---|---|
| 446 | | Free | 433[M + Na]+ 409[M − H]− | $^1$H NMR (400 MHz, CD$_3$OD) δ ppm 2.83 (3 H, s), 3.10 (3 H, s), 5.52 (1 H, s), 7.50-8.00 (4 H, m), 8.42 (1 H, s), 8.90 (1 H, s), 9.13 (1 H, s) | C |
| 447 | | Free | 395[M + Na]+ 371[M − H]− | $^1$H NMR (400 MHz, CD$_3$OD) δ ppm 2.70 (3 H, s), 3.01 (3 H, s), 3.86 (3 H, s), 7.40-7.80 (5 H, m), 8.10-8.20 (1 H, m), 8.30-8.50 (1 H, m) | C |
| 448 | | Free | 383[M + Na]+ 359[M − H]− | $^1$H NMR (400 MHz, CD$_3$OD) δ ppm 2.82 (3 H, s), 3.10 (3 H, s), 7.50-7.90 (5 H, m), 8.40-8.60 (2 H, m) | B |
| 449 | | Free | 395[M + Na]+ 371[M − H]− | $^1$H NMR (400 MHz, CD$_3$OD) δ ppm 2.82 (3 H, s), 3.10 (3 H, s), 3.95 (3 H, s), 5.51 (1 H, s), 6.90 (1 H, d, J = 8.8 Hz), 7.45-7.80 (4 H, m), 7.94-8.04 (1 H, m), 8.43 (1 H, s) | B |
| 450 | | Free | 357[M + H]+ 355[M − H]− | $^1$H NMR (400 MHz, CD$_3$OD) δ ppm 2.49 (3 H, s), 2.73 (3 H, s), 3.01 (3 H, s), 7.32 (1 H, d, J = 7.8 Hz), 7.35-7.90 (4 H, m), 7.94 (1 H, d, J = 7.8 Hz), 8.61 (1 H, s) | C |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 451 | 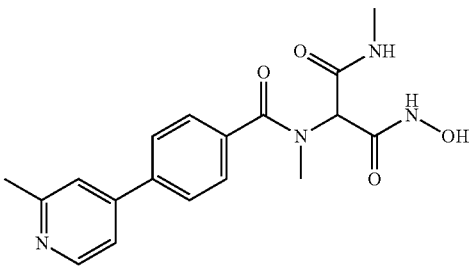 [SMILES: CNC(=O)C(C(=O)NO)N(C)C(=O)c1ccc(-c2ccnc(C)c2)cc1] | Free | 357[M + H]+ 355[M − H]− | ¹H NMR (400 MHz, DMSO-$d_6$) δ ppm 2.55 (3 H, s), 2.66-2.67 (3 H, m), 2.91 (3 H, s), 5.38 (1 H, s), 7.35-7.70 (2 H, m), 7.84-7.87 (2 H, m), 8.15-8.17 (1 H, m), 8.53 (1 H, d, J = 5.1 Hz), 9.08 (1 H, s), 10.85-11.00 (1 H, m) | B |
| 452 | 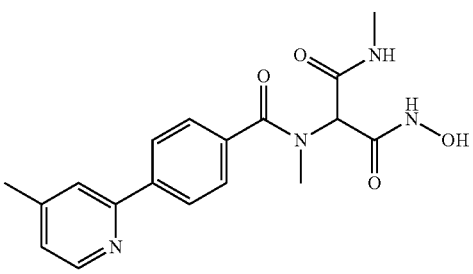 [SMILES: CNC(=O)C(C(=O)NO)N(C)C(=O)c1ccc(-c2cc(C)ccn2)cc1] | Free | 357[M + H]+ 355[M − H]− | ¹H NMR (400 MHz, CD$_3$OD) δ ppm 2.46 (3 H, s), 2.83 (3 H, s), 3.10 (3 H, s), 7.20-7.30 (1 H, m), 7.45-7.70 (2 H, m), 7.75 (1 H, s), 8.00-8.10 (2 H, m), 8.45-8.50 (1 H, m) | C |
| 453 | 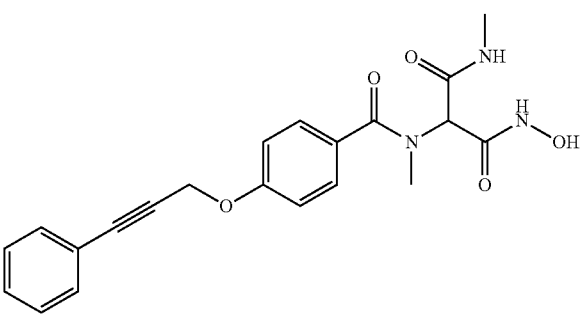 [SMILES: CNC(=O)C(C(=O)NO)N(C)C(=O)c1ccc(OCC#Cc2ccccc2)cc1] | Free | 418[M + Na]+ 394[M − H]− | ¹H NMR (400 MHz, CD$_3$OD) δ ppm 2.80 (3 H, s), 3.09 (3 H, s), 5.02 (2 H, s), 7.13 (2 H, d, J = 8.8 Hz), 7.28-7.43 (5 H, m), 7.45-7.60 (2 H, m) | B |
| 454 | 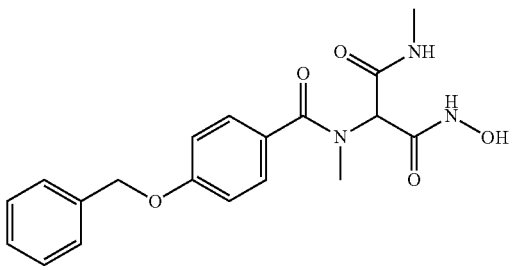 [SMILES: CNC(=O)C(C(=O)NO)N(C)C(=O)c1ccc(OCc2ccccc2)cc1] | Free | 394[M + Na]+ 370[M − H]− | ¹H NMR (400 MHz, CD$_3$OD) δ ppm 2.80 (3 H, s), 3.08 (3 H, s), 5.14 (2 H, s), 7.04-7.09 (2 H, m), 7.27-7.55 (7 H, m) | B |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 455 | | Free | 367[M + H]+<br>365[M − H]− | ¹H NMR (400 MHz, CD$_3$OD) δ ppm 2.73-2.88 (3 H, m), 3.12 (3 H, s), 5.54 (1 H, s), 7.34-7.48 (3 H, m), 7.51-7.64 (2 H, m), 7.70-7.90 (1 H, m), 8.00-8.18 (1 H, m), 8.68-8.80 (1 H, m) | C |
| 456 | | Free | 368[M + Na]+<br>344[M − H]− | ¹H NMR (400 MHz, CD$_3$OD) δ ppm 2.36 (3 H, s), 2.81 (3 H, s), 3.10 (3 H, s), 5.48 (1 H, br. s.), 6.13 (1 H, d, J = 2.6 Hz), 6.75 (1 H, d, J = 2.6 Hz), 7.35-7.62 (2 H, m), 7.71 (2 H, d, J = 8.0 Hz) | NT |
| 457 | | Free | 391[M + H]+<br>389[M − H]− | ¹H NMR (400 MHz, CD$_3$OD) δ ppm 2.82 (3 H, s), 3.14 (3 H, s), 3.86 (3 H, s), 6.90-7.15 (2 H, m), 7.75-8.00 (3 H, m), 8.62 (1 H, br. s.) | B |
| 458 | | Free | 405[M + H]+<br>403[M − H]− | ¹H NMR (400 MHz, CD$_3$OD) δ ppm 2.82 (3 H, s), 3.13 (3 H, s), 6.04 (2 H, s), 6.95 (1 H, d, J = 8.0 Hz), 7.45-7.65 (2 H, m), 7.83 (1 H, br. s.), 8.61 (1 H, br. s.) | B |
| 459 | | Free | 418[M + Na]+<br>394[M − H]− | ¹H NMR (400 MHz, CD$_3$OD) δ ppm 2.82 (3 H, s), 3.10 (3 H, s), 5.50 (1 H, s), 7.00-7.15 (2 H, m), 7.20-7.60 (4 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 460 | | Free | 414[M + Na]+ 390[M − H]− | ¹H NMR (400 MHz, CD$_3$OD) δ ppm 2.40 (3 H, s), 2.82 (3 H, s), 3.10 (3 H, s), 5.50 (1 H, s), 7.00-7.15 (2 H, m), 7.20-7.55 (4 H, m) | A |
| 461 | | Free | 378[M + Na]+ 354[M − H]− | ¹H NMR (400 MHz, CD$_3$OD) δ ppm 2.81 (3 H, s), 3.07 (3 H, s), 6.56 (1 H, br. s.), 7.35-7.59 (5 H, m), 7.84 (1 H, br. s.) | B |
| 462 | | Free | 383[M + Na]+ 359[M − H]− | ¹H NMR (400 MHz, DMSO-d$_6$) δ ppm 2.67 (3 H, s), 2.98 (3 H, s), 5.38 (1 H, br. s.), 7.30-7.35 (1 H, m), 7.35-7.65 (2 H, m), 7.83 (2 H, d, J = 7.6 Hz), 8.10-8.20 (1 H, m), 8.30-8.40 (1 H, m), 8.62 (1 H, s), 9.08 (1 H, s), 10.90 (1 H, br. s.) | NT |
| 463 | | Free | 401[M + H]+ 399[M − H]− | ¹H NMR (400 MHz, DMSO-d$_6$) δ ppm 1.20 (3 H, t, J = 7.4 Hz), 2.55-2.70 (5 H, m), 2.98 (3 H, s), 3.94 (3 H, s), 5.37 (1 H, br. s.), 7.35-7.65 (2 H, m), 7.77 (2 H, d, J = 7.3 Hz), 7.90 (1 H, s), 8.16 (1 H, br. s.), 8.37 (1 H, br. s.), 9.07 (1 H, s), 10.89 (1 H, br. s.) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 464 | | Free | 381[M + H]+ 379[M − H]− | ¹H NMR (400 MHz, CD$_3$OD) δ ppm 2.45 (3 H, s), 2.73 (3 H, s), 3.20 (3 H, s), 7.22-7.28 (1 H, m), 7.32-7.38 (1 H, m), 7.44-8.00 (4 H, m), 8.30-8.38 (1 H, m) | B |
| 465 | | Free | 509[M + H]+ 507[M − H]− | ¹H NMR (400 MHz, CD$_3$OD) δ ppm 1.87-1.95 (2 H, m), 2.40-2.52 (6 H, m), 2.72 (3 H, s), 2.99 (3 H, s), 3.58-3.65 (4 H, m), 3.98 (2 H, t, J = 6.0 Hz), 6.84 (2 H, d, J = 8.8 Hz), 7.36 (2 H, d, J = 8.8 Hz), 7.40-7.50 (4 H, m) | A |
| 466 | | Free | 369[M + H]+ 367[M − H]− | ¹H NMR (400 MHz, DMSO-d$_6$) δ ppm 2.66 (3 H, br. s.), 3.01 (3 H, s), 5.37 (1 H, br. s.), 7.30-7.50 (4 H, m), 7.55-7.80 (3 H, m), 7.76 (1 H, d, J = 15.8 Hz), 7.92 (1 H, br. s.), 8.18 (1 H, br. s.), 8.68 (1 H, br. s.), 9.10 (1 H, s), 10.91 (1 H, br. s.) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 467 | 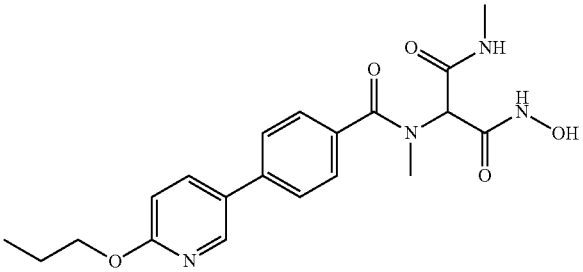 [SMILES: CCCOc1ccc(-c2ccc(C(=O)N(C)C(C(=O)NC)C(=O)NO)cc2)cn1] | Free | 401[M + H]+ 399[M − H]− | ¹H NMR (400 MHz, DMSO-$d_6$) δ ppm 0.98 (3 H, t, J = 7.4 Hz), 1.70-1.82 (2 H, m), 2.66 (3 H, br. s.), 2.98 (3 H, s), 4.26 (2 H, t, J = 6.7 Hz), 5.37 (1 H, br. s.), 6.85-6.95 (1 H, m), 7.30-7.65 (2 H, m), 7.76 (2 H, d, J = 7.6 Hz), 8.00-8.10 (1 H, m), 8.10-8.20 (1 H, m), 8.50-8.55 (1 H, m), 9.07 (1 H, s), 10.89 (1 H, br. s.) | A |
| 468 | 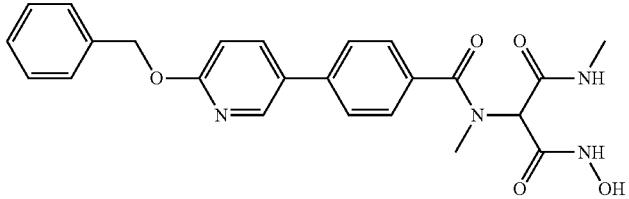 [SMILES: CNC(=O)C(C(=O)NO)N(C)C(=O)c1ccc(-c2ccc(OCc3ccccc3)nc2)cc1] | Free | 449[M + H]+ 447[M − H]− | ¹H NMR (400 MHz, DMSO-$d_6$) δ ppm 2.66 (3 H, s), 2.98 (3 H, s), 5.37 (1 H, s), 5.42 (2 H, s), 7.00 (1 H, d, J = 8.5 Hz), 7.30-7.65 (7 H, m), 7.77 (2 H, d, J = 7.3 Hz), 8.09-8.16 (2 H, m), 8.56 (1 H, s), 9.07 (1 H, s), 10.89 (1 H, s) | A |
| 469 | 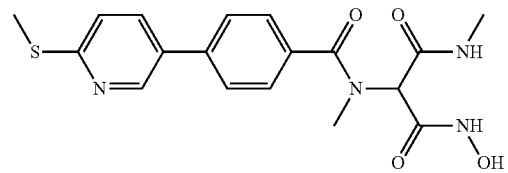 [SMILES: CNC(=O)C(C(=O)NO)N(C)C(=O)c1ccc(-c2ccc(SC)nc2)cc1] | Free | 389[M + H]+ 387[M − H]− | ¹H NMR (400 MHz, DMSO-$d_6$) δ ppm 2.56 (3 H, s), 2.67 (3 H, s), 2.98 (3 H, s), 5.37 (1 H, s), 7.35-7.65 (3 H, m), 7.81 (2 H, d, J = 7.6 Hz), 8.01 (1 H, d, J = 5.9 Hz), 8.16 (1 H, br. s.), 8.82 (1 H, s), 9.07 (1 H, s), 10.89 (1 H, s) | B |
| 470 | 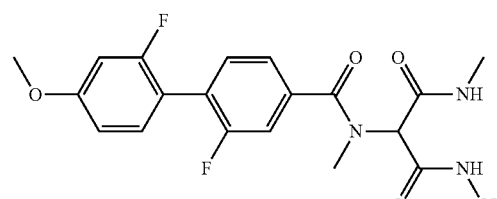 | Free | 430[M + Na]+ 406[M − H]− | ¹H NMR (400 MHz, DMSO-$d_6$) δ ppm 2.66 (3 H, s), 2.98 (3 H, s), 3.90 (3 H, s), 5.35 (1 H, s), 7.15-7.65 (5 H, m), 7.65-7.75 (1 H, m), 8.17 (1 H, br. s.), 9.09 (1 H, br. s.), 10.89 (1 H, br. s.) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 471 | | Free | 417[M + H]+ 415[M − H]− | ¹H NMR (400 MHz, CD$_3$OD) δ ppm 2.82 (3 H, s), 3.09 (3 H, s), 7.40-7.73 (5 H, m), 7.85-7.92 (1 H, m), 8.04 (1 H, d, J = 8.4 Hz), 8.18 (1 H, br. s.), 8.36-8.42 (1 H, m), 8.87 (1 H, dd, J = 4.4, 1.6 Hz) | NT |
| 472 | | Free | 417[M + H]+ 415[M − H]− | ¹H NMR (400 MHz, CD$_3$OD) δ ppm 2.82 (3 H, s), 3.29 (3 H, s), 5.50 (1 H, s), 7.40-7.90 (6 H, m), 8.11-8.18 (2 H, m), 8.45-8.50 (1 H, m), 9.25 (1 H, s) | NT |
| 473 | | Free | 464[M + H]+ 462[M − H]− | ¹H NMR (400 MHz, CD$_3$OD) δ ppm 2.40 (3 H, s), 2.64-2.85 (11 H, m), 3.08 (3 H, s), 5.48 (1 H, br. s.), 6.96 (2 H, d, J = 8.4 Hz), 7.34-7.60 (6 H, m) | B |
| 474 | | Free | 399[M + H]+ 397[M − H]− | ¹H NMR (400 MHz, CD$_3$OD) δ ppm 0.97 (3 H, t, J = 7.3 Hz), 1.38-1.46 (2 H, m), 1.69-1.76 (2 H, m), 2.75-2.90 (5 H, m), 3.11 (3 H, s), 7.41 (1 H, d, J = 8.1 Hz), 7.45-7.85 (4 H, m), 8.05 (1 H, d, J = 6.6 Hz), 8.72 (1 H, s) | B |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 475 | | Free | 429[M + H]+<br>427[M − H]− | ¹H NMR (400 MHz, CD$_3$OD) δ ppm 0.92-0.95 (3 H, m), 1.38-1.43 (4 H, m), 1.61-1.65 (2 H, m), 2.82 (3 H, s), 3.11 (3 H, s), 3.20-3.40 (2 H, m), 6.57-6.65 (1 H, m), 7.40-7.70 (4 H, m), 7.72-7.83 (1 H, m), 8.24 (1 H, d, J = 1.0 Hz) | B |
| 476 | | Free | 459[M + H]+<br>457[M − H]− | ¹H NMR (400 MHz, CD$_3$OD) δ ppm 0.39-0.54 (4 H, m), 2.12-2.20 (1 H, m), 2.85 (3 H, s), 3.10 (3 H, s), 3.86 (2 H, s), 7.42 (2 H, d, J = 8.1 Hz), 7.53-7.70 (6 H, m) | A |
| 477 | | Free | 461[M + H]+<br>459[M − H]− | ¹H NMR (400 MHz, CD$_3$OD) δ ppm 0.39-0.55 (4 H, m), 2.12-2.20 (1 H, m), 2.85 (3 H, s), 3.12 (3 H, s), 3.85 (2 H, s), 6.64 (1 H, d, J = 16.3 Hz), 7.10 (1 H, d, J = 16.3 Hz), 7.35-7.70 (8 H, m) | A |
| 478 | | Free | 423[M + H]+<br>421[M − H]− | ¹H NMR (400 MHz, CD$_3$OD) δ ppm 2.82 (3 H, s), 3.07 (3 H, s), 3.92 (3 H s), 6.44 (1 H, d, J = 16.3 Hz), 6.80 (1 H, d, J = 8.8 Hz), 7.04 (1 H, d, J = 16.3 Hz), 7.30-7.65 (4 H, m), 7.89-7.93 (1 H, m), 8.15-8.25 (1 H, m) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 479 | | Free | 507[M + H]+ 505[M − H]− | ¹H NMR (400 MHz, CD$_3$OD) δ ppm 2.49 (4 H, m), 2.73 (3 H, s), 3.03 (3 H, s), 3.53-3.65 (6 H, m), 5.42 (1 H, s), 6.34 (1 H, d, J = 3.2 Hz), 6.70 (1 H, d, J = 3.2 Hz), 7.35-7.75 (8 H, m) | A |
| 480 | | Free | 429[M + H]+ 427[M − H]− | ¹H NMR (400 MHz, CD$_3$OD) δ ppm 0.95 (3 H, t, J = 7.1 Hz), 1.38-1.50 (4 H, m), 1.76-1.83 (2 H, m), 2.82 (3 H, s), 3.11 (3 H, s), 4.30 (2 H, t, J = 6.6 Hz), 6.85-6.95 (1 H, m), 7.45-7.80 (4 H, m), 7.95-8.05 (1 H, m), 8.41 (1 H, s) | NT |
| 481 | | Free | 461[M + H]+ 459[M − H]− | ¹H NMR (400 MHz, CD$_3$OD) δ ppm 0.47-0.63 (4 H, m), 2.21-2.30 (1 H, m), 2.91 (3 H, s), 3.17 (3 H, s), 3.92 (2 H, s), 6.58 (1 H, d, J = 16.2 Hz), 7.17 (1 H, d, J = 16.2 Hz), 7.45 (2 H, d, J = 8.0 Hz), 7.54-7.68 (6 H, m) | A |
| 482 | | Free | 490[M + H]+ 488[M − H]− | ¹H NMR (400 MHz, CD$_3$OD) δ ppm 2.41 (3 H, s), 2.81 (3 H, s), 3.08 (3 H, s), 3.70-3.80 (4 H, m), 6.17 (1 H, s), 7.38 (2 H, d, J = 8.3 Hz), 7.40-7.65 (6 H, m) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 483 | | Free | 455[M + H]+<br>453[M − H]− | ¹H NMR (400 MHz, CD$_3$OD) δ ppm 2.46-2.53 (4 H, m), 2.81 (3 H, s), 3.07 (3 H, s), 3.57 (2 H, s), 3.66-3.72 (4 H, m), 6.47 (1 H, s), 7.35-7.62 (4 H, m), 7.81 (1 H, s) | A |
| 484 | | Free | 402[M + Na]+<br>378[M − H]− | ¹H NMR (400 MHz, CD$_3$OD) δ ppm 2.81 (3 H, s), 3.05 (3 H, s), 5.48 (1 H, br. s.), 6.54-6.59 (1 H, m), 7.36-7.66 (5 H, m), 7.90-7.94 (1 H, m) | A |
| 485 | | Free | 476[M + H]+<br>474[M − H]− | ¹H NMR (400 MHz, CD$_3$OD) δ ppm 2.81 (3 H, s), 3.08 (3 H, s), 3.80 (2 H, s), 3.89 (2 H, s), 7.13 (1 H, s), 7.35-7.65 (8 H, m), 7.88 (1 H, s) | A |
| 486 | | Free | 503[M + H]+<br>501[M − H]− | ¹H NMR (400 MHz, CD$_3$OD) δ ppm 2.81 (3 H, s), 3.08 (3 H, s), 3.75-3.80 (4 H, m), 6.60 (1 H, s), 7.03-7.08 (2 H, m), 7.34-7.39 (4 H, m), 7.50-7.60 (6 H, m) | NT |
| 487 | | Free | 517[M + H]+<br>515[M − H]− | ¹H NMR (400 MHz, CD$_3$OD) δ ppm 2.81 (3 s), 3.08 (3 H, s), 3.85 (2 H, s), 6.98-7.03 (2 H, m), 7.20-7.23 (2 H, m), 7.36-7.38 (2 H, m), 7.40-7.62 (6 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 488 | 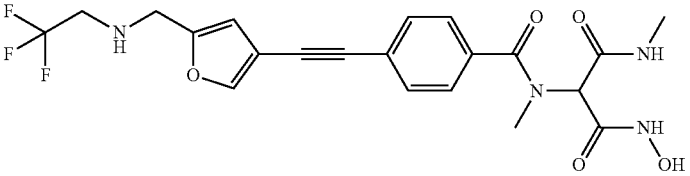 [SMILES: CNC(=O)C(C(=O)NO)N(C)C(=O)c1ccc(C#Cc2coc(CNCC(F)(F)F)c2)cc1] | Free | 489[M + Na]+ 465[M − H]− | ¹H NMR (400 MHz, CD$_3$OD) δ ppm 2.81 (3 H, s), 3.07 (3 H, s), 3.20 (2 H, q, J = 9.8 Hz), 3.83 (2 H, s), 6.43 (1 H, s), 7.40-7.59 (4 H, m), 7.79 (1 H, s) | A |
| 489 | 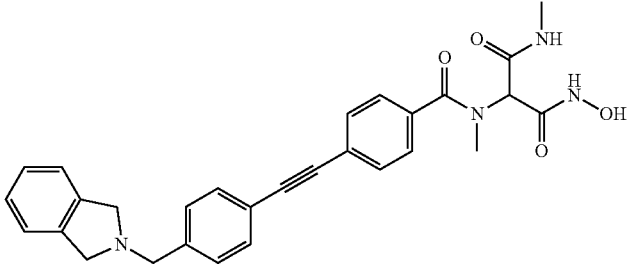 [SMILES: CNC(=O)C(C(=O)NO)N(C)C(=O)c1ccc(C#Cc2ccc(CN3Cc4ccccc4C3)cc2)cc1] | Free | 497[M + H]+ 495[M − H]− | ¹H NMR (400 MHz, CD$_3$OD) δ ppm 2.82 (3 H, s), 3.08 (3 H, s), 3.90-3.95 (6 H, m), 7.15-7.25 (4 H, m), 7.35-7.70 (8 H, m) | A |
| 490 |  | Free | 511[M + H]+ 509[M − H]− | ¹H NMR (400 MHz, CD$_3$OD) δ ppm 2.76-2.82 (5 H, m), 2.89-2.92 (2 H, m), 3.08 (3 H, s), 3.63 (2 H, s), 3.67-3.73 (2 H, m), 6.98-7.00 (1 H, m), 7.07-7.11 (3 H, m), 7.43-7.45 (2 H, m), 7.52-7.63 (6 H, m) | NT |
| 491 | 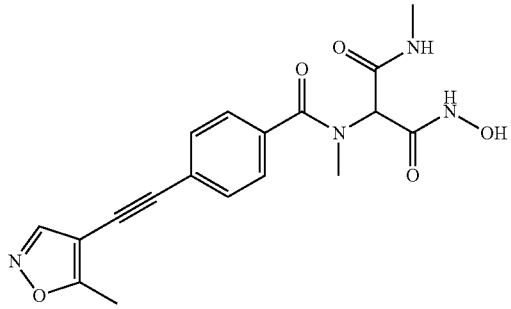 [SMILES: CNC(=O)C(C(=O)NO)N(C)C(=O)c1ccc(C#Cc2cnoc2C)cc1] | Free | 393[M + Na]+ 369[M − H]− | ¹H NMR (400 MHz, CD$_3$OD) δ ppm 2.55 (3 H, s), 2.80 (3 H, s), 3.05 (3 H, s), 7.30-7.65 (4 H, m), 8.44 (1 H, s) | NT |
| 492 |  | Free | 502[M + H]+ 500[M − H]− | ¹H NMR (400 MHz, CD$_3$OD) δ ppm 2.35 (3 H, s), 2.40-2.74 (8 H, br. s.), 2.85 (3 H, s), 3.10 (3 H, s), 3.60 (2 H, s), 7.41 (2 H, d, J = 8.3 Hz), 7.52-7.70 (6 H, m) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 493 | | Free | 489[M + H]+ 487[M − H]− | ¹H NMR (400 MHz, CD₃OD) δ ppm 0.96 (9 H, s), 2.39 (2 H, m), 2.85 (3 H, s), 3.10 (3 H, s), 3.88 (2 H, s), 7.44 (2 H, d, J = 8.1 Hz), 7.53-7.70 (6 H, m) | A |
| 494 | | Free | 511[M + H]+ 509[M − H]− | ¹H NMR (400 MHz, CD₃OD) δ ppm 1.90-2.10 (1 H, m), 2.30-2.50 (1 H, m), 2.75-2.95 (4 H, m), 3.00-3.15 (4 H, m), 3.80-3.95 (2 H, m), 4.25-4.40 (1 H, m), 4.80-5.00 (1 H, m), 7.15-7.30 (3 H, m), 7.35-7.70 (9 H, m) | NT |
| 495 | | Free | 499[M + H]+ 497[M − H]− | ¹H NMR (400 MHz, CD₃OD) δ ppm 2.17 (3 H, s), 2.81 (3 H, s), 3.08 (3 H, s), 3.45-3.60 (4 H, m), 7.20-7.65 (13 H, m) | A |
| 496 | | Free | 534[M + H]+ 532[M − H]− | ¹H NMR (400 MHz, CD₃OD) δ ppm 1.54-1.69 (2 H, m), 2.00-2.10 (2 H, m), 2.35-2.48 (1 H, m), 2.61-2.69 (2 H, m), 2.74-2.88 (2 H, m), 2.85 (3 H, s), 3.12 (3 H, s), 3.70-3.77 (6 H, m), 3.87-3.95 (2 H, s), 5.52 (1 H, br. s.), 6.99 (2 H, d, J = 9.0 Hz), 7.41 (2 H, d, J = 8.8 Hz), 7.51-7.62 (4 H, m) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 497 | | Free | 475[M + H]+<br>473[M − H]− | ¹H NMR (400 MHz, CD$_3$OD) δ ppm 2.81 (3 H, s), 3.08 (3 H, s), 3.74-3.79 (4 H, m), 6.26-6.29 (1 H, m), 6.34-6.38 (1 H, m), 7.37 (2 H, d, J = 8.0 Hz), 7.44-7.64 (7 H, m) | NT |
| 498 | | Free | 511[M + H]+<br>509[M − H]− | ¹H NMR (400 MHz, DMSO-d$_6$) δ ppm 2.65-2.67 (3 H, m), 2.84-2.88 (2 H, m), 2.92-2.96 (5 H, m), 3.89 (4 H, s), 7.17-7.24 (4 H, m), 7.32 (2 H, d, J = 8.0 Hz), 7.49-7.53 (4 H, m), 7.62-7.63 (2 H, m), 8.15 (1 H, br. s.), 9.07 (1 H, s), 10.90 (1 H, br. s.) | NT |
| 499 | | Free | 436[M − H]− | ¹H NMR (400 MHz, CD$_3$OD) δ ppm 2.74 (3 H, s), 3.03 (3 H, s), 4.50 (2 H, s), 5.42 (1 H, br. s.), 6.33 (1 H, d, J = 3.3 Hz), 6.51 (1 H, s), 6.69 (1 H, d, J = 3.3 Hz), 7.35-7.90 (6 H, m) | A |
| 500 | | Free | 473[M + H]+<br>471[M − H]− | ¹H NMR (400 MHz, CD$_3$OD) δ ppm 1.71-1.87 (2 H, m), 1.90-2.06 (2 H, m), 2.19-2.30 (2 H, m), 2.81 (3 H, s), 3.06 (3 H, s), 3.42-3.54 (1 H, m), 3.86 (2 H, s), 7.39-7.47 (2 H, m), 7.52-7.67 (6 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 501 | | Free | 449[M + Na]+ 425[M − H]− | ¹H NMR (400 MHz, CD₃OD) δ ppm [1.29], 1.34 (3 H, t, J = 7.1 Hz), 2.81 (3 H, s), 3.07 (3 H, s), [4.19], 4.28 (2 H, q, J = 7.1 Hz), [6.76], 6.87 (1 H, d, J = 3.6 Hz), [6.83], 7.25 (1 H, d, J = 3.6 Hz), 7.38-7.69 (4 H, m), [7.43], 7.98 (1 H, s) | A |
| 502 | | Free | 481[M − H]− | ¹H NMR (400 MHz, CD₃OD) δ ppm 1.77-1.84 (4 H, m), 2.48-2.53 (2 H, m), 2.58-2.62 (2 H, m), 2.67-2.73 (7 H, m), 3.02 (3 H, s), 3.61-3.69 (4 H, m), 7.22 (2 H, d, J = 8.0 Hz), 7.35-7.55 (4 H, m), 7.62 (2 H, d, J = 7.6 Hz) | B |
| 503 | | Free | 352[M + Na]+ 328[M − H]− | ¹H NMR (400 MHz, CD₃OD) δ ppm 0.80-0.90 (2 H, m), 0.95-1.05 (2 H, m), 1.53-1.62 (1 H, m), 2.90 (3 H, s), 3.15 (3 H, s), 5.56 (1 H, br. s.), 7.35-7.61 (4 H, m) | C |
| 504 | | Free | 392[M + Na]+ 368[M − H]− | ¹H NMR (400 MHz, CD₃OD) δ ppm 2.91 (3 H, s), 3.17 (3 H, s), 4.00 (3 H, s), 5.58 (1 H, br. s.), 7.35-7.70 (4 H, m), 7.73 (1 H, s), 7.96 (1 H, s) | B |
| 505 | | Free | 465[M + H]+ 463[M − H]− | ¹H NMR (400 MHz, CD₃OD) δ ppm 2.81 (3 H, s), 3.02-3.15 (2 H, m), 3.08 (3 H, s), 3.25 (3 H, s), 3.54-3.64 (2 H, m), 3.69 (2 H, s), 4.02-4.09 (1 H, m), 7.32 (2 H, d, J = 8.0 Hz), 7.47-7.65 (6 H, m) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 506 | | Free | 449[M + Na]+ 425[M − H]− | ¹H NMR (400 MHz, CD$_3$OD) δ ppm [1.21], [1.28], 1.36 (3 H, t, J = 7.1 Hz), 2.81 (3 H, s), 3.07 (3 H, s), 3.55-4.33 (2 H, m), [5.52], [6.53], 6.82 (1 H, s), 7.26-7.62 (5 H, m), [7.82], [7.92], 7.98 (1 H, s) | A |
| 507 | | Free | 376[M + Na]+ 352[M − H]− | ¹H NMR (400 MHz, CD$_3$OD) δ ppm 0.73-0.80 (2 H, m), 0.87-0.95 (2 H, m), 1.41-1.50 (1 H, m), 2.80 (3 H, s), 3.04 (3 H, s), 7.30-7.57 (4 H, m) | NT |
| 508 | | Free | 467[M + Na]+ 465[M − H]− | ¹H NMR (400 MHz, CD$_3$OD) δ ppm 1.27 (6 H, s), 2.81 (3 H, s), 3.08 (3 H, s), 3.39 (2 H, s), 4.61-4.62 (2 H, m), 7.40-7.42 (2 H, m), 7.48-7.58 (6 H, m) | B |
| 509 | | Free | 413[M + Na]+ 389[M − H]− | ¹H NMR (400 MHz, CD$_3$OD) δ ppm 2.81 (3 H, m), 3.05 (3 H, s), 5.49 (1 H, s), 7.50-7.70 (6 H, m), 8.54-8.62 (2 H, m) | NT |
| 510 | | Free | 493[M + H]+ 491[M − H]− | ¹H NMR (400 MHz, CD$_3$OD) δ ppm 0.79 (9 H, br. s.), 1.11-1.12 (4 H, m), 2.26 (2 H, s), 2.72 (3 H, s), 2.98 (3 H, s), 3.72 (2 H, s), 7.28-7.52 (8 H, m) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 511 | | Free | 416[M + Na]+ 392[M − H]− | ¹H NMR (400 MHz, CD$_3$OD) δ ppm 2.81 (3 H, s), 3.05 (3 H, s), 3.89 (3 H, s), 7.35-7.63 (4 H, m), 7.66 (1 H, s), 7.91 (1 H, s) | A |
| 512 | | Free | 463[M + H]+ 461[M − H]− | ¹H NMR (400 MHz, CD$_3$OD) δ ppm 1.20 (3 H, d, J = 6.1 Hz), 1.45-1.52 (1 H, m), 1.68-1.76 (2 H, m), 1.98-2.05 (1 H, m), 2.23-2.29 (1 H, m), 2.52-2.53 (1 H, m), 2.81 (3 H, s), 2.88-2.93 (1 H, m), 3.08 (3 H, s), 3.20-3.40 (1 H, m), 4.07 (1 H, d, J = 12.9 Hz), 7.38 (2 H, d, J = 8.1 Hz), 7.49-7.62 (6 H, m) | NT |
| 513 | | Free | 492[M + H]+ 490[M − H]− | ¹H NMR (400 MHz, CD$_3$OD) δ ppm 0.93 (6 H, s), 1.23-1.26 (2 H, m), 1.61-1.64 (2 H, m), 2.04 (2 H, br. s.), 2.35-2.38 (2 H, m), 2.81 (3 H, s), 3.08 (3 H, s), 3.47 (2 H, s), 7.36 (2 H, d, J = 8.1 Hz), 7.46-7.62 (6 H, m) | A |
| 514 | | Free | 422[M + Na]+ 398[M − H]− | ¹H NMR (400 MHz, CD$_3$OD) δ ppm 2.81 (3 H, s), 3.07 (3 H, s), 3.34 (3 H, s), 4.39 (2 H, s), 6.53 (1 H, s), 7.48-7.60 (4 H, m), 7.82 (1 H, s) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 515 | | Free | 461[M + H]+ 459[M − H]− | ¹H NMR (400 MHz, CD$_3$OD) δ ppm 0.33-0.42 (1 H, m), 0.70-0.78 (1 H, m), 1.35-1.43 (2 H, m), 2.37-2.47 (2 H, m), 2.81 (3 H, s), 2.87-2.97 (2 H, m), 3.08 (3 H, s), 3.62 (2 H, s), 7.32 (2 H, d, J = 8.3 Hz), 7.33-7.68 (6 H, m) | A |
| 516 | | Free | 449[M + H]+ 447[M − H]− | ¹H NMR (400 MHz, CD$_3$OD) δ ppm 1.11 (3 H, d, J = 6.1 Hz), 1.21-1.26 (3 H, m), 2.53-2.62 (1 H, m), 2.81 (3 H, s), 3.04-3.13 (4 H, m), 3.59-3.63 (1 H, m), 3.84-3.88 (1 H, m), 4.28 (1 H, d, J = 12.9 Hz), 7.21-7.25 (1 H, m), 7.39-7.61 (6 H, m) | B |
| 517 | | Free | 406[M + Na]+ 382[M − H]− | ¹H NMR (400 MHz, CD$_3$OD) δ ppm 1.46 (3 H, t, J = 7.3 Hz), 2.81 (3 H, s), 3.07 (3 H, s), 4.19 (2 H, q, J = 7.3 Hz), 7.34-7.60 (4 H, m), 7.65 (1 H, 3), 7.91 (1 H, s) | B |
| 518 | | Free | 436[M + Na]+ 412[M − H]− | ¹H NMR (400 MHz, CD$_3$OD) δ ppm 2.81 (3 H, s), 3.07 (3 H, s), 3.34 (3 H, s), 3.73 (2 H, t, J = 5.1 Hz), 4.30 (2 H, t, J = 5.1 Hz), 7.30-7.60 (4 H, m), 7.66 (1 H, s), 7.89 (1 H, s) | B |
| 519 | | Free | 461[M + Na]+ 437[M − H]− | ¹H NMR (400 MHz, CD$_3$OD) δ ppm 2.81 (3 H, s), 3.12 (3 H, s), 4.68-4.69 (2 H, m), 6.86 (1 H, s), 7.45-8.00 (8 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 520 | | Free | 556[M + H]+ 554[M − H]− | ¹H NMR (400 MHz, CD₃OD) δ ppm 1.86-1.98 (2 H, m), 2.66-2.76 (4 H, m), 3.12 (3 H, s), 3.65-3.75 (4 H, m), 3.77-3.85 (2 H, m), 4.40-4.78 (2 H, m), 7.28-7.65 (10 H, m), 7.77-7.87 (1 H, m), 8.45-8.55 (1 H, m) | A |
| 521 | | Free | 570[M + H]+ 568[M − H]− | ¹H NMR (400 MHz, CD₃OD) δ ppm 1.85 (3 H, s), 1.88-1.95 (2 H, m), 2.66-2.76 (4 H, m), 3.19 (3 H, s), 3.65-3.75 (4 H, m), 3.78-3.84 (2 H, m), 4.50-4.64 (2 H, m), 7.25-7.31 (1 H, m), 7.39 (2 H, d, J = 8.4 Hz), 7.46-7.53 (3 H, m), 7.53-7.63 (4 H, m), 7.73-7.80 (1 H, m), 8.45-8.48 (1 H, m) | A |
| 522 | | Free | 481[M + H]+ 479[M − H]− | ¹H NMR (400 MHz, CD₃OD) δ ppm 1.84-1.99 (4 H, m), 2.37-2.47 (2 H, m), 2.55-2.66 (2 H, m), 2.81 (3 H, s), 3.08 (3 H, s), 3.55 (2 H, s), 4.67-4.95 (1 H, m), 7.37 (2 H, d, J = 8.1 Hz), 7.47-7.64 (6 H, m) | NT |
| 523 | | Free | 392[M + Na]+ 368[M − H]− | ¹H NMR (400 MHz, CD₃OD) δ ppm 1.62-1.71 (4 H, m), 2.15-2.20 (4 H, m), 2.81 (3 H, s), 3.05 (3 H, s), 6.20 (1 H, s), 7.30-7.55 (4 H, m) | B |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | $^1$H-NMR | Enzyme inhibitory activity |
|---|---|---|---|---|---|
| 524 | | Free | 475[M + H]+ 473[M − H]− | $^1$H NMR (400 MHz, CD$_3$OD) δ ppm 1.08-1.12 (4 H, m), 1.78-1.83 (2 H, m), 2.10-2.16 (4 H, m), 2.81 (3 H, s), 3.06 (3 H, s), 3.67 (2 H, s), 7.31-7.32 (2 H, m), 7.49-7.59 (6 H, m) | B |
| 525 | | Free | 463[M + H]+ 461[M − H]− | $^1$H NMR (400 MHz, CD$_3$OD) δ ppm 1.24 (6 H, s), 2.81 (3 H, s), 3.08 (3 H, s), 3.16 (4 H, s), 3.74 (2 H, s), 7.33-7.35 (2 H, m), 7.49-7.62 (6 H, m) | B |
| 526 | | Free | 449[M + H]+ 447[M − H]− | $^1$H NMR (400 MHz, CD$_3$OD) δ ppm 3.16 (3 H, s), 3.83 (3 H, s), 4.59 (2 H, s), 7.02 (2 H, d, J = 8.3 Hz), 7.27-7.35 (1 H, m), 7.37-7.75 (7 H, m), 7.77-7.85 (1 H, m), 8.45-8.53 (1 H, m) | NT |
| 527 | | Free | 476[M + H]+ 474[M − H]− | $^1$H NMR (400 MHz, CD$_3$OD) δ ppm 1.42-1.43 (4 H, m), 1.80 (4 H, br. s.), 2.81 (3 H, s), 3.07 (3 H, s), 3.20-3.50 (2 H, m), 3.64 (2 H, s), 7.42-7.44 (2 H, m), 7.51-7.60 (6 H, m) | B |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 528 | | Free | 436[M + Na]+ 412[M − H]− | ¹H NMR (400 MHz, CD₃OD) δ ppm 1.76 (3 H, s), 2.78 (3 H, s), 3.16 (3 H, s), 3.34 (3 H, s), 4.39 (2 H, s), 6.53 (1 H, s), 7.52-7.60 (4 H, m), 7.82 (1 H, s) | A |
| 529 | | Free | 430[M + Na]+ 406[M − H]− | ¹H NMR (400 MHz, CD₃OD) δ ppm 1.76 (3 H, s), 2.78 (3 H, s), 3.14 (3 H, s), 3.89 (3 H, s), 7.66 (1 H, s), 7.49-7.63 (4 H, m), 7.91 (1 H, s) | NT |
| 530 | | Free | 491[M + H]+ 489[M − H]− | ¹H NMR (400 MHz, CD₃OD) δ ppm 2.81 (3 H, s), 3.08 (3 H, s), 3.28 (3 H, s), 3.80 (2 H, s), 3.83 (2 H, d, J = 6.4 Hz), 3.97 (2 H, s), 4.03 (2 H, s), 5.35-5.45 (1 H, m), 7.34-7.36 (2 H, m), 7.49-7.62 (6 H, m) | A |
| 531 | | Free | 493[M + H]+ 491[M − H]− | ¹H NMR (400 MHz, CD₃OD) δ ppm 1.16 (3 H, t, J = 7.1 Hz), 1.77 (3 H, s), 2.79 (3 H, s), 3.02-3.09 (2 H, m), 3.16 (3 H, s), 3.43 (2 H, q, J = 7.1 Hz), 3.56-3.62 (2 H, m), 3.68 (2 H, s), 4.09-4.18 (1 H, m), 7.32 (2 H, d, J = 8.3 Hz), 7.47-7.53 (2 H, m), 7.53-7.63 (4 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 532 | | Free | 506[M + H]+ 504[M − H]− | ¹H NMR (400 MHz, CD$_3$OD) δ ppm 1.75-1.77 (4 H, m), 2.81 (3 H, s), 3.08 (3 H, s), 3.20 (4 H, s), 3.58 (4 H, br. s.), 3.73 (2 H, br. s.), 7.33-7.35 (2 H, m), 7.49-7.59 (6 H, m) | NT |
| 533 | | Free | 480[M + H]+ 478[M − H]− | ¹H NMR (400 MHz, CD$_3$OD) δ ppm 1.45 (3 H, s), 2.81 (3 H, s), 3.08 (3 H, s), 3.19 (3 H, s), 3.22-3.26 (4 H, m), 3.72 (2 H, s), 7.33-7.35 (2 H, m), 7.49-7.61 (6 H, m) | NT |
| 534 | | Free | 507[M + H]+ 505[M − H]− | ¹H NMR (400 MHz, CD$_3$OD) δ ppm 1.11 (6 H, d, J = 6.1 Hz), 1.77 (3 H, s), 2.79 (3 H, s), 2.99-3.06 (2 H, m), 3.16 (3 H, s), 3.56-3.66 (3 H, m), 3.68 (2 H, s), 4.15-4.24 (1 H, m), 7.32 (2 H, d, J = 8.3 Hz), 7.48-7.53 (2 H, m), 7.53-7.63 (4 H, m) | NT |
| 535 | | Free | 479[M + H]+ 477[M − H]− | ¹H NMR (400 MHz, CD$_3$OD) δ ppm 1.16 (3 H, t, J = 7.1 Hz), 2.81 (3 H, s), 3.02-3.11 (2 H, m), 3.08 (3 H, s), 3.43 (2 H, q, J = 7.1 Hz), 3.57-3.63 (2 H, m), 3.69 (2 H, s), 4.09-4.17 (1 H, m), 7.32 (2 H, d, J = 8.3 Hz), 7.47-7.64 (6 H, m) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 536 | | Free | 483[M + H]+<br>481[M − H]− | ¹H NMR (400 MHz, CD$_3$OD) δ ppm 2.48-2.51 (4 H, m), 2.81 (3 H, s), 3.07 (3 H, s), 3.60 (2 H, s), 3.67-3.73 (4 H, m), 7.24-7.31 (1 H, m), 7.31-7.38 (1 H, m), 7.43-7.49 (2 H, m), 7.52-7.66 (3 H, m) | NT |
| 537 | | Free | 494[M + H]+<br>492[M − H]− | ¹H NMR (400 MHz, CD$_3$OD) δ ppm 1.16 (3 H, t, J = 7.0 Hz), 1.46 (3 H, s), 2.82 (3 H, s), 3.08 (3 H, s), 3.15-3.42 (6 H, m), 3.71 (2 H, s), 7.30-7.65 (8 H, m) | NT |
| 538 | | Free | 493[M + H]+<br>491[M − H]− | ¹H NMR (400 MHz, CD$_3$OD) δ ppm 0.85 (3 H, t, J = 7.3 Hz), 1.80-1.88 (2 H, m), 2.81 (3 H, s), 3.08 (3 H, s), 3.15 (3 H, s), 3.17-3.26 (4 H, m), 3.72 (2 H, s), 7.30-7.70 (8 H, m) | NT |
| 539 | | Free | 497[M + H]+<br>495[M − H]− | ¹H NMR (400 MHz, CD$_3$OD) δ ppm 2.81 (3 H, s), 3.03-3.14 (2 H, m), 3.08 (3 H, s), 3.56-3.75 (7 H, m), 4.40-4.44 (1 H, m), 4.53-4.56 (1 H, m), 7.30-7.40 (2 H, m), 7.49-7.62 (6 H, m) | NT |
| 540 | | Free | 449[M + H]+<br>447[M − H]− | ¹H NMR (400 MHz, CD$_3$OD) δ ppm 0.38-0.54 (4 H, m), 1.71-1.78 (1 H, m), 2.28 (3 H, s), 2.82 (3 H, s), 3.08 (3 H, s), 3.70 (2 H, s), 7.34 (2 H, d, J = 8.0 Hz), 7.46-7.64 (6 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 541 | | Free | 464[M + H]+<br>462[M − H]− | ¹H NMR (400 MHz, CD$_3$OD) δ ppm 0.70-0.90 (4 H, m), 1.77 (3 H, s), 2.52 (3 H, br. s.), 2.58-2.66 (1 H, m), 2.79 (3 H, s), 3.17 (3 H, s), 3.99 (2 H, br. s.), 7.38-7.46 (2 H, m), 7.50-7.66 (6 H, m) | NT |
| 542 | | Free | 505[M + H]+<br>503[M − H]− | ¹H NMR (400 MHz, CD$_3$OD) δ ppm 1.45-1.57 (1 H, m), 1.60-1.74 (1 H, m), 1.84-1.98 (2 H, m), 2.10-2.24 (2 H, m), 2.81 (3 H, s), 3.03-3.14 (2 H, m), 3.08 (3 H, s), 3.56-3.76 (4 H, m), 3.86-3.98 (1 H, m), 4.06-4.18 (1 H, m), 7.28-7.36 (2 H, m), 7.46-7.66 (6 H, m) | NT |
| 543 | | Free | 477[M + H]+<br>475[M − H]− | ¹H NMR (400 MHz, CD$_3$OD) δ ppm 0.90 (3 H, t, J = 7.3 Hz), 1.20-1.29 (2 H, m), 1.48-1.56 (2 H, m), 2.46-2.56 (1 H, m), 2.81 (3 H, s), 2.90-2.96 (2 H, m), 3.08 (3 H, s), 3.40-3.54 (2 H, m), 3.60-3.73 (2 H, m), 7.32 (2 H, d, J = 8.0 Hz), 7.42-7.62 (6 H, m) | NT |
| 544 | | Free | 493[M + H]+<br>491[M − H]− | ¹H NMR (400 MHz, CD$_3$OD) δ ppm 1.86-1.93 (2 H, m), 2.38 (3 H, s), 2.66-2.73 (4 H, m), 2.82 (3 H, s), 3.08 (3 H, s), 3.64 (2 H, s), 3.68-3.72 (2 H, m), 3.78-3.84 (2 H, m), 7.30-7.62 (7 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 545 | | Free | 497[M + H]+ 495[M − H]− | ¹H NMR (400 MHz, CD$_3$OD) δ ppm 1.88-1.96 (2 H, m), 2.70-2.78 (4 H, m), 2.81 (3 H, s), 3.13 (3 H, s), 3.66-3.83 (6 H, m), 7.27 (1 H, d, J = 10.0 Hz), 7.34 (1 H, d, J = 7.6 Hz), 7.40-7.70 (5 H, m) | NT |
| 546 | | Free | 455[M + H]+ 453[M − H]− | ¹H NMR (400 MHz, CD$_3$OD) δ ppm 2.29 (3 H, s), 2.70 (1 H, t, J = 4.9 Hz), 2.77 (1 H, t, J = 4.9 Hz), 2.82 (3 H, s), 3.08 (3 H, s), 3.62 (2 H, s), 4.50 (1 H, t, J = 4.9 Hz), 4.62 (1 H, t, J = 4.9 Hz), 7.37 (2 H, d, J = 8.0 Hz), 7.47-7.66 (6 H, m) | NT |
| 547 | | Free | 498[M + H]+ 496[M − H]− | ¹H NMR (400 MHz, CD$_3$OD) δ ppm 1.88-1.95 (2 H, m), 2.66-2.74 (4 H, m), 2.82 (3 H, s), 3.07 (3 H, s), 3.66-3.76 (4 H, m), 3.78-3.84 (2 H, m), 7.18-7.26 (2 H, m), 7.35-7.65 (5 H, m) | NT |
| 548 | | Free | 470[M + H]+ 468[M − H]− | ¹H NMR (400 MHz, CD$_3$OD) δ ppm 1.68 (3 H, s), 2.21 (3 H, s), 2.58-2.76 (2 H, m), 2.70 (3 H, s), 3.08 (3 H, s), 3.54 (2 H, s), 4.42 (1 H, t, J = 4.9 Hz), 4.48-4.60 (1 H, m), 7.29 (2 H, d, J = 8.3 Hz), 7.38-7.58 (6 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 549 | | Free | 450[M + H]+ 448[M − H]− | ¹H NMR (400 MHz, CD$_3$OD) δ ppm 0.37-0.51 (4 H, m), 1.76 (3 H, s), 2.10-2.20 (1 H, m), 2.78 (3 H, s), 3.16 (3 H, s), 3.83 (2 H, s), 7.38 (2 H, d, J = 8.3 Hz), 7.45-7.64 (6 H, m) | NT |
| 550 | | Free | 436[M + Na]+ 412[M − H]− | ¹H NMR (400 MHz, CDCl$_3$) δ ppm 1.80 (3 H, s), 2.83 (3 H, d, J = 4.6 Hz), 3.17 (3 H, s), 3.38 (3 H, s), 4.39 (2 H, s), 6.45 (1 H, s), 6.80-7.00 (1 H, m), 7.30-7.60 (5 H, m), 7.68 (1 H, br. s.), 10.54 (1 H, br. s.) | A |
| 551 | | Free | 464[M + H]+ 462[M − H]− | ¹H NMR (400 MHz, CD$_3$OD) δ ppm 1.70-1.75 (2 H, m), 1.93-1.98 (2 H, m), 2.04-2.08 (5 H, m), 2.82 (3 H, s), 2.92-2.95 (1 H, m), 3.08 (3 H, s), 3.45 (2 H, s), 7.35 (2 H, d, J = 8.1 Hz), 7.50-7.62 (6 H, m) | NT |
| 552 | | Free | 480[M + H]+ 478[M − H]− | ¹H NMR (400 MHz, CD$_3$OD) δ ppm 0.91 (9 H, s), 2.23 (3 H, s), 2.25 (2 H, s), 2.81 (3 H, s), 3.08 (3 H, s), 3.59 (2 H, s), 7.40 (2 H, d, J = 8.3 Hz), 7.47-7.62 (6 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 553 | | Free | 450[M + H]+ 448[M − H]− | ¹H NMR (400 MHz, CD$_3$OD) δ ppm 0.35-0.50 (4 H, m), 1.77 (3 H, s), 2.08-2.17 (1 H, m), 2.79 (3 H, s), 3.17 (3 H, s), 3.82 (2 H, s), 7.38 (2 H, d, J = 8.5 Hz), 7.46-7.61 (6 H, m) | NT |
| 554 | | Free | 455[M + H]+ 453[M − H]− | ¹H NMR (400 MHz, CD$_3$OD) δ ppm 1.73 (3 H, s), 2.75 (3 H, s), 2.86-3.00 (2 H, m), 3.12 (3 H, s), 3.84 (2 H, s), 4.43-4.52 (1 H, m), 4.55-4.63 (1 H, m), 7.36 (2 H, d, J = 8.3 Hz), 7.44-7.63 (6 H, m) | NT |
| 555 | | Free | 463[M + H]+ 461[M − H]− | ¹H NMR (400 MHz, CD$_3$OD) δ ppm 1.15-1.35 (2 H, m), 1.50-2.05 (7 H, m), 2.10-2.30 (1 H, m), 2.82 (3 H, s), 3.20 (3 H, s), 3.79 (2 H, s), 7.42 (2 H, d, J = 8.5 Hz), 7.47-7.70 (6 H, m) | NT |
| 556 | | Free | 480[M + H]+ 478[M − H]− | ¹H NMR (400 MHz, CD$_3$OD) δ ppm 0.93 (9 H, s), 1.77 (3 H, s), 2.38 (2 H, s), 2.79 (3 H, s), 3.17 (3 H, s), 3.85 (2 H, s), 7.40 (2 H, d, J = 8.3 Hz), 7.48-7.63 (6 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 557 | | Free | 493[M + H]+<br>491[M − H]− | ¹H NMR (400 MHz, CD₃OD) δ ppm 1.16 (3 H, t, J = 7.0 Hz), 1.77 (3 H, s), 2.79 (3 H, s), 3.06-3.12 (2 H, m), 3.16 (3 H, s), 3.35-3.50 (2 H, m), 3.58-3.76 (4 H, m), 4.08-4.20 (1 H, m), 7.25-7.40 (2 H, m), 7.45-7.70 (6 H, m) | A |
| 558 | | Free | 493[M + H]+<br>492[M − H]− | ¹H NMR (400 MHz, CD₃OD) δ ppm 1.45 (3 H, s), 1.77 (3 H, s), 2.79 (3 H, s), 3.05-3.35 (4 H, m), 3.16 (3 H, s), 3.19 (3 H, s), 3.71 (2 H, br. s.), 7.25-7.40 (2 H, m), 7.45-7.65 (6 H, m) | NT |
| 559 | | Free | 512[M + H]+<br>510[M − H]− | ¹H NMR (400 MHz, CD₃OD) δ ppm 1.77 (3 H, s), 2.79 (3 H, s), 3.08-3.14 (2 H, m), 3.16 (3 H, s), 3.56-3.74 (4 H, m), 3.70 (2 H, s), 4.16-4.25 (1 H, m), 4.40-4.45 (1 H, m), 4.52-4.57 (1 H, m), 7.25-7.40 (2 H, m), 7.45-7.65 (6 H, m) | NT |
| 560 | | Free | 493[M + H]+<br>491[M − H]− | ¹H NMR (400 MHz, CD₃OD) δ ppm 0.98-1.04 (3 H, m), 1.68 (3 H, s), 1.70-1.80 (1 H, m), 2.00-2.15 (1 H, m), 2.57-2.70 (2 H, m), 2.70 (3 H, s), 3.07 (3 H, s), 3.44 (2 H, s), 3.48-3.66 (2 H, m), 3.68-3.76 (1 H, m), 7.28 (2 H, d, J = 8.3 Hz), 7.36-7.54 (6 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 561 | | Free | 479[M + H]+ 477[M − H]− | ¹H NMR (400 MHz, CD$_3$OD) δ ppm 1.77 (3 H, s), 2.40-2.50 (4 H, m), 2.79 (3 H, s), 3.17 (3 H, s), 3.54 (2 H, s), 3.65-3.75 (4 H, m), 7.38 (2 H, d, J = 8.3 Hz), 7.50 (2 H, d, J = 8.1 Hz), 7.56 (2 H, d, J = 8.3 Hz), 7.60 (2 H, d, J = 8.5 Hz) | NT |
| 562 | | Free | 494[M + H]+ 492[M − H]− | ¹H NMR (400 MHz, CD$_3$OD) δ ppm 1.17 (3 H, t, J = 7.1 Hz), 2.33 (3 H, s), 2.81 (3 H, s), 3.05-3.15 (5 H, m), 3.44 (2 H, q, J = 7.1 Hz), 3.60-3.75 (4 H, m), 4.10-4.20 (1 H, m), 7.24-7.26 (1 H, m), 7.32-7.35 (2 H, m), 7.57-7.61 (4 H, m) | A |
| 563 | | Free | 498[M + H]+ 496[M − H]− | ¹H NMR (400 MHz, CD$_3$OD) δ ppm 1.16 (3 H, t, J = 7.1 Hz), 2.81 (3 H, s), 3.00-3.15 (5 H, m), 3.39-3.51 (2 H, m), 3.61-3.72 (4 H, m), 4.08-4.14 (1 H, m), 7.25-7.70 (7 H, m) | A |
| 564 | | Free | 498[M + H]+ 496[M − H]− | ¹H NMR (400 MHz, CD$_3$OD) δ ppm 1.16 (3 H, t, J = 7.1 Hz), 2.82 (3 H, s), 3.00-3.08 (5 H, m), 3.43 (2 H, q, J = 7.1 Hz), 3.55-3.75 (4 H, m), 4.10-4.20 (1 H, m), 7.13-7.25 (2 H, m), 7.35-7.70 (5 H, m) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 565 | | Free | 507[M + H]+<br>505[M − H]− | ¹H NMR (400 MHz, CD$_3$OD) δ ppm 1.51-1.64 (2 H, m), 1.77 (3 H, s), 1.86-1.96 (2 H, m), 2.18-2.32 (2 H, m), 2.65-2.85 (2 H, m), 2.79 (3 H, s), 3.17 (3 H, s), 3.20-3.35 (1 H, m), 3.28 (3 H, s), 3.56 (2 H, s), 7.35-7.40 (2 H, m), 7.45-7.65 (6 H, m) | NT |
| 566 | | Free | 521[M + H]+<br>519[M − H]− | ¹H NMR (400 MHz, CD$_3$OD) δ ppm 1.18 (3 H, t, J = 7.1 Hz), 1.77 (5 H, br. s.), 1.90-2.05 (2 H, m), 2.51-2.58 (2 H, m), 2.79 (3 H, s), 3.04 (2 H, br. s.), 3.16 (3 H, s), 3.45-3.58 (3 H, m), 3.92 (2 H, br. s.), 7.45 (2 H, d, J = 8.0 Hz), 7.50-7.65 (6 H, m) | NT |
| 567 | | Free | 479[M + H]+<br>477[M − H]− | ¹H NMR (400 MHz, CD$_3$OD) δ ppm 1.77 (3 H, s), 2.79 (3 H, s), 3.02-3.12 (2 H, m), 3.16 (3 H, s), 3.25 (3 H, s), 3.56-3.64 (2 H, m), 3.69 (2 H, s), 4.02-4.13 (1 H, m), 7.32 (2 H, d, J = 8.3 Hz), 7.45-7.65 (6 H, m) | NT |
| 568 | | Free | 493[M + H]+<br>491[M − H]− | ¹H NMR (400 MHz, CD$_3$OD) δ ppm 1.16 (3 H, t, J = 7.1 Hz), 2.50 (3 H, s), 2.77 (3 H, s), 3.00-3.10 (5 H, m), 3.40-3.46 (2 H, m), 3.50-3.75 (4 H, m), 4.05-4.15 (1 H, m), 7.11-7.15 (1 H, m), 7.22 (1 H, s), 7.40-7.70 (5 H, m) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 569 | | Free | 507[M + H]+ 505[M − H]− | ¹H NMR (400 MHz, CD₃OD) δ ppm 0.92 (3 H, t, J = 7.3 Hz), 1.51-1.58 (2 H, m), 1.77 (3 H, s), 2.79 (3 H, s), 3.04-3.10 (2 H, m), 3.16 (3 H, s), 3.30-3.34 (2 H, m), 3.56-3.64 (2 H, m), 3.69 (2 H, s), 4.08-4.16 (1 H, m), 7.33 (2 H, d, J = 8.3 Hz), 7.49-7.62 (6 H, m) | NT |
| 570 | | Free | 519[M + H]+ 517[M − H]− | ¹H NMR (400 MHz, CD₃OD) δ ppm 0.15-0.22 (2 H, m), 0.47-0.54 (2 H, m), 0.92-1.04 (1 H, m), 1.76 (3 H, s), 2.78 (3 H, s), 3.04-3.12 (2 H, m), 3.16 (3 H, s), 3.23 (2 H, d, J = 6.8 Hz), 3.58-3.66 (2 H, m), 3.69 (2 H, s), 4.12-4.22 (1 H, m), 7.33 (2 H, d, J = 8.0 Hz), 7.50 (2 H, d, J = 8.0 Hz), 7.53-7.65 (4 H, m) | NT |
| 571 | | Free | 465[M + H]+ 463[M − H]− | ¹H NMR (400 MHz, CD₃OD) δ ppm 1.03 (6 H, d, J = 6.8 Hz), 1.77 (3 H, s), 1.99-2.04 (1 H, m), 2.79 (3 H, s), 2.85 (2 H, d, J = 7.3 Hz), 3.16 (3 H, s), 4.19 (2 H, s), 7.50-7.68 (8 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 572 | | Free | 509[M + H]+ 507[M − H]− | ¹H NMR (400 MHz, CD$_3$OD) δ ppm 1.16 (3 H, t, J = 7.1 Hz), 2.82 (3 H, s), 3.00-3.14 (5 H, m), 3.42 (2 H, q, J = 7.1 Hz), 3.61-3.73 (4 H, m), 3.87 (3 H, s), 4.05-4.20 (1 H, m), 7.05-7.15 (2 H, m), 7.22-7.25 (1 H, m), 7.35-7.65 (4 H, m) | B |
| 573 | | Free | 547[M + H]+ 545[M − H]− | ¹H NMR (400 MHz, CD$_3$OD) δ ppm 1.17 (3 H, t, J = 7.1 Hz), 2.82 (3 H, s), 3.04-3.13 (5 H, m), 3.42-3.48 (2 H, m), 3.66-3.70 (2 H, m), 3.86 (2 H, s), 4.13-4.19 (1 H, m), 7.40-7.90 (7 H, m) | A |
| 574 | | Free | 547[M + H]+ 545[M − H]− | ¹H NMR (400 MHz, CD$_3$OD) δ ppm 1.16 (3 H, t, J = 7.0 Hz), 2.82 (3 H, s), 3.05-3.15 (2 H, m), 3.08 (3 H, s), 3.40-3.46 (2 H, m), 3.58-3.62 (2 H, m), 3.75 (2 H, s), 4.13-4.20 (1 H, m), 7.40-7.80 (7 H, m) | A |
| 575 | | Free | 407[M + Na]+ 383[M − H]− | ¹H NMR (400 MHz, CD$_3$OD) δ ppm 1.76 (3 H, s), 2.47 (3 H, s), 2.78 (3 H, s), 3.15 (3 H, s), 7.54-7.64 (4 H, m), 8.10 (1 H, s) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 576 | | Free | 407[M + Na]+<br>383[M − H]− | ¹H NMR (400 MHz, CD$_3$OD) δ ppm 1.77 (3 H, s), 2.46 (3 H, s), 2.79 (3 H, s), 3.15 (3 H, s), 6.35 (1 H, s), 7.57-7.62 (2 H, m), 7.65-7.70 (2 H, m) | A |
| 577 | | Free | 523[M + H]+<br>521[M − H]− | ¹H NMR (400 MHz, CD$_3$OD) δ ppm 1.77 (3 H, s), 2.79 (3 H, s), 3.16 (3 H, s), 3.35 (3 H, s), 3.44-3.62 (6 H, m), 3.88-3.96 (2 H, m), 4.00 (2 H, s), 4.24-4.32 (1 H, m), 7.39 (2 H, d, J = 8.3 Hz), 7.52-7.65 (6 H, m) | NT |
| 578 | | Free | 493[M + H]+<br>491[M − H]− | ¹H NMR (400 MHz, CD$_3$OD) δ ppm 1.32 (3 H, s), 1.77 (3 H, s), 277 (2 H, s), 279 (3 H, s), 3.17 (3 H, s), 3.83 (2 H, s), 4.33 (2 H, d, J = 5.9 Hz), 4.45 (2 H, d, J = 5.9 Hz), 7.35-7.45 (2 H, m), 7.45-7.65 (6 H, m) | NT |
| 579 | | Free | 513[M + H]+ | ¹H NMR (400 MHz, CD$_3$OD) δ ppm 1.17 (3 H, t, J = 7.1 Hz), 2.81 (3 H, s), 3.07 (3 H, s), 3.09-3.13 (2 H, m), 3.41-3.46 (2 H, m), 3.66-3.69 (2 H, m), 3.81 (2 H, s), 4.14-4.17 (1 H, m), 7.41-7.64 (7 H, m) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 580 | | Free | 515[M + H]+ 513[M − H]− | ¹H NMR (400 MHz, CD$_3$OD) δ ppm 1.16 (3 H, t, J = 7.1 Hz), 2.81 (3 H, s), 3.07-3.13 (5 H, m), 3.40-3.46 (2 H, m), 3.61-3.65 (2 H, m), 3.75 (2 H, s), 4.11-4.14 (1 H, m), 7.16-7.20 (1 H, m), 7.32-7.35 (1 H, m), 7.45-7.68 (4 H, m) | A |
| 581 | | Free | 498[M + H]+ 496[M − H]− | ¹H NMR (400 MHz, CD$_3$OD) δ ppm 1.16 (3 H, t, J = 7.1 Hz), 2.81 (3 H, s), 3.03-3.13 (5 H, m), 3.43 (2 H, q, J = 7.1 Hz), 3.59-3.62 (2 H, m), 3.69 (2 H, s), 4.11-4.17 (1 H, m), 7.15-7.41 (4 H, m), 7.52 (2 H, d, J = 8.0 Hz), 7.63-7.66 (1 H, m) | A |
| 582 | | Free | 494[M + H]+ 492[M − H]− | ¹H NMR (400 MHz, CD$_3$OD) δ ppm 1.16 (3 H, t, J = 7.1 Hz), 2.54 (3 H, s), 2.82 (3 H, s), 3.05-3.12 (5 H, m), 3.42 (2 H, q, J = 7.1 Hz), 3.58-3.62 (2 H, m), 3.69 (2 H, s), 4.12-4.15 (1 H, m), 7.32-7.34 (3 H, m), 7.46-7.56 (4 H, m) | A |
| 583 | | Free | 483[M + H]+ 481[M − H]− | ¹H NMR (400 MHz, CD$_3$OD) δ ppm 1.77 (3 H, s), 1.85-2.00 (2 H, m), 2.73-2.80 (4 H, m), 2.79 (3 H, s), 3.16 (3 H, s), 3.70-3.82 (6 H, m), 6.46 (1 H, br. s.), 7.52-7.58 (4 H, m), 7.81 (1 H, d, J = 1.0 Hz) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 584 | | Free | 483[M + H]+<br>481[M − H]− | ¹H NMR (400 MHz, CD$_3$OD) δ ppm 1.16 (3 H, t, J = 6.9 Hz), 1.76 (3 H, s), 2.78 (3 H, s), 3.05-3.20 (2 H, m), 3.15 (3 H, s), 3.43 (2 H, q, J = 6.9 Hz), 3.57-3.74 (4 H, m), 4.06-4.18 (1 H, m), 6.43 (1 H, s), 7.52-7.58 (4 H, m), 7.79 (1 H, s) | A |
| 585 | | Free | 439[M + H]+<br>437[M − H]− | ¹H NMR (400 MHz, CD$_3$OD) δ ppm −0.03-0.02 (2 H, m), 0.08-0.13 (2 H, m), 1.39 (3 H, s), 1.75-1.83 (1 H, m), 2.41 (3 H, s), 2.78 (3 H, s), 3.43 (2 H, s), 6.05 (1 H, s), 7.12-7.20 (4 H, m), 7.41 (1 H, s) | A |
| 586 | | Free | 423[M + Na]+<br>399[M − H]− | ¹H NMR (400 MHz, CD$_3$OD) δ ppm 1.77 (3 H, s), 2.72 (3 H, s), 2.79 (3 H, s), 3.16 (3 H, s), 7.55-7.60 (2 H, m), 7.62-7.65 (2 H, m), 7.70 (1 H, s) | B |
| 587 | | Free | 505[M + H]+<br>503[M − H]− | ¹H NMR (400 MHz, CD$_3$OD) δ ppm 1.04 (3 H, s), 1.35-1.52 (4 H, m), 1.56-1.73 (4 H, m), 1.77 (3 H, s), 2.66 (2 H, br. s.), 2.79 (3 H, s), 3.16 (3 H, s), 4.03 (2 H, br. s.), 7.47 (2 H, d, J = 7.8 Hz), 7.50-7.65 (6 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 588 | | Free | 446[M + Na]+ 422[M − H]− | ¹H NMR (400 MHz, CD₃OD) δ ppm 1.77 (3 H, s), 2.79 (3 H, s), 3.16 (3 H, s), 5.99 (2 H, s), 6.84 (1 H, d, J = 8.0 Hz), 6.98 (1 H, d, J = 1.6 Hz), 7.07 (1 H, dd, J = 8.0, 1.6 Hz), 7.52-7.59 (4 H, m) | NT |
| 589 | | Free | 468[M + Na]+ 444[M − H]− | ¹H NMR (400 MHz, CD₃OD) δ ppm 1.77 (3 H, s), 2.79 (3 H, s), 3.16 (3 H, s), 6.89 (1 H, t, J = 74.0 Hz), 7.17 (2 H, d, J = 8.8 Hz), 7.54-7.63 (6 H, m) | NT |
| 590 | | Free | 437[M + Na]+ 413[M − H]− | ¹H NMR (400 MHz, CD₃OD) δ ppm 1.45-1.53 (2 H, m), 1.65-1.69 (2 H, m), 1.76 (3 H, s), 2.36-2.41 (1 H, m), 2.78 (3 H, s), 3.15 (3 H,s), 3.43-3.49 (2 H, m), 3.93-3.96 (2 H, m), 5.74-5.79 (1 H, m), 6.22 (1 H, dd, J = 16.1, 6.8 Hz), 7.47 (2 H, d, J = 8.5 Hz), 7.51 (2 H, d, J = 8.5 Hz) | A |
| 591 | | Free | 477[M + H]+ 475[M − H]− | ¹H NMR (400 MHz, CD₃OD) δ ppm 0.35-0.50 (2 H, m), 0.65-0.80 (2 H, m), 1.08 (3 H, d, J = 5.8 Hz), 1.77 (3 H, s), 2.70-2.85 (2 H, m), 2.79 (3 H, s), 3.17 (3 H, s), 4.06 (2 H, s), 7.47 (2 H, d, J = 8.3 Hz), 7.50-7.65 (6 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 592 | 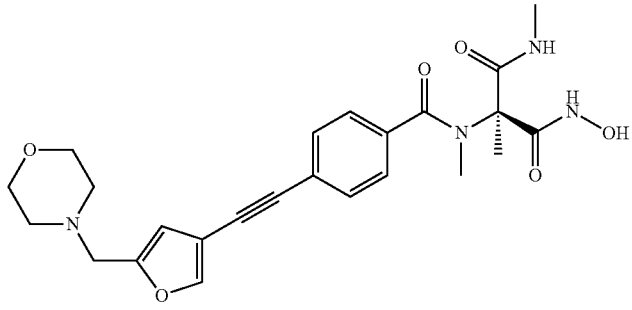 [SMILES: CNC(=O)[C@@](C)(C(=O)NO)N(C)C(=O)c1ccc(C#Cc2coc(CN3CCOCC3)c2)cc1] | Free | 469[M + H]+<br>467[M − H]− | ¹H NMR (400 MHz, CD$_3$OD) δ ppm 1.76 (3 H, s), 2.47-2.56 (4 H, m), 2.78 (3 H, s), 3.15 (3 H, s), 3.57 (2 H, s), 3.66-3.76 (4 H, m), 6.47 (1 H, s), 7.52-7.58 (4 H, m), 7.81 (1 H, s) | A |
| 593 | 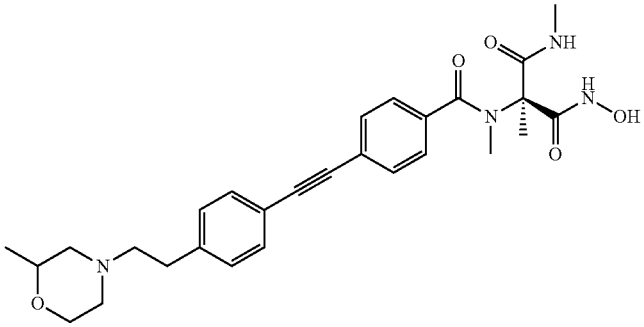 [SMILES: CNC(=O)[C@@](C)(C(=O)NO)N(C)C(=O)c1ccc(C#Cc2ccc(CCN3CCOC(C)C3)cc2)cc1] | Free | 507[M + H]+<br>505[M − H]− | ¹H NMR (400 MHz, CD$_3$OD) δ ppm 1.13 (3 H, d, J = 6.4 Hz), 1.77 (3 H, s), 1.84-1.92 (1 H, m), 2.10-2.25 (1 H, m), 2.58-2.66 (2 H, m), 2.75-2.95 (4 H, m), 2.79 (3 H, s), 3.17 (3 H, s), 3.60-3.75 (2 H, m), 3.82-3.90 (1 H, m), 7.26 (2 H, d, J = 8.3 Hz), 7.42-7.50 (2 H, m), 7.50-7.70 (4 H, m) | NT |
| 594 | 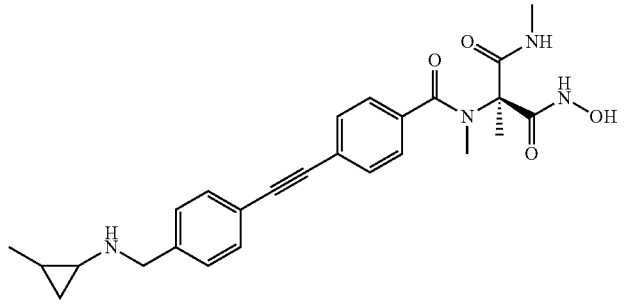 [SMILES: CNC(=O)[C@@](C)(C(=O)NO)N(C)C(=O)c1ccc(C#Cc2ccc(CNC3CC3C)cc2)cc1] | Free | 463[M + H]+ | ¹H NMR (400 MHz, CD$_3$OD) δ ppm 0.25-0.45 (1 H, m), 0.55-0.75 (1 H, m), 0.75-0.95 (1 H, m), 0.97-1.02 (3 H, m), 1.77 (3 H, s), 1.85-2.05 (1 H, m), 2.79 (3 H, s), 3.17 (3 H, s), 3.94 (2 H, br. s.), 7.35-7.45 (2 H, m), 7.50-7.65 (6 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 595 | 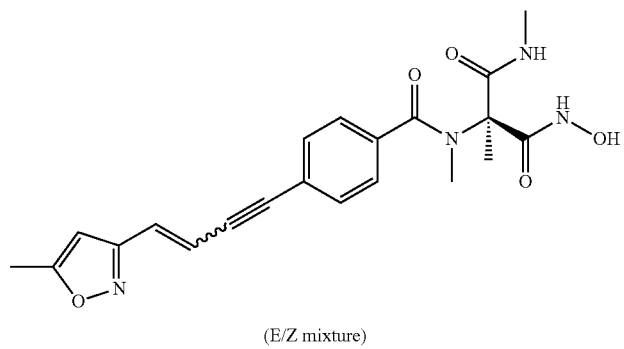 [SMILES: CNC(=O)[C@@](C)(C(=O)NO)N(C)C(=O)c1ccc(C#CC=Cc2cc(C)on2)cc1]<br>(E/Z mixture) | Free | 433[M + H]+<br>409[M − H]− | ¹H NMR (400 MHz, CD$_3$OD) δ ppm 1.76 (1.5 H, s), 1.77 (1.5 H, s), 2.42 (1.5 H, s), 2.47 (1.5 H, s), 2.78 (1.5 H, s), 2.79 (1.5 H, s), 3.15 (1.5 H, s), 3.16 (1.5 H, s), 6.29 (0.5 H, d, J = 11.7 Hz), 6.44 (0.5 H, s), 6.63 (0.5 H, d, J = 16.4 Hz), 6.81 (0.5 H, d, J = 11.7 Hz), 6.90 (0.5 H, s), 6.97 (0.5 H, d, J = 16.4 Hz), 7.53-7.65 (4 H, m) | NT |
| 596 | 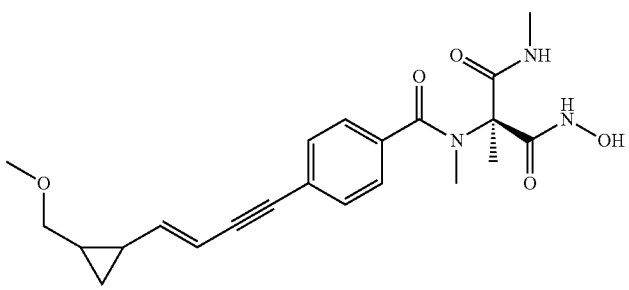 [SMILES: CNC(=O)[C@@](C)(C(=O)NO)N(C)C(=O)c1ccc(C#C/C=C/C2CC2COC)cc1] | Free | 413[M − H]− | ¹H NMR (400 MHz, DMSO-d$_6$) δ ppm 0.75-0.83 (2 H, m), 1.22-1.33 (1 H, m), 1.48-1.56 (1 H, m), 1.61 (3 H, s), 2.63 (3 H, d, J = 4.4 Hz), 2.99 (3 H, s), 3.17 (1 H, dd, J = 10.5, 7.1 Hz), 3.20-3.27 (1 H, m), 3.23 (3 H, s), 5.82-5.92 (2 H, m), 7.45-7.56 (4 H, m), 8.45-8.55 (1 H, m), 8.96 (1 H, s), 10.94 (1 H, s) | A |
| 597 | 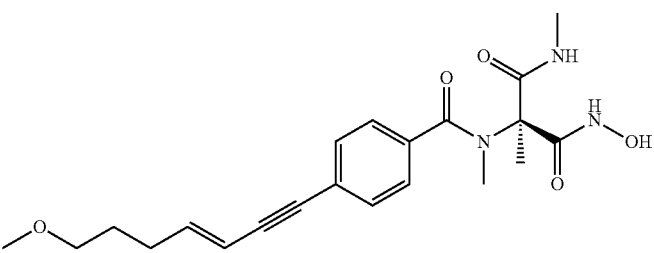 [SMILES: CNC(=O)[C@@](C)(C(=O)NO)N(C)C(=O)c1ccc(C#C/C=C/CCCOC)cc1] | Free | 401[M − H]− | ¹H NMR (400 MHz, CD$_3$OD) δ ppm 1.65-1.73 (2 H, m), 1.75 (3 H, s), 2.20-2.29 (2 H, m), 2.78 (3 H, s), 3.15 (3 H, s), 3.33 (3 H, s), 3.38-3.44 (2 H, m), 5.71-5.79 (1 H, m), 6.22-6.32 (1 H, m), 7.44-7.55 (4 H, m) | A |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 598 | | Free | 555[M + H]+ 553[M − H]− | ¹H NMR (400 MHz, CD$_3$OD) δ ppm 1.77 (3 H, s), 2.79 (3 H, s), 3.05-3.12 (2 H, m), 3.16 (3 H, s), 3.52-3.60 (2 H, m), 3.67 (2 H, s), 4.18-4.28 (1 H, m), 4.45 (2 H, s), 7.25-7.40 (7 H, m), 7.45-7.65 (6 H, m) | NT |
| 599 | | Free | 493[M + H]+ 491[M − H]− | ¹H NMR (400 MHz, CD$_3$OD) δ ppm 1.68 (3 H, s), 2.58-2.72 (4 H, m), 2.70 (3 H, s), 2.90-2.96 (2 H, m), 3.07 (3 H, s), 3.15 (3 H, s), 3.49-3.55 (2 H, m), 3.90-3.98 (1 H, m), 7.16 (2 H, d, J = 8.0 Hz), 7.37 (2 H, d, J = 7.8 Hz), 7.44-7.53 (4 H, m) | NT |
| 600 | | Free | 511[M + H]+ 509[M − H]− | ¹H NMR (400 MHz, CD$_3$OD) δ ppm 1.77 (3 H, s), 2.73-2.80 (1 H, m), 2.79 (3 H, s), 2.80-2.85 (1 H, m), 3.08-3.15 (2 H, m), 3.17 (3 H, s), 3.62-3.70 (2 H, m), 4.20-4.28 (1 H, m), 4.35-4.40 (1 H, m), 4.45-4.52 (1 H, m), 4.48 (2 H, s), 7.38 (2 H, d, J = 8.3 Hz), 7.52 (2 H, d, J = 8.0 Hz), 7.53-7.63 (4 H, m) | NT |
| 601 | | Free | 398[M + Na]+ 374[M − H]− | ¹H NMR (400 MHz, CD$_3$OD) δ ppm 1.75 (3 H, s), 1.80-1.88 (2 H, m), 2.47-2.53 (2 H, m), 2.78 (3 H, s), 3.14 (3 H, s), 3.35 (3 H, s), 3.51-3.56 (2 H, m), 7.42-7.50 (4 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | 1H-NMR | Enzyme inhibitory activity |
|---|---|---|---|---|---|
| 602 | 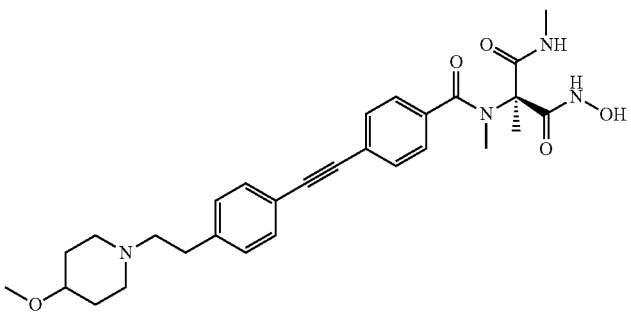 [SMILES: CNC(=O)[C@@](C)(C(=O)NO)N(C)C(=O)c1ccc(C#Cc2ccc(CCN3CCC(OC)CC3)cc2)cc1] | Free | 521[M + H]+ 519[M − H]− | 1H NMR (400 MHz, CD3OD) δ ppm 1.53-1.68 (2 H, m), 1.73 (3 H, s), 1.85-2.00 (2 H, m), 2.30-2.45 (2 H, m), 2.60-2.68 (2 H, m), 2.75 (3 H, s), 2.79-2.90 (4 H, m), 3.13 (3 H, s), 3.30 (3 H, s), 4.45-4.65 (1 H, m), 7.22 (2 H, d, J = 7.8 Hz), 7.38-7.46 (2 H, m), 7.48-7.60 (4 H, m) | NT |
| 603 | 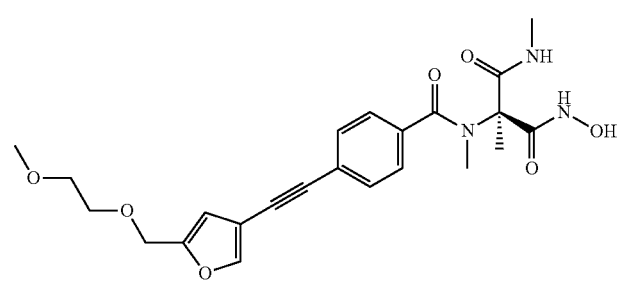 [SMILES: CNC(=O)[C@@](C)(C(=O)NO)N(C)C(=O)c1ccc(C#Cc2coc(COCCOC)c2)cc1] | Free | 480[M + Na]+ 456[M − H]− | 1H NMR (400 MHz, CD3OD) δ ppm 1.76 (3 H, s), 2.78 (3 H, s), 3.16 (3 H, s), 3.35 (3 H, s), 3.50-3.58 (2 H, m), 3.60-3.65 (2 H, m), 4.49 (2 H, s), 6.54 (1 H, s), 7.52-7.58 (4 H, m), 7.82 (1 H, s) | NT |
| 604 | 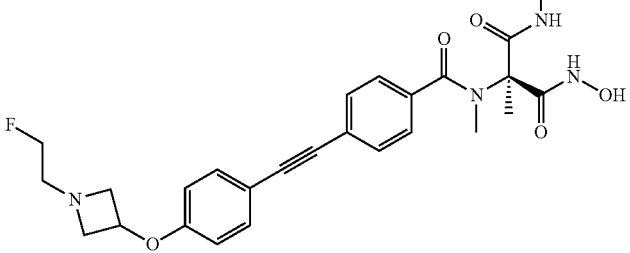 | Free | 497[M + H]+ 495[M − H]− | 1H NMR (400 MHz, CD3OD) δ ppm 1.76 (3 H, s), 2.79 (3 H, s), 2.80-2.92 (2 H, m), 3.16 (3 H, s), 3.25-3.38 (2 H, m), 3.85-3.93 (2 H, m), 4.39-4.56 (2 H, m), 4.77-4.93 (1 H, m), 6.82-6.87 (2 H, m), 7.43-7.48 (2 H, m), 7.52-7.59 (4 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 605 | | Free | 450[M + Na]+ 426[M − H]− | ¹H NMR (400 MHz, CHLOROFORM-d) δ ppm 1.82 (3 H, s), 2.85 (3 H, d, J = 4.6 Hz), 2.91 (2 H, t, J = 6.5 Hz), 3.21 (3 H, s), 3.37 (3 H, s), 3.65 (2 H, t, J = 6.5 Hz), 6.22 (1 H, s), 6.65-6.75 (1 H, m), 7.43-7.56 (4 H, m), 7.59 (1 H, s), 10.62 (1 H, br. s.) | NT |
| 606 | | Free | 475[M + H]+ 473[M − H]− | ¹H NMR (400 MHz, CD₃OD) δ ppm 1.75 (3 H, s), 2.78 (3 H, s), 3.07-3.17 (2 H, m), 3.14 (3 H, s), 3.23-3.38 (1 H, m), 3.52-3.58 (2 H, m), 3.64 (2 H, s), 5.79 (1 H, dd, J = 15.8, 1.0 Hz), 6.40 (1 H, dd, J = 15.8, 8.2 Hz), 7.23-7.35 (5 H, m), 7.45-7.54 (4 H, m) | NT |
| 607 | | Free | 545[M + H]+ 543[M − H]− | ¹H NMR (400 MHz, CD₃OD) δ ppm 1.77 (3 H, s), 2.79 (3 H, s), 2.92-3.02 (2 H, m), 3.16 (3 H, s), 3.46-3.54 (2 H, m), 3.64 (2 H, s), 4.12-4.24 (1 H, m), 4.42 (2 H, s), 6.32-6.38 (2 H, m), 7.30 (2 H, d, J = 8.5 Hz), 7.46-7.51 (3 H, m), 7.54-7.62 (4 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 608 | | Free | 507[M + H]+ 505[M − H]− | ¹H NMR (400 MHz, CD$_3$OD) δ ppm 1.64-1.74 (2 H, m), 1.77 (3 H, s), 2.51-2.59 (2 H, m), 2.65 (2 H, t, J = 7.6 Hz), 279 (3 H, s), 2.98-3.05 (2 H, m), 3.17 (3 H, s), 3.24 (3 H, s), 3.60-3.66 (2 H, m), 4.00-4.08 (1 H, m), 7.23 (2 H, d, J = 8.3 Hz), 7.45 (2 H, d, J = 8.3 Hz), 7.53-7.62 (4 H, m) | NT |
| 609 | | Free | 450[M +Na]+ 426[M − H]− | ¹H NMR (600 MHz, CD3OD) δ ppm 1.47 (3 H, d, J = 6.6 Hz), 1.77 (3 H, s), 2.79 (3 H, s), 3.16 (3 H, s), 3.27 (3 H, s), 4.32-4.44 (1 H, m), 6.48 (1 H, s), 7.43-7.59 (4 H, m), 7.81 (1 H, s) | NT |
| 610 | | Free | 444[M + Na]+ 420[M − H]− | ¹H NMR (600 MHz, CD$_3$OD) δ ppm 1.77 (3 H, s), 2.61 (3 H, s), 2.79 (3 H, s), 3.18 (3 H, s), 7.57-7.68 (6 H, m), 8.00-8.04 (2 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 611 | | Free | 493[M + H]+ 491[M − H]− | ¹H NMR (600 MHz, CD₃OD) δ ppm 1.50-1.59 1.59 (1 H, m), 1.78 (3 H, s), 1.86-1.93 (2 H, m), 1.98-2.05 (1 H, m), 2.60-2.69 (2 H, m), 2.80 (3 H, s), 3.17 (3 H, s), 3.74 (1 H, q, J = 7.4 Hz), 3.80-3.87 (3 H, m), 4.00-4.06 (1 H, m), 7.39 (2 H, d, J = 8.3 Hz), 7.52 (2 H, d, J = 8.3 Hz), 7.55-7.63 (4 H, m) | NT |
| 612 | | Free | 450[M + Na]+ 426[M − H]− | ¹H NMR (600 MHz, CD₃OD) δ ppm 1.16-1.22 (3 H, m), 1.77 (3 H, s), 2.79 (3 H, s), 3.16 (3 H, s), 3.50-3.58 (2 H, m), 4.44 (2 H, s), 6.52 (1 H, s), 7.53-7.57 (4 H, m), 7.80-7.83 (1 H, m) | A |
| 613 | | Free | 507[M + H]+ 505[M − H]− | ¹H NMR (600 MHz, CD₃OD) δ ppm 1.12 (6 H, d, J = 5.8 Hz), 1.78 (3 H, s), 2.80 (3 H, s), 3.00-3.05 (2 H, m), 3.17 (3 H, s), 3.59-3.65 (3 H, m), 3.68 (2 H, s), 4.17-4.23 (1 H, m), 7.33 (2 H, d, J = 8.3 Hz), 7.51 (2 H, d, J = 8.3 Hz), 7.55-7.63 (4 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 614 | | Free | 467[M + H]+<br>465[M − H]− | ¹H NMR (600 MHz, CD$_3$OD) δ ppm 1.50-1.59 (1 H, m), 1.78 (3 H, s), 1.86-1.93 (2 H, m), 1.98-2.05 (1 H, m), 2.60-2.69 (2 H, m), 2.80 (3 H, s), 3.17 (3 H, s), 3.74 (1 H, q, J = 7.4 Hz), 3.80-3.87 (3 H, m), 4.00-4.06 (1 H, m), 7.39 (2 H, d, J = 8.3 Hz), 7.52 (2 H, d, J = 8.3 Hz), 7.55-7.63 (4 H, m) | NT |
| 615 | | Free | 519[M + H]+<br>517[M − H]− | ¹H NMR (600 MHz, CD$_3$OD) δ ppm 1.73-1.82 1.82 (5 H, m), 2.12-2.28 (2 H, m), 2.63-2.69 (2 H, m), 2.80 (3 H, s), 3.17 (3 H, s), 3.79 (2 H, br. s), 7.36-7.41 (2 H, m), 7.49-7.53 (2 H, m), 7.55-7.63 (4 H, m) | NT |
| 616 | | Free | 422[M + Na]+<br>398[M − H]− | ¹H NMR (600 MHz, CD$_3$OD) δ ppm 1.77 (3 H, s), 2.79 (3 H, s), 3.16 (3 H, s), 4.51 (2 H, s), 6.45 (1 H, s), 7.47-7.60 (4 H, m), 7.79 (1 H, s) | A |
| 617 | | Free | 491[M + H]+<br>489[M − H]− | ¹H NMR (600 MHz, CD$_3$OD) δ ppm 1.77 (3 H, s), 2.79 (3 H, s), 2.81-2.87 (2 H, m), 3.17 (3 H, s), 3.26-3.34 (2 H, m), 3.57-3.62 (2 H, m), 3.64 (2 H, s), 4.46-4.52 (2 H, m), 7.28-7.63 (8 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 618 | 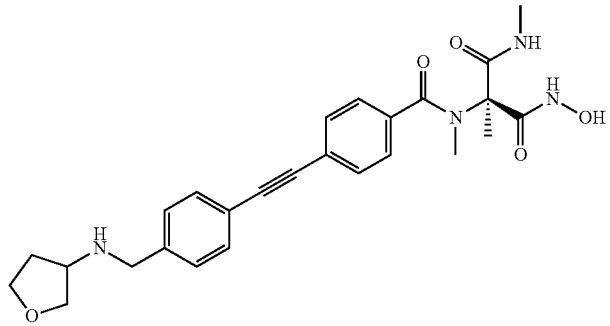 [SMILES: CNC(=O)[C@@](C)(C(=O)NO)N(C)C(=O)c1ccc(C#Cc2ccc(CNC3CCOC3)cc2)cc1] | Free | 479[M + H]+ 477[M − H]− | ¹H NMR (600 MHz, CD$_3$OD) δ ppm 1.75 (3 H, s), 1.77-1.84 (1 H, m), 2.07-2.16 (1 H, m), 2.77 (3 H, s), 3.15 (3 H, s), 3.37-3.45 (1 H, m), 3.55-3.63 (1 H, m), 3.69-3.84 (4 H, m), 3.88-3.95 (1 H, m), 7.36-7.61 (8 H, m) | NT |
| 619 | 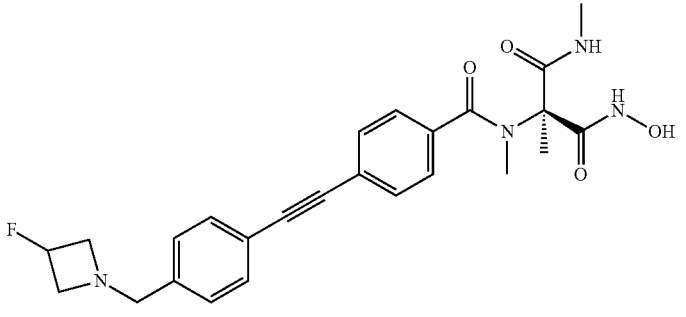 [SMILES: CNC(=O)[C@@](C)(C(=O)NO)N(C)C(=O)c1ccc(C#Cc2ccc(CN3CC(F)C3)cc2)cc1] | Free | 467[M + H]+ 465[M − H]− | ¹H NMR (600 MHz, CD$_3$OD) δ ppm 1.75 (3 H, s), 2.77 (3 H, s), 3.15 (3 H, s), 3.24-3.32 (2 H, m), 3.57-3.66 (2 H, m), 3.69 (2 H, s), 5.04-5.19 (1 H, m), 7.29-7.61 (8 H, m) | NT |
| 620 | 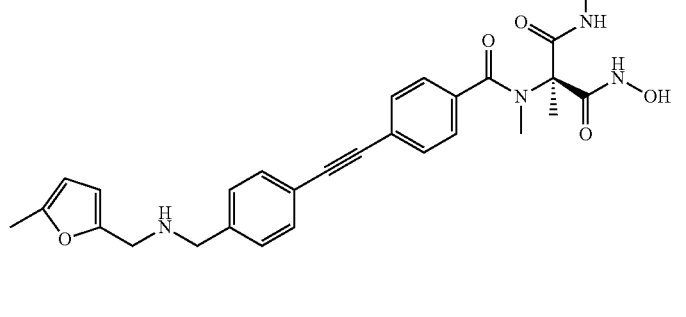 | Free | 503[M + H]+ 501[M − H]− | ¹H NMR (600 MHz, CD$_3$OD) δ ppm 1.77 (3 H, s), 2.27 (3 H, s), 2.77 (3 H, s), 3.18 (3 H, s), 3.69 (2 H, s), 3.77 (2 H, s), 5.92-5.93 (1 H, d, J = 2.9 Hz), 6.12-6.13 (1 H, d, J = 2.9 Hz) 7.34-7.39 (2 H, m), 7.50-7.52 (2 H, m), 7.55-7.57 (2 H, m), 7.60-7.61 (2 H, m) | NT |
| 621 | 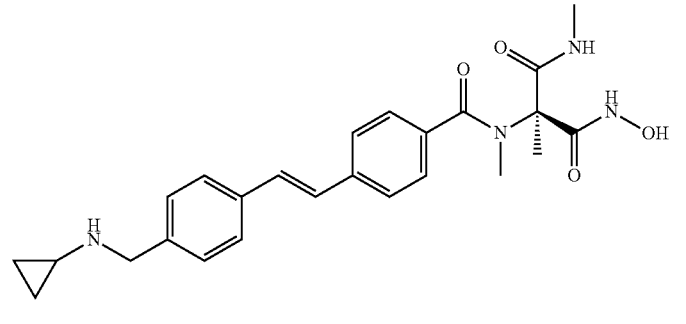 [SMILES: CNC(=O)[C@@](C)(C(=O)NO)N(C)C(=O)c1ccc(/C=C/c2ccc(CNC3CC3)cc2)cc1] | Free | 451[M + H]+ 449[M − H]− | ¹H NMR (600 MHz, CD$_3$OD) δ ppm 0.35-0.51 0.51 (4 H, m), 1.77 (3 H, s), 2.10-2.19 (1 H, m), 2.79 (3 H, s), 3.20 (3 H, s), 3.81 (2 H, s), 7.15-7.32 (2 H, m), 7.36 (2 H, d, J = 7.8 Hz), 7.51-7.58 (4 H, m), 7.65 (2 H, d, J = 8.3 Hz) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 622 | 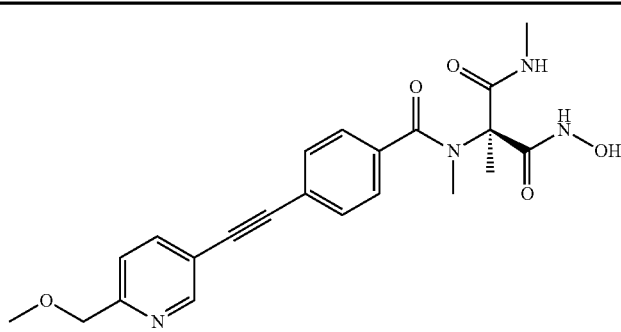 | Free | 425[M + H]+ 447[M + Na]+ 423[M − H]− | ¹H NMR (600 MHz, CD$_3$OD) δ ppm 1.80 (3 H, s), 2.78 (3 H, s), 3.20 (3 H, s), 3.44 (3 H, s), 4.57 (2 H, s), 7.52-7.55 (1 H, m), 7.57-7.60 (2 H, m), 7.65-7.67 (2 H, m), 7.97-7.99 (1 H, m), 8.65-8.66 (1 H, m) | NT |
| 623 | 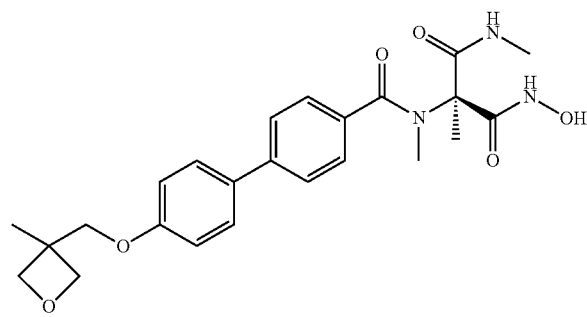 [SMILES: CNC(=O)[C@@](C)(C(=O)NO)N(C)C(=O)c1ccc(-c2ccc(OCC3(C)COC3)cc2)cc1] | Free | 478[M + Na]+ 454[M − H]− | ¹H NMR (600 MHz, CD$_3$OD) δ ppm 1.45 (3 H, s), 1.78 (3 H, s), 2.80 (3 H, s), 3.22 (3 H, s), 4.10 (2 H, s), 4.46 (2 H, d, J = 6.0 Hz), 4.68 (2 H, d, J = 6.0 Hz), 7.02-7.13 (2 H, m), 7.55-7.74 (6 H, m) | NT |
| 624 | 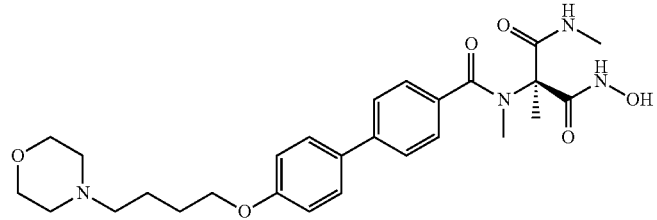 [SMILES: CNC(=O)[C@@](C)(C(=O)NO)N(C)C(=O)c1ccc(-c2ccc(OCCCCN3CCOCC3)cc2)cc1] | Free | 513[M + H]+ 511[M − H]− | ¹H NMR (600 MHz, CD$_3$OD) δ ppm 1.69-1.79 (5 H, m), 1.80-1.87 (2 H, m), 2.42-2.54 (6 H, m), 2.80 (3 H, s), 3.21 (3 H, s), 3.64-3.75 (4 H, m), 4.06 (2 H, t, J = 6.4 Hz), 6.95-7.06 (2 H, m), 7.51-7.74 (6 H, m) | NT |
| 625 | 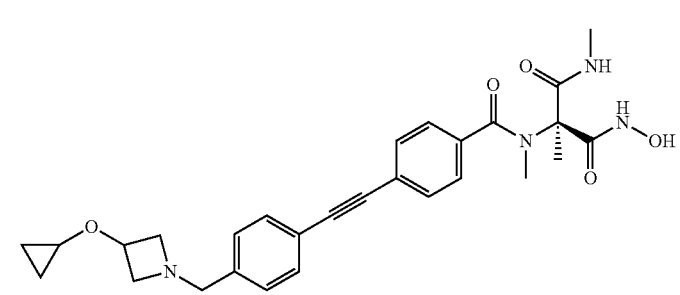 [SMILES: CNC(=O)[C@@](C)(C(=O)NO)N(C)C(=O)c1ccc(C#Cc2ccc(CN3CC(OC4CC4)C3)cc2)cc1] | Free | 505[M + H]+ 503[M − H]− | ¹H NMR (300 MHz, CD$_3$OD) δ ppm 0.40-0.48 (2 H, m), 0.49-0.57 (2 H, m), 1.77 (3 H, s), 2.79 (3 H, s), 3.02-3.11 (2 H, m), 3.17 (3 H, s), 3.23-3.29 (1 H, m), 3.56-3.64 (2 H, m), 3.67 (2 H, s), 4.26 (1 H, quin, J = 6.1 Hz), 7.32 (2 H, d, J = 8.1 Hz), 7.50 (2 H, d, J = 8.1 Hz), 7.53-7.65 (4 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 626 | | Free | 492[M + Na]+ 468[M − H]− | ¹H NMR (600 MHz, CD$_3$OD) δ ppm 1.41-1.50 (2 H, m), 1.72-1.80 (5 H, m), 2.03-2.12 (1 H, m), 2.78 (3 H, s), 3.19 (3 H, s), 3.43-3.49 (2 H, m), 3.87 (2 H, d, J = 6.6 Hz), 3.97 (2 H, dd, J = 11.1, 4.1 Hz), 7.00 (2 H, d, J = 8.7 Hz), 7.55-7.60 (4 H, m), 7.64-7.68 (2 H, m) | NT |
| 627 | | Free | 467[M + H]+ 465[M − H]− | ¹H NMR (600 MHz, CD3OD) δ ppm 1.77 (3 H, s), 2.79 (3 H, s), 3.20 (3 H, s), 3.70 (2 H, s), 3.96-4.05 (1 H, m), 4.39-4.45 (2 H, m), 4.67-4.73 (2 H, m), 7.16-7.37 (4 H, m), 7.50-7.59 (4 H, m), 7.66 (2 H, d, J = 8.3 Hz) | NT |
| 628 | | Free | 495[M + H]+ 493[M − H]− | ¹H NMR (600 MHz, CD3OD) δ ppm 1.77 (3 H, s), 1.86-1.95 (2 H, m), 2.69-2.76 (4 H, m), 2.79 (3 H, s), 3.20 (3 H, s), 3.64-3.76 (4 H, m), 3.77-3.84 (2 H, m), 7.17-7.40 (4 H, m), 7.50-7.60 (4 H, m), 7.66 (2 H, d, J = 8.3 Hz) | NT |
| 629 | | Free | 441[M + Na]+ 417[M − H]− | ¹H NMR (300 MHz, CD$_3$OD) δ ppm 1.78 (3 H, s), 2.75-2.84 (6 H, m), 3.22 (3 H, s), 6.61 (1 H, dd, J = 8.4, 2.5 Hz), 6.69 (1 H, d, J = 2.5 Hz), 7.13 (1 H, d, J = 8.4 Hz), 7.45-7.61 (4 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | ¹H-NMR | Enzyme inhibitory activity |
|---|---|---|---|---|---|
| 630 | | Free | 436[M + Na]+ 412[M − H]− | ¹H NMR (600 MHz, CD$_3$OD) δ ppm 1.77 (3 H, s), 2.79 (3 H, s), 3.16 (3 H, s), 3.34 (3 H, s), 4.41 (2 H, s), 6.46 (1 H, d, J = 2.9 Hz), 6.72 (1 H, d, J = 2.9 Hz), 7.50-7.64 (4 H, m) | NT |
| 631 | | Free | 438[M + Na]+ | ¹H NMR (400 MHz, CD$_3$OD) δ ppm 1.31 (3 H, s), 1.54-1.64 (2 H, m), 1.75 (3 H, s), 1.79-1.86 (2 H, m), 2.47 (2 H, t, J = 7.0 Hz), 2.78 (3 H, s), 3.14 (3 H, s), 4.36 (2 H, d, J = 5.6 Hz), 4.47 (2 H, d, J = 5.6 Hz), 7.42-7.52 (4 H, m) | NT |
| 632 | | Free | 432[M + Na]+ 408[M − H]− | ¹H NMR (600 MHz, CD$_3$OD) δ ppm 1.77 (3 H, s), 2.79 (3 H, s), 3.17 (3 H, s), 4.63 (2 H, s), 7.32-7.42 (2 H, m), 7.46-7.65 (6 H, m) | NT |
| 633 | | Free | 420[M + Na]+ 396[M − H]− | ¹H NMR (600 MHz, CD$_3$OD) δ ppm 1.77 (3 H, s), 2.41 (3 H, s), 2.79 (3 H, s), 3.17 (3 H, s), 3.80 (3 H, s), 7.49-7.58 (5 H, m) | NT |

TABLE 3-1-continued

Structural formulae of compounds, as well as their spectral data and inhibitory activity on *Pseudomonas aeruginosa* LpxC enzyme

| Compound No. | Structural formulae | Kind of salt | MS(ESI) | $^1$H-NMR | Enzyme inhibitory activity |
|---|---|---|---|---|---|
| 634 | | Free | 491[M + H]+ 489[M − H]− | $^1$H NMR (600 MHz, CD$_3$OD) δ ppm 1.77 (3 H, s), 2.38-2.42 (2 H, m), 2.79 (3 H, s), 3.09-3.13 (2 H, m), 3.17 (3 H, s), 3.88 (2 H, s), 4.62-4.66 (2 H, m), 4.98-5.02 (2 H, m), 7.35-7.66 (8 H, m) | NT |

TABLE 4

Inhibitory activity on LpxC enzymes (in *Pseudomonas aeruginosa* and *E. coli*) of compounds representative of the compounds listed in Table 3, and their antimicrobial activity (against *Pseudomonas aeruginosa*, *E. coli*, and *Klebsiella pneumoniae*)

| Compound No. | *Pseudomonas aeruginosa* LpxC IC$_{50}$ (nM) | *E. coli* LpxC IC$_{50}$ (nM) | *Pseudomonas aeruginosa* TS88 strain MIC (µg/mL) | *E. coli* ATCC 25922 strain MIC (µg/mL) | *Klebsiella pneumoniae* ATCC 13883 strain MIC µg/mL) |
|---|---|---|---|---|---|
| 168 | 4.2 | 119 | 0.5 | 0.5 | 2 |
| 211 | 3.1 | 109 | 0.5 | 1 | 8 |
| 301 | 6.1 | 100 | 1 | 1 | 4 |
| 376 | 2.0 | 129 | 0.5 | 0.25 | 1 |
| 396 | 3.1 | 46 | 2 | 0.5 | 2 |
| 399 | NT | 13 | 0.5 | 0.125 | 0.5 |
| 402 | NT | 4.9 | 1 | 0.125 | 1 |
| 405 | 2.9 | NT | 0.5 | 0.5 | 4 |
| 406 | NT | NT | 0.5 | 0.125 | 0.5 |
| 410 | NT | 78 | 1 | 0.25 | 1 |
| 416 | NT | NT | 1 | 0.5 | 2 |
| 417 | NT | NT | 0.5 | 0.0625 | 0.25 |
| 425 | 5.1 | 121 | 8 | 2 | 8 |
| 434 | 2.8 | 55 | 1 | 0.25 | 1 |
| 435 | NT | NT | 1 | 1 | 2 |
| 477 | 4.3 | 33 | 0.5 | 0.25 | 1 |
| 481 | 9.1 | 78 | 1 | 0.25 | 2 |
| 507 | NT | 12 | 0.25 | 0.125 | 1 |
| 528 | 4.8 | 25 | 0.5 | 0.25 | 2 |
| 550 | 1.6 | 12 | 0.5 | 0.25 | 1 |
| 553 | NT | 159 | 0.5 | 0.25 | 0.5 |
| 554 | NT | 120 | 0.5 | 0.5 | 1 |
| 557 | 2.3 | 108 | 0.5 | 0.25 | 1 |
| 558 | NT | 235 | 1 | 0.5 | 2 |
| 559 | NT | 115 | 1 | 0.25 | 1 |
| 561 | NT | 30 | 0.5 | 0.125 | 0.5 |
| 563 | 3.9 | NT | 1 | 1 | 4 |
| 565 | NT | NT | 1 | 0.5 | 2 |
| 567 | NT | 177 | 1 | 0.5 | 2 |
| 585 | 3.4 | 88 | 0.5 | 0.5 | 1 |

The compound names shown in Table 1 are as follows:
Compound 1 2-[(biphenyl-4-ylcarbonyl)(methyl)amino]-N-hydroxy-N'-methylpropanediamide,
Compound 2 N-hydroxy-N'-methyl-2-(methyl{[4'-(methylamino)biphenyl-4-yl]carbonyl}amino)propanediamide,
Compound 3 2-(biphenyl-4-ylmethoxy)-N-hydroxy-N'-methylpropanediamide,
Compound 4 N-hydroxy-2-[{[4'-(methoxymethyl)biphenyl-4-yl]carbonyl}(methyl)amino]-N'-methylpropanediamide,
Compound 5 N-hydroxy-N'-methyl-2-{methyl[(4'-methylbiphenyl-4-yl)carbonyl]amino}propanediamide,
Compound 6 2-{[(4'-fluorobiphenyl-4-yl)carbonyl](methyl)amino}-N-hydroxy-N'-methylpropanediamide, Compound 7 N-hydroxy-N'-methyl-2-[methyl({4'-[3-(morpholin-4-yl)propoxy]biphenyl-4-yl}carbonyl)amino]propanediamide, Compound 7b N-hydroxy-N'-methyl-2-[methyl({4'-[3-(morpholin-4-yl)propoxy]biphenyl-4-yl}carbonyl)amino]propanediamide tosylate, Compound 8 2-{[4-(1,3-benzodioxol-5-yl)benzoyl](methyl)amino}-N-hydroxy-N'-methylpropanediamide, Compound 40 N-hydroxy-N'-methyl-2-{methyl[4-(1-methyl-2,3-dihydro-1H-indol-5-yl)benzoyl]amino}propanediamide, Compound 43 2-[{[4'-(dimethylamino)biphenyl-4-yl]carbonyl}(methyl)amino]-N-hydroxy-N'-methylpropanediamide, Compound 52 N-hydroxy-N'-methyl-2-(methyl {[4'-(trifluoromethoxy)biphenyl-4-yl]carbonyl}amino)propanediamide, Compound 56 N-hydroxy-N'-methyl-2-(methyl {[4'-(trifluoromethyl)biphenyl-4-yl]carbonyl}amino)propanediamide, Compound 58 N-hydroxy-N'-methyl-2-{methyl[(4'-{[5-(morpholin-4-yl)pentyl]amino}biphenyl-4-yl)carbonyl]amino}propanediamide, Compound 61 2-{[(2-fluorobiphenyl-4-yl)carbonyl](methyl)amino}-N-hydroxy-N'-methylpropanediamide, Compound 77 N-hydroxy-2-(methyl {[4'-(methylamino)biphenyl-4-yl]carbonyl}amino)-N'-[(5-methyl-1,2-oxazol-3-yl)methyl]propanediamide, Compound 94 N-hydroxy-2-{[4-(2-methoxy-1,3-benzodioxol-5-yl)benzoyl](methyl)amino}-N'-methylpropanediamide, Compound 153 N-hydroxy-2-[{[4'-(2-hydroxyethoxy)biphenyl-4-yl]carbonyl}(methyl)amino]-N'-methylpropanediamide, Compound 172 2-[(biphenyl-4-ylcarbonyl)(methyl)amino]-N-hydroxy-N'-[(5-methyl-1,2-oxazol-3-yl)methyl]propanediamide, Compound 188 2-{[4-(2,3-dihydro-1-benzofuran-5-yl)benzoyl](methyl)amino}-N-hydroxy-N'-methylpropanediamide, Compound 218 N-hydroxy-N'-methyl-2-{methyl[4-(phenylethynyl)benzoyl]amino}propanediamide, Compound 237 2-[{[4'-(fluoromethyl)biphenyl-4-yl]carbonyl}(methyl)amino]-N-hydroxy-N'-methylpropanediamide, Compound 271 2-{[4-(2,3-dihydro-1-benzofuran-6-yl)benzoyl](methyl)amino}-N-hydroxy-N'-methylpropanediamide.

The compound names shown in Table 2 are as follows:

Compound 9 N-(cyclopropylmethyl)-N'-hydroxy-2-({[4'-(2-hydroxyethoxy)biphenyl-4-yl]carbonyl}amino)propanediamide, Compound 10 N-hydroxy-2-({[4'-(2-hydroxyethoxy)biphenyl-4-yl]carbonyl}amino)-N'-[2-(propan-2-yloxy)ethyl]propanediamide, Compound 11 N-hydroxy-2-({[4'-(2-hydroxyethoxy)biphenyl-4-yl]carbonyl}amino)-N'-(1,3-thiazol-5-ylmethyl)propanediamide, Compound 12 N-(furan-2-ylmethyl)-N'-hydroxy-2-({[4'-(2-hydroxyethoxy)biphenyl-4-yl]carbonyl}amino)propanediamide, Compound 13 N-hydroxy-2-{[(4'-{2-[2-(2-hydroxyethoxy)ethoxy]ethoxy}biphenyl-4-yl)carbonyl]amino}-N'-methylpropanediamide, Compound 14 N-hydroxy-2-[({4'-[2-(2-hydroxyethoxy)ethoxy]biphenyl-4-yl}carbonyl)amino]-N'-methylpropanediamide, Compound 15 N-hydroxy-2-[({4'-[2-(2-hydroxyethoxy)ethoxy]biphenyl-4-yl}carbonyl)(methyl)amino]-N'-methylpropanediamide, Compound 16 N-hydroxy-N'-methyl-2-{[4-(trifluoromethoxy)benzoyl]amino}propanediamide, Compound 17 2-[(biphenyl-4-ylcarbonyl)(methoxy)amino]-N-hydroxy-N'-methylpropanediamide, Compound 18 N-hydroxy-N'-methyl-2-{methyl[(2'-methylbiphenyl-4-yl)carbonyl]amino}propanediamide, Compound 19 N-hydroxy-N'-methyl-2-{methyl[4-(1-methyl-1H-indol-5-yl)benzoyl]amino}propanediamide, Compound 20 N-hydroxy-2-[({4'-[(4-hydroxybutyl)amino]biphenyl-4-yl}carbonyl)(methyl)amino]-N'-methylpropanediamide, Compound 21 N-hydroxy-N'-methyl-2-{methyl[(3-methylbiphenyl-4-yl)carbonyl]amino}propanediamide, Compound 22 N-hydroxy-N'-methyl-2-{methyl[4-(trifluoromethoxy)benzoyl]amino}propanediamide, Compound 23 2-{[(2'-fluoro-4'-methylbiphenyl-4-yl)carbonyl](methyl)amino}-N-hydroxy-N'-methylpropanediamide, Compound 24 N-hydroxy-2-{[(3-hydroxybiphenyl-4-yl)carbonyl](methyl)amino}-N'-methylpropanediamide, Compound 25 N-hydroxy-N'-methyl-2-{methyl[4-(octyloxy)benzoyl]amino}propanediamide, Compound 26 N-hydroxy-2-[{4-[1-(4-hydroxybutyl)-1H-indol-5-yl]benzoyl}(methyl)amino]-N'-methylpropanediamide, Compound 27 2-{[(3-fluorobiphenyl-4-yl)carbonyl](methyl)amino}-N-hydroxy-N'-methylpropanediamide, Compound 28 2-{[(3'-fluoro-4'-methylbiphenyl-4-yl)carbonyl](methyl)amino}-N-hydroxy-N'-methylpropanediamide, Compound 29 N-hydroxy-N'-methyl-2-{methyl[(3'-methylbiphenyl-4-yl)carbonyl]amino}propanediamide, Compound 30 2-[(4-cyclohexylbenzoyl)(methyl)amino]-N-hydroxy-N'-methylpropanediamide, Compound 31 N-hydroxy-2-[{4-[1-(2-hydroxyethyl)-1H-indol-5-yl]benzoyl}(methyl)amino]-N'-methylpropanediamide, Compound 32 2-[{[4'-(ethylamino)biphenyl-4-yl]carbonyl}(methyl)amino]-N-hydroxy-N'-methylpropanediamide, Compound 33 N-hydroxy-2-[(4-{2-[(methoxymethoxy)methyl]-1-methyl-1H-indol-5-yl}benzoyl)(methyl)amino]-N'-methylpropanediamide, Compound 34 tert-butyl[(1R)-1-(4'-{[1-(hydroxyamino)-3-(methylamino)-1,3-dioxopropan-2-yl](methyl)carbamoyl}biphenyl-4-yl)ethyl]carbamate, Compound 35 2-[(4-butoxybenzoyl)(methyl)amino]-N-hydroxy-N'-methylpropanediamide, Compound 36 N-hydroxy-N'-methyl-2-{methyl[4-(1-methyl-1H-indol-6-yl)benzoyl]amino}propanediamide, Compound 37 2-[(4-butylbenzoyl)(methyl)amino]-N-hydroxy-N'-methylpropanediamide, Compound 38 2-[{[3'-fluoro-4'-(methylamino)biphenyl-4-yl]carbonyl}(methyl)amino]-N-hydroxy-N'-methylpropanediamide, Compound 39 2-{[4-(2,3-dihydro-1H-indol-5-yl)benzoyl](methyl)amino}-N-hydroxy-N'-methylpropanediamide, Compound 41 N-hydroxy-2-[{4-[2-(hydroxymethyl)-1-methyl-1H-indol-5-yl]benzoyl}(methyl)amino]-N'-methylpropanediamide, Compound 42 N-hydroxy-N'-methyl-2-(methyl {[4'-(methylsulfanyl)biphenyl-4-yl]carbonyl}amino)propanediamide, Compound 44 tert-butyl(4'-{[1-(hydroxyamino)-3-(methylamino)-1,3-dioxopropan-2-yl](methyl)carbamoyl}-3-methylbiphenyl-4-yl)methylcarbamate, Compound 45 N-hydroxy-N'-methyl-2-(methyl {[3'-methyl-4'-(methylamino)biphenyl-4-yl]carbonyl}amino)propanediamide, Compound 46 N-hydroxy-N'-methyl-2-(methyl {4-[1-methyl-2-(morpholin-4-ylmethyl)-1H-indol-5-yl]benzoyl}amino)propanediamide, Compound 47 N-hydroxy-N'-methyl-2-{methyl[4-(1,1,2,2-tetrafluoroethoxy)benzoyl]amino}propanediamide, Compound 48 N-hydroxy-2-{[(3'-hydroxybiphenyl-4-yl)carbonyl](methyl)amino}-N'-methylpropanediamide, Compound 49 N-hydroxy-2-{[(4'-hydroxybiphenyl-4-yl)carbonyl](methyl)amino}-N'-methylpropanediamide, Compound 50 N-hydroxy-2-[{[3'-methoxy-4'-(methylamino)biphenyl-4-yl]carbonyl}(methyl)amino]-N'-methylpropanediamide, Compound 51 2-[{[4'-(difluoromethoxy)biphenyl-4-yl]carbonyl}(methyl)amino]-N-hydroxy-N'-methylpropanediamide, Compound 53 N-hydroxy-N'-methyl-2-(methyl {[4'-(morpholin-4-yl)biphenyl-4-yl]carbonyl}amino)propanediamide, Compound 54 2-[{[4'-(dimethylamino)-3'-fluorobiphenyl-4-yl]carbonyl}(methyl)amino]-N-hydroxy-N'-methylpropanediamide, Compound 55 2-{[(3',4'-dimethoxybiphenyl-4-yl)carbonyl](methyl)amino}-N-hydroxy-N'-methylpropanediamide, Compound 57 2-{[4-(1,2-dimethyl-1H-indol-5-yl)benzoyl](methyl)amino}-N-hydroxy-N'-methylpropanediamide, Compound 59 2-{[(2'-fluorobiphenyl-4-yl)carbonyl](methyl)amino}-N-hydroxy-N'-methylpropanediamide, Compound 60 N-hydroxy-N'-methyl-2-(methyl {[4'-(2H-tetrazol-5-ylmethyl)biphenyl-4-yl]carbonyl}amino)propanediamide, Compound 62 N-benzyl-2-[(biphenyl-4-ylcarbonyl)(methyl)amino]-N'-hydroxypropanediamide, Compound 63 N-hydroxy-N'-methyl-2-(methyl {4-[(E)-2-phenylethenyl]benzoyl}amino)propanediamide, Compound 64 N-hydroxy-2-{[(4'-{3-[(2-methoxyethyl)(methyl)amino]propoxy}biphenyl-4-yl)carbonyl](methyl)amino}-N'-methylpropanediamide, Compound 65 N-hydroxy-N'-methyl-2-[methyl({4'-[(pyridin-3-ylmethyl)amino]biphenyl-4-yl}carbonyl)amino]propanediamide, Compound 66 2-[({3'-fluoro-4'-[(2-methoxyethyl)amino]biphenyl-4-yl}carbonyl)(methyl)amino]-N-hydroxy-N'-methylpropanediamide, Compound 67 2-[{[2',5'-difluoro-4'-(methylamino)biphenyl-4-yl]carbonyl}(methyl)amino]-N-hydroxy-N'-methylpropanediamide, Compound 68 N-hydroxy-N'-methyl-2-(methyl{[4'-(methylamino)-3'-(trifluoromethyl)biphenyl-4-yl]carbonyl}amino)propanediamide, Compound 69 2-[{[3',5'-difluoro-4'-(methylamino)biphenyl-4-yl]carbonyl}(methyl)amino]-N-hydroxy-N'-methylpropanediamide, Compound 70 2-{[(4'-{3-[benzyl(methyl)amino]propoxy}biphenyl-4-yl)carbonyl](methyl)amino}-N-hydroxy-N'-methylpropanediamide, Compound 71 N-hydroxy-N'-methyl-2-[methyl({4'-[3-(2-oxo-1,3-oxazolidin-3-yl)propoxy]biphenyl-4-yl}carbonyl)amino]propanediamide, Compound 72 N-hydroxy-N'-methyl-2-(methyl {[2',3',5',6'-tetrafluoro-4'-(methylamino)biphenyl-4-yl]carbonyl}amino)propanediamide, Compound 73 2-{[(2,2'-difluorobiphenyl-4-yl)carbonyl](methyl)amino}-N-hydroxy-N'-methylpropanediamide, Compound 74 2-{[(4'-{[(2,2-dimethylpropyl)amino]methyl}biphenyl-4-yl)carbonyl](methyl)amino}-N-hydroxy-N'-methylpropanediamide, Compound 75 N-hydroxy-N'-methyl-2-[methyl({4'-[3-(phenylamino)propoxy]biphenyl-4-yl}carbonyl)amino]propanediamide, Compound 76 2-[(biphenyl-4-ylcarbonyl)(methyl)amino]-N-hydroxy-N'-(2-phenylethyl)propanediamide, Compound 78 N-hydroxy-N'-methyl-2-[methyl({4'-[(propylsulfonyl)amino]biphenyl-4-yl}carbonyl)amino]propanediamide, Compound 79 2-[({4'-[(cyclopropylmethyl)amino]biphenyl-4-yl}carbonyl)(methyl)amino]-N-hydroxy-N'-methylpropanediamide, Compound 80 2-[(biphenyl-4-ylcarbonyl)(methyl)amino]-N'-hydroxy-N,N-dimethylpropanediamide, Compound 81 2-{[4-(2,3-dihydro-1,4-benzodioxin-6-yl)benzoyl](methyl)amino}-N-hydroxy-N'-methylpropanediamide, Compound 82 N-hydroxy-N'-methyl-2-{methyl[4-(4-methyl-3-oxo-3,4-dihydro-2H-1,4-benzoxazin-6-yl)benzoyl]amino}propanediamide, Compound 83 N-hydroxy-N'-methyl-2-(methyl {[4'-(1,1,2,2-tetrafluoroethoxy)biphenyl-4-yl]carbonyl}amino)propanediamide, Compound 84 N-hydroxy-N'-methyl-2-[methyl({4'-[3-(4-phenylpiperazin-1-yl)propoxy]biphenyl-4-yl}carbonyl)amino]propanediamide, Compound 85 2-[({4'-[(cyclopropylmethyl)(methyl)amino]biphenyl-4-yl}carbonyl)(methyl)amino]-N-hydroxy-N'-methylpropanediamide, Compound 86 N-hydroxy-N'-methyl-2-{methyl[(4'-{[3-(morpholin-4-yl)propyl]amino}biphenyl-4-yl)carbonyl]amino}propanediamide, Compound 87 N-hydroxy-N'-methyl-2-{methyl[(4'-{[3-(morpholin-4-ylmethyl)benzyl]oxy}biphenyl-4-yl)carbonyl]amino}propanediamide, Compound 88 2-[({4'-[3-(2,6-dimethylmorpholin-4-yl)propoxy]biphenyl-4-yl}carbonyl)(methyl)amino]-N-hydroxy-N'-methylpropanediamide, Compound 89 N-hydroxy-N'-methyl-2-{methyl[(4'-{2-[methyl(phenyl)amino]ethoxy}biphenyl-4-yl)carbonyl]amino}propanediamide, Compound 90 N-hydroxy-N'-methyl-2-{methyl[(4'-{[4-(4-methylpiperazin-1-yl)benzyl]oxy}biphenyl-4-yl)carbonyl]amino}propanediamide, Compound 91 N-hydroxy-N'-methyl-2-{methyl[(4'-{[4-(morpholin-4-ylmethyl)benzyl]oxy}biphenyl-4-yl)carbonyl]amino}propanediamide, Compound 92 2-{[(4'-{3-[(2,6-difluorobenzyl)(methyl)amino]propoxy}biphenyl-4-yl)carbonyl](methyl)amino}-N-hydroxy-N'-methylpropanediamide, Compound 93 N-hydroxy-N'-methyl-2-{methyl[(4'-{[4-(1H-tetrazol-5-yl)benzyl]oxy}biphenyl-4-yl)carbonyl]amino}propanediamide, Compound 95 N-hydroxy-N'-methyl-2-[methyl({4'-[(3-methyloxetan-3-yl)methoxy]biphenyl-4-yl}carbonyl)amino]propanediamide, Compound 96 N-hydroxy-2-[({4'-[3-(1H-imidazol-1-yl)propoxy]biphenyl-4-yl}carbonyl)(methyl)amino]-N'-methylpropanediamide, Compound 97 2-[{[4'-({3-[benzyl(methyl)amino]propyl}amino)biphenyl-4-yl]carbonyl}(methyl)amino]-N-hydroxy-N'-methylpropanediamide, Compound 98 4-{[(4'-{[1-(hydroxyamino)-3-(methylamino)-1,3-dioxopropan-2-yl](methyl)carbamoyl}biphenyl-4-yl)oxy]methyl}benzoate,
Compound 99 N-hydroxy-N'-methyl-2-[methyl({4'-[(2-methyl-1,3-oxazol-4-yl)methoxy]biphenyl-4-yl}carbonyl)amino]propanediamide,
Compound 100 N-hydroxy-N'-methyl-2-{methyl[(4'-{[3-(phenylamino)propyl]amino}biphenyl-4-yl)carbonyl]amino}propanediamide,
Compound 101 2-[{[2,4'-bis(methylamino)biphenyl-4-yl]carbonyl}(methyl)amino]-N-hydroxy-N'-methylpropanediamide,
Compound 102 N-hydroxy-N'-methyl-2-{methyl[(4'-{[1-(morpholin-4-ylmethyl)cyclopropyl]methoxy}biphenyl-4-yl)carbonyl]amino}propanediamide,
Compound 103 N-hydroxy-N'-methyl-2-[methyl({4'-[({2-[(phenylamino)methyl]cyclopropyl}methyl)amino]biphenyl-4-yl}carbonyl)amino]propanediamide,
Compound 104 2-(phosphonooxy)ethyl(4'-{[1-(hydroxyamino)-3-(methylamino)-1,3-dioxopropan-2-yl](methyl)carbamoyl}biphenyl-4-yl)methylcarbamate,
Compound 105 2-{[4-(furan-3-yl)benzoyl](methyl)amino}-N-hydroxy-N'-methylpropanediamide,
Compound 106 2-[{[4'-{3-[benzyl(methyl)amino]propoxy}-2'-(methylamino)biphenyl-4-yl]carbonyl}(methyl)amino]-N-hydroxy-N'-methylpropanediamide,
Compound 107 2-{[4-(3-fluoropyridin-2-yl)benzoyl](methyl)amino}-N-hydroxy-N'-methylpropanediamide,
Compound 108 2-{[4-(5-fluoropyridin-2-yl)benzoyl](methyl)amino}-N-hydroxy-N'-methylpropanediamide,
Compound 109 2-[(biphenyl-4-ylcarbonyl)amino]-N,N'-dihydroxypropanediamide,
Compound 110 2-[(biphenyl-4-ylcarbonyl)amino]-N-hydroxy-N'-methylpropanediamide,
Compound 111 2-[(biphenyl-4-ylcarbonyl)amino]-N-hydroxypropanediamide,
Compound 112 N-hydroxy-N'-methyl-2-[({4'-[3-(1,4-oxazepan-4-yl)propoxy]biphenyl-4-yl}carbonyl)amino]propanediamide,
Compound 113 N-hydroxy-2-({[4'-(2-hydroxyethoxy)biphenyl-4-yl]carbonyl}amino)-N'-methylpropanediamide,
Compound 114 N-hydroxy-2-[({4'-[(2-hydroxyethyl)amino]biphenyl-4-yl}carbonyl)amino]-N'-methylpropanediamide,
Compound 115 N-hydroxy-2-{[4-({4-[(2-hydroxyethyl)amino]phenyl}ethynyl)benzoyl]amino}-N'-methylpropanediamide,
Compound 116 N-hydroxy-2-({[4'-(2-hydroxyethoxy)biphenyl-4-yl]carbonyl}amino)-N'-(pyridin-3-yl)propanediamide,
Compound 117 N-hydroxy-N'-methyl-2-[(4-{[4-(1,4-oxazepan-4-ylmethyl)phenyl]ethynyl}benzoyl)amino]propanediamide,
Compound 118 N'-hydroxy-2-({[4'-(2-hydroxyethoxy)biphenyl-4-yl]carbonyl}amino)-N,N-dimethylpropanediamide,
Compound 119 N-tert-butyl-N'-hydroxy-2-({[4'-(2-hydroxyethoxy)biphenyl-4-yl]carbonyl}amino)propanediamide,
Compound 120 N-benzyl-N'-hydroxy-2-({[4'-(2-hydroxyethoxy)biphenyl-4-yl]carbonyl}amino)propanediamide,
Compound 121 N-cyclopropyl-N'-hydroxy-2-({[4'-(2-hydroxyethoxy)biphenyl-4-yl]carbonyl}amino)propanediamide,
Compound 122 N-hydroxy-2-({[4'-(2-hydroxyethoxy)biphenyl-4-yl]carbonyl}amino)-N'-(2-hydroxyethyl)propanediamide,
Compound 123 N-[2-(dimethylamino)ethyl]-N'-hydroxy-2-({[4'-(2-hydroxyethoxy)biphenyl-4-yl]carbonyl}amino)propanediamide,
Compound 124 N-hydroxy-2-({[4'-(2-hydroxyethoxy)biphenyl-4-yl]carbonyl}amino)-N'-(pyridin-4-ylmethyl)propanediamide,
Compound 125 N-hydroxy-2-({[4'-(2-hydroxyethoxy)biphenyl-4-yl]carbonyl}amino)-N'-(2-phenylethyl)propanediamide,
Compound 126 N-hydroxy-2-({[4'-(2-hydroxyethoxy)biphenyl-4-yl]carbonyl}amino)-N'-(3-phenylpropyl)propanediamide,
Compound 127 2-[(biphenyl-4-ylcarbonyl)(cyclopropyl)amino]-N-hydroxy-N'-methylpropanediamide,
Compound 128 N-(cyclobutylmethyl)-N'-hydroxy-2-({[4'-(2-hydroxyethoxy)biphenyl-4-yl]carbonyl}amino)propanediamide,
Compound 129 N-hydroxy-2-({[4'-(2-hydroxyethoxy)biphenyl-4-yl]carbonyl}amino)-N'-(pyridin-3-ylmethyl)propanediamide,
Compound 130 N-hydroxy-2-({[4'-(2-hydroxyethoxy)biphenyl-4-yl]carbonyl}amino)-N'-(pyridin-2-ylmethyl)propanediamide,
Compound 131 N-hydroxy-2-({[4'-(2-hydroxyethoxy)biphenyl-4-yl]carbonyl}amino)-N'-(2-methoxyethyl)propanediamide,
Compound 132 N-hydroxy-2-({[4'-(2-hydroxyethoxy)biphenyl-4-yl]carbonyl}amino)-N'-[2-(methylsulfanyl)ethyl]propanediamide,
Compound 133 N-hydroxy-2-({[4'-(2-hydroxyethoxy)biphenyl-4-yl]carbonyl}amino)-N'-[(5-methyl-1,2-oxazol-3-yl)methyl]propanediamide,
Compound 134 N-hydroxy-2-({[4'-(2-hydroxyethoxy)biphenyl-4-yl]carbonyl}amino)-N'-(tetrahydrofuran-2-ylmethyl)propanediamide,
Compound 135 N-[2-(acetylamino)ethyl]-N'-hydroxy-2-({[4'-(2-hydroxyethoxy)biphenyl-4-yl]carbonyl}amino)propanediamide,
Compound 136 N-(2,2-dimethylpropyl)-N'-hydroxy-2-({[4'-(2-hydroxyethoxy)biphenyl-4-yl]carbonyl}amino)propanediamide,
Compound 137 N-(2,2-difluoroethyl)-N'-hydroxy-2-({[4'-(2-hydroxyethoxy)biphenyl-4-yl]carbonyl}amino)propanediamide,
Compound 138 N-hydroxy-2-({[4'-(2-hydroxyethoxy)biphenyl-4-yl]carbonyl}amino)-N'-(2-phenoxyethyl)propanediamide,
Compound 139 N-ethyl-N'-hydroxy-2-({[4'-(2-hydroxyethoxy)biphenyl-4-yl]carbonyl}amino)propanediamide,
Compound 140 N-hydroxy-2-({[4'-(2-hydroxyethoxy)biphenyl-4-yl]carbonyl}amino)-N'-[(1-methyl-1H-pyrazol-3-yl)methyl]propanediamide,
Compound 141 N-hydroxy-2-({[4'-(2-hydroxyethoxy)biphenyl-4-yl]carbonyl}amino)-N'-[2-oxo-2-(pyrrolidin-1-yl)ethyl]propanediamide,
Compound 142 N-hydroxy-2-({[4'-(2-hydroxyethoxy)biphenyl-4-yl]carbonyl}amino)-N'-propylpropanediamide,
Compound 143 N-hydroxy-2-({[4'-(2-hydroxyethoxy)biphenyl-4-yl]carbonyl}amino)-N'-(propan-2-yl)propanediamide,
Compound 144 N-[2-(dimethylamino)-2-oxoethyl]-N'-hydroxy-2-({[4'-(2-hydroxyethoxy)biphenyl-4-yl]carbonyl}amino)propanediamide,
Compound 145 N-{2-[acetyl(methyl)amino]ethyl}-N'-hydroxy-2-({[4'-(2-hydroxyethoxy)biphenyl-4-yl]carbonyl}amino)propanediamide, Compound 146 N-hydroxy-2-({[4'-(2-hydroxyethoxy)biphenyl-4-yl]carbonyl}amino)-N'-[(1-methyl-1H-pyrazol-5-yl)methyl]propanediamide, Compound 147 N-hydroxy-2-({[4'-(2-hydroxyethoxy)biphenyl-4-yl]carbonyl}amino)-N'-[(1-methyl-1H-pyrazol-4-yl)methyl]propanediamide, Compound 148 N,N'-dihydroxy-2-({[4'-(2-hydroxyethoxy)biphenyl-4-yl]carbonyl}amino)propanediamide, Compound 149 N-(2,3-dihydro-1,4-benzodioxin-2-ylmethyl)-N'-hydroxy-2-({[4'-(2-hydroxyethoxy)biphenyl-4-yl]carbonyl}amino)propanediamide, Compound 150 N-hydroxy-2-({[4'-(2-hydroxyethoxy)biphenyl-4-yl]carbonyl}amino)-N'-[(6-methylpyridin-2-yl)methyl]propanediamide, Compound 151 N-hydroxy-2-({[4'-(2-hydroxyethoxy)biphenyl-4-yl]carbonyl}amino)-N'-[2-(pyridin-2-yl)ethyl]propanediamide, Compound 152 N-hydroxy-2-({[4'-(2-hydroxyethoxy)biphenyl-4-yl]carbonyl}amino)-N'-[(3-oxo-3,4-dihydro-2H-pyrido[3,2-b][1,4]oxazin-6-yl)methyl]propanediamide, Compound 154 2-(cyclopropyl {[4'-(2-hydroxyethoxy)biphenyl-4-yl]carbonyl}amino)-N-hydroxy-N'-methylpropanediamide, Compound 155 N-hydroxy-2-({[4'-(2-hydroxyethoxy)biphenyl-4-yl]carbonyl}amino)-N'-[(5-methyl-1,3,4-thiadiazol-2-yl)methyl]propanediamide, Compound 156 N-hydroxy-2-({[4'-(2-hydroxyethoxy)biphenyl-4-yl]carbonyl}amino)-N'-[(1-methyl-1H-imidazol-2-yl)methyl]propanediamide, Compound 157 N-hydroxy-2-({[4'-(2-hydroxyethoxy)biphenyl-4-yl]carbonyl}amino)-N'-(1,3-oxazol-4-ylmethyl)propanediamide, Compound 158 N-hydroxy-2-({[4'-(2-hydroxyethoxy)biphenyl-4-yl]carbonyl}amino)-N'-[(1-methyl-1H-imidazol-4-yl)methyl]propanediamide, Compound 159 2-[(biphenyl-4-ylcarbonyl)(ethyl)amino]-N-hydroxy-N'-methylpropanediamide, Compound 160 N-[(4-benzylmorpholin-2-yl)methyl]-N'-hydroxy-2-({[4'-(2-hydroxyethoxy)biphenyl-4-yl]carbonyl}amino)propanediamide, Compound 161 2-[(biphenyl-4-ylcarbonyl)(methyl)amino]-N-hydroxy-N'-(pyridin-2-ylmethyl)propanediamide, Compound 162 N-hydroxy-2-({[4'-(2-hydroxyethoxy)biphenyl-4-yl]carbonyl}amino)-N'-(morpholin-2-ylmethyl)propanediamide, Compound 163 2-[(biphenyl-4-ylcarbonyl)(cyclobutyl)amino]-N-hydroxy-N'-methylpropanediamide, Compound 164 2-[(biphenyl-4-ylcarbonyl)amino]-N-hydroxy-N',2-dimethylpropanediamide, Compound 165 N-hydroxy-2-[{[4'-(3-hydroxypropyl)biphenyl-4-yl]carbonyl}(methyl)amino]-N'-methylpropanediamide, Compound 166 2-[(biphenyl-4-ylcarbonyl)(2-methoxyethyl)amino]-N-hydroxy-N'-methylpropanediamide, Compound 167 N-hydroxy-N'-methyl-2-[methyl(4-{[4-(morpholin-4-ylmethyl)phenyl]ethynyl}benzoyl)amino]propanediamide, Compound 168 N-hydroxy-N'-methyl-2-[methyl(4-{[4-(1,4-oxazepan-4-ylmethyl)phenyl]ethynyl}benzoyl)amino]propanediamide, Compound 169 N-hydroxy-N'-methyl-2-{methyl[4-(pyridin-4-yl)benzoyl]amino}propanediamide, Compound 170 2-[(biphenyl-4-ylcarbonyl)(methyl)amino]-N-hydroxy-N'-(pyrimidin-2-ylmethyl)propanediamide, Compound 171 2-[(biphenyl-4-ylcarbonyl)(methyl)amino]-N-hydroxy-N'-propylpropanediamide, Compound 173 2-[(biphenyl-4-ylcarbonyl)(methyl)amino]-N-[2-(dimethylamino)-2-oxoethyl]-N'-hydroxypropanediamide, Compound 174 2-[(biphenyl-4-ylcarbonyl)(2,2-difluoroethyl)amino]-N-hydroxy-N'-methylpropanediamide, Compound 175 2-[(biphenyl-4-ylcarbonyl)(methyl)amino]-N-cyclopropyl-N'-hydroxypropanediamide, Compound 176 N-hydroxy-2-{[4-(2-{4-[(2-hydroxyethyl)amino]phenyl}ethyl)benzoyl](methyl)amino}-N'-methylpropanediamide, Compound 177 2-[(biphenyl-4-ylcarbonyl)(methyl)amino]-N-hydroxy-N'-(pyridin-3-ylmethyl)propanediamide, Compound 178 2-[(biphenyl-4-ylcarbonyl)(methyl)amino]-N-hydroxy-N'-(pyridin-4-ylmethyl)propanediamide, Compound 179 N-hydroxy-2-[({4'-[(2-hydroxyethyl)amino]biphenyl-4-yl}carbonyl)(methyl)amino]-N'-methylpropanediamide, Compound 180 N-hydroxy-2-[{[4'-(4-hydroxybutoxy)biphenyl-4-yl]carbonyl}(methyl)amino]-N'-methylpropanediamide, Compound 181 2-[{[4'-(3,4-dihydroxybutoxy)biphenyl-4-yl]carbonyl}(methyl)amino]-N-hydroxy-N'-methylpropanediamide, Compound 182 N-hydroxy-N'-methyl-2-{methyl[(4'-propylbiphenyl-4-yl)carbonyl]amino}propanediamide, Compound 183 N-hydroxy-2-{[4-({4-[(2-hydroxyethyl)amino]phenyl}ethynyl)benzoyl](methyl)amino}-N'-methylpropanediamide, Compound 184 2-{[4-(1-benzofuran-5-yl)benzoyl](methyl)amino}-N-hydroxy-N'-methylpropanediamide, Compound 185 N-hydroxy-2-[{[3-hydroxy-4'-(3-hydroxypropyl)biphenyl-4-yl]carbonyl}(methyl)amino]-N'-methylpropanediamide, Compound 186 2-[(biphenyl-4-ylcarbonyl)(methyl)amino]-N-hydroxypropanediamide, Compound 187 2-[{[4'-(1,3-dioxolan-2-yl)biphenyl-4-yl]carbonyl}(methyl)amino]-N-hydroxy-N'-methylpropanediamide, Compound 189 2-{[4-(2,1,3-benzoxadiazol-5-yl)benzoyl](methyl)amino}-N-hydroxy-N'-methylpropanediamide, Compound 190 N-hydroxy-N'-methyl-2-{methyl[(6-phenylpyridin-3-yl)carbonyl]amino}propanediamide, Compound 191 N-hydroxy-2-[{[4'-(2-methoxyethoxy)biphenyl-4-yl]carbonyl}(methyl)amino]-N'-methylpropanediamide, Compound 192 N-hydroxy-N'-methyl-2-{methyl[4-(quinolin-3-yl)benzoyl]amino}propanediamide, Compound 193 2-[(biphenyl-4-ylcarbonyl)(2-fluoroethyl)amino]-N-hydroxy-N'-methylpropanediamide, Compound 194 2-[({4'-[(dimethylamino)methyl]biphenyl-4-yl}carbonyl)(methyl)amino]-N-hydroxy-N'-methylpropanediamide, Compound 195 N-hydroxy-2-[({4'-[(E)-(hydroxyimino)methyl]biphenyl-4-yl}carbonyl)(methyl)amino]-N'-methylpropanediamide, Compound 196 N-hydroxy-N'-methyl-2-{methyl[4-(1-methyl-1H-indazol-5-yl)benzoyl]amino}propanediamide, Compound 197 N-hydroxy-N'-methyl-2-{methyl[4-(2-methyl-2H-indazol-5-yl)benzoyl]amino}propanediamide, Compound 198 2-[cyclopropyl({4'-[3-(morpholin-4-yl)propoxy]biphenyl-4-yl}carbonyl)amino]-N-hydroxy-N'-methylpropanediamide, Compound 199 2-{[4-(1,3-benzothiazol-6-yl)benzoyl](methyl)amino}-N-hydroxy-N'-methylpropanediamide, Compound 200 N-hydroxy-N'-methyl-2-{methyl[4-(quinolin-6-yl)benzoyl]amino}propanediamide, Compound 201 N-hydroxy-2-{[4-(1H-indol-5-yl)benzoyl](methyl)amino}-N'-methylpropanediamide, Compound 202 2-{[4-({4-[(dimethylamino)methyl]phenyl}ethynyl)benzoyl](methyl)amino}-N-hydroxy-N'-methylpropanediamide, Compound 203 N-hydroxy-N'-methyl-2-{methyl[4-(2-methyl-1H-indol-5-yl)benzoyl]amino}propanediamide, Compound 204 2-{[(4'-{[(2,2-difluoroethyl)amino]methyl}biphenyl-4-yl)carbonyl](methyl)amino}-N-hydroxy-N'-methylpropanediamide, Compound 205 2-[({4'-[(cyclopropylamino)methyl]biphenyl-4-yl}carbonyl)(methyl)amino]-N-hydroxy-N'-methylpropanediamide, Compound 206 N-hydroxy-N'-methyl-2-{methyl[4-({4-[2-(morpholin-4-yl)ethyl]phenyl}ethynyl)benzoyl]amino}propanediamide, Compound 207 N-hydroxy-N'-methyl-2-{methyl[4-({4-[2-(1,4-oxazepan-4-yl)ethyl]phenyl}ethynyl)benzoyl]amino}propanediamide, Compound 208 2-[({3'-fluoro-4'-[3-(morpholin-4-yl)propoxy]biphenyl-4-yl}carbonyl)(methyl)amino]-N-hydroxy-N'-methylpropanediamide, Compound 209 N-hydroxy-N'-methyl-2-{methyl[4-(2-{4-[2-(morpholin-4-yl)ethyl]phenyl}ethyl)benzoyl]amino}propanediamide, Compound 210 N-hydroxy-N'-methyl-2-{methyl[4-(2-{4-[2-(1,4-oxazepan-4-yl)ethyl]phenyl}ethyl)benzoyl]amino}propanediamide, Compound 211 2-{[(4'-ethoxybiphenyl-4-yl)carbonyl](methyl)amino}-N-hydroxy-N'-methylpropanediamide, Compound 212 N-hydroxy-N'-methyl-2-{methyl[(4'-propoxybiphenyl-4-yl)carbonyl]amino}propanediamide, Compound 213 N-hydroxy-N'-methyl-2-(methyl {[4'-(propan-2-yloxy)biphenyl-4-yl]carbonyl}amino)propanediamide, Compound 214 N-hydroxy-N'-methyl-2-(methyl {[4'-(2-methylpropoxy)biphenyl-4-yl]carbonyl}amino)propanediamide, Compound 215 N-hydroxy-2-[{[4'-(4-methoxybutoxy)biphenyl-4-yl]carbonyl}(methyl)amino]-N'-methylpropanediamide, Compound 216 2-{[(3'-fluoro-4'-methoxybiphenyl-4-yl)carbonyl](methyl)amino}-N-hydroxy-N'-methylpropanediamide, Compound 217 2-[({4'-[3-(cyclopropylamino)propoxy]biphenyl-4-yl}carbonyl)(methyl)amino]-N-hydroxy-N'-methylpropanediamide, Compound 219 N-hydroxy-2-[{4-[(6-methoxypyridin-3-yl)ethynyl]benzoyl}(methyl)amino]-N'-methylpropanediamide, Compound 220 N-hydroxy-N'-methyl-2-{methyl[(3',4',5'-trifluorobiphenyl-4-yl)carbonyl]amino}propanediamide, Compound 221 N-hydroxy-N'-methyl-2-[methyl({4'-[4-(morpholin-4-yl)butyl]biphenyl-4-yl}carbonyl)amino]propanediamide, Compound 222 2-{[(3',5'-dichlorobiphenyl-4-yl)carbonyl](methyl)amino}-N-hydroxy-N'-methylpropanediamide, Compound 223 2-{[(3'-chloro-4'-fluorobiphenyl-4-yl)carbonyl](methyl)amino}-N-hydroxy-N'-methylpropanediamide, Compound 224 2-{[(3',4'-dichlorobiphenyl-4-yl)carbonyl](methyl)amino}-N-hydroxy-N'-methylpropanediamide, Compound 225 2-[(2,2-difluoroethyl)({4'-[3-(morpholin-4-yl)propoxy]biphenyl-4-yl}carbonyl)amino]-N-hydroxy-N'-methylpropanediamide, Compound 226 2-[{[2'-fluoro-4'-(methylamino)biphenyl-4-yl]carbonyl}(methyl)amino]-N-hydroxy-N'-methylpropanediamide, Compound 227 2-[{[3'-chloro-4'-(methylamino)biphenyl-4-yl]carbonyl}(methyl)amino]-N-hydroxy-N'-methylpropanediamide, Compound 228 N-hydroxy-2-[({4'-[(3-methoxypropyl)amino]biphenyl-4-yl}carbonyl)(methyl)amino]-N'-methylpropanediamide, Compound 229 N-hydroxy-2-[{[4'-(3-methoxyazetidin-1-yl)biphenyl-4-yl]carbonyl}(methyl)amino]-N'-methylpropanediamide, Compound 230 2-[{[4'-(ethylamino)-3'-fluorobiphenyl-4-yl]carbonyl}(methyl)amino]-N-hydroxy-N'-methylpropanediamide, Compound 231 2-[{[3'-fluoro-4'-(propylamino)biphenyl-4-yl]carbonyl}(methyl)amino]-N-hydroxy-N'-methylpropanediamide, Compound 232 N-hydroxy-N'-methyl-2-(methyl {[4'-(morpholin-4-ylmethyl)biphenyl-4-yl]carbonyl}amino)propanediamide, Compound 233 2-{[(2',6'-difluorobiphenyl-4-yl)carbonyl](methyl)amino}-N-hydroxy-N'-methylpropanediamide, Compound 234 N-hydroxy-N'-methyl-2-[methyl(4-{[4-(piperidin-1-ylmethyl)phenyl]ethynyl}benzoyl)amino]propanediamide, Compound 235 2-(ethyl {[4'-(methylamino)biphenyl-4-yl]carbonyl}amino)-N-hydroxy-N'-methylpropanediamide, Compound 236 N-hydroxy-N'-methyl-2-[methyl({4'-[2-(morpholin-4-yl)ethyl]biphenyl-4-yl}carbonyl)amino]propanediamide, Compound 238 2-[{[4'-(2-fluoroethyl)biphenyl-4-yl]carbonyl}(methyl)amino]-N-hydroxy-N'-methylpropanediamide, Compound 239 2-{[(4'-{[acetyl(methyl)amino]methyl}biphenyl-4-yl)carbonyl](methyl)amino}-N-hydroxy-N'-methylpropanediamide, Compound 240 2-{[(4'-tert-butylbiphenyl-4-yl)carbonyl](methyl)amino}-N-hydroxy-N'-methylpropanediamide, Compound 241 2-[({4'-[(acetylamino)methyl]biphenyl-4-yl}carbonyl)(methyl)amino]-N-hydroxy-N'-methylpropanediamide, Compound 242 2-[(biphenyl-4-ylcarbonyl)(methyl)amino]-N-ethyl-N'-hydroxypropanediamide, Compound 243 N-hydroxy-N'-methyl-2-[methyl({4'-[2-(morpholin-4-yl)ethoxy]biphenyl-4-yl}carbonyl)amino]propanediamide, Compound 244 N-hydroxy-2-[{[4'-(3-hydroxyazetidin-1-yl)biphenyl-4-yl]carbonyl}(methyl)amino]-N'-methylpropanediamide, Compound 245 N-hydroxy-N'-methyl-2-(methyl {[4'-(propylamino)biphenyl-4-yl]carbonyl}amino)propanediamide, Compound 246 N-hydroxy-2-[{[4'-(2-methoxyethyl)biphenyl-4-yl]carbonyl}(methyl)amino]-N'-methylpropanediamide, Compound 247 N-hydroxy-N'-methyl-2-(methyl {[4'-(2-oxo-1,3-oxazolidin-3-yl)biphenyl-4-yl]carbonyl}amino)propanediamide, Compound 248 N'-tert-butyl-N-[1-(hydroxyamino)-3-(methylamino)-1,3-dioxopropan-2-yl]-N-methylbiphenyl-4,4'-dicarboxamide, Compound 249 N-hydroxy-N'-methyl-2-{methyl[4-(3-phenylazetidin-1-yl)benzoyl]amino}propanediamide, Compound 250 2-{[4-(1,3-dihydro-2H-isoindol-2-yl)benzoyl](methyl)amino}-N-hydroxy-N'-methylpropanediamide, Compound 251 2-[{[4'-(1,1-difluoropropyl)biphenyl-4-yl]carbonyl}(methyl)amino]-N-hydroxy-N'-methylpropanediamide, Compound 252 N-[1-(hydroxyamino)-3-(methylamino)-1,3-dioxopropan-2-yl]-N,N',N'-trimethylbiphenyl-4,4'-dicarboxamide, Compound 253 2-[{[4'-(1,1-difluoroethyl)biphenyl-4-yl]carbonyl}(methyl)amino]-N-hydroxy-N'-methylpropanediamide, Compound 254 N-hydroxy-N'-methyl-2-(methyl{[4'-(2-methyl-1,3-dioxolan-2-yl)biphenyl-4-yl]carbonyl}amino)propanediamide, Compound 255 2-[{[4'-(2-fluoroethoxy)biphenyl-4-yl]carbonyl}(methyl)amino]-N-hydroxy-N'-methylpropanediamide, Compound 256 N-hydroxy-N'-methyl-2-(methyl{[4'-(pyrrolidin-1-yl)biphenyl-4-yl]carbonyl}amino)propanediamide, Compound 257 N-[1-(hydroxyamino)-3-(methylamino)-1,3-dioxopropan-2-yl]-N-methyl-N'-propylbiphenyl-4,4'-dicarboxamide, Compound 258 2-{[4-(2,2-difluoro-1,3-benzodioxol-5-yl)benzoyl](methyl)amino}-N-hydroxy-N'-methylpropanediamide, Compound 259 N-hydroxy-2-{[(4'-{[methoxy(methyl)amino]methyl}biphenyl-4-yl)carbonyl](methyl)amino}-N'-methylpropanediamide, Compound 260 N-hydroxy-2-[({4'-[(E)-(methoxyimino)methyl]biphenyl-4-yl}carbonyl)(methyl)amino]-N'-methylpropanediamide, Compound 261 N-hydroxy-2-[{[4'-(1-hydroxyethyl)biphenyl-4-yl]carbonyl}(methyl)amino]-N'-methylpropanediamide, Compound 262 N-hydroxy-2-[{[4'-(2-hydroxypropan-2-yl)biphenyl-4-yl]carbonyl}(methyl)amino]-N'-methylpropanediamide, Compound 263 2-[({4'-[3-(3,6-dihydropyridin-1(2H)-yl)propoxy]biphenyl-4-yl}carbonyl)(methyl)amino]-N-hydroxy-N'-methylpropanediamide, Compound 264 2-[({4'-[3-(4,4-difluoropiperidin-1-yl)propoxy]biphenyl-4-yl}carbonyl)(methyl)amino]-N-hydroxy-N'-methylpropanediamide, Compound 265 2-[({4'-[2-(dimethylamino)-2-oxoethyl]biphenyl-4-yl}carbonyl)(methyl)amino]-N-hydroxy-N'-methylpropanediamide, Compound 266 2-[({4'-[3-(dimethylamino)-3-oxopropyl]biphenyl-4-yl}carbonyl)(methyl)amino]-N-hydroxy-N'-methylpropanediamide, Compound 267 N-hydroxy-N'-methyl-2-(methyl{[4'-(4-methylpiperazin-1-yl)biphenyl-4-yl]carbonyl}amino)propanediamide, Compound 268 2-[{[4'-(cyclobutylamino)biphenyl-4-yl]carbonyl}(methyl)amino]-N-hydroxy-N'-methylpropanediamide, Compound 269 2-{[4-(2,2-dimethyl-1,3-benzodioxol-5-yl)benzoyl](methyl)amino}-N-hydroxy-N'-methylpropanediamide, Compound 270 2-{[4-(1-benzofuran-6-yl)benzoyl](methyl)amino}-N-hydroxy-N'-methylpropanediamide, Compound 272 N-hydroxy-2-{[(4'-{[(E)-(hydroxyamino)methylidene]amino}biphenyl-4-yl)carbonyl](methyl)amino}-N'-methylpropanediamide, Compound 273 2-[{[4-(4-chlorophenyl)cyclohexyl]carbonyl}(methyl)amino]-N-hydroxy-N'-methylpropanediamide, Compound 274 2-[({4'-[3-(dimethylamino)propoxy]biphenyl-4-yl}carbonyl)(methyl)amino]-N-hydroxy-N'-methylpropanediamide, Compound 275 2-[({4'-[(E)-(dimethylhydrazinylidene)methyl]biphenyl-4-yl}carbonyl)(methyl)amino]-N-hydroxy-N'-methylpropanediamide, Compound 276 N-hydroxy-2-[({4'-[3-(3-methoxyazetidin-1-yl)propoxy]biphenyl-4-yl}carbonyl)(methyl)amino]-N'-methylpropanediamide, Compound 277 N-hydroxy-N'-methyl-2-[methyl({4'-[3-(1,4-oxazepan-4-yl)propoxy]biphenyl-4-yl}carbonyl)amino]propanediamide, Compound 278 N-hydroxy-N'-methyl-2-(methyl{[3'-(methylamino)biphenyl-4-yl]carbonyl}amino)propanediamide, Compound 279 N-hydroxy-2-{[(3'-methoxybiphenyl-4-yl)carbonyl](methyl)amino}-N'-methylpropanediamide, Compound 280 N-hydroxy-2-[{[4'-(2-hydroxy-2-methylpropoxy)biphenyl-4-yl]carbonyl}(methyl)amino]-N'-methylpropanediamide, Compound 281 N-hydroxy-N'-methyl-2-{methyl[4-(1-methyl-1H-benzimidazol-5-yl)benzoyl]amino}propanediamide, Compound 282 N-hydroxy-N'-methyl-2-{methyl[4-(1-methyl-1H-benzimidazol-6-yl)benzoyl]amino}propanediamide, Compound 283 2-[({4'-[2-fluoro-3-(morpholin-4-yl)propoxy]biphenyl-4-yl}carbonyl)(methyl)amino]-N-hydroxy-N'-methylpropanediamide, Compound 284 2-{[(4'-aminobiphenyl-4-yl)carbonyl](methyl)amino}-N-hydroxy-N'-methylpropanediamide, Compound 285 2-[{[4'-(ethoxymethyl)biphenyl-4-yl]carbonyl}(methyl)amino]-N-hydroxy-N'-methylpropanediamide, Compound 286 N-hydroxy-N'-methyl-2-{methyl[(4'-{[3-(morpholin-4-yl)propyl]sulfanyl}biphenyl-4-yl)carbonyl]amino}propanediamide, Compound 287 N-hydroxy-N'-methyl-2-[methyl({4'-[3-(morpholin-4-ylmethyl)pyrrolidin-1-yl]biphenyl-4-yl}carbonyl)amino]propanediamide, Compound 288 N-hydroxy-N'-methyl-2-[methyl({4'-[3-(thiomorpholin-4-yl)propoxy]biphenyl-4-yl}carbonyl)amino]propanediamide, Compound 289 2-[({4'-[3-(1,1-dioxidothiomorpholin-4-yl)propoxy]biphenyl-4-yl}carbonyl)(methyl)amino]-N-hydroxy-N'-methylpropanediamide, Compound 290 2-[{[4-(1,3-dihydro-2-benzofuran-5-yl)phenyl]carbonyl}(methyl)amino]-N-hydroxy-N'-methylpropanediamide, Compound 291 N-hydroxy-2-[({4'-[(2-methoxyethyl)sulfanyl]biphenyl-4-yl}carbonyl)(methyl)amino]-N'-methylpropanediamide, Compound 292 N-hydroxy-N'-methyl-2-(methyl{[4-(thiophen-3-yl)phenyl]carbonyl}amino)propanediamide, Compound 293 2-[{[4'-({3-[(2-fluorophenyl)amino]propyl}amino)biphenyl-4-yl]carbonyl}(methyl)amino]-N-hydroxy-N'-methylpropanediamide, Compound 294 N-hydroxy-N'-methyl-2-(methyl{[4'-({3-[3-(methylamino)phenoxy]propyl}amino)biphenyl-4-yl]carbonyl}amino)propanediamide, Compound 295 N-hydroxy-N'-methyl-2-(methyl{[4-(6-methylpyridin-2-yl)phenyl]carbonyl}amino)propanediamide, Compound 296 N-hydroxy-2-[{[4-(6-methoxypyridin-2-yl)phenyl]carbonyl}(methyl)amino]-N'-methylpropanediamide, Compound 297 N-hydroxy-N'-methyl-2-[methyl({4-[5-(trifluoromethyl)pyridin-2-yl]phenyl}carbonyl)amino]propanediamide,
Compound 298 N-hydroxy-2-[{[4-(imidazo[1,2-a]pyridin-7-yl)phenyl]carbonyl}(methyl)amino]-N'-methylpropanediamide,
Compound 299 N-hydroxy-N'-methyl-2-{methyl[(5-phenylpyrazin-2-yl)carbonyl]amino}propanediamide.

The compound names shown in Table 3 are as follows:
Compound 300 2-[({4-[(4-{[(2-fluoroethyl)amino]methyl}phenyl)ethynyl]phenyl}carbonyl)(methyl)amino]-N-hydroxy-N'-methylpropanediamide,
Compound 301 2-[{[4-({4-[(cyclopropylamino)methyl]phenyl}ethynyl)phenyl]carbonyl}(methyl)amino]-N-hydroxy-N'-methylpropanediamide,
Compound 302 2-[({4-[(4-{[(2,2-difluoroethyl)amino]methyl}phenyl)ethynyl]phenyl}carbonyl)(methyl)amino]-N-hydroxy-N'-methylpropanediamide,
Compound 303 N-hydroxy-N'-methyl-2-{methyl[(4-{[4-(8-oxa-3-azabicyclo[3.2.1]oct-3-ylmethyl)phenyl]ethynyl}phenyl)carbonyl]amino}propanediamide,
Compound 304 N-hydroxy-N'-methyl-2-(methyl {[4-({4-[(4-methylpiperazin-1-yl)methyl]phenyl}ethynyl)phenyl]carbonyl}amino)propanediamide,
Compound 305 2-[{[4-({4-[(1,1-dioxidothiomorpholin-4-yl)methyl]phenyl}ethynyl)phenyl]carbonyl}(methyl)amino]-N-hydroxy-N'-methylpropanediamide,
Compound 306 N-hydroxy-2-{[(4-{[4-(hydroxymethyl)phenyl]ethynyl}phenyl)carbonyl](methyl)amino}-N'-methylpropanediamide,
Compound 307 N-hydroxy-N'-methyl-2-(methyl {[4-(1H-pyrrol-1-yl)phenyl]carbonyl}amino)propanediamide,
Compound 308 N-hydroxy-N'-methyl-2-(methyl {[4-(thiophen-2-yl)phenyl]carbonyl}amino)propanediamide,
Compound 309 N-hydroxy-N'-methyl-2-(methyl {[4-(pyrazin-2-yl)phenyl]carbonyl}amino)propanediamide,
Compound 310 N-hydroxy-N'-methyl-2-(methyl {[4-(1,3-oxazol-5-yl)phenyl]carbonyl}amino)propanediamide,
Compound 311 N-hydroxy-N'-methyl-2-(methyl {[4-(pyrimidin-2-yl)phenyl]carbonyl}amino)propanediamide,
Compound 312 2-[{[4-(1-benzofuran-2-yl)phenyl]carbonyl}(methyl)amino]-N-hydroxy-N'-methylpropanediamide,
Compound 313 2-[{[4-({4-[(3-fluoroazetidin-1-yl)methyl]phenyl}ethynyl)phenyl]carbonyl}(methyl)amino]-N-hydroxy-N'-methylpropanediamide,
Compound 314 N-hydroxy-N'-methyl-2-[methyl({4-[(4-{[(tetrahydro-2H-pyran-4-ylmethyl)amino]methyl}phenyl)ethynyl]phenyl}carbonyl)amino]propanediamide,
Compound 315 2-[({4-[(4-{[bis(2-hydroxyethyl)amino]methyl}phenyl)ethynyl]phenyl}carbonyl)(methyl)amino]-N-hydroxy-N'-methylpropanediamide,
Compound 316 2-[{[4-({4-[(cyclobutylamino)methyl]phenyl}ethynyl)phenyl]carbonyl}(methyl)amino]-N-hydroxy-N'-methylpropanediamide,
Compound 317 2-[{[4-({4-[(cyclopentylamino)methyl]phenyl}ethynyl)phenyl]carbonyl}(methyl)amino]-N-hydroxy-N'-methylpropanediamide,
Compound 318 2-[{[4-({4-[(cyclohexylamino)methyl]phenyl}ethynyl)phenyl]carbonyl}(methyl)amino]-N-hydroxy-N'-methylpropanediamide,
Compound 319 N-hydroxy-2-[({4-[(4-methoxybenzyl)oxy]phenyl}carbonyl)(methyl)amino]-N'-methylpropanediamide,
Compound 320 2-{[(4-{[4-(2,3-dihydroxypropoxy)phenyl]ethynyl}phenyl)carbonyl](methyl)amino}-N-hydroxy-N'-methylpropanediamide,
Compound 321 N-hydroxy-2-[{[4-({4-[(3-hydroxy-3-methylazetidin-1-yl)methyl]phenyl}ethynyl)phenyl]carbonyl}(methyl)amino]-N'-methylpropanediamide,
Compound 322 N-hydroxy-N'-methyl-2-{methyl[(4-{[4-(2-oxa-6-azaspiro[3.3]hept-6-ylmethyl)phenyl]ethynyl}phenyl)carbonyl]amino}propanediamide,
Compound 323 N-hydroxy-2-[({4-[(4-{[(3-hydroxy-3-methylbutyl)amino]methyl}phenyl)ethynyl]phenyl}carbonyl)(methyl)amino]-N'-methylpropanediamide,
Compound 324 2-[(biphenyl-4-ylcarbonyl)(methyl)amino]-N-hydroxy-N',2-dimethylpropanediamide,
Compound 325 N-hydroxy-N'-methyl-2-{methyl[(4-{[4-({[3-(2-oxopyrrolidin-1-yl) propyl]amino}methyl)phenyl]ethynyl}phenyl)carbonyl]amino}propanediamide,
Compound 326 N-hydroxy-N'-methyl-2-{methyl[(4-{[4-({[2-(pyrrolidin-1-yl)ethyl]amino}methyl)phenyl]ethynyl}phenyl)carbonyl]amino}propanediamide,
Compound 327 2-[({4-[(4-{[cyclohexyl(methyl)amino]methyl}phenyl)ethynyl]phenyl}carbonyl)(methyl)amino]-N-hydroxy-N'-methylpropanediamide,
Compound 328 2-[{[4-{4-[(tert-butylamino)methyl]phenyl}ethynyl)phenyl]carbonyl}(methyl)amino]-N-hydroxy-N'-methylpropanediamide,
Compound 329 2-[({4-[(4-{[(2,2-dimethylpropyl)amino]methyl}phenyl)ethynyl]phenyl}carbonyl)(methyl)amino]-N-hydroxy-N'-methylpropanediamide,
Compound 330 2-[{[4-({4-[(benzylamino)methyl]phenyl}ethynyl)phenyl]carbonyl}(methyl)amino]-N-hydroxy-N'-methylpropanediamide,
Compound 331 N-hydroxy-N'-methyl-2-{methyl[(4-{[4-({[2-(morpholin-4-yl)ethyl]amino}methyl)phenyl]ethynyl}phenyl)carbonyl]amino}propanediamide,
Compound 332 N-hydroxy-N'-methyl-2-(methyl {[4-({4-[(2-methyl-1-oxo-2,8-diazaspiro[4.5]dec-8-yl)methyl]phenyl}ethynyl)phenyl]carbonyl}amino)propanediamide,
Compound 333 N-hydroxy-2-[{[4-({4-[(3-hydroxypyrrolidin-1-yl)methyl]phenyl}ethynyl)phenyl]carbonyl}(methyl)amino]-N'-methylpropanediamide,
Compound 334 N-hydroxy-2-[{[4-({4-[(4-hydroxypiperidin-1-yl)methyl]phenyl}ethynyl)phenyl]carbonyl}(methyl)amino]-N'-methylpropanediamide,
Compound 335 2-[{[4-({4-[(1,3-dihydroxypropan-2-yl)oxy]phenyl}ethynyl)phenyl]carbonyl}(methyl)amino]-N-hydroxy-N'-methylpropanediamide,
Compound 336 2-{ethyl[(4-{[4-(1,4-oxazepan-4-ylmethyl)phenyl]ethynyl}phenyl)carbonyl]amino}-N-hydroxy-N'-methylpropanediamide,
Compound 337 N-hydroxy-N'-methyl-2-(methyl {[4-({4-[(oxetan-3-ylamino)methyl]phenyl}ethynyl)phenyl]carbonyl}amino)propanediamide,
Compound 338 N-hydroxy-N'-methyl-2-(methyl {[4-(4-phenylpiperazin-1-yl)phenyl]carbonyl}amino)propanediamide,
Compound 339 1-{[1-(hydroxyamino)-3-(methylamino)-1,3-dioxopropan-2-yl](methyl)carbamoyl}-4-[(4-{[1-methoxy-3-(methylamino)-1,3-dioxopropan-2-yl](methyl)carbamoyl}phenyl)ethynyl]benzene,
Compound 340 2,2'-{ethyne-1,2-diylbis[benzene-4,1-diylcarbonyl(methylimino)]}bis(N-1-hydroxy-N-3-methylpropanediamide),
Compound 341 (2S)-2-[(biphenyl-4-ylcarbonyl)(methyl)amino]-N-hydroxy-N',2-dimethylpropanediamide,
Compound 342 2-[(biphenyl-4-ylcarbonyl)(methyl)amino]-2-ethyl-N-hydroxy-N'-methylpropanediamide, Compound 343 (2R)-2-[(biphenyl-4-ylcarbonyl)(methyl)amino]-N-hydroxy-N',2-dimethylpropanediamide, Compound 344 2-[{[4-(1,3-benzothiazol-2-yl)phenyl]carbonyl}(methyl)amino]-N-hydroxy-N'-methylpropanediamide, Compound 345 N-hydroxy-N',2-dimethyl-2-(methyl {[4-(phenylethynyl)phenyl]carbonyl}amino)propanediamide, Compound 346 N-hydroxy-N',2-dimethyl-2-{methyl[(4-{[4-(1,4-oxazepan-4-ylmethyl)phenyl]ethynyl}phenyl)carbonyl]amino}propanediamide, Compound 347 2-[{[4-(1,3-benzoxazol-2-yl)phenyl]carbonyl}(methyl)amino]-N-hydroxy-N'-methylpropanediamide, Compound 348 N-hydroxy-2-{[(4'-methoxybiphenyl-4-yl)carbonyl](methyl)amino}-N',2-dimethylpropanediamide, Compound 349 N-hydroxy-N',2-dimethyl-2-{methyl[(4'-methylbiphenyl-4-yl)carbonyl]amino}propanediamide, Compound 350 N-hydroxy-N',2-dimethyl-2-[methyl({4'-[3-(morpholin-4-yl)propoxy]biphenyl-4-yl}carbonyl)amino]propanediamide, Compound 351 2-[({4'-[2-(benzyloxy)ethoxy]biphenyl-4-yl}carbonyl)(methyl)amino]-N-hydroxy-N',2-dimethylpropanediamide, Compound 352 N-hydroxy-N'-methyl-2-(methyl {[4'-(methylsulfonyl)biphenyl-4-yl]carbonyl}amino)propanediamide, Compound 353 2-[{[4-({4-[(3,3-difluoroazetidin-1-yl)methyl]phenyl}ethynyl)phenyl]carbonyl}(methyl)amino]-N-hydroxy-N'-methylpropanediamide, Compound 354 N-hydroxy-N'-methyl-2-[methyl({4-[(4-{[(3-phenylpropyl)amino]methyl}phenyl)ethynyl]phenyl}carbonyl)amino]propanediamide, Compound 355 2-[({4-[(4-{[ethyl(2-methoxyethyl)amino]methyl}phenyl)ethynyl]phenyl}carbonyl)(methyl)amino]-N-hydroxy-N'-methylpropanediamide, Compound 356 N-hydroxy-N'-methyl-2-{methyl[(4-{[4-({[(1-methyl-1H-imidazol-2-yl)methyl]amino}methyl)phenyl]ethynyl}phenyl)carbonyl]amino}propanediamide, Compound 357 2-[{[4-({4-[1-(cyclopropylamino)ethyl]phenyl}ethynyl)phenyl]carbonyl}(methyl)amino]-N-hydroxy-N'-methylpropanediamide, Compound 358 2-{[(4-{[4-(1-amino ethyl)phenyl]ethynyl}phenyl)carbonyl](methyl)amino}-N-hydroxy-N'-methylpropanediamide, Compound 359 N-hydroxy-N'-methyl-2-{methyl[(4-{[4-({[(5-methylpyrazin-2-yl)methyl]amino}methyl)phenyl]ethynyl}phenyl)carbonyl]amino}propanediamide, Compound 360 N-hydroxy-N'-methyl-2-[methyl({4-[(4-{[(pyrimidin-2-ylmethyl)amino]methyl}phenyl)ethynyl]phenyl}carbonyl)amino]propanediamide, Compound 361 2-[({4-[(4-{[(cycloheptylmethyl)amino]methyl}phenyl)ethynyl]phenyl}carbonyl)(methyl)amino]-N-hydroxy-N'-methylpropanediamide, Compound 362 2-[({4-[(4-{[(cyclohexylmethyl)amino]methyl}phenyl)ethynyl]phenyl}carbonyl)(methyl)amino]-N-hydroxy-N'-methylpropanediamide, Compound 363 N-hydroxy-N'-methyl-2-[methyl({4-[(4-{[(pyridin-2-ylmethyl)amino]methyl}phenyl)ethynyl]phenyl}carbonyl)amino]propanediamide, Compound 364 N-hydroxy-2-[{[4'-(4-hydroxybutoxy)biphenyl-4-yl]carbonyl}(methyl)amino]-N',2-dimethylpropanediamide, Compound 365 2-[{[4-({4-[(3,3-difluoropyrrolidin-1-yl)methyl]phenyl}ethynyl)phenyl]carbonyl}(methyl)amino]-N-hydroxy-N'-methylpropanediamide, Compound 366 2-[({4-[(4-{[bis(2-methoxyethyl)amino]methyl}phenyl)ethynyl]phenyl}carbonyl)(methyl)amino]-N-hydroxy-N'-methylpropanediamide, Compound 367 N-hydroxy-N'-methyl-2-(methyl {[4-({4-[1-(morpholin-4-yl)ethyl]phenyl}ethynyl)phenyl]carbonyl}amino)propanediamide, Compound 368 N-hydroxy-N'-methyl-2-[methyl({4-[(4-{[methyl(2-phenylethyl)amino]methyl}phenyl)ethynyl]phenyl}carbonyl)amino]propanediamide, Compound 369 N-hydroxy-N'-methyl-2-{methyl[(4-{[4-({[2-(pyridin-4-yl)ethyl]amino}methyl)phenyl]ethynyl}phenyl)carbonyl]amino}propanediamide, Compound 370 2-[({4-[(4-{[(1,1-dioxidotetrahydrothiophen-3-yl)(methyl)amino]methyl}phenyl)ethynyl]phenyl}carbonyl)(methyl)amino]-N-hydroxy-N'-methylpropanediamide, Compound 371 N-hydroxy-N'-methyl-2-(methyl {[4-({4-[(tetrahydro-2H-thiopyran-4-ylamino)methyl]phenyl}ethynyl)phenyl]carbonyl}amino)propanediamide, Compound 372 N-hydroxy-N'-methyl-2-[methyl({4-[(4-{[(tetrahydrofuran-2-ylmethyl)amino]methyl}phenyl)ethynyl]phenyl}carbonyl)amino]propanediamide, Compound 373 2-[{[4-({4-[(4-acetylpiperazin-1-yl)methyl]phenyl}ethynyl)phenyl]carbonyl}(methyl)amino]-N-hydroxy-N'-methylpropanediamide, Compound 374 N-hydroxy-N'-methyl-2-[methyl({4-[(4-{[(pyridin-3-ylmethyl)amino]methyl}phenyl)ethynyl]phenyl}carbonyl)amino]propanediamide, Compound 375 N-hydroxy-N'-methyl-2-{methyl[(4-{[3-(morpholin-4-ylmethyl)phenyl]ethynyl}phenyl)carbonyl]amino}propanediamide, Compound 376 (2S)-N-hydroxy-N',2-dimethyl-2-{methyl[(4-{[4-(1,4-oxazepan-4-ylmethyl)phenyl]ethynyl}phenyl)carbonyl]amino}propanediamide, Compound 377 (2R)-N-hydroxy-N',2-dimethyl-2-{methyl[(4-{[4-(1,4-oxazepan-4-ylmethyl)phenyl]ethynyl}phenyl)carbonyl]amino}propanediamide, Compound 378 N-hydroxy-N'-methyl-2-{methyl[(4-{[4-({[2-(methylsulfonyl)ethyl]amino}methyl)phenyl]ethynyl}phenyl)carbonyl]amino}propanediamide, Compound 379 2-[{[4-({3-[(cyclopropylamino)methyl]phenyl}ethynyl)phenyl]carbonyl}(methyl)amino]-N-hydroxy-N'-methylpropanediamide, Compound 380 N-hydroxy-N',2-dimethyl-2-{[(4-{[4-(1,4-oxazepan-4-ylmethyl)phenyl]ethynyl}phenyl)carbonyl]amino}propanediamide, Compound 381 N-hydroxy-N'-methyl-2-(methyl {[4-({4-[2-(1,4-oxazepan-4-yl)ethoxy]phenyl}ethynyl)phenyl]carbonyl}amino)propanediamide, Compound 382 N-hydroxy-N'-methyl-2-(methyl {[4-({4-[2-(morpholin-4-yl)ethoxy]phenyl}ethynyl)phenyl]carbonyl}amino)propanediamide, Compound 383 N-hydroxy-2-[{[4-({4-[(4-methoxypiperidin-1-yl)methyl]phenyl}ethynyl)phenyl]carbonyl}(methyl)amino]-N'-methylpropanediamide, Compound 384 2-[({4-[(4-{[(2R,6S)-2,6-dimethylmorpholin-4-yl]methyl}phenyl)ethynyl]phenyl}carbonyl)(methyl)amino]-N-hydroxy-N'-methylpropanediamide, Compound 385 2-[({4-[(2-cyclopropyl-2,3-dihydro-1H-isoindol-5-yl)ethynyl]phenyl}carbonyl)(methyl)amino]-N-hydroxy-N'-methylpropanediamide, Compound 386 N-hydroxy-N'-methyl-2-[methyl({4-[(4-{[4-(trifluoromethyl)piperidin-1-yl]methyl}phenyl)ethynyl]phenyl}carbonyl)amino]propanediamide, Compound 387 N-hydroxy-N'-methyl-2-[methyl({4-[(4-{[3-(trifluoromethyl)piperidin-1-yl]methyl}phenyl)ethynyl]phenyl}carbonyl)amino]propanediamide, Compound 388 2-[({4-[(4-{[cyclopropyl(2-methoxyethyl)amino]methyl}phenyl)ethynyl]phenyl}carbonyl)(methyl)amino]-N-hydroxy-N'-methylpropanediamide, Compound 389 N-hydroxy-2-{[[4'-(3-hydroxyprop-1-yn-1-yl)biphenyl-4-yl]carbonyl}(methyl)amino]-N'-methylpropanediamide, Compound 390 N-hydroxy-N'-methyl-2-[methyl({4'-[3-(morpholin-4-yl)prop-1-yn-1-yl]biphenyl-4-yl}carbonyl)amino]propanediamide, Compound 391 N-hydroxy-N'-methyl-2-(methyl {[4-({4-[(3-oxopiperazin-1-yl)methyl]phenyl}ethynyl)phenyl]carbonyl}amino)propanediamide, Compound 392 2-{[(4-{[4-(1,4-dioxa-8-azaspiro[4.5]dec-8-ylmethyl)phenyl]ethynyl}phenyl)carbonyl](methyl)amino}-N-hydroxy-N'-methylpropanediamide, Compound 393 N-hydroxy-2-[{[4-({4-[(3-methoxypyrrolidin-1-yl)methyl]phenyl}ethynyl)phenyl]carbonyl}(methyl)amino]-N'-methylpropanediamide, Compound 394 2-{[(4-{[4-(1-aminocyclopropyl)phenyl]ethynyl}phenyl)carbonyl](methyl)amino}-N-hydroxy-N'-methylpropanediamide, Compound 395 N-hydroxy-2-[({4-[(4-{[3-(hydroxycarbamoyl)azetidin-1-yl]methyl}phenyl)ethynyl]phenyl}carbonyl)(methyl)amino]-N'-methylpropanediamide, Compound 396 (2S)-N-hydroxy-N',2-dimethyl-2-(methyl {[4-({4-[(oxetan-3-ylamino)methyl]phenyl}ethynyl)phenyl]carbonyl}amino)propanediamide, Compound 397 (2S)-N-hydroxy-N',2-dimethyl-2-[methyl ({4-[(4-{[methyl(oxetan-3-yl)amino]methyl}phenyl)ethynyl]phenyl}carbonyl)amino]propanediamide, Compound 398 2-[{[4'-(cyclopropylethynyl)biphenyl-4-yl]carbonyl}(methyl)amino]-N-hydroxy-N'-methylpropanediamide, Compound 399 (2S)-2-{[(4'-ethoxybiphenyl-4-yl)carbonyl](methyl)amino}-N-hydroxy-N',2-dimethylpropanediamide, Compound 400 N-hydroxy-N'-methyl-2-{methyl[(4'-{3-[2-(morpholin-4-yl)ethoxy]prop-1-yn-1-yl}biphenyl-4-yl)carbonyl]amino}propanediamide, Compound 401 (2S)-N-hydroxy-N',2-dimethyl-2-(methyl {[4-(1-methyl-2,3-dihydro-1H-indol-5-yl)phenyl]carbonyl}amino)propanediamide, Compound 402 (2S)-N-hydroxy-N',2-dimethyl-2-(methyl {[4-(1-methyl-1H-indol-5-yl)phenyl]carbonyl}amino) propanediamide, Compound 403 (2S)-N-hydroxy-2-{[(4-{[4-(methoxymethyl)phenyl]ethynyl}phenyl)carbonyl](methyl)amino}-N',2-dimethylpropanediamide, Compound 404 (2S)-2-{[(4-{[441-aminocyclopropyl)phenyl]ethynyl}phenyl)carbonyl](methyl)amino}-N-hydroxy-N',2-dimethylpropanediamide, Compound 405 N-hydroxy-2-[{[4'-(3-methoxyprop-1-yn-1-yl)biphenyl-4-yl]carbonyl}(methyl)amino]-N'-methylpropanediamide, Compound 406 (2S)-N-hydroxy-N',2-dimethyl-2-(methyl {[4'-(methylsulfanyl)biphenyl-4-yl]carbonyl}amino)propanediamide, Compound 407 N-hydroxy-N'-methyl-2-{methyl[(4-{[5-(propylamino)pyridin-2-yl]ethynyl}phenyl)carbonyl]amino}propanediamide, Compound 408 (2S)-N-hydroxy-2-[({4'-[(E)-(methoxyimino)methyl]biphenyl-4-yl}carbonyl)(methyl)amino]-N',2-dimethylpropanediamide, Compound 409 (2S)-2-[{[4-({4-[(4-fluoropiperidin-1-yl)methyl]phenyl}ethynyl)phenyl]carbonyl}(methyl)amino]-N-hydroxy-N',2-dimethylpropanediamide, Compound 410 (2S)-N-hydroxy-N',2-dimethyl-2-(methyl {[4-({4-[2-(morpholin-4-yl)ethyl]phenyl}ethynyl)phenyl]carbonyl}amino)propanediamide, Compound 411 (2S)-2-[{[4-(1,3-benzodioxol-5-yl)phenyl]carbonyl}(methyl)amino]-N-hydroxy-N',2-dimethylpropanediamide, Compound 412 (2S)-N-hydroxy-N',2-dimethyl-2-{[(4'-methoxybiphenyl-4-yl)carbonyl](methyl)amino}-N',2-dimethylpropanediamide, Compound 413 (2S)-2-[{[4-(2,3-dihydro-1,4-benzodioxin-6-yl)phenyl]carbonyl}(methyl)amino]-N-hydroxy-N',2-dimethylpropanediamide, Compound 414 (2S)-N-hydroxy-N',2-dimethyl-2-(methyl {[4-({4-[(methylamino)methyl]phenyl}ethynyl)phenyl]carbonyl}amino)propanediamide, Compound 415 (2S)-2-{[(4'-fluorobiphenyl-4-yl)carbonyl](methyl)amino}-N-hydroxy-N',2-dimethylpropanediamide, Compound 416 (2S)-N-hydroxy-N',2-dimethyl-2-{methyl [(4-{[4-(2-oxa-6-azaspiro[3.3]hept-6-ylmethyl)phenyl]ethynyl}phenyl)carbonyl]amino}propanediamide, Compound 417 (2S)-2-[({4-[(4-{[(furan-2-ylmethyl)amino]methyl}phenyl)ethynyl]phenyl}carbonyl)(methyl)amino]-N-hydroxy-N',2-dimethylpropanediamide, Compound 418 N-hydroxy-N'-methyl-2-[methyl({4-[(1-methyl-1H-pyrazol-3-yl)ethynyl]phenyl}carbonyl)amino] propanediamide, Compound 419 (2S)-N-hydroxy-N',2-dimethyl-2-[methyl ({4-[(4-{[(pyridin-3-ylmethyl)amino]methyl}phenyl)ethynyl]phenyl}carbonyl)amino]propanediamide, Compound 420 N-hydroxy-N'-methyl-2-{methyl[(4-{[4-(trifluoromethyl)phenyl]ethynyl}phenyl)carbonyl]amino}propanediamide, Compound 421 (2S)-N-hydroxy-N',2-dimethyl-2-[methyl ({4-[(4-{[(pyridin-2-ylmethyl)amino]methyl}phenyl)ethynyl]phenyl}carbonyl)amino]propanediamide, Compound 422 (2S)-N-hydroxy-N',2-dimethyl-2-(methyl {[4-({4-[(methylsulfonyl)methyl]phenyl}ethynyl)phenyl]carbonyl}amino)propanediamide, Compound 423 (2S)-2-{[(4'-ethylbiphenyl-4-yl)carbonyl](methyl)amino}-N-hydroxy-N',2-dimethylpropanediamide, Compound 424 N-hydroxy-N'-methyl-2-[methyl({4-[(1-methyl-1H-pyrrol-3-yl)ethynyl]phenyl}carbonyl)amino]propanediamide, Compound 425 (2S)-N-hydroxy-N',2-dimethyl-2-{methyl [(4-{2-[4-(morpholin-4-ylmethyl)phenyl]ethyl}phenyl)carbonyl]amino}propanediamide, Compound 426 (2S)-N-hydroxy-2-{[[4'-(3-hydroxypropyl)biphenyl-4-yl]carbonyl}(methyl)amino]-N',2-dimethylpropanediamide, Compound 427 (2S)-2-[({4-[(4-{[(2-cyanoethyl)amino]methyl}phenyl)ethynyl]phenyl}carbonyl)(methyl)amino]-N-hydroxy-N',2-dimethylpropanediamide, Compound 428 N-hydroxy-2-[({4-[(4-methoxyphenyl)ethynyl]phenyl}carbonyl)(methyl)amino]-N'-methylpropanediamide, Compound 429 (2S)-2-[({4-[(4-{[(2,2-difluoroethyl)amino]methyl}phenyl)ethynyl]phenyl}carbonyl)(methyl)amino]-N-hydroxy-N',2-dimethylpropanediamide, Compound 430 (2S)-2-{[4-({4-[(3-fluoropyrrolidin-1-yl)methyl]phenyl}ethynyl)benzoyl](methyl)amino}-N-hydroxy-N',2-dimethylpropanediamide, Compound 431 (2S)-N-hydroxy-N',2-dimethyl-2-(methyl{[4-({4-[(tetrahydro-2H-pyran-4-ylamino)methyl]phenyl}ethynyl)phenyl]carbonyl}amino)propanediamide, Compound 432 (2S)-N-hydroxy-N',2-dimethyl-2-[methyl({4-[(4-{[(tetrahydro-2H-pyran-4-ylmethyl)amino]methyl}phenyl)ethynyl]phenyl}carbonyl)amino]propanediamide, Compound 433 (2S)-N-hydroxy-N',2-dimethyl-2-[methyl({4-[(1-methyl-1H-pyrazol-4-yl)ethynyl]phenyl}carbonyl)amino]propanediamide, Compound 434 (2S)-N-hydroxy-N',2-dimethyl-2-{methyl[(4-{(E)-2-[4-(morpholin-4-ylmethyl)phenyl]ethenyl}phenyl)carbonyl]amino}propanediamide, Compound 435 (2S)-N-hydroxy-N',2-dimethyl-2-(methyl{[4-({4-[1-(methylamino)cyclopropyl]phenyl}ethynyl)phenyl]carbonyl}amino)propanediamide, Compound 436 N-hydroxy-2-[(4-{[5-(methoxymethyl)thiophen-3-yl]ethynyl}benzoyl)(methyl)amino]-N'-methylpropanediamide, Compound 437 (2S)-N-hydroxy-N',2-dimethyl-2-[methyl({4'-[2-(morpholin-4-yl)ethoxy]biphenyl-4-yl}carbonyl)amino]propanediamide, Compound 438 (2S)-N-hydroxy-N',2-dimethyl-2-{methyl[4-({4-[2-(1,4-oxazepan-4-yl)ethyl]phenyl}ethynyl)benzoyl]amino}propanediamide, Compound 439 (2S)-2-[{4-[(4-{[(cyanomethyl)amino]methyl}phenyl)ethynyl]benzoyl}(methyl)amino]-N-hydroxy-N',2-dimethylpropanediamide, Compound 440 (2S)-2-[(4-{[4-(1,4-dioxa-8-azaspiro[4.5]dec-8-ylmethyl)phenyl]ethynyl}benzoyl)(methyl)amino]-N-hydroxy-N',2-dimethylpropanediamide, Compound 441 (2S)-N-hydroxy-2-[{4-[(4-{[(3-methoxypropyl)amino]methyl}phenyl)ethynyl]benzoyl}(methyl)amino]-N',2-dimethylpropanediamide, Compound 442 N-hydroxy-N'-methyl-2-{methyl[(5-phenylthiophen-2-yl)carbonyl]amino}propanediamide, Compound 443 N-hydroxy-N'-methyl-2-{methyl[(4-phenoxyphenyl)carbonyl]amino}propanediamide, Compound 444 2-[{[4-(cyclohex-2-en-1-yloxy)phenyl]carbonyl}(methyl)amino]-N-hydroxy-N'-methylpropanediamide, Compound 445 2-{[(4-benzylphenyl)carbonyl](methyl)amino}-N-hydroxy-N'-methylpropanediamide, Compound 446 N-hydroxy-N'-methyl-2-[methyl({4-[5-(trifluoromethyl)pyridin-3-yl]phenyl}carbonyl)amino]propanediamide, Compound 447 N-hydroxy-2-[{[4-(5-methoxypyridin-3-yl)phenyl]carbonyl}(methyl)amino]-N'-methylpropanediamide, Compound 448 2-[{[4-(3-fluoropyridin-4-yl)phenyl]carbonyl}(methyl)amino]-N-hydroxy-N'-methylpropanediamide, Compound 449 N-hydroxy-2-[{[4-(6-methoxypyridin-3-yl)phenyl]carbonyl}(methyl)amino]-N'-methylpropanediamide, Compound 450 N-hydroxy-N'-methyl-2-(methyl{[4-(6-methylpyridin-3-yl)phenyl]carbonyl}amino)propanediamide, Compound 451 N-hydroxy-N'-methyl-2-(methyl{[4-(2-methylpyridin-4-yl)phenyl]carbonyl}amino)propanediamide, Compound 452 N-hydroxy-N'-methyl-2-(methyl{[4-(4-methylpyridin-2-yl)phenyl]carbonyl}amino)propanediamide, Compound 453 N-hydroxy-N'-methyl-2-[methyl({4-[(3-phenylprop-2-yn-1-yl)oxy]phenyl}carbonyl)amino]propanediamide, Compound 454 2-[{[4-(benzyloxy)phenyl]carbonyl}(methyl)amino]-N-hydroxy-N'-methylpropanediamide, Compound 455 N-hydroxy-N'-methyl-2-(methyl{[5-(phenylethynyl)pyridin-2-yl]carbonyl}amino)propanediamide, Compound 456 N-hydroxy-N'-methyl-2-(methyl{[4-(5-methylfuran-2-yl)phenyl]carbonyl}amino)propanediamide, Compound 457 2-[{[5-fluoro-6-(4-methoxyphenyl)pyridin-3-yl]carbonyl}(methyl)amino]-N-hydroxy-N'-methylpropanediamide, Compound 458 2-[{[6-(1,3-benzodioxol-5-yl)-5-fluoropyridin-3-yl]carbonyl}(methyl)amino]-N-hydroxy-N'-methylpropanediamide, Compound 459 N-hydroxy-N'-methyl-2-{methyl[(2,2',4'-trifluorobiphenyl-4-yl)carbonyl]amino}propanediamide, Compound 460 2-{[(2,2'-difluoro-4'-methylbiphenyl-4-yl)carbonyl](methyl)amino}-N-hydroxy-N'-methylpropanediamide, Compound 461 2-[{[4-(furan-3-ylethynyl)phenyl]carbonyl}(methyl)amino]-N-hydroxy-N'-methylpropanediamide, Compound 462 2-[{[4-(6-fluoropyridin-3-yl)phenyl]carbonyl}(methyl)amino]-N-hydroxy-N'-methylpropanediamide, Compound 463 2-[{[4-(5-ethyl-6-methoxypyridin-3-yl)phenyl]carbonyl}(methyl)amino]-N-hydroxy-N'-methylpropanediamide, Compound 464 N-hydroxy-N'-methyl-2-[methyl({4-[(2-methylpyridin-4-yl)ethynyl]phenyl}carbonyl)amino]propanediamide, Compound 465 N-hydroxy-N'-methyl-2-(methyl{[4-({4-[3-(morpholin-4-yl)propoxy]phenyl}ethynyl)phenyl]carbonyl}amino)propanediamide, Compound 466 N-hydroxy-N'-methyl-2-[methyl({6-[(E)-2-phenylethenyl]pyridin-3-yl}carbonyl)amino]propanediamide, Compound 467 N-hydroxy-N'-methyl-2-(methyl{[4-(6-propoxypyridin-3-yl)phenyl]carbonyl}amino)propanediamide, Compound 468 2-[({4-[6-(benzyloxy)pyridin-3-yl]phenyl}carbonyl)(methyl)amino]-N-hydroxy-N'-methylpropanediamide, Compound 469 N-hydroxy-N'-methyl-2-[methyl({4-[6-(methylsulfanyl)pyridin-3-yl]phenyl}carbonyl)amino]propanediamide, Compound 470 2-{[(2,2'-difluoro-4'-methoxybiphenyl-4-yl)carbonyl](methyl)amino}-N-hydroxy-N'-methylpropanediamide, Compound 471 N-hydroxy-N'-methyl-2-(methyl{[4-(quinolin-6-ylethynyl)phenyl]carbonyl}amino)propanediamide, Compound 472 N-hydroxy-2-[{[4-(isoquinolin-6-ylethynyl)phenyl]carbonyl}(methyl)amino]-N'-methylpropanediamide, Compound 473 N-hydroxy-N'-methyl-2-{methyl[(4-{[4-(4-methylpiperazin-1-yl)phenyl]ethynyl}phenyl)carbonyl]amino}propanediamide, Compound 474 2-[{[4-(6-butylpyridin-3-yl)phenyl]carbonyl}(methyl)amino]-N-hydroxy-N'-methylpropanediamide, Compound 475 N-hydroxy-N'-methyl-2-[methyl({4-[6-(pentylamino)pyridin-3-yl]phenyl}carbonyl)amino]propanediamide, Compound 476 2-[{[4-(4-{4-[(cyclopropylamino)methyl]phenyl}buta-1,3-diyn-1-yl)phenyl]carbonyl}(methyl)amino]-N-hydroxy-N'-methylpropanediamide, Compound 477 2-[({4-[(1E)-4-{4-[(cyclopropylamino)methyl]phenyl}but-1-en-3-yn-1-yl]phenyl}carbonyl)(methyl)amino]-N-hydroxy-N'-methylpropanediamide, Compound 478 N-hydroxy-2-[({4-[(3E)-4-(6-methoxypyridin-3-yl)but-3-en-1-yn-1-yl]phenyl}carbonyl)(methyl)amino]-N'-methylpropanediamide, Compound 479 N-hydroxy-N'-methyl-2-[methyl({4'-[5-(morpholin-4-ylmethyl)furan-2-yl]biphenyl-4-yl}carbonyl)amino]propanediamide, Compound 480 N-hydroxy-N'-methyl-2-[methyl({4-[6-(pentyloxy)pyridin-3-yl]phenyl}carbonyl)amino]propanediamide, Compound 481 2-[({4-[(3E)-4-{4-[(cyclopropylamino)methyl]phenyl}but-3-en-1-yn-1-yl]phenyl}carbonyl)(methyl)amino]-N-hydroxy-N'-methylpropanediamide, Compound 482 N-hydroxy-N'-methyl-2-{methyl[(4-{[4-({[(5-methyl-1,2-oxazol-3-yl)methyl]amino}methyl)phenyl]ethynyl}phenyl)carbonyl]amino}propanediamide, Compound 483 N-hydroxy-N'-methyl-2-{methyl[(4-{[5-(morpholin-4-ylmethyl)furan-3-yl]ethynyl}phenyl)carbonyl]amino}propanediamide, Compound 484 2-[({4-[4-(furan-3-yl)buta-1,3-diyn-1-yl]phenyl}carbonyl)(methyl)amino]-N-hydroxy-N'-methylpropanediamide, Compound 485 N-hydroxy-N'-methyl-2-[methyl({4-[(4-{[(1,3-oxazol-2-ylmethyl)amino]methyl}phenyl)ethynyl]phenyl}carbonyl)amino]propanediamide, Compound 486 2-[({4-[(4-{[(4-fluorobenzyl)amino]methyl}phenyl)ethynyl]phenyl}carbonyl)(methyl)amino]-N-hydroxy-N'-methylpropanediamide, Compound 487 2-{[(4-{[4-({[2-(4-fluorophenyl)ethyl]amino}methyl)phenyl]ethynyl}phenyl)carbonyl](methyl)amino}-N-hydroxy-N'-methylpropanediamide, Compound 488 N-hydroxy-N'-methyl-2-[methyl({4-[(5-{[(2,2,2-trifluoroethyl)amino]methyl}furan-3-yl)ethynyl]phenyl}carbonyl)amino]propanediamide, Compound 489 2-{[(4-{[4-(1,3-dihydro-2H-isoindol-2-ylmethyl)phenyl]ethynyl}phenyl)carbonyl](methyl)amino}-N-hydroxy-N'-methylpropanediamide, Compound 490 2-{[(4-{[4-(3,4-dihydroisoquinolin-2(1H)-ylmethyl)phenyl]ethynyl}phenyl)carbonyl](methyl)amino}-N-hydroxy-N'-methylpropanediamide, Compound 491 N-hydroxy-N'-methyl-2-[methyl({4-[(5-methyl-1,2-oxazol-4-yl)ethynyl]phenyl}carbonyl)amino]propanediamide, Compound 492 N-hydroxy-N'-methyl-2-(methyl {[4-(4-{4-[(4-methylpiperazin-1-yl)methyl]phenyl}buta-1,3-diyn-1-yl)phenyl]carbonyl}amino)propanediamide, Compound 493 2-[({4-[4-(4-{[(2,2-dimethylpropyl)amino]methyl}phenyl)buta-1,3-diyn-1-yl]phenyl}carbonyl)(methyl)amino]-N-hydroxy-N'-methylpropanediamide, Compound 494 2-[{[4-({4-[(2,3-dihydro-1H-inden-1-ylamino)methyl]phenyl}ethynyl)phenyl]carbonyl}(methyl)amino]-N-hydroxy-N'-methylpropanediamide, Compound 495 2-[({4-[(4-{[benzyl(methyl)amino]methyl}phenyl)ethynyl]phenyl}carbonyl)(methyl)amino]-N-hydroxy-N'-methylpropanediamide, Compound 496 N-hydroxy-N'-methyl-2-(methyl {[4-({4-[4-(morpholin-4-yl)piperidin-1-yl]phenyl}ethynyl)phenyl]carbonyl}amino)propanediamide, Compound 497 2-[({4-[(4-{[(furan-2-ylmethyl)amino]methyl}phenyl)ethynyl]phenyl}carbonyl)(methyl)amino]-N-hydroxy-N'-methylpropanediamide, Compound 498 2-[{[4-({4-[2-(1,3-dihydro-2H-isoindol-2-yl)ethyl]phenyl}ethynyl)phenyl]carbonyl}(methyl)amino]-N-hydroxy-N'-methylpropanediamide, Compound 499 N-hydroxy-2-[({4'-[5-(hydroxymethyl)furan-2-yl]biphenyl-4-yl}carbonyl)(methyl)amino]-N'-methylpropanediamide, Compound 500 2-[{[4-(4-{4-[(cyclobutylamino)methyl]phenyl}buta-1,3-diyn-1-yl)phenyl]carbonyl}(methyl)amino]-N-hydroxy-N'-methylpropanediamide, Compound 501 2-[{[4-({5-[(E)-(ethoxyimino)methyl]furan-2-yl}ethynyl)phenyl]carbonyl}(methyl)amino]-N-hydroxy-N'-methylpropanediamide, Compound 502 N-hydroxy-N'-methyl-2-[methyl({4'-[3-(1,4-oxazepan-4-yl)propyl]biphenyl-4-yl}carbonyl)amino]propanediamide, Compound 503 2-[{[4-(cyclopropylethynyl)phenyl]carbonyl}(methyl)amino]-N-hydroxy-N'-methylpropanediamide, Compound 504 N-hydroxy-N'-methyl-2-[methyl({4-[(1-methyl-1H-pyrazol-4-yl)ethynyl]phenyl}carbonyl)amino]propanediamide, Compound 505 N-hydroxy-2-[{[4-({4-[(3-methoxyazetidin-1-yl)methyl]phenyl}ethynyl)phenyl]carbonyl}(methyl)amino]-N'-methylpropanediamide, Compound 506 2-[{[4-({5-[(E)-(ethoxyimino)methyl]furan-3-yl}ethynyl)phenyl]carbonyl}(methyl)amino]-N-hydroxy-N'-methylpropanediamide, Compound 507 2-[{[4-(4-cyclopropylbuta-1,3-diyn-1-yl)phenyl]carbonyl}(methyl)amino]-N-hydroxy-N'-methylpropanediamide, Compound 508 2-[{[4-({4-[(2-amino-2-methylpropoxy)methyl]phenyl}ethynyl)phenyl]carbonyl}(methyl)amino]-N-hydroxy-N'-methylpropanediamide, Compound 509 N-hydroxy-N'-methyl-2-[methyl({4-[4-(pyridin-4-yl)buta-1,3-diyn-1-yl]phenyl}carbonyl)amino]propanediamide, Compound 510 2-[({4-[(4-{[(2,2-dimethylpentyl)amino]methyl}phenyl)ethynyl]phenyl}carbonyl)(methyl)amino]-N-hydroxy-N'-methylpropanediamide, Compound 511 N-hydroxy-N'-methyl-2-[methyl({4-[4-(1-methyl-1H-pyrazol-4-yl)buta-1,3-diyn-1-yl]phenyl}carbonyl)amino]propanediamide, Compound 512 N-hydroxy-N'-methyl-2-(methyl {[4-({4-[(2-methylpyrrolidin-1-yl)methyl]phenyl}ethynyl)phenyl]carbonyl}amino)propanediamide, Compound 513 2-[{[4-({4-[(3,3-dimethylpiperidin-1-yl)methyl]phenyl}ethynyl)phenyl]carbonyl}(methyl)amino]-N-hydroxy-N'-methylpropanediamide, Compound 514 N-hydroxy-2-{[(4-{[5-(methoxymethyl)furan-3-yl]ethynyl}phenyl)carbonyl](methyl)amino}-N'-methylpropanediamide, Compound 515 2-{[(4-{[4-(3-azabicyclo[3.1.0]hex-3-ylmethyl)phenyl]ethynyl}phenyl)carbonyl](methyl)amino}-N-hydroxy-N'-methylpropanediamide, Compound 516 2-{[(4-{[(1R)-2-ethyl-1-methyl-2,3-dihydro-1H-isoindol-5-yl]ethynyl}phenyl)carbonyl](methyl)amino}-N-hydroxy-N'-methylpropanediamide, Compound 517 2-[({4-[(1-ethyl-1H-pyrazol-4-yl)ethynyl]phenyl}carbonyl)(methyl)amino]-N-hydroxy-N'-methylpropanediamide, Compound 518 N-hydroxy-2-{[(4-{[1-(2-methoxyethyl)-1H-pyrazol-4-yl]ethynyl}phenyl)carbonyl](methyl)amino}-N'-methylpropanediamide, Compound 519 N-hydroxy-2-[({4'-[3-(hydroxymethyl)-1,2-oxazol-5-yl]biphenyl-4-yl}carbonyl)(methyl)amino]-N'-methylpropanediamide, Compound 520 N-hydroxy-2-{methyl[(4-{[4-(1,4-oxazepan-4-ylmethyl)phenyl]ethynyl}phenyl)carbonyl]amino}-N'-(pyridin-2-ylmethyl)propanediamide, Compound 521 N-hydroxy-2-methyl-2-{methyl[(4-{[4-(1,4-oxazepan-4-ylmethyl)phenyl]ethynyl}phenyl)carbonyl]amino}-N'-(pyridin-2-ylmethyl)propanediamide, Compound 522 2-[{[4-({4-[(4-fluoropiperidin-1-yl)methyl]phenyl}ethynyl)phenyl]carbonyl}(methyl)amino]-N-hydroxy-N'-methylpropanediamide, Compound 523 2-[{[4-(cyclohex-1-en-1-ylethynyl)phenyl]carbonyl}(methyl)amino]-N-hydroxy-N'-methylpropanediamide, Compound 524 2-{[(4-{[4-(2-azaspiro[3.3]hept-2-ylmethyl)phenyl]ethynyl}phenyl)carbonyl](methyl)amino}-N-hydroxy-N'-methylpropanediamide, Compound 525 2-[{[4-({4-[(3,3-dimethylazetidin-1-yl)methyl]phenyl}ethynyl)phenyl]carbonyl}(methyl)amino]-N-hydroxy-N'-methylpropanediamide, Compound 526 N-hydroxy-2-{[(4'-methoxybiphenyl-4-yl)carbonyl](methyl)amino}-N'-(pyridin-2-ylmethyl)propanediamide, Compound 527 2-{[(4-{[4-(7-azabicyclo[2.2.1]hept-7-ylmethyl)phenyl]ethynyl}phenyl)carbonyl](methyl)amino}-N-hydroxy-N'-methylpropanediamide, Compound 528 N-hydroxy-2-{[(4-{[5-(methoxymethyl)furan-3-yl]ethynyl}phenyl)carbonyl](methyl)amino]-N',2-dimethylpropanediamide, Compound 529 N-hydroxy-N',2-dimethyl-2-[methyl({4-[4-(1-methyl-1H-pyrazol-4-yl)buta-1,3-diyn-1-yl]phenyl}carbonyl)amino]propanediamide, Compound 530 N-hydroxy-2-[({4-[(4-{[3-(2-methoxyethylidene)azetidin-1-yl]methyl}phenyl)ethynyl]phenyl}carbonyl)(methyl)amino]-N'-methylpropanediamide, Compound 531 2-[{[4-({4-[(3-ethoxyazetidin-1-yl)methyl]phenyl}ethynyl)phenyl]carbonyl}(methyl)amino]-N-hydroxy-N',2-dimethylpropanediamide, Compound 532 N-hydroxy-N'-methyl-2-{methyl[(4-{[4-(7-oxa-2-azaspiro[3.5]non-2-ylmethyl)phenyl]ethynyl}phenyl)carbonyl]amino}propanediamide, Compound 533 N-hydroxy-2-[{[4-({4-[(3-methoxy-3-methylazetidin-1-yl)methyl]phenyl}ethynyl)phenyl]carbonyl}(methyl)amino]-N'-methylpropanediamide, Compound 534 N-hydroxy-N',2-dimethyl-2-[methyl({4-[(4-{[3-(propan-2-yloxy)azetidin-1-yl]methyl}phenyl)ethynyl]phenyl}carbonyl)amino]propanediamide, Compound 535 2-[{[4-({4-[(3-ethoxyazetidin-1-yl)methyl]phenyl}ethynyl)phenyl]carbonyl}(methyl)amino]-N-hydroxy-N'-methylpropanediamide, Compound 536 2-{[(4-{[3-fluoro-4-(morpholin-4-ylmethyl)phenyl]ethynyl}phenyl)carbonyl](methyl)amino}-N-hydroxy-N'-methylpropanediamide, Compound 537 2-[{[4-({4-[(3-ethoxy-3-methylazetidin-1-yl)methyl]phenyl}ethynyl)phenyl]carbonyl}(methyl)amino]-N-hydroxy-N'-methylpropanediamide, Compound 538 2-[{[4-({4-[(3-ethyl-3-methoxyazetidin-1-yl)methyl]phenyl}ethynyl)phenyl]carbonyl}(methyl)amino]-N-hydroxy-N'-methylpropanediamide, Compound 539 2-[({4-[(4-{[3-(2-fluoroethoxy)azetidin-1-yl]methyl}phenyl)ethynyl]phenyl}carbonyl)(methyl)amino]-N-hydroxy-N'-methylpropanediamide, Compound 540 2-[({4-[(4-{[cyclopropyl(methyl)amino]methyl}phenyl)ethynyl]phenyl}carbonyl)(methyl)amino]-N-hydroxy-N'-methylpropanediamide, Compound 541 2-[({4-[(4-{[cyclopropyl(methyl)amino]methyl}phenyl)ethynyl]phenyl}carbonyl)(methyl)amino]-N-hydroxy-N',2-dimethylpropanediamide, Compound 542 2-[({4-[(4-{[3-(cyclobutyloxy)azetidin-1-yl]methyl}phenyl)ethynyl]phenyl}carbonyl)(methyl)amino]-N-hydroxy-N'-methylpropanediamide, Compound 543 N-hydroxy-N'-methyl-2-(methyl {[4-({4-[(3-propylazetidin-1-yl)methyl]phenyl}ethynyl)phenyl]carbonyl}amino)propanediamide, Compound 544 N-hydroxy-N'-methyl-2-{methyl[(4-{[3-methyl-4-(1,4-oxazepan-4-ylmethyl)phenyl]ethynyl}phenyl)carbonyl]amino}propanediamide, Compound 545 2-{[(4-{[3-fluoro-4-(1,4-oxazepan-4-ylmethyl)phenyl]ethynyl}phenyl)carbonyl](methyl)amino}-N-hydroxy-N'-methylpropanediamide, Compound 546 2-[(({4-[(4-{[(2-fluoroethyl)(methyl)amino]methyl}phenyl)ethynyl]phenyl}carbonyl)(methyl)amino]-N-hydroxy-N'-methylpropanediamide, Compound 547 2-{[(4-{[2-fluoro-4-(1,4-oxazepan-4-ylmethyl)phenyl]ethynyl}phenyl)carbonyl](methyl)amino}-N-hydroxy-N'-methylpropanediamide, Compound 548 2-[({4-[(4-{[(2-fluoroethyl)(methyl)amino]methyl}phenyl)ethynyl]phenyl}carbonyl)(methyl)amino]-N-hydroxy-N',2-dimethylpropanediamide, Compound 549 2-[{[4-({4-[(cyclopropylamino)methyl]phenyl}ethynyl)phenyl]carbonyl}(methyl)amino]-N-hydroxy-N',2-dimethylpropanediamide, Compound 550 (2S)-N-hydroxy-2-{[(4-{[5-(methoxymethyl)furan-3-yl]ethynyl}phenyl)carbonyl](methyl)amino}-N',2-dimethylpropanediamide, Compound 551 2-[({4-[(4-{[cyclobutyl(methyl)amino]methyl}phenyl)ethynyl]phenyl}carbonyl)(methyl)amino]-N-hydroxy-N'-methylpropanediamide, Compound 552 2-[({4-[(4-{[(2,2-dimethylpropyl)(methyl)amino]methyl}phenyl)ethynyl]phenyl}carbonyl)(methyl)amino]-N-hydroxy-N'-methylpropanediamide, Compound 553 (2S)-2-[{[4-({4-[(cyclopropylamino)methyl]phenyl}ethynyl)phenyl]carbonyl}(methyl)amino]-N-hydroxy-N',2-dimethylpropanediamide, Compound 554 (2S)-2-[({4-[(4-{[(2-fluoroethyl)amino]methyl}phenyl)ethynyl]phenyl}carbonyl)(methyl)amino]-N-hydroxy-N',2-dimethylpropanediamide, Compound 555 (2S)-2-[{[4-({4-[(cyclobutylamino)methyl]phenyl}ethynyl)phenyl]carbonyl}(methyl)amino]-N-hydroxy-N',2-dimethylpropanediamide, Compound 556 (2S)-2-[({4-[(4-{[(2,2-dimethylpropyl)amino]methyl}phenyl)ethynyl]phenyl}carbonyl)(methyl)amino]-N-hydroxy-N',2-dimethylpropanediamide, Compound 557 (2S)-2-[{[4-({4-[(3-ethoxyazetidin-1-yl)methyl]phenyl}ethynyl)phenyl]carbonyl}(methyl)amino]-N-hydroxy-N',2-dimethylpropanediamide, Compound 558 (2S)-N-hydroxy-2-[{[4-({4-[(3-methoxy-3-methylazetidin-1-yl)methyl]phenyl}ethynyl)phenyl]carbonyl}(methyl)amino]-N',2-dimethylpropanediamide, Compound 559 (2S)-2-[({4-[(4-{[3-(2-fluoroethoxy)azetidin-1-yl]methyl}phenyl)ethynyl]phenyl}carbonyl)(methyl)amino]-N-hydroxy-N',2-dimethylpropanediamide, Compound 560 (2S)-N-hydroxy-N',2-dimethyl-2-(methyl {[4-({4-[(2-methylmorpholin-4-yl)methyl]phenyl}ethynyl)phenyl]carbonyl}amino)propanediamide, Compound 561 (2S)-N-hydroxy-N',2-dimethyl-2-{methyl[(4-{[4-(morpholin-4-ylmethyl)phenyl]ethynyl}phenyl)carbonyl]amino}propanediamide, Compound 562 2-[{[4-({4-[(3-ethoxyazetidin-1-yl)methyl]-3-methylphenyl}ethynyl)phenyl]carbonyl}(methyl)amino]-N-hydroxy-N'-methylpropanediamide, Compound 563 2-[{[4-({4-[(3-ethoxyazetidin-1-yl)methyl]-3-fluorophenyl}ethynyl)phenyl]carbonyl}(methyl)amino]-N-hydroxy-N'-methylpropanediamide, Compound 564 2-[{[4-({4-[(3-ethoxyazetidin-1-yl)methyl]-2-fluorophenyl}ethynyl)phenyl]carbonyl}(methyl)amino]-N-hydroxy-N'-methylpropanediamide, Compound 565 (2S)-N-hydroxy-2-[{[4-({4-[(4-methoxypiperidin-1-yl)methyl]phenyl}ethynyl)phenyl]carbonyl}(methyl)amino]-N',2-dimethylpropanediamide, Compound 566 (2S)-2-[{[4-({4-[(4-ethoxypiperidin-1-yl)methyl]phenyl}ethynyl)phenyl]carbonyl}(methyl)amino]-N-hydroxy-N',2-dimethylpropanediamide, Compound 567 (2S)-N-hydroxy-2-[{[4-({4-[(3-methoxyazetidin-1-yl)methyl]phenyl}ethynyl)phenyl]carbonyl}(methyl)amino]-N',2-dimethylpropanediamide, Compound 568 2-[{[4-({4-[(3-ethoxyazetidin-1-yl)methyl]-2-methylphenyl}ethynyl)phenyl]carbonyl}(methyl)amino]-N-hydroxy-N'-methylpropanediamide, Compound 569 (2S)-N-hydroxy-N',2-dimethyl-2-(methyl{[4-({4-[(3-propoxyazetidin-1-yl)methyl]phenyl}ethynyl)phenyl]carbonyl}amino)propanediamide, Compound 570 (2S)-2-[({4-[(4-{[3-(cyclopropylmethoxy)azetidin-1-yl]methyl}phenyl)ethynyl]phenyl}carbonyl)(methyl)amino]-N-hydroxy-N',2-dimethylpropanediamide, Compound 571 (2S)-N-hydroxy-N',2-dimethyl-2-[methyl({4-[(4-{[(2-methylpropyl)amino]methyl}phenyl)ethynyl]phenyl}carbonyl)amino]propanediamide, Compound 572 2-[{[4-({4-[(3-ethoxyazetidin-1-yl)methyl]-3-methoxyphenyl}ethynyl)phenyl]carbonyl}(methyl)amino]-N-hydroxy-N'-methylpropanediamide, Compound 573 2-[{[4-({4-[(3-ethoxyazetidin-1-yl)methyl]-3-(trifluoromethyl)phenyl}ethynyl)phenyl]carbonyl}(methyl)amino]-N-hydroxy-N'-methylpropanediamide, Compound 574 2-[{[4-({4-[(3-ethoxyazetidin-1-yl)methyl]-2-(trifluoromethyl)phenyl}ethynyl)phenyl]carbonyl}(methyl)amino]-N-hydroxy-N'-methylpropanediamide, Compound 575 (2S)-N-hydroxy-N',2-dimethyl-2-[methyl({4-[(2-methyl-1,3-oxazol-4-yl)ethynyl]phenyl}carbonyl)amino]propanediamide, Compound 576 (2S)-N-hydroxy-N',2-dimethyl-2-[methyl({4-[(5-methyl-1,2-oxazol-3-yl)ethynyl]phenyl}carbonyl)amino]propanediamide, Compound 577 (2S)-N-hydroxy-2-[({4-[(4-{[3-(2-methoxyethoxy)azetidin-1-yl]methyl}phenyl)ethynyl]phenyl}carbonyl)(methyl)amino]-N',2-dimethylpropanediamide, Compound 578 (2S)-N-hydroxy-N',2-dimethyl-2-{methyl[(4-{[4-({[(3-methyloxetan-3-yl)methyl]amino}methyl)phenyl]ethynyl}phenyl)carbonyl]amino}propanediamide, Compound 579 2-[{[4-({3-chloro-4-[(3-ethoxyazetidin-1-yl)methyl]phenyl}ethynyl)phenyl]carbonyl}(methyl)amino]-N-hydroxy-N'-methylpropanediamide, Compound 580 2-[{[4-({4-[(3-ethoxyazetidin-1-yl)methyl]-2,3-difluorophenyl}ethynyl)phenyl]carbonyl}(methyl)amino]-N-hydroxy-N'-methylpropanediamide, Compound 581 2-[{[4-({4-[(3-ethoxyazetidin-1-yl)methyl]phenyl}ethynyl)-3-fluorophenyl]carbonyl}(methyl)amino]-N-hydroxy-N'-methylpropanediamide, Compound 582 2-[{[4-({4-[(3-ethoxyazetidin-1-yl)methyl]phenyl}ethynyl)-3-methylphenyl]carbonyl}(methyl)amino]-N-hydroxy-N'-methylpropanediamide, Compound 583 (2S)-N-hydroxy-N',2-dimethyl-2-{methyl[(4-{[5-(1,4-oxazepan-4-ylmethyl)furan-3-yl]ethynyl}phenyl)carbonyl]amino}propanediamide, Compound 584 (2S)-2-[{[4-({5-[(3-ethoxyazetidin-1-yl)methyl]furan-3-yl}ethynyl)phenyl]carbonyl}(methyl)amino]-N-hydroxy-N',2-dimethylpropanediamide, Compound 585 (2S)-2-[{[4-({5-[(cyclopropylamino)methyl]furan-3-yl}ethynyl)phenyl]carbonyl}(methyl)amino]-N-hydroxy-N',2-dimethylpropanediamide, Compound 586 (2S)-N-hydroxy-N',2-dimethyl-2-[methyl({4-[(2-methyl-1,3-thiazol-4-yl)ethynyl]phenyl}carbonyl)amino]propanediamide, Compound 587 (2S)-N-hydroxy-N',2-dimethyl-2-{methyl[(4-{[4-({[(1-methylcyclopentyl)methyl]amino}methyl)phenyl]ethynyl}phenyl)carbonyl]amino}propanediamide, Compound 588 (2S)-2-[{[4-(1,3-benzodioxol-5-ylethynyl)phenyl]carbonyl}(methyl)amino]-N-hydroxy-N',2-dimethylpropanediamide, Compound 589 (2S)-2-{[(4-{[4-(difluoromethoxy)phenyl]ethynyl}phenyl)carbonyl](methyl)amino}-N-hydroxy-N',2-dimethylpropanediamide, Compound 590 (2S)-N-hydroxy-N',2-dimethyl-2-(methyl{4-[(3E)-4-(tetrahydro-2H-pyran-4-yl)but-3-en-1-yn-1-yl]benzoyl}amino)propanediamide, Compound 591 (2S)-N-hydroxy-N',2-dimethyl-2-[methyl(4-{[4-({[(2-methylcyclopropyl)methyl]amino}methyl)phenyl]ethynyl}benzoyl)amino]propanediamide, Compound 592 (2S)-N-hydroxy-N',2-dimethyl-2-[methyl(4-{[5-(morpholin-4-ylmethyl)furan-3-yl]ethynyl}benzoyl)amino]propanediamide, Compound 593 (2S)-N-hydroxy-N',2-dimethyl-2-{methyl[4-({4-[2-(2-methylmorpholin-4-yl)ethyl]phenyl}ethynyl)benzoyl]amino}propanediamide, Compound 594 (2S)-N-hydroxy-N',2-dimethyl-2-(methyl{4-[(4-{[(2-methylcyclopropyl)amino]methyl}phenyl)ethynyl]benzoyl}amino)propanediamide, Compound 595 a mixture of (2S)-N-hydroxy-N',2-dimethyl-2-(methyl{4-[(3E)-4-(5-methyl-1,2-oxazol-3-yl)but-3-en-1-yn-1-yl]benzoyl}amino)propanediamide and (2S)-N-hydroxy-N',2-dimethyl-2-(methyl{4-[(3Z)-4-(5-methyl-1,2-oxazol-3-yl)but-3-en-1-yn-1-yl]benzoyl}amino)propanediamide, Compound 596 (2S)-N-hydroxy-2-[(4-{(3E)-4-[2-(methoxymethyl)cyclopropyl]but-3-en-1-yn-1-yl}benzoyl)(methyl)amino]-N',2-dimethylpropanediamide, Compound 597 (2S)-N-hydroxy-2-[{4-[(3E)-7-methoxyhept-3-en-1-yn-1-yl]benzoyl}(methyl)amino]-N',2-dimethylpropanediamide, Compound 598 (2S)-2-[{4-[(4-{[3-(benzyloxy)azetidin-1-yl]methyl}phenyl)ethynyl]benzoyl}(methyl)amino]-N-hydroxy-N',2-dimethylpropanediamide, Compound 599 (2S)-N-hydroxy-2-{[4-({4-[2-(3-methoxyazetidin-1-yl)ethyl]phenyl}ethynyl)benzoyl](methyl)amino}-N',2-dimethylpropanediamide, Compound 600 (2S)-2-[(4-{[4-({[1-(2-fluoroethyl)azetidin-3-yl]oxy}methyl)phenyl]ethynyl}benzoyl)(methyl)amino]-N-hydroxy-N',2-dimethylpropanediamide, Compound 601 (2S)-N-hydroxy-2-{[4-(5-methoxypent-1-yn-1-yl)benzoyl](methyl)amino}-N',2-dimethylpropanediamide, Compound 602 (2S)-N-hydroxy-2-{[4-({4-[2-(4-methoxypiperidin-1-yl)ethyl]phenyl}ethynyl)benzoyl](methyl)amino}-N',2-dimethylpropanediamide, Compound 603 (2S)-N-hydroxy-2-{[4-({5-[(2-methoxyethoxy)methyl]furan-3-yl}ethynyl)benzoyl](methyl)amino}-N',2-dimethylpropanediamide, Compound 604 (2S)-2-[{4-[(4-{[1-(2-fluoroethyl)azetidin-3-yl]oxy}phenyl)ethynyl]benzoyl}(methyl)amino]-N-hydroxy-N',2-dimethylpropanediamide, Compound 605 (2S)-N-hydroxy-2-[(4-{[5-(2-methoxyethyl)furan-3-yl]ethynyl}benzoyl)(methyl)amino]-N',2-dimethylpropanediamide, Compound 606 (2S)-2-[({4-[(3E)-4-(1-benzylazetidin-3-yl)but-3-en-1-yn-1-yl]phenyl}carbonyl)(methyl)amino]-N-hydroxy-N',2-dimethylpropanediamide, Compound 607 (2S)-2-[({4-[(4-{[3-(furan-2-ylmethoxy)azetidin-1-yl]methyl}phenyl)ethynyl]phenyl}carbonyl)(methyl)amino]-N-hydroxy-N',2-dimethylpropanediamide, Compound 608 (2S)-N-hydroxy-2-[{[4-({4-[3-(3-methoxyazetidin-1-yl)propyl]phenyl}ethynyl)phenyl]carbonyl}(methyl)amino]-N',2-dimethylpropanediamide, Compound 609 (2S)-N-hydroxy-2-{[(4-{[5-(1-methoxyethyl)furan-3-yl]ethynyl}phenyl)carbonyl](methyl)amino}-N',2-dimethylpropanediamide, Compound 610 (2S)-2-[({4-[(4-acetylphenyl)ethynyl]phenyl}carbonyl)(methyl)amino]-N-hydroxy-N',2-dimethylpropanediamide, Compound 611 (2S)-N-hydroxy-N',2-dimethyl-2-(methyl{4-[(4-{[(tetrahydrofuran-2-ylmethyl)amino]methyl}phenyl)ethynyl]benzoyl}amino)propanediamide, Compound 612 (2S)-2-[(4-{[5-(ethoxymethyl)furan-3-yl]ethynyl}benzoyl)(methyl)amino]-N-hydroxy-N',2-dimethylpropanediamide, Compound 613 (2S)-N-hydroxy-N',2-dimethyl-2-(methyl{4-[(4-{[3-(propan-2-yloxy)azetidin-1-yl]methyl}phenyl)ethynyl]benzoyl}amino)propanediamide, Compound 614 (2S)-N-hydroxy-2-[{4-[(4-{[(2-methoxyethyl)amino]methyl}phenyl)ethynyl]benzoyl}(methyl)amino]-N',2-dimethylpropanediamide, Compound 615 (2S)-N-hydroxy-N',2-dimethyl-2-(methyl{4-[(4-{[(4,4,4-trifluorobutyl)amino]methyl}phenyl)ethynyl]benzoyl}amino)propanediamide, Compound 616 (2S)-N-hydroxy-2-[(4-{[5-(hydroxymethyl)furan-3-yl]ethynyl}benzoyl)(methyl)amino]-N',2-dimethylpropanediamide, Compound 617 (2S)-N-hydroxy-N',2-dimethyl-2-[methyl(4-{[4-(1-oxa-6-azaspiro[3.3]hept-6-ylmethyl)phenyl]ethynyl}benzoyl)amino]propanediamide, Compound 618 (2S)-N-hydroxy-N',2-dimethyl-2-{methyl[4-({4-[(tetrahydrofuran-3-ylamino)methyl]phenyl}ethynyl)benzoyl]amino}propanediamide, Compound 619 (2S)-2-{[4-({4-[(3-fluoroazetidin-1-yl)methyl]phenyl}ethynyl)benzoyl](methyl)amino}-N-hydroxy-N',2-dimethylpropanediamide, Compound 620 (2S)-N-hydroxy-N',2-dimethyl-2-{methyl[(4-{[4-({[(5-methylfuran-2-yl)methyl]amino}methyl)phenyl]ethynyl}phenyl)carbonyl]amino}propanediamide, Compound 621 (2S)-2-[({4-[(E)-2-{4-[(cyclopropylamino)methyl]phenyl}ethenyl]phenyl}carbonyl)(methyl)amino]-N-hydroxy-N',2-dimethylpropanediamide Compound 622 (2S)-N-hydroxy-2-{[(4-{[6-(methoxymethyl)pyridin-3-yl]ethynyl}phenyl)carbonyl](methyl)amino}-N',2-dimethylpropanediamide Compound 623 (2S)-N-hydroxy-N',2-dimethyl-2-[methyl({4'-[(3-methyloxetan-3-yl)methoxy]biphenyl-4-yl}carbonyl)amino]propanediamide, Compound 624 (2S)-N-hydroxy-N',2-dimethyl-2-[methyl({4'-[4-(morpholin-4-yl)butoxy]biphenyl-4-yl}carbonyl)amino]propanediamide, Compound 625 (2S)-2-[({4-[(4-{[3-(cyclopropyloxy)azetidin-1-yl]methyl}phenyl)ethynyl]phenyl}carbonyl)(methyl)amino]-N-hydroxy-N',2-dimethylpropanediamide, Compound 626 (2S)-N-hydroxy-N',2-dimethyl-2-(methyl{[4'-(tetrahydro-2H-pyran-4-ylmethoxy)biphenyl-4-yl]carbonyl}amino)propanediamide, Compound 627 (2S)-N-hydroxy-N',2-dimethyl-2-[methyl({4-[(E)-2-{4-[(oxetan-3-ylamino)methyl]phenyl}ethenyl]phenyl}carbonyl)amino]propanediamide, Compound 628 (2S)-N-hydroxy-N',2-dimethyl-2-{methyl[(4-{(E)-2-[4-(1,4-oxazepan-4-ylmethyl)phenyl]ethenyl}phenyl)carbonyl]amino}propanediamide, Compound 629 (2S)-2-[{[2'-chloro-4'-(methylamino)biphenyl-4-yl]carbonyl}(methyl)amino]-N-hydroxy-N',2-dimethylpropanediamide, Compound 630 (2S)-N-hydroxy-2-{[(4-{[5-(methoxymethyl)furan-2-yl]ethynyl}phenyl)carbonyl](methyl)amino}-N',2-dimethylpropanediamide, Compound 631 (2S)-N-hydroxy-N',2-dimethyl-2-[methyl({4-[5-(3-methyloxetan-3-yl)pent-1-yn-1-yl]phenyl}carbonyl)amino]propanediamide, Compound 632 (2S)-N-hydroxy-2-{[(4-{[4-(hydroxymethyl)phenyl]ethynyl}phenyl)carbonyl](methyl)amino}-N',2-dimethylpropanediamide, Compound 633 (2S)-2-[({4-[(1,5-dimethyl-1H-pyrazol-4-yl)ethynyl]phenyl}carbonyl)(methyl)amino]-N-hydroxy-N',2-dimethylpropanediamide, Compound 634 (2S)-N-hydroxy-N',2-dimethyl-2-{methyl[(4-{[4-(6-oxa-1-azaspiro[3.3]hept-1-ylmethyl)phenyl]ethynyl}phenyl)carbonyl]amino}propanediamide.

The invention claimed is:

1. A compound represented by the following formula [1] or a pharmaceutically acceptable salt thereof:

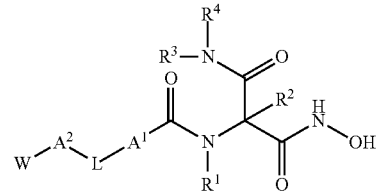

[1]

wherein $R^1$ and $R^2$ are the same or different and each represent a hydrogen atom, a $C_{1-6}$ alkyl group, a $C_{3-8}$ cycloalkyl group or a $C_{1-6}$ alkoxy group (the $C_{1-6}$ alkyl group, the $C_{1-6}$ alkoxy group and the $C_{3-8}$ cycloalkyl group may be substituted with 1 to 3 substituents which are the same or different and are selected from "a halogen atom, a hydroxy group, a $C_{3-8}$ cycloalkyl group, a $C_{1-6}$ alkoxy group, a $C_{3-8}$ cycloalkoxy group, an amino group, a $C_{1-6}$ alkylamino group, a di($C_{1-6}$ alkyl)amino group, —N($R^{11}$)COR$^{12}$, —N($R^{11}$)SO$_2$R$^{12}$, a cyano group, a carboxy group, a carbamoyl group, —CON($R^{13}$)($R^{14}$), —SO$_2$N($R^{13}$)($R^{14}$), a $C_{1-6}$ alkylthio group, a $C_{1-6}$ alkylsulfonyl group, an aryloxy group, an aryl group, and a heterocyclic group"), $R^{11}$, $R^{12}$, $R^{13}$ and $R^{14}$ are the same or different and each represent a hydrogen atom or a $C_{1-6}$ alkyl group, $R^{13}$ and $R^{14}$, together with the nitrogen atom to which they are attached, may form a saturated or unsaturated 5- or 6-membered ring which may further contain one or more nitrogen atoms, oxygen atoms or sulfur atoms, $R^3$ represents a hydrogen atom or a $C_{1-6}$ alkyl group (the $C_{1-6}$ alkyl group may be substituted with 1 to 3 substituents which are the same or different and are selected from "a halogen atom, a hydroxy group, a $C_{1-6}$ alkoxy group, a $C_{3-8}$ cycloalkoxy group, an amino group, a $C_{1-6}$ alkylamino group, and a di($C_{1-6}$ alkyl)amino group"), $R^4$ represents a hydrogen atom, a hydroxy group, a $C_{1-6}$ alkoxy group, a $C_{3-8}$ cycloalkoxy group,
an amino group,
a $C_{1-6}$ alkylamino group,
a di($C_{1-6}$ alkyl)amino group,
a $C_{1-6}$ alkyl group, a $C_{3-8}$ cycloalkyl group
(the $C_{1-6}$ alkyl group and the $C_{3-8}$ cycloalkyl group may be substituted with 1 to 3 substituents which are the same or different and are selected from
"a halogen atom, a hydroxy group, a $C_{3-8}$ cycloalkyl group, a $C_{1-6}$ alkoxy group, a $C_{3-8}$ cycloalkoxy group, an amino group, a $C_{1-6}$ alkylamino group, a di($C_{1-6}$ alkyl)amino group, —N($R^{41}$)CO$R^{42}$, —N($R^{41}$)SO$_2R^{42}$, a cyano group, a carboxy group, —CON($R^{43}$)($R^{44}$), —SO$_2$N($R^{43}$)($R^{44}$), a $C_{1-6}$ alkylthio group, a $C_{1-6}$ alkylsulfonyl group, an aryl group, an aryloxy group, and a heterocyclic group (the aryl group, the aryloxy group, and the heterocyclic group may be substituted with 1 to 3 substituents which are the same or different and are selected from "a halogen atom, a $C_{1-6}$ alkyl group, a $C_{3-8}$ cycloalkyl group, a benzyl group, a $C_{1-6}$ haloalkyl group, a $C_{1-6}$ hydroxyalkyl group, a $C_{2-8}$ alkoxyalkyl group, a hydroxy group, a $C_{1-6}$ alkoxy group, a $C_{3-8}$ cycloalkoxy group, an amino group, a $C_{1-6}$ alkylamino group, a di($C_{1-6}$ alkyl)amino group, —N($R^{45}$)COR$^{46}$, —N($R^{45}$)SO$_2R^{46}$, a cyano group, a carboxy group, —CON($R^{47}$)($R^{48}$), —SO$_2$N($R^{47}$)($R^{48}$), a $C_{1-6}$ alkylthio group, and a $C_{1-6}$ alkylsulfonyl group") "),
an aryl group, or a heterocyclic group
(the aryl group and the heterocyclic group may be substituted with 1 to 3 substituents which are the same or different and are selected from "a halogen atom, a $C_{1-6}$ alkyl group, a $C_{3-8}$ cycloalkyl group, a $C_{1-6}$ haloalkyl group, a $C_{1-6}$ hydroxyalkyl group, a $C_{2-8}$ alkoxyalkyl group, a hydroxy group, a $C_{1-6}$ alkoxy group, a $C_{3-8}$ cycloalkoxy group, an amino group, a $C_{1-6}$ alkylamino group, a di($C_{1-6}$ alkyl)amino group, —N($R^{45}$)COR$^{46}$, —N($R^{45}$)SO$_2R^{46}$, a cyano group, a carboxy group, —CON($R^{47}$)($R^{48}$), —SO$_2$N($R^{47}$)($R^{48}$), a $C_{1-6}$ alkylthio group, and a $C_{1-6}$ alkylsulfonyl group"),
$R^{41}$, $R^{42}$, $R^{43}$, $R^{44}$, $R^{45}$, $R^{46}$, $R^{47}$ and $R^{48}$ are the same or different and each represent a hydrogen atom or a $C_{1-6}$ alkyl group,
$R^{43}$ and $R^{44}$, together with the nitrogen atom to which they are attached, may form a saturated or unsaturated 5- or 6-membered ring which may further contain one or more nitrogen atoms, oxygen atoms or sulfur atoms,
$R^{47}$ and $R^{48}$, together with the nitrogen atom to which they are attached, may form a saturated or unsaturated 5- or 6-membered ring which may further contain one or more nitrogen atoms, oxygen atoms or sulfur atoms,
$R^3$ and $R^4$, together with the nitrogen atom to which they are attached, may form a saturated or unsaturated 5- or 6-membered ring which may further contain one or more nitrogen atoms, oxygen atoms or sulfur atoms,
$A^1$ represents a divalent aryl group which may be substituted with 1 to 4 substituents which are the same or different and are selected from the following group of substituents, $R^a$):
the group of substituents, $R^a$, consists of a halogen atom, a hydroxy group, an amino group (the amino group may be substituted with a $C_{2-6}$ alkanoyl group or one or two $C_{1-6}$ alkyl groups), a carboxy group, a carbamoyl group, a $C_{1-6}$ alkyl group, a $C_{3-8}$ cycloalkyl group, a $C_{2-6}$ alkenyl group, and a $C_{1-6}$ alkoxy group (the $C_{1-6}$ alkyl group, the $C_{3-8}$ cycloalkyl group, the $C_{2-6}$ alkenyl group, and the $C_{1-6}$ alkoxy group may be substituted with 1 to 4 substituents which are the same or different and are selected from "a halogen atom, a hydroxy group, an amino group, a carboxy group, a $C_{1-6}$ alkylaminocarbonyl group, and a $C_{1-6}$ alkoxycarbonyl group"),
L represents —C≡C—, —C≡C—C≡C—, —CH=CH—, —CH=CH—C≡C—, or —C≡C—CH=CH—,
$R^5$ represents a hydrogen atom, a $C_{1-6}$ alkyl group, a $C_{3-8}$ cycloalkyl group, or an aryl group,
m denotes 1, 2 or 3,
$A^2$ represents a divalent aryl group which may be substituted with 1 to 4 substituents which are the same or different and are selected from the following group of substituents, $R^b$):
the group of substituents, $R^b$, consists of a halogen atom, an optionally protected hydroxy group, a mercapto group, a cyano group, a nitro group, an optionally protected amino group, an optionally protected formyl group, an optionally protected carboxy group, a carbamoyl group, a sulfo group, a ureido group, a guanidido group, a $C_{1-6}$ alkyl group, a $C_{3-8}$ cycloalkyl group, a $C_{1-6}$ haloalkyl group, a $C_{1-6}$ hydroxyalkyl group, a $C_{1-6}$ alkoxy group, a $C_{1-6}$ alkylamino group, a di($C_{1-6}$ alkyl)amino group, a $C_{1-6}$ alkoxycarbonyl group, a $C_{2-6}$ alkanoyl group, and an aryl group,
W represents $R^6$—$X^1$—, $R^6$—$X^2$—$Y^1$—$X^1$—, $R^6$—$X^4$—$Y^1$—$X^2$—$Y^3$—$X^3$—, Q-$X^1$—$Y^2$—$X^3$—, or Q-$X^1$—$Y^1$—$X^2$—$Y^3$—$X^3$—,
$Y^2$ represents —O—, —$NR^7$—, —CO—, —$NR^7$CO—, —CON$R^7$—, —S(O)$_n$—, —OCO—, —COO—, —$NR^7$SO$_2$—, —SO$_2$—$NR^7$—, —OCOO—, —OCON$R^7$—, —$NR^7$CON$R^8$—, or a bond,
$Y^1$ and $Y^3$ are the same or different and each represent —O—, —$NR^7$—, —CO—, —$NR^7$CO—, —CON$R^7$—, —S(O)$_n$—, —OCO—, —COO—, —$NR^7$SO$_2$—, —SO$_2NR^7$—, —OCOO—, —OCON$R^7$—, or —$NR^7$CON$R^8$—,
n denotes 0, 1 or 2,
$X^1$ and $X^3$ are the same or different and each represent a $C_{1-10}$ alkylene group, a $C_{2-10}$ alkenylene group, a $C_{2-10}$ alkynylene group, a $C_{3-8}$ cycloalkylene group, —$C_{1-6}$ alkylene-$C_{3-8}$ cycloalkylene-$C_{1-6}$ alkylene- (the $C_{1-10}$ alkylene group, the $C_{2-10}$ alkenylene group, the $C_{2-10}$ alkynylene group, the $C_{3-8}$ cycloalkylene group, and the —$C_{1-6}$ alkylene-$C_{3-8}$ cycloalkylene-$C_{1-6}$ alkylene- may be substituted with 1 to 4 substituents which are the same or different and are selected from a group of substituents, $R^c$, to be shown below), or a bond,
$X^2$ and $X^4$ are the same or different and each represent a $C_{1-10}$ alkylene group, a $C_{2-10}$ alkenylene group, a $C_{2-10}$ alkynylene group, or —$C_{1-6}$ alkylene-$C_{3-8}$ cycloalkylene-$C_{1-6}$ alkylene-(the $C_{1-10}$ alkylene group, the $C_{2-10}$ alkenylene group, the $C_{2-10}$ alkynylene group, and the -$C_{1-6}$ alkylene-$C_{3-8}$ cycloalkylene-$C_{1-6}$ alkylene- may be substituted with 1 to 4 substituents which are the same or different and are selected from the group of substituents, $R^c$, to be shown below),
Q represents a $C_{3-8}$ cycloalkyl group, an aryl group, or a heterocyclic group (the $C_{3-8}$ cycloalkyl group, the aryl group and the heterocyclic group may be substituted with 1 to 4 substituents which are the same or different and are selected from the group of substituents, $R^c$, to be shown below, and the heterocyclic group may have the different carbon atoms on the ring bridged with a $C_{1-6}$ alkylene group or —$C_{1-6}$ alkylene-O—$C_{1-6}$ alkylene-),

531

$R^6$ represents a hydrogen atom, a halogen atom, an optionally protected hydroxy group, a mercapto group, a cyano group, a nitro group, an optionally protected amino group, an optionally protected formyl group, an optionally protected carboxy group, a carbamoyl group, a sulfo group, an optionally protected phosphate group, a ureido group, a guanidido group, $R^7$—O—$NR^8$—CO—, $R^8$—ON=$CR^9$—, $R^8$—ON=$CR^9$—NH—, $R^7$—O—$NR^8$—CH=N—, $(R^7)(R^8)N$—N=CH—, $R^8$—O—$NR^8$—, N≡C—$NR^8$— or a $C_{1-6}$ alkoxy group (the $C_{1-6}$ alkoxy group may be substituted with 1 to 3 hydroxy groups), $R^7$ and $R^8$ are the same or different and each represent a hydrogen atom, a $C_{1-6}$ alkyl group, a $C_{3-8}$ cycloalkyl group, an aryl group, or a heterocyclic group (the $C_{1-6}$ alkyl group, the $C_{3-8}$ cycloalkyl group, the aryl group and the heterocyclic group may be substituted with 1 to 4 substituents which are the same or different and are selected from the group of substituents, $R^c$, to be shown below), $R^9$ represents a hydrogen atom, a $C_{1-6}$ alkyl group, a $C_{3-8}$ cycloalkyl group, an amino group, or a $C_{1-6}$ alkylamino group, and the group of substituents, $R^c$, consists of a halogen atom, a hydroxy group, a cyano group, a nitro group, an amino group (the amino group may be substituted with a $C_{2-6}$ alkanoyl group or one or two $C_{1-6}$ alkyl groups), a carboxy group, a carbamoyl group, a ureido group, a guanidido group, a $C_{1-6}$ alkyl group (the $C_{1-6}$ alkyl group may be substituted with a heterocyclic group), a $C_{1-6}$ hydroxyalkyl group, a $C_{1-6}$ haloalkyl group, a $C_{3-8}$ cycloalkyl group, a $C_{1-6}$ alkoxy group (the $C_{1-6}$ alkoxy group may be substituted with 1 to 3 substituents which are the same or different and are selected from a hydroxy group, a halogen atom, a $C_{3-8}$ cycloalkyl group, a $C_{1-6}$ alkoxy group, an aryl group and a heterocyclic group), a $C_{3-8}$ cycloalkoxy group, a $C_{1-6}$ alkoxycarbonyl group, a $C_{1-6}$ alkoxycarbonylamino group, a $C_{2-6}$ alkanoyl group, a $C_{1-6}$ alkylsulfonyl group, a $C_{1-6}$ alkylthio group, an aryl group, a heterocyclic group (the aryl group and the heterocyclic group may be substituted with 1 to 4 substituents which are the same or different and are selected from "a halogen atom, a hydroxy group, a cyano group, a nitro group, an amino group, a carboxy group and a $C_{1-6}$ alkyl group"), a $C_{1-6}$ alkylidene group (the $C_{1-6}$ alkylidene group may be substituted with a $C_{1-6}$ alkoxy group), a $C_{3-8}$ cycloalkylidene group, a monocyclic saturated heteroclidene group (the monocyclic saturated heteroclidene group may be substituted with 1 to 2 $C_{1-6}$ alkyl groups), and a hydroxyaminocarbonyl group.

2. The compound represented by the following formula [1] or the pharmaceutically acceptable salt thereof, according to claim 1:

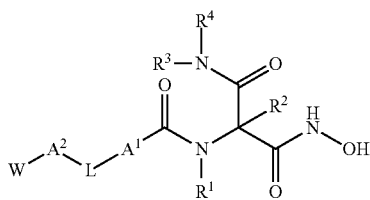

[1]

532 wherein $R^1$ and $R^2$ are the same or different and each represent a hydrogen atom, a $C_{1-6}$ alkyl group, a $C_{3-8}$ cycloalkyl group or a $C_{1-6}$ alkoxy group (the $C_{1-6}$ alkyl group, the $C_{1-6}$ alkoxy group and the $C_{3-8}$ cycloalkyl group may be substituted with 1 to 3 substituents which are the same or different and are selected from "a halogen atom, a hydroxy group, a $C_{3-8}$ cycloalkyl group, a $C_{1-6}$ alkoxy group, a $C_{3-8}$ cycloalkoxy group, an amino group, a $C_{1-6}$ alkylamino group, a di($C_{1-6}$ alkyl)amino group, —$N(R^{11})COR^{12}$, —$N(R^{11})SO_2R^{12}$, a cyano group, a carboxy group, a carbamoyl group, —$CON(R^{13})(R^{14})$, —$SO_2N(R^{13})(R^{14})$, a $C_{1-6}$ alkylthio group, a $C_{1-6}$ alkylsulfonyl group, an aryloxy group, an aryl group, and a heterocyclic group"), $R^{11}$, $R^{12}$, $R^{13}$ and $R^{14}$ are the same or different and each represent a hydrogen atom or a $C_{1-6}$ alkyl group, $R^{13}$ and $R^{14}$, together with the nitrogen atom to which they are attached, may form a saturated or unsaturated 5- or 6-membered ring which may further contain one or more nitrogen atoms, oxygen atoms or sulfur atoms, $R^3$ represents a hydrogen atom or a $C_{1-6}$ alkyl group (the $C_{1-6}$ alkyl group may be substituted with 1 to 3 substituents which are the same or different and are selected from "a halogen atom, a hydroxy group, a $C_{1-6}$ alkoxy group, a $C_{3-8}$ cycloalkoxy group, an amino group, a $C_{1-6}$ alkylamino group, and a di($C_{1-6}$ alkyl)amino group"), $R^4$ represents
a hydrogen atom,
a hydroxy group,
a $C_{1-6}$ alkoxy group,
a $C_{3-8}$ cycloalkoxy group,
an amino group,
a $C_{1-6}$ alkylamino group,
a di($C_{1-6}$ alkyl)amino group,
a $C_{1-6}$ alkyl group, a $C_{3-8}$ cycloalkyl group
(the $C_{1-6}$ alkyl group and the $C_{3-8}$ cycloalkyl group may be substituted with 1 to 3 substituents which are the same or different and are selected from
"a halogen atom, a hydroxy group, a $C_{3-8}$ cycloalkyl group, a $C_{1-6}$ alkoxy group, a $C_{3-8}$ cycloalkoxy group, an amino group, a $C_{1-6}$ alkylamino group, a di($C_{1-6}$ alkyl)amino group, —$N(R^{41})COR^{42}$, —$N(R^{41})SO_2R^{42}$, a cyano group, a carboxy group, —$CON(R^{43})(R^{44})$, —$SO_2N(R^{43})(R^{44})$, a $C_{1-6}$ alkylthio group, a $C_{1-6}$ alkylsulfonyl group, an aryl group, an aryloxy group, and a heterocyclic group (the aryl group, the aryloxy group, and the heterocyclic group may be substituted with 1 to 3 substituents which are the same or different and are selected from "a halogen atom, a $C_{1-6}$ alkyl group, a $C_{3-8}$ cycloalkyl group, a benzyl group, a $C_{1-6}$ haloalkyl group, a $C_{1-6}$ hydroxyalkyl group, a $C_{2-8}$ alkoxyalkyl group, a hydroxy group, a $C_{1-6}$ alkoxy group, a $C_{3-8}$ cycloalkoxy group, an amino group, a $C_{1-6}$ alkylamino group, a di($C_{1-6}$ alkyl)amino group, —$N(R^{45})COR^{46}$, —$N(R^{45})SO_2R^{46}$, a cyano group, a carboxy group, —$CON(R^{47})(R^{48})$, —$SO_2N(R^{47})(R^{48})$, a $C_{1-6}$ alkylthio group, and a $C_{1-6}$ alkylsulfonyl group") "), an aryl group, or a heterocyclic group
(the aryl group and the heterocyclic group may be substituted with 1 to 3 substituents which are the same or different and are selected from "a halogen atom, a $C_{1-6}$ alkyl group, a $C_{3-8}$ cycloalkyl group, a $C_{1-6}$ haloalkyl group, a $C_{1-6}$ hydroxyalkyl group, a $C_{2-8}$ alkoxyalkyl group, a hydroxy group, a $C_{1-6}$ alkoxy group, a $C_{3-8}$ cycloalkoxy group, an amino group, a $C_{1-6}$ alkylamino group, a di($C_{1-6}$ alkyl)amino group, —N($R^{45}$)CO$R^{46}$, —N($R^{45}$)SO$_2R^{46}$, a cyano group, a carboxy group, —CON($R^{47}$)($R^{48}$), —SO$_2$N($R^{47}$)($R^{48}$)SO$_2$N($R^{47}$)($R^{48}$), a $C_{1-6}$ alkylthio group, and a $C_{1-6}$ alkylsulfonyl group"), $R^{41}$, $R^{42}$, $R^{43}$, $R^{44}$, $R^{45}$, $R^{46}$, $R^{47}$ and $R^{48}$ are the same or different and each represent a hydrogen atom or a $C_{1-6}$ alkyl group, $R^{43}$ and $R^{44}$, together with the nitrogen atom to which they are attached, may form a saturated or unsaturated 5- or 6-membered ring which may further contain one or more nitrogen atoms, oxygen atoms or sulfur atoms, $R^{47}$ and $R^{48}$, together with the nitrogen atom to which they are attached, may form a saturated or unsaturated 5- or 6-membered ring which may further contain one or more nitrogen atoms, oxygen atoms or sulfur atoms, $R^3$ and $R^4$, together with the nitrogen atom to which they are attached, may form a saturated or unsaturated 5- or 6-membered ring which may further contain one or more nitrogen atoms, oxygen atoms or sulfur atoms, $A^1$ represents a divalent aryl group which may be substituted with 1 to 4 substituents which are the same or different and are selected from the following group of substituents, $R^a$):

the group of substituents, $R^a$, consists of a halogen atom, a hydroxy group, an amino group (the amino group may be substituted with a $C_{2-6}$ alkanoyl group or one or two $C_{1-6}$ alkyl groups), a carboxy group, a carbamoyl group, a $C_{1-6}$ alkyl group, a $C_{3-8}$ cycloalkyl group, a $C_{2-6}$ alkenyl group, and a $C_{1-6}$ alkoxy group (the $C_{1-6}$ alkyl group, the $C_{3-8}$ cycloalkyl group, the $C_{2-6}$ alkenyl group, and the $C_{1-6}$ alkoxy group may be substituted with 1 to 4 substituents which are the same or different and are selected from "a halogen atom, a hydroxy group, an amino group, a carboxy group, a $C_{1-6}$ alkylaminocarbonyl group, and a $C_{1-6}$ alkoxycarbonyl group"), L represents —C≡C— or —C≡C—C≡C—, $R^5$ represents a hydrogen atom, a $C_{1-6}$ alkyl group, a $C_{3-8}$ cycloalkyl group, or an aryl group, m denotes 1, 2 or 3, $A^2$ represents a divalent aryl group which may be substituted with 1 to 4 substituents which are the same or different and are selected from the following group of substituents, $R^b$):

the group of substituents, $R^b$, consists of a halogen atom, an optionally protected hydroxy group, a mercapto group, a cyano group, a nitro group, an optionally protected amino group, an optionally protected formyl group, an optionally protected carboxy group, a carbamoyl group, a sulfo group, a ureido group, a guanidido group, a $C_{1-6}$ alkyl group, a $C_{3-8}$ cycloalkyl group, a $C_{1-6}$ haloalkyl group, a $C_{1-6}$ hydroxyalkyl group, a $C_{1-6}$ alkoxy group, a $C_{1-6}$ alkylamino group, a di($C_{1-6}$ alkyl)amino group, a $C_{1-6}$ alkoxycarbonyl group, a $C_{2-6}$ alkanoyl group, and an aryl group, W represents $R^6$—$X^1$—, $R^6$—$X^2$—$Y^1$—$X^1$—, $R^6$—$X^4$—$Y^1$—$X^2$—$Y^3$—$X^3$—, Q-$X^1$—$Y^2$—$X^3$—, or Q-$X^1$—$Y^1$—$X^2$—$Y^3$—$X^3$—, $Y^2$ represents —O—, —N$R^7$—, —CO—, —N$R^7$CO—, —CON$R^7$—, —S(O)$_n$—, —OCO—, —COO—, —N$R^7$SO$_2$—, —SO$_2$—N$R^7$—, —OCOO—, —OCON$R^7$—, —N$R^7$—CON$R^8$—, or a bond, $Y^1$ and $Y^3$ are the same or different and each represent —O—, —N$R^7$—, —CO—, —N$R^7$CO—, —CON$R^7$—, —S(O)$_n$—, —OCO—, —COO—, —N$R^7$SO$_2$, —SO$_2$N$R^7$—, —OCOO—, —OCON$R^7$—, or —N$R^7$CON$R^8$—, n denotes 0, 1 or 2, $X^1$ and $X^3$ are the same or different and each represent a $C_{1-10}$ alkylene group, a $C_{2-10}$ alkenylene group, a $C_{2-10}$ alkynylene group (the $C_{1-10}$ alkylene group, the $C_{2-10}$ alkenylene group and the $C_{2-10}$ alkynylene group may be substituted with 1 to 4 substituents which are the same or different and are selected from a group of substituents, $R^c$, to be shown below), or a bond, $X^2$ and $X^4$ are the same or different and each represent a $C_{1-10}$ alkylene group, a $C_{2-10}$ alkenylene group, a $C_{2-10}$ alkynylene group, or -$C_{1-6}$ alkylene-$C_{3-8}$ cycloalkylene-$C_{1-6}$ alkylene -(the $C_{1-10}$ alkylene group, the $C_{2-10}$ alkenylene group, the $C_{2-10}$ alkynylene group, and the -$C_{1-6}$ alkylene-$C_{3-8}$ cycloalkylene-$C_{1-6}$ alkylene—may be substituted with 1 to 4 substituents which are the same or different and are selected from the group of substituents, $R^c$, to be shown below), Q represents a $C_{3-8}$ cycloalkyl group, an aryl group, or a heterocyclic group (the $C_{3-8}$ cycloalkyl group, the aryl group and the heterocyclic group may be substituted with 1 to 4 substituents which are the same or different and are selected from the group of substituents, $R^c$, to be shown below), $R^6$ represents a hydrogen atom, a halogen atom, an optionally protected hydroxy group, a mercapto group, a cyano group, a nitro group, an optionally protected amino group, an optionally protected formyl group, an optionally protected carboxy group, a carbamoyl group, a sulfo group, an optionally protected phosphate group, a ureido group, a guanidido group, $R^7$—O—N$R^8$—CO—, $R^8$—ON═C$R^9$—, $R^8$—ON═C$R^9$—NH—, $R^7$—O—N$R^8$—CH═N—, ($R^7$)($R^8$)N—N═CH—, $R^8$—O—N$R^8$—, or N≡C—N$R^8$—, $R^7$ and $R^8$ are the same or different and each represent a hydrogen atom, a $C_{1-6}$ alkyl group, a $C_{3-8}$ cycloalkyl group, an aryl group, or a heterocyclic group (the $C_{1-6}$ alkyl group, the $C_{3-8}$ cycloalkyl group, the aryl group and the heterocyclic group may be substituted with 1 to 4 substituents which are the same or different and are selected from the group of substituents, $R^c$, to be shown below), $R^9$ represents a hydrogen atom, a $C_{1-6}$ alkyl group, a $C_{3-8}$ cycloalkyl group, an amino group, or a $C_{1-6}$ alkylamino group, and the group of substituents, $R^c$, consists of a halogen atom, a hydroxy group, a cyano group, a nitro group, an amino group (the amino group may be substituted with a $C_{2-6}$ alkanoyl group or one or two $C_{1-6}$ alkyl groups), a carboxy group, a carbamoyl group, a ureido group, a guanidido group, a $C_{1-6}$ alkyl group (the $C_{1-6}$ alkyl group may be substituted with a heterocyclic group), a $C_{1-6}$ hydroxyalkyl group, a $C_{1-6}$ haloalkyl group, a $C_{3-8}$ cycloalkyl group, a $C_{1-6}$ alkoxy group (the $C_{1-6}$ alkoxy group may be substituted with 1 to 3 hydroxy groups), a $C_{3-8}$ cycloalkoxy group, a $C_{1-6}$ alkoxycarbonyl group, a $C_{1-6}$ alkoxycarbonylamino group, a $C_{2-6}$ alkanoyl group, a $C_{1-6}$ alkylsulfonyl group, a $C_{1-6}$ alkylthio group, an aryl group, and a heterocyclic group (the aryl group and the heterocyclic group may be substituted with 1 to 4 substituents which are the same or different and are selected from "a halogen atom, a hydroxy group, a cyano group, a nitro group, an amino group, a carboxy group and a $C_{1-6}$ alkyl group").

3. The compound or the pharmaceutically acceptable salt thereof, according to claim 1, wherein $R^1$ is a hydrogen atom or a $C_{1-6}$ alkyl group (the $C_{1-6}$ alkyl group may be substituted with the same or different 1 to 3 halogen atoms).

4. The compound or the pharmaceutically acceptable salt thereof, according to claim 3, wherein $R^1$ is a $C_{1-6}$ alkyl group (the $C_{1-6}$ alkyl group may be substituted with the same or different 1 to 3 halogen atoms).

5. The compound or the pharmaceutically acceptable salt thereof, according to claim 4, wherein $R^1$ is a methyl group.

6. The compound or the pharmaceutically acceptable salt thereof, according to claim 1, wherein $R^2$ is a hydrogen atom.

7. The compound or the pharmaceutically acceptable salt thereof, according to claim 1, wherein $R^2$ is a methyl group.

8. The compound or the pharmaceutically acceptable salt thereof, according to claim 1, wherein
$R^3$ is a hydrogen atom, and
$R^4$ is a $C_{1-6}$ alkyl group (the $C_{1-6}$ alkyl group may be substituted with a phenyl group or a monocyclic aromatic heterocyclic group (the phenyl group and the monocyclic aromatic heterocyclic group may be substituted with 1 to 3 substituents which are the same or different and are selected from "a halogen atom, a $C_{1-6}$ alkyl group, a $C_{3-8}$ cycloalkyl group, a $C_{1-6}$ haloalkyl group, a $C_{1-6}$ hydroxyalkyl group, a $C_{2-8}$ alkoxyalkyl group, a hydroxy group, a $C_{1-6}$ alkoxy group, a $C_{3-8}$ cycloalkoxy group, an amino group, a $C_{1-6}$ alkylamino group, a di($C_{1-6}$ alkyl)amino group, —N($R^{45}$)COR$^{46}$, —CON($R^{47}$)($R^{48}$)")).

9. The compound or the pharmaceutically acceptable salt thereof, according to claim 8, wherein $R^3$ is a hydrogen atom, and $R^4$ is a methyl group.

10. The compound or the pharmaceutically acceptable salt thereof, according to claim 1, wherein $A^1$ is a phenylene group (the phenylene group may be substituted with 1 to 4 substituents which are the same or different and are selected from "a halogen atom, a hydroxy group, an amino group and a $C_{1-6}$ alkyl group").

11. The compound or the pharmaceutically acceptable salt thereof, according to claim 10, wherein $A^1$ is a phenylene group.

12. The compound or the pharmaceutically acceptable salt thereof, according to claim 1, wherein L is —C≡C—.

13. The compound or the pharmaceutically acceptable salt thereof, according to claim 1, wherein
W is $R^6$—$X^1$—,
$X^1$ is a methylene group or a bond,
$R^6$ is a hydrogen atom, an optionally protected hydroxy group, or $R^8$—ON=CR$^9$—,
$R^8$ is a hydrogen atom or a $C_{1-6}$ alkyl group (the $C_{1-6}$ alkyl group may be substituted with 1 to 4 substituents which are the same or different and are selected from a group of substituents, $R^c$, to be shown below),
$R^9$ is a hydrogen atom, a $C_{1-6}$ alkyl group, a $C_{3-8}$ cycloalkyl group, an amino group, or a $C_{1-6}$ alkylamino group, and
the group of substituents, $R^c$, consists of a halogen atom and a hydroxy group.

14. The compound or the pharmaceutically acceptable salt thereof, according to claim 1, wherein
W is $R^6$—$X^2$—$Y^1$—$X^1$—,
$Y^1$ is —O— or —NR$^7$—,
$X^1$ is a methylene group, an ethylene group (the methylene group and the ethylene group may be substituted with 1 to 2 methyl groups), a $C_{3-8}$ cycloalkylene group, or a bond,
$X^2$ is a $C_{1-4}$ alkylene group (the $C_{1-4}$ alkylene group may be substituted with 1 to 4 substituents which are the same or different and are selected from a group of substituents, $R^c$, to be shown below),
$R^6$ is a hydrogen atom, a halogen atom, an optionally protected hydroxy group, or a $C_{1-6}$ alkoxy group,
$R^7$ is a hydrogen atom, a $C_{1-6}$ alkyl group or a $C_{3-8}$ cycloalkyl group (the $C_{1-6}$ alkyl group and the $C_{3-8}$ cycloalkyl group may be substituted with 1 to 4 substituents which are the same or different and are selected from the following group of substituents, $R^c$), and
the group of substituents, $R^c$, consists of a halogen atom, a hydroxy group, and a $C_{1-6}$ alkyl group.

15. The compound or the pharmaceutically acceptable salt thereof, according to claim 1, wherein
W is Q-$X^1$—$Y^2$—$X^3$—,
$Y^2$ is —O—, —NR$^7$—, or a bond,
$X^1$ is a $C_{1-4}$ alkylene group (the $C_{1-4}$ alkylene group may be substituted with 1 to 4 substituents which are the same or different and are selected from a group of substituents, $R^c$, to be shown below), or a bond,
$X^3$ is a methylene group, an ethylene group (the methylene group and the ethylene group may be substituted with 1 to 2 methyl groups), a $C_{3-8}$ cycloalkylene group, or a bond,
Q is a $C_{3-8}$ cycloalkyl group, an aryl group, or a heterocyclic group (the $C_{3-8}$ cycloalkyl group, the aryl group, or the heterocyclic group may be substituted with 1 to 4 substituents which are the same or different and are selected from the group of substituents, $R^c$, shown below)
$R^7$ is a hydrogen atom, a $C_{1-6}$ alkyl group or a $C_{3-8}$ cycloalkyl group (the $C_{1-6}$ alkyl group and the $C_{3-8}$ cycloalkyl group may be substituted with 1 to 4 substituents which are the same or different and are selected from the following group of substituents, $R^c$), and
the group of substituents, $R^c$, consists of a halogen atom, a hydroxy group, a $C_{1-6}$ alkyl group, a $C_{1-6}$ hydroxyalkyl group, a $C_{1-6}$ haloalkyl group, a $C_{3-8}$ cycloalkyl group, a $C_{1-6}$ alkoxy group (the $C_{1-6}$ alkoxy group may be substituted with 1 to 3 hydroxy groups or halogen atoms), a $C_{3-8}$ cycloalkoxy group, a $C_{2-6}$ alkanoyl group, a $C_{1-6}$ alkylidene group (the $C_{1-6}$ alkylidene group may be substituted with a $C_{1-6}$ alkoxy group), and a hydroxyaminocarbonyl group.

16. The compound or the pharmaceutically acceptable salt thereof, according to claim 1, wherein
W is a hydrogen atom, a halogen atom, a $C_{1-6}$ alkyl group, a $C_{1-6}$ alkoxy group, or a $C_{1-6}$ alkylamino group (the $C_{1-6}$ alkyl group, the $C_{1-6}$ alkoxy group and the $C_{1-6}$ alkylamino group may be substituted with 1 to 3 substituents which are the same or different and are selected from "a halogen atom, a hydroxy group, a $C_{1-6}$ alkoxy group and a morpholino group").

17. A pharmaceutical composition comprising the compound or the pharmaceutically acceptable salt thereof according to claim 1 and a pharmaceutically acceptable carrier, excipient or diluent.

* * * * *